(12) United States Patent
Schwaeble et al.

(10) Patent No.: US 11,884,742 B2
(45) Date of Patent: Jan. 30, 2024

(54) METHODS FOR TREATING CONDITIONS ASSOCIATED WITH MASP-2 DEPENDENT COMPLEMENT ACTIVATION

(71) Applicants: Omeros Corporation, Seattle, WA (US); University of Leicester, Leicestershire (GB)

(72) Inventors: Hans-Wilhelm Schwaeble, Cambridge (GB); Clark E. Tedford, Poulsbo, WA (US); James B. Parent, Bainbridge Island, WA (US); Thomas Dudler, Bellevue, WA (US); Gregory A. Demopulos, Mercer Island, WA (US)

(73) Assignees: Omeros Corporation, Seattle, WA (US); University of Leicester, Leicester (GB)

( * ) Notice: Subject to any disclaimer, the term of this patent is extended or adjusted under 35 U.S.C. 154(b) by 967 days.

(21) Appl. No.: 16/591,418

(22) Filed: Oct. 2, 2019

(65) Prior Publication Data

US 2020/0157245 A1 May 21, 2020

Related U.S. Application Data

(60) Continuation of application No. 14/459,656, filed on Aug. 14, 2014, now abandoned, which is a continuation of application No. 13/083,441, filed on Apr. 8, 2011, now Pat. No. 8,840,893, which is a continuation-in-part of application No. 12/896,754, filed on Oct. 1, 2010, now abandoned, which is a continuation of application No. 12/561,202, filed on Sep. 16, 2009, now abandoned, which is a division of application No. 11/645,359, filed on Dec. 22, 2006, now Pat. No. 7,919,094, which is a continuation-in-part of application No. 11/150,883, filed on Jun. 9, 2005, now abandoned.

(60) Provisional application No. 61/322,722, filed on Apr. 9, 2010, provisional application No. 60/788,876, filed on Apr. 3, 2006, provisional application No. 60/578,847, filed on Jun. 10, 2004.

(51) Int. Cl.
| | | |
|---|---|---|
| C07K 16/40 | (2006.01) |
| A61K 39/395 | (2006.01) |
| A01N 1/02 | (2006.01) |
| A61K 45/06 | (2006.01) |
| A61K 39/00 | (2006.01) |

(52) U.S. Cl.
CPC ............ *C07K 16/40* (2013.01); *A01N 1/0205* (2013.01); *A61K 39/395* (2013.01); *A61K 39/3955* (2013.01); *A61K 45/06* (2013.01); *A61K 2039/505* (2013.01); *C07K 2317/21* (2013.01); *C07K 2317/24* (2013.01); *C07K 2317/54* (2013.01); *C07K 2317/55* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,331,647 A | 5/1982 | Goldenberg |
| 4,394,370 A | 7/1983 | Jefferies |
| 4,526,909 A | 7/1985 | Urist |
| 4,563,489 A | 1/1986 | Urist |
| 4,816,567 A | 3/1989 | Cabilly |
| 4,946,778 A | 8/1990 | Ladner |
| 4,975,527 A | 12/1990 | Koezuka |
| 5,211,657 A | 5/1993 | Yamada |
| 5,223,409 A | 6/1993 | Ladner |
| 5,403,484 A | 4/1995 | Ladner |
| 5,552,157 A | 9/1996 | Yagi |
| 5,565,213 A | 10/1996 | Nakamori |
| 5,567,434 A | 10/1996 | Szoka, Jr. |
| 5,571,698 A | 11/1996 | Ladner |
| 5,610,288 A | 3/1997 | Rubenstein |
| 5,693,762 A | 12/1997 | Queen |
| 5,718,709 A | 2/1998 | Considine |

(Continued)

FOREIGN PATENT DOCUMENTS

| | | |
|---|---|---|
| CN | 101018565 A | 10/2007 |
| EP | 0 321 201 | 12/1994 |

(Continued)

OTHER PUBLICATIONS

Lehmann et al. (Transplantation, vol. 66(6), Sep. 27, 1998, pp. 717-722). (Year: 1998).*

(Continued)

*Primary Examiner* — Zachary S Skelding

(74) *Attorney, Agent, or Firm* — Tineka J. Quinton

(57) ABSTRACT

In one aspect, the invention provides methods of inhibiting the effects of MASP-2-dependent complement activation in a living subject. The methods comprise the step of administering, to a subject in need thereof, an amount of a MASP-2 inhibitory agent effective to inhibit MASP-2-dependent complement activation. In some embodiments, the MASP-2 inhibitory agent inhibits cellular injury associated with MASP-2-mediated alternative complement pathway activation, while leaving the classical (C1q-dependent) pathway component of the immune system intact. In another aspect, the invention provides compositions for inhibiting the effects of lectin-dependent complement activation, comprising a therapeutically effective amount of a MASP-2 inhibitory agent and a pharmaceutically acceptable carrier.

14 Claims, 69 Drawing Sheets

Specification includes a Sequence Listing.

(56) References Cited

U.S. PATENT DOCUMENTS

| | | | |
|---|---|---|---|
| 5,738,868 | A | 4/1998 | Shinkarenko |
| 5,739,119 | A | 4/1998 | Galli |
| 5,741,516 | A | 4/1998 | Webb |
| 5,759,829 | A | 6/1998 | Shewmaker |
| 5,789,573 | A | 8/1998 | Baker |
| 5,795,587 | A | 8/1998 | Gao |
| 5,801,154 | A | 9/1998 | Baracchini |
| 6,075,181 | A | 6/2000 | Kucherlapati et al. |
| 6,235,494 | B1 | 5/2001 | Hugli |
| 6,297,024 | B1 | 10/2001 | Hugli et al. |
| 6,407,213 | B1 | 6/2002 | Carter |
| 6,420,432 | B2 | 7/2002 | Demopulos |
| 6,492,332 | B1 | 12/2002 | Demopulos et al. |
| 6,645,168 | B2 | 11/2003 | Demopulos |
| 6,649,592 | B1 | 11/2003 | Larson |
| 6,969,601 | B2 | 11/2005 | Jensenius |
| 7,060,267 | B2 | 6/2006 | Jensenius |
| 7,083,786 | B2 | 8/2006 | Jensenius |
| 7,112,414 | B2 | 9/2006 | Jensenius |
| 7,919,094 | B2 | 4/2011 | Schwaeble et al. |
| 8,652,477 | B2 | 2/2014 | Schwaeble et al. |
| 8,840,893 | B2 | 9/2014 | Schwaeble et al. |
| 2002/0019369 | A1 | 2/2002 | Li |
| 2002/0082208 | A1 | 6/2002 | Jensenius |
| 2002/0082209 | A1 | 6/2002 | Jensenius |
| 2002/0094332 | A1 | 7/2002 | Bell |
| 2003/0049260 | A1 | 3/2003 | Bell |
| 2003/0091995 | A1 | 5/2003 | Buechler et al. |
| 2003/0186419 | A1 | 10/2003 | Jensenius |
| 2003/0207309 | A1 | 11/2003 | Hageman |
| 2003/0235582 | A1 | 12/2003 | Singh |
| 2004/0038297 | A1 | 2/2004 | Jensenius |
| 2004/0081619 | A1 | 4/2004 | Bell |
| 2004/0219147 | A1 | 11/2004 | Bell |
| 2004/0259771 | A1 | 12/2004 | Stahl |
| 2005/0004031 | A1 | 1/2005 | Subasinghe |
| 2005/0169921 | A1 | 8/2005 | Bell et al. |
| 2005/0191298 | A1 | 9/2005 | Bell et al. |
| 2005/0222027 | A1 | 10/2005 | Chiang |
| 2006/0002937 | A1 | 1/2006 | Schwaeble |
| 2006/0018896 | A1 | 1/2006 | Schwaeble |
| 2006/0140939 | A1 | 6/2006 | Fung |
| 2006/0240476 | A1 | 10/2006 | Soejima et al. |
| 2006/0275764 | A1 | 12/2006 | Thiel |
| 2007/0009528 | A1 | 1/2007 | Larsen |
| 2007/0015703 | A1 | 1/2007 | Wagner et al. |
| 2007/0031420 | A1 | 2/2007 | Jensenius |
| 2007/0172483 | A1 | 7/2007 | Schwaeble et al. |
| 2009/0042217 | A1 | 2/2009 | Brenner et al. |
| 2011/0002931 | A1 | 1/2011 | Tamburini |
| 2011/0020337 | A1 | 1/2011 | Schwaeble et al. |
| 2011/0091450 | A1 | 4/2011 | Schwaeble et al. |
| 2012/0282285 | A1 | 11/2012 | Garred et al. |
| 2015/0166675 | A1 | 6/2015 | Demopulos et al. |
| 2015/0166676 | A1 | 6/2015 | Demopulos et al. |

FOREIGN PATENT DOCUMENTS

| | | |
|---|---|---|
| JP | 7-238100 | 9/1995 |
| JP | 2007-520494 | 7/2007 |
| JP | 2009-532493 | 9/2009 |
| WO | WO 95/23161 | 8/1995 |
| WO | WO 00/35483 | 6/2000 |
| WO | WO 01/07067 | 2/2001 |
| WO | WO 01/12212 | 2/2001 |
| WO | WO 02/06460 | 1/2002 |
| WO | WO 03/009803 | 2/2003 |
| WO | WO 03/061765 | 7/2003 |
| WO | WO 03/063799 | 8/2003 |
| WO | WO 03/081206 A2 | 10/2003 |
| WO | WO 2004/009664 | 1/2004 |
| WO | WO 2004/022096 | 3/2004 |
| WO | WO 2004/050907 | 6/2004 |
| WO | WO 2004/075837 | 9/2004 |
| WO | WO 2004/106384 | 12/2004 |
| WO | WO 2005/002627 | 1/2005 |
| WO | WO 2005/024013 | 3/2005 |
| WO | WO 2005/074607 | 8/2005 |
| WO | WO 2005/120222 | 12/2005 |
| WO | WO 2005/123128 | 12/2005 |
| WO | WO 2005/123776 | 12/2005 |
| WO | WO 2007/103549 A2 | 9/2007 |
| WO | WO 2007/117996 | 10/2007 |
| WO | WO 2010/054403 A1 | 5/2010 |
| WO | WO 2011/047346 | 4/2011 |
| WO | WO 2011/057158 A1 | 5/2011 |

OTHER PUBLICATIONS

Stasi, K., et al., "Complement component 1Q (C1Q) upregulation in retina in murine, primate, and human glaucomatous eyes," *Invest Ophthalmol Vis Sci* 47:1024-1029 (2006).

Kuehn, M.H., et al., "Retinal synthesis and deposition of complement components induced by ocular hypertension," *Experimental Eye Research* 83:620-628 (2006).

Plaimauer, B., et al., "Recombinant ADAMTS13 normalizes von Willebrand factor-cleaving activity in plasma of acquired TTP patients by overriding inhibitory antibodies," *Journal of Thrombosis and Haemostasis* 9:936-944 (2011).

Bobbio-Pallavicini, E., et al., "Vincristine sulfate for the treatment of thrombotic thrombocytopenic purpura refractory to plasma-exhange," *Eur J Haematol* 52:222-226 (1994).

Miller, D.P., et al., "Incidence of thrombotic thrombocytopenic purpura/hemolytic uremic syndrome," *Epidemiology* 15:208-215 (2004).

Coleman, A.L., et al., "Risk factors for glaucoma onset and progression," *Survey of Ophthalmology* 53(Suppl 1):S3-S10 (2008).

Parker, C., "Complement and Hematology," *The Hematologist* 8(1):1-5 (2011). Mini Review Jan. 17, 2011. https://doi.org/10.1182/hem.V8.1.6324.

Desch, K., et al., "Is there a shared pathophysiology for thrombotic thrombocytopenic purpura and hemolytic-uremic syndrome?" *J Am Soc Nephrol* 18:2457-2460 (2007).

Chen, C.-B., and R. Wallis, "Stoichiometry of Complexes Between Mannose—Binding Protein and Its Associated Serine Proteases," *Journal of Biological Chemistry* 276(28):25894-25902, Jul. 2001.

Feinberg, H., et al., "Crystal Structure of the CUB1-EGF-CUB2 Region of Mannose-Binding Protein Associated Serine Protease-2," *EMBO Journal* 22(10):2348-2359, May 2003.

Ji, H., et al., "Arthritis Critically Dependent on Innate Immune System Players," *Immunity* 16(2):157-168, Feb. 2002.

Lynch, N.J., et al., "L-ficolin specifically binds to lipoteichoic acid, a cell wall constituent of Gram-positive bacteria, and activates the lectin pathway of complement," *J. Immunol.* 172:1198-1202 (2004).

Stover, C.M., et al., "Two constituents of the initiation complex of the mannan-binding lectin activation pathway of complement are encoded by a single structural gene," *J. Immunol.* 162:3481-3490 (1999).

Stover, C.M., et al., "The Rat and Mouse Homologues of MASP-2 and MAp19, Components of the Lectin Activation Pathway of Complement," *Journal of Immunology* 163(12):6848-6859, Dec. 1999.

Thiel, S., et al., "A second serine protease associated with mannan-binding lectin that activates complement," *Nature* 386:506-510 (1997).

Thiel, S., et al., "Interaction of C1q and mannan-binding lectin (MBL) with C1r, C1s, MBL-associated serine proteases 1 and 2, and the MBL-associated protein MAp19," *J. Immunol.* 165(2):878-887 (2000).

Vorup-Jensen, T., et al., "Distinct pathways of mannan-binding lectin (MBL)- and C1-complex autoactivation revealed by reconstitution of MBL with recombinant MBL-associated serine protease-2," *J. Immunol.* 165(4):2093-2100 (2000).

Gupta-bansal, R., et al., "Inhibition of Complement Alternative Pathway Function With Anti-Properdin Monoclonal Antibodies," *Molecular Immunology* 37(5):191-201, Apr. 2000.

Pillemer, L. et al., "The properdin system and immunity. III. The zymosan assay of properdin," *J. Exp. Med.* 103:1-13 (1956).

(56) References Cited

OTHER PUBLICATIONS

Haeffner-Cavaillon, N., et al., "C3a(C3adesArg) induces production and release of interleukin 1 by cultured human monocytes," *J Immunol* 139(3):794-799 (1987).
Lepow, I.H., "Presidential address to American Association of Immunologists in Anaheim, California, Apr. 16,1980. Louis Pillemer, Properdin, and scientific controversy," *J. Immunol.* 125:471-475 (1980).
Rothman, B.L., et al., "Cytokine regulation of C3 and C5 production by the human type II pneumocyte cell line, A549," *J Immunol* 145(2):592-598 (1990).
Rehrig, S., et al., "Complement inhibitor, complement receptor 1-related gene/protein y-Ig attenuates intestinal damage after the onset of mesenteric ischemia/reperfusion injury in mice," *J Immunol* 167:5921-5927 (2001).
Reid, R.R., et al., "Functional activity of natural antibody is altered in Cr2-deficient mice," *J Immunol* 169:5433-5440 (2002).
Huber-Lang, M.S., et al., "Complement-Induced Impairment of Innate Immunity During Sepsis," *Journal of Immunology* 169(6):3223-3231, Sep. 2002.
Matsushita, M., et al., "Cutting Edge: Complement-Activating Complex of Ficolin and Mannose-Binding Lectin-Associated Serine Protease," Journal of Immunology 164(5):2281-2284, Mar. 2000.
Matsushita, M., et al., "Proteolytic Activites of Two Types of Mannose—Binding Lectin-Associated Serine Protease," *Journal of Immunology* 165(5):2637-2642, Sep. 2000.
Fleming, S.D., et al., "Mice deficient in complement receptors 1 and 2 lack a tissue injury-inducing subset of the natural antibody repertoire," *J. Immunol.* 169:2126-2133 (2002).
Drouin, S.M., et al., "Absence of the complement anaphylatoxin C3a receptor suppresses Th2 effector functions in a murine model of pulmonary allergy," *J Immunol* 169:5926-33 (2002).
Amsterdam, E.A., et al., "Limitation of reperfusion injury by a monoclonal antibody to C5a during myocardial infarction in pigs," *Am J Physiol* 268:H448-H457 (1995).
Gralinski, M.R., et al., "Selective Inhibition of the Alternative Complement Pathway by sCR1 [desLHR-A] Protects the Rabbit Isolated Heart From Human Complement-Mediated Damage," *Immunopharmacology* 34(2-3):79-88, Sep. 1996.
Molina, H., "Update on Complement in the Pathogenesis of Systemic Lupus Erythematosus," *Current Opinion in Rheumatology* 14(5):492-497, Sep. 2002.
Fitch, J.C., et al., "Pharmacology and biological efficacy of a recombinant, humanized, single-chain antibody C5 complement inhibitor in patients undergoing coronary artery bypass graft surgery with cardiopulmonary bypass," *Circulation* 100(25):2499-2506 (1999).
Wang, H., et al., "Complement Inhibition With an Anti-C5 Monoclonal Antibody Prevents Hyperacute Rejection in a Xenograft Heart Transplantation Model," Transplantation 68(11):1643-1651, Dec. 1999.
Wang, Y., et al., "Anti-C5 Monoclonal Antibody Therapy Prevents Collagen-Induced Arthritis and Ameliorates Established Disease," *Proceedings of the National Academy of Sciences of the United States of America* 92(19):8955-8959, Sep. 1995.
Haeger, M., "The Role of Complement in Pregnancy—Induced Hypertensive Disease," *International Journal of Gynecology and Obstetrics* 43(2):113-127, Nov. 1993.
D'cruz, O.J., et al., "Recombinant Soluble Human Complement Receptor Type 1 Inhibits Antisperm Antibody- and Neutrophil—Mediated Injury to Human Sperm," Biology of Reproduction 54(6):1217-1228, Jun. 1996.
Xu, C., et al., "A Critical Role for Murine Complement Regulator Crry in Fetomaternal Tolerance," *Science* 287(5452):498-501, Jan. 2000.
Stein, J.H., et al., "The role of complement in the pathogenesis of postischemic acute renal failure," *Miner Electrolyte Metab* 11(4):256-261 (1985).

Ohsawa, I., et al., "Cryoprecipitate of Patients With Cryoglobulinemic Glomerulonephritis Contains Molecules of the Lectin Complement Pathway," *Clinical Immunology* 101(1):59-66, Oct. 2001.
Endo, M., et al., "Regulation of in Situ Complement Activation Via the Lectin Pathway in Patients With IgA Nephropathy," *Clinical Nephrology* 55(3):185-191, Mar. 2001.
Rinder, C.S., et al., "Role of C3 cleavage in monocyte activation during extracorporeal circulation," *Circulation* 100(5):553-558 (1999).
Rinder, C.S., et al., "Selective blockade of membrane attack complex formation during simulated extracorporeal circulation inhibits platelet but not leukocyte activation," *J Thorac Cardiovasc Surg* 118(3):460-466 (1999).
Vallhonrat, H. et al., "Rapid activation of the alternative pathway of complement by extracorporeal membrane oxygenation," *ASAIO J* 45(1):113-114 (1999).
Craddock, P.R., et al., "Complement and leukocyte-mediated pulmonary dysfunction in hemodialysis," *N. Engl J Med* 296:769-774 (1977).
Johnson, R.J., "Complement activation during extracorporeal therapy: biochemistry, cell biology and clinical relevance," *Nephrol Dial Transplant* 9 Suppl 2:36-45 (1994).
Verrier, E.D., et al., "Terminal Complement Blockade With Pexelizumab During Coronary Artery Bypass Graft Surgery Requiring Cardiopulmonary Bypass: a Randomized Trial," *Journal of the American Medical Association* 291(19):2319-2327, May 2004.
Steinberg, J.B., et al., "Cytokine and complement levels in patients undergoing cardiopulmonary bypass," *J Thorac Cardiovasc Surg* 106(6):1008-1016 (1993).
Wan, S., et al., "Inflammatory response to cardiopulmonary bypass: mechanisms involved and possible therapeutic strategies," *Chest* 112(3):676-692 (1997).
Kirklin, J.K., et al., "Complement and the damaging effects of cardiopulmonary bypass," *J Thorac Cardiovasc Surg* 86(6):845-857 (1983).
Woodruff, T.M., et al., "A Potent Human C5a Receptor Antagonist Protects against Disease Pathology in a Rat Model of Inflammatory Bowel Disease," *J Immunol* 171:5514-5520 (2003).
Lin, F., et al., "Decay-accelerating factor deficiency increases susceptibility to dextran sulfate sodium-induced colitis: role for complement in inflammatory bowel disease," *J Immunol* 172.
Shen, Y., and S. Meri, "Yin and Yang: Complement Activation and Regulation in Alzheimer's Disease," *Progress in Neurobiology* 70(6):463-472, Aug. 2003.
Gasque, P., et al., "Complement Components of the Innate Immune System in Health and Disease in the CNS," *Immunopharmacology* 49(1-2):171-186, Aug. 2000.
Piddlesden, S.J., et al., "Soluble Complement Receptor 1 (sCR1) Protects Against Experimental Autoimmune Myasthenia Gravis," *Journal of Neuroimmunology* 71(1-2):173-177, Dec. 1996.
Barnum, S.R., "Complement in Central Nervous System Inflammation," *Immunologic Research* 26(1-3):7-13, Aug. 2002.
Hill, J.H., et al., "The phlogistic role of C3 leukotactic fragments in myocardial infarcts of rats," *J. Exp. Med.* 133(4):885-900 (1971).
Buerke, M., et al., "Cardioprotective effects of a C1 esterase inhibitor in myocardial ischemia and reperfusion," *Circulation* 91:393-402 (1995).
Maroko, P.R., et al., "Reduction by cobra venom factor of myocardial necrosis after coronary artery occlusion," *J. Clin. Invest* 61:661-670 (1978).
Vakeva, A., et al., "Myocardial infarction and apoptosis after myocardial ischemia and reperfusion: role of the terminal complement components and inhibition by anti-C5 therapy," *Circulation* 97(22):2259-2297 (1998).
Mulligan, M.S., et al., "Requirement and Role of C5a in Acute Lung Inflammatory Injury in Rats," *J Clin Invest* 98:503-512 (1996).
Bautch, W., et al., "Cutting edge: guinea pigs with a natural C3a-receptor defect exhibit decreased bronchoconstriction in allergic airway disease: evidence for an involvement of the C3a anaphylatoxin in the pathogenesis of asthma," *J Immunol* 165(10):5401-5405 (2000).
Humbles, A.A., et al., "A role for the C3a anaphylatoxin receptor in the effector phase of asthma," *Nature* 406:998-1001 (2000).

(56) References Cited

OTHER PUBLICATIONS

Lachmann, P.J., et al., "Initiation of complement activation," *Springer Semin. Immunopathol.* 7:143-162 (1984).
Weiser, M.R., et al., "Reperfusion injury of ischemic skeletal muscle is mediated by natural antibody and complement," *J Exp Med* 183:2343-2348 (1996).
Williams, J.P., et al., "Intestinal reperfusion injury is mediated by IgM and complement," *J Appl Physiol* 86(3):938-942 (1999).
Riedemann, N.C., et al., "Complement in ischemia reperfusion injury," *Am. J. Pathol.* 162(2):363-367 (2003).
Bhakdi, S., et al., "Complement and atherogenesis: binding of CRP to degraded, nonoxidized LDL enhances complement activation," *Arterioscler.Thromb. Vasc.Biol.*19(10):2348-2354 (1999).
Geertinger, P., et al., "On the Reduced Atherogenic Effect of Cholesterol Feeding in Rabbits with Congenital Complement (C6) Deficiency," *Artery* 1:177-184 (1977).
Schmiedt, W., et al., "Complement C6 deficiency protects against diet-induced atherosclerosis in rabbits," *Arterioscler Thromb Vasc. Biol* 18(1):1790-1795 (1998).
Seifert, P.S., et al., "Isolation and characterization of a complement—activating lipid extracted from human atherosclerotic lesions," *J. Exp. Med.* 172(2):547-557 (1990).
Seifert, P.S., et al., "Generation of complement anaphylatoxins and C5b-9 by crystalline cholesterol oxidation derivatives depends on hydroxyl group number and position," *Mol. Immunol.* 24(12):1303-1308 (1987).
Seifert, P.S., et al., "The complement system in atherosclerosis," *Atherosclerosis* 73:91-104 (1988).
Niculescu, F., et al., "Complement activation and atherosclerosis," *Mol Immunol* 36:949-955 (1999).
Seifert, P.S., et al., "Prelesional complement activation in experimental atherosclerosis. Terminal C5b-9 complement deposition coincides with cholesterol accumulation in the aortic intima of hypercholesterolemic rabbits," *Lab Invest* 60:747-754 (1989).
Matsushita, M., et al., "Activation of the lectin complement pathway by H-ficolin (Hakata antigen)," *J. Immunol.* 168(7):3502-3506 (2002).
Fung, M., et al., "Inhibition of complement, neutrophil, and platelet activation by an anti-factor D monoclonal antibody in simulated cardiopulmonary bypass circuits," *J THorac Cardiovasc Surg* 122(1):113-122 (2001).
Stengaard-Pedersen, K., et al., "Inherited deficiency of mannan-binding lectin-associated serine protease 2," *N. Engl. J. Med.* 349(6):554-560 (2003).
Takahashi, M., et al., "A Truncated Form of Mannose-Binding Lectin—Associated Serine Protease (MASP)-2 Expressed by Alternative Polyadenylation is a Component of the Lectin Complement Pathway," *International Immunology* 11(5):859-863, May 1999.
Terui, T., "Inflammatory and Immune Reactions Associated With Stratum Corneum and Neutrophils in Sterile Pustular Dermatoses," *Tohoku Journal of Experimental Medicine* 190(4):239-248, Apr. 2000.
Ambrus, G., et al., "Natural substrates and inhibitors of mannan-binding lectin-associated serine protease-1 and -2: a study on recombinant catalytic fragments,"*J. Immunol.* 170:1374-1382 (2003).
Moller-Kristensen, M., et al., "Levels of mannan-binding lectin-associated serine protease-2 in healthy individuals," *J. Immunol. Methods* 282:159-167 (2003).
Petersen, S.V., et al., "Control of the Classical and the MBL Pathway of Complement Activation," *Molecular Immunology* 37(14):803-811, Oct. 2000.
Dahl, M.R., et al., "Masp-3 and its association with distinct complexes of the mannan-binding lectin complement activation pathway," *Immunity* 15(1):127-135 (2001).
Petersen, S.V., et al., "An Assay for the Mannan-Binding Lectin Pathway of Complement Activation," *Journal of Immunological Methods* 257(1-2):107-116, Nov. 2001.
Endo, M., et al., "Complement activation through the lectin pathway in patients with Henoch-Schonlein purpura nephritis," *Am J Kidney Dis* 35(3):401-407 (2000).
Collard, C.D., et al., "Complement activation after oxidative stress: role of the lectin complement pathway," *Am. J. Path.* 156(5):1549-1556 (2000).
Lu, J., et al., "Collections ad Ficolins: Sugar Pattern Recognition Molecules of the Mammalian Irate Immune System," *Biochim. Biophys. Acta* 1572:387-400 (2002).
Schweinle, J.E., et al., "Human Mannose-Binding Protein Activates the Alternative Complement Pathway and Enhances Serum Bactericidal Activity on a Mannose-Rich Isolate of *Salmonella,"* *Journal of Clinical Investigation* 84(6):1821-1829, Dec. 1989.
Jordan, J.E., et al., "Inhibition of mannose-binding lectin reduces postischemic myocardial reperfusion injury," *Circulation* 104(12):1413-1418 (2001).
Maynard, Y., et al., "Characterization of a mannose and N-acetylglucosamine-specific lectin present in rat hepatocytes," *J. Biol. Chem.* 257(7):3788-3794 (1982).
Stahl, G.L., et al., "Role for the alternative complement pathway in ischemia/reperfusion injury," *Am J Pathol* 162(2):449-455 (2003).
Lee, R.T., et al., "Multivalent ligand binding by serum mannose-binding protein," *Arch. Biochem. Biophys.* 299:129-136 (1992).
Collard, C.D., et al., "Endothelial oxidative stress activates the lectin complement pathway: role of cytokeratin 1," *Am. J. Pathol.* 159(3):1045-1054 (2001).
Ji, Y.H., et al., "Activation of the C4 and C2 components of complement by a proteinase in serum bactericidal factor, Ra reactive factor," *J. Immunol.* 150(2):571-578 (1993).
Kilpatrick, D.C., "Mannan-binding lectin: clinical significance and applications," *Biochim.Biophys. Acta* 1572:401-413 (2002).
Weis, W.I., et al., "Structure of a C-type Mannose-Binding Protein Complexes with an Oligosaccharide," *Nature* 360:127-134 (1992).
Kalli, K.R., et al., "Therapeutic Uses of Recombinant Complement Protein Inhibitors," *Springer Semin. Immunopathol.* 15(4):417-431 (1994).
Mulligan, M.S., et al., "Protective effects of soluble CR1 in complement- and neutrophil-mediated tissue injury," *J Immunol* 148:1479-1485 (1992).
Chai, P.J., et al., "Soluble complement receptor-1 protects heart, lung, and cardiac myofilament function from cardiopulmonary bypass damage," *Circulation* 101(5):541-546 (2000).
Czermak, B.J., et al., "Protective effects of C5a blockade in sepsis," *Nature Medicine* 5(7):788-792 (1999).
Goodfellow, R.M., et al., "Soluble Complement Receptor One (sCR1) Inhibits the Development and Progression of Rat Collagen-Induced Arthritis," Clinical Experimental Immunology 119(1):210-216, Jan. 2000.
Goodfellow, R.M., et al. "Local therapy with soluble complement receptor 1 (sCR1) suppresses inflammation in rat mono-articular arthritis," *Clin Exp Immunol* 110:45-52 (1997).
Morgan, K., et al., "Native Type II Collagen-Induced Arthritis in the Rat: The Effect of Complement Depletion by Cobra Venom Factor," *Arthritis and Rheumatism* 24(11):1356-1362, Nov. 1981.
Van Lent, P.L.E.M., et al., "Cationic Immune Complex Arthritis in Mice—A New Model: Synergistic Effect of Complement and Interleukin-1," *American Journal of Pathology* 140(6):1451-1461, Jun. 1992.
Kemp, P.A., et al., "Immunohistochemical Determination of Complement Activation in Joint Tissues of Patients With Rheumatoid Arthritis and Osteoarthritis Using Neoantigen-Specific Monoclonal Antibodies," *Journal of Clinical and Laboratory Immunology* 37(4):147-162, 1992.
Kaczorowski, S.L., et al., "Effect of Soluble Complement Receptor-1 on Neutrophil Accumulation After Traumatic Brain Injury in Rats," *Journal of Cerebral Blood Flow and Metabolism* 15(5):860-864, Sep. 1995.
Sanders, M.E., et al., "Detection of Activated Terminal Complement (C5b-9) in Cerebrospinal Fluid From Patients With Central Nervous System Involvement of Primary Sjogren's Syndrome or Systemic Lupus Erythematosus," *Journal of Immunology* 138(7):2095-2099, Apr. 1987.
Pangburn, M.K., et al., "Formation of the initial C3 convertase of the alternative complement pathway. Acquisition of C3b-like activities by spontaneous hydrolysis of the putative thioester in native C3," *J. Exp. Med.* 154(3):856-867 (1981).

(56) References Cited

OTHER PUBLICATIONS

Pangburn, M.K., "Alternative pathway of complement," *Methods Enzymol.* 162:639-653 (1988).
Wallis, R., et al., "Localization of the Serine Protease-Binding Sites in the Collagen-Like Domain of Mannose-Binding Protein," *Journal of Biological Chemistry* 279(14):14065-14073, Apr. 2004.
Chen, C.B., et al., "Two mechanisms for mannose-binding protein modulation of the activity of its associated serine proteases," *J Biol Chem* 279(25):26058-26065 (2004).
Zhao, H., et al., "Identification of human mannose binding lectin (MBL) recognition sites for novel inhibitory antibodies," *Hybrid Hybridomics* 21(1):25-36 (2002).
Jensenius, J.C., et al., "Recombinant Mannan-Binding Lectin (MBL) for Therapy," *Biochemical Society Transactions* 31(Pt 4):763-767, Aug. 2003.
Wallis, R., and R.B. Dodd, "Interaction of Mannose-Binding Protein With Associated Serine Proteases: Effects of Naturally Occurring Mutations," *Journal of Biological Chemistry* 275(40):30962-30969, Oct. 2000.
Sim, R.B., et al., "Innate Immunity," *Biochemical Society Transactions* 28(5):545-550 (2000).
Petersen, S.V., et al., "Generation of Antibodies Towards MASP-1 and MASP-2 Using Bacterial Expression Systems," *Molecular Immunology* 35(6-7):409, Apr. 1998 (meeting abstract).
Cruickshank, A.M., et al., "Response of serum interleukin-6 in patients undergoing elective surgery of varying severity," *Clin Sci (Loud)* 79(2):161-165 (1990).
Chenoweth, D.E., "Complement activation in extracorporeal circuits," *Ann NY Acad Sci* 516:306-313 (1987).
Butler, J., et al., "Inflammatory response to cardiopulmonary bypass," *Ann Thorac Surg* 55(2):552-559 (1993).
Bone, R.C., et al., "Definitions for Sepsis and Organ Failure," *Critical Care Medicine* 20(6):724-726, Jun. 1992.
Campbell, L.A., et al., "Detection of Chlamydia pneumoniae TWAR in human coronary atherectomy tissues," *J.Infect.Dis.* 172(2):585-588 (1995).
Cheung, A.K., "Biocompatibility of hemodialysis membranes," *J Am Soc Nephrol* 1(2):150-161 (1990).
Couser, W.G., et al., "The Effects of Soluble Recombinant Complement Receptor 1 on Complement-Mediated Experimental Glomerulonephritis," *Journal of the American Society of Nephrology* 5(11):1888-1894, May 1995.
Cines, D.B., et al., "Presence of complement-fixing anti-endothelial cell antibodies in systemic lupus erythematosus," *J Clin Invest* 73:611-625 (1984).
Bartlow, B.G., et al., "Nonimmunoglobulin C3 Activating Factor in Membranoproliferative Glomerulonephritis," *Kidney International* 151(3):294-302 Mar. 1979.
Cecic, I., et al., "Mediators of peripheral blood neutrophilia induced by photodynamic therapy of solid tumors," *Cancer Letters* 183:43-51 (2002).
Johnson, L.V., et al., "Complement Activation and Inflammatory Processes in Drusen Formation and Age Related Macular Degeneration," *Experimental Eye Research* 73(6):887-896, Dec. 2001.
Halstensen, T.S., et al., "Local complement activation in inflammatory bowel disease," *Immunol Res* 10:485-492 (1991).
Hugli, T.E., "Biochemistry and biology of anaphylatoxins," *Complement* 3:111-127 (1986).
Hageman, G.S., et al., "An Integrated Hypothesis That Considers Drusen as Biomarkers of Immune-Mediated Processes at the RPE-Bruch's Membrane Interface in Aging and Age-Related Macular Degeneration," *Progress in Retinal and Eye Research* 20(6):705-732, Nov. 2001.
Edmunds, L.H., "Inflammatory response to cardiopulmonary bypass," *Ann Thorac Surg* 66(5 Supp):S12-S16 (1998).
Fujie, K., et al., "Release of neutrophil elastase and its role in tissue injury in acute inflammation: effect of the elastase inhibitor, FR134043," *Eur J Pharmacol* 374:117-125 (1999).

Gerl, V.B., et al., "Extensive Deposits of Complement C3d and C5b-9 in the Choriocapillaris of Eyes of Patients With Diabetic Retinopathy," *Investigative Ophthalmology & Visual Science* 43(4):1104-1108, Apr. 2002.
Evangelist, V., et al., "Platelet/polymorphonuclear leukocyte interaction: P-selectin triggers protein-tyrosine phosphorylation-dependent CD11b/CD18 adhesion: role of PSGL-1 as a signaling molecule," *Blood* 93(3):876-885 (1999).
Geertinger, P., et al., "Complement as a factor in arteriosclerosis," *Acta. Pathol. Microbiol. Scand.(A)* 78:284-288 (1970).
Fletcher, M.P., et al., "C5a-induced myocardial ischemia: role for CD18-dependent PMN localization and PMN-platelet interactions," *Am J Physiol* 265(5 Pt 2):H1750-H1761 (1993).
Francis, K., et al., "Complement C3a Receptors in the Pituitary Gland: A Novel Pathway by Which an Innate Immune Molecule Releases Hormones Involved in the Control of Inflammation," *FASEB Journal* 17(15):2266-2268, Dec. 2003.
Foreman, K.E., et al., "C5a-induced expression of P-selectin in endothelial cells," *J Clin Invest* 94:1147-1155 (1994).
Van Dijk, H., et al., "Study of the optimal reaction conditions for assay of the mouse alternative complement pathway," *J. Immunol. Methods* 85(2):233-243 (1985).
Finn, A., et al., "Interleukin-8 release and neutrophil degranulation after pediatric cardiopulmonary bypass," *J Thorac Cardiovasc Surg* 105(2):234-241 (1993).
Czlonkowska, A., et al., "Immune Processes in the Pathogenesis of Parkinson's Disease—A Potential Role for Microglia and Nitric Oxide," *Medical Science Monitor* 8(8):RA165-RA177, Aug. 2002.
Elmgreen, J., "Complement and function of neutrophils in chronic inflammatory bowel disease," *Dan Med Bull* 33(5):222-228 (1986).
Brenchley, P.E., et al., "Urinary C3dg and C5b 9 Indicate Active Immune Disease in Human Membranous Nephropathy," *Kidney International* 41(4):933-937, Apr. 1992.
Asimakopoulos, G., "Mechanisms of the systemic inflammatory response," 14(4):269-277 (1999).
Salant, D.J., et al., "Heymann Nephritis: Mechanisms of Renal Injury," *Kidney International* 35(4):976-984, Apr. 1989.
Rus, H.G., et al., "Cells carrying C5b-9 complement complexes in human atherosclerotic wall," *Immunol Lett.* 20(4):305-310 (1989).
Seelen, M.A., et al., "Autoantibodies against mannose-binding lectin in systemic lupus erythematosus," *Clin Exp Immunol* 134:335-343 (2003).
Seegar, W., et al., "Reproduction of transfusion-related acute lung injury in an ex vivo lung model," *Blood* 76(7):1438-1444 (1990).
Schwaeble, W., et al., "The mannan-binding lectin-associated serine proteases (MASPs) and MAp19: four components of the lectin pathway activation complex encoded by two genes," *Immunobiology* 205:455-466 (2002).
Taskinens, S., et al., "Binding of C-reactive protein to modified low-density-lipoprotein particles: identification of cholesterol as a novel ligand for C-reactive protein" *Biochem J* 367:403-412 (2002).
Tada, T., et al., "Membrane attack complex of complement and 20 kDa homologous restriction factor (CD59) in myocardial infarction," *Vichows Arch* 430:327-332 (1997).
Patel, S., et al., "ApoE(−/−) mice develop atherosclerosis in the absence of complement component C5," *Biochem Biophys Res Commun* 286:164-170 (2001).
Ohkohchi, K., et al., "Plasma Concentrations of Complement—Modulating Proteins (C1 Inhibitor, C4 Binding Protein, Factor H and Factor I) in Inflammatory Dermatoses With Special Reference to Psoriasis," *Dermatologica* 179(Suppl 1):30-34, 1989.
Kerjaschki, D., "The Pathogenesis of Membranous Glomerulonephritis: From Morphology to Molecules," *Virchows Archiv B: Cell Pathology* 58(4):253-271, 1990.
Rinder, C., et al., "Amplification of the inflammatory response: adhesion molecules associated with platelet/white cell responses," *J Cardiovasc Pharmacol* 27 Suppl 1:S6-12 (1996).
Vlaicu, R., et al., "Immunohistochemical localization of the terminal C5b-9 complement complex in human aortic fibrous plaque," *Atherosclerosis* 57:163-177 (1985).
Witztum, J.L., "The oxidation hypothesis of atherosclerosis," *Lancet* 344:793-795 (1994).

(56) References Cited

OTHER PUBLICATIONS

Solomkin, J.S., "Complement activation and clearance in acute illness and injury: evidence for C5a as a cell-directed mediator of the adult respiratory distress syndrome in man," *Surgery* 97(6):668-678 (1985).
Gatenby, P.A., "The Role of Complement in the Aetiopathogenesis of Systemic Lupus Erythematosus," *Autoimmunity* 11(1):61-66, Jan. 1991.
Weisman, H.F., et al., "Soluble human complement receptor type 1: in vivo inhibitor of complement suppressing post-ischemic myocardial inflammation and necrosis," *Science* 249:146-151 (1990).
Yasojima, K., et al., "Complement components, but not complement inhibitors, are upregulated in atherosclerotic plaques," *Arterioscler Thromb Vasc Biol* 21(7):1214-1219 (2001).
Ward, P.A., "Rous-Whipple Award Lecture. Role of complement in lung inflammatory injury," *Am J Pathol* 149:1081-1086 (1996).
Till, G.O., et al., "Activation of C5 by cobra venom factor is required in neutrophil-mediated lung injury in the rat," *Am J Pathol* 129:44-53 (1987).
Terui, T., et al., "Role of Neutrophils in Induction of Acute Inflammation in T-Cell-Mediated Immune Dermatosis, Psoriasis: A Neutrophil-Associated Inflammation-Boosting Loop," *Experimental Dermatology* 9(1):1-10, Feb. 2000.
Van Der Kolk, L.E., et al., "Complement Activation Plays a Key Role in the Side-Effects of Rituximab Treatment," *British Journal of Haematology* 115(4):807-811, Dec. 2001.
Trouw, L.A., et al., "Autoantibodies to Complement Components," *Molecular Immunology* 38(2-3):199-206, Aug. 2001.
Xiao, F., et al., "Complement-mediated lung injury and neutrophil retention after intestinal ischemia-reperfusion," *J Appl Physiol* 82(5):1459-1465 (1997).
Zhou, W., et al., "Predominant role for C5b-9 in renal ischemia/reperfusion injury," *J Clin Invest* 105(10):1363-1371 (2000).
Zhang, J., et al., "Early Complement Activation and Decreased Levels of Glycosylphosphatidylinositol—Anchored Complement Inhibitors in Human and Experimental Diabetic Retinopathy," *Diabetes* 51(12):3499-3504, Dec. 2002.
Zwaka, T.P., et al, "Complement and dilated cardiomyopathy: a role of sublytic terminal complement complex-induced tumor necrosis factor—alpha synthesis in cardiac myocytes," *Am J Pathol* 161(2):449-457 (2002).
Ware, L.B., "The acute respiratory distress syndrome," *N Engl J Med* 342:1334-1349 (2000).
Walters, D.M., et al., "Complement factor 3 mediates particulate matter—induced airway hyperresponsiveness," *Am J Respir Cell Mol Biol* 27:413-418 (2002).
Takematsu, H., and H. Tagami, "Activation of the Alternative Pathway of Complement in Psoriatic Lesional Skin," *Dermatologica* 181(4):289-292, 1990.
Scandrett, A.L., et al., "Acute Inflammation is the Harbinger of Glomerulosclerosis in Anti-Glomerular Basement Membrane Nephritis," *American Journal of Physiology* 268(2 Pt 2):F258-F265, Feb. 1995.
Rumfeld, W.R., et al., "The Ninth Complement Component in Rheumatoid Arthritis, Behçet's Disease and Other Rheumatic Diseases," *British Journal of Rheumatology* 25(3):266-270, Aug. 1986.
Tripathy, N.K., et al., "Complement and cell mediated cytotoxicity by antiendothelial cell antibodies in Takayasu's arteritis," *J Rheumatol* 28(4):805-808 (2001).
Van de Graaf, E.A., et al., "ELISA of complement C3a in bronchoalveolar lavage fluid," *J. Immunol Methods* 147:241-250 (1992).
Wachtfogel, Y.T., et al., "Formation of C1s-C1-inhibitor, kallikrein-C1-inhibitor, and plasmin-alpha 2-plasmin-inhibitor complexes during cardiopulmonary bypass," *Blood* 73(2):468-471 (1989).
Tomooka, K., "Serum Complement Levels in Patients with Rheumatoid Arthritis and Vasculitis," *Fukuoka Acta Med* 80(10):456-466 (1989).

Ravirajan, C.T., et al., "Effect of Neutralizing Antibodies to IL-10 and C5 on the Renal Damage Caused by a Pathogenic Human Anti-dsDNA Antibody," *Rheumatology* 43(4):442-447, Apr. 2004.
Halstensen, T.S., et al., "Epithelial deposition of immunoglobulin G1 and activated complement (C3b and terminal complement complex) in ulcerative colitis," *Gastroenterology* 98:1294-1271 (1990).
Hakim, R.M., "Clinical implications of hemodialysis membrane biocompatibility," *Kidney Int* 44(3):484-494 (1993).
Hammerschmidt, D.E., et al., "Association of Complement Activation and Elevated Plasma-C5a with Adult Respiratory Distress Syndrome," *Lancet* 1(8175):947-949 (1980).
Glover, G.I., et al., "Synthetic Peptide Inhibitors of Complement Serine Proteases-I. Identification of Functionally Equivalent Protease Inhibitor Sequences in Serpins and Inhibition of C1s and D," *Molecular Immunology* 25(12):1261-1267, Dec. 1988.
Chenoweth, D.E., et al., "Complement activation during cardiopulmonary bypass: evidence for generation of C3a and C5a anaphylatoxins," *N Engl J Med* 304:497-503 (1981).
Hetland, G., et al., "Human alveolar macrophages synthesize the functional alternative pathway of complement and active C5 and C9 in vitro," *Scand J Immunol* 24:603-608 (1986).
Haslam, P.L., et al., "Complement activation during cardiopulmonary bypass," *Anaesthesia* 35:22-26 (1980).
Hogaboam, C.M., et al., "Mannose-binding lectin deficiency alters the development of fungal asthma: effects on airway response, inflammation, and cytokine profile," *J Leukoc Biol* 75(5):805-814 (2004).
Holm-Bentzen, M., et al., "A Prospective Double-Blind Clinically Controlled Multicenter Trial of Sodium Pentosanpolysulfate in the Treatment of Interstitial Cystitis and Related Painful Bladder Disease," *Journal of Urology* 138(3):503-507, Sep. 1987.
Hansson, G.K., et al., "Accumulation of IgG and complement factor C3 in human arterial endothelium and atherosclerotic lesions," *Acta Pathol Microbiol Immunol Scand (A)* 92(6):429-435 (1984).
Kalluri, R., et al., "Goodpasture syndrome involving overlap with Wegener's granulomatosis and anti-glomerular basement membrane disease," *J Am Soc Nephrol* 8(11):1795-1800 (1997).
Kinkade, J.M., et al., "Differential distribution of distinct forms of myeloperoxidase in different azurophilic granule subpopulations from human neutrophils," *Biochem Biophys Res Commun* 114(1):296-303 (1983).
Kitano, A., et al., "Multifunctional effects of anticomplementary agent K-76 on carrageenan-induced colitis in the rabbit," *Clin Exp Immunol* 94(2):348-353 (1993).
Matsushita, M., et al., "Activation of the classical complement pathway by mannose-binding protein in association with a novel C1s-like serine protease," *J. Exp. Med.* 176(6):1497-1502 (1992).
Kawamura, T., et al., "Elevation of cytokines during open heart surgery with cardiopulmonary bypass: participation of interleukin 8 and 6 in reperfusion injury," *Can J Anaesth* 40:1016-1021 (1993).
Morgan, B.P., "Clinical Complementology: Recent Progress and Future Trends," *Eur. J. Clin. Invest.* 24(4):219-228 (1994).
Kawana, S., et al., "Membrane attack complex of complement in Henoch-Schonlein purpura skin and nephritis," *Arch Dermatol Res* 282(3):183-187 (1990).
Kirklin, J.K., et al., "Effects of protamine administration after cardiopulmonary bypass on complement, blood elements, and the hemodynamic state," *Ann Thorac Surg* 41(2):193-199 (1986).
Holmskov, U., et al., "Collections and Ficolins: humoral lectins of the innate immune defense," *Annu. Rev. Immunol.* 21:457-578 (2003).
Ikeda, K., et al., "Serum lectin with known structure activates complement through the classical pathway," *J. Biol. Chem.* 262:7451-7454 (1987).
Karp, C.L., et al., "Identification of complement factor 5 as a susceptibility locus for experimental allergic asthma," *Nat Immunol* 1(3):221-226 (2000).
Kyriakides, C., et al., "Moderation of skeletal muscle reperfusion injury by a sLe(x)-glycosylated complement inhibitory protein," *Am J Physiol Cell Physiol* 281:C224-C230 (2001).

(56) References Cited

OTHER PUBLICATIONS

Krug, N., et al., "Complement factors C3a and C5a are increased in bronchoalveolar lavage fluid after segmental allergen provocation in subjects with asthma," *Am J Respir Crit Care Med* 164:1841-1843 (2001).

Kondo, C., et al., "The role of C5a in the development of thrombotic glomerulonephritis in rats," *Clin Exp Immunol* 124(2):323-329 (2001).

Kohl, J., "Anaphylatoxins and infectious and non-infectious inflammatory diseases," *Mol Immunol* 38:175-187 (2001).

Linton, S.M., and B.P. Morgan, "Complement Activation and Inhibition in Experimental Models of Arthritis," *Molecular Immunology* 36(13-14):905-914, Sep. Oct. 1999.

Baldwin, W.M., et al., "Complement in Transplant Rejection: Diagnostic and Mechanistic Considerations," *Springer Seminars in Immunopathology* 25(2):181-197, Sep. 2003.

Austen, W.G., et al., "Intestinal ischemia-reperfusion injury is mediated by the membrane attack complex," *Surgery* 126:343-348 (1999).

Mahaffey, K.W., et al., "Effect of pexelizumab, an anti-C5 complement antibody, as adjunctive therapy to fibrinolysis in acute myocardial infarction: the COMPlement inhibition in myocardial infarction treated with thromboLYtics (COMPLY) trial," *Circulation* 108:1176-1183 (2003).

Neth, O., et al., "Mannose-Binding Lectin Binds to a Range of Clinically Relevant Microorganisms and Promotes Complement Deposition," *Infection and Immunity* 68(2):688-693, Feb. 2000.

Lamb, N.J., et al., "Oxidative damage to proteins of bronchoalveolar lavage fluid in patients with acute respiratory distress syndrome: evidence for neutrophil—mediated hydroxylation, nitration, and chlorination," *Crit Care Med* 27(9):1738-1744 (1999).

Kitano, A., et al., "New Treatment of Ulcerative Colitis with K-76," *Dis Colon Rectum* 35:560-567 (1992).

Kolios, G., et al., "Mediators of inflammation: production and implication in inflammatory bowel disease," *Hepatogastroenterology* 45:1601-1609 (1998).

Lentsch, A.B., et al., "Regulation of inflammatory vascular damage," *J Pathol* 190(3):343-348 (2000).

Kuhlman, M., et al. "The Human Mannose-Binding Protein Functions as an Opsonin," *J Exp Med* 169:1733-1745 (1989).

Lonberg, N., et al., "Antigen-specific human antibodies from mice comprising four distinct genetic modifications," *Nature* 368:856-859 (1994).

Meri, S., et al., "Activation of the Alternative Pathway of Complement by Monoclonal λ Light Chains in Membranoproliferative Glomerulonephritis," *Journal of Experimental Medicine* 175(4):939-950, Apr. 1992.

Matsushita, M., et al., "A novel human serum lectin with collagen- and fibrinogen-like domains that functions as an opsonin," *J. Biol. Chem.* 271(5):2448-2454 (1996).

Moore, F.D., et al., "The effects of complement activation during cardiopulmonary bypass. Attenuation by hypothermia, heparin, and hemodilution," *Ann Surg* 208(1):95-103 (1988).

Mollnes, T.E., and A. Paus, "Complement Activation in Synovial Fluid and Tissue From Patients With Juvenile Rheumatoid Arthritis," *Arthritis and Rheumatism* 29(11):1359-1364, Nov. 1986.

Niculescu, F., et al., "Persistent Complement Activation on Tumor Cells in breast Cancer," *Am J Pathol* 140(5):1039-1043 (1992).

Nilsson, B., et al., "Compstatin inhibits complement and cellular activation in whole blood in two models of extracorporeal circulation," *Blood* 92(5):1661-1667 (1998).

Riedemann, N.C., et al., "Increased C5a Receptor Expression in Sepsis," *Journal of Clinical Investigation* 110(1):101-108, Jul. 2002.

Polotsky, V.Y., et al., "Interactions of Human Mannose-Binding Protein With Lipoteichoic Acids," *Infection and Immunity* 64(1):380-383, Jan. 1996.

Schindler, R., et al., "Recombinant C5a stimulates transcription rather than translation of interleukin-1 (IL-1) and tumor necrosis factor: translational signal provided by lipopolysaccharide or IL-1 itself," *Blood* 76(8):1631-1638 (1990).

Ashraf, S.S., et al., "Proinflammatory cytokine release during pediatric cardiopulmonary bypass: influence of centrifugal and roller pumps," *J Cardiothorac Vasc Anesth* 11(6):718-722 (1997).

Buono, C., et al., "Influence of C3 deficiency on atherosclerosis," *Circulation* 105(25):3025-3031 (2002).

Marc, M.M., et al., "Complement factors c3a, c4a, and c5a in chronic obstructive pulmonary disease and asthma," *Am J Respir Cell Mol Biol* 31:216-219 (2004).

Brandt, J., et al., "Role of the Complement Membrane Attack Complex (C5b 9) in Mediating Experimental Mesangioproliferative Glomerulonephritis," Kidney International 49(2):335-343, Feb. 1996.

Klein, R.J., et al., "Complement Factor H Polymorphism in Age-Related Macular Degeneration," *Science* 308(5720):385-389, Apr. 2005.

Haines, J.L., et al., "Complement Factor H Variant Increases the Risk of Age-Related Macular Degeneration," *Science* 308(5720):419-421, Apr. 2005.

Edwards, A.O., et al., "Complement Factor H Polymorphism and Age-Related Macular Degeneration," Science 308(5720):421-424, Apr. 2005.

Iwaki, D., and T. Fujita, "Production and Purification of Recombinants of Mouse MASP-2 and sMAP," *Journal of Endotoxin Research* 11(1):47-50, Feb. 2005.

Hart, M.L., et al., "Gastrointestinal ischemia-reperfusion injury is lectin complement pathway dependent without involving C1q," *J Immunol* 174:6373-80 (2005).

Walsh, M.C., et al., "Mannose-binding lectin is a regulator of inflammation that accompanies myocardial ischemia and reperfusion injury," *J Immunol* 175:541-546 (2005).

Roos, A., et al., "Human IgA Activates the Complement System Via the Mannan-Binding Lectin Pathway," Journal of Immunology 167(5):2861-2868, Sep. 2001.

Banda, N.K., et al., "Prevention of Collagen-Induced Arthritis in Mice Transgenic for the Complement Inhibitor Complement Receptor 1-Related Gene/Protein y," *Journal of Immunology* 171(4):2109-2115, Aug. 2003.

Celik, I., et al., "Role of the Classical Pathway of Complement Activation in Experimentally Induced Polymicrobial Peritonitis," *Infection and Immunity* 69(12):7304-7309, Dec. 2001.

Pratt, J.R., et al., "Nontransgenic Hyperexpression of a Complement Regulator in Donor Kidney Modulates Transplant Ischemia/Reperfusion Damage, Acute Rejection, and Chronic Nephropathy," *American Journal of Pathology* 163(4):1457-1465, Oct. 2003.

Turnberg, D., et al., "CD59a Deficiency Exacerbates Ischemia—Reperfusion Injury in Mice," *American Journal of Pathology* 165(3):825-832, Sep. 2004.

Takahashi, M., et al., "Role of MASP-1 and/or MASP-3 in Activation of the Lectin Pathway," in "Oral Session 1: Mechanisms of Activation," *International Immunopharmacology* 2(9):1220, Aug. 2002.

Casanova, J.-L., and L. Abel, "Human Mannose-Binding Lectin in Immunity: Friend, Foe, or Both?" Journal of Experimental Medicine 199(10):1295-1299, May 2004.

Malhotra, R., et al., "Glycosylation Changes of IgG Associated With Rheumatoid Arthritis Can Activate Complement Via the Mannose-Binding Protein," *Nature Medicine* 1(3):237-243, Mar. 1995.

Hansen, T.K., et al., "Elevated Levels of Mannan-Binding Lectin in Patients With Type 1 Diabetes," *Journal of Clinical Endocrinology & Metabolism* 88(10):4857-4861, Oct. 2003.

Hovind, P., et al., "Mannose-Binding Lectin as a Predictor of Microalbuminuria in Type 1 Diabetes: An Inception Cohort Study," *Diabetes* 54(5):1523-1527, May 2005.

Hansen, T.K., et al., "Mannose-Binding Lectin and Mortality in Type 2 Diabetes," *Archives of Internal Medicine* 166(18):2007-2013, Oct. 2006.

Hansen, T.K., et al., "Association Between Mannose-Binding Lectin and Vascular Complications in Type 1 Diabetes," *Diabetes* 53(6):1570-1576, Jun. 2004.

De Vries, B., et al., "The mannose-binding lectin-pathway is involved in complement activation in the course of renal ischemia-reperfusion injury," *Am J Pathol* 165:1677-1688 (2004).

(56) References Cited

OTHER PUBLICATIONS

Nozaki, M., et al., "Drusen Complement Components C3a and C5a Promote Choroidal Neovascularization," *Proceedings of the National Academy of Sciences of the United States of America* 103(7):2328-2333, Feb. 2006.
Bora, P.S., et al., "Role of Complement and Complement Membrane Attack Complex in Laser-Induced Choroidal Neovascularization," *Journal of Immunology* 174(1):491-497, Jan. 2005.
Connolly, a.M., et al., "Complement 3 Deficiency and Oral Prednisolone Improve Strength and Prolong Survival of Laminin α2-Deficient Mice," *Journal of Neuroimmunology* 127(1):80-87, Jun. 2002.
Spuler, S., and A.G. Engel, "Unexpected Sarcolemmal Complement Membrane Attack Complex Deposits on Nonnecrotic Muscle Fibers in Muscular Dystrophies," *Neurology* 50(1):41-46, Jan. 1998.
Liu, J., et al., "Dysferlin, a Novel Skeletal Muscle Gene, is Mutated in Miyoshi Myopathy and Limb Girdle Muscular Dystrophy," *Nature Genetics* 20(1):31-36, Sep. 1998.
Porter, J.D., et al., "A Chronic Inflammatory Response Dominates the Skeletal Muscle Molecular Signature in Dystrophin-Deficient mdx Mice," *Human Molecular Genetics* 11(3):263-272, Feb. 2002.
Cuchacovich, M., et al., "Potential Pathogenicity of Deglycosylated IgG Cross Reactive With Streptokinase and Fibronectin in the Serum of Patients With Rheumatoid Arthritis," *Journal of Rheumatology* 23(1):44-51, Jan. 1996.
Baelder, R., et al., "Pharmacological targeting of anaphylatoxin receptors during the effector phase of allergic asthma suppresses airway hyperresponsiveness and airway inflammation," *J Immunol* 174:783-789 (2005).
Taube, C., et al., "Inhibition of complement activation decreases airway inflammation and hyperresponsiveness," *Am J Respir Crit Care Med* 168:1333-1341 (2003).
Drouin, S.M., et al., "Cutting edge: the absence of C3 demonstrates a role for complement in Th2 effector functions in a murine model of pulmonary allergy," *J Immunol* 167(8):4141-4145 (2001).
Peng, T., et al., "Role of C5 in the development of airway inflammation, airway hyperresponsiveness, and ongoing airway response," *J Clin Invest* 115(6):1590-1600 (2005).
Huang, Z., "Structural Chemistry and Therapeutic Intervention of Protein Protein Interactions in Immune Response, Human Immunodeficiency Virus Entry, and Apoptosis," *Pharmacology & Therapeutics* 86(3):201-215, Jun. 2000.
Khan, A.U., and S.K. Lal, "Ribozymes: A Modern Tool in Medicine," *Journal of Biomedical Scencei* 10(5):457-467, Sep.-Oct. 2003.
Shoji, Y., and H. Nakashima, "Current Status of Delivery Systems to Improve Target Efficacy of Oligonucleotides," *Current Pharmaceutical Design* 10(7):785-796, Mar. 2004.
Takahashi, M., et al., "Essential role of mannose-binding lectin-associated serine protease-1 in activation of the complement factor D," *J Exp Med* 207(1):29-37 (2010).
Rieben, R., et al., "Immunoglobulin M-Enriched Human Intravenous Immunoglobulin Prevents Complement Activation in Vitro and in Vivo in a Rat Model of Acute Inflammation," *Blood* 93(3):942-951, Feb. 1999.
Simon, H.U., and P.J. Späth, "IVIG—Mechanisms of Action," *Allergy* 58(7): 543-552, Jul. 2003.
Harlow, E., and D. Lane, "Using Antibodies: a Laboratory Manual," Cold Spring Harbor Press, Cold Spring Harbor, N.Y., 1999, pp. 44, 45, and 52.
Tan, S., et al., "Improvements on the Purification of Mannan-Binding Lectin and Demonstration of Its $Ca^{2+}$-Independent Association With a C1s-Like Serine Protease," *Biochemical Journal* 319(Pt 2):329-332, Oct. 1996.
MacKinnon, C.M., et al., "Molecular Cloning of cDNA for Human Complement Component C1s: The Complete Amino Acid Sequence," *European Journal of Biochemistry* 169(3):547-553, Dec. 1987.
Journet, A., and M. Tosi, "Cloning and Sequencing of Full-Length cDNA Encoding the Precursor of Human Complement Component C1r," *Biochemical Journal* 240(3):783-787, Dec. 1986.

Endo, Y., et al., "Exon Structure of the Gene Encoding the Human Mannose- Binding Protein-Associated Serine Protease Light Chain: Comparison With Complement C1r and C1s Genes," *International Immunology* 8(9):1355-1358, Sep. 1996.
Baatrup, G., et al., "Demonstration in Human Plasma of a Lectin Activity Analogous to That of Bovine Conglutinin," *Scandinavian Journal of Immunology* 26(4):355-361, Oct. 1987.
Jack, D.L., and M.W. Turner, "Anti-Microbial Activities of Mannose-Binding Lectin," *Biochemical Society Transactions* 31(Pt 4)753-757, Aug. 2003.
Kuehn, M.H., et al., "Disruption of the complement cascade delays retinal ganglion cell death following retinal ischemia-reperfusion," *Exp Eye Res* 87(2):89-95 (2008).
Lindorfer, M.A., et al., "A novel approach to preventing the hemolysis of paroxysmal nocturnal hemoglobinuria: both complement-mediated cytolysis and C3 deposition are blocked by a monoclonal antibody specific for the alternative pathway of complement," *Blood* 115(11):2283-2291 (2010).
Ng, Y.C., et al., "Monoclonal rheumatoid factor-IgG immune complexes. Poor fixation of opsonic C4 and C3 despite efficient complement activation," *Arthritis Rheum* 31(1):99-107 (1988).
Pickering, M.C., et al., "Spontaneous hemolytic uremic syndrome triggered by complement factor H lacking surface recognition domains," *J Exp Med* 204(6):1249-1256 (2007).
Tezel, G., et al., "Oxidative stress and the regulation of complement activation in human glaucoma," *Invest Ophthalmol Vis Sci* 51(10):5071-5082 (2010).
Wilcox, L.A., et al., "Molecular basis of the enhanced susceptibility of the erythrocytes of paroxysmal nocturnal hemoglobinuria to hemolysis in acidified serum," *Blood* 78(3):820-829 (1991).
Zhang, X., et al., "A protective role for C5a in the development of allergic asthma associated with altered levels of B7-H1 and B7-DC on plasmacytoid dendritic cells," *J Immunol* 182(8):5123-5130 (2009).
Zipfel, P.F., et al., "Deletion of complement factor H-related genes CFHR1 and CFHR3 is associated with atypical hemolytic uremic syndrome," *PLoS Genet* 3(3):e41 (2007).
Bally, I., et al., "Residue GLN340, at the Interface Between the CCP1 and CCP2 Modules of C1s, is a Key Element of C4 Recognition," *International Immunopharmacology* 2(9):1228, Aug. 2002 [abstract].
Barton, G.J., "Protein Multiple Sequence Alignment and Flexible Pattern Matching," *Methods in Enzymology* 183:403-428, 1990.
Davies, E.J., et al., "Mannose-Binding Protein Gene Polymorphism in Systemic Lupus Erythematosus," *Arthritis & Rheumatism* 38(1):110-114, Jan. 1995.
Deng, Y.-J., and A.L. Notkins, "Molecular Determinants of Polyreactive Antibody Binding: HCDR3 and Cyclic Peptides," *Clinical and Experimental Immunology* 119(1):69-76, Jan. 2000.
Garred, P., et al., "Increased Frequency of Homozygosity of Abnormal Mannan-Binding-Protein Alleles in Patients With Suspected Immunodeficiency," *Lancet* 346(8980):941-943, Oct. 1995.
Garred, P., et al., "Susceptibility to HIV Infection and Progression of AIDS in Relation to Variant Alleles of Mannose-Binding Lectin," *Lancet* 349(9047):236-240, Jan. 1997.
Garred, P., et al., "Diallelic Polymorphism May Explain Variations of the Blood Concentration of Mannan-Binding Protein in Eskimos, But Not in Black Africans," *European Journal of Immunogenetics* 19(6):403-412, Dec. 1992.
Jensenius, J.C., "Mannan-Binding Lectin (MBL): From Investigations on Fish and Chickens to Substitution Therapy in an Infant With Severe Infections," in M.W. Steward (ed.), *Immunology: Joint Congress of BSI and NVVI Abstracts* 86(Suppl 1):100, Dec. 1995.
Jensenius, J.C., et al., "Eggs: Conveniently Packaged Antibodies. Methods for Purification of Yolk IgG," *Journal of Immunological Methods* 46(1):63-68, Oct. 1981.
Kawasaki, T., et al., "Isolation and Characterization of a Mannan-Binding Protein From Rabbit Liver," *Biochemical and Biophysical Research Communications* 81(3):1018-1024, Apr. 1978.
Kawasaki, N., et al., "A Serum Lectin (Mannan-Binding Protein) Has Complement-Dependent Bactericidal Activity," *Journal of Biochemistry* 106(3):483-489, Sep. 1989.

(56) References Cited

OTHER PUBLICATIONS

Kilpatrick, D.C., "Mannan Binding Protein in Sera Positive for Rheumatoid Factor," *British Journal of Rheumatology* 36(2):207-209, Feb. 1997.
Klein, J., and V. Hofejgi, "B-Cell Receptors, Immunoglobulins and FC Receptors," in "Immunology," 2d ed., Blackwell Science, Oxford, United Kingdom, 1997, Chapter 8, pp. 229-240.
Law, S.K.A. and K.B.M. Reid, "Complement," 2d ed., IRL Press, Oxford, United Kingdom, 1995, 27 pages.
Leytus, S.P. et al., "Nucleotide Sequence of the cDNA Coding for Human Complement C1r," *Biochemistry* 25(17):4855-4863, Aug. 1986.
Lipscombe, R.J., et al., "High Frequencies in African and Non-African Populations of Independent Mutations in the Mannose-Binding Protein Gene," *Human Molecular Genetics* 1(9):709-715, Dec. 1992.
Madsen, H.O., et al, "A New Frequent Allele is the Missing Link in the Structural Polymorphism of the Human Mannan-Binding Protein," *Immunogenetics* 40(1):37-44, Jan. 1994.
Matsushita, M., and T. Fujita, "Cleavage of the Third Component of Complement (C3) by Mannose Binding Protein Associated Serine Protease (MASP) With Subsequent Complement Activation," *Immunobiology* 194:443 448, Nov. 1995.
Nielsen, S.L., et al., "The Level of the Serum Opsonin, Mannan-Binding Protein in HIV-1 Antibody-Positive Patients," Clinical and Experimental Immunology 100(2):219-222, May 1995.
Rossi, V., et al., "Baculovirus-Mediated Expression of Truncated Modular Fragments From the Catalytic Region of Human Complement Serine Protease C1s," *Journal of Biological Chemistry* 273(2):1232-1239, Jan. 1998.
Rossi, V., et al., "C1s/MASP-2 Chimeras: Tools to Determine the Relative Contributions of the CCP Modules and Serine Protease Domain of MASP-2 to Its Higher C4 Cleaving Activity," *International Immunopharmacology* 2(9):1253, Aug. 2002 [abstract].
Rossi, V., et al., "Substrate Specificities of Recombinant Mannan—Binding Lectin-Associated Serine Proteases-1 and -2," *Journal of Biological Chemistry* 276(44):40880-40887, Nov. 2001.
Sato, T., et al., "Molecular Characterization of a Novel Serine Protease Involved in Activation of the Complement System by Mannose-Binding Protein," *International Immunology* 6(4):665-669, Jan. 1994.
Sumiya, M., et al., "Molecular Basis of Opsonic Defect in Immunodeficient Children," *Lancet* 337(8757):1569-1570, Jun. 1991.
Summerfield, J.A., et al., "Mannose-Binding Protein Gene Mutations Associated With Unusual and Severe Infections in Adults," *Lancet* 345(8954):886-889, Apr. 1995.
Super, M., et al., "Association of Low Levels of Mannan-Binding Protein With a Common Defect of Opsonisation," *Lancet* 11(8674):1236-1239, Nov. 1989.
Takada, F., et al., "A New Member of the C1s Family of Complement Proteins Found in a Bactericidal Factor, Ra-Reactive Factor, in Human Serum," *Biochemical and Biophysical Research Communications* 196(2):1003-1009, Oct. 1993.
Thiel, S., et al., "Identification of a New Mannan-Binding Protein Associated Serine Protease (MASP-2)," *Immunology* 86(Suppl. 1):101, Dec. 1995 [abstract].
Tosi, M., et al., "Complete cDNA Sequence of Human Complement C1s and Close Physical Linkage of the Homologous Genes C1s and C1r," *Biochemistry* 26(26):8516-8524, Dec. 1987.
Turner, M.W., "Mannose-Binding Lectin (MBL) in Health and Disease," *Immunobiology* 199(2):327-339, Aug. 1998.
Turner, M.W., "Mannose-Binding Lectin: The Pluripotent Molecule of the Innate Immune System," *Immunology Today* 17(11):532-540, Nov. 1996.
Van De Geijn, F.E., et al., "Mannose-Binding Lectin Polymorphisms Are Not Associated With Rheumatoid Arthritis—Confirmation in Two Large Cohorts," *Rheumatology* 47(8):1168-1171, Aug. 2008.
Abaza, M.S., et al., "Effects of amino acid substitutions outside an antigenic site on protein binding to monoclonal antibodies of predetermined specificity obtained by peptide immunization: demonstration with region 94-100 (antigenic site 3) of myoglobin," *J Protein Chem* 11(5):433-444 (1992).
Colman, P.M., "Effects of amino acid sequence changes on antibody-antigen interactions," *Res Immunol* 145(1):33-36 (1994).
Harlow, E., et al., "Antibodies: A Laboratory Manual," Cold Spring Harbor Laboratory, Cold Spring Harbor, N.Y., 1988, pp. 567-569.
Lederman, S., et al., "A single amino acid substitution in a common African allele of the CD4 molecule ablates binding of the monoclonal antibody, OKT4," *Mol Immunol* 28(11):1171-1181 (1991).
Krarup, A., et al., "Simultaneous activation of complement and coagulation by MBL-associated serine protease 2," *PLoS One* 2(7):e623 (2007).
Walsh, M.C., et al., "Complement activation and tissue injury following myocardial ischemia and reperfusion is dependent on MBL," *Molecular Immunology* 41:322-323 (2004).
Schwaeble, W., et al., "Targeting of mannan-binding lectin-associated serine protease-2 confers protection from myocardial and gastrointestinal ischemia/reperfusion injury," *Proc Natl Acad Sci USA* 108(18):7523-7528 (2011).
Norwood, M.G., et al., "Consumption of mannan-binding lectin during abdominal aortic aneurysm repair," *Eur J Vasc Endovasc Surg* 31(3):239-243 (2006).
Fidler, K.J., et al., "Increased incidence and severity of the systemic inflammatory response syndrome in patients deficient in mannose-binding lectin," *Intensive Care Med* 30(7):1438-1445 (2004).
Schlapbach, L.J., et al., "Differential role of the lectin pathway of complement activation in susceptibility to neonatal sepsis," *Clin Infect Dis* 51(2):153-162 (2010).
Garred, P., et al., "Genetic Susceptibility to Sepsis: A Possible Role for Mannose-binding Lectin," *Curr Infect Dis Rep* 6(5):367-373 (2004).
Garred, P., et al., "Association of mannose-binding lectin polymorphisms with sepsis and fatal outcome, in patients with systemic inflammatory response syndrome," *J Infect Dis* 188(9):1394-1403 (2003).
Hibberd, M.L., et al., "Variation in the mannose binding lectin (MBL) gene and susceptibility to sepsis," *Sepsis* 4(3):201-207 (2001).
Hjelmesaeth, J., et al., "Early posttransplant serum osteoprotegerin levels predict long-term (8-year) patient survival and cardiovascular death in renal transplant patients," *J Am Soc Nephrol* 17(6):1746-1754 (2006).
Olesen, H.V., et al., "The mannan-binding lectin pathway and lung disease in cystic fibrosis—dysfunction of mannan-binding lectin-associated serine protease 2 (MASP-Z) may be a major modifier," *Clin Immunol* 121(3):324-331 (2006).
Carlsson, M., et al., "Cystic fibrosis patients heterozygous for MASP-2 gene mutation have lowered MASP-2 concentration, without relation to clinical findings," *Molecular Immunology* 40(2-4):208 (2003).
Sorensen, R., et al., "Mannan-binding-lectin-associated serine proteases, characteristics and disease associations," *Springer Semin Immunopathol* 27(3):299-319 (2005).
Banda, N. K., et al., "Essential role of complement mannose-binding lectin-associated serine proteases-1/3 in the murine collagen antibody-induced model of inflammatory arthritis," *J Immunol*, 185(9): 5598-5606, (2010).
Weimann, A., et al., "Role of MBL, MASP2 and NOD2 polymorphisms in patients with inflammatory blowel disease," *DGKL Congress of Clinical Chemistry and Laboratory Medicine* 2004 42(10):A145 (2004). (Abstract only).
Novovic, S., et al., "Mannan-binding lectin and mannan-binding lectin-associated serine protease 2 in acute pancreatitis," *Pancreas* 40(7):1097-1102 (2011).
Ali, M., et al., "The deficiency of the lectin pathway functional activity in MASP-2 deficient mice does not effect the survival drom acute polymicrobial septic peritonitis," *Molecular Immunology* 45:4181 (P207) (2008). (Abstract only).
Chrysanthou, E., et al., "The lectin pathway of complement activation in cerebral ischaemia and reperfusion injury," Neuroscience 2011 Presentation Abstact.
Orsini, F., et al., "Mannose-binding lectin as a target for cerebral ischemic injury," *Molecular Immunology* 48(14):1677 (2011). (Abstract only).

(56) References Cited

OTHER PUBLICATIONS

Arumugam, T.V., et al., "Neuroprotection in stroke by complement inhibition and immunoglobulin therapy," *Neuroscience* 158(3):1074-1089 (2009).
Ostergaard, J., et al., "Complement activation and diabetic vascular complications," *Clinica Chimica* 361:10-19 (2005).
Rasmussen, H.H., et al., "Toweards a comprehensive database of proteins from the urine of patients with bladder cancer," *Journal of Urology* 155:2113-2119 (1996).
Takahashi, K., et al., "Mannose-binding lectin and its associated proteases (MASPs) mediate coagulation and its deficiency is a risk factor in developing complications from infection, including disseminated intravascular coagulation," *Immunobiology* 216:96-102 (2011).
Stover, C., et al., "Functional MASP2 single nucleotide polymorphism plays no role in psoriasis," *Br Assoc Dermatol* 152:1313-1315 (2005).
Moller-Kristensen, M., et al., "Burn injury reveals altered phenotype in mannan-binding lectin-deficient mice," *J Invest Dermatol* 127:1524-1531 (2007).
Miller, C., et al., "Molecular defects in the mannose binding lectin pathway in dermatological disease: Case report and literature review," *Clinical and Molecular Allergy* 8:6-14 (2010).
Glovsky, M.M., et al., "Complement determinations in human disease," *Ann Allergy Asthma Immunol* 93:513-523 (2004).
Ammitzboll, C.G., et al., "Levels of lectin pathway proteins in plasma and suynovial fluid of rheumatoid arthritis and osteoarthritis," *Rheumatol Int* Apr. 3, 2011 retrieved from the interne at URL/http/www.springerlink.com.
Farrar, C.A., et al., "Role of complement and neutrophil migration in renal ischaemia/reperfusion injury," *Molecular Immunology* 38:87 (2001). (Abstract only).
Roos, A., et al., "Glomerular activation of the lectin pathway of complement in IgA nephropathy is associated with more severe renal disease," *J Am Soc Nephrol* 17:1724-1734 (2006).
Farrar, C.A., et al., "Mannan binding lectin associated serine protease-2 (MASP-2) is a critical player in the pathophysiology of renal ischaemia reperfusion (I/R) injury and mediates tissue injury in absence of complement C4," *Molecular Immunology* 46:2832 (2009). (Abstract only).
Farrar, C.A., et al., "The role of complement in renal ischaemia/reperfusion injury," *Immunobiology* 98(Suppl.1):101 (1999). (Abstract only).
Ytting, H., et al., "Serum mannan-binding lectin-associated serine protease 2 levels in colorectal cancer: Relation to recurrence and mortality," *Clinical Cancer Research* 11:1441-1446 (2005).
Ytting, H., et al., "Increased acitivity of the mannan-binding lectin complement activation pathway in patients with colorectal cancer," *Scand J Gastroenteral* 39:674-679 (2004).
Verma, A., et al., "Clinical significance of mannose-binding lectin-associated serine protease-2 expression in esophageal squamous cell carcinoma," *Int J Cancer* 118:2930-2935 (2006).
Ytting, H., et al., "The postoperative levels of MASP-2, a marker of survival in primary colorectal cancer," *Proc Am Assoc Cancer Res Annual Meeting* 46:Abstract 1205 (Apr. 2012).
Nielsen, H.J., et al., "Soluble Masp-2 and Timp-1 protein levels as selection marker for adjuvant therapy in colon cancer," *Gstroenterology* 128(4)(Suppl.2):A71 (2005). (Abstract only).
Berger, S.P., et al., "Complement in glomerular injury," *Semin Immunopathol* 29:375-384 (2007).
Teh, C., et al., "M-ficolin is expressed on monocytes and is a lectin binding to N-acetyl-D-glucosamine and mediates monocyte adhesion and phagocytosis of *Escherichia coli*," *Immunology* 101(2):225-232 (200).
Hansen, S., et al., "Collectin 11 (CL-11, CL-K1) is a MASP-1/3-associated plasma collectin with microbial-binding activity," *J. Immunol.* 185(10):6096-6104 (2010).
Schwaeble, W., et al., "Does properdin crosslink the cellular and the humoral immune response?," *Immunol. Today* 20(1):17-21 (1999).

Noris, M., et al., "Relative role of genetic complement abnormalities in sporadic and familial aHUS and their impact on clinical phenotype," *Clin J Am Soc Nephrol*, 5(10): 1844-1859, (2010).
Wagner, E., et al., "Therapeutic potential of complement modulation," *Nature Reviews* 9:43-56 (2010).
Taylor, C.M., "Enterohaemorrhagic *Escherichia coli* and *Shigella dysenteriae* type 1-induced haemolytic uraemic syndrome," *Pediatr Nephrol* 23:1425-1431 (2008).
Gando, S., et al., "Increased Neutrophil Elastase, Persistent Intravascular Coagulation, and Decreased Fibrinolytic Activity in Patients with Postraumatic Acute Respiratory Distress Syndrome," *J Trauma, Injury, Infect, Crit Care* 42(6):1068-1072 (1997).
Preston, F.E., et al., "Disseminated intravascular coagulation as a consequence of cerebral damage," *J Neurology, Neyrosurgery, and Psychiatry* 37:241-248 (1974).
Tamano, M., et al., "Complement Activation in Cisplatin Nephrology," *Nephron* 81:442-443 (1999).
Fuke, Y., et al., "The role of complement activation, detected by urinary C5b-9 and urinary factor H, in the excretion of urinary albumin in cisplatin nephropathy," *Clin Nephrol* 71(2):110-117 (2009).
Racz, M. J., et al., "A comparison of short- and long-term outcomes after off-pump and on-pump coronary artery bypass graft surgery with sternotomy," *J Am Coll Cardiol* 43(4):557-64 (2004).
Fiane, A.E., et al., "Mechanism of complement activation and its role in the inflammatory response after thoracoabdominal aortic aneurysm repair," *Circulation* 108:849-856 (2003).
Ardehali, A., et al., "Modified reperfusion and ischemia-reperfusion injury in human lung transplantation," *J Thorac Cardiovasc Surg* 126(6):1929-1934 (2003).
Gulla, K. C., et al., "Activation of mannan-binding lectin-associated serine proteases leads to generation of a fibrin clot," *Immunology*, 129(4): 482-495, (2009).
Beinrohr, L., et al., "C1, MBL-MASPs and C1-inhibitor: novel approaches for targeting complement-mediated inflammation," *Trends in Molecular Medicine* 14(12):511-521 (2008).
Skjoedt, M. O., et al., "A novel mannose-binding lectin/ficolin-associated protein is highly expressed in heart and skeletal muscle tissues and inhibits complement activation," *J Biol Chem*, 285(11):8234-8243, (2010).
Abe, M., et al., "Contribution of anaphylatoxin C5a to late airway responses after repeated exposure of antigen to allergic rats," *J Immunol* 167(8):4651-4660 (2001).
Kaur, S., et al., "Elevated levels of mannan-binding lectin [corrected] (MBL) and eosinophilia in patients of bronchial asthma with allergic rhinitis and allergic bronchopulmonary aspergillosis associate with a novel intronic polymorphism in MBL," *Clin Exp Immunol* 143:414-419 (2006).
Jacquet, M., et al., "Deciphering Complement Receptor Type 1 Interactions with Recognition Proteins of the Lectin Complement Pathway," *J Immunology* 190:3721-3731 (2013).
Wan, S., et al., "Human cytokine responses to cardiac transplantation and coronary artery bypass grafting," *J Thorac Cardiovasc Surg* 111(2):469-477 (1996).
Demers, P., et al., "Coronary artery endothelial dysfunction after ischemia-reperfusion and acute untreated rejection in a canine heterotopic heart transplantation model," *Transplantation* 71(1):26-32 (2001).
Thurman, J. M., et al., "Alternative pathway of complement in children with diarrhea—associated hemolytic uremic syndrome," *Clin J Am Soc Nephrol*, 4(12): 1920-1924, (2009).
Orth, D., et al., "Shiga toxin activates complement and binds factor H: evidence for an active role of complement in hemolytic uremic syndrome," *J Immunol*, 182(10): 6394-6400, (2009).
Torzewski, J., et al., "Complement-induced release of monocyte chemotactic protein-1 from human smooth muscle cells. A possible initiating event in atherosclerotic lesion formation," *Arterioscler Thromb Vasc Biol* 16:673-677 (1996).
Shanley, T.P., "Cytokines in inflammatory diseases: role and therapeutic targets in acute respiratory distress syndrome," *Emerging Therapeutic Targets* 2:1-16 (1998).

(56) References Cited

OTHER PUBLICATIONS

Torzewski, J., et al., "C-reactive protein frequently colocalizes with the terminal complement complex in the intima of early atherosclerotic lesions of human coronary arteries," *Arterioscler Thromb Vasc Biol* 18:1386-92 (1998).
Saito, E., "Effects of K-76 COONa, an Anticomplementary Agent, on Experimental Atherosclerosis in Rabbits," *J Drug Dev* 3:147-154 (1990).
Sacks, S.H., et al., "Role of the complement system in rejection," *Curr Opin Immunol* 15(5):487-492 (2003).
Sund, S., et al., "Complement activation in early protocol kidney graft biopsies after living-donor transplantation," *Transplantation* 75(8):1204-1213 (2003).
Hill, A., et al., "Recent developments in the understanding and management of paroxysmal nocturnal haemoglobinuria," *Br J Haematol* 137(3):181-192 (2007).
Winter, G., et al., "Making antibodies by phage display technology," *Annu Rev Immunol* 12:433-455 (1994).
Bruchim, Y., et al., "Disseminated intravascular coagulation," *Compend Contin Educ Vet* 30(10):E3 (2008).
Ward, J.R., et al., "Agonists of toll-like receptor (TLR)2 and TLR4 are unable to modulate platelet activation by adenosine diphosphate and platelet activating factor," *Thromb Haemost* 94(4):831-838 (2005).
Holers, V.M., "The spectrum of complement alternative pathway-mediated diseases," *Immunol Rev* 223:300-316 (2008).
Goldberg, R. J., et al., "The role of endothelial cell injury in thrombotic microangiopathy," *Am J Kidney Dis*, 56(6): 1168-1174, (2010).
Meri, S., (2001) *Complement regulatory proteins* in Encyclopedia of Life Sciences, Nature Publishing Group.
Kienast, J., et al., "Treatment effects of high-dose antithrombin without concomitant heparin in patients with severe sepsis with or without disseminated intravascular coagulation," *Journal of Thrombosis and Haemostasis* 4:90-97 (2006).
Pedersen, E. D., et al., "Systemic complement activation following human acute ischaemic stroke," *Clin Exp Immunol*, 137(1): 117-122, (2004).
De Simoni, M. G., et al., "The powerful neuroprotective action of C1-inhibitor on brain ischemia-reperfusion injury does not require C1q," *Am J Pathol*, 164(5): 1857-1863, (2004).
Maurer, M., et al., "Differentiation between intracerebral hemorrhage and ischemic stroke by transcranial color-coded duplex-sonography," *Stroke*, 29(12): 2563-2567, (1998).
Rodrigues, M. E., et al., "Technological progresses in monoclonal antibody production systems," *Biotechnol Prog*, 26(2): 332-351, (2010).
Endo, Y., et al., "Interactions of ficolin and mannose-binding lectin with fibrinogen/fibrin augment the lectin complement pathway," *J Innate Immun*, 2(1): 33-42, (2010).
Schroeder, V., et al., "MBL-associated serine protease-1 (MASP-1)—A novel link between inflammation and thrombosis?" *Hamostaseologie* 31(1):A18 (2011). Abstract Only.
Well, J.A., et al., "Reaching for high-hanging fruit in drug discovery at protein-protein interfaces," *Nature* 450(7172):1001-1009 (2007).
De Jorge, E.G., et al., "The Development of Atypical Hemolytic Uremic Syndrome Depends on Complement C5," *J Am Soc Nephrol* 22:137-145 (2011).
Tektonidou, M.G., "Risk Factors for Thrombosis and Primary Thrombosis Preventionin Patients With Systemic Lupus Erythematosus With of Without Antiphospholipid," *Arthritis & Rheumatism (Arthritis Care & Research)* 61(1):29-36 (2009).
Vilacosta, I., et al., "Risk of Embolization After Institution of Antibiotic Therapy for Infective Endocarditis," *J Am Coll Cardiol* 39(9):1489-1495 (2002).
Gonzalez-Juanatey, C., et al., "Rheumatic Manifestations of Infective Endocarditis in Non-Addicts. A 12 Year Study," *Medicine (Baltimore)* 80(1):9-19 (2001).
Shapiro, W., Hemolytic Uremic Syndrome: WebMD; 2007 [updated Jan. 11, 2007].
Stahl, A. L., et al., "Complement activation on platelet-leukocyte complexes and microparticles in enterohemorrhagic *Escherichia coli*-induced hemolytic uremic syndrome," *Blood*, 117(20): 5503-5513, (2011).
Walsh, M., "Myocardial Ischemia-Reperfusion Injury is Dependent on Lectin Complement Activation," *Journal of the American College of Cardiology* 43 (Supplement A(5):305A (2003).
Baldwin, W. M., III, et al., "Complement deposition in early cardiac transplant biopsies is associated with ischemic injury and subsequent rejection episodes," *Transplantation* 68(6):894-900 (1999).
Stengaard-Pedersen, K., et al., "Inherited Deficiency of Mannan-binding Lectin-Associated Serine Protease 2," *N Engl J Med* 349:554-560 (2003).
Minchinton, R. M., et al., "Analysis of the relationship between mannose-binding lectin (MBL) genotype, MBL levels and function in an Australian blood donor population," *Scand J Immunol* 56(6):630-641 (2002).
Mudge, G. J., "Cardiac transplantation," *Cardiology Rounds* 4(9):1-6 (2000).
Welborn, M. B., et al., "The relationship between Visceral ischemia, proinflammatory cytokines, and organ injury in patients undergoing thoracoabdominal aortic aneurysm repair." *Crit Care Med* 28(9):3191-3197 (2000).
Fink, M. P., "Thoracoabdominal aortic aneurysm repair: a human model of ischemia/reperfusion-induced cytokine-driven multiple organ dysfunction syndrome." *Crit Care Med* 28(9): 3356-3357 (2000).
Hafez, H. M., et al., "Myocardial injury in major aortic surgery." *J Vasc Surg* 31(4):742-750 (2000).

\* cited by examiner

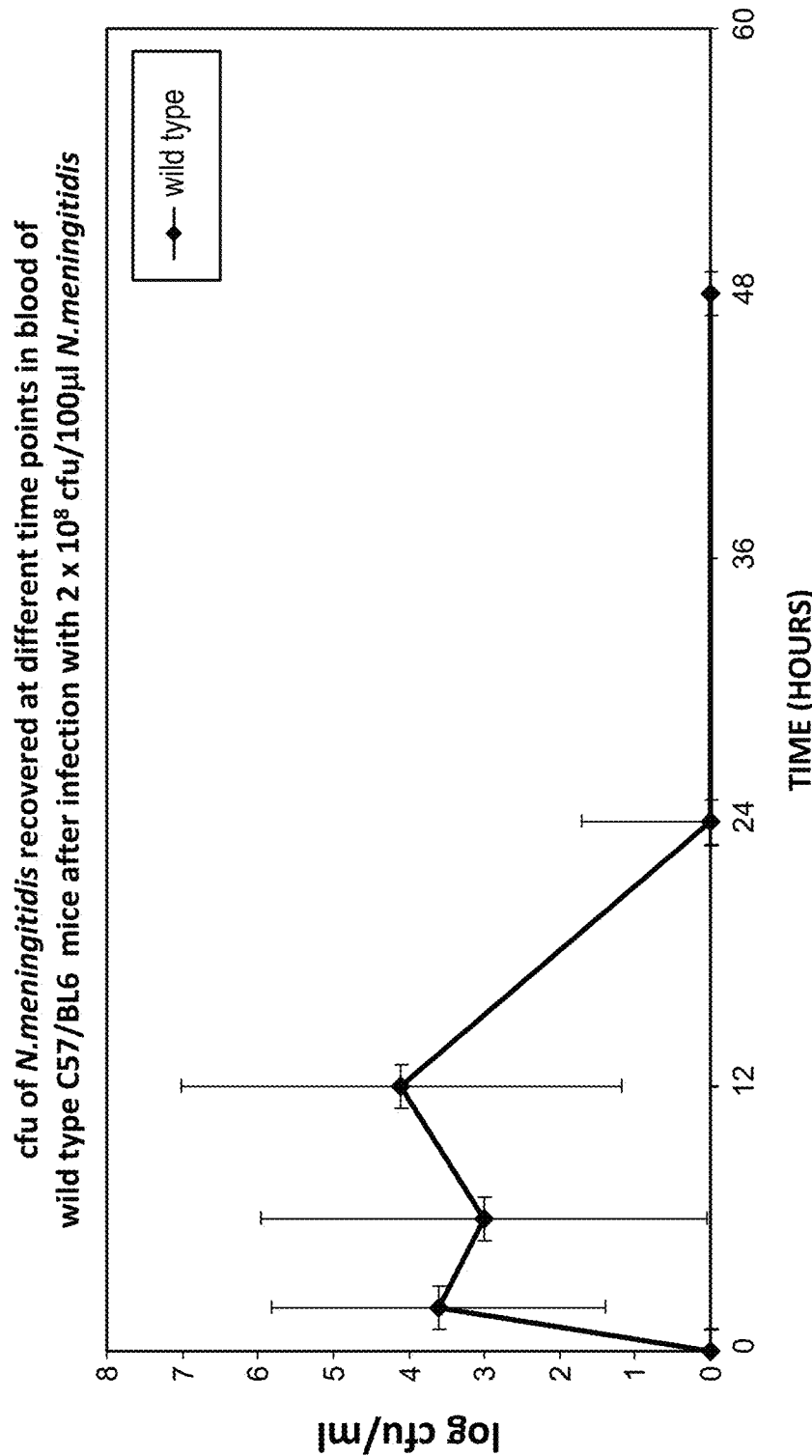

WT (+/+)

SEQUENCE LISTING

<160> NUMBER OF SEQ ID NOS: 65

<210> SEQ ID NO 1
<211> LENGTH: 725
<212> TYPE: DNA
<213> ORGANISM: Homo sapiens
<220> FEATURE:
<221> NAME/KEY: CDS
<222> LOCATION: (27)..(584)

<400> SEQUENCE: 1

```
ggccaggcca gctggacggg cacacc atg agg ctg ctg acc ctc ctg ggc ctt     53
                               Met Arg Leu Leu Thr Leu Leu Gly Leu
                               1               5 ctg tgt ggc tcg gtg gcc acc ccc ttg ggc ccg aag tgg cct gaa cct    101
Leu Cys Gly Ser Val Ala Thr Pro Leu Gly Pro Lys Trp Pro Glu Pro
```

```
                 10                 15                      20                      25
gtg ttc ggg cgc ctg gca tcc ccc ggc ttt cca ggg gag tat gcc aat      149
Val Phe Gly Arg Leu Ala Ser Pro Gly Phe Pro Gly Glu Tyr Ala Asn
             30                      35                      40 gac cag gag cgg cgc tgg acc ctg act gca ccc ccc ggc tac cgc ctg      197
Asp Gln Glu Arg Arg Trp Thr Leu Thr Ala Pro Pro Gly Tyr Arg Leu
         45                      50                      55 cgc ctc tac ttc acc cac ttc gac ctg gag ctc tcc cac ctc tgc gag      245
Arg Leu Tyr Phe Thr His Phe Asp Leu Glu Leu Ser His Leu Cys Glu
                 60                      65                      70 tac gac ttc gtc aag ctg agc tcg ggg gcc aag gtg ctg gcc acg ctg      293
Tyr Asp Phe Val Lys Leu Ser Ser Gly Ala Lys Val Leu Ala Thr Leu
     75                      80                      85 tgc ggg cag gag agc aca gac acg gag cgg gcc cct ggc aag gac act      341
Cys Gly Gln Glu Ser Thr Asp Thr Glu Arg Ala Pro Gly Lys Asp Thr
 90                      95                      100                     105 ttc tac tcg ctg ggc tcc agc ctg gac att acc ttc cgc tcc gac tac      389
Phe Tyr Ser Leu Gly Ser Ser Leu Asp Ile Thr Phe Arg Ser Asp Tyr
                 110                     115                     120 tcc aac gag aag ccg ttc acg ggg ttc gag gcc ttc tat gca gcc gag      437
Ser Asn Glu Lys Pro Phe Thr Gly Phe Glu Ala Phe Tyr Ala Ala Glu
             125                     130                     135 gac att gac gag tgc cag gtg gcc ccg gga gag gcg ccc acc tgc gac      485
Asp Ile Asp Glu Cys Gln Val Ala Pro Gly Glu Ala Pro Thr Cys Asp
         140                     145                     150 cac cac tgc cac aac cac ctg ggc ggt ttc tac tgc tcc tgc cgc gca      533
His His Cys His Asn His Leu Gly Gly Phe Tyr Cys Ser Cys Arg Ala
                 155                     160                     165 ggc tac gtc ctg cac cgt aac aag cgc acc tgc tca gag cag agc ctc      581
Gly Tyr Val Leu His Arg Asn Lys Arg Thr Cys Ser Glu Gln Ser Leu
170                     175                     180                     185 tag cctcccctgg agctccggcc tgcccagcag gtcagaagcc agagccagcc           634
tgctggcctc agctccgggt tgggctgaga tggctgtgcc ccaactccca ttcacccacc    694
atggacccaa taataaacct ggccccaccc c                                   725

<210> SEQ ID NO 2
<211> LENGTH: 185
<212> TYPE: PRT
<213> ORGANISM: Homo sapiens

<400> SEQUENCE: 2

Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr
        35                  40                  45

Leu Thr Ala Pro Pro Gly Tyr Arg Leu Arg Leu Tyr Phe Thr His Phe
    50                  55                  60

Asp Leu Glu Leu Ser His Leu Cys Glu Tyr Asp Phe Val Lys Leu Ser
65                  70                  75                  80

Ser Gly Ala Lys Val Leu Ala Thr Leu Cys Gly Gln Glu Ser Thr Asp
                85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
        115                 120                 125
```

```
Gly Phe Glu Ala Phe Tyr Ala Ala Glu Asp Ile Asp Glu Cys Gln Val
        130                 135                 140

Ala Pro Gly Glu Ala Pro Thr Cys Asp His His Cys His Asn His Leu
145                 150                 155                 160

Gly Gly Phe Tyr Cys Ser Cys Arg Ala Gly Tyr Val Leu His Arg Asn
                165                 170                 175

Lys Arg Thr Cys Ser Glu Gln Ser Leu
            180                 185

<210> SEQ ID NO 3
<211> LENGTH: 170
<212> TYPE: PRT
<213> ORGANISM: Homo sapiens

<400> SEQUENCE: 3

Thr Pro Leu Gly Pro Lys Trp Pro Glu Pro Val Phe Gly Arg Leu Ala
1               5                   10                  15

Ser Pro Gly Phe Pro Gly Glu Tyr Ala Asn Asp Gln Glu Arg Arg Trp
            20                  25                  30

Thr Leu Thr Ala Pro Pro Gly Tyr Arg Leu Arg Leu Tyr Phe Thr His
        35                  40                  45

Phe Asp Leu Glu Leu Ser His Leu Cys Glu Tyr Asp Phe Val Lys Leu
    50                  55                  60

Ser Ser Gly Ala Lys Val Leu Ala Thr Leu Cys Gly Gln Glu Ser Thr
65                  70                  75                  80

Asp Thr Glu Arg Ala Pro Gly Lys Asp Thr Phe Tyr Ser Leu Gly Ser
                85                  90                  95

Ser Leu Asp Ile Thr Phe Arg Ser Asp Tyr Ser Asn Glu Lys Pro Phe
            100                 105                 110

Thr Gly Phe Glu Ala Phe Tyr Ala Ala Glu Asp Ile Asp Glu Cys Gln
        115                 120                 125

Val Ala Pro Gly Glu Ala Pro Thr Cys Asp His His Cys His Asn His
    130                 135                 140

Leu Gly Gly Phe Tyr Cys Ser Cys Arg Ala Gly Tyr Val Leu His Arg
145                 150                 155                 160

Asn Lys Arg Thr Cys Ser Glu Gln Ser Leu
                165                 170

<210> SEQ ID NO 4
<211> LENGTH: 2460
<212> TYPE: DNA
<213> ORGANISM: Homo sapiens
<220> FEATURE:
<221> NAME/KEY: CDS
<222> LOCATION: (22)..(2082)

<400> SEQUENCE: 4
ggccagctgg acgggcacac c atg agg ctg ctg acc ctc ctg ggc ctt ctg     51
                        Met Arg Leu Leu Thr Leu Leu Gly Leu Leu
                        1               5                   10 tgt ggc tcg gtg gcc acc ccc ttg ggc ccg aag tgg cct gaa cct gtg     99
Cys Gly Ser Val Ala Thr Pro Leu Gly Pro Lys Trp Pro Glu Pro Val
                15                  20                  25 ttc ggg cgc ctg gca tcc ccc ggc ttt cca ggg gag tat gcc aat gac    147
Phe Gly Arg Leu Ala Ser Pro Gly Phe Pro Gly Glu Tyr Ala Asn Asp
            30                  35                  40 cag gag cgg cgc tgg acc ctg act gca ccc ccc ggc tac cgc ctg cgc    195
Gln Glu Arg Arg Trp Thr Leu Thr Ala Pro Pro Gly Tyr Arg Leu Arg
```

-continued

```
              45                  50                  55
ctc tac ttc acc cac ttc gac ctg gag ctc tcc cac ctc tgc gag tac      243
Leu Tyr Phe Thr His Phe Asp Leu Glu Leu Ser His Leu Cys Glu Tyr
        60                  65                  70 gac ttc gtc aag ctg agc tcg ggg gcc aag gtg ctg gcc acg ctg tgc      291
Asp Phe Val Lys Leu Ser Ser Gly Ala Lys Val Leu Ala Thr Leu Cys
 75                  80                  85                  90 ggg cag gag agc aca gac acg gag cgg gcc cct ggc aag gac act ttc      339
Gly Gln Glu Ser Thr Asp Thr Glu Arg Ala Pro Gly Lys Asp Thr Phe
                     95                 100                 105 tac tcg ctg ggc tcc agc ctg gac att acc ttc cgc tcc gac tac tcc      387
Tyr Ser Leu Gly Ser Ser Leu Asp Ile Thr Phe Arg Ser Asp Tyr Ser
                110                 115                 120 aac gag aag ccg ttc acg ggg ttc gag gcc ttc tat gca gcc gag gac      435
Asn Glu Lys Pro Phe Thr Gly Phe Glu Ala Phe Tyr Ala Ala Glu Asp
                125                 130                 135 att gac gag tgc cag gtg gcc ccg gga gag gcg ccc acc tgc gac cac      483
Ile Asp Glu Cys Gln Val Ala Pro Gly Glu Ala Pro Thr Cys Asp His
140                 145                 150 cac tgc cac aac cac ctg ggc ggt ttc tac tgc tcc tgc cgc gca ggc      531
His Cys His Asn His Leu Gly Gly Phe Tyr Cys Ser Cys Arg Ala Gly
155                 160                 165                 170 tac gtc ctg cac cgt aac aag cgc acc tgc tca gcc ctg tgc tcc ggc      579
Tyr Val Leu His Arg Asn Lys Arg Thr Cys Ser Ala Leu Cys Ser Gly
                175                 180                 185 cag gtc ttc acc cag agg tct ggg gag ctc agc agc cct gaa tac cca      627
Gln Val Phe Thr Gln Arg Ser Gly Glu Leu Ser Ser Pro Glu Tyr Pro
                190                 195                 200 cgg ccg tat ccc aaa ctc tcc agt tgc act tac agc atc agc ctg gag      675
Arg Pro Tyr Pro Lys Leu Ser Ser Cys Thr Tyr Ser Ile Ser Leu Glu
                205                 210                 215 gag ggg ttc agt gtc att ctg gac ttt gtg gag tcc ttc gat gtg gag      723
Glu Gly Phe Ser Val Ile Leu Asp Phe Val Glu Ser Phe Asp Val Glu
220                 225                 230 aca cac cct gaa acc ctg tgt ccc tac gac ttt ctc aag att caa aca      771
Thr His Pro Glu Thr Leu Cys Pro Tyr Asp Phe Leu Lys Ile Gln Thr
235                 240                 245                 250 gac aga gaa gaa cat ggc cca ttc tgt ggg aag aca ttg ccc cac agg      819
Asp Arg Glu Glu His Gly Pro Phe Cys Gly Lys Thr Leu Pro His Arg
                255                 260                 265 att gaa aca aaa agc aac acg gtg acc atc acc ttt gtc aca gat gaa      867
Ile Glu Thr Lys Ser Asn Thr Val Thr Ile Thr Phe Val Thr Asp Glu
                270                 275                 280 tca gga gac cac aca ggc tgg aag atc cac tac acg agc aca gcg cag      915
Ser Gly Asp His Thr Gly Trp Lys Ile His Tyr Thr Ser Thr Ala Gln
                285                 290                 295 cct tgc cct tat ccg atg gcg cca cct aat ggc cac gtt tca cct gtg      963
Pro Cys Pro Tyr Pro Met Ala Pro Pro Asn Gly His Val Ser Pro Val
300                 305                 310 caa gcc aaa tac atc ctg aaa gac agc ttc tcc atc ttt tgc gag act     1011
Gln Ala Lys Tyr Ile Leu Lys Asp Ser Phe Ser Ile Phe Cys Glu Thr
315                 320                 325                 330 ggc tat gag ctt ctg caa ggt cac ttg ccc ctg aaa tcc ttt act gca     1059
Gly Tyr Glu Leu Leu Gln Gly His Leu Pro Leu Lys Ser Phe Thr Ala
                335                 340                 345 gtt tgt cag aaa gat gga tct tgg gac cgg cca atg ccc gcg tgc agc     1107
Val Cys Gln Lys Asp Gly Ser Trp Asp Arg Pro Met Pro Ala Cys Ser
                350                 355                 360 att gtt gac tgt ggc cct cct gat gat cta ccc agt ggc cga gtg gag     1155
Ile Val Asp Cys Gly Pro Pro Asp Asp Leu Pro Ser Gly Arg Val Glu
```

```
Ile Val Asp Cys Gly Pro Pro Asp Leu Pro Ser Gly Arg Val Glu
            365                 370                 375 tac atc aca ggt cct gga gtg acc acc tac aaa gct gtg att cag tac    1203
Tyr Ile Thr Gly Pro Gly Val Thr Thr Tyr Lys Ala Val Ile Gln Tyr
    380                 385                 390 agc tgt gaa gag acc ttc tac aca atg aaa gtg aat gat ggt aaa tat    1251
Ser Cys Glu Glu Thr Phe Tyr Thr Met Lys Val Asn Asp Gly Lys Tyr
395                 400                 405                 410 gtg tgt gag gct gat gga ttc tgg acg agc tcc aaa gga gaa aaa tca    1299
Val Cys Glu Ala Asp Gly Phe Trp Thr Ser Ser Lys Gly Glu Lys Ser
                415                 420                 425 ctc cca gtc tgt gag cct gtt tgt gga cta tca gcc cgc aca aca gga    1347
Leu Pro Val Cys Glu Pro Val Cys Gly Leu Ser Ala Arg Thr Thr Gly
            430                 435                 440 ggg cgt ata tat gga ggg caa aag gca aaa cct ggt gat ttt cct tgg    1395
Gly Arg Ile Tyr Gly Gly Gln Lys Ala Lys Pro Gly Asp Phe Pro Trp
        445                 450                 455 caa gtc ctg ata tta ggt gga acc aca gca gca ggt gca ctt tta tat    1443
Gln Val Leu Ile Leu Gly Gly Thr Thr Ala Ala Gly Ala Leu Leu Tyr
460                 465                 470 gac aac tgg gtc cta aca gct gct cat gcc gtc tat gag caa aaa cat    1491
Asp Asn Trp Val Leu Thr Ala Ala His Ala Val Tyr Glu Gln Lys His
475                 480                 485                 490 gat gca tcc gcc ctg gac att cga atg ggc acc ctg aaa aga cta tca    1539
Asp Ala Ser Ala Leu Asp Ile Arg Met Gly Thr Leu Lys Arg Leu Ser
                495                 500                 505 cct cat tat aca caa gcc tgg tct gaa gct gtt ttt ata cat gaa ggt    1587
Pro His Tyr Thr Gln Ala Trp Ser Glu Ala Val Phe Ile His Glu Gly
            510                 515                 520 tat act cat gat gct ggc ttt gac aat gac ata gca ctg att aaa ttg    1635
Tyr Thr His Asp Ala Gly Phe Asp Asn Asp Ile Ala Leu Ile Lys Leu
        525                 530                 535 aat aac aaa gtt gta atc aat agc aac atc acg cct att tgt ctg cca    1683
Asn Asn Lys Val Val Ile Asn Ser Asn Ile Thr Pro Ile Cys Leu Pro
540                 545                 550 aga aaa gaa gct gaa tcc ttt atg agg aca gat gac att gga act gca    1731
Arg Lys Glu Ala Glu Ser Phe Met Arg Thr Asp Asp Ile Gly Thr Ala
555                 560                 565                 570 tct gga tgg gga tta acc caa agg ggt ttt ctt gct aga aat cta atg    1779
Ser Gly Trp Gly Leu Thr Gln Arg Gly Phe Leu Ala Arg Asn Leu Met
                575                 580                 585 tat gtc gac ata ccg att gtt gac cat caa aaa tgt act gct gca tat    1827
Tyr Val Asp Ile Pro Ile Val Asp His Gln Lys Cys Thr Ala Ala Tyr
            590                 595                 600 gaa aag cca ccc tat cca agg gga agt gta act gct aac atg ctt tgt    1875
Glu Lys Pro Pro Tyr Pro Arg Gly Ser Val Thr Ala Asn Met Leu Cys
        605                 610                 615 gct ggc tta gaa agt ggg ggc aag gac agc tgc aga ggt gac agc gga    1923
Ala Gly Leu Glu Ser Gly Gly Lys Asp Ser Cys Arg Gly Asp Ser Gly
620                 625                 630 ggg gca ctg gtg ttt cta gat agt gaa aca gag agg tgg ttt gtg gga    1971
Gly Ala Leu Val Phe Leu Asp Ser Glu Thr Glu Arg Trp Phe Val Gly
635                 640                 645                 650 gga ata gtg tcc tgg ggt tcc atg aat tgt ggg gaa gca ggt cag tat    2019
Gly Ile Val Ser Trp Gly Ser Met Asn Cys Gly Glu Ala Gly Gln Tyr
                655                 660                 665 gga gtc tac aca aaa gtt att aac tat att ccc tgg atc gag aac ata    2067
Gly Val Tyr Thr Lys Val Ile Asn Tyr Ile Pro Trp Ile Glu Asn Ile
            670                 675                 680
```

```
att agt gat ttt taa cttgcgtgtc tgcagtcaag gattcttcat ttttagaaat    2122
Ile Ser Asp Phe
        685 gcctgtgaag accttggcag cgacgtggct cgagaagcat tcatcattac tgtggacatg    2182 gcagttgttg ctccacccaa aaaaacagac tccaggtgag gctgctgtca tttctccact    2242 tgccagttta attccagcct tacccattga ctcaagggga cataaaccac gagagtgaca    2302 gtcatctttg cccacccagt gtaatgtcac tgctcaaatt acatttcatt accttaaaaa    2362 gccagtctct tttcatactg gctgttggca tttctgtaaa ctgcctgtcc atgctctttg    2422 tttttaaact tgttcttatt gaaaaaaaaa aaaaaaaa                            2460

<210> SEQ ID NO 5
<211> LENGTH: 686
<212> TYPE: PRT
<213> ORGANISM: Homo sapiens

<400> SEQUENCE: 5

Met Arg Leu Leu Thr Leu Leu Gly Leu Leu Cys Gly Ser Val Ala Thr
1               5                  10                  15

Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr
        35                  40                  45

Leu Thr Ala Pro Pro Gly Tyr Arg Leu Arg Leu Tyr Phe Thr His Phe
    50                  55                  60

Asp Leu Glu Leu Ser His Leu Cys Glu Tyr Asp Phe Val Lys Leu Ser
65                  70                  75                  80

Ser Gly Ala Lys Val Leu Ala Thr Leu Cys Gly Gln Glu Ser Thr Asp
                85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
        115                 120                 125

Gly Phe Glu Ala Phe Tyr Ala Ala Glu Asp Ile Asp Glu Cys Gln Val
    130                 135                 140

Ala Pro Gly Glu Ala Pro Thr Cys Asp His His Cys His Asn His Leu
145                 150                 155                 160

Gly Gly Phe Tyr Cys Ser Cys Arg Ala Gly Tyr Val Leu His Arg Asn
                165                 170                 175

Lys Arg Thr Cys Ser Ala Leu Cys Ser Gly Gln Val Phe Thr Gln Arg
            180                 185                 190

Ser Gly Glu Leu Ser Ser Pro Glu Tyr Pro Arg Pro Tyr Pro Lys Leu
        195                 200                 205

Ser Ser Cys Thr Tyr Ser Ile Ser Leu Glu Glu Gly Phe Ser Val Ile
    210                 215                 220

Leu Asp Phe Val Glu Ser Phe Asp Val Glu Thr His Pro Glu Thr Leu
225                 230                 235                 240

Cys Pro Tyr Asp Phe Leu Lys Ile Gln Thr Asp Arg Glu Glu His Gly
                245                 250                 255

Pro Phe Cys Gly Lys Thr Leu Pro His Arg Ile Glu Thr Lys Ser Asn
            260                 265                 270

Thr Val Thr Ile Thr Phe Val Thr Asp Glu Ser Gly Asp His Thr Gly
        275                 280                 285

Trp Lys Ile His Tyr Thr Ser Thr Ala Gln Pro Cys Pro Tyr Pro Met
```

```
            290                 295                 300
Ala Pro Pro Asn Gly His Val Ser Pro Val Gln Ala Lys Tyr Ile Leu
305                 310                 315                 320

Lys Asp Ser Phe Ser Ile Phe Cys Glu Thr Gly Tyr Glu Leu Leu Gln
                325                 330                 335

Gly His Leu Pro Leu Lys Ser Phe Thr Ala Val Cys Gln Lys Asp Gly
                340                 345                 350

Ser Trp Asp Arg Pro Met Pro Ala Cys Ser Ile Val Asp Cys Gly Pro
                355                 360                 365

Pro Asp Asp Leu Pro Ser Gly Arg Val Glu Tyr Ile Thr Gly Pro Gly
                370                 375                 380

Val Thr Thr Tyr Lys Ala Val Ile Gln Tyr Ser Cys Glu Glu Thr Phe
385                 390                 395                 400

Tyr Thr Met Lys Val Asn Asp Gly Lys Tyr Val Cys Glu Ala Asp Gly
                405                 410                 415

Phe Trp Thr Ser Ser Lys Gly Glu Lys Ser Leu Pro Val Cys Glu Pro
                420                 425                 430

Val Cys Gly Leu Ser Ala Arg Thr Thr Gly Gly Arg Ile Tyr Gly Gly
                435                 440                 445

Gln Lys Ala Lys Pro Gly Asp Phe Pro Trp Gln Val Leu Ile Leu Gly
                450                 455                 460

Gly Thr Thr Ala Ala Gly Ala Leu Leu Tyr Asp Asn Trp Val Leu Thr
465                 470                 475                 480

Ala Ala His Ala Val Tyr Glu Gln Lys His Asp Ala Ser Ala Leu Asp
                485                 490                 495

Ile Arg Met Gly Thr Leu Lys Arg Leu Ser Pro His Tyr Thr Gln Ala
                500                 505                 510

Trp Ser Glu Ala Val Phe Ile His Glu Gly Tyr Thr His Asp Ala Gly
                515                 520                 525

Phe Asp Asn Asp Ile Ala Leu Ile Lys Leu Asn Asn Lys Val Val Ile
                530                 535                 540

Asn Ser Asn Ile Thr Pro Ile Cys Leu Pro Arg Lys Glu Ala Glu Ser
545                 550                 555                 560

Phe Met Arg Thr Asp Asp Ile Gly Thr Ala Ser Gly Trp Gly Leu Thr
                565                 570                 575

Gln Arg Gly Phe Leu Ala Arg Asn Leu Met Tyr Val Asp Ile Pro Ile
                580                 585                 590

Val Asp His Gln Lys Cys Thr Ala Ala Tyr Glu Lys Pro Pro Tyr Pro
                595                 600                 605

Arg Gly Ser Val Thr Ala Asn Met Leu Cys Ala Gly Leu Glu Ser Gly
                610                 615                 620

Gly Lys Asp Ser Cys Arg Gly Asp Ser Gly Gly Ala Leu Val Phe Leu
625                 630                 635                 640

Asp Ser Glu Thr Glu Arg Trp Phe Val Gly Gly Ile Val Ser Trp Gly
                645                 650                 655

Ser Met Asn Cys Gly Glu Ala Gly Gln Tyr Gly Val Tyr Thr Lys Val
                660                 665                 670

Ile Asn Tyr Ile Pro Trp Ile Glu Asn Ile Ile Ser Asp Phe
                675                 680                 685

<210> SEQ ID NO 6
<211> LENGTH: 671
<212> TYPE: PRT
<213> ORGANISM: Homo sapiens
```

<400> SEQUENCE: 6

```
Thr Pro Leu Gly Pro Lys Trp Pro Glu Pro Val Phe Gly Arg Leu Ala
1               5                   10                  15

Ser Pro Gly Phe Pro Gly Glu Tyr Ala Asn Asp Gln Glu Arg Arg Trp
            20                  25                  30

Thr Leu Thr Ala Pro Pro Gly Tyr Arg Leu Arg Leu Tyr Phe Thr His
        35                  40                  45

Phe Asp Leu Glu Leu Ser His Leu Cys Glu Tyr Asp Phe Val Lys Leu
50                  55                  60

Ser Ser Gly Ala Lys Val Leu Ala Thr Leu Cys Gly Gln Glu Ser Thr
65                  70                  75                  80

Asp Thr Glu Arg Ala Pro Gly Lys Asp Thr Phe Tyr Ser Leu Gly Ser
                85                  90                  95

Ser Leu Asp Ile Thr Phe Arg Ser Asp Tyr Ser Asn Glu Lys Pro Phe
            100                 105                 110

Thr Gly Phe Glu Ala Phe Tyr Ala Ala Glu Asp Ile Asp Glu Cys Gln
        115                 120                 125

Val Ala Pro Gly Glu Ala Pro Thr Cys Asp His His Cys His Asn His
130                 135                 140

Leu Gly Gly Phe Tyr Cys Ser Cys Arg Ala Gly Tyr Val Leu His Arg
145                 150                 155                 160

Asn Lys Arg Thr Cys Ser Ala Leu Cys Ser Gly Gln Val Phe Thr Gln
                165                 170                 175

Arg Ser Gly Glu Leu Ser Ser Pro Glu Tyr Pro Arg Pro Tyr Pro Lys
            180                 185                 190

Leu Ser Ser Cys Thr Tyr Ser Ile Ser Leu Glu Glu Gly Phe Ser Val
        195                 200                 205

Ile Leu Asp Phe Val Glu Ser Phe Asp Val Glu Thr His Pro Glu Thr
210                 215                 220

Leu Cys Pro Tyr Asp Phe Leu Lys Ile Gln Thr Asp Arg Glu Glu His
225                 230                 235                 240

Gly Pro Phe Cys Gly Lys Thr Leu Pro His Arg Ile Glu Thr Lys Ser
                245                 250                 255

Asn Thr Val Thr Ile Thr Phe Val Thr Asp Glu Ser Gly Asp His Thr
            260                 265                 270

Gly Trp Lys Ile His Tyr Thr Ser Thr Ala Gln Pro Cys Pro Tyr Pro
        275                 280                 285

Met Ala Pro Pro Asn Gly His Val Ser Pro Val Gln Ala Lys Tyr Ile
290                 295                 300

Leu Lys Asp Ser Phe Ser Ile Phe Cys Glu Thr Gly Tyr Glu Leu Leu
305                 310                 315                 320

Gln Gly His Leu Pro Leu Lys Ser Phe Thr Ala Val Cys Gln Lys Asp
                325                 330                 335

Gly Ser Trp Asp Arg Pro Met Pro Ala Cys Ser Ile Val Asp Cys Gly
            340                 345                 350

Pro Pro Asp Asp Leu Pro Ser Gly Arg Val Glu Tyr Ile Thr Gly Pro
        355                 360                 365

Gly Val Thr Thr Tyr Lys Ala Val Ile Gln Tyr Ser Cys Glu Glu Thr
370                 375                 380

Phe Tyr Thr Met Lys Val Asn Asp Gly Lys Tyr Val Cys Glu Ala Asp
385                 390                 395                 400

Gly Phe Trp Thr Ser Ser Lys Gly Glu Lys Ser Leu Pro Val Cys Glu
```

|  |  |  | 405 |  |  |  | 410 |  |  |  | 415 |
|---|---|---|---|---|---|---|---|---|---|---|---|

Pro Val Cys Gly Leu Ser Ala Arg Thr Thr Gly Gly Arg Ile Tyr Gly
            420                      425                  430

Gly Gln Lys Ala Lys Pro Gly Asp Phe Pro Trp Gln Val Leu Ile Leu
            435                      440                  445

Gly Gly Thr Thr Ala Ala Gly Ala Leu Leu Tyr Asp Asn Trp Val Leu
    450                        455                  460

Thr Ala Ala His Ala Val Tyr Glu Gln Lys His Asp Ala Ser Ala Leu
465                      470                  475                  480

Asp Ile Arg Met Gly Thr Leu Lys Arg Leu Ser Pro His Tyr Thr Gln
                485                      490                  495

Ala Trp Ser Glu Ala Val Phe Ile His Glu Gly Tyr Thr His Asp Ala
            500                      505                  510

Gly Phe Asp Asn Asp Ile Ala Leu Ile Lys Leu Asn Asn Lys Val Val
    515                        520                  525

Ile Asn Ser Asn Ile Thr Pro Ile Cys Leu Pro Arg Lys Glu Ala Glu
530                      535                  540

Ser Phe Met Arg Thr Asp Asp Ile Gly Thr Ala Ser Gly Trp Gly Leu
545                      550                  555                  560

Thr Gln Arg Gly Phe Leu Ala Arg Asn Leu Met Tyr Val Asp Ile Pro
                565                      570                  575

Ile Val Asp His Gln Lys Cys Thr Ala Ala Tyr Glu Lys Pro Pro Tyr
            580                      585                  590

Pro Arg Gly Ser Val Thr Ala Asn Met Leu Cys Ala Gly Leu Glu Ser
                595                      600                  605

Gly Gly Lys Asp Ser Cys Arg Gly Asp Ser Gly Gly Ala Leu Val Phe
    610                        615                  620

Leu Asp Ser Glu Thr Glu Arg Trp Phe Val Gly Gly Ile Val Ser Trp
625                      630                  635                  640

Gly Ser Met Asn Cys Gly Glu Ala Gly Gln Tyr Gly Val Tyr Thr Lys
                645                      650                  655

Val Ile Asn Tyr Ile Pro Trp Ile Glu Asn Ile Ile Ser Asp Phe
            660                      665                  670

<210> SEQ ID NO 7
<211> LENGTH: 4900
<212> TYPE: DNA
<213> ORGANISM: Homo sapiens

<400> SEQUENCE: 7

| cctgtcctgc | ctgcctggaa | ctctgagcag | gctggagtca | tggagtcgat | tcccagaatc | 60 |
|---|---|---|---|---|---|---|
| ccagagtcag | ggaggctggg | ggcaggggca | ggtcactgga | caaacagatc | aaaggtgaga | 120 |
| ccagcgtagg | actgcagacc | aggccaggcc | agctggacgg | gcacaccatg | aggtaggtgg | 180 |
| gcgccacagc | ctccctgcag | ggtgtggggt | gggagcacag | gcctgggcct | caccgcccct | 240 |
| gccctgccca | taggctgctg | accctcctgg | gccttctgtg | tggctcggtg | gccacccect | 300 |
| taggcccgaa | gtggcctgaa | cctgtgttcg | ggcgcctggc | atccccggc | tttccagggg | 360 |
| agtatgccaa | tgaccaggag | cggcgctgga | ccctgactgc | accccccggc | taccgcctgc | 420 |
| gcctctactt | cacccacttc | gacctggagc | tctcccacct | ctgcgagtac | gacttcgtca | 480 |
| aggtgccgtc | agacgggagg | gctggggttt | ctcaggtcg | ggggtcccc | aaggagtagc | 540 |
| cagggttcag | ggacacctgg | gagcaggggc | caggcttggc | caggagggag | atcaggcctg | 600 |
| ggtcttgcct | tcactccctg | tgacacctga | ccccacagct | gagctcgggg | gccaaggtgc | 660 |

```
tggccacgct gtgcgggcag gagagcacag acacggagcg ggcccctggc aaggacactt      720
tctactcgct gggctccagc ctggacatta ccttccgctc cgactactcc aacgagaagc      780
cgttcacggg gttcgaggcc ttctatgcag ccgagggtga gccaagaggg gtcctgcaac      840
atctcagtct gcgcagctgg ctgtgggggt aactctgtct taggccaggc agccctgcct      900
tcagtttccc cacctttccc agggcagggg agaggcctct ggcctgacat catccacaat      960
gcaaagacca aaacagccgt gacctccatt cacatgggct gagtgccaac tctgagccag     1020
ggatctgagg acagcatcgc ctcaagtgac gcagggactg gccgggcgcg gcagctcacg     1080
cctgtaattc cagcactttg ggaggccgag gctggcttga taatttgagg gtcaggagtt     1140
caaggccagc cagggcaaca cggtgaaact ctatctccac taaaactaca aaaattagct     1200
gggcgtggtg gtgcgcacct ggaatcccag ctactaggga ggctgaggca ggagaattgc     1260
ttgaacctgc gaggtggagg ctgcagtgaa cagagattgc accactacac tccacctggg     1320
cgacagacta gactccgtct caaaaaacaa aaaacaaaaa ccacgcaggg ccagggccc       1380 atttacaagc tgacaaagtg ggccctgcca gcgggagcgc tgcaggatgt tgatttttca     1440
gatcccagtc cctgcagaga ccaactgtgt gacctctggc aagtggctca atttctctgc     1500
tccttagaag ctgctgcaag ggttcagcgc tgtagccccg cccctgggt ttgattgact        1560 cccctcatta gctgggtgac ctcggccgga cactgaaact cccactggtt taacagaggt     1620
gatgtttgca tctttctccc agcgctgctg ggagcttgca gcgaccctag gcctgtaagg     1680
tgattggccc ggcaccagtc ccgcacccta gacaggacct aggcctcctc tgaggtccac     1740
tctgaggtca tggatctcct gggaggagtc caggctggat cccgcctctt tccctcctga     1800
cggcctgcct ggccctgcct ctcccccaga cattgacgag tgccaggtgg ccccgggaga     1860
ggcgcccacc tgcgaccacc actgccacaa ccacctgggc ggtttctact gctcctgccg     1920
cgcaggctac gtcctgcacc gtaacaagcg cacctgctca ggtgagggag gctgcctggg     1980
ccccaacgca ccctctcctg ggatacccgg ggctcctcag ggccattgct gctctgccca     2040
ggggtgcgga gggcctgggc ctggacactg ggtgcttcta ggccctgctg cctccagctc     2100
cccttctcag ccctgcttcc cctctcagca gccaggctca tcagtgccac cctgccctag     2160
cactgagact aattctaaca tcccactgtg tacctggttc cacctgggct ctgggaaccc     2220
ctcatgtagc cacgggagag tcggggtatc taccctcgtt ccttggactg ggttcctgtt     2280
ccctgcactg ggggacgggc cagtgctctg gggcgtgggc agccccaccc tgtggcgctg     2340
accctgctcc cccgactcgg tttctcctct cggggtctct ccttgcctct ctgatctctc     2400
ttccagagca gagcctctag cctcccctgg agctccggct gcccagcagg tcagaagcca     2460
gagccaggct gctggcctca gctccgggtt ggctgagat gctgtgcccc aactcccatt      2520
cacccaccat ggacccaata taaacctgg ccccaccccca cctgctgccg cgtgtctctg     2580
gggtgggagg gtcgggaggc ggtggggcgc gctcctctct gcctaccctc ctcacagcct     2640
catgaacccc aggtctgtgg gagcctcctc catggggcca cacggtcctt ggcctcaccc     2700
cctgttttga agatgggca ctgaggccgg agaggggtaa ggcctcgctc gagtccaggt       2760
ccccagaggc tgagcccaga gtaatcttga accacccca ttcagggtct ggcctggagg       2820
agcctgaccc acagaggaga caccctggga gatattcatt gaggggtaat ctggtccccc     2880
gcaaatccag gggtgattcc cactgcccca taggcacagc cacgtggaag aaggcaggca     2940
atgttggggc tcctcacttc ctagaggcct cacaactcaa atgccccca ctgcagctgg       3000
```

```
                                         -continued
gggtggggtg gtggtatggg atggggacca agccttcctt gaaggataga gcccagccca      3060
acaccccgcc ccgtggcagc agcatcacgt gttccagcga ggaaggagag caccagactc      3120
agtcatgatc actgttgcct tgaacttcca agaacagccc agggcaagg gtcaaaacag       3180 gggaaagggg gtgatgagag atccttcttc cggatgttcc tccaggaacc aggggggctgg    3240 ctggtcttgg ctgggttcgg gtaggagacc catgatgaat aaacttggga atcactgggg     3300
tggctgtaag ggaatttagg ggagctccga aggggccctt aggctcgagg agatgctcct     3360
ctcttttccc gaattcccag ggacccagga gagtgtccct tcttcctctt cctgtgtgtc      3420
catccacccc cgccccccgc cctggcgagg ctggtggaac tcagtgctct agcccctacc     3480
ctggggttgc gactctggct caggacacca ccacgctccc tgggggtgtg agtgagggcc     3540
tgtgcgctcc atcccgagtg ctgcctgttt cagctaaagc tcaaagcaa gagaaacccc     3600 ctctctaagc ggcccctcag ccatcgggtg ggtcgtttgg tttctgggta ggcctcaggg     3660
gctggccacc tgcagggccc agcccaaccc agggatgcag atgtcccagc cacatccctg     3720
tcccagtttc ctgctcccca aggcatccac cctgctgttg gtgcgagggc tgatagaggg     3780
cacgccaagt cactcccctg cccttccctc cttccagccc tgtgctccgg ccaggtcttc     3840
acccagaggt ctggggagct cagcagccct gaatacccac ggccgtatcc caaactctcc     3900
agttgcactt acagcatcag cctggaggag gggttcagtg tcattctgga ctttgtggag     3960
tccttcgatg tggagacaca ccctgaaacc ctgtgtccct acgactttct caaggtctgg    4020
ctcctgggcc cctcatcttg tcccagatcc tccccccttca gcccagctgc acccccctact   4080 tcctgcagca tggcccccac cacgttcccg tcacctcgg tgaccccacc tcttcaggtg     4140
ctctatggag gtcaaggctg gggcttcgag tacaagtgtg ggaggcagag tggggagggg    4200 cacccccaatc catggcctgg gttggcctca ttggctgtcc ctgaaatgct gaggaggtgg   4260
gttacttccc tccgcccagg ccagacccag gcagctgctc cccagctttc atgagcttct     4320
ttctcagatt caaacagaca gagaagaaca tgggcccattc tgtgggaaga cattgccccca  4380 caggattgaa acaaaaagca acacggtgac catcaccttt gtcacagatg aatcaggaga     4440
ccacacaggc tggaagatcc actacacgag cacagtgagc aagtgggctc agatccttgg    4500
tggaagcgca gagctgcctc tctctggagt gcaaggagct gtagagtgta gggctcttct     4560
gggcaggact aggaagggac accaggttta gtggtgctga ggtctgaggc agcagcttct    4620 aagggaagc acccgtgccc tcctcagcag cacccagcat cttcaccact cattcttcaa     4680
ccacccattc acccatcact catcttttac ccacccaccc tttgccactc atccttctgt     4740
ccctcatcct tccaaccatt catcaatcac ccacccatcc atcctttgcc acacaaccat    4800
ccacccattc ttctacctac ccatcctatc catccatcct tctatcagca tccttctacc     4860
acccatcctt cgttcggtca tccatcatca tccatccatc                           4900
```

<210> SEQ ID NO 8
<211> LENGTH: 136
<212> TYPE: PRT
<213> ORGANISM: Homo sapiens

<400> SEQUENCE: 8

Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr

```
            35                  40                  45
Leu Thr Ala Pro Pro Gly Tyr Arg Leu Arg Leu Tyr Phe Thr His Phe
 50                  55                  60

Asp Leu Glu Leu Ser His Leu Cys Glu Tyr Asp Phe Val Lys Leu Ser
 65                  70                  75                  80

Ser Gly Ala Lys Val Leu Ala Thr Leu Cys Gly Gln Glu Ser Thr Asp
                 85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
            115                 120                 125

Gly Phe Glu Ala Phe Tyr Ala Ala
            130                 135
```

<210> SEQ ID NO 9
<211> LENGTH: 181
<212> TYPE: PRT
<213> ORGANISM: Homo sapiens

<400> SEQUENCE: 9

```
Met Arg Leu Leu Thr Leu Leu Gly Leu Leu Cys Gly Ser Val Ala Thr
  1               5                  10                  15

Pro Leu Gly Pro Lys Trp Pro Glu Pro Val Phe Gly Arg Leu Ala Ser
                 20                  25                  30

Pro Gly Phe Pro Gly Glu Tyr Ala Asn Asp Gln Glu Arg Arg Trp Thr
            35                  40                  45

Leu Thr Ala Pro Pro Gly Tyr Arg Leu Arg Leu Tyr Phe Thr His Phe
 50                  55                  60

Asp Leu Glu Leu Ser His Leu Cys Glu Tyr Asp Phe Val Lys Leu Ser
 65                  70                  75                  80

Ser Gly Ala Lys Val Leu Ala Thr Leu Cys Gly Gln Glu Ser Thr Asp
                 85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
            115                 120                 125

Gly Phe Glu Ala Phe Tyr Ala Ala Glu Asp Ile Asp Glu Cys Gln Val
            130                 135                 140

Ala Pro Gly Glu Ala Pro Thr Cys Asp His His Cys His Asn His Leu
145                 150                 155                 160

Gly Gly Phe Tyr Cys Ser Cys Arg Ala Gly Tyr Val Leu His Arg Asn
                165                 170                 175

Lys Arg Thr Cys Ser
            180
```

<210> SEQ ID NO 10
<211> LENGTH: 293
<212> TYPE: PRT
<213> ORGANISM: Homo sapiens

<400> SEQUENCE: 10

```
Met Arg Leu Leu Thr Leu Leu Gly Leu Leu Cys Gly Ser Val Ala Thr
  1               5                  10                  15

Pro Leu Gly Pro Lys Trp Pro Glu Pro Val Phe Gly Arg Leu Ala Ser
                 20                  25                  30

Pro Gly Phe Pro Gly Glu Tyr Ala Asn Asp Gln Glu Arg Arg Trp Thr
```

```
            35                  40                  45
Leu Thr Ala Pro Pro Gly Tyr Arg Leu Arg Leu Tyr Phe Thr His Phe
 50                  55                  60

Asp Leu Glu Leu Ser His Leu Cys Glu Tyr Asp Phe Val Lys Leu Ser
 65                  70                  75                  80

Ser Gly Ala Lys Val Leu Ala Thr Leu Cys Gly Gln Glu Ser Thr Asp
                 85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
        115                 120                 125

Gly Phe Glu Ala Phe Tyr Ala Ala Glu Asp Ile Asp Glu Cys Gln Val
130                 135                 140

Ala Pro Gly Glu Ala Pro Thr Cys Asp His His Cys His Asn His Leu
145                 150                 155                 160

Gly Gly Phe Tyr Cys Ser Cys Arg Ala Gly Tyr Val Leu His Arg Asn
                165                 170                 175

Lys Arg Thr Cys Ser Ala Leu Cys Ser Gly Gln Val Phe Thr Gln Arg
            180                 185                 190

Ser Gly Glu Leu Ser Ser Pro Glu Tyr Pro Arg Pro Tyr Pro Lys Leu
        195                 200                 205

Ser Ser Cys Thr Tyr Ser Ile Ser Leu Glu Glu Gly Phe Ser Val Ile
210                 215                 220

Leu Asp Phe Val Glu Ser Phe Asp Val Glu Thr His Pro Glu Thr Leu
225                 230                 235                 240

Cys Pro Tyr Asp Phe Leu Lys Ile Gln Thr Asp Arg Glu Glu His Gly
                245                 250                 255

Pro Phe Cys Gly Lys Thr Leu Pro His Arg Ile Glu Thr Lys Ser Asn
            260                 265                 270

Thr Val Thr Ile Thr Phe Val Thr Asp Glu Ser Gly Asp His Thr Gly
        275                 280                 285

Trp Lys Ile His Tyr
    290

<210> SEQ ID NO 11
<211> LENGTH: 41
<212> TYPE: PRT
<213> ORGANISM: Homo sapiens

<400> SEQUENCE: 11

Glu Asp Ile Asp Glu Cys Gln Val Ala Pro Gly Glu Ala Pro Thr Cys
 1               5                  10                  15

Asp His His Cys His Asn His Leu Gly Gly Phe Tyr Cys Ser Cys Arg
                20                  25                  30

Ala Gly Tyr Val Leu His Arg Asn Lys
            35                  40

<210> SEQ ID NO 12
<211> LENGTH: 242
<212> TYPE: PRT
<213> ORGANISM: Homo sapiens

<400> SEQUENCE: 12

Ile Tyr Gly Gly Gln Lys Ala Lys Pro Gly Asp Phe Pro Trp Gln Val
 1               5                  10                  15

Leu Ile Leu Gly Gly Thr Thr Ala Ala Gly Ala Leu Leu Tyr Asp Asn
```

```
                20                  25                  30

Trp Val Leu Thr Ala Ala His Ala Val Tyr Glu Gln Lys His Asp Ala
            35                  40                  45

Ser Ala Leu Asp Ile Arg Met Gly Thr Leu Lys Arg Leu Ser Pro His
        50                  55                  60

Tyr Thr Gln Ala Trp Ser Glu Ala Val Phe Ile His Glu Gly Tyr Thr
65                  70                  75                  80

His Asp Ala Gly Phe Asp Asn Asp Ile Ala Leu Ile Lys Leu Asn Asn
                85                  90                  95

Lys Val Val Ile Asn Ser Asn Ile Thr Pro Ile Cys Leu Pro Arg Lys
            100                 105                 110

Glu Ala Glu Ser Phe Met Arg Thr Asp Asp Ile Gly Thr Ala Ser Gly
        115                 120                 125

Trp Gly Leu Thr Gln Arg Gly Phe Leu Ala Arg Asn Leu Met Tyr Val
    130                 135                 140

Asp Ile Pro Ile Val Asp His Gln Lys Cys Thr Ala Ala Tyr Glu Lys
145                 150                 155                 160

Pro Pro Tyr Pro Arg Gly Ser Val Thr Ala Asn Met Leu Cys Ala Gly
                165                 170                 175

Leu Glu Ser Gly Gly Lys Asp Ser Cys Arg Gly Asp Ser Gly Gly Ala
            180                 185                 190

Leu Val Phe Leu Asp Ser Glu Thr Glu Arg Trp Phe Val Gly Gly Ile
        195                 200                 205

Val Ser Trp Gly Ser Met Asn Cys Gly Glu Ala Gly Gln Tyr Gly Val
    210                 215                 220

Tyr Thr Lys Val Ile Asn Tyr Ile Pro Trp Ile Glu Asn Ile Ile Ser
225                 230                 235                 240

Asp Phe

<210> SEQ ID NO 13
<211> LENGTH: 16
<212> TYPE: PRT
<213> ORGANISM: Artificial Sequence
<220> FEATURE:
<223> OTHER INFORMATION: Synthetic

<400> SEQUENCE: 13

Gly Lys Asp Ser Cys Arg Gly Asp Ala Gly Gly Ala Leu Val Phe Leu
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic

<400> SEQUENCE: 14

Thr Pro Leu Gly Pro Lys Trp Pro Glu Pro Val Phe Gly Arg Leu
1               5                   10                  15

<210> SEQ ID NO 15
<211> LENGTH: 43
<212> TYPE: PRT
<213> ORGANISM: Artificial Sequence
<220> FEATURE:
<223> OTHER INFORMATION: Synthetic

<400> SEQUENCE: 15
```

Thr Ala Pro Pro Gly Tyr Arg Leu Arg Leu Tyr Phe Thr His Phe Asp
1               5                   10                  15

Leu Glu Leu Ser His Leu Cys Glu Tyr Asp Phe Val Lys Leu Ser Ser
            20                  25                  30

Gly Ala Lys Val Leu Ala Thr Leu Cys Gly Gln
        35                  40

<210> SEQ ID NO 16
<211> LENGTH: 8
<212> TYPE: PRT
<213> ORGANISM: Artificial
<220> FEATURE:
<223> OTHER INFORMATION: Synthetic

<400> SEQUENCE: 16

Thr Phe Arg Ser Asp Tyr Ser Asn
1               5

<210> SEQ ID NO 17
<211> LENGTH: 25
<212> TYPE: PRT
<213> ORGANISM: Artificial Sequence
<220> FEATURE:
<223> OTHER INFORMATION: Synthetic

<400> SEQUENCE: 17

Phe Tyr Ser Leu Gly Ser Ser Leu Asp Ile Thr Phe Arg Ser Asp Tyr
1               5                   10                  15

Ser Asn Glu Lys Pro Phe Thr Gly Phe
            20                  25

<210> SEQ ID NO 18
<211> LENGTH: 9
<212> TYPE: PRT
<213> ORGANISM: Artificial
<220> FEATURE:
<223> OTHER INFORMATION: Synthetic

<400> SEQUENCE: 18

Ile Asp Glu Cys Gln Val Ala Pro Gly
1               5

<210> SEQ ID NO 19
<211> LENGTH: 25
<212> TYPE: PRT
<213> ORGANISM: Artificial Sequence
<220> FEATURE:
<223> OTHER INFORMATION: Synthetic

<400> SEQUENCE: 19

Ala Asn Met Leu Cys Ala Gly Leu Glu Ser Gly Gly Lys Asp Ser Cys
1               5                   10                  15

Arg Gly Asp Ser Gly Gly Ala Leu Val
            20                  25

<210> SEQ ID NO 20
<211> LENGTH: 960
<212> TYPE: DNA
<213> ORGANISM: Homo sapiens
<220> FEATURE:
<221> NAME/KEY: CDS
<222> LOCATION: (51)..(797)

<400> SEQUENCE: 20
attaactgag attaaccttc cctgagtttt ctcacaccaa ggtgaggacc atg tcc         56

```
                                                    Met Ser
                                                      1
ctg ttt cca tca ctc cct ctc ctt ctc ctg agt atg gtg gca gcg tct    104
Leu Phe Pro Ser Leu Pro Leu Leu Leu Leu Ser Met Val Ala Ala Ser
      5                  10                  15 tac tca gaa act gtg acc tgt gag gat gcc caa aag acc tgc cct gca    152
Tyr Ser Glu Thr Val Thr Cys Glu Asp Ala Gln Lys Thr Cys Pro Ala
 20                  25                  30 gtg att gcc tgt agc tct cca ggc atc aac ggc ttc cca ggc aaa gat    200
Val Ile Ala Cys Ser Ser Pro Gly Ile Asn Gly Phe Pro Gly Lys Asp
 35                  40                  45                  50 ggg cgt gat ggc acc aag gga gaa aag ggg gaa cca ggc caa ggg ctc    248
Gly Arg Asp Gly Thr Lys Gly Glu Lys Gly Glu Pro Gly Gln Gly Leu
                 55                  60                  65 aga ggc tta cag ggc ccc cct gga aag ttg ggg cct cca gga aat cca    296
Arg Gly Leu Gln Gly Pro Pro Gly Lys Leu Gly Pro Pro Gly Asn Pro
          70                  75                  80 ggg cct tct ggg tca cca gga cca aag ggc caa aaa gga gac cct gga    344
Gly Pro Ser Gly Ser Pro Gly Pro Lys Gly Gln Lys Gly Asp Pro Gly
      85                  90                  95 aaa agt ccg gat ggt gat agt agc ctg gct gcc tca gaa aga aaa gct    392
Lys Ser Pro Asp Gly Asp Ser Ser Leu Ala Ala Ser Glu Arg Lys Ala
100                 105                 110 ctg caa aca gaa atg gca cgt atc aaa aag tgg ctc acc ttc tct ctg    440
Leu Gln Thr Glu Met Ala Arg Ile Lys Lys Trp Leu Thr Phe Ser Leu
115                 120                 125                 130 ggc aaa caa gtt ggg aac aag ttc ttc ctg acc aat ggt gaa ata atg    488
Gly Lys Gln Val Gly Asn Lys Phe Phe Leu Thr Asn Gly Glu Ile Met
                135                 140                 145 acc ttt gaa aaa gtg aag gcc ttg tgt gtc aag ttc cag gcc tct gtg    536
Thr Phe Glu Lys Val Lys Ala Leu Cys Val Lys Phe Gln Ala Ser Val
            150                 155                 160 gcc acc ccc agg aat gct gca gag aat gga gcc att cag aat ctc atc    584
Ala Thr Pro Arg Asn Ala Ala Glu Asn Gly Ala Ile Gln Asn Leu Ile
        165                 170                 175 aag gag gaa gcc ttc ctg ggc atc act gat gag aag aca gaa ggg cag    632
Lys Glu Glu Ala Phe Leu Gly Ile Thr Asp Glu Lys Thr Glu Gly Gln
    180                 185                 190 ttt gtg gat ctg aca gga aat aga ctg acc tac aca aac tgg aac gag    680
Phe Val Asp Leu Thr Gly Asn Arg Leu Thr Tyr Thr Asn Trp Asn Glu
195                 200                 205                 210 ggt gaa ccc aac aat gct ggt tct gat gaa gat tgt gta ttg cta ctg    728
Gly Glu Pro Asn Asn Ala Gly Ser Asp Glu Asp Cys Val Leu Leu Leu
                215                 220                 225 aaa aat ggc cag tgg aat gac gtc ccc tgc tcc acc tcc cat ctg gcc    776
Lys Asn Gly Gln Trp Asn Asp Val Pro Cys Ser Thr Ser His Leu Ala
            230                 235                 240 gtc tgt gag ttc cct atc tga aggtcatat cactcaggcc ctccttgtct        827
Val Cys Glu Phe Pro Ile
        245 tttactgca acccacaggc ccacagtatg cttgaaaaga taaattatat caatttcctc    887
atatccagta ttgttccttt tgtgggcaat cactaaaaat gatcactaac agcaccaaca    947
aagcaataat agt                                                      960

<210> SEQ ID NO 21
<211> LENGTH: 248
<212> TYPE: PRT
<213> ORGANISM: Homo sapiens
```

```
<400> SEQUENCE: 21

Met Ser Leu Phe Pro Ser Leu Pro Leu Leu Leu Ser Met Val Ala
1               5                   10                  15

Ala Ser Tyr Ser Glu Thr Val Thr Cys Glu Asp Ala Gln Lys Thr Cys
            20                  25                  30

Pro Ala Val Ile Ala Cys Ser Ser Pro Gly Ile Asn Gly Phe Pro Gly
            35                  40                  45

Lys Asp Gly Arg Asp Gly Thr Lys Gly Glu Lys Gly Glu Pro Gly Gln
50                  55                  60

Gly Leu Arg Gly Leu Gln Gly Pro Pro Gly Lys Leu Gly Pro Pro Gly
65                  70                  75                  80

Asn Pro Gly Pro Ser Gly Ser Pro Gly Pro Lys Gly Gln Lys Gly Asp
                85                  90                  95

Pro Gly Lys Ser Pro Asp Gly Asp Ser Ser Leu Ala Ala Ser Glu Arg
            100                 105                 110

Lys Ala Leu Gln Thr Glu Met Ala Arg Ile Lys Lys Trp Leu Thr Phe
            115                 120                 125

Ser Leu Gly Lys Gln Val Gly Asn Lys Phe Phe Leu Thr Asn Gly Glu
130                 135                 140

Ile Met Thr Phe Glu Lys Val Lys Ala Leu Cys Val Lys Phe Gln Ala
145                 150                 155                 160

Ser Val Ala Thr Pro Arg Asn Ala Ala Glu Asn Gly Ala Ile Gln Asn
                165                 170                 175

Leu Ile Lys Glu Glu Ala Phe Leu Gly Ile Thr Asp Glu Lys Thr Glu
            180                 185                 190

Gly Gln Phe Val Asp Leu Thr Gly Asn Arg Leu Thr Tyr Thr Asn Trp
            195                 200                 205

Asn Glu Gly Glu Pro Asn Asn Ala Gly Ser Asp Glu Asp Cys Val Leu
            210                 215                 220

Leu Leu Lys Asn Gly Gln Trp Asn Asp Val Pro Cys Ser Thr Ser His
225                 230                 235                 240

Leu Ala Val Cys Glu Phe Pro Ile
                245

<210> SEQ ID NO 22
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 represents
      hydroxyproline
<220> FEATURE:
<221> NAME/KEY: MISC_FEATURE
<222> LOCATION: (4)..(4)
<223> OTHER INFORMATION: Wherein X at position 4 represents hydrophobic
      residue

<400> SEQUENCE: 22

Xaa Gly Lys Xaa Gly Pro
1               5

<210> SEQ ID NO 23
<211> LENGTH: 5
<212> TYPE: PRT
<213> ORGANISM: Artificial Sequence
<220> FEATURE:
```

```
<223> OTHER INFORMATION: Synthetic
<220> FEATURE:
<221> NAME/KEY: MISC_FEATURE
<222> LOCATION: (1)..(1)
<223> OTHER INFORMATION: Wherein X represents hydroxyproline

<400> SEQUENCE: 23

Xaa Gly Lys Leu Gly
1               5

<210> SEQ ID NO 24
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(15)
<223> OTHER INFORMATION: Wherein X at positions 9 and 15 represents
      hydroxyproline

<400> SEQUENCE: 24

Gly Leu Arg Gly Leu Gln Gly Pro Xaa Gly Lys Leu Gly Pro Xaa Gly
1               5                   10                  15

<210> SEQ ID NO 25
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(27)
<223> OTHER INFORMATION: Wherein X at positions 3, 6, 15, 21, 24, 27
      represents hydroxyproline

<400> SEQUENCE: 25

Gly Pro Xaa Gly Pro Xaa Gly Leu Arg Gly Leu Gln Gly Pro Xaa Gly
1               5                   10                  15

Lys Leu Gly Pro Xaa Gly Pro Xaa Gly Pro Xaa
            20                  25

<210> SEQ ID NO 26
<211> LENGTH: 53
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid

<400> SEQUENCE: 26
```

```
Gly Lys Asp Gly Arg Asp Gly Thr Lys Gly Glu Lys Gly Glu Pro Gly
1               5                   10                  15

Gln Gly Leu Arg Gly Leu Gln Gly Pro Xaa Gly Lys Leu Gly Pro Xaa
                20                  25                  30

Gly Asn Xaa Gly Pro Ser Gly Ser Xaa Gly Pro Lys Gly Gln Lys Gly
            35                  40                  45

Asp Xaa Gly Lys Ser
    50

<210> SEQ ID NO 27
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(33)
<223> OTHER INFORMATION: Wherein X at positions 3, 6, 12, 18, 21, 30,
      33 represents hydroxyproline

<400> SEQUENCE: 27

Gly Ala Xaa Gly Ser Xaa Gly Glu Lys Gly Ala Xaa Gly Pro Gln Gly
1               5                   10                  15

Pro Xaa Gly Pro Xaa Gly Lys Met Gly Pro Lys Gly Glu Xaa Gly Asp
                20                  25                  30

Xaa

<210> SEQ ID NO 28
<211> LENGTH: 45
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(45)
<223> OTHER INFORMATION: Wherein X at positions 3, 6, 9, 27, 30, 36,
      42, 45 represents hydroxyproline

<400> SEQUENCE: 28

Gly Cys Xaa Gly Leu Xaa Gly Ala Xaa Gly Asp Lys Gly Glu Ala Gly
1               5                   10                  15

Thr Asn Gly Lys Arg Gly Glu Arg Gly Pro Xaa Gly Pro Xaa Gly Lys
                20                  25                  30

Ala Gly Pro Xaa Gly Pro Asn Gly Ala Xaa Gly Glu Xaa
            35                  40                  45

<210> SEQ ID NO 29
<211> LENGTH: 24
<212> TYPE: PRT
<213> ORGANISM: Artificial Sequence
<220> FEATURE:
<223> OTHER INFORMATION: Synthetic

<400> SEQUENCE: 29

Leu Gln Arg Ala Leu Glu Ile Leu Pro Asn Arg Val Thr Ile Lys Ala
1               5                   10                  15

Asn Arg Pro Phe Leu Val Phe Ile
                20

<210> SEQ ID NO 30
<211> LENGTH: 559
```

```
<212> TYPE: DNA
<213> ORGANISM: Homo sapiens

<400> SEQUENCE: 30
atgaggctgc tgaccctcct gggccttctg tgtggctcgg tggccacccc cttgggcccg      60
aagtggcctg aacctgtgtt cgggcgcctg catcccccg gctttccagg ggagtatgcc     120
aatgaccagg agcggcgctg gaccctgact gcacccccg gctaccgcct gcgcctctac     180
ttcacccact cgacctgga gctctcccac ctctgcgagt acgacttcgt caagctgagc     240
tcgggggcca aggtgctggc cacgctgtgc gggcaggaga gcacagacac ggagcgggcc     300
cctggcaagg acactttcta ctcgctgggc tccagcctgg acattacctt ccgctccgac     360
tactccaacg agaagccgtt cacggggttc gaggccttct atgcagccga ggacattgac     420
gagtgccagg tgccccggg agaggcgccc acctgcgacc accactgcca caaccacctg     480
ggcggtttct actgctcctg ccgcgcaggc tacgtcctgc accgtaacaa gcgcacctgc     540
tcagccctgt gctccggcc                                                 559

<210> SEQ ID NO 31
<211> LENGTH: 34
<212> TYPE: DNA
<213> ORGANISM: Artificial Sequence
<220> FEATURE:
<223> OTHER INFORMATION: Synthetic

<400> SEQUENCE: 31
cgggcacacc atgaggctgc tgaccctcct gggc                                 34

<210> SEQ ID NO 32
<211> LENGTH: 33
<212> TYPE: DNA
<213> ORGANISM: Artificial Sequence
<220> FEATURE:
<223> OTHER INFORMATION: Synthetic

<400> SEQUENCE: 32
gacattacct tccgctccga ctccaacgag aag                                  33

<210> SEQ ID NO 33
<211> LENGTH: 33
<212> TYPE: DNA
<213> ORGANISM: Artificial Sequence
<220> FEATURE:
<223> OTHER INFORMATION: Synthetic

<400> SEQUENCE: 33
agcagccctg aatacccacg gccgtatccc aaa                                  33

<210> SEQ ID NO 34
<211> LENGTH: 26
<212> TYPE: DNA
<213> ORGANISM: Artificial Sequence
<220> FEATURE:
<223> OTHER INFORMATION: Synthetic

<400> SEQUENCE: 34
cgggatccat gaggctgctg accctc                                          26

<210> SEQ ID NO 35
<211> LENGTH: 19
<212> TYPE: DNA
<213> ORGANISM: Artificial Sequence
<220> FEATURE:
```

```
<223> OTHER INFORMATION: Synthetic

<400> SEQUENCE: 35
ggaattccta ggctgcata                                              19

<210> SEQ ID NO 36
<211> LENGTH: 19
<212> TYPE: DNA
<213> ORGANISM: Artificial Sequence
<220> FEATURE:
<223> OTHER INFORMATION: Synthetic

<400> SEQUENCE: 36
ggaattccta cagggcgct                                              19

<210> SEQ ID NO 37
<211> LENGTH: 19
<212> TYPE: DNA
<213> ORGANISM: Artificial Sequence
<220> FEATURE:
<223> OTHER INFORMATION: Synthetic

<400> SEQUENCE: 37
ggaattccta gtagtggat                                              19

<210> SEQ ID NO 38
<211> LENGTH: 25
<212> TYPE: DNA
<213> ORGANISM: Artificial Sequence
<220> FEATURE:
<223> OTHER INFORMATION: Synthetic

<400> SEQUENCE: 38
tgcggccgct gtaggtgctg tcttt                                       25

<210> SEQ ID NO 39
<211> LENGTH: 23
<212> TYPE: DNA
<213> ORGANISM: Artificial Sequence
<220> FEATURE:
<223> OTHER INFORMATION: Synthetic

<400> SEQUENCE: 39
ggaattcact cgttattctc gga                                         23

<210> SEQ ID NO 40
<211> LENGTH: 17
<212> TYPE: DNA
<213> ORGANISM: Artificial Sequence
<220> FEATURE:
<223> OTHER INFORMATION: Synthetic

<400> SEQUENCE: 40
tccgagaata acgagtg                                                17

<210> SEQ ID NO 41
<211> LENGTH: 29
<212> TYPE: DNA
<213> ORGANISM: Artificial Sequence
<220> FEATURE:
<223> OTHER INFORMATION: Synthetic

<400> SEQUENCE: 41
cattgaaagc tttggggtag aagttgttc                                   29
```

```
<210> SEQ ID NO 42
<211> LENGTH: 27
<212> TYPE: DNA
<213> ORGANISM: Artificial Sequence
<220> FEATURE:
<223> OTHER INFORMATION: Synthetic

<400> SEQUENCE: 42
cgcggccgca gctgctcaga gtgtaga                                              27

<210> SEQ ID NO 43
<211> LENGTH: 28
<212> TYPE: DNA
<213> ORGANISM: Artificial Sequence
<220> FEATURE:
<223> OTHER INFORMATION: Synthetic

<400> SEQUENCE: 43
cggtaagctt cactggctca gggaaata                                             28

<210> SEQ ID NO 44
<211> LENGTH: 37
<212> TYPE: DNA
<213> ORGANISM: Artificial Sequence
<220> FEATURE:
<223> OTHER INFORMATION: Synthetic

<400> SEQUENCE: 44
aagaagcttg ccgccaccat ggattggctg tggaact                                   37

<210> SEQ ID NO 45
<211> LENGTH: 31
<212> TYPE: DNA
<213> ORGANISM: Artificial Sequence
<220> FEATURE:
<223> OTHER INFORMATION: Synthetic

<400> SEQUENCE: 45
cgggatcctc aaactttctt gtccaccttg g                                         31

<210> SEQ ID NO 46
<211> LENGTH: 36
<212> TYPE: DNA
<213> ORGANISM: Artificial Sequence
<220> FEATURE:
<223> OTHER INFORMATION: Synthetic

<400> SEQUENCE: 46
aagaaagctt gccgccacca tgttctcact agctct                                    36

<210> SEQ ID NO 47
<211> LENGTH: 26
<212> TYPE: DNA
<213> ORGANISM: Artificial Sequence
<220> FEATURE:
<223> OTHER INFORMATION: Synthetic

<400> SEQUENCE: 47
cgggatcctt ctccctctaa cactct                                               26

<210> SEQ ID NO 48
<211> LENGTH: 9
<212> TYPE: PRT
<213> ORGANISM: Artificial Sequence
<220> FEATURE:
<223> OTHER INFORMATION: Synthetic
```

<400> SEQUENCE: 48

Glu Pro Lys Ser Cys Asp Lys Thr His
1               5

<210> SEQ ID NO 49
<211> LENGTH: 4960
<212> TYPE: DNA
<213> ORGANISM: Homo sapiens

<400> SEQUENCE: 49

| | | | | | |
|---|---|---|---|---|---|
| ccggacgtgg | tggcgcatgc | ctgtaatccc | agctactcgg | gaggctgagg | caggagaatt | 60 |
| gctcgaaccc | cggaggcaga | ggtttggtgg | ctcacacctg | taatcccagc | actttgcgag | 120 |
| gctgaggcag | gtgcatcgct | ttggctcagg | agttcaagac | cagcctgggc | aacacaggga | 180 |
| gaccccatc | tctacaaaaa | acaaaaacaa | atataaaggg | gataaaaaaa | aaaaaaagac | 240 |
| aagacatgaa | tccatgagga | cagagtgtgg | aagaggaagc | agcagcctca | aagttctgga | 300 |
| agctggaaga | acagataaac | aggtgtgaaa | taactgcctg | gaaagcaact | tctttttttt | 360 |
| ttttttttt | tttgaggtgg | agtctcactc | tgtcgtccag | gctggagtgc | agtggtgcga | 420 |
| tctcggatca | ctgcaacctc | cgcctcccag | gctcaagcaa | ttctcctgcc | tcagcctccc | 480 |
| gagtagctgg | gattataagt | gcgcgctgcc | acacctggat | gattttttgta | ttttagtag | 540 |
| agatgggatt | tcaccatgtt | ggtcaggctg | gtctcaaact | cccaacctcg | tgatccaccc | 600 |
| accttggcct | cccaaagtgc | tgggattaca | ggtataagcc | accgagccca | gccaaaagcg | 660 |
| acttctaagc | ctgcaaggga | atcgggaatt | ggtggcacca | ggtccttctg | acagggttta | 720 |
| agaaattagc | cagcctgagg | ctgggcacgg | tggctcacac | ctgtaatccc | agcactttgg | 780 |
| gaggctaagg | caggtggatc | acctgagggc | aggagttcaa | gaccagcctg | accaacatgg | 840 |
| agaaacccca | tccctaccaa | aaataaaaaa | ttagccaggt | gtggtggtgc | tcgcctgtaa | 900 |
| tcccagctac | ttgggaggct | gaggtggag | gattgcttga | acacaggaag | tagaggctgc | 960 |
| agtgagctat | gattgcagca | ctgcactgaa | gccggggcaa | cagaacaaga | tccaaaaaaa | 1020 |
| agggaggggt | gaggggcaga | gccaggattt | gtttccaggc | tgttgttacc | taggtccgac | 1080 |
| tcctggctcc | cagagcagcc | tgtcctgcct | gcctggaact | ctgagcaggc | tggagtcatg | 1140 |
| gagtcgattc | ccagaatccc | agagtcaggg | aggctggggg | caggggcagg | tcactggaca | 1200 |
| aacagatcaa | aggtgagacc | agcgtagggc | tgcagaccag | gccaggccag | ctggacgggc | 1260 |
| acaccatgag | gtaggtgggc | gcccacagcc | tccctgcagg | gtgtggggtg | ggagcacagg | 1320 |
| cctgggccct | caccgcccct | gccctgccca | taggctgctg | accctcctgg | gccttctgtg | 1380 |
| tggctcggtg | gccacccct | tgggcccgaa | gtggcctgaa | cctgtgttcg | ggcgcctggc | 1440 |
| atccccggc | tttccagggg | agtatgccaa | tgaccaggag | cggcgctgga | ccctgactgc | 1500 |
| acccccggc | taccgcctgc | gcctctactt | cacccacttc | gacctggagc | tctcccacct | 1560 |
| ctgcgagtac | gacttcgtca | aggtgccgta | aggacgggag | ggctgggtt | tctcagggtc | 1620 |
| gggggtccc | caaggagtag | ccagggttca | gggacacctg | ggagcagggg | ccaggcttgg | 1680 |
| ccaggaggga | gatcaggcct | gggtcttgcc | ttcactccct | gtgacacctg | accccacagc | 1740 |
| tgagctcggg | ggccaaggtg | ctggccacgc | tgtgcgggca | ggagagcaca | gacacggagc | 1800 |
| gggcccctgg | caaggacact | ttctactcgc | tgggctccag | cctggacatt | accttccgct | 1860 |
| ccgactactc | caacgagaag | ccgttcacgg | ggttcgagcc | cttctatgca | gccgagggtg | 1920 |
| agccaagagg | ggtcctgcaa | catctcagtc | tgcgcagctg | gctgtggggg | taactctgtc | 1980 |

```
ttaggccagg cagccctgcc ttcagtttcc ccaccttcc cagggcaggg gagaggcctc    2040
tggcctgaca tcatccacaa tgcaaagacc aaaacagccg tgacctccat tcacatgggc    2100
tgagtgccaa ctctgagcca gggatctgag gacagcatcg cctcaagtga cgcagggact    2160
ggccgggcgc agcagctcac gcctgtaatt ccagcacttt gggaggccga ggctggctga    2220
tcatttgagg tcaggagttc aaggccagcc agggcaacac ggtgaaactc tatctccact    2280
aaaactacaa aaattagctg gcgtggtgg tgcgcacctg gaatcccagc tactagggag    2340
gctgaggcag gagaattgct tgaacctgcg aggtggaggc tgcagtgaac agagattgca    2400
ccactacact ccagcctggg cgacagagct agactccgtc tcaaaaaaca aaaaacaaaa    2460
acgacgcagg ggccgagggc cccatttaca gctgacaaag tggggccctg ccagcgggag    2520
cgctgccagg atgtttgatt tcagatccca gtccctgcag agaccaactg tgtgacctct    2580
ggcaagtggc tcaatttctc tgctccttag gaagctgctg caagggttca gcgctgtagc    2640
cccgccccct gggtttgatt gactcccctc attagctggg tgacctcggg ccggacactg    2700
aaactcccac tggtttaaca gaggtgatgt ttgcatcttt ctcccagcgc tgctgggagc    2760
ttgcagcgac cctaggcctg taaggtgatt ggcccggcac cagtcccgca ccctagacag    2820
gacgaggcct cctctgaggt ccactctgag gtcatggatc tcctggggag agtccaggct    2880
ggatcccgcc tctttccctc ctgacggcct gcctggccct gcctctcccc cagacattga    2940
cgagtgccag gtggccccgg gagaggcgcc cacctgcgac caccactgcc acaaccacct    3000
gggcggtttc tactgctcct gccgcgcagg ctacgtcctg caccgtaaca agcgcacctg    3060
ctcagccctg tgctccggcc aggtcttcac ccagaggtct ggggagctca gcagccctga    3120
atacccacgg ccgtatccca aactctccag ttgcacttac agcatcagcc tggaggaggg    3180
gttcagtgtc attctggact tgtggagtc cttcgatgtg gagacacacc ctgaaaccct    3240
gtgtccctac gactttctca agattcaaac agacagagaa gaacatggcc cattctgtgg    3300
gaagacattg ccccacagga ttgaaacaaa agcaacacg gtgaccatca cctttgtcac    3360
agatgaatca ggagaccaca caggctggaa gatccactac acgagcacag cgcacgcttg    3420
cccttatccg atggcgccac ctaatggcca cgtttcacct gtgcaagcca atacatcct    3480
gaaagacagc ttctccatct tttgcgagac tggctatgag cttctgcaag gtcacttgcc    3540
cctgaaatcc tttactgcag tttgtcagaa agatggatct tgggaccggc caatgcccgc    3600
gtgcagcatt gttgactgtg gccctcctga tgatctaccc agtggccgag tggagtacat    3660
cacaggtcct ggagtgacca cctacaaagc tgtgattcag tacagctgtg aagagacctt    3720
ctacacaatg aaagtgaatg atggtaaata tgtgtgtgag gctgatggat tctggacgag    3780
ctccaaagga gaaaatcac tcccagtctg tgagcctgtt tgtggactat cagcccgcac    3840
aacaggaggg cgtatatatg gagggcaaaa ggcaaaacct ggtgattttc cttggcaagt    3900
cctgatatta ggtggaacca cagcagcagg tgcactttta tatgacaact gggtcctaac    3960
agctgctcat gccgtctatg agcaaaaaca tgatgcatcc gccctggaca ttcgaatggg    4020
caccctgaaa agactatcac ctcattatac acaagcctgg tctgaagctg ttttatacat    4080
tgaaggttat actcatgatg ctggctttga caatgacata gcactgatta aattgaataa    4140
caaagttgta atcaatagca acatcacgcc tatttgtctg ccaagaaaag aagctgaatc    4200
ctttatgagg acagatgaca ttggaactgc atctggatgg ggattaaccc aaaggggttt    4260
tcttgctaga aatctaatgt atgtcgacat accgattgtt gaccatcaaa aatgtactgc    4320
tgcatatgaa aagccacct atccaagggg aagtgtaact gctaacatgc tttgtgctgg    4380
```

```
cttagaaagt gggggcaagg acagctgcag aggtgacagc ggaggggcac tggtgtttct    4440
agatagtgaa acagagaggt ggtttgtggg aggaatagtg tcctgggtt ccatgaattg     4500 tggggaagca ggtcagtatg gagtctacac aaaagttatt aactatattc cctggatcga    4560
gaacataatt agtgattttt aacttgcgtg tctgcagtca aggattcttc attttagaa     4620 atgcctgtga agaccttggc agcgacgtgg ctcgagaagc attcatcatt actgtggaca    4680
tggcagttgt tgctccaccc aaaaaaacag actccaggtg aggctgctgt catttctcca    4740
cttgccagtt taattccagc cttacccatt gactcaaggg gacataaacc acgagagtga    4800
cagtcatctt tgcccaccca gtgtaatgtc actgctcaaa ttacatttca ttaccttaaa    4860
aagccagtct cttttcatac tggctgttgg catttctgta aactgcctgt ccatgctctt    4920 tgttttaaa cttgttctta ttgaaaaaaa aaaaaaaaa                             4960

<210> SEQ ID NO 50
<211> LENGTH: 2090
<212> TYPE: DNA
<213> ORGANISM: Murine
<220> FEATURE:
<221> NAME/KEY: CDS
<222> LOCATION: (33)..(2090)

<400> SEQUENCE: 50
ggcgctggac tgcagagcta tggtggcaca cc atg agg cta ctc atc ttc ctg           53
                                    Met Arg Leu Leu Ile Phe Leu
                                     1               5 ggt ctg ctg tgg agt ttg gtg gcc aca ctt ctg ggt tca aag tgg cct          101
Gly Leu Leu Trp Ser Leu Val Ala Thr Leu Leu Gly Ser Lys Trp Pro
            10                  15                  20 gaa cct gta ttc ggg cgc ctg gtg tcc cct ggc ttc cca gag aag tat         149
Glu Pro Val Phe Gly Arg Leu Val Ser Pro Gly Phe Pro Glu Lys Tyr
        25                  30                  35 gct gac cat caa gat cga tcc tgg aca ctg act gca ccc cct ggc tac         197
Ala Asp His Gln Asp Arg Ser Trp Thr Leu Thr Ala Pro Pro Gly Tyr
 40                  45                  50                  55 cgc ctg cgc ctc tac ttc acc cac ttt gac ctg gaa ctc tct tac cgc         245
Arg Leu Arg Leu Tyr Phe Thr His Phe Asp Leu Glu Leu Ser Tyr Arg
                 60                  65                  70 tgc gag tat gac ttt gtc aag ttg agc tca ggg acc aag gtg ctg gcc         293
Cys Glu Tyr Asp Phe Val Lys Leu Ser Ser Gly Thr Lys Val Leu Ala
            75                  80                  85 aca ctg tgt ggg cag gag agt aca gac act gag cag gca cct ggc aat         341
Thr Leu Cys Gly Gln Glu Ser Thr Asp Thr Glu Gln Ala Pro Gly Asn
        90                  95                 100 gac acc ttc tac tca ctg ggt ccc agc cta aag gtc acc ttc cac tcc         389
Asp Thr Phe Tyr Ser Leu Gly Pro Ser Leu Lys Val Thr Phe His Ser
    105                 110                 115 gac tac tcc aat gag aag ccg ttc aca ggg ttt gag gcc ttc tat gca         437
Asp Tyr Ser Asn Glu Lys Pro Phe Thr Gly Phe Glu Ala Phe Tyr Ala
120                 125                 130                 135 gcg gag gat gtg gat gaa tgc aga gtg tct ctg gga gac tca gtc cct         485
Ala Glu Asp Val Asp Glu Cys Arg Val Ser Leu Gly Asp Ser Val Pro
                140                 145                 150 tgt gac cat tat tgc cac aac tac ttg ggc ggc tac tat tgc tcc tgc         533
Cys Asp His Tyr Cys His Asn Tyr Leu Gly Gly Tyr Tyr Cys Ser Cys
            155                 160                 165 aga gcg ggc tac att ctc cac cag aac aag cac acg tgc tca gcc ctt         581
Arg Ala Gly Tyr Ile Leu His Gln Asn Lys His Thr Cys Ser Ala Leu
        170                 175                 180
```

```
tgt tca ggc cag gtg ttc aca gga aga tct ggg tat ctc agt agc cct    629
Cys Ser Gly Gln Val Phe Thr Gly Arg Ser Gly Tyr Leu Ser Ser Pro
    185                 190                 195 gag tac ccg cag cca tac ccc aag ctc tcc agc tgc acc tac agc atc    677
Glu Tyr Pro Gln Pro Tyr Pro Lys Leu Ser Ser Cys Thr Tyr Ser Ile
200                 205                 210                 215 cgc ctg gag gac ggc ttc agt gtc atc ctg gac ttc gtg gag tcc ttc    725
Arg Leu Glu Asp Gly Phe Ser Val Ile Leu Asp Phe Val Glu Ser Phe
                220                 225                 230 gat gtg gag acg cac cct gaa gcc cag tgc ccc tat gac tcc ctc aag    773
Asp Val Glu Thr His Pro Glu Ala Gln Cys Pro Tyr Asp Ser Leu Lys
            235                 240                 245 att caa aca gac aag ggg gaa cac ggc cca ttt tgt ggg aag acg ctg    821
Ile Gln Thr Asp Lys Gly Glu His Gly Pro Phe Cys Gly Lys Thr Leu
        250                 255                 260 cct ccc agg att gaa act gac agc cac aag gtg acc atc acc ttt gcc    869
Pro Pro Arg Ile Glu Thr Asp Ser His Lys Val Thr Ile Thr Phe Ala
    265                 270                 275 act gac gag tcg ggg aac cac aca ggc tgg aag ata cac tac aca agc    917
Thr Asp Glu Ser Gly Asn His Thr Gly Trp Lys Ile His Tyr Thr Ser
280                 285                 290                 295 aca gca cgg ccc tgc cct gat cca acg gcg cca cct aat ggc agc att    965
Thr Ala Arg Pro Cys Pro Asp Pro Thr Ala Pro Pro Asn Gly Ser Ile
                300                 305                 310 tca cct gtg caa gcc acg tat gtc ctg aag gac agg ttt tct gtc ttc    1013
Ser Pro Val Gln Ala Thr Tyr Val Leu Lys Asp Arg Phe Ser Val Phe
            315                 320                 325 tgc aag aca ggc ttc gag ctt ctg caa ggt tct gtc ccc ctg aaa tca    1061
Cys Lys Thr Gly Phe Glu Leu Leu Gln Gly Ser Val Pro Leu Lys Ser
        330                 335                 340 ttc act gct gtc tgt cag aaa gat gga tct tgg gac cgg ccg atg cca    1109
Phe Thr Ala Val Cys Gln Lys Asp Gly Ser Trp Asp Arg Pro Met Pro
    345                 350                 355 gag tgc agc att att gat tgt ggc cct ccc gat gac cta ccc aat ggc    1157
Glu Cys Ser Ile Ile Asp Cys Gly Pro Pro Asp Asp Leu Pro Asn Gly
360                 365                 370                 375 cat gtg gac tat atc aca ggc cct caa gtg act acc tac aaa gct gtg    1205
His Val Asp Tyr Ile Thr Gly Pro Gln Val Thr Thr Tyr Lys Ala Val
                380                 385                 390 att cag tac agc tgt gaa gag act ttc tac aca atg agc agc aat ggt    1253
Ile Gln Tyr Ser Cys Glu Glu Thr Phe Tyr Thr Met Ser Ser Asn Gly
            395                 400                 405 aaa tat gtg tgt gag gct gat gga ttc tgg acg agc tcc aaa gga gaa    1301
Lys Tyr Val Cys Glu Ala Asp Gly Phe Trp Thr Ser Ser Lys Gly Glu
        410                 415                 420 aaa ctc ccc ccg gtt tgt gag cct gtt tgt ggg ctg tcc aca cac act    1349
Lys Leu Pro Pro Val Cys Glu Pro Val Cys Gly Leu Ser Thr His Thr
    425                 430                 435 ata gga gga cgc ata gtt gga ggg cag cct gca aag cct ggt gac ttt    1397
Ile Gly Gly Arg Ile Val Gly Gly Gln Pro Ala Lys Pro Gly Asp Phe
440                 445                 450                 455 cct tgg caa gtc ttg ttg ctg ggt caa act aca gca gca ggt gca    1445
Pro Trp Gln Val Leu Leu Leu Gly Gln Thr Thr Ala Ala Ala Gly Ala
                460                 465                 470 ctt ata cat gac aat tgg gtc cta aca gcc gct cat gct gta tat gag    1493
Leu Ile His Asp Asn Trp Val Leu Thr Ala Ala His Ala Val Tyr Glu
            475                 480                 485 aaa aga atg gca gcg tcc tcc ctg aac atc cga atg ggc atc ctc aaa    1541
Lys Arg Met Ala Ala Ser Ser Leu Asn Ile Arg Met Gly Ile Leu Lys
```

```
                490             495             500
agg ctc tca cct cat tac act caa gcc tgg ccc gag gaa atc ttt ata   1589
Arg Leu Ser Pro His Tyr Thr Gln Ala Trp Pro Glu Glu Ile Phe Ile
505             510             515 cat gaa ggc tac act cac ggt gct ggt ttt gac aat gat ata gca ttg   1637
His Glu Gly Tyr Thr His Gly Ala Gly Phe Asp Asn Asp Ile Ala Leu
520             525             530             535 att aaa ctc aag aac aaa gtc aca atc aac gga agc atc atg cct gtt   1685
Ile Lys Leu Lys Asn Lys Val Thr Ile Asn Gly Ser Ile Met Pro Val
        540             545             550 tgc cta ccg cga aaa gaa gct gca tcc tta atg aga aca gac ttc act   1733
Cys Leu Pro Arg Lys Glu Ala Ala Ser Leu Met Arg Thr Asp Phe Thr
    555             560             565 gga act gtg gct ggc tgg ggg tta acc cag aag ggg ctt ctt gct aga   1781
Gly Thr Val Ala Gly Trp Gly Leu Thr Gln Lys Gly Leu Leu Ala Arg
570             575             580 aac cta atg ttt gtg gac ata cca att gct gac cac caa aaa tgt acc   1829
Asn Leu Met Phe Val Asp Ile Pro Ile Ala Asp His Gln Lys Cys Thr
585             590             595 acc gtg tat gaa aag ctc tat cca gga gta aga gta agc gct aac atg   1877
Thr Val Tyr Glu Lys Leu Tyr Pro Gly Val Arg Val Ser Ala Asn Met
600             605             610             615 ctc tgt gct ggc tta gag act ggt ggc aag gac agc tgc aga ggt gac   1925
Leu Cys Ala Gly Leu Glu Thr Gly Gly Lys Asp Ser Cys Arg Gly Asp
        620             625             630 agt ggg ggg gca tta gtg ttt cta gat aat gag aca cag cga tgg ttt   1973
Ser Gly Gly Ala Leu Val Phe Leu Asp Asn Glu Thr Gln Arg Trp Phe
    635             640             645 gtg gga gga ata gtt tcc tgg ggt tcc att aat tgt ggg gcg gca ggc   2021
Val Gly Gly Ile Val Ser Trp Gly Ser Ile Asn Cys Gly Ala Ala Gly
650             655             660 cag tat ggg gtc tac aca aaa gtc atc aac tat att ccc tgg aat gag   2069
Gln Tyr Gly Val Tyr Thr Lys Val Ile Asn Tyr Ile Pro Trp Asn Glu
665             670             675 aac ata ata agt aat ttc taa                                        2090
Asn Ile Ile Ser Asn Phe
680             685
```

<210> SEQ ID NO 51
<211> LENGTH: 685
<212> TYPE: PRT
<213> ORGANISM: Murine

<400> SEQUENCE: 51

```
Met Arg Leu Leu Ile Phe Leu Gly Leu Leu Trp Ser Leu Val Ala Thr
1               5                   10                  15

Leu Leu Gly Ser Lys Trp Pro Glu Pro Val Phe Gly Arg Leu Val Ser
                20                  25                  30

Pro Gly Phe Pro Glu Lys Tyr Ala Asp His Gln Asp Arg Ser Trp Thr
            35                  40                  45

Leu Thr Ala Pro Pro Gly Tyr Arg Leu Arg Leu Tyr Phe Thr His Phe
        50                  55                  60

Asp Leu Glu Leu Ser Tyr Arg Cys Glu Tyr Asp Phe Val Lys Leu Ser
65                  70                  75                  80

Ser Gly Thr Lys Val Leu Ala Thr Leu Cys Gly Gln Glu Ser Thr Asp
                85                  90                  95

Thr Glu Gln Ala Pro Gly Asn Asp Thr Phe Tyr Ser Leu Gly Pro Ser
            100                 105                 110
```

```
Leu Lys Val Thr Phe His Ser Asp Tyr Ser Asn Glu Lys Pro Phe Thr
        115                 120                 125

Gly Phe Glu Ala Phe Tyr Ala Ala Glu Asp Val Asp Glu Cys Arg Val
130                 135                 140

Ser Leu Gly Asp Ser Val Pro Cys Asp His Tyr Cys His Asn Tyr Leu
145                 150                 155                 160

Gly Gly Tyr Tyr Cys Ser Cys Arg Ala Gly Tyr Ile Leu His Gln Asn
                165                 170                 175

Lys His Thr Cys Ser Ala Leu Cys Ser Gly Gln Val Phe Thr Gly Arg
            180                 185                 190

Ser Gly Tyr Leu Ser Ser Pro Glu Tyr Pro Gln Pro Tyr Pro Lys Leu
        195                 200                 205

Ser Ser Cys Thr Tyr Ser Ile Arg Leu Glu Asp Gly Phe Ser Val Ile
210                 215                 220

Leu Asp Phe Val Glu Ser Phe Asp Val Glu Thr His Pro Glu Ala Gln
225                 230                 235                 240

Cys Pro Tyr Asp Ser Leu Lys Ile Gln Thr Asp Lys Gly Glu His Gly
                245                 250                 255

Pro Phe Cys Gly Lys Thr Leu Pro Pro Arg Ile Glu Thr Asp Ser His
        260                 265                 270

Lys Val Thr Ile Thr Phe Ala Thr Asp Glu Ser Gly Asn His Thr Gly
            275                 280                 285

Trp Lys Ile His Tyr Thr Ser Thr Ala Arg Pro Cys Pro Asp Pro Thr
        290                 295                 300

Ala Pro Pro Asn Gly Ser Ile Ser Pro Val Gln Ala Thr Tyr Val Leu
305                 310                 315                 320

Lys Asp Arg Phe Ser Val Phe Cys Lys Thr Gly Phe Glu Leu Leu Gln
                325                 330                 335

Gly Ser Val Pro Leu Lys Ser Phe Thr Ala Val Cys Gln Lys Asp Gly
        340                 345                 350

Ser Trp Asp Arg Pro Met Pro Glu Cys Ser Ile Ile Cys Gly Pro
            355                 360                 365

Pro Asp Asp Leu Pro Asn Gly His Val Asp Tyr Ile Thr Gly Pro Gln
370                 375                 380

Val Thr Thr Tyr Lys Ala Val Ile Gln Tyr Ser Cys Glu Glu Thr Phe
385                 390                 395                 400

Tyr Thr Met Ser Ser Asn Gly Lys Tyr Val Cys Glu Ala Asp Gly Phe
                405                 410                 415

Trp Thr Ser Ser Lys Gly Glu Lys Leu Pro Pro Val Cys Glu Pro Val
        420                 425                 430

Cys Gly Leu Ser Thr His Thr Ile Gly Gly Arg Ile Val Gly Gly Gln
            435                 440                 445

Pro Ala Lys Pro Gly Asp Phe Pro Trp Gln Val Leu Leu Leu Gly Gln
450                 455                 460

Thr Thr Ala Ala Ala Gly Ala Leu Ile His Asp Asn Trp Val Leu Thr
465                 470                 475                 480

Ala Ala His Ala Val Tyr Glu Lys Arg Met Ala Ala Ser Ser Leu Asn
                485                 490                 495

Ile Arg Met Gly Ile Leu Lys Arg Leu Ser Pro His Tyr Thr Gln Ala
            500                 505                 510

Trp Pro Glu Glu Ile Phe Ile His Gly Tyr Thr His Gly Ala Gly
        515                 520                 525

Phe Asp Asn Asp Ile Ala Leu Ile Lys Leu Lys Asn Lys Val Thr Ile
```

```
                530            535             540
Asn Gly Ser Ile Met Pro Val Cys Leu Pro Arg Lys Glu Ala Ala Ser
545                 550             555                 560

Leu Met Arg Thr Asp Phe Thr Gly Thr Val Ala Gly Trp Gly Leu Thr
                565             570             575

Gln Lys Gly Leu Leu Ala Arg Asn Leu Met Phe Val Asp Ile Pro Ile
            580             585                 590

Ala Asp His Gln Lys Cys Thr Thr Val Tyr Glu Lys Leu Tyr Pro Gly
        595             600             605

Val Arg Val Ser Ala Asn Met Leu Cys Ala Gly Leu Glu Thr Gly Gly
        610             615             620

Lys Asp Ser Cys Arg Gly Asp Ser Gly Gly Ala Leu Val Phe Leu Asp
625             630             635                 640

Asn Glu Thr Gln Arg Trp Phe Val Gly Ile Val Ser Trp Gly Ser
                645             650             655

Ile Asn Cys Gly Ala Ala Gly Gln Tyr Gly Val Tyr Thr Lys Val Ile
            660             665             670

Asn Tyr Ile Pro Trp Asn Glu Asn Ile Ile Ser Asn Phe
        675             680             685

<210> SEQ ID NO 52
<211> LENGTH: 670
<212> TYPE: PRT
<213> ORGANISM: Murine

<400> SEQUENCE: 52

Thr Leu Leu Gly Ser Lys Trp Pro Glu Pro Val Phe Gly Arg Leu Val
1               5                   10                  15

Ser Pro Gly Phe Pro Glu Lys Tyr Ala Asp His Gln Asp Arg Ser Trp
            20                  25                  30

Thr Leu Thr Ala Pro Pro Gly Tyr Arg Leu Arg Leu Tyr Phe Thr His
            35                  40                  45

Phe Asp Leu Glu Leu Ser Tyr Arg Cys Glu Tyr Asp Phe Val Lys Leu
    50                  55                  60

Ser Ser Gly Thr Lys Val Leu Ala Thr Leu Cys Gly Gln Glu Ser Thr
65                  70                  75                  80

Asp Thr Glu Gln Ala Pro Gly Asn Asp Thr Phe Tyr Ser Leu Gly Pro
                85                  90                  95

Ser Leu Lys Val Thr Phe His Ser Asp Tyr Ser Asn Glu Lys Pro Phe
            100                 105                 110

Thr Gly Phe Glu Ala Phe Tyr Ala Ala Glu Asp Val Asp Glu Cys Arg
            115                 120                 125

Val Ser Leu Gly Asp Ser Val Pro Cys Asp His Tyr Cys His Asn Tyr
        130                 135                 140

Leu Gly Gly Tyr Tyr Cys Ser Cys Arg Ala Gly Tyr Ile Leu His Gln
145                 150                 155                 160

Asn Lys His Thr Cys Ser Ala Leu Cys Ser Gly Gln Val Phe Thr Gly
                165                 170                 175

Arg Ser Gly Tyr Leu Ser Ser Pro Glu Tyr Pro Gln Pro Tyr Pro Lys
            180                 185                 190

Leu Ser Ser Cys Thr Tyr Ser Ile Arg Leu Glu Asp Gly Phe Ser Val
        195                 200                 205

Ile Leu Asp Phe Val Glu Ser Phe Asp Val Glu Thr His Pro Glu Ala
    210                 215                 220
```

```
Gln Cys Pro Tyr Asp Ser Leu Lys Ile Gln Thr Asp Lys Gly Glu His
225                 230                 235                 240

Gly Pro Phe Cys Gly Lys Thr Leu Pro Pro Arg Ile Glu Thr Asp Ser
                245                 250                 255

His Lys Val Thr Ile Thr Phe Ala Thr Asp Glu Ser Gly Asn His Thr
            260                 265                 270

Gly Trp Lys Ile His Tyr Thr Ser Thr Ala Arg Pro Cys Pro Asp Pro
        275                 280                 285

Thr Ala Pro Pro Asn Gly Ser Ile Ser Pro Val Gln Ala Thr Tyr Val
    290                 295                 300

Leu Lys Asp Arg Phe Ser Val Phe Cys Lys Thr Gly Phe Glu Leu Leu
305                 310                 315                 320

Gln Gly Ser Val Pro Leu Lys Ser Phe Thr Ala Val Cys Gln Lys Asp
                325                 330                 335

Gly Ser Trp Asp Arg Pro Met Pro Glu Cys Ser Ile Ile Asp Cys Gly
                340                 345                 350

Pro Pro Asp Asp Leu Pro Asn Gly His Val Asp Tyr Ile Thr Gly Pro
                355                 360                 365

Gln Val Thr Thr Tyr Lys Ala Val Ile Gln Tyr Ser Cys Glu Glu Thr
370                 375                 380

Phe Tyr Thr Met Ser Ser Asn Gly Lys Tyr Val Cys Glu Ala Asp Gly
385                 390                 395                 400

Phe Trp Thr Ser Ser Lys Gly Glu Lys Leu Pro Pro Val Cys Glu Pro
                405                 410                 415

Val Cys Gly Leu Ser Thr His Thr Ile Gly Gly Arg Ile Val Gly Gly
                420                 425                 430

Gln Pro Ala Lys Pro Gly Asp Phe Pro Trp Gln Val Leu Leu Leu Gly
                435                 440                 445

Gln Thr Thr Ala Ala Ala Gly Ala Leu Ile His Asp Asn Trp Val Leu
    450                 455                 460

Thr Ala Ala His Ala Val Tyr Glu Lys Arg Met Ala Ala Ser Ser Leu
465                 470                 475                 480

Asn Ile Arg Met Gly Ile Leu Lys Arg Leu Ser Pro His Tyr Thr Gln
                485                 490                 495

Ala Trp Pro Glu Glu Ile Phe Ile His Glu Gly Tyr Thr His Gly Ala
                500                 505                 510

Gly Phe Asp Asn Asp Ile Ala Leu Ile Lys Leu Lys Asn Lys Val Thr
            515                 520                 525

Ile Asn Gly Ser Ile Met Pro Val Cys Leu Pro Arg Lys Glu Ala Ala
    530                 535                 540

Ser Leu Met Arg Thr Asp Phe Thr Gly Thr Val Ala Gly Trp Gly Leu
545                 550                 555                 560

Thr Gln Lys Gly Leu Leu Ala Arg Asn Leu Met Phe Val Asp Ile Pro
                565                 570                 575

Ile Ala Asp His Gln Lys Cys Thr Thr Val Tyr Glu Lys Leu Tyr Pro
            580                 585                 590

Gly Val Arg Val Ser Ala Asn Met Leu Cys Ala Gly Leu Glu Thr Gly
                595                 600                 605

Gly Lys Asp Ser Cys Arg Gly Asp Ser Gly Gly Ala Leu Val Phe Leu
            610                 615                 620

Asp Asn Glu Thr Gln Arg Trp Phe Val Gly Gly Ile Val Ser Trp Gly
625                 630                 635                 640

Ser Ile Asn Cys Gly Ala Ala Gly Gln Tyr Gly Val Tyr Thr Lys Val
```

```
                           645                 650                 655
Ile Asn Tyr Ile Pro Trp Asn Glu Asn Ile Ile Ser Asn Phe
                660                 665                 670

<210> SEQ ID NO 53
<211> LENGTH: 2091
<212> TYPE: DNA
<213> ORGANISM: Rattus
<220> FEATURE:
<221> NAME/KEY: CDS
<222> LOCATION: (10)..(2067)

<400> SEQUENCE: 53 tggcacaca atg agg cta ctg atc gtc ctg ggt ctg ctt tgg agt ttg gtg         51
          Met Arg Leu Leu Ile Val Leu Gly Leu Leu Trp Ser Leu Val
            1               5                  10 gcc aca ctt ttg ggc tcc aag tgg cct gag cct gta ttc ggg cgc ctg           99
Ala Thr Leu Leu Gly Ser Lys Trp Pro Glu Pro Val Phe Gly Arg Leu
 15                  20                  25                  30 gtg tcc ctg gcc ttc cca gag aag tat ggc aac cat cag gat cga tcc          147
Val Ser Leu Ala Phe Pro Glu Lys Tyr Gly Asn His Gln Asp Arg Ser
                 35                  40                  45 tgg acg ctg act gca ccc cct ggc ttc cgc ctg cgc ctc tac ttc acc          195
Trp Thr Leu Thr Ala Pro Pro Gly Phe Arg Leu Arg Leu Tyr Phe Thr
             50                  55                  60 cac ttc aac ctg gaa ctc tct tac cgc tgc gag tat gac ttt gtc aag          243
His Phe Asn Leu Glu Leu Ser Tyr Arg Cys Glu Tyr Asp Phe Val Lys
         65                  70                  75 ttg acc tca ggg acc aag gtg cta gcc acg ctg tgt ggg cag gag agt          291
Leu Thr Ser Gly Thr Lys Val Leu Ala Thr Leu Cys Gly Gln Glu Ser
 80                  85                  90 aca gat act gag cgg gca cct ggc aat gac acc ttc tac tca ctg ggt          339
Thr Asp Thr Glu Arg Ala Pro Gly Asn Asp Thr Phe Tyr Ser Leu Gly
 95                 100                 105                 110 ccc agc cta aag gtc acc ttc cac tcc gac tac tcc aat gag aag cca          387
Pro Ser Leu Lys Val Thr Phe His Ser Asp Tyr Ser Asn Glu Lys Pro
                115                 120                 125 ttc aca gga ttt gag gcc ttc tat gca gcg gag gat gtg gat gaa tgc          435
Phe Thr Gly Phe Glu Ala Phe Tyr Ala Ala Glu Asp Val Asp Glu Cys
            130                 135                 140 aga aca tcc ctg gga gac tca gtc cct tgt gac cat tat tgc cac aac          483
Arg Thr Ser Leu Gly Asp Ser Val Pro Cys Asp His Tyr Cys His Asn
        145                 150                 155 tac ctg ggc ggc tac tac tgc tcc tgc cga gtg ggc tac att ctg cac          531
Tyr Leu Gly Gly Tyr Tyr Cys Ser Cys Arg Val Gly Tyr Ile Leu His
160                 165                 170 cag aac aag cat acc tgc tca gcc ctt tgt tca ggc cag gtg ttc act          579
Gln Asn Lys His Thr Cys Ser Ala Leu Cys Ser Gly Gln Val Phe Thr
175                 180                 185                 190 ggg agg tct ggc ttt ctc agt agc cct gag tac cca cag cca tac ccc          627
Gly Arg Ser Gly Phe Leu Ser Ser Pro Glu Tyr Pro Gln Pro Tyr Pro
                195                 200                 205 aaa ctc tcc agc tgt gcc tac aac atc cgc ctg gag gaa ggc ttc agt          675
Lys Leu Ser Ser Cys Ala Tyr Asn Ile Arg Leu Glu Glu Gly Phe Ser
            210                 215                 220 atc acc ctg gac ttc gtg gag tcc ttt gat gtg gag atg cac cct gaa          723
Ile Thr Leu Asp Phe Val Glu Ser Phe Asp Val Glu Met His Pro Glu
        225                 230                 235 gcc cag tgc ccc tac gac tcc ctc aag att caa aca gac aag agg gaa          771
Ala Gln Cys Pro Tyr Asp Ser Leu Lys Ile Gln Thr Asp Lys Arg Glu
240                 245                 250
```

-continued

| | |
|---|---|
| tac ggc ccg ttt tgt ggg aag acg ctg ccc ccc agg att gaa act gac<br>Tyr Gly Pro Phe Cys Gly Lys Thr Leu Pro Pro Arg Ile Glu Thr Asp<br>255                260                265              270 | 819 |
| agc aac aag gtg acc att acc ttt acc acc gac gag tca ggg aac cac<br>Ser Asn Lys Val Thr Ile Thr Phe Thr Thr Asp Glu Ser Gly Asn His<br>                275                280              285 | 867 |
| aca ggc tgg aag ata cac tac aca agc aca gca cag ccc tgc cct gat<br>Thr Gly Trp Lys Ile His Tyr Thr Ser Thr Ala Gln Pro Cys Pro Asp<br>        290                295              300 | 915 |
| cca acg gcg cca cct aat ggt cac att tca cct gtg caa gcc acg tat<br>Pro Thr Ala Pro Pro Asn Gly His Ile Ser Pro Val Gln Ala Thr Tyr<br>305                310                315 | 963 |
| gtc ctg aag gac agc ttt tct gtc ttc tgc aag act ggc ttc gag ctt<br>Val Leu Lys Asp Ser Phe Ser Val Phe Cys Lys Thr Gly Phe Glu Leu<br>        320                325              330 | 1011 |
| ctg caa ggt tct gtc ccc ctg aag tca ttc act gct gtc tgt cag aaa<br>Leu Gln Gly Ser Val Pro Leu Lys Ser Phe Thr Ala Val Cys Gln Lys<br>335                340                345              350 | 1059 |
| gat gga tct tgg gac cgg ccg ata cca gag tgc agc att att gac tgt<br>Asp Gly Ser Trp Asp Arg Pro Ile Pro Glu Cys Ser Ile Ile Asp Cys<br>                355                360              365 | 1107 |
| ggc cct ccc gat gac cta ccc aat ggc cac gtg gac tat atc aca ggc<br>Gly Pro Pro Asp Asp Leu Pro Asn Gly His Val Asp Tyr Ile Thr Gly<br>        370                375              380 | 1155 |
| cct gaa gtg acc acc tac aaa gct gtg att cag tac agc tgt gaa gag<br>Pro Glu Val Thr Thr Tyr Lys Ala Val Ile Gln Tyr Ser Cys Glu Glu<br>385                390                395 | 1203 |
| act ttc tac aca atg agc agc aat ggt aaa tat gtg tgt gag gct gat<br>Thr Phe Tyr Thr Met Ser Ser Asn Gly Lys Tyr Val Cys Glu Ala Asp<br>        400                405              410 | 1251 |
| gga ttc tgg acg agc tcc aaa gga gaa aaa tcc ctc ccg gtt tgc aag<br>Gly Phe Trp Thr Ser Ser Lys Gly Glu Lys Ser Leu Pro Val Cys Lys<br>415                420                425              430 | 1299 |
| cct gtc tgt gga ctg tcc aca cac act tca gga ggc cgt ata att gga<br>Pro Val Cys Gly Leu Ser Thr His Thr Ser Gly Gly Arg Ile Ile Gly<br>                435                440              445 | 1347 |
| gga cag cct gca aag cct ggt gac ttt cct tgg caa gtc ttg tta ctg<br>Gly Gln Pro Ala Lys Pro Gly Asp Phe Pro Trp Gln Val Leu Leu Leu<br>        450                455              460 | 1395 |
| ggt gaa act aca gca gca ggt gct ctt ata cat gac gac tgg gtc cta<br>Gly Glu Thr Thr Ala Ala Gly Ala Leu Ile His Asp Asp Trp Val Leu<br>465                470                475 | 1443 |
| aca gcg gct cat gct gta tat ggg aaa aca gag gcg atg tcc tcc ctg<br>Thr Ala Ala His Ala Val Tyr Gly Lys Thr Glu Ala Met Ser Ser Leu<br>        480                485              490 | 1491 |
| gac atc cgc atg ggc atc ctc aaa agg ctc tcc ctc att tac act caa<br>Asp Ile Arg Met Gly Ile Leu Lys Arg Leu Ser Leu Ile Tyr Thr Gln<br>495                500                505              510 | 1539 |
| gcc tgg cca gag gct gtc ttt atc cat gaa ggc tac act cac gga gct<br>Ala Trp Pro Glu Ala Val Phe Ile His Glu Gly Tyr Thr His Gly Ala<br>                515                520              525 | 1587 |
| ggt ttt gac aat gat ata gca ctg att aaa ctc aag aac aaa gtc aca<br>Gly Phe Asp Asn Asp Ile Ala Leu Ile Lys Leu Lys Asn Lys Val Thr<br>        530                535              540 | 1635 |
| atc aac aga aac atc atg ccg att tgt cta cca aga aaa gaa gct gca<br>Ile Asn Arg Asn Ile Met Pro Ile Cys Leu Pro Arg Lys Glu Ala Ala<br>545                550                555 | 1683 |
| tcc tta atg aaa aca gac ttc gtt gga act gtg gct ggc tgg ggg tta<br>Ser Leu Met Lys Thr Asp Phe Val Gly Thr Val Ala Gly Trp Gly Leu | 1731 |

```
                560                 565                 570
acc cag aag ggg ttt ctt gct aga aac cta atg ttt gtg gac ata cca    1779
Thr Gln Lys Gly Phe Leu Ala Arg Asn Leu Met Phe Val Asp Ile Pro
575                 580                 585                 590 att gtt gac cac caa aaa tgt gct act gcg tat aca aag cag ccc tac    1827
Ile Val Asp His Gln Lys Cys Ala Thr Ala Tyr Thr Lys Gln Pro Tyr
                595                 600                 605 cca gga gca aaa gtg act gtt aac atg ctc tgt gct ggc cta gac cgc    1875
Pro Gly Ala Lys Val Thr Val Asn Met Leu Cys Ala Gly Leu Asp Arg
            610                 615                 620 ggt ggc aag gac agc tgc aga ggt gac agc gga ggg gca tta gtg ttt    1923
Gly Gly Lys Asp Ser Cys Arg Gly Asp Ser Gly Gly Ala Leu Val Phe
        625                 630                 635 cta gac aat gaa aca cag aga tgg ttt gtg gga gga ata gtt tcc tgg    1971
Leu Asp Asn Glu Thr Gln Arg Trp Phe Val Gly Gly Ile Val Ser Trp
640                 645                 650 ggt tct att aac tgt ggg ggg tca gaa cag tat ggg gtc tac acg aaa    2019
Gly Ser Ile Asn Cys Gly Gly Ser Glu Gln Tyr Gly Val Tyr Thr Lys
655                 660                 665                 670 gtc acg aac tat att ccc tgg att gag aac ata ata aat aat ttc taa    2067
Val Thr Asn Tyr Ile Pro Trp Ile Glu Asn Ile Ile Asn Asn Phe
                675                 680                 685 tttgcaaaaa aaaaaaaaaa aaaa                                         2091

<210> SEQ ID NO 54
<211> LENGTH: 685
<212> TYPE: PRT
<213> ORGANISM: Rattus

<400> SEQUENCE: 54

Met Arg Leu Leu Ile Val Leu Gly Leu Leu Trp Ser Leu Val Ala Thr
1               5                   10                  15

Leu Leu Gly Ser Lys Trp Pro Glu Pro Val Phe Gly Arg Leu Val Ser
            20                  25                  30

Leu Ala Phe Pro Glu Lys Tyr Gly Asn His Gln Asp Arg Ser Trp Thr
        35                  40                  45

Leu Thr Ala Pro Pro Gly Phe Arg Leu Arg Leu Tyr Phe Thr His Phe
    50                  55                  60

Asn Leu Glu Leu Ser Tyr Arg Cys Glu Tyr Asp Phe Val Lys Leu Thr
65                  70                  75                  80

Ser Gly Thr Lys Val Leu Ala Thr Leu Cys Gly Gln Glu Ser Thr Asp
                85                  90                  95

Thr Glu Arg Ala Pro Gly Asn Asp Thr Phe Tyr Ser Leu Gly Pro Ser
            100                 105                 110

Leu Lys Val Thr Phe His Ser Asp Tyr Ser Asn Glu Lys Pro Phe Thr
        115                 120                 125

Gly Phe Glu Ala Phe Tyr Ala Ala Glu Asp Val Asp Glu Cys Arg Thr
    130                 135                 140

Ser Leu Gly Asp Ser Val Pro Cys Asp His Tyr Cys His Asn Tyr Leu
145                 150                 155                 160

Gly Gly Tyr Tyr Cys Ser Cys Arg Val Gly Tyr Ile Leu His Gln Asn
                165                 170                 175

Lys His Thr Cys Ser Ala Leu Cys Ser Gly Gln Val Phe Thr Gly Arg
            180                 185                 190

Ser Gly Phe Leu Ser Ser Pro Glu Tyr Pro Gln Pro Tyr Pro Lys Leu
        195                 200                 205
```

```
Ser Ser Cys Ala Tyr Asn Ile Arg Leu Glu Glu Gly Phe Ser Ile Thr
210             215                 220

Leu Asp Phe Val Glu Ser Phe Asp Val Glu Met His Pro Glu Ala Gln
225                 230                 235                 240

Cys Pro Tyr Asp Ser Leu Lys Ile Gln Thr Asp Lys Arg Glu Tyr Gly
                245                 250                 255

Pro Phe Cys Gly Lys Thr Leu Pro Pro Arg Ile Glu Thr Asp Ser Asn
            260                 265                 270

Lys Val Thr Ile Thr Phe Thr Asp Glu Ser Gly Asn His Thr Gly
            275                 280                 285

Trp Lys Ile His Tyr Thr Ser Thr Ala Gln Pro Cys Pro Asp Pro Thr
290                 295                 300

Ala Pro Pro Asn Gly His Ile Ser Pro Val Gln Ala Thr Tyr Val Leu
305                 310                 315                 320

Lys Asp Ser Phe Ser Val Phe Cys Lys Thr Gly Phe Glu Leu Leu Gln
                325                 330                 335

Gly Ser Val Pro Leu Lys Ser Phe Thr Ala Val Cys Gln Lys Asp Gly
            340                 345                 350

Ser Trp Asp Arg Pro Ile Pro Glu Cys Ser Ile Ile Asp Cys Gly Pro
        355                 360                 365

Pro Asp Asp Leu Pro Asn Gly His Val Asp Tyr Ile Thr Gly Pro Glu
        370                 375                 380

Val Thr Thr Tyr Lys Ala Val Ile Gln Tyr Ser Cys Glu Glu Thr Phe
385                 390                 395                 400

Tyr Thr Met Ser Ser Asn Gly Lys Tyr Val Cys Glu Ala Asp Gly Phe
                405                 410                 415

Trp Thr Ser Ser Lys Gly Glu Lys Ser Leu Pro Val Cys Lys Pro Val
            420                 425                 430

Cys Gly Leu Ser Thr His Thr Ser Gly Arg Ile Ile Gly Gly Gln
        435                 440                 445

Pro Ala Lys Pro Gly Asp Phe Pro Trp Gln Val Leu Leu Leu Gly Glu
    450                 455                 460

Thr Thr Ala Ala Gly Ala Leu Ile His Asp Asp Trp Val Leu Thr Ala
465                 470                 475                 480

Ala His Ala Val Tyr Gly Lys Thr Glu Ala Met Ser Ser Leu Asp Ile
                485                 490                 495

Arg Met Gly Ile Leu Lys Arg Leu Ser Leu Ile Tyr Thr Gln Ala Trp
            500                 505                 510

Pro Glu Ala Val Phe Ile His Glu Gly Tyr Thr His Gly Ala Gly Phe
    515                 520                 525

Asp Asn Asp Ile Ala Leu Ile Lys Leu Lys Asn Lys Val Thr Ile Asn
530                 535                 540

Arg Asn Ile Met Pro Ile Cys Leu Pro Arg Lys Glu Ala Ala Ser Leu
545                 550                 555                 560

Met Lys Thr Asp Phe Val Gly Thr Val Ala Gly Trp Gly Leu Thr Gln
                565                 570                 575

Lys Gly Phe Leu Ala Arg Asn Leu Met Phe Val Asp Ile Pro Ile Val
            580                 585                 590

Asp His Gln Lys Cys Ala Thr Ala Tyr Thr Lys Gln Pro Tyr Pro Gly
        595                 600                 605

Ala Lys Val Thr Val Asn Met Leu Cys Ala Gly Leu Asp Arg Gly Gly
        610                 615                 620

Lys Asp Ser Cys Arg Gly Asp Ser Gly Gly Ala Leu Val Phe Leu Asp
```

```
                625                 630                 635                 640
Asn Glu Thr Gln Arg Trp Phe Val Gly Gly Ile Val Ser Trp Gly Ser
                    645                 650                 655
Ile Asn Cys Gly Gly Ser Glu Gln Tyr Gly Val Tyr Thr Lys Val Thr
                    660                 665                 670
Asn Tyr Ile Pro Trp Ile Glu Asn Ile Ile Asn Asn Phe
                    675                 680                 685

<210> SEQ ID NO 55
<211> LENGTH: 670
<212> TYPE: PRT
<213> ORGANISM: Rattus

<400> SEQUENCE: 55

Thr Leu Leu Gly Ser Lys Trp Pro Glu Pro Val Phe Gly Arg Leu Val
1               5                   10                  15
Ser Leu Ala Phe Pro Glu Lys Tyr Gly Asn His Gln Asp Arg Ser Trp
                20                  25                  30
Thr Leu Thr Ala Pro Pro Gly Phe Arg Leu Arg Leu Tyr Phe Thr His
                35                  40                  45
Phe Asn Leu Glu Leu Ser Tyr Arg Cys Glu Tyr Asp Phe Val Lys Leu
    50                  55                  60
Thr Ser Gly Thr Lys Val Leu Ala Thr Leu Cys Gly Gln Glu Ser Thr
65                  70                  75                  80
Asp Thr Glu Arg Ala Pro Gly Asn Asp Thr Phe Tyr Ser Leu Gly Pro
                85                  90                  95
Ser Leu Lys Val Thr Phe His Ser Asp Tyr Ser Asn Glu Lys Pro Phe
                100                 105                 110
Thr Gly Phe Glu Ala Phe Tyr Ala Ala Glu Asp Val Asp Glu Cys Arg
                115                 120                 125
Thr Ser Leu Gly Asp Ser Val Pro Cys Asp His Tyr Cys His Asn Tyr
                130                 135                 140
Leu Gly Gly Tyr Tyr Cys Ser Cys Arg Val Gly Tyr Ile Leu His Gln
145                 150                 155                 160
Asn Lys His Thr Cys Ser Ala Leu Cys Ser Gly Gln Val Phe Thr Gly
                165                 170                 175
Arg Ser Gly Phe Leu Ser Ser Pro Glu Tyr Pro Gln Pro Tyr Pro Lys
                180                 185                 190
Leu Ser Ser Cys Ala Tyr Asn Ile Arg Leu Glu Glu Gly Phe Ser Ile
                195                 200                 205
Thr Leu Asp Phe Val Glu Ser Phe Asp Val Glu Met His Pro Glu Ala
                210                 215                 220
Gln Cys Pro Tyr Asp Ser Leu Lys Ile Gln Thr Asp Lys Arg Glu Tyr
225                 230                 235                 240
Gly Pro Phe Cys Gly Lys Thr Leu Pro Pro Arg Ile Glu Thr Asp Ser
                245                 250                 255
Asn Lys Val Thr Ile Thr Phe Thr Thr Asp Glu Ser Gly Asn His Thr
                260                 265                 270
Gly Trp Lys Ile His Tyr Thr Ser Thr Ala Gln Pro Cys Pro Asp Pro
                275                 280                 285
Thr Ala Pro Pro Asn Gly His Ile Ser Pro Val Gln Ala Thr Tyr Val
                290                 295                 300
Leu Lys Asp Ser Phe Ser Val Phe Cys Lys Thr Gly Phe Glu Leu Leu
305                 310                 315                 320
```

```
Gln Gly Ser Val Pro Leu Lys Ser Phe Thr Ala Val Cys Gln Lys Asp
                325                 330                 335
Gly Ser Trp Asp Arg Pro Ile Pro Glu Cys Ser Ile Ile Asp Cys Gly
            340                 345                 350
Pro Pro Asp Asp Leu Pro Asn Gly His Val Asp Tyr Ile Thr Gly Pro
            355                 360                 365
Glu Val Thr Thr Tyr Lys Ala Val Ile Gln Tyr Ser Cys Glu Glu Thr
        370                 375                 380
Phe Tyr Thr Met Ser Ser Asn Gly Lys Tyr Val Cys Glu Ala Asp Gly
385                 390                 395                 400
Phe Trp Thr Ser Ser Lys Gly Glu Lys Ser Leu Pro Val Cys Lys Pro
                405                 410                 415
Val Cys Gly Leu Ser Thr His Thr Ser Gly Arg Ile Ile Gly Gly
                420                 425                 430
Gln Pro Ala Lys Pro Gly Asp Phe Pro Trp Gln Val Leu Leu Leu Gly
                435                 440                 445
Glu Thr Thr Ala Ala Gly Ala Leu Ile His Asp Trp Val Leu Thr
        450                 455                 460
Ala Ala His Ala Val Tyr Gly Lys Thr Glu Ala Met Ser Ser Leu Asp
465                 470                 475                 480
Ile Arg Met Gly Ile Leu Lys Arg Leu Ser Leu Ile Tyr Thr Gln Ala
                485                 490                 495
Trp Pro Glu Ala Val Phe Ile His Glu Gly Tyr Thr His Gly Ala Gly
                500                 505                 510
Phe Asp Asn Asp Ile Ala Leu Ile Lys Leu Lys Asn Lys Val Thr Ile
                515                 520                 525
Asn Arg Asn Ile Met Pro Ile Cys Leu Pro Arg Lys Glu Ala Ala Ser
530                 535                 540
Leu Met Lys Thr Asp Phe Val Gly Thr Val Ala Gly Trp Gly Leu Thr
545                 550                 555                 560
Gln Lys Gly Phe Leu Ala Arg Asn Leu Met Phe Val Asp Ile Pro Ile
                565                 570                 575
Val Asp His Gln Lys Cys Ala Thr Ala Tyr Thr Lys Gln Pro Tyr Pro
                580                 585                 590
Gly Ala Lys Val Thr Val Asn Met Leu Cys Ala Gly Leu Asp Arg Gly
                595                 600                 605
Gly Lys Asp Ser Cys Arg Gly Asp Ser Gly Gly Ala Leu Val Phe Leu
                610                 615                 620
Asp Asn Glu Thr Gln Arg Trp Phe Val Gly Gly Ile Val Ser Trp Gly
625                 630                 635                 640
Ser Ile Asn Cys Gly Gly Ser Glu Gln Tyr Gly Val Tyr Thr Lys Val
                645                 650                 655
Thr Asn Tyr Ile Pro Trp Ile Glu Asn Ile Ile Asn Asn Phe
                660                 665                 670
```

<210> SEQ ID NO 56
<211> LENGTH: 28
<212> TYPE: DNA
<213> ORGANISM: Artificial Sequence
<220> FEATURE:
<223> OTHER INFORMATION: Homo sapiens MASP-2 PCR primer

<400> SEQUENCE: 56
atgaggctgc tgaccctcct gggccttc                                   28

<210> SEQ ID NO 57
<211> LENGTH: 23
<212> TYPE: DNA
<213> ORGANISM: Artificial Sequence
<220> FEATURE:
<223> OTHER INFORMATION: Homo sapiens MASP-2 PCR primer

<400> SEQUENCE: 57
gtgcccctcc tgcgtcacct ctg                                              23

<210> SEQ ID NO 58
<211> LENGTH: 23
<212> TYPE: DNA
<213> ORGANISM: Artificial Sequence
<220> FEATURE:
<223> OTHER INFORMATION: Homo sapiens MASP-2 PCR primer

<400> SEQUENCE: 58
cagaggtgac gcaggagggg cac                                              23

<210> SEQ ID NO 59
<211> LENGTH: 27
<212> TYPE: DNA
<213> ORGANISM: Artificial Sequence
<220> FEATURE:
<223> OTHER INFORMATION: Homo sapiens MASP-2 PCR primer

<400> SEQUENCE: 59
ttaaaatcac taattatgtt ctcgatc                                          27

<210> SEQ ID NO 60
<211> LENGTH: 22
<212> TYPE: DNA
<213> ORGANISM: Artificial Sequence
<220> FEATURE:
<223> OTHER INFORMATION: Murine MASP-2 PCR primer

<400> SEQUENCE: 60
atgaggctac tcatcttcct gg                                               22

<210> SEQ ID NO 61
<211> LENGTH: 23
<212> TYPE: DNA
<213> ORGANISM: Artificial Sequence
<220> FEATURE:
<223> OTHER INFORMATION: Murine MASP-2 PCR primer

<400> SEQUENCE: 61
ctgcagaggt gacgcagggg ggg                                              23

<210> SEQ ID NO 62
<211> LENGTH: 23
<212> TYPE: DNA
<213> ORGANISM: Artificial Sequence
<220> FEATURE:
<223> OTHER INFORMATION: Murine MASP-2 PCR primer

<400> SEQUENCE: 62
ccccccctgc gtcacctctg cag                                              23

<210> SEQ ID NO 63
<211> LENGTH: 29
<212> TYPE: DNA
<213> ORGANISM: Artificial Sequence
<220> FEATURE:
<223> OTHER INFORMATION: Murine MASP-2 PCR primer

```
<400> SEQUENCE: 63
ttagaaatta cttattatgt tctcaatcc                                29

<210> SEQ ID NO 64
<211> LENGTH: 29
<212> TYPE: DNA
<213> ORGANISM: Artificial Sequence
<220> FEATURE:
<223> OTHER INFORMATION: Oligonucleotide from rat MASP-2

<400> SEQUENCE: 64
gaggtgacgc aggaggggca ttagtgttt                                29

<210> SEQ ID NO 65
<211> LENGTH: 37
<212> TYPE: DNA
<213> ORGANISM: Artificial Sequence
<220> FEATURE:
<223> OTHER INFORMATION: Oligonucleotide from rat MASP-2

<400> SEQUENCE: 65
ctagaaacac taatgccct cctgcgtcac ctctgca                        37
```

METHODS FOR TREATING CONDITIONS ASSOCIATED WITH MASP-2 DEPENDENT COMPLEMENT ACTIVATION

CROSS-REFERENCES TO RELATED APPLICATIONS

This application is a continuation of pending U.S. patent application Ser. No. 14/459,656, filed Aug. 14, 2014, which is a continuation of U.S. patent application Ser. No. 13/083, 441, filed Apr. 8, 2011 (now U.S. Pat. No. 8,840,893), which claims the benefit of Provisional Patent Application No. 61/322,722, filed Apr. 9, 2010, and is a continuation-in-part of patent application Ser. No. 12/896,754, filed Oct. 1, 2010, which is a continuation of patent application Ser. No. 12/561,202, filed Sep. 16, 2009 (now abandoned), which is a division of patent application Ser. No. 11/645,359, filed Dec. 22, 2006 (now U.S. Pat. No. 7,919,094), which claims the benefit of Provisional Patent Application No. 60/788, 876, filed Apr. 3, 2006, and which is a continuation-in-part of application Ser. No. 11/150,883, filed Jun. 9, 2005 (now abandoned), which claims the benefit of Provisional Patent Application No. 60/578,847, filed Jun. 10, 2004, all of which are hereby incorporated by reference in their entirety.

STATEMENT REGARDING SEQUENCE LISTING

The sequence listing associated with this application is provided in text format in lieu of a paper copy and is hereby incorporated by reference into the specification. The name of the text file containing the sequence listing is MP_1_0112_US3_Sequence_Listing_20191002.txt. The text file is 109 KB; was created on Oct. 2, 2019; and is being submitted via EFS-Web with the filing of the specification.

BACKGROUND

The complement system provides an early acting mechanism to initiate and amplify the inflammatory response to microbial infection and other acute insults (M. K. Liszewski and J. P. Atkinson, 1993, in *Fundamental Immunology*, Third Edition, edited by W. E. Paul, Raven Press, Ltd., New York). While complement activation provides a valuable first-line defense against potential pathogens, the activities of complement that promote a protective inflammatory response can also represent a potential threat to the host (K. R. Kalli, et al., *Springer Semin. Immunopathol.* 15:417-431, 1994; B. P. Morgan, *Eur. J. Clinical Investig.* 24:219-228, 1994). For example, C3 and C5 proteolytic products recruit and activate neutrophils. These activated cells are indiscriminate in their release of destructive enzymes and may cause organ damage. In addition, complement activation may cause the deposition of lytic complement components on nearby host cells as well as on microbial targets, resulting in host cell lysis.

The complement system has been implicated as contributing to the pathogenesis of numerous acute and chronic disease states, including: myocardial infarction, revascularization following stroke, ARDS, reperfusion injury, septic shock, capillary leakage following thermal burns, postcardiopulmonary bypass inflammation, transplant rejection, rheumatoid arthritis, multiple sclerosis, myasthenia gravis, and Alzheimer's disease. In almost all of these conditions, complement is not the cause but is one of several factors involved in pathogenesis. Nevertheless, complement activation may be a major pathological mechanism and represents an effective point for clinical control in many of these disease states. The growing recognition of the importance of complement-mediated tissue injury in a variety of disease states underscores the need for effective complement inhibitory drugs. No drugs have been approved for human use that specifically target and inhibit complement activation.

Currently, it is widely accepted that the complement system can be activated through three distinct pathways: the classical pathway, the lectin pathway, and the alternative pathway. The classical pathway is usually triggered by antibody bound to a foreign particle (i.e., an antigen) and thus requires prior exposure to that antigen for the generation of specific antibody. Since activation of the classical pathway is associated with development of an immune response, the classical pathway is part of the acquired immune system. In contrast, both the lectin and alternative pathways are independent of clonal immunity and are part of the innate immune system.

The first step in activation of the classical pathway is the binding of a specific recognition molecule, C1q, to antigen-bound IgG and IgM. The activation of the complement system results in the sequential activation of serine protease zymogens. C1q is associated with the C1r and C1s serine protease proenzymes as a complex called C1 and, upon binding of C1q to an immune complex, autoproteolytic cleavage of the Arg-Ile site of C1r is followed by C1r activation of C1s, which thereby acquires the ability to cleave C4 and C2. The cleavage of C4 into two fragments, designated C4a and C4b, allows the C4b fragments to form covalent bonds with adjacent hydroxyl or amino groups and the subsequent generation of C3 convertase (C4b2b) through noncovalent interaction with the C2b fragment of activated C2. C3 convertase (C4b2b) activates C3 leading to generation of the C5 convertase (C4b2b3b) and formation of the membrane attack complex (C5b-9) that can cause microbial lysis. The activated forms of C3 and C4 (C3b and C4b) are covalently deposited on the foreign target surfaces, which are recognized by complement receptors on multiple phagocytes.

Independently, the first step in activation of the complement system by the lectin pathway is also the binding of specific recognition molecules, which is followed by the activation of associated serine proteases. However, rather than the binding of immune complexes by C1q, the recognition molecules in the lectin pathway are carbohydrate-binding proteins (mannan-binding lectin (MBL), H-ficolin, M-ficolin, L-ficolin and C-type lectin CL-11). See J. Lu et al., *Biochim. Biophys. Acta* 1572:387-400, 2002; Holmskov et al., *Annu. Rev. Immunol.* 21:547-578 (2003); Teh et al., *Immunology* 101:225-232 (2000)). See also J. Luet et al., *Biochim Biophys Acta* 1572:387-400 (2002); Holmskov et al, *Annu Rev Immunol* 21:547-578 (2003); Teh et al., *Immunology* 101:225-232 (2000); Hansen S. et al. "Collectin 11 (CL-11, CL-K1) is a MASP1/3-associated plasma collectin with microbial-binding activity," *J. Immunol* 185(10):6096-6104 (2010).

Ikeda et al. first demonstrated that, like C1q, MBL could activate the complement system upon binding to yeast mannan-coated erythrocytes in a C4-dependent manner (K. Ikeda et al., *J. Biol. Chem.* 262:7451-7454, 1987). MBL, a member of the collectin protein family, is a calcium-dependent lectin that binds carbohydrates with 3- and 4-hydroxy groups oriented in the equatorial plane of the pyranose ring. Prominent ligands for MBL are thus D-mannose and N-acetyl-D-glucosamine, while carbohydrates not fitting this steric requirement have undetectable affinity for MBL (Weis, W. I., et al., *Nature* 360:127-134, 1992). The interaction between MBL and monovalent sugars is extremely weak, with dissociation constants typically in the 2 mM range. MBL achieves tight, specific binding to glycan ligands by interaction with multiple monosaccharide residues simultaneously (Lee, R. T., et al., *Archiv. Biochem. Biophys.* 299:129-136, 1992). MBL recognizes the carbohydrate patterns that commonly decorate microorganisms such as bacteria, yeast, parasites and certain viruses. In contrast, MBL does not recognize D-galactose and sialic acid, the penultimate and ultimate sugars that usually decorate "mature" complex glycoconjugates present on mammalian plasma and cell surface glycoproteins. This binding specificity is thought to help protect from self activation. However, MBL does bind with high affinity to clusters of high-mannose "precursor" glycans on N-linked glycoproteins and glycolipids sequestered in the endoplasmic reticulum and Golgi of mammalian cells (Maynard, Y., et al., *J. Biol. Chem.* 257:3788-3794, 1982). Therefore, damaged cells are potential targets for lectin pathway activation via MBL binding.

The ficolins possess a different type of lectin domain than MBL, called the fibrinogen-like domain. Ficolins bind sugar residues in a $Ca^{++}$-independent manner. In humans, three kinds of ficolins, L-ficolin, M-ficolin and H-ficolin, have been identified. Both serum ficolins L-ficolin, H-ficolin have in common a specificity for N-acetyl-D-glucosamine; however, H-ficolin also binds N-acetyl-D-galactosamine. The difference in sugar specificity of L-ficolin, H-ficolin, CL-11 and MBL means that the different lectins may be complementary and target different, though overlapping, glycoconjugates. This concept is supported by the recent report that, of the known lectins in the lectin pathway, only L-ficolin binds specifically to lipoteichoic acid, a cell wall glycoconjugate found on all Gram-positive bacteria (Lynch, N. J., et al., *J. Immunol.* 172:1198-1202, 2004). The collectins (i.e., MBL) and the ficolins bear no significant similarity in amino acid sequence. However, the two groups of proteins have similar domain organizations and, like C1q, assemble into oligomeric structures, which maximize the possibility of multisite binding. The serum concentrations of MBL are highly variable in healthy populations and this is genetically controlled by the polymorphism/mutations in both the promoter and coding regions of the MBL gene. As an acute phase protein, the expression of MBL is further upregulated during inflammation. L-ficolin is present in serum at similar concentrations as MBL. Therefore, the L-ficolin arm of the lectin pathway is potentially comparable to the MBL arm in strength. MBL and ficolins can also function as opsonins, which require interaction of these proteins with phagocyte receptors (Kuhlman, M., et al., *J. Exp. Med.* 169:1733, 1989; Matsushita, M., et al., *J. Biol. Chem.* 271:2448-54, 1996). However, the identities of the receptor(s) on phagocytic cells have not been established.

Human MBL forms a specific and high affinity interaction through its collagen-like domain with unique C1r/C1s-like serine proteases, termed MBL-associated serine proteases (MASPs). To date, three MASPs have been described. First, a single enzyme "MASP" was identified and characterized as the enzyme responsible for the initiation of the complement cascade (i.e., cleaving C2 and C4) (Matsushita M and Fujita T., J Exp Med 176(6):1497-1502 (1992), Ji, Y. H., et al., *J. Immunol.* 150:571-578, 1993). Later, it turned out that MASP is in fact a mixture of two proteases: MASP-1 and MASP-2 (Thiel, S., et al., *Nature* 386:506-510, 1997). However, it was demonstrated that the MBL-MASP-2 complex alone is sufficient for complement activation (Vorup-Jensen, T., et al., *J. Immunol.* 165:2093-2100, 2000). Furthermore, only MASP-2 cleaved C2 and C4 at high rates (Ambrus, G., et al., *J. Immunol.* 170:1374-1382, 2003). Therefore, MASP-2 is the protease responsible for activating C4 and C2 to generate the C3 convertase, C4b2b. This is a significant difference from the C1 complex, where the coordinated action of two specific serine proteases (C1r and C1s) leads to the activation of the complement system. Recently, a third novel protease, MASP-3, has been isolated (Dahl, M. R., et al., *Immunity* 15:127-35, 2001). MASP-1 and MASP-3 are alternatively spliced products of the same gene. The biological functions of MASP-1 and MASP-3 remain to be resolved.

MASPs share identical domain organizations with those of C1r and C1s, the enzymatic components of the C1 complex (Sim, R. B., et al., *Biochem. Soc. Trans.* 28:545, 2000). These domains include an N-terminal C1r/C1s/sea urchin Vegf/bone morphogenic protein (CUB) domain, an epidermal growth factor-like domain, a second CUB domain, a tandem of complement control protein domains, and a serine protease domain. As in the C1 proteases, activation of MASP-2 occurs through cleavage of an Arg-Ile bond adjacent to the serine protease domain, which splits the enzyme into disulfide-linked A and B chains, the latter consisting of the serine protease domain. Recently, a genetically determined deficiency of MASP-2 was described (Stengaard-Pedersen, K., et al., *New Eng. J. Med.* 349:554-560, 2003). The mutation of a single nucleotide leads to an Asp-Gly exchange in the CUB1 domain and renders MASP-2 incapable of binding to MBL.

MBL is also associated with a nonenzymatic protein referred to as MBL-associated protein of 19 kDa (MAp19) (Stover, C. M., *J. Immunol.* 162:3481-90, 1999) or small MBL-associated protein (sMAP) (Takahashi, M., et al., *Int. Immunol.* 11:859-863, 1999). MAp19 is formed by alternative splicing of the MASP 2 gene product and comprises the first two domains of MASP-2, followed by an extra sequence of four unique amino acids. The MASP 1 and MASP 2 genes are located on human chromosomes 3 and 1, respectively (Schwaeble, W., et al., *Immunobiology* 205: 455-466, 2002).

Several lines of evidence suggest that there are different MBL-MASPs complexes and a large fraction of the total MASPs in serum is not complexed with MBL (Thiel, S., et al., *J. Immunol.* 165:878-887, 2000). Both H- and L-ficolin are associated with MASP and activate the lectin complement pathway, as does MBL (Dahl, M. R., et al., *Immunity* 15:127-35, 2001; Matsushita, M., et al., *J. Immunol.* 168: 3502-3506, 2002). Both the lectin and classical pathways form a common C3 convertase (C4b2b) and the two pathways converge at this step.

The lectin pathway is widely thought to have a major role in host defense against infection. Strong evidence for the involvement of MBL in host defense comes from analysis of patients with decreased serum levels of functional MBL (Kilpatrick, D. C., *Biochim. Biophys. Acta* 1572:401-413, 2002). Such patients display susceptibility to recurrent bacterial and fungal infections. These symptoms are usually evident early in life, during an apparent window of vulnerability as maternally derived antibody titer wanes, but before a full repertoire of antibody responses develops. This syndrome often results from mutations at several sites in the collagenous portion of MBL, which interfere with proper formation of MBL oligomers. However, since MBL can function as an opsonin independent of complement, it is not known to what extent the increased susceptibility to infection is due to impaired complement activation.

Although there is extensive evidence implicating both the classical and alternative complement pathways in the pathogenesis of non-infectious human diseases, the role of the lectin pathway is just beginning to be evaluated. Recent studies provide evidence that activation of the lectin pathway can be responsible for complement activation and related inflammation in ischemia/reperfusion injury. Collard et al. (2000) reported that cultured endothelial cells subjected to oxidative stress bind MBL and show deposition of C3 upon exposure to human serum (Collard, C. D., et al., *Am. J. Pathol.* 156:1549-1556, 2000). In addition, treatment of human sera with blocking anti-MBL monoclonal antibodies inhibited MBL binding and complement activation. These findings were extended to a rat model of myocardial ischemia-reperfusion in which rats treated with a blocking antibody directed against rat MBL showed significantly less myocardial damage upon occlusion of a coronary artery than rats treated with a control antibody (Jordan, J. E., et al., *Circulation* 104:1413-1418, 2001). The molecular mechanism of MBL binding to the vascular endothelium after oxidative stress is unclear; a recent study suggests that activation of the lectin pathway after oxidative stress may be mediated by MBL binding to vascular endothelial cytokeratins, and not to glycoconjugates (Collard, C. D., et al., *Am. J. Pathol.* 159:1045-1054, 2001). Other studies have implicated the classical and alternative pathways in the pathogenesis of ischemia/reperfusion injury and the role of the lectin pathway in this disease remains controversial (Riedermann, N. C., et al., *Am. J. Pathol.* 162:363-367, 2003).

In contrast to the classical and lectin pathways, no initiators of the alternative pathway have been found to fulfill the recognition functions that C1q and lectins perform in the other two pathways. Currently it is widely accepted that the alternative pathway is spontaneously triggered by foreign or other abnormal surfaces (bacteria, yeast, virally infected cells, or damaged tissue). There are four plasma proteins directly involved in the alternative pathway: C3, factors B and D, and properdin.

A recent study has shown that MASP-1 (and possibly also MASP-3) is required to convert the alternative pathway activation enzyme Factor D from its zymogen form into its enzymatically active form. See Takahashi M. et al., "Essential Role of Mannose-binding lectin-associated serine protease-1 in activation of the complement factor D," *J Exp Med* 207(1):29-37 (2010)). The physiological importance of this process is underlined by the absence of alternative pathway functional activity in plasma of MASP-1/3 deficient mice. Proteolytic generation of C3b from native C3 is required for the alternative pathway to function. Since the alternative pathway C3 convertase (C3bBb) contains C3b as an essential subunit, the question regarding the origin of the first C3b via the alternative pathway has presented a puzzling problem and has stimulated considerable research.

C3 belongs to a family of proteins (along with C4 and α-2 macroglobulin) that contain a rare posttranslational modification known as a thioester bond. The thioester group is composed of a glutamine whose terminal carbonyl group is bound to the sulfhydryl group of a cysteine three amino acids away. This bond is unstable and the electrophilic carbonyl group of glutamine can form a covalent bond with other molecules via hydroxyl or amino groups. The thioester bond is reasonably stable when sequestered within a hydrophobic pocket of intact C3. However, proteolytic cleavage of C3 to C3a and C3b results in exposure of the highly reactive thioester bond on C3b and by this mechanism C3b covalently attaches to a target. In addition to its well-documented role in covalent attachment of C3b to complement targets, the C3 thioester is also thought to have a pivotal role in triggering the alternative pathway. According to the widely accepted "tick-over theory", the alternative pathway is initiated by the generation of a fluid-phase convertase, iC3Bb, which is formed from C3 with hydrolyzed thioester (iC3; $C3(H_2O)$) and factor B (Lachmann, P. J., et al., *Springer Semin. Immunopathol.* 7:143-162, 1984). The C3b-like iC3 is generated from native C3 by a slow spontaneous hydrolysis of the internal thioester in the protein (Pangburn, M. K., et al., *J. Exp. Med.* 154:856-867, 1981). Through the activity of the iC3Bb convertase, C3b molecules are deposited on the target surface thereby initiating the alternative pathway.

Very little is known about the initiators of activation of the alternative pathway. Activators are thought to include yeast cell walls (zymosan), many pure polysaccharides, rabbit erythrocytes, certain immunoglobulins, viruses, fungi, bacteria, animal tumor cells, parasites, and damaged cells. The only feature common to these activators is the presence of carbohydrate, but the complexity and variety of carbohydrate structures has made it difficult to establish the shared molecular determinants, which are recognized. It is widely accepted that alternative pathway activation is controlled through the fine balance between inhibitory regulatory components of this pathway, such as Factor H, DAF, and CR1 and properdin, the only positive regulator of the alternative pathway. See Schwaeble W. J. and Reid K. B., "Does properdin crosslink the cellular and the humoral immune response?, *Immunol Today* 20(1):17-21 (1999)).

The alternative pathway can also provide a powerful amplification loop for the lectin/classical pathway C3 convertase (C4b2b) since any C3b generated can participate with factor B in forming additional alternative pathway C3 convertase (C3bBb). The alternative pathway C3 convertase is stabilized by the binding of properdin. Properdin extends the alternative pathway C3 convertase half-life six to ten fold. Addition of C3b to the C3 convertase leads to the formation of the alternative pathway C5 convertase.

All three pathways (i.e., the classical, lectin and alternative) have been thought to converge at C5, which is cleaved to form products with multiple proinflammatory effects. The converged pathway has been referred to as the terminal complement pathway. C5a is the most potent anaphylatoxin, inducing alterations in smooth muscle and vascular tone, as well as vascular permeability. It is also a powerful chemotaxin and activator of both neutrophils and monocytes. C5a-mediated cellular activation can significantly amplify inflammatory responses by inducing the release of multiple additional inflammatory mediators, including cytokines, hydrolytic enzymes, arachidonic acid metabolites and reactive oxygen species. C5 cleavage leads to the formation of C5b-9, also known as the membrane attack complex (MAC). There is now strong evidence that sublytic MAC deposition may play an important role in inflammation in addition to its role as a lytic pore-forming complex.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present invention provides a method of inhibiting the adverse effects of MASP-2-dependent complement activation in a living subject. The method includes the step of administering to a subject in need thereof, an amount of a MASP-2 inhibitory agent effective to inhibit MASP-2-dependent complement activation. In this context, the phrase "MASP-2-dependent complement activation" refers to alternative pathway complement activation that occurs via the lectin-dependent MASP-2 system. In another aspect of the invention, the MASP-2 inhibitory agent inhibits complement activation via the lectin-dependent MASP-2 system without substantially inhibiting complement activation via the classical or C1q-dependent system, such that the C1q-dependent system remains functional.

In some embodiments of these aspects of the invention, the MASP-2 inhibitory agent is an anti-MASP-2 antibody or fragment thereof. In further embodiments, the anti-MASP-2 antibody has reduced effector function. In some embodiments, the MASP-2 inhibitory agent is a MASP-2 inhibitory peptide or a non-peptide MASP-2 inhibitor.

In another aspect, the present invention provides compositions for inhibiting the adverse effects of MASP-2-dependent complement activation, comprising a therapeutically effective amount of a MASP-2 inhibitory agent and a pharmaceutically acceptable carrier. Methods are also provided for manufacturing a medicament for use in inhibiting the adverse effects of MASP-2-dependent complement activation in living subjects in need thereof, comprising a therapeutically effective amount of a MASP-2 inhibitory agent in a pharmaceutical carrier. Methods are also provided for manufacturing medicaments for use in inhibiting MASP-2-dependent complement activation for treatment of each of the conditions, diseases and disorders described herein below.

The methods, compositions and medicaments of the invention are useful for inhibiting the adverse effects of MASP-2-dependent complement activation in vivo in mammalian subjects, including humans suffering from an acute or chronic pathological condition or injury as further described herein. Such conditions and injuries include without limitation MASP-2 mediated complement activation in associated autoimmune disorders and/or inflammatory conditions.

In another aspect of the invention, methods are provided for inhibiting MASP-2-dependent complement activation in a subject suffering from a blood disorder, by administering a therapeutically effective amount of a MASP-2 inhibitory agent in a pharmaceutical carrier to such a subject.

In one aspect of the invention, methods are provided for inhibiting MASP-2 dependent complement activation in a subject suffering from a blood disorder selected from the group consisting of sepsis, severe sepsis, septic shock, acute respiratory distress syndrome resulting from sepsis, systemic inflammatory response syndrome, hemorrhagic shock, hemolytic anemia, autoimmune thrombotic thrombocytopenic purpura and hemolytic uremic syndrome.

In another aspect of the invention, methods are provided for inhibiting MASP-2 dependent complement activation in a subject suffering from a complement mediated ischemia reperfusion injury comprising administering to the subject a composition comprising an amount of a MASP-2 inhibitory agent effective to inhibit MASP-2 dependent complement activation.

In one aspect, methods are provided for inhibiting MASP-2 dependent complement activation in a subject suffering from an ischemia reperfusion injury selected from the group consisting of myocardial ischemia reperfusion injury, gastrointestinal ischemia reperfusion injury, cerebral ischemia reperfusion injury, and renal ischemia reperfusion injury.

In another aspect of the invention, methods are provided for inhibiting MASP-2 dependent complement activation in a subject that has undergone, is undergoing, or will undergo an organ or tissue transplant procedure comprising administering to the subject a composition comprising an amount of a MASP-2 inhibitory agent effective to inhibit MASP-2 dependent complement activation. In one embodiment, methods are provided for inhibiting MASP-2 dependent complement activation in a subject that has undergone, is undergoing, or will undergo a kidney transplant procedure.

In another aspect of the invention, methods are provided for inhibiting MASP-2 dependent complement activation in a subject suffering from an ophthalmologic condition, comprising administering to the subject a composition comprising an amount of a MASP-2 inhibitory agent effective to inhibit MASP-2 dependent complement activation. In one embodiment, the ophthalmologic condition is age-related macular degeneration.

In another aspect of the invention, methods are provided for inhibiting MASP-2 dependent complement activation in a subject at risk for developing or is suffering from diabetic neuropathy, diabetic nephropathy, diabetic retinopathy, or diabetic macular edema comprising administering to the subject a composition comprising an amount of a MASP-2 inhibitory agent effective to inhibit MASP-2 dependent complement activation.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 40B graphically illustrates the log cfu/ml of *N. meningitidis* recovered at different time points in blood samples taken from the WT (+/+) mice infected with $2\times10^8$ cfu/100 μl *N. meningitidis*, as described in Example 40;

DESCRIPTION OF THE SEQUENCE LISTING

Figure 1:
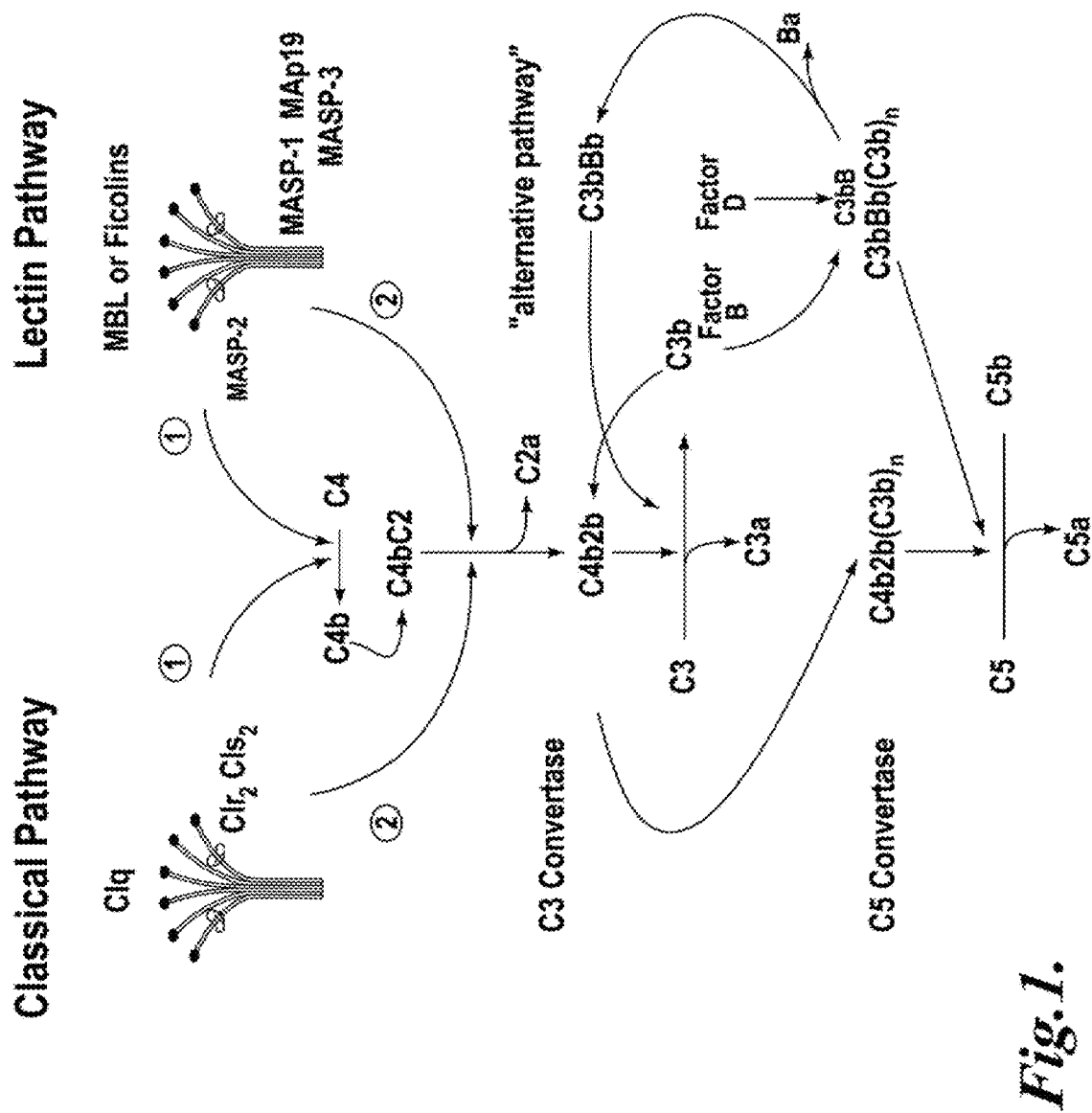
FIG. 1 is a flowchart illustrating the new discovery that the alternative complement pathway requires lectin pathway-dependent MASP-2 activation for complement activation.

SEQ ID NO:1 human MAp19 cDNA
SEQ ID NO:2 human MAp19 protein (with leader)
SEQ ID NO:3 human MAp19 protein (mature)
SEQ ID NO:4 human MASP-2 cDNA
SEQ ID NO:5 human MASP-2 protein (with leader)
SEQ ID NO:6 human MASP-2 protein (mature)
SEQ ID NO:7 human MASP-2 gDNA (exons 1-6)
Antigens: (In Reference to the MASP-2 Mature Protein)
SEQ ID NO:8 CUBI sequence (aa 1-121)
SEQ ID NO:9 CUBEGF sequence (aa 1-166)
SEQ ID NO:10 CUBEGFCUBII (aa 1-293)
SEQ ID NO:11 EGF region (aa 122-166)
SEQ ID NO:12 serine protease domain (aa 429-671)
SEQ ID NO:13 serine protease domain inactive (aa 610-625 with Ser618 to Ala mutation)
SEQ ID NO:14 TPLGPKWPEPVFGRL (CUB1 peptide)
SEQ ID NO:15
TAPPGYRLRLYFTHFDLELSHLCEY-DFVKLSSGAKVLATLCGQ
(CUBI peptide)
SEQ ID NO:16 TFRSDYSN (MBL binding region core)
SEQ ID NO:17 FYSLGSSLDITFRSDYSNEKPFTGF (MBL binding region)
SEQ ID NO:18 IDECQVAPG (EGF PEPTIDE)
SEQ ID NO:19 ANMLCAGLESGGKDSCRGDSG-GALV (serine protease binding core)Detailed Description Peptide Inhibitors:
SEQ ID NO:20 MBL full length cDNA
SEQ ID NO:21 MBL full length protein
SEQ ID NO:22 OGK-X-GP (consensus binding)
SEQ ID NO:23 OGKLG
SEQ ID NO:24 GLR GLQ GPO GKL GPO G
SEQ ID NO:25 GPO GPO GLR GLQ GPO GKL GPO GPO GPO
SEQ ID NO:26 GKDGRDGTKGEKGEPGQGLR-GLQGPOGKLGPOG
SEQ ID NO:27 GAOGSOGEK-GAOGPQGPOGPOGKMGPKGEOGDO (human h-ficolin)
SEQ ID NO:28
GCOGLOGAOGDKGEAGTNGKRG-ERGPOGPOGKAGPOGPNGA
OGEO (human ficolin p35)
SEQ ID NO:29 LQRALEILPNRVTIKANRPFLVFI (C4 cleavage site)
Expression Inhibitors:
SEQ ID NO:30 cDNA of CUBI-EGF domain (nucleotides 22-680 of SEQ ID NO:4)
SEQ ID NO:31
5' CGGGCACACCAT-GAGGCTGCTGACCCTCCTGGGC 3'
Nucleotides 12-45 of SEQ ID NO:4 including the MASP-2 translation start site (sense)
SEQ ID NO:32
5'GACATTACCTTCCGCTCCGACTC-CAACGAGAAG3'
Nucleotides 361-396 of SEQ ID NO:4 encoding a region comprising the MASP-2 MBL binding site (sense)
SEQ ID NO:33
5'AGCAGCCCTGAATACCCACGGCCGTATCC-CAAA3'
Nucleotides 610-642 of SEQ ID NO:4 encoding a region comprising the CUBII domain
Cloning Primers:
SEQ ID NO:34 CGGGATCCAT-GAGGCTGCTGACCCTC (5' PCR for CUB)
SEQ ID NO:35 GGAATTCCTAGGCTGCATA (3' PCR FOR CUB)
SEQ ID NO:36 GGAATTCCTACAGGGCGCT (3' PCR FOR CUBIEGF)
SEQ ID NO:37 GGAATTCCTAGTAGTGGAT (3' PCR FOR CUBIEGFCUBII)
SEQ ID NOS:38-47 are cloning primers for humanized antibody
SEQ ID NO:48 is 9 aa peptide bond Expression Vector:
  SEQ ID NO:49 is the MASP-2 minigene insert
  SEQ ID NO: 50 is the murine MASP-2 cDNA
  SEQ ID NO: 51 is the murine MASP-2 protein (w/leader)
  SEQ ID NO: 52 is the mature murine MASP-2 protein
  SEQ ID NO: 53 the rat MASP-2 cDNA
  SEQ ID NO: 54 is the rat MASP-2 protein (w/leader)
  SEQ ID NO: 55 is the mature rat MASP-2 protein
  SEQ ID NO: 56-59 are the oligonucleotides for site-directed mutagenesis of human MASP-2 used to generate human MASP-2A
  SEQ ID NO: 60-63 are the oligonucleotides for site-directed mutagenesis of murine MASP-2 used to generate murine MASP-2A
  SEQ ID NO: 64-65 are the oligonucleotides for site-directed mutagenesis of rat MASP-2 used to generate rat MASP-2A

DETAILED DESCRIPTION

The present invention is based upon the surprising discovery by the present inventors that MASP-2 is needed to initiate alternative complement pathway activation. Through the use of a knockout mouse model of MASP-2−/−, the present inventors have shown that it is possible to inhibit alternative complement pathway activation via the lectin mediated MASP-2 pathway while leaving the classical pathway intact, thus establishing the lectin-dependent MASP-2 activation as a requirement for alternative complement activation in absence of the classical pathway. The present invention also describes the use of MASP-2 as a therapeutic target for inhibiting cellular injury associated with lectin-mediated alternative complement pathway activation while leaving the classical (C1q-dependent) pathway component of the immune system intact.

I. Definitions

Unless specifically defined herein, all terms used herein have the same meaning as would be understood by those of ordinary skill in the art of the present invention. The following definitions are provided in order to provide clarity with respect to the terms as they are used in the specification and claims to describe the present invention.

As used herein, the term "MASP-2-dependent complement activation" refers to alternative pathway complement activation that occurs via lectin-dependent MASP-2 activation.

As used herein, the term "alternative pathway" refers to complement activation that is triggered, for example, by zymosan from fungal and yeast cell walls, lipopolysaccharide (LPS) from Gram negative outer membranes, and rabbit erythrocytes, as well as from many pure polysaccharides, rabbit erythrocytes, viruses, bacteria, animal tumor cells, parasites and damaged cells, and which has traditionally been thought to arise from spontaneous proteolytic generation of C3b from complement factor C3.

As used herein, the term "lectin pathway" refers to complement activation that occurs via the specific binding of serum and non-serum carbohydrate-binding proteins including mannan-binding lectin (MBL) and the ficolins.

As used herein, the term "classical pathway" refers to complement activation that is triggered by antibody bound to a foreign particle and requires binding of the recognition molecule C1q.

As used herein, the term "MASP-2 inhibitory agent" refers to any agent that binds to or directly interacts with MASP-2 and effectively inhibits MASP-2-dependent complement activation, including anti-MASP-2 antibodies and MASP-2 binding fragments thereof, natural and synthetic peptides, small molecules, soluble MASP-2 receptors, expression inhibitors and isolated natural inhibitors, and also encompasses peptides that compete with MASP-2 for binding to another recognition molecule (e.g., MBL, H-ficolin, M-ficolin, or L-ficolin) in the lectin pathway, but does not encompass antibodies that bind to such other recognition molecules. MASP-2 inhibitory agents useful in the method of the invention may reduce MASP-2-dependent complement activation by greater than 20%, such as greater than 50%, such as greater than 90%. In one embodiment, the MASP-2 inhibitory agent reduces MASP-2-dependent complement activation by greater than 90% (i.e., resulting in MASP-2 complement activation of only 10% or less).

As used herein, the term "antibody" encompasses antibodies and antibody fragments thereof, derived from any antibody-producing mammal (e.g., mouse, rat, rabbit, and primate including human), that specifically bind to MASP-2 polypeptides or portions thereof. Exemplary antibodies include polyclonal, monoclonal and recombinant antibodies; multispecific antibodies (e.g., bispecific antibodies); humanized antibodies; murine antibodies; chimeric, mouse-human, mouse-primate, primate-human monoclonal antibodies; and anti-idiotype antibodies, and may be any intact molecule or fragment thereof.

As used herein, the term "antibody fragment" refers to a portion derived from or related to a full-length anti-MASP-2 antibody, generally including the antigen binding or variable region thereof. Illustrative examples of antibody fragments include Fab, Fab', F(ab)$_2$, F(ab')$_2$ and Fv fragments, scFv fragments, diabodies, linear antibodies, single-chain antibody molecules and multispecific antibodies formed from antibody fragments.

As used herein, a "single-chain Fv" or "scFv" antibody fragment comprises the V$_H$ and V$_L$ domains of an antibody, wherein these domains are present in a single polypeptide chain. Generally, the Fv polypeptide further comprises a polypeptide linker between the V$_H$ and V$_L$ domains, which enables the scFv to form the desired structure for antigen binding.

As used herein, a "chimeric antibody" is a recombinant protein that contains the variable domains and complementarity-determining regions derived from a non-human species (e.g., rodent) antibody, while the remainder of the antibody molecule is derived from a human antibody.

As used herein, a "humanized antibody" is a chimeric antibody that comprises a minimal sequence that conforms to specific complementarity-determining regions derived from non-human immunoglobulin that is transplanted into a human antibody framework. Humanized antibodies are typically recombinant proteins in which only the antibody complementarity-determining regions are of non-human origin.

As used herein, the term "mannan-binding lectin" ("MBL") is equivalent to mannan-binding protein ("MBP").

As used herein, the "membrane attack complex" ("MAC") refers to a complex of the terminal five complement components (C5-C9) that inserts into and disrupts membranes. Also referred to as C5b-9.

As used herein, "a subject" includes all mammals, including without limitation humans, non-human primates, dogs, cats, horses, sheep, goats, cows, rabbits, pigs and rodents.

As used herein, the amino acid residues are abbreviated as follows: alanine (Ala;A), asparagine (Asn;N), aspartic acid (Asp;D), arginine (Arg;R), cysteine (Cys;C), glutamic acid (Glu;E), glutamine (Gln;Q), glycine (Gly;G), histidine (His; H), isoleucine (Ile;I), leucine (Leu;L), lysine (Lys;K), methionine (Met;M), phenylalanine (Phe;F), proline (Pro; P), serine (Ser; S), threonine (Thr;T), tryptophan (Trp;W), tyrosine (Tyr;Y), and valine (Val;V).

In the broadest sense, the naturally occurring amino acids can be divided into groups based upon the chemical characteristic of the side chain of the respective amino acids. By "hydrophobic" amino acid is meant either Ile, Leu, Met, Phe, Trp, Tyr, Val, Ala, Cys or Pro. By "hydrophilic" amino acid is meant either Gly, Asn, Gln, Ser, Thr, Asp, Glu, Lys, Arg or His. This grouping of amino acids can be further subclassed as follows. By "uncharged hydrophilic" amino acid is meant either Ser, Thr, Asn or Gln. By "acidic" amino acid is meant either Glu or Asp. By "basic" amino acid is meant either Lys, Arg or His.

As used herein the term "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine.

The term "oligonucleotide" as used herein refers to an oligomer or polymer of ribonucleic acid (RNA) or deoxyribonucleic acid (DNA) or mimetics thereof. This term also covers those oligonucleobases composed of naturally-occurring nucleotides, sugars and covalent internucleoside (backbone) linkages as well as oligonucleotides having non-naturally-occurring modifications.

II. The Alternative Pathway: A New Understanding

Figure 7A:
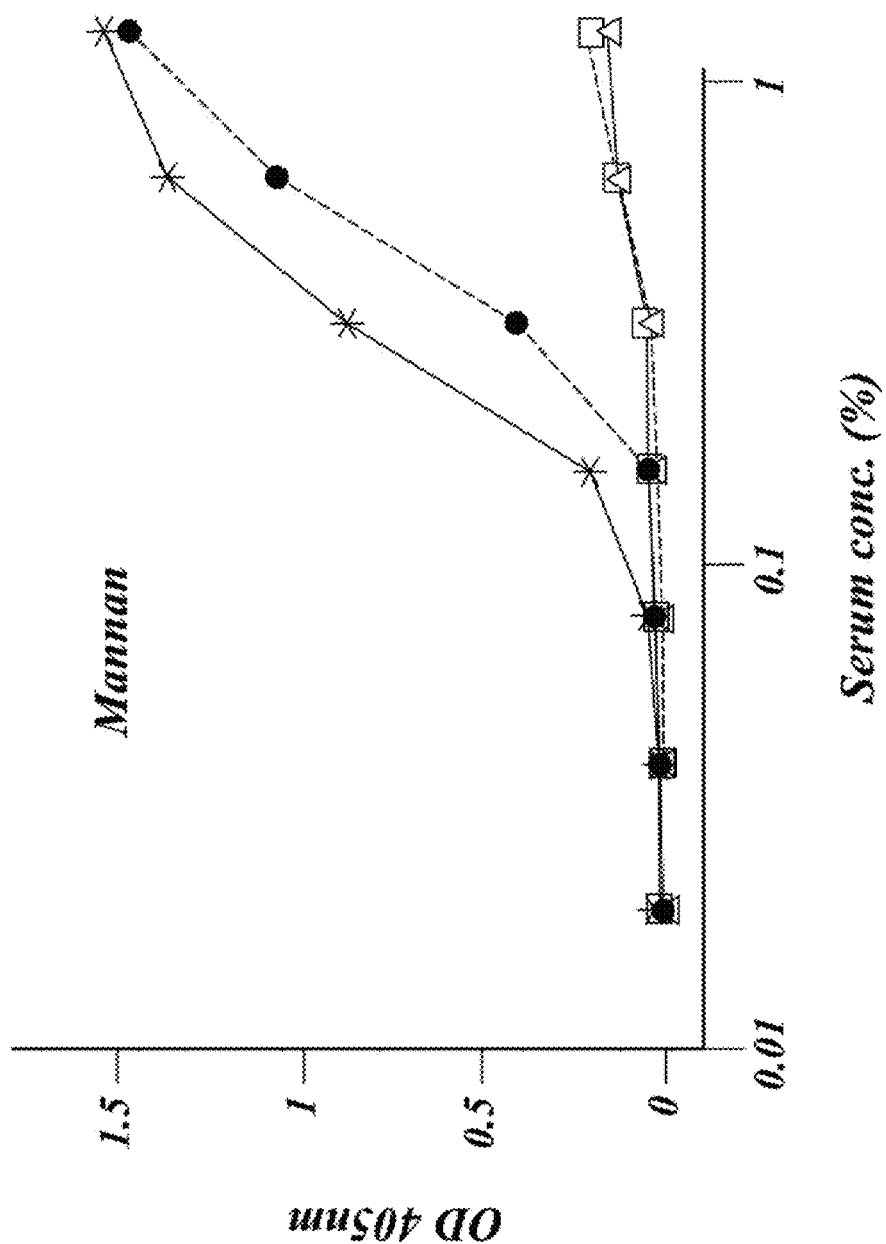
FIG. 7A presents results demonstrating that MASP-2-deficiency leads to the loss of both lectin-pathway-mediated and alternative pathway mediated C3 activation as measured by lack of C3b deposition on mannan.
Figure 7B:
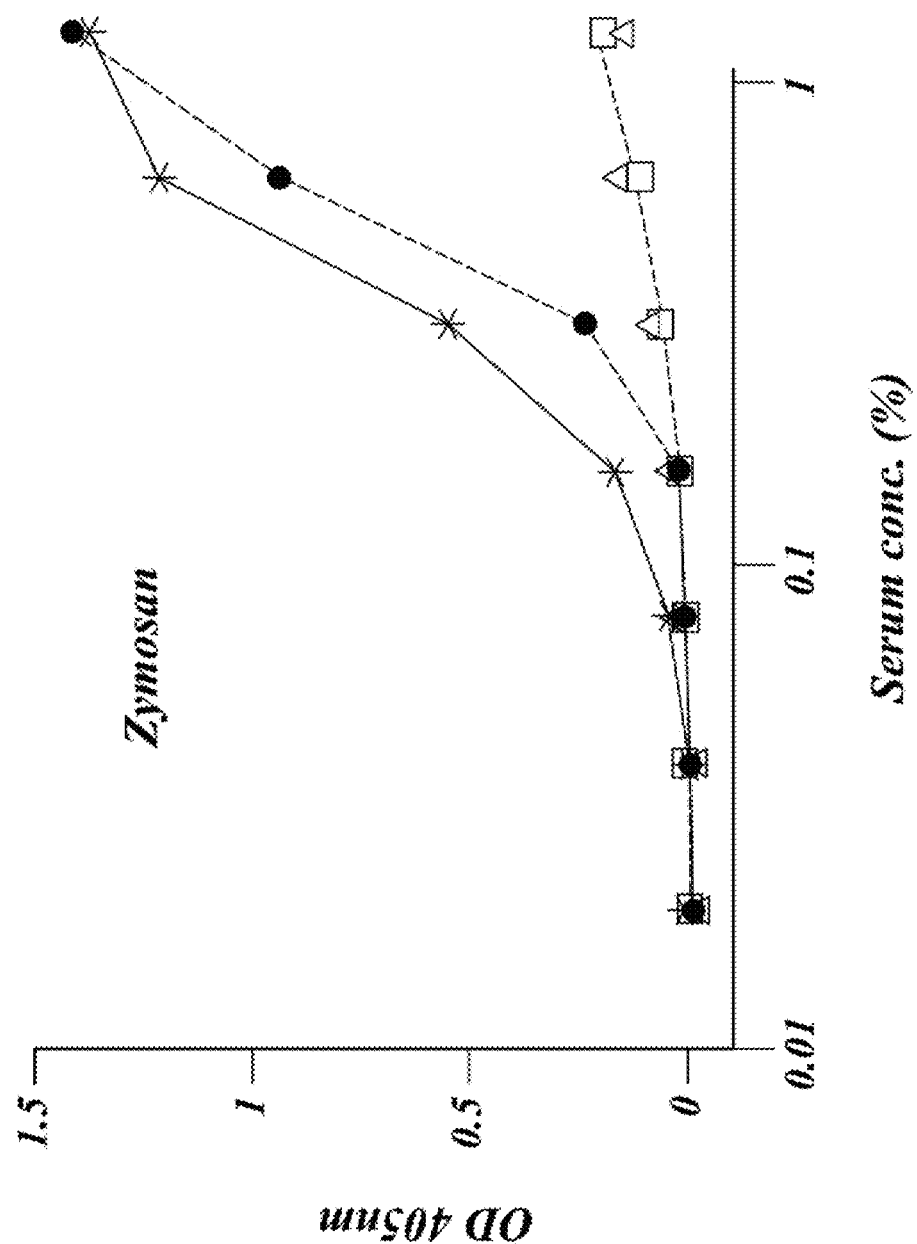
FIG. 7B presents results demonstrating that MASP-2-deficiency leads to the loss of both lectin-pathway-mediated and alternative pathway mediated C3 activation as measured by lack of C3b deposition on zymosan.

The alternative pathway of complement was first described by Louis Pillemer and his colleagues in early 1950s based on studies in which zymosan made from yeast cell walls was used to activate complement (Pillemer, L. et al., *J. Exp. Med.* 103:1-13, 1956; Lepow, I. H., *J. Immunol.* 125:471-478, 1980). Ever since then, zymosan is considered as the canonical example of a specific activator of the alternative pathway in human and rodent serum (Lachmann, P. J., et al., *Springer Semin. Immunopathol.* 7:143-162, 1984; Van Dijk, H., et al., *J. Immunol. Methods* 85:233-243, 1985; Pangburn, M. K., *Methods in Enzymol.* 162:639-653, 1988). A convenient and widely used assay for alternative pathway activation is to incubate serum with zymosan coated onto plastic wells and to determine the amount of C3b deposition onto the solid phase following the incubation. As expected, there is substantial C3b deposition onto zymosan-coated wells following incubation with normal mouse serum (FIG. 7B). However, incubation of serum from homozygous MASP-2-deficient mice with zymosan-coated wells results in a substantial reduction in C3b deposition compared to that of normal serum. Furthermore, use of serum from mice heterozygous for deficiency in the MASP 2 gene in this assay results in levels of C3b deposition that are intermediate between those obtained with serum from homozygous MASP-2-deficient mice and normal mouse serum. Parallel results are also obtained using wells coated with mannan, another polysaccharide known to activate the alternative pathway (FIG. 7A). Since the normal and MASP-2 deficient mice share the same genetic background, except for the MASP 2 gene, these unexpected results demonstrate that MASP-2 plays an essential role in activation of the alternative pathway.

These results provide strong evidence that the alternative pathway is not an independent, stand-alone pathway of complement activation as described in essentially all current medical textbooks and recent review articles on complement. The current and widely held scientific view is that the alternative pathway is activated on the surface of certain particulate targets (microbes, zymosan, rabbit erythrocytes) through the amplification of spontaneous "tick-over" C3 activation. However, the absence of significant alternative pathway activation in serum from MASP-2 knockout mice by two well-known "activators" of the alternative pathway makes it unlikely that the "tick-over theory" describes an important physiological mechanism for complement activation.

Figure 6A:
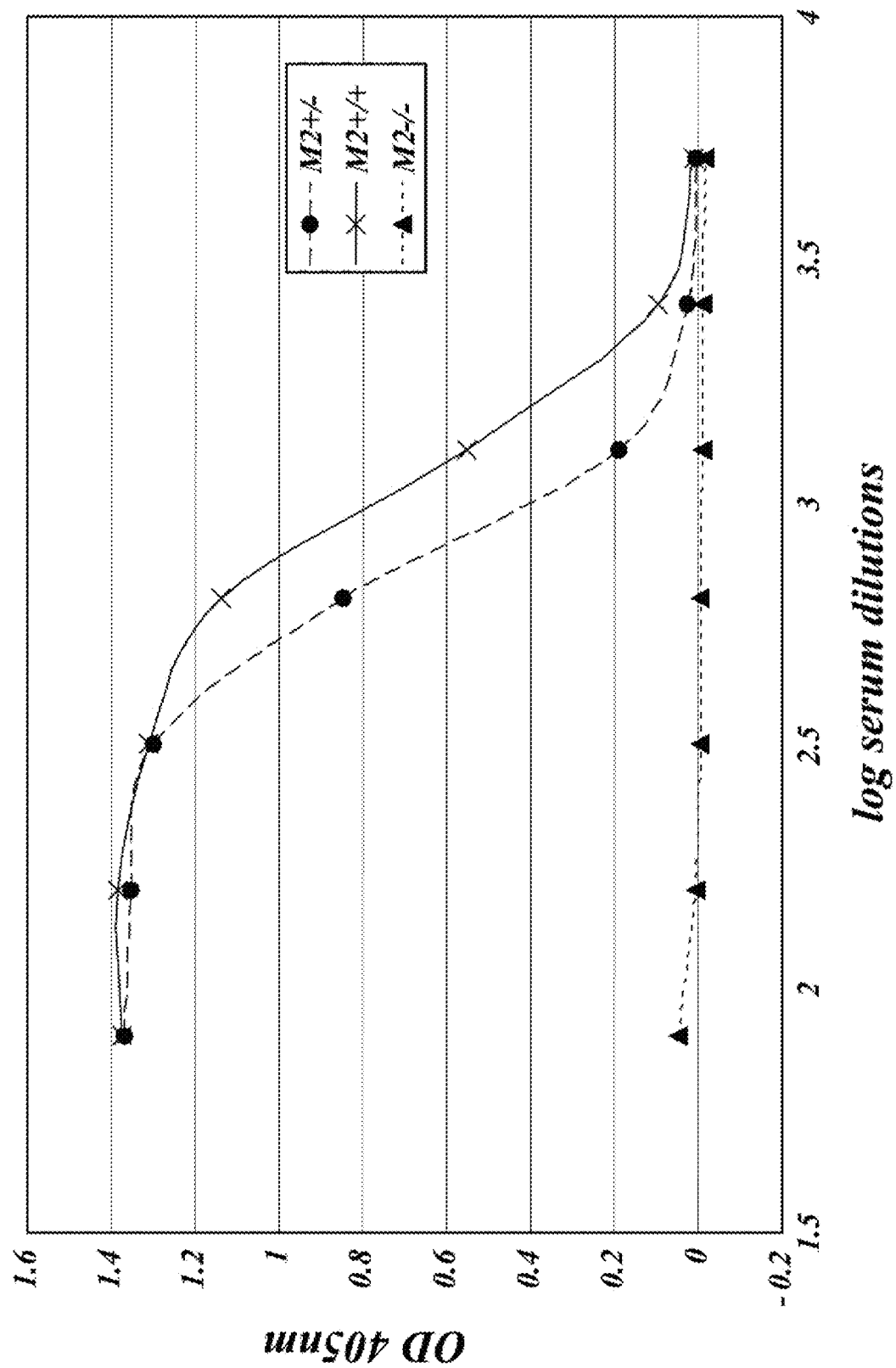
FIG. 6A presents results demonstrating that MASP-2-deficiency leads to the loss of lectin-pathway-mediated C4 activation as measured by lack of C4b deposition on mannan.
Figure 6B:
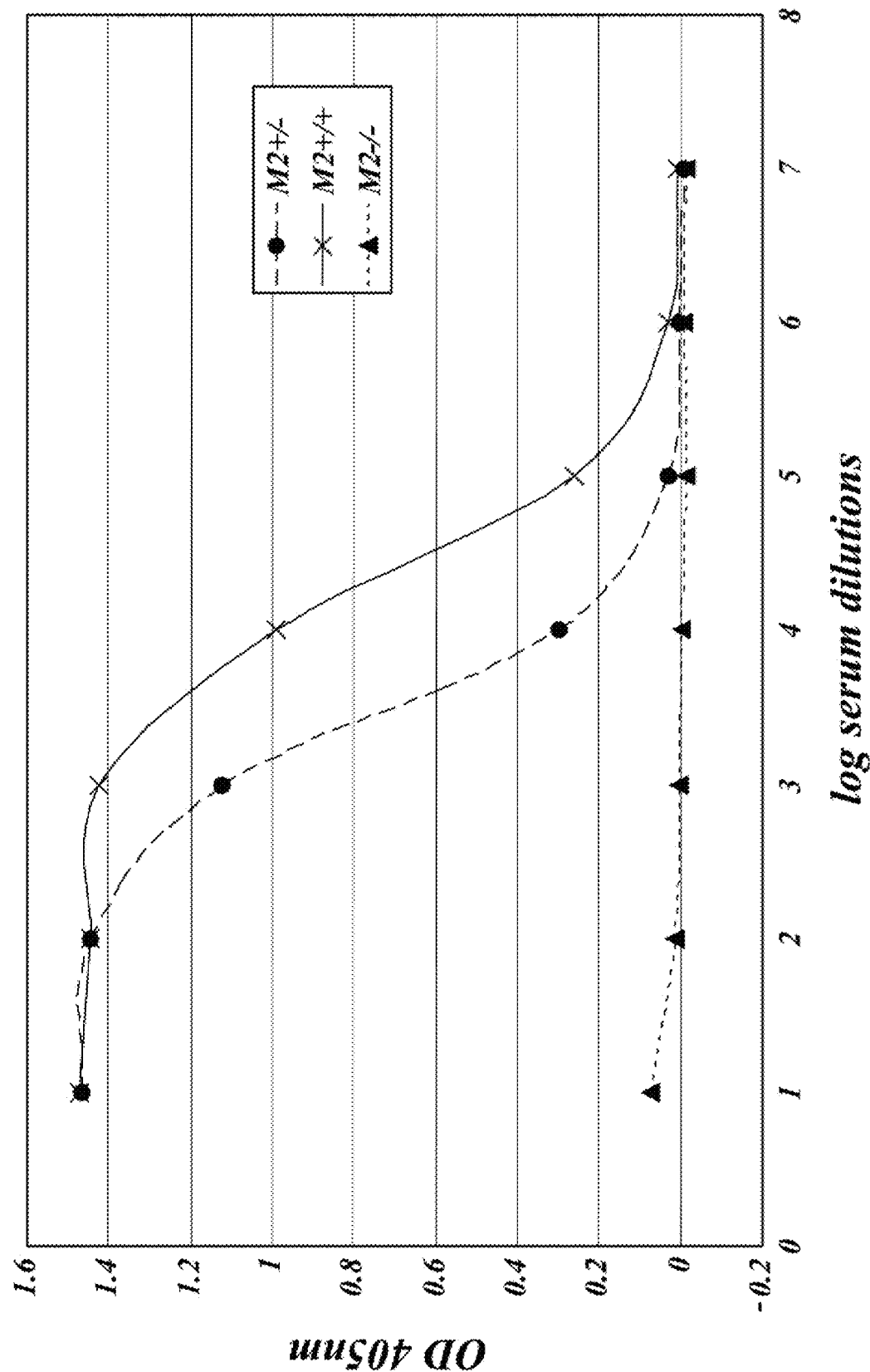
FIG. 6B presents results demonstrating that MASP-2-deficiency leads to the loss of lectin-pathway-mediated C4 activation as measured by lack of C4b deposition on zymosan.
Figure 6C:
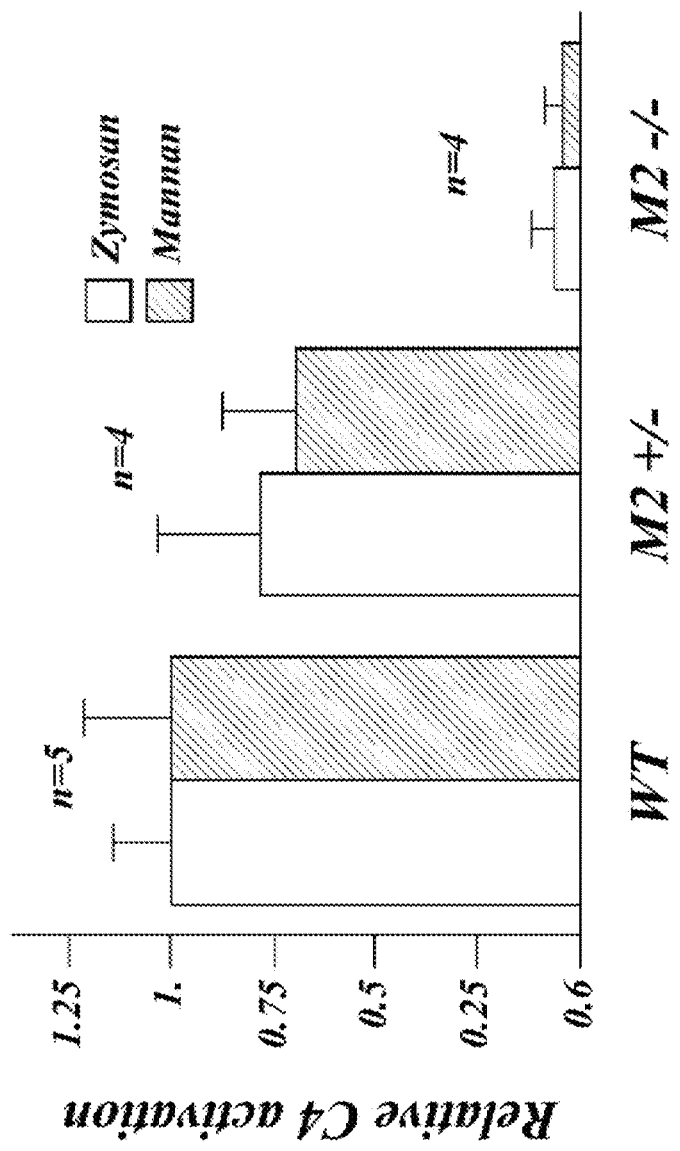
FIG. 6C presents results demonstrating the relative C4 activation levels of serum samples obtained from MASP-2+/−; MASP-2−/− and wild-type strains as measure by C4b deposition on mannan and on zymosan.

Since MASP-2 protease is known to have a specific and well-defined role as the enzyme responsible for the initiation of the lectin complement cascade, these results implicate activation of the lectin pathway by zymosan and mannan as a critical first step for subsequent activation of the alternative pathway. C4b is an activation product generated by the lectin pathway but not by the alternative pathway. Consistent with this concept, incubation of normal mouse serum with zymosan- or mannan-coated wells results in C4b deposition onto the wells and this C4b deposition is substantially reduced when the coated wells are incubated with serum from MASP-2-deficient mice (FIGS. 6A, 6B and 6C).

The alternative pathway, in addition to its widely accepted role as an independent pathway for complement activation, can also provide an amplification loop for complement activation initially triggered via the classical and lectin pathways (Liszewski, M. K. and J. P. Atkinson, 1993, in *Fundamental Immunology*, Third Edition, edited by W. E. Paul, Raven Press, Ltd., New York; Schweinie, J. E., et al., *J. Clin. Invest.* 84:1821-1829, 1989). In this alternative pathway-mediated amplification mechanism, C3 convertase (C4b2b) generated by activation of either the classical or lectin complement cascades cleaves C3 into C3a and C3b, and thereby provides C3b that can participate in forming C3bBb, the alternative pathway C3 convertase. The likely explanation for the absence of alternative pathway activation in MASP-2 knockout serum is that the lectin pathway is required for initial complement activation by zymosan, mannan, and other putative "activators" of the alternative pathway, while the alternative pathway plays a crucial role for amplifying complement activation. In other words, the alternative pathway is a feedforward amplification loop dependent upon the lectin and classical complement pathways for activation, rather than an independent linear cascade.

Rather than the complement cascade being activated through three distinct pathways (classical, alternative and lectin pathways) as previously envisioned, our results indicate that it is more accurate to view complement as being composed of two major systems, which correspond, to a first approximation, to the innate (lectin) and acquired (classical) wings of the complement immune defense system. Lectins (MBP, M-ficolin, H-ficolin, and L-ficolin) are the specific recognition molecules that trigger the innate complement system and the system includes the lectin pathway and the associated alternative pathway amplification loop. C1q is the specific recognition molecule that triggers the acquired complement system and the system includes the classical pathway and associated alternative pathway amplification loop. We refer to these two major complement activation systems as the lectin-dependent complement system and the C1q-dependent complement system, respectively.

In addition to its essential role in immune defense, the complement system contributes to tissue damage in many clinical conditions. Thus, there is a pressing need to develop therapeutically effective complement inhibitors to prevent these adverse effects. With recognition that complement is composed of two major complement activation systems comes the realization that it would be highly desirable to specifically inhibit only the complement activation system causing a particular pathology without completely shutting down the immune defense capabilities of complement. For example, in disease states in which complement activation is mediated predominantly by the lectin-dependent complement system, it would be advantageous to specifically inhibit only this system. This would leave the C1q-dependent complement activation system intact to handle immune complex processing and to aid in host defense against infection.

The preferred protein component to target in the development of therapeutic agents to specifically inhibit the lectin-dependent complement system is MASP-2. Of all the protein components of the lectin-dependent complement system (MBL, H-ficolin, M-ficolin, L-ficolin, MASP-2, C2-C9, Factor B, Factor D, and properdin), only MASP-2 is both unique to the lectin-dependent complement system and required for the system to function. The lectins (MBL, H-ficolin, M-ficolin and L-ficolin) are also unique components in the lectin-dependent complement system. However, loss of any one of the lectin components would not necessarily inhibit activation of the system due to lectin redundancy. It would be necessary to inhibit all four lectins in order to guarantee inhibition of the lectin-dependent complement activation system. Furthermore, since MBL and the ficolins are also known to have opsonic activity independent of complement, inhibition of lectin function would result in the loss of this beneficial host defense mechanism against infection. In contrast, this complement-independent lectin opsonic activity would remain intact if MASP-2 was the inhibitory target. An added benefit of MASP-2 as the therapeutic target to inhibit the lectin-dependent complement activation system is that the plasma concentration of MASP-2 is among the lowest of any complement protein ($\approx$500 ng/ml); therefore, correspondingly low concentrations of high-affinity inhibitors of MASP-2 may be required to obtain full inhibition (Moller-Kristensen, M., et al., *J. Immunol Methods* 282:159-167, 2003).

III. Role of Masp-2 in Various Diseases and Conditions and Therapeutic Methods Using Masp-2 Inhibitory Agents Ischemia Reperfusion Injury Ischemia reperfusion injury (FR) occurs when blood flow is restored after an extended period of ischemia. It is a common source of morbidity and mortality in a wide spectrum of diseases. Surgical patients are vulnerable after aortic aneurysm repair, cardiopulmonary bypass, vascular reanastomosis in connection with, for example, organ transplants (e.g., heart, lung, liver, kidney) and digit/extremity replantation, stroke, myocardial infarction and hemodynamic resuscitation following shock and/or surgical procedures. Patients with atherosclerotic diseases are prone to myocardial infarctions, strokes, and emboli-induced intestinal and lower-extremity ischemia. Patients with trauma frequently suffer from temporary ischemia of the limbs. In addition, any cause of massive blood loss leads to a whole-body I/R reaction.

The pathophysiology of FR injury is complex, with at least two major factors contributing to the process: complement activation and neutrophil stimulation with accompanying oxygen radical-mediated injury. In I/R injury, complement activation was first described during myocardial infarction over 30 years ago, and has led to numerous investigations on the contribution of the complement system to FR tissue injury (Hill, J. H., et al., *J. Exp. Med.* 133:885-900, 1971). Accumulating evidence now points to complement as a pivotal mediator in I/R injury. Complement inhibition has been successful in limiting injury in several animal models of I/R. In early studies, C3 depletion was achieved following infusion of cobra venom factor, reported to be beneficial during I/R in kidney and heart (Maroko, P. R., et al., 1978, *J. Clin Invest.* 61:661-670, 1978; Stein, S. H., et al., *Miner Electrolyte Metab.* 11:256-61, 1985). However, the soluble form of complement receptor 1 (sCR1) was the first complement-specific inhibitor utilized for the prevention of myocardial I/R injury (Weisman, H. F., et al., *Science* 249:146-51, 1990). sCR1 treatment during myocardial I/R attenuates infarction associated with decreased deposition of C5b-9 complexes along the coronary endothelium and decreased leukocyte infiltration after reperfusion.

In experimental myocardial I/R, C1 esterase inhibitor (C1 INH) administered before reperfusion prevents deposition of C1q and significantly reduced the area of cardiac muscle necrosis (Buerke, M., et al., 1995, *Circulation* 91:393-402, 1995). Animals genetically deficient in C3 have less local tissue necrosis after skeletal muscle or intestinal ischaemia (Weiser, M. R., et al., *J. Exp. Med.* 183:2343-48, 1996).

The membrane attack complex is the ultimate vehicle of complement-directed injury and studies in CS-deficient animals have shown decreased local and remote injury in models of I/R injury (Austen, W. G. Jr., et al., *Surgery* 126:343-48, 1999). An inhibitor of complement activation, soluble Crry (complement receptor-related gene Y), has been shown to be effective against injury when given both before and after the onset of murine intestinal reperfusion (Rehrig, S., et al., *J. Immunol.* 167:5921-27, 2001). In a model of skeletal muscle ischemia, the use of soluble complement receptor 1 (sCR1) also reduced muscle injury when given after the start of reperfusion (Kyriakides, C., et al., *Am. J. Physiol. Cell Physiol.* 281:C244-30, 2001). In a porcine model of myocardial I/R, animals treated with monoclonal antibody ("MoAb") to the anaphylatoxin C5a prior to reperfusion showed attenuated infarction (Amsterdam, E. A., et al., *Am. J. Physiol. Heart Circ. Physiol.* 268:H448-57, 1995). Rats treated with C5 MoAb demonstrated attenuated infarct size, neutrophil infiltration and apoptosis in the myocardium (Vakeva, A., et al., *Circulation* 97:2259-67, 1998). These experimental results highlight the importance of complement activation in the pathogenesis of FR injury.

It is unclear which complement pathway (classical, lectin or alternative) is predominantly involved in complement activation in I/R injury. Weiser et al. demonstrated an important role of the lectin and/or classical pathways during skeletal I/R by showing that C3- or C4-knockout mice were protected against FR injury based on a significant reduction in vascular permeability (Weiser, M. R., et al., *J. Exp. Med.* 183:2343-48, 1996). In contrast, renal I/R experiments with C4 knockout mice demonstrate no significant tissue protection, while C3-, C5-, and C6-knockout mice were protected from injury, suggesting that complement activation during renal FR injury occurs via the alternative pathway (Zhou, W., et al., *J. Clin. Invest.* 105:1363-71, 2000). Using factor D deficient mice, Stahl et al. recently presented evidence for an important role of the alternative pathway in intestinal I/R in mice (Stahl, G., et al., *Am. J. Pathol.* 162:449-55, 2003). In contrast, Williams et al. suggested a predominant role of the classical pathway for initiation of I/R injury in the intestine of mice by showing reduced organ staining for C3 and protection from injury in C4 and IgM (Rag1−/−) deficient mice (Williams, J. P., et al., *J. Appl. Physiol.* 86:938-42, 1999).

Treatment of rats in a myocardial I/R model with monoclonal antibodies against rat mannan-binding lectin (MBL) resulted in reduced postischemic reperfusion injury (Jordan, J. E., et al., *Circulation* 104:1413-18, 2001). MBL antibodies also reduced complement deposition on endothelial cells in vitro after oxidative stress indicating a role for the lectin pathway in myocardial I/R injury (Collard, C. D., et al., *Am. J. Pathol.* 156:1549-56, 2000). There is also evidence that I/R injury in some organs may be mediated by a specific category of IgM, termed natural antibodies, and activation of the classical pathway (Fleming, S. D., et al., *J. Immunol.* 169:2126-33, 2002; Reid, R. R., et al., *J. Immunol.* 169: 5433-40, 2002).

Several inhibitors of complement activation have been developed as potential therapeutic agents to prevent morbidity and mortality resulting from myocardial I/R complications. Two of these inhibitors, sCR1 (TP10) and humanized anti-C5 scFv (Pexelizumab), have completed Phase II clinical trials. Pexelizumab has additionally completed a Phase III clinical trial. Although TP10 was well tolerated and beneficial to patients in early Phase I/II trials, results from a Phase II trial ending in February 2002 failed to meet its primary endpoint. However, sub-group analysis of the data from male patients in a high-risk population undergoing open-heart procedures demonstrated significantly decreased mortality and infarct size. Administration of a humanized anti-C5 scFv decreased overall patient mortality associated with acute myocardial infarction in the COMA and COMPLY Phase II trials, but failed to meet the primary endpoint (Mahaffey, K. W., et al., *Circulation* 108:1176-83, 2003). Results from a recent Phase III anti-C5 scFv clinical trial (PRIMO-CABG) for improving surgically induced outcomes following coronary artery bypass were recently released. Although the primary endpoint for this study was not reached, the study demonstrated an overall reduction in postoperative patient morbidity and mortality.

Dr. Walsh and colleagues have demonstrated that mice lacking MBL, and hence devoid of MBL-dependent lectin pathway activation but with fully-active classical complement pathways, are protected from cardiac reperfusion injury with resultant preservation of cardiac function (Walsh et al., *J. Immunol.* 175:541-46, 2005). Significantly, mice that lack C1q, the recognition component of the classical complement pathway, but that have intact MBL complement pathway, are not protected from injury. These results indicate that the lectin pathway has a major role in the pathogenesis of myocardial reperfusion ischemic injury.

Complement activation is known to play an important role in tissue injury associated with gastrointestinal ischemia-reperfusion (I/R). Using a murine model of GI/R, a recent study by Hart and colleagues reports that mice genetically deficient in MBL are protected from gut injury after gastrointestinal I/R (Hart et al., *J. Immunol.* 174:6373-80, 2005). Addition of recombinant MBL to MBL-deficient mice significantly increased injury compared to untreated MBL-deficient mice after gastrointestinal I/R. In contrast, mice that genetically lack C1q, the classical pathway recognition component, are not protected from tissue injury after gastrointestinal I/R.

Kidney I/R is an important cause of acute renal failure. The complement system appears to be essentially involved in renal I/R injury. In a recent study, de Vries and colleagues report that the lectin pathway is activated in the course of experimental as well as clinical renal I/R injury (de Vries et al., *Am. J. Path.* 165:1677-88, 2004). Moreover, the lectin pathway precedes and co-localizes with complement C3, C6, and C9 deposition in the course of renal I/R. These results indicate that the lectin pathway of complement activation is involved in renal I/R injury.

One aspect of the invention is thus directed to the treatment of ischemia reperfusion injuries by treating a subject experiencing ischemic reperfusion with a therapeutically effective amount of a MASP-2 inhibitory agent in a pharmaceutical carrier. The MASP-2 inhibitory agent may be administered to the subject by intra-arterial, intravenous, intracranial, intramuscular, subcutaneous, or other parenteral administration, and potentially orally for non-peptidergic inhibitors, and most suitably by intra-arterial or intravenous administration. Administration of the MASP-2 inhibitory compositions of the present invention suitably commences immediately after or as soon as possible after an ischemia reperfusion event. In instances where reperfusion occurs in a controlled environment (e.g., following an aortic aneurism repair, organ transplant or reattachment of severed or traumatized limbs or digits), the MASP-2 inhibitory agent may be administered prior to and/or during and/or after reperfusion. Administration may be repeated periodically as determined by a physician for optimal therapeutic effect.

Atherosclerosis

There is considerable evidence that complement activation is involved in atherogenesis in humans. A number of studies have convincingly shown that, although no significant complement activation takes place in normal arteries, complement is extensively activated in atherosclerotic lesions and is especially strong in vulnerable and ruptured plaques. Components of the terminal complement pathway are frequently found in human atheromas (Niculescu, F., et al., *Mol. Immunol.* 36:949-55.10-12, 1999; Rus, H. G., et al., *Immunol. Lett.* 20:305-310, 1989; Torzewski, M., et al., *Arterioscler. Thromb. Vasc. Biol.* 18:369-378, 1998). C3 and C4 deposition in arterial lesions has also been demonstrated (Hansson, G. K., et al., *Acta Pathol. Microbiol. Immunol. Scand.* (A) 92:429-35, 1984). The extent of C5b-9 deposition was found to correlate with the severity of the lesion (Vlaicu, R., et al., *Atherosclerosis* 57:163-77, 1985). Deposition of complement iC3b, but not C5b-9, was especially strong in ruptured and vulnerable plaques, suggesting that complement activation may be a factor in acute coronary syndromes (Taskinen S., et al., *Biochem. J.* 367:403-12, 2002). In experimental atheroma in rabbits, complement activation was found to precede the development of lesions (Seifer, P. S., et al., *Lab Invest.* 60:747-54, 1989).

In atherosclerotic lesions, complement is activated via the classic and alternative pathways, but there is little evidence, as yet, of complement activation via the lectin pathway. Several components of the arterial wall may trigger complement activation. The classical pathway of complement may be activated by C-reactive protein (CRP) bound to enzymatically degraded LDL (Bhakdi, S., et al., *Arterioscler. Thromb. Vasc. Biol.* 19:2348-54, 1999). Consistent with this view is the finding that the terminal complement proteins colocalize with CRP in the intima of early human lesions (Torzewski, J., et al., *Arterioscler. Thromb. Vasc. Biol.* 18:1386-92, 1998). Likewise, immunoglobulin M or IgG antibodies specific for oxidized LDL within lesions may activate the classical pathway (Witztum, J. L., *Lancet* 344: 793-95, 1994). Lipids isolated from human atherosclerotic lesions have a high content of unesterified cholesterol and are able to activate the alternative pathway (Seifert P. S., et al., *J. Exp. Med.* 172:547-57, 1990). *Chlamydia pneumoniae*, a Gram-negative bacteria frequently associated with atherosclerotic lesions, may also activate the alternative pathway of complement (Campbell L. A., et al., *J. Infect. Dis.* 172:585-8, 1995). Other potential complement activators present in atherosclerotic lesions include cholesterol crystals and cell debris, both of which can activate the alternative pathway (Seifert, P. S., et al., *Mol. Immunol.* 24:1303-08, 1987).

Byproducts of complement activation are known to have many biological properties that could influence the development of atherosclerotic lesions. Local complement activation may induce cell lysis and generate at least some of the cell debris found in the necrotic core of advanced lesions (Niculescu, F. et al., *Mol. Immunol.* 36:949-55.10-12, 1999). Sublytic complement activation could be a significant factor contributing to smooth muscle cell proliferation and to monocyte infiltration into the arterial intima during atherogenesis (Torzewski J., et al., *Arterioscler. Thromb. Vasc. Biol.* 18:673-77, 1996). Persistent activation of complement may be detrimental because it may trigger and sustain inflammation. In addition to the infiltration of complement components from blood plasma, arterial cells express messenger RNA for complement proteins and the expression of various complement components is upregulated in atherosclerotic lesions (Yasojima, K., et al., *Arterioscler. Thromb. Vasc. Biol.* 21:1214-19, 2001).

A limited number of studies on the influence of complement protein deficiencies on atherogenesis have been reported. The results in experimental animal models have been conflicting. In the rat, the formation of atherosclerotic-like lesions induced by toxic doses of vitamin D was diminished in complement-depleted animals (Geertinger P., et al., *Acta. Pathol. Microbiol. Scand.* (A) 78:284-88, 1970). Furthermore, in cholesterol-fed rabbits, complement inhibition either by genetic C6 deficiency (Geertinger, P., et al., *Artery* 1:177-84, 1977; Schmiedt, W., et al., *Arterioscl. Thromb. Vasc. Biol.* 18:1790-1795, 1998) or by anticomplement agent K-76 COONa (Saito, E., et al., *J. Drug Dev.* 3:147-54, 1990) suppressed the development of atherosclerosis without affecting the serum cholesterol levels. In contrast, a recent study reported that C5 deficiency does not reduce the development of atherosclerotic lesions in apolipoprotein E (ApoE) deficient mice (Patel, S., et al., *Biochem. Biophys. Res. Commun.* 286:164-70, 2001). However, in another study the development of atherosclerotic lesions in LDLR-deficient (ldlr-) mice with or without C3 deficiency was evaluated (Buono, C., et al., *Circulation* 105:3025-31, 2002). They found that the maturation of atheromas to atherosclerotic-like lesions depends in part of the presence of an intact complement system.

One aspect of the invention is thus directed to the treatment or prevention of atherosclerosis by treating a subject suffering from or prone to atherosclerosis with a therapeutically effective amount of a MASP-2 inhibitory agent in a pharmaceutical carrier. The MASP-2 inhibitory agent may be administered to the subject by intra-arterial, intravenous, intrathecal, intracranial, intramuscular, subcutaneous or other parenteral administration, and potentially orally for non-peptidergic inhibitors. Administration of the MASP-2 inhibitory composition may commence after diagnosis of atherosclerosis in a subject or prophylactically in a subject at high risk of developing such a condition. Administration may be repeated periodically as determined by a physician for optimal therapeutic effect.

Other Vascular Diseases and Conditions

The endothelium is largely exposed to the immune system and is particularly vulnerable to complement proteins that are present in plasma. Complement-mediated vascular injury has been shown to contribute to the pathophysiology of several diseases of the cardiovascular system, including atherosclerosis (Seifert, P. S., et al., *Atherosclerosis* 73:91-104, 1988), ischemia-reperfusion injury (Weisman, H. F., *Science* 249:146-51, 1990) and myocardial infarction (Tada, T., et al., *Virchows Arch* 430:327-332, 1997). Evidence suggests that complement activation may extend to other vascular conditions.

For example, there is evidence that complement activation contributes to the pathogenesis of many forms of vasculitis, including: Henoch-Schonlein purpura nephritis, systemic lupus erythematosus-associated vasculitis, vasculitis associated with rheumatoid arthritis (also called malignant rheumatoid arthritis), immune complex vasculitis, and Takayasu's disease. Henoch-Schonlein purpura nephritis is a form of systemic vasculitis of the small vessels with immune pathogenesis, in which activation of complement through the lectin pathway leading to C5b-9-induced endothelial damage is recognized as an important mechanism (Kawana, S., et al., *Arch. Dermatol. Res.* 282:183-7, 1990; Endo, M., et al., *Am J. Kidney Dis.* 35:401-7, 2000). Systemic lupus erythematosus (SLE) is an example of systemic autoimmune diseases that affects multiple organs, including skin, kidneys, joints, serosal surfaces, and central nervous system, and is frequently associated with severe vasculitis. IgG anti-endothelial antibodies and IgG complexes capable of binding to endothelial cells are present in the sera of patients with active SLE, and deposits of IgG immune complexes and complement are found in blood vessel walls of patients with SLE vasculitis (Cines, D. B., et al., *J. Clin. Invest.* 73:611-25, 1984). Rheumatoid arthritis associated with vasculitis, also called malignant rheumatoid arthritis (Tomooka, K., *Fukuoka Igaku Zasshi* 80:456-66, 1989), immune-complex vasculitis, vasculitis associated with hepatitis A, leukocytoclastic vasculitis, and the arteritis known as Takayasu's disease, form another pleomorphic group of human diseases in which complement-dependent cytotoxicity against endothelial and other cell types plays a documented role (Tripathy, N. K., et al., *J. Rheumatol.* 28:805-8, 2001).

Evidence also suggests that complement activation plays a role in dilated cardiomyopathy. Dilated cardiomyopathy is a syndrome characterized by cardiac enlargement and impaired systolic function of the heart. Recent data suggests that ongoing inflammation in the myocardium may contribute to the development of disease. C5b-9, the terminal membrane attack complex of complement, is known to significantly correlate with immunoglobulin deposition and myocardial expression of TNF-alpha. In myocardial biopsies from 28 patients with dilated cardiomyopathy, myocardial accumulation of C5b-9 was demonstrated, suggesting that chronic immunoglobulin-mediated complement activation in the myocardium may contribute in part to the progression of dilated cardiomyopathy (Zwaka, T. P., et al., *Am. J. Pathol.* 161(2):449-57, 2002).

One aspect of the invention is thus directed to the treatment of a vascular condition, including cardiovascular conditions, cerebrovascular conditions, peripheral (e.g., musculoskeletal) vascular conditions, renovascular conditions, and mesenteric/enteric vascular conditions, by administering a composition comprising a therapeutically effective amount of a MASP-2 inhibitory agent in a pharmaceutical carrier. Conditions for which the invention is believed to be suited include, without limitation: vasculitis, including Henoch-Schonlein purpura nephritis, systemic lupus erythematosus-associated vasculitis, vasculitis associated with rheumatoid arthritis (also called malignant rheumatoid arthritis), immune complex vasculitis, and Takayasu's disease; dilated cardiomyopathy; diabetic angiopathy; Kawasaki's disease (arteritis); and venous gas embolus (VGE). Also, given that complement activation occurs as a result of luminal trauma and the foreign-body inflammatory response associated with cardiovascular interventional procedures, it is believed that the MASP-2 inhibitory compositions of the present invention may also be used in the inhibition of restenosis following stent placement, rotational atherectomy and/or percutaneous transluminal coronary angioplasty (PTCA), either alone or in combination with other restenosis inhibitory agents such as are disclosed in U.S. Pat. No. 6,492,332 to Demopulos.

The MASP-2 inhibitory agent may be administered to the subject by intra-arterial, intravenous, intramuscular, intrathecal, intracranial, subcutaneous or other parenteral administration, and potentially orally for non-peptidergic inhibitors. Administration may be repeated periodically as determined by a physician for optimal therapeutic effect. For the inhibition of restenosis, the MASP-2 inhibitory composition may be administered before and/or during and/or after the placement of a stent or the atherectomy or angioplasty procedure. Alternately, the MASP-2 inhibitory composition may be coated on or incorporated into the stent.

Gastrointestinal Disorders

Ulcerative colitis and Crohn's disease are chronic inflammatory disorders of the bowel that fall under the banner of inflammatory bowel disease (IBD). IBD is characterized by spontaneously occurring, chronic, relapsing inflammation of unknown origin. Despite extensive research into the disease in both humans and experimental animals, the precise mechanisms of pathology remain to be elucidated. However, the complement system is believed to be activated in patients with IBD and is thought to play a role in disease pathogenesis (Kolios, G., et al., *Hepato-Gastroenterology* 45:1601-9, 1998; Elmgreen, J., *Dan. Med. Bull.* 33:222, 1986).

It has been shown that C3b and other activated complement products are found at the luminal face of surface epithelial cells, as well as in the muscularis mucosa and submucosal blood vessels in IBD patients (Halstensen, T. S., et al., *Immunol. Res.* 10:485-92, 1991; Halstensen, T. S., et al., *Gastroenterology* 98:1264, 1990). Furthermore, polymorphonuclear cell infiltration, usually a result of C5a generation, characteristically is seen in the inflammatory bowel (Kohl, J., *Mol. Immunol.* 38:175, 2001). The multifunctional complement inhibitor K-76, has also been reported to produce symptomatic improvement of ulcerative colitis in a small clinical study (Kitano, A., et al., *Dis. Colon Rectum* 35:560, 1992), as well as in a model of carrageenan-induced colitis in rabbits (Kitano, A., et al., *Clin. Exp. Immunol.* 94:348-53, 1993).

A novel human C5a receptor antagonist has been shown to protect against disease pathology in a rat model of IBD (Woodruff, T. M., et al., *J. Immunol.* 171:5514-20, 2003). Mice that were genetically deficient in decay-accelerating factor (DAF), a membrane complement regulatory protein, were used in a model of IBD to demonstrate that DAF deficiency resulted in markedly greater tissue damage and increased proinflammatory cytokine production (Lin, F., et al., *J. Immunol.* 172:3836-41, 2004). Therefore, control of complement is important in regulating gut homeostasis and may be a major pathogenic mechanism involved in the development of IBD.

The present invention thus provides methods for inhibiting MASP-2-dependent complement activation in subjects suffering from inflammatory gastrointestinal disorders, including but not limited to pancreatitis, diverticulitis and bowel disorders including Crohn's disease, ulcerative colitis, and irritable bowel syndrome, by administering a composition comprising a therapeutically effect amount of a MASP-2 inhibitory agent in a pharmaceutical carrier to a patient suffering from such a disorder. The MASP-2 inhibitory agent may be administered to the subject by intra-arterial, intravenous, intramuscular, subcutaneous, intrathecal, intracranial or other parenteral administration, and potentially orally for non-peptidergic inhibitors. Administration may suitably be repeated periodically as determined by a physician to control symptoms of the disorder being treated.

Pulmonary Conditions

Complement has been implicated in the pathogenesis of many lung inflammatory disorders, including: acute respiratory distress syndrome (ARDS) (Ware, I., et al., *N. Engl. J. Med.* 342:1334-49, 2000); transfusion-related acute lung injury (TRALI) (Seeger, W., et al., *Blood* 76:1438-44, 1990); ischemia/reperfusion acute lung injury (Xiao, F., et al., *J. Appl. Physiol.* 82:1459-65, 1997); chronic obstructive pulmonary disease (COPD) (Marc, M. M., et al., *Am. J. Respir. Cell Mol. Biol.* (Epub ahead of print), Mar. 23, 2004); asthma (Krug, N., et al., *Am. J. Respir. Crit. Care Med.* 164:1841-43, 2001); Wegener's granulomatosis (Kalluri, R., et al., *J. Am. Soc. Nephrol.* 8:1795-800, 1997); and anti-glomerular basement membrane disease (Goodpasture's disease) (Kondo, C., et al., *Clin. Exp. Immunol.* 124:323-9, 2001).

It is now well accepted that much of the pathophysiology of ARDS involves a dysregulated inflammatory cascade that begins as a normal response to an infection or other inciting event, but ultimately causes significant autoinjury to the host (Stanley, T. P., *Emerging Therapeutic Targets* 2:1-16, 1998). Patients with ARDS almost universally show evidence of extensive complement activation (increased plasma levels of complement components C3a and C5a), and the degree of complement activation has been correlated with the development and outcome of ARDS (Hammerschmidt, D. F., et al., *Lancet* 1:947-49, 1980; Solomkin, J. S., et al., *J. Surgery* 97:668-78, 1985).

Various experimental and clinical data suggest a role for complement activation in the pathophysiology of ARDS. In animal models, systemic activation of complement leads to acute lung injury with histopathology similar to that seen in human ARDS (Till, G. O., et al., *Am. J. Pathol.* 129:44-53, 1987; Ward, P. A., *Am. J. Pathol.* 149:1081-86, 1996). Inhibiting the complement cascade by general complement depletion or by specific inhibition of C5a confers protection in animal models of acute lung injury (Mulligan, M. S., et al., *J. Clin. Invest.* 98:503-512, 1996). In rat models, sCR1 has a protective effect in complement- and neutrophil-mediated lung injury (Mulligan, M. S., Yeh, et al., *J. Immunol.* 148:1479-85, 1992). In addition, virtually all complement components can be produced locally in the lung by type II alveolar cells, alveolar macrophages and lung fibroblasts (Hetland, G., et al., *Scand. J. Immunol.* 24:603-8, 1986; Rothman, B. I., et al., *J. Immunol.* 145:592-98, 1990). Thus the complement cascade is well positioned to contribute significantly to lung inflammation and, consequently, to lung injury in ARDS.

Asthma is, in essence, an inflammatory disease. The cardinal features of allergic asthma include airway hyperresponsiveness to a variety of specific and nonspecific stimuli, excessive airway mucus production, pulmonary eosinophilia, and elevated concentration of serum IgE. Although asthma is multifactorial in origin, it is generally accepted that it arises as a result of inappropriate immunological responses to common environmental antigens in genetically susceptible individuals. The fact that the complement system is highly activated in the human asthmatic lung is well documented (Humbles, A. A., et al., *Nature* 406:998-01, 2002; van de Graf, E. A., et al., *J. Immunol. Methods* 147:241-50, 1992). Furthermore, recent data from animal models and humans provide evidence that complement activation is an important mechanism contributing to disease pathogenesis (Karp, C. L., et al., *Nat. Immunol.* 1:221-26, 2000; Bautsch, W., et al., *J. Immunol.* 165:5401-5, 2000; Drouin, S. M., et al., *J. Immunol.* 169:5926-33, 2002; Walters, D. M., et al., *Am. J. Respir. Cell Mol. Biol.* 27:413-18, 2002). A role for the lectin pathway in asthma is supported by studies using a murine model of chronic fungal asthma. Mice with a genetic deficiency in mannan-binding lectin develop an altered airway hyperresponsiveness compared to normal animals in this asthma model (Hogaboam, C. M., et al., *J. Leukoc. Biol.* 75:805-14, 2004).

Complement may be activated in asthma via several pathways, including: (a) activation through the classical pathway as a result of allergen-antibody complex formation; (b) alternative pathway activation on allergen surfaces; (c) activation of the lectin pathway through engagement of carbohydrate structures on allergens; and (d) cleavage of C3 and C5 by proteases released from inflammatory cells. Although much remains to be learned about the complex role played by complement in asthma, identification of the complement activation pathways involved in the development of allergic asthma may provide a focus for development of novel therapeutic strategies for this increasingly important disease.

A number of studies using animal models have demonstrated a critical role for C3 and its cleavage product, C3a, in the development of the allergic phenotype. Drouin and colleagues used C3-deficient mice in the ovalbumin (OVA)/ *Aspergillus fumigatus* asthma model (Drouin et al., *J. Immunol.* 167:4141-45, 2001). They found that, when challenged with allergen, mice deficient in C3 exhibit strikingly diminished AHR and lung eosinophilia compared to matched wild type control mice. Furthermore, these C3-deficient mice had dramatically reduced numbers of IL-4 producing cells and attenuated Ag-specific IgE and IgG1 responses. Taube and colleagues obtained similar results in the OVA model of asthma by blocking complement activation at the level of C3 and C4 using a soluble recombinant form of the mouse complement receptor Crry (Taube et al., *Am. J. Respir. Crit. Care Med.* 168:1333-41, 2003). Humbles and colleagues deleted the C3aR in mice to examine the role of C3a in eosinophil function (Humbles et al., *Nature* 406:998-1001, 2000). Using the OVA model of asthma, they observed near complete protection from the development of AHR to aerosolized methacholine. Drouin and colleagues (2002) have used C3aR-deficient mice in the OVA/*A. fumigatus* asthma model and demonstrated an attenuated allergic response very similar to C3-deficient animals with diminished AHR, eosinophil recruitment, TH2 cytokine production, and mucus secretion in the lung, as well as reduced Ag-specific IgE and IgG1 responses (Drouin et al., *J. Immunol.* 169: 5926-33, 2002). Bautsch and colleagues performed investigations using a strain of guinea pigs that have a natural deletion of C3aR (Bautsch et al., *J. Immunol.* 165:5401-05, 2000). Using an OVA model of allergic asthma, they observed significant protection from airway bronchoconstriction following antigen challenge.

A number of recent studies using animal models have demonstrated a critical role for C5 and its cleavage product C5a, in the development of the allergic phenotype. Abe and colleagues have reported evidence that links C5aR activation to airway inflammation, cytokine production and airway responsiveness (Abe et al., *J. Immunol.* 167:4651-60, 2001). In their studies, inhibition of complement activation by soluble CR1, futhan (an inhibitor of complement activation) or synthetic hexapeptide C5a antagonist blocked the inflammatory response and airway responsiveness to methacholine. In studies using a blocking anti-C5 monoclonal antibody Peng and colleagues found that C5 activation contributed substantially to both airway inflammation and AHR in the OVA model of asthma (Peng et al., *J. Clin. Invest.* 115:1590-1600, 2005). Also, Baelder and colleagues reported that blockade of the C5aR substantially reduced AHR in the *A. fumigatus* model of asthma (Baelder et al., *J. Immunol.* 174:783-89, 2005). Furthermore, blockade of both the C3aR and the C5aR significantly reduced airway inflammation as demonstrated by reduced numbers of neutrophils and eosinophils in BAL.

Although the previously listed studies highlight the importance of complement factors C3 and C5 and their cleavage products in the pathogenesis of experimental allergic asthma, these studies provide no information about the contribution of each of the three complement activation pathways since C3 and C5 are common to all three activation pathways. However, a recent study by Hogaboam and colleagues indicates that the lectin pathway may have a major role in the pathogenesis of asthma (Hogaboam et al., *J. Leukocyte Biol.* 75:805-814, 2004). These studies used mice genetically deficient in mannan-binding lectin-A (MBL-A), a carbohydrate binding protein that functions as the recognition component for activation of the lectin complement pathway. In a model of chronic fungal asthma, MBL-A(+/+) and MBL-A(−/−) *A. fumigatus*-sensitized mice were examined at days 4 and 28 after an i. t. challenge with *A. fumigatus* conidia. AHR in sensitized MBL-A(−/−) mice was significantly attenuated at both times after conidia challenge compared with the sensitized MBL-A (+/+) group. They found that lung TH2 cytokine levels (IL-4, IL-5 and IL-13) were significantly lower in *A. fumigatus*-sensitized MBL-A(−/−) mice compared to the wild-type group at day 4 after conidia. Their results indicate that MBL-A and the lectin pathway have a major role in the development and maintenance of AHR during chronic fungal asthma.

Results from a recent clinical study in which the association between a specific MBL polymorphism and development of asthma provides further evidence that the lectin pathway may play an important pathological role in this disease (Kaur et al., *Clin. Experimental Immunol.* 143:414-19, 2006). Plasma concentrations of MBL vary widely between individuals, and this is primarily attributable to the genetic polymorphisms within the MBL gene. They found that individuals who carry at least one copy of a specific MBL polymorphism that up regulates MBL expression two- to four-fold have an almost five-fold increased risk of developing bronchial asthma. There was also an increased severity of disease markers in bronchial asthma patients who carry this MBL polymorphism.

An aspect of the invention thus provides a method for treating pulmonary disorders, by administering a composition comprising a therapeutically effective amount of a MASP-2 inhibitory agent in a pharmaceutical carrier to a subject suffering from pulmonary disorders, including without limitation, acute respiratory distress syndrome, transfusion-related acute lung injury, ischemia/reperfusion acute lung injury, chronic obstructive pulmonary disease, asthma, Wegener's granulomatosis, antiglomerular basement membrane disease (Goodpasture's disease), meconium aspiration syndrome, bronchiolitis obliterans syndrome, idiopathic pulmonary fibrosis, acute lung injury secondary to burn, non-cardiogenic pulmonary edema, transfusion-related respiratory depression, and emphysema. The MASP-2 inhibitory agent may be administered to the subject systemically, such as by intra-arterial, intravenous, intramuscular, inhalational, nasal, subcutaneous or other parenteral administration, or potentially by oral administration for non-peptidergic agents. The MASP-2 inhibitory agent composition may be combined with one or more additional therapeutic agents, including anti-inflammatory agents, antihistamines, corticosteroids or antimicrobial agents. Administration may be repeated as determined by a physician until the condition has been resolved.

Extracorporeal Circulation

There are numerous medical procedures during which blood is diverted from a patient's circulatory system (extracorporeal circulation systems or ECC). Such procedures include hemodialysis, plasmapheresis, leukopheresis, extracorporeal membrane oxygenator (ECMO), heparin-induced extracorporeal membrane oxygenation LDL precipitation (HELP) and cardiopulmonary bypass (CPB). These procedures expose blood or blood products to foreign surfaces that may alter normal cellular function and hemostasis. In pioneering studies Craddock et al. identified complement activation as the probable cause of granulocytopenia during hemodialysis (Craddock, P. R., et al., *N. Engl. J. Med.* 296:769-74, 1977). The results of numerous studies between 1977 and the present time indicate that many of the adverse events experienced by patients undergoing hemodialysis or CPB are caused by activation of the complement system (Chenoweth, D. E., *Ann. N.Y. Acad. Sci.* 5/6:306-313, 1987; Hugli, T. E., *Complement* 3:111-127, 1986; Cheung, A. K., *J. Am. Soc. Nephrol.* 1:150-161, 1990; Johnson, R. J., *Nephrol. Dial. Transplant* 9:36-45 1994). For example, the complement activating potential has been shown to be an important criterion in determination of the biocompatibility of hemodialyzers with respect to recovery of renal function, susceptibility to infection, pulmonary dysfunction, morbidity, and survival rate of patients with renal failure (Hakim, R. M., *Kidney Int.* 44:484-4946, 1993).

It has been largely believed that complement activation by hemodialysis membranes occurs by alternative pathway mechanisms due to weak C4a generation (Kirklin, J. K., et al., *J. Thorac. Cardiovasc. Surg.* 86:845-57, 1983; Vallhonrat, H., et al., *ASAIO J.* 45:113-4, 1999), but recent work suggests that the classical pathway may also be involved (Wachtfogel, Y. T., et al., *Blood* 73:468-471, 1989). However, there is still inadequate understanding of the factors initiating and controlling complement activation on artificial surfaces including biomedical polymers. For example, Cuprophan membrane used in hemodialysis has been classified as a very potent complement activator. While not wishing to be limited by theory, the inventors theorize that this could perhaps be explained in part by its polysaccharide nature. The MASP-2-dependent complement activation system identified in this patent provides a mechanism whereby activation of the lectin pathway triggers alternative pathway activation.

Patients undergoing ECC during CPB suffer a systemic inflammatory reaction, which is partly caused by exposure of blood to the artificial surfaces of the extracorporeal circuit, but also by surface-independent factors like surgical trauma and ischemia-reperfusion injury (Butler, J., et al., *Ann. Thorac. Surg.* 55:552-9, 1993; Edmunds, L. H., *Ann. Thorac. Surg.* 66(Suppl):S12-6, 1998; Asimakopoulos, G., *Perfusion* 14:269-77, 1999). The CPB-triggered inflammatory reaction can result in postsurgical complications, generally termed "postperfusion syndrome." Among these postoperative events are cognitive deficits (Fitch, J., et al., *Circulation* 100(25):2499-2506, 1999), respiratory failure, bleeding disorders, renal dysfunction and, in the most severe cases, multiple organ failure (Wan, S., et al., *Chest* 112:676-692, 1997). Coronary bypass surgery with CPB leads to profound activation of complement, in contrast to surgery without CPB but with a comparable degree of surgical trauma (E. Fosse, 1987). Therefore, the primary suspected cause of these CPB-related problems is inappropriate activation of complement during the bypass procedure (Chenoweth, K., et al., *N. Engl. J. Med.* 304:497-503, 1981; Haslam, P., et al., *Anaesthesia* 25:22-26, 1980; J. K. Kirklin, et al., *J. Thorac. Cardiovasc. Surg.* 86:845-857, 1983; Moore, F. D., et al., *Ann. Surg* 208:95-103, 1988; Steinberg, J., et al., *J. Thorac. Cardiovasc. Surg* 106:1901-1918, 1993). In CPB circuits, the alternative complement pathway plays a predominant role in complement activation, resulting from the interaction of blood with the artificial surfaces of the CPB circuits (Kirklin, J. K., et al., *J. Thorac. Cardiovasc. Surg.* 86:845-57, 1983; Kirklin, J. K., et al., *Ann. Thorac. Surg.* 41:193-199, 1986; Vallhonrat H., et al., *ASAIO J.* 45:113-4, 1999). However, there is also evidence that the classical complement pathway is activated during CPB (Wachtfogel, Y. T., et al., *Blood* 73:468-471, 1989).

Primary inflammatory substances are generated after activation of the complement system, including anaphylatoxins C3a and C5a, the opsonin C3b, and the membrane attack complex C5b-9. C3a and C5a are potent stimulators of neutrophils, monocytes, and platelets (Haeffner-Cavaillon, N., et al., *J. Immunol.* 139:794-9, 1987; Fletcher, M. P., et al., *Am. J. Physiol.* 265:H1750-61, 1993; Rinder, C. S., et al., *J. Clin. Invest.* 96:1564-72, 1995; Rinder, C. S., et al., *Circulation* 100:553-8, 1999). Activation of these cells results in release of proinflammatory cytokines (IL-1, IL-6, IL-8, TNF alpha), oxidative free radicals and proteases (Schindler, R., et al., *Blood* 76:1631-8, 1990; Cruickshank, A. M., et al., *Clin Sci. (Lond)* 79:161-5, 1990; Kawamura, T., et al., *Can. J. Anaesth.* 40:1016-21, 1993; Steinberg, J. B., et al., *J. Thorac. Cardiovasc. Surg.* 106:1008-1, 1993; Finn, A., et al., *J. Thorac. Cardiovasc. Surg.* 105:234-41, 1993; Ashraf, S. S., et al., *J. Cardiothorac. Vasc. Anesth.* 11:718-22, 1997). C5a has been shown to upregulate adhesion molecules CD11b and CD18 of Mac-1 in polymorphonuclear cells (PMNs) and to induce degranulation of PMNs to release proinflammatory enzymes. Rinder, C., et al., *Cardiovasc Pharmacol.* 27(Suppl 1):56-12, 1996; Evangelista, V., et al., *Blood* 93:876-85, 1999; Kinkade, J. M., Jr., et al., *Biochem. Biophys. Res. Commun.* 114:296-303, 1983; Lamb, N. J., et al., *Crit. Care Med.* 27:1738-44, 1999; Fujie, K., et al., *Eur. J. Pharmacol.* 374:117-25, 1999. C5b-9 induces the expression of adhesion molecule P-selectin (CD62P) on platelets (Rinder, C. S., et al., *J. Thorac. Cardiovasc. Surg.* 118:460-6, 1999), whereas both C5a and C5b-9 induce surface expression of P-selectin on endothelial cells (Foreman, K. E., et al., *J. Clin. Invest.* 94:1147-55, 1994). These adhesion molecules are involved in the interaction among leukocytes, platelets and endothelial cells. The expression of adhesion molecules on activated endothelial cells is responsible for sequestration of activated leukocytes, which then mediate tissue inflammation and injury (Evangelista, V., *Blood* 1999; Foreman, K. E., *J. Clin. Invest.* 1994; Lentsch, A. B., et al., *J. Pathol.* 190:343-8, 2000). It is the actions of these complement activation products on neutrophils, monocytes, platelets and other circulatory cells that likely lead to the various problems that arise after CPB.

Several complement inhibitors are being studied for potential applications in CPB. They include a recombinant soluble complement receptor 1 (sCR1) (Chai, P. J., et al., *Circulation* 101:541-6, 2000), a humanized single chain anti-C5 antibody (h5G1.1-scFv or Pexelizumab) (Fitch, J. C. K., et al., *Circulation* 100:3499-506, 1999), a recombinant fusion hybrid (CAB-2) of human membrane cofactor protein and human decay accelerating factor (Rinder, C. S., et al., *Circulation* 100:553-8, 1999), a 13-residue C3-binding cyclic peptide (Compstatin) (Nilsson, B., et al., *Blood* 92:1661-7, 1998) and an anti-factor D MoAb (Fung, M., et al., *J. Thoracic Cardiovasc. Surg.* 122:113-22, 2001). SCR1 and CAB-2 inhibit the classical and alternative complement pathways at the steps of C3 and C5 activation. Compstatin inhibits both complement pathways at the step of C3 activation, whereas h5G1.1-scFv does so only at the step of C5 activation. Anti-factor D MoAb inhibits the alternative pathway at the steps of C3 and C5 activation. However, none of these complement inhibitors would specifically inhibit the MASP-2-dependent complement activation system identified in this patent.

Results from a large prospective phase 3 clinical study to investigate the efficacy and safety of the humanized single chain anti-C5 antibody (h5G1.1-scFv, pexelizu mab) in reducing perioperative MI and mortality in coronary artery bypass graft (CABG) surgery has been reported (Verner, E. D., et al., *JAMA* 291:2319-27, 2004). Compared with placebo, pexelizu mab was not associated with a significant reduction in the risk of the composite end point of death or MI in 2746 patients who had undergone CABG surgery. However, there was a statistically significant reduction 30 days after the procedure among all 3099 patients undergoing CABG surgery with or without valve surgery. Since pexelizu mab inhibits at the step of C5 activation, it inhibits C5a and sC5b-9 generation but has no effect on generation of the other two potent complement inflammatory substances, C3a and opsonic C3b, which are also known to contribute to the CPB-triggered inflammatory reaction.

One aspect of the invention is thus directed to the prevention or treatment of extracorporeal exposure-triggered inflammatory reaction by treating a subject undergoing an extracorporeal circulation procedure with a composition comprising a therapeutically effective amount of a MASP-2 inhibitory agent in a pharmaceutical carrier, including patients undergoing hemodialysis, plasmapheresis, leukopheresis, extracorporeal membrane oxygenation (ECMO), heparin-induced extracorporeal membrane oxygenation LDL precipitation (HELP) and cardiopulmonary bypass (CPB). MASP-2 inhibitory agent treatment in accordance with the methods of the present invention is believed to be useful in reducing or preventing the cognitive dysfunction that sometimes results from CPB procedures. The MASP-2 inhibitory agent may be administered to the subject preprocedurally and/or intraprocedurally and/or postprocedurally, such as by intra-arterial, intravenous, intramuscular, subcutaneous or other parenteral administration. Alternately, the MASP-2 inhibitory agent may be introduced to the subject's bloodstream during extracorporeal circulation, such as by injecting the MASP-2 inhibitory agent into tubing or a membrane through or past which the blood is circulated or by contacting the blood with a surface that has been coated with the MASP-2 inhibitory agent such as an interior wall of the tubing, membrane or other surface such as a CPB device.

Inflammatory and Non-Inflammatory Arthritides and Other Musculoskeletal Diseases Activation of the complement system has been implicated in the pathogenesis of a wide variety of rheumatological diseases; including rheumatoid arthritis (Linton, S. M., et al., *Molec. Immunol.* 36:905-14, 1999), juvenile rheumatoid arthritis (Mollnes, T. E., et al., *Arthritis Rheum.* 29:1359-64, 1986), osteoarthritis (Kemp, P. A., et al., *J. Clin. Lab. Immunol.* 37:147-62, 1992), systemic lupus erythematosis (SLE) (Molina, H., *Current Opinion in Rheumatol.* 14:492-497, 2002), Behcet's syndrome (Rumfeld, W. R., et al., *Br. J. Rheumatol.* 25:266-70, 1986) and Sjogren's syndrome (Sanders, M. E., et al., *J. Immunol.* 138:2095-9, 1987).

There is compelling evidence that immune-complex-triggered complement activation is a major pathological mechanism that contributes to tissue damage in rheumatoid arthritis (RA). There are numerous publications documenting that complement activation products are elevated in the plasma of RA patients (Morgan, B. P., et al., *Clin. Exp. Immunol,* 73:473-478, 1988; Auda, G., et al., *Rheumatol. Int.* 10:185-189, 1990; Rumfeld, W. R., et al., *Br. J. Rheumatol.* 25:266-270, 1986). Complement activation products such as C3a, C5a, and sC5b-9 have also been found within inflamed rheumatic joints and positive correlations have been established between the degree of complement activation and the severity of RA (Makinde, V. A., et al., *Ann. Rheum. Dis.* 48:302-306, 1989; Brodeur, J. P., et al., *Arthritis Rheumatism* 34:1531-1537, 1991). In both adult and juvenile rheumatoid arthritis, elevated serum and synovial fluid levels of alternative pathway complement activation product Bb compared to C4d (a marker for classical pathway activation), indicate that complement activation is mediated predominantly by the alternative pathway (El-Ghobarey, A. F. et al., *J. Rheumatology* 7:453-460, 1980; Agarwal, A., et al., *Rheumatology* 39:189-192, 2000). Complement activation products can directly damage tissue (via C5b-9) or indirectly mediate inflammation through recruitment of inflammatory cells by the anaphylatoxins C3a and C5a.

Animal models of experimental arthritis have been widely used to investigate the role of complement in the pathogenesis of RA. Complement depletion by cobra venom factor in animal models of RA prevents the onset of arthritis (Morgan, K., et al., *Arthritis Rheumat.* 24:1356-1362, 1981; Van Lent, P. L., et al., *Am. J. Pathol.* 140:1451-1461, 1992). Intra-articular injection of the soluble form of complement receptor 1 (sCR1), a complement inhibitor, suppressed inflammation in a rat model of RA (Goodfellow, R. M., et al., *Clin. Exp. Immunol.* 110:45-52, 1997). Furthermore, sCR1 inhibits the development and progression of rat collagen-induced arthritis (Goodfellow, R. M., et al., *Clin Exp. Immunol.* 119:210-216, 2000). Soluble CR1 inhibits the classical and alternative complement pathways at the steps of C3 and C5 activation in both the alternative pathway and the classical pathway, thereby inhibiting generation of C3a, C5a and sC5b-9.

In the late 1970s it was recognized that immunization of rodents with heterologous type II collagen (CII; the major collagen component of human joint cartilage) led to the development of an autoimmune arthritis (collagen-induced arthritis, or CIA) with significant similarities to human RA (Courtenay, J. S., et al., *Nature* 283:666-68 (1980), Banda et al., *J. of Immunol.* 171:2109-2115 (2003)). The autoimmune response in susceptible animals involves a complex combination of factors including specific major histocompatability complex (MHC) molecules, cytokines and CII-specific B- and T-cell responses (reviewed by Myers, L. K., et al., *Life Sciences* 61:1861-78, 1997). The observation that almost 40% of inbred mouse strains have a complete deficiency in complement component C5 (Cinader, B., et al., *J. Exp. Med.* 120:897-902, 1964) has provided an indirect opportunity to explore the role of complement in this arthritic model by comparing CIA between C5-deficient and sufficient strains. Results from such studies indicate that C5 sufficiency is an absolute requirement for the development of CIA (Watson et al., 1987; Wang, Y., et al., *J. Immunol.* 164:4340-4347, 2000). Further evidence of the importance of C5 and complement in RA has been provided by the use of anti-C5 monoclonal antibodies (MoAbs). Prophylactic intraperitoneal administration of anti-C5 MoAbs in a murine model of CIA almost completely prevented disease onset while treatment during active arthritis resulted in both significant clinical benefit and milder histological disease (Wang, Y., et al., *Proc. Natl. Acad. Sci. USA* 92:8955-59, 1995).

Additional insights about the potential role of complement activation in disease pathogenesis have been provided by studies using K/BxN T-cell receptor transgenic mice, a recently developed model of inflammatory arthritis (Korganow, A. S., et al., *Immunity* 10:451-461, 1999). All K/BxN animals spontaneously develop an autoimmune disease with most (although not all) of the clinical, histological and immunological features of RA in humans. Furthermore, transfer of serum from arthritic K/BxN mice into healthy animals provokes arthritis within days via the transfer of arthritogenic immunoglobulins. To identify the specific complement activation steps required for disease development, serum from arthritic K/BxN mice was transferred into various mice genetically deficient for a particular complement pathway product (Ji, H., et al., *Immunity* 16:157-68, 2002). Interestingly, the results of the study demonstrated that alternative pathway activation is critical, whereas classical pathway activation is dispensable. In addition, the generation of C5a is critical since both C5-deficient mice and C5aR-deficient mice were protected from disease development. Consistent with these results, a previous study reported that genetic ablation of C5a receptor expression protects mice from arthritis (Grant, E. P., et al., *J. Exp. Med.* 196:1461-1471, 2002).

A humanized anti-C5 MoAb (5G1.1) that prevents the cleavage of human complement component C5 into its pro-inflammatory components is under development by Alexion Pharmaceuticals, Inc., New Haven, Conn., as a potential treatment for RA.

Two research groups have independently proposed that the lectin pathway promotes inflammation in RA patients via interaction of MBL with specific IgG glycoforms (Malhotra et al., *Nat. Med.* 1:237-243, 1995; Cuchacovich et al., *J. Rheumatol.* 23:44-51, 1996). RA is associated with a marked increase in IgG glycoforms that lack galactose (referred to as IgG0 glycoforms) in the Fc region of the molecule (Rudd et al., *Trends Biotechnology* 22:524-30, 2004). The percentage of IgG0 glycoforms increases with disease progression, and returns to normal when patients go into remission. In vivo, IgG0 is deposited on synovial tissue and MBL is present at increased levels in synovial fluid in individuals with RA. Aggregated agalactosyl IgG (IgG0) on the clustered IgG associated with RA can bind mannose-binding lectin (MBL) and activate the lectin pathway of complement. Furthermore, results from a recent clinical study looking at allelic variants of MBL in RA patients suggest that MBL may have an inflammatory-enhancing role in the disease (Garred et al., *J. Rheumatol.* 27:26-34, 2000). Therefore, the lectin pathway may have an important role in the pathogenesis of RA.

Systemic lupus erythematosus (SLE) is an autoimmune disease of undefined etiology that results in production of autoantibodies, generation of circulating immune complexes, and episodic, uncontrolled activation of the complement system. Although the origins of autoimmunity in SLE remain elusive, considerable information is now available implicating complement activation as an important mechanism contributing to vascular injury in this disease (Abramson, S. B., et al., *Hospital Practice* 33:107-122, 1998). Activation of both the classical and alternative pathways of complement are involved in the disease and both C4d and Bb are sensitive markers of moderate-to-severe lupus disease activity (Manzi, S., et al., *Arthrit. Rheumat.* 39:1178-1188, 1996). Activation of the alternative complement pathway accompanies disease flares in systemic lupus erythematosus during pregnancy (Buyon, J. P., et al., *Arthritis Rheum.* 35:55-61, 1992). In addition, the lectin pathway may contribute to disease development since autoantibodies against MBL have recently been identified in sera from SLE patients (Seelen, M. A., et al., *Clin Exp. Immunol.* 134:335-343, 2003).

Immune complex-mediated activation of complement through the classic pathway is believed to be one mechanism by which tissue injury occurs in SLE patients. However, hereditary deficiencies in complement components of the classic pathway increase the risk of lupus and lupus-like disease (Pickering, M. C., et al., *Adv. Immunol.* 76:227-324, 2000). SLE, or a related syndrome occurs in more than 80% of persons with complete deficiency of C1q, C1r/C1s, C4 or C3. This presents an apparent paradox in reconciling the harmful effects with the protective effects of complement in lupus.

An important activity of the classical pathway appears to be promotion of the removal of immune complexes from the circulation and tissues by the mononuclear phagocytic system (Kohler, P. F., et al., *Am. J. Med.* 56:406-11, 1974). In addition, complement has recently been found to have an important role in the removal and disposal of apoptotic bodies (Mevorarch, D., et al., *J. Exp. Med.* 188:2313-2320, 1998). Deficiency in classical pathway function may predispose subjects to the development of SLE by allowing a cycle to develop in which immune complexes or apoptotic cells accumulate in tissues, cause inflammation and the release of autoantigens, which in turn stimulate the production of autoantibodies and more immune complexes and thereby evoke an autoimmune response (Botto, M., et al., *Nat. Genet.* 19:56-59, 1998; Botto, M., *Arthritis Res.* 3:201-10, 2001). However, these "complete" deficiency states in classical pathway components are present in approximately one of 100 patients with SLE. Therefore, in the vast majority of SLE patients, complement deficiency in classical pathway components does not contribute to the disease etiology and complement activation may be an important mechanism contributing to SLE pathogenesis. The fact that rare individuals with permanent genetic deficiencies in classical pathway components frequently develop SLE at some point in their lives testifies to the redundancy of mechanisms capable of triggering the disease.

Results from animal models of SLE support the important role of complement activation in pathogenesis of the disease. Inhibiting the activation of C5 using a blocking anti-C5 MoAb decreased proteinuria and renal disease in NZB/NZW F1 mice, a mouse model of SLE (Wang Y., et al., *Proc. Natl. Acad. Sci. USA* 93:8563-8, 1996). Furthermore, treatment with anti-C5 MoAb of mice with severe combined immunodeficiency disease implanted with cells secreting anti-DNA antibodies results in improvement in the proteinuria and renal histologic picture with an associated benefit in survival compared to untreated controls (Ravirajan, C. T., et al., *Rheumatology* 43:442-7, 2004). The alternative pathway also has an important role in the autoimmune disease manifestations of SLE since backcrossing of factor B-deficient mice onto the MRL/lpr model of SLE revealed that the lack of factor B lessened the vasculitis, glomerular disease, C3 consumption and IgG3 RF levels typically found in this model without altering levels of other autoantibodies (Watanabe, H., et al., *J. Immunol.* 164:786-794, 2000). A humanized anti-C5 MoAb is under investigation as a potential treatment for SLE. This antibody prevents the cleavage of C5 to C5a and C5b. In Phase I clinical trials, no serious adverse effects were noted, and more human trials are under way to determine the efficacy in SLE (Strand, V., *Lupus* 10:216-221, 2001).

Results from both human and animal studies support the possibility that the complement system contributes directly to the pathogenesis of muscular dystrophy. Studies of human dystrophic biopsies have shown that C3 and C9 are deposited on both necrotic and non-necrotic fibers in dystrophic muscle (Cornelio and Dones, *Ann. Neurol.* 16:694-701, 1984; Spuler and Engel, A. G., *Neurology* 50:41-46, 1998). Using DNA microarray methods, Porter and colleagues found markedly enhanced gene expression of numerous complement-related mRNAs in dystrophin-deficient (mdv) mice coincident with development of the dystrophic disease (Porter et al., *Hum. Mol. Genet.* 11:263-72, 2002).

Mutations in the human gene encoding dysferlin, a transmembrane muscle protein, have been identified as major risk factors for two forms of skeletal muscle disease, namely limb girdle muscular dystrophy (LGMD) and Miyoshi myopathy (Liu et al., *Nat. Genet.* 20:31-6, 1998). Several mouse model with mutations in dysferlin have been developed and they also develop progressive muscular dystrophy. Activation of the complement cascade has been identified on the surface of nonnecrotic muscle fibers in some patients with LGMD (Spuler and Engel., *Neurology* 50:41-46, 1998). In a recent study, Wenzel and colleagues showed that both murine and human dysferlin-deficient muscle fibers lack the complement inhibitory factor, CD33/DAF, a specific inhibitor of C5b-9 MAC (membrane attack complex) (Wenzel et al., *J. Immunol.* 175:6219-25, 2005). As a consequence, dysferlin-deficient nonnecrotic muscle cells are more susceptible to complement-mediated cell lysis. Wenzel and colleagues suggest that complement-mediated lysis of skeletal muscle cells may be a major pathological mechanism involved in the development of LGMD and Miyoshi myopathy in patients. Connolly and colleagues studied the role of complement C3 in the pathogenesis of a severe model of congenital dystrophy, the dy-/- mouse, which is laminin α2-deficient (Connolly et al., *J. Neuroimmunol.* 127:80-7, 2002). They generated animals genetically deficient in both C3 and laminin α2 and found that the absence of C3 prolonged survival in the dy-/- model of muscular dystrophy. Furthermore, the double knockout (C3-/-, dy-/-) mice demonstrated more muscular strength than the dy-/- mice. This work suggests that the complement system may contribute directly to the pathogenesis of this form of congenital dystrophy.

One aspect of the invention is thus directed to the prevention or treatment of inflammatory and non-inflammatory arthritides and other musculoskeletal disorders, including but not limited to osteoarthritis, rheumatoid arthritis, juvenile rheumatoid arthritis, gout, neuropathic arthropathy, psoriatic arthritis, ankylosing spondylitis or other spondyloarthropathies and crystalline arthropathies, muscular dystrophy or systemic lupus erythematosus (SLE), by administering a composition comprising a therapeutically effective amount of a MASP-2 inhibitory agent in a pharmaceutical carrier to a subject suffering from such a disorder. The MASP-2 inhibitory agent may be administered to the subject systemically, such as by intra-arterial, intravenous, intramuscular, subcutaneous or other parenteral administration, or potentially by oral administration for non-peptidergic agents. Alternatively, administration may be by local delivery, such as by intra-articular injection. The MASP-2 inhibitory agent may be administered periodically over an extended period of time for treatment or control of a chronic condition, or may be by single or repeated administration in the period before, during and/or following acute trauma or injury, including surgical procedures performed on the joint.

Renal Conditions

Activation of the complement system has been implicated in the pathogenesis of a wide variety of renal diseases; including, mesangioproliferative glomerulonephritis (IgA-nephropathy, Berger's disease) (Endo, M., et al., *Clin. Nephrology* 55:185-191, 2001), membranous glomerulonephritis (Kerjashki, D., *Arch B Cell Pathol.* 58:253-71, 1990; Brenchley, P. E., et al., *Kidney Int.,* 41:933-7, 1992; Salant, D. J., et al., *Kidney Int.* 35:976-84, 1989), membranoproliferative glomerulonephritis (mesangiocapillary glomerulonephritis) (Bartlow, B. G., et al., *Kidney Int.* 15:294-300, 1979; Meri, S., et al., *J. Exp. Med.* 175:939-50, 1992), acute postinfectious glomerulonephritis (poststreptococcal glomerulonephritis), cryoglobulinemic glomerulonephritis (Ohsawa, I., et al., *Clin Immunol.* 101:59-66, 2001), lupus nephritis (Gatenby, P. A., *Autoimmunity* 11:61-6, 1991), and Henoch-Schonlein purpura nephritis (Endo, M., et al., *Am. J. Kidney Dis.* 35:401-407, 2000). The involvement of complement in renal disease has been appreciated for several decades but there is still a major discussion on its exact role in the onset, the development and the resolution phase of renal disease. Under normal conditions the contribution of complement is beneficial to the host, but inappropriate activation and deposition of complement may contribute to tissue damage.

There is substantial evidence that glomerulonephritis, inflammation of the glomeruli, is often initiated by deposition of immune complexes onto glomerular or tubular structures which then triggers complement activation, inflammation and tissue damage. Kahn and Sinniah demonstrated increased deposition of C5b-9 in tubular basement membranes in biopsies taken from patients with various forms of glomerulonephritis (Kahn, T. N., et al., *Histopath.* 26:351-6, 1995). In a study of patients with IgA nephrology (Alexopoulos, A., et al., *Nephrol. Dial. Transplant* 10:1166-1172, 1995), C5b-9 deposition in the tubular epithelial/basement membrane structures correlated with plasma creatinine levels. Another study of membranous nephropathy demonstrated a relationship between clinical outcome and urinary sC5b-9 levels (Kon, S. P., et al., *Kidney Int.* 48:1953-58, 1995). Elevated sC5b-9 levels were correlated positively with poor prognosis. Lehto et al., measured elevated levels of CD59, a complement regulatory factor that inhibits the membrane attack complex in plasma membranes, as well as C5b-9 in urine from patients with membranous glomerulonephritis (Lehto, T., et al., *Kidney Int.* 47:1403-11, 1995). Histopathological analysis of biopsy samples taken from these same patients demonstrated deposition of C3 and C9 proteins in the glomeruli, whereas expression of CD59 in these tissues was diminished compared to that of normal kidney tissue. These various studies suggest that ongoing complement-mediated glomerulonephritis results in urinary excretion of complement proteins that correlate with the degree of tissue damage and disease prognosis.

Inhibition of complement activation in various animal models of glomerulonephritis has also demonstrated the importance of complement activation in the etiology of the disease. In a model of membranoproliferative glomerulonephritis (MPGN), infusion of anti-Thy1 antiserum in C6-deficient rats (that cannot form C5b-9) resulted in 90% less glomerular cellular proliferation, 80% reduction in platelet and macrophage infiltration, diminished collagen type IV synthesis (a marker for mesangial matrix expansion), and 50% less proteinuria than in C6+ normal rats (Brandt, J., et al., *Kidney Int.* 49:335-343, 1996). These results implicate C5b-9 as a major mediator of tissue damage by complement in this rat anti-thymocyte serum model. In another model of glomerulonephritis, infusion of graded dosages of rabbit anti-rat glomerular basement membrane produced a dose-dependent influx of polymorphonuclear leukocytes (PMN) that was attenuated by prior treatment with cobra venom factor (to consume complement) (Scandrett, A. L., et al., *Am. J. Physiol.* 268:F256-F265, 1995). Cobra venom factor-treated rats also showed diminished histopathology, decreased long-term proteinuria, and lower creatinine levels than control rats. Employing three models of GN in rats (anti-thymocyte serum, Con A anti-Con A, and passive Heymann nephritis), Couser et al., demonstrated the potential therapeutic efficacy of approaches to inhibit complement by using the recombinant sCR1 protein (Couser, W. G., et al., *J. Am. Soc. Nephrol.* 5:1888-94, 1995). Rats treated with sCR1 showed significantly diminished PMN, platelet and macrophage influx, decreased mesangiolysis, and proteinuria versus control rats. Further evidence for the importance of complement activation in glomerulonephritis has been provided by the use of an anti-C5 MoAb in the NZB/W F1 mouse model. The anti-C5 MoAb inhibits cleavage of C5, thus blocking generation of C5a and C5b-9. Continuous therapy with anti-C5 MoAb for 6 months resulted in significant amelioration of the course of glomerulonephritis. A humanized anti-C5 MoAb monoclonal antibody (5G1.1) that prevents the cleavage of human complement component C5 into its pro-inflammatory components is under development by Alexion Pharmaceuticals, Inc., New Haven, Conn., as a potential treatment for glomerulonephritis.

Direct evidence for a pathological role of complement in renal injury is provided by studies of patients with genetic deficiencies in specific complement components. A number of reports have documented an association of renal disease with deficiencies of complement regulatory factor H (Ault, B. H., *Nephrol.* 14:1045-1053, 2000; Levy, M., et al., *Kidney Int.* 30:949-56, 1986; Pickering, M. C., et al., *Nat. Genet.* 31:424-8, 2002). Factor H deficiency results in low plasma levels of factor B and C3 and in consumption of C5b-9. Both atypical membranoproliferative glomerulonephritis (MPGN) and idiopathic hemolytic uremic syndrome (HUS) are associated with factor H deficiency. Factor H deficient pigs (Jansen, J. H., et al., *Kidney Int.* 53:331-49, 1998) and factor H knockout mice (Pickering, M. C., 2002) display MPGN-like symptoms, confirming the importance of factor H in complement regulation. Deficiencies of other complement components are associated with renal disease, secondary to the development of systemic lupus erythematosus (SLE) (Walport, M. J., Davies, et al., *Ann. N.Y. Acad. Sci.* 8/5:267-81, 1997). Deficiency for C1q, C4 and C2 predispose strongly to the development of SLE via mechanisms relating to defective clearance of immune complexes and apoptotic material. In many of these SLE patients lupus nephritis occurs, characterized by the deposition of immune complexes throughout the glomerulus.

Further evidence linking complement activation and renal disease has been provided by the identification in patients of autoantibodies directed against complement components, some of which have been directly related to renal disease (Trouw, L. A., et al., *Mol. Immunol.* 38:199-206, 2001). A number of these autoantibodies show such a high degree of correlation with renal disease that the term nephritic factor (NeF) was introduced to indicate this activity. In clinical studies, about 50% of the patients positive for nephritic factors developed MPGN (Spitzer, R. E., et al., *Clin. Immunol. Immunopathol.* 64:177-83, 1992). C3NeF is an autoantibody directed against the alternative pathway C3 convertase (C3bBb) and it stabilizes this convertase, thereby promoting alternative pathway activation (Daha, M. R., et al., *J. Immunol.* 116:1-7, 1976). Likewise, autoantibody with a specificity for the classical pathway C3 convertase (C4b2a), called C4NeF, stabilizes this convertase and thereby promotes classical pathway activation (Daha, M. R. et al., *J. Immunol.* 125:2051-2054, 1980; Halbwachs, L., et al., *J. Clin. Invest.* 65:1249-56, 1980). Anti-C1q autoantibodies have been described to be related to nephritis in SLE patients (Hovath, L., et al., *Clin. Exp. Rheumatol.* 19:667-72, 2001; Siegert, C., et al., *J. Rheumatol.* 18:230-34, 1991; Siegert, C., et al., *Clin. Exp. Rheumatol.* 10:19-23, 1992), and a rise in the titer of these anti-C1q autoantibodies was reported to predict a flare of nephritis (Coremans, I. E., et al., *Am. J. Kidney Dis.* 26:595-601, 1995). Immune deposits eluted from postmortem kidneys of SLE patients revealed the accumulation of these anti-C1q autoantibodies (Mannick, M., et al., *Arthritis Rheumatol.* 40:1504-11, 1997). All these facts point to a pathological role for these autoantibodies. However, not all patients with anti-C1q autoantibodies develop renal disease and also some healthy individuals have low titer anti-C1q autoantibodies (Siegert, C. E., et al., *Clin. Immunol. Immunopathol.* 67:204-9, 1993).

In addition to the alternative and classical pathways of complement activation, the lectin pathway may also have an important pathological role in renal disease. Elevated levels of MBL, MBL-associated serine protease and complement activation products have been detected by immunohistochemical techniques on renal biopsy material obtained from patients diagnosed with several different renal diseases, including Henoch-Schonlein purpura nephritis (Endo, M., et al., *Am. J. Kidney Dis.* 35:401-407, 2000), cryoglobulinemic glomerulonephritis (Ohsawa, I., et al., *Clin. Immunol.* 101:59-66, 2001) and IgA neuropathy (Endo, M., et al., *Clin. Nephrology* 55:185-191, 2001). Therefore, despite the fact that an association between complement and renal diseases has been known for several decades, data on how complement exactly influences these renal diseases is far from complete.

One aspect of the invention is thus directed to the treatment of renal conditions including but not limited to mesangioproliferative glomerulonephritis, membranous glomerulonephritis, membranoproliferative glomerulonephritis (mesangiocapillary glomerulonephritis), acute postinfectious glomerulonephritis (poststreptococcal glomerulonephritis), cryoglobulinemic glomerulonephritis, lupus nephritis, Henoch-Schonlein purpura nephritis or IgA nephropathy, by administering a composition comprising a therapeutically effective amount of a MASP-2 inhibitory agent in a pharmaceutical carrier to a subject suffering from such a disorder. The MASP-2 inhibitory agent may be administered to the subject systemically, such as by intra-arterial, intravenous, intramuscular, subcutaneous or other parenteral administration, or potentially by oral administration for non-peptidergic agents. The MASP-2 inhibitory agent may be administered periodically over an extended period of time for treatment or control of a chronic condition, or may be by single or repeated administration in the period before, during or following acute trauma or injury.

Skin Disorders

Psoriasis is a chronic, debilitating skin condition that affects millions of people and is attributed to both genetic and environmental factors. Topical agents as well as UVB and PUVA phototherapy are generally considered to be the first-line treatment for psoriasis. However, for generalized or more extensive disease, systemic therapy is indicated as a primary treatment or, in some cases, to potentiate UVB and PUVA therapy.

The underlying etiology of various skins diseases such as psoriasis support a role for immune and proinflammatory processes including the involvement of the complement system. Moreover, the role of the complement system has been established as an important nonspecific skin defense mechanism. Its activation leads to the generation of products that not only help to maintain normal host defenses, but also mediate inflammation and tissue injury. Proinflammatory products of complement include large fragments of C3 with opsonic and cell-stimulatory activities (C3b and C3bi), low molecular weight anaphylatoxins (C3a, C4a, and C5a), and membrane attack complexes. Among them, C5a or its degradation product C5a des Arg, seems to be the most important mediator because it exerts a potent chemotactic effect on inflammatory cells. Intradermal administration of C5a anaphylatoxin induces skin changes quite similar to those observed in cutaneous hypersensitivity vasculitis that occurs through immune complex-mediated complement activation. Complement activation is involved in the pathogenesis of the inflammatory changes in autoimmune bullous dermatoses. Complement activation by pemphigus antibody in the epidermis seems to be responsible for the development of characteristic inflammatory changes termed eosinophilic spongiosis. In bullous pemphigoid (BP), interaction of basement membrane zone antigen and BP antibody leads to complement activation that seems to be related to leukocytes lining the dermoepidermal junction. Resultant anaphylatoxins not only activate the infiltrating leukocytes but also induce mast cell degranulation, which facilitates dermoepidermal separation and eosinophil infiltration. Similarly, complement activation seems to play a more direct role in the dermoepidermal separation noted in epidermolysis bullosa acquisita and herpes gestationis.

Evidence for the involvement of complement in psoriasis comes from recent experimental findings described in the literature related to the pathophysiological mechanisms for the inflammatory changes in psoriasis and related diseases. A growing body of evidence has indicated that T-cell-mediated immunity plays an important role in the triggering and maintenance of psoriatic lesions. It has been revealed that lymphokines produced by activated T-cells in psoriatic lesions have a strong influence on the proliferation of the epidermis. Characteristic neutrophil accumulation under the stratum corneum can be observed in the highly inflamed areas of psoriatic lesions. Neutrophils are chemotactically attracted and activated there by synergistic action of chemokines, IL-8 and Gro-alpha released by stimulated keratinocytes, and particularly by C5a/C5a des-arg produced via the alternative complement pathway activation (Terui, T., Tahoku J. Exp. Med. 190:239-248, 2000; Terui, T., Exp. Dermatol. 9:1-10, 2000).

Psoriatic scale extracts contain a unique chemotactic peptide fraction that is likely to be involved in the induction of rhythmic transepidermal leukocyte chemotaxis. Recent studies have identified the presence of two unrelated chemotactic peptides in this fraction, i.e., C5a/C5a des Arg and interleukin 8 (IL-8) and its related cytokines. To investigate their relative contribution to the transepidermal leukocyte migration as well as their interrelationship in psoriatic lesions, concentrations of immunoreactive C5a/C5a desArg and IL-8 in psoriatic lesional scale extracts and those from related sterile pustular dermatoses were quantified. It was found that the concentrations of C5a/C5a desArg and IL-8 were more significantly increased in the horny-tissue extracts from lesional skin than in those from non-inflammatory orthokeratotic skin. The increase of C5a/C5a desArg concentration was specific to the lesional scale extracts. Based on these results, it appears that C5a/C5a desArg is generated only in the inflammatory lesional skin under specific circumstances that preferentially favor complement activation. This provides a rationale for the use of an inhibitor of complement activation to ameliorate psoriatic lesions.

While the classical pathway of the complement system has been shown to be activated in psoriasis, there are fewer reports on the involvement of the alternative pathway in the inflammatory reactions in psoriasis. Within the conventional view of complement activation pathways, complement fragments C4d and Bb are released at the time of the classical and alternative pathway activation, respectively. The presence of the C4d or Bb fragment, therefore, denotes a complement activation that proceeds through the classical and/or alternative pathway. One study measured the levels of C4d and Bb in psoriatic scale extracts using enzyme immunoassay techniques. The scales of these dermatoses contained higher levels of C4d and Bb detectable by enzyme immunoassay than those in the stratum corneum of noninflammatory skin (Takematsu, H., et al., Dermatologica 181: 289-292, 1990). These results suggest that the alternative pathway is activated in addition to the classical pathway of complement in psoriatic lesional skin.

Additional evidence for the involvement of complement in psoriasis and atopic dermatitis has been obtained by measuring normal complement components and activation products in the peripheral blood of 35 patients with atopic dermatitis (AD) and 24 patients with psoriasis at a mild to intermediate stage. Levels of C3, C4 and C1 inactivator (C1 INA) were determined in serum by radial immunodiffusion, whereas C3a and C5a levels were measured by radioimmunoassay. In comparison to healthy non-atopic controls, the levels of C3, C4 and C1 INA were found to be significantly increased in both diseases. In AD, there was a tendency towards increased C3a levels, whereas in psoriasis, C3a levels were significantly increased. The results indicate that, in both AD and psoriasis, the complement system participates in the inflammatory process (Ohkonohchi, K., et al., Dermatologica 179:30-34, 1989).

Complement activation in psoriatic lesional skin also results in the deposition of terminal complement complexes within the epidermis as defined by measuring levels of SC5b-9 in the plasma and horny tissues of psoriatic patients. The levels of SC5b-9 in psoriatic plasma have been found to be significantly higher than those of controls or those of patients with atopic dermatitis. Studies of total protein extracts from lesional skin have shown that, while no SC5b-9 can be detected in the noninflammatory horny tissues, there were high levels of SC5b-9 in lesional horny tissues of psoriasis. By immunofluorescence using a monoclonal antibody to the C5b-9 neoantigen, deposition of C5b-9 has been observed only in the stratum corneum of psoriatic skin. In summary, in psoriatic lesional skin, the complement system is activated and complement activation proceeds all the way to the terminal step, generating membrane attack complex.

New biologic drugs that selectively target the immune system have recently become available for treating psoriasis. Four biologic drugs that are either currently FDA approved or in Phase 3 studies are: alefacept (Amevive®) and efalizuMoAb (Raptiva®) which are T-cell modulators; etanercept (Enbrel®), a soluble TNF-receptor; and inflixiMoAb (Remicade®), an anti-TNF monoclonal antibody. Raptiva is an immune response modifier, wherein the targeted mechanism of action is a blockade of the interaction between LFA-1 on lymphocytes and ICAM-1 on antigen-presenting cells and on vascular endothelial cells. Binding of CD11a by Raptiva results in saturation of available CD11a binding sites on lymphocytes and down-modulation of cell surface CD11a expression on lymphocytes. This mechanism of action inhibits T-cell activation, cell trafficking to the dermis and epidermis and T-cell reactivation. Thus, a plurality of scientific evidence indicates a role for complement in inflammatory disease states of the skin and recent pharmaceutical approaches have targeted the immune system or specific inflammatory processes. None, however, have identified MASP-2 as a targeted approach. Based on the inventors' new understanding of the role of MASP-2 in complement activation, the inventors believe MASP-2 to be an effective target for the treatment of psoriasis and other skin disorders.

One aspect of the invention is thus directed to the treatment of psoriasis, autoimmune bullous dermatoses, eosinophilic spongiosis, bullous pemphigoid, epidermolysis bullosa acquisita, atopic dermatitis, herpes gestationis and other skin disorders, and for the treatment of thermal and chemical burns including capillary leakage caused thereby, by administering a composition comprising a therapeutically effective amount of a MASP-2 inhibitory agent in a pharmaceutical carrier to a subject suffering from such a skin disorder. The MASP-2 inhibitory agent may be administered to the subject topically, by application of a spray, lotion, gel, paste, salve or irrigation solution containing the MASP-2 inhibitory agent, or systemically such as by intra-arterial, intravenous, intramuscular, subcutaneous or other parenteral administration, or potentially by oral administration for non-peptidergic inhibitors. Treatment may involve a single administration or repeated applications or dosings for an acute condition, or by periodic applications or dosings for control of a chronic condition.

Transplantation

Activation of the complement system significantly contributes to the inflammatory reaction after solid organ transplantation. In allotransplantation, the complement system may be activated by ischemia/reperfusion and, possibly, by antibodies directed against the graft (Baldwin, W. M., et al., *Springer Seminol Immunopathol.* 25:181-197, 2003). In xenotransplantation from nonprimates to primates, the major activators for complement are preexisting antibodies. Studies in animal models have shown that the use of complement inhibitors may significantly prolong graft survival (see below). Thus, there is an established role of the complement system in organ injury after organ transplantation, and therefore the inventors believe that the use of complement inhibitors directed to MASP-2 may prevent damage to the graft after allo- or xenotransplantation.

Innate immune mechanisms, particularly complement, play a greater role in inflammatory and immune responses against the graft than has been previously recognized. For example, alternative complement pathway activation appears to mediate renal ischemia/reperfusion injury, and proximal tubular cells may be both the source and the site of attack of complement components in this setting. Locally produced complement in the kidney also plays a role in the development of both cellular and antibody-mediated immune responses against the graft.

C4d is the degradation product of the activated complement factor C4, a component of the classical and lectin-dependent pathways. C4d staining has emerged as a useful marker of humoral rejection both in the acute and in the chronic setting and led to renewed interest in the significance of anti-donor antibody formation. The association between C4d and morphological signs of acute cellular rejection is statistically significant. C4d is found in 24-43% of Type I episodes, in 45% of type II rejection and 50% of type III rejection (Nickeleit, V., et al., *J. Am. Soc. Nephrol.* 13:242-251, 2002; Nickeleit, V., et al., *Nephrol. Dial. Transplant* 18:2232-2239, 2003). A number of therapies are in development that inhibit complement or reduce local synthesis as a means to achieve an improved clinical outcome following transplantation.

Activation of the complement cascade occurs as a result of a number of processes during transplantation. Present therapy, although effective in limiting cellular rejection, does not fully deal with all the barriers faced. These include humoral rejection and chronic allograft nephropathy or dysfunction. Although the overall response to the transplanted organ is a result of a number of effector mechanisms on the part of the host, complement may play a key role in some of these. In the setting of renal transplantation, local synthesis of complement by proximal tubular cells appears of particular importance.

The availability of specific inhibitors of complement may provide the opportunity for an improved clinical outcome following organ transplantation. Inhibitors that act by a mechanism that blocks complement attack may be particularly useful, because they hold the promise of increased efficacy and avoidance of systemic complement depletion in an already immuno-compromised recipient.

Complement also plays a critical role in xenograft rejection. Therefore, effective complement inhibitors are of great interest as potential therapeutic agents. In pig-to-primate organ transplantation, hyperacute rejection (HAR) results from antibody deposition and complement activation. Multiple strategies and targets have been tested to prevent hyperacute xenograft rejection in the pig-to-primate combination. These approaches have been accomplished by removal of natural antibodies, complement depletion with cobra venom factor, or prevention of C3 activation with the soluble complement inhibitor sCR1. In addition, complement activation blocker-2 (CAB-2), a recombinant soluble chimeric protein derived from human decay accelerating factor (DAF) and membrane cofactor protein, inhibits C3 and C5 convertases of both classical and alternative pathways. CAB-2 reduces complement-mediated tissue injury of a pig heart perfused ex vivo with human blood. A study of the efficacy of CAB-2 when a pig heart was transplanted heterotopically into rhesus monkeys receiving no immunosuppression showed that graft survival was markedly prolonged in monkeys that received CAB-2 (Salerno, C. T., et al., *Xenotransplantation* 9:125-134, 2002). CAB-2 markedly inhibited complement activation, as shown by a strong reduction in generation of C3a and SCSb-9. At graft rejection, tissue deposition of iC3b, C4 and C9 was similar or slightly reduced from controls, and deposition of IgG, IgM, C1q and fibrin did not change. Thus, this approach for complement inhibition abrogated hyperacute rejection of pig hearts transplanted into rhesus monkeys. These studies demonstrate the beneficial effects of complement inhibition on survival and the inventors believe that MASP-2 inhibition may also be useful in xenotransplantation.

Another approach has focused on determining if anti-complement 5 (C5) monoclonal antibodies could prevent hyperacute rejection (HAR) in a rat-to-presensitized mouse heart transplantation model and whether these MoAb, combined with cyclosporine and cyclophosphamide, could achieve long-term graft survival. It was found that anti-CS MoAb prevents HAR (Wang, H., et al., *Transplantation* 68:1643-1651, 1999). The inventors thus believe that other targets in the complement cascade, such as MASP-2, may also be valuable for preventing HAR and acute vascular rejection in future clinical xenotransplantation.

While the pivotal role of complement in hyperacute rejection seen in xenografts is well established, a subtler role in allogeneic transplantation is emerging. A link between complement and the acquired immune response has long been known, with the finding that complement-depleted animals mounted subnormal antibody responses following antigenic stimulation. Opsonization of antigen with the complement split product C3d has been shown to greatly increase the effectiveness of antigen presentation to B cells, and has been shown to act via engagement of complement receptor type 2 on certain B cells. This work has been extended to the transplantation setting in a skin graft model in mice, where C3- and C4-deficient mice had a marked defect in allo-antibody production, due to failure of class switching to high-affinity IgG. The importance of these mechanisms in renal transplantation is increased due to the significance of anti-donor antibodies and humoral rejection.

Previous work has already demonstrated upregulation of C3 synthesis by proximal tubular cells during allograft rejection following renal transplantation. The role of locally synthesized complement has been examined in a mouse renal transplantation model. Grafts from C3-negative donors transplanted into C3-sufficient recipients demonstrated prolonged survival (>100 days) as compared with control grafts from C3-positive donors, which were rejected within 14 days. Furthermore, the anti-donor T-cell proliferative response in recipients of C3-negative grafts was markedly reduced as compared with that of controls, indicating an effect of locally synthesized C3 on T-cell priming.

These observations suggest the possibility that exposure of donor antigen to T-cells first occurs in the graft and that locally synthesized complement enhances antigen presentation, either by opsonization of donor antigen or by providing additional signals to both antigen-presenting cells and T-cells. In the setting of renal transplantation, tubular cells that produce complement also demonstrate complement deposition on their cell surface.

One aspect of the invention is thus directed to the prevention or treatment of inflammatory reaction resulting from tissue or solid organ transplantation by administering a composition comprising a therapeutically effective amount of a MASP-2 inhibitory agent in a pharmaceutical carrier to the transplant recipient, including subjects that have received allotransplantation or xenotransplantation of whole organs (e.g., kidney, heart, liver, pancreas, lung, cornea, etc.) or grafts (e.g., valves, tendons, bone marrow, etc.). The MASP-2 inhibitory agent may be administered to the subject by intra-arterial, intravenous, intramuscular, subcutaneous or other parenteral administration, or potentially by oral administration for non-peptidergic inhibitors. Administration may occur during the acute period following transplantation and/or as long-term posttransplantation therapy. Additionally or in lieu of posttransplant administration, the subject may be treated with the MASP-2 inhibitory agent prior to transplantation and/or during the transplant procedure, and/or by pretreating the organ or tissue to be transplanted with the MASP-2 inhibitory agent. Pretreatment of the organ or tissue may entail applying a solution, gel or paste containing the MASP-2 inhibitory agent to the surface of the organ or tissue by spraying or irrigating the surface, or the organ or tissue may be soaked in a solution containing the MASP-2 inhibitor.

Central and Peripheral Nervous System Disorders and Injuries

Activation of the complement system has been implicated in the pathogenesis of a variety of central nervous system (CNS) or peripheral nervous system (PNS) diseases or injuries, including but not limited to multiple sclerosis (MS), myasthenia gravis (MG), Huntington's disease (HD), amyotrophic lateral sclerosis (ALS), Guillain Barre syndrome, reperfusion following stroke, degenerative discs, cerebral trauma, Parkinson's disease (PD) and Alzheimer's disease (AD). The initial determination that complement proteins are synthesized in CNS cells including neurons, astrocytes and microglia, as well as the realization that anaphylatoxins generated in the CNS following complement activation can alter neuronal function, has opened up the potential role of complement in CNS disorders (Morgan, B. P., et al., *Immunology Today* 17(10):461-466, 1996). It has now been shown that C3a receptors and C5a receptors are found on neurons and show widespread distribution in distinct portions of the sensory, motor and limbic brain systems (Barum, S. R., *Immunologic Research* 26:7-13, 2002). Moreover, the anaphylatoxins C5a and C3a have been shown to alter eating and drinking behavior in rodents and can induce calcium signaling in microglia and neurons. These findings raise possibilities regarding the therapeutic utility of inhibiting complement activation in a variety of CNS inflammatory diseases including cerebral trauma, demyelination, meningitis, stroke and Alzheimer's disease.

Brain trauma or hemorrhage is a common clinical problem, and complement activation may occur and exacerbate resulting inflammation and edema. The effects of complement inhibition have been studied in a model of brain trauma in rats (Kaczorowski et al., *J. Cereb. Blood Flow Metab.* 15:860-864, 1995). Administration of sCR1 immediately prior to brain injury markedly inhibited neutrophil infiltration into the injured area, indicating complement was important for recruitment of phagocytic cells. Likewise, complement activation in patients following cerebral hemorrhage is clearly implicated by the presence of high levels of multiple complement activation products in both plasma and cerebrospinal fluid (CSF). Complement activation and increased staining of C5b-9 complexes have been demonstrated in sequestered lumbar disc tissue and could suggest a role in disc herniation tissue-induced sciatica (Gronblad, M., et al., *Spine* 28(2):114-118, 2003).

MS is characterized by a progressive loss of myelin ensheathing and insulating axons within the CNS. Although the initial cause is unknown, there is abundant evidence implicating the immune system (Prineas, J. W., et al., *Lab Invest.* 38:409-421, 1978; Ryberg, B., *J. Neurol. Sci.* 54:239-261, 1982). There is also clear evidence that complement plays a prominent role in the pathophysiology of CNS or PNS demyelinating diseases including MS, Guillain-Barre syndrome and Miller-Fisher syndrome (Gasque, P., et al., *Immunopharmacology* 49:171-186, 2000; Barnum, S. R. in Bondy S. et al. (eds.) *Inflammatory events in neurodegeneration*, Prominent Press, pp. 139-156, 2001). Complement contributes to tissue destruction, inflammation, clearance of myelin debris and even remyelination of axons. Despite clear evidence of complement involvement, the identification of complement therapeutic targets is only now being evaluated in experimental allergic encephalomyelitis (EAE), an animal model of multiple sclerosis. Studies have established that EAE mice deficient in C3 or factor B showed attenuated demyelination as compared to EAE control mice (Barnum, *Immunologic Research* 26:7-13, 2002). EAE mouse studies using a soluble form of a complement inhibitor coined "sCrry" and C3−/− and factor B−/− demonstrated that complement contributes to the development and progression of the disease model at several levels. In addition, the marked reduction in EAE severity in factor B−/− mice provides further evidence for the role of the alternative pathway of complement in EAE (Nataf et al., *J. Immunology* 165:5867-5873, 2000).

MG is a disease of the neuromuscular junction with a loss of acetylcholine receptors and destruction of the end plate. sCR1 is very effective in an animal model of MG, further indicating the role of complement in the disease (Piddelesden et al., *J. Neuroimmunol.* 1997).

The histological hallmarks of AD, a neurodegenerative disease, are senile plaques and neurofibrillary tangles (McGeer et al., *Res. Immunol.* 143:621-630, 1992). These pathological markers also stain strongly for components of the complement system. Evidence points to a local neuroinflammatory state that results in neuronal death and cognitive dysfunction. Senile plaques contain abnormal amyloid-β☐ peptide (Aβ☐, a peptide derived from amyloid precursor protein. Aβ has been shown to bind C1 and can trigger complement activation (Rogers et al., *Res. Immunol.* 143: 624-630, 1992). In addition, a prominent feature of AD is the association of activated proteins of the classical complement pathway from C1q to C5b-9, which have been found highly localized in the neuritic plaques (Shen, Y., et al., *Brain Research* 769:391-395, 1997; Shen, Y., et al., *Neurosci. Letters* 305(3):165-168, 2001). Thus, Aβ not only initiates the classical pathway, but a resulting continual inflammatory state may contribute to the neuronal cell death. Moreover, the fact that complement activation in AD has progressed to the terminal C5b-9 phase indicates that the regulatory mechanisms of the complement system have been unable to halt the complement activation process.

Several inhibitors of the complement pathway have been proposed as potential therapeutic approaches for AD, including proteoglycan as inhibitors of C1Q binding, Nafamstat as an inhibitor of C3 convertase, and C5 activation blockers or inhibitors of C5a receptors (Shen, Y., et al., *Progress in Neurobiology* 70:463-472, 2003). The role of MASP-2 as an initiation step in the innate complement pathway, as well as for alternative pathway activation, provides a potential new therapeutic approach and is supported by the wealth of data suggesting complement pathway involvement in AD.

In damaged regions in the brains of PD patients, as in other CNS degenerative diseases, there is evidence of inflammation characterized by glial reaction (especially microglia), as well as increased expression of HLA-DR antigens, cytokines, and components of complement. These observations suggest that immune system mechanisms are involved in the pathogenesis of neuronal damage in PD. The cellular mechanisms of primary injury in PD have not been clarified, however, but it is likely that mitochondrial mutations, oxidative stress and apoptosis play a role. Furthermore, inflammation initiated by neuronal damage in the striatum and the substantia nigra in PD may aggravate the course of the disease. These observations suggest that treatment with complement inhibitory drugs may act to slow progression of PD (Czlonkowska, A., et al., *Med. Sci. Monit.* 8:165-177, 2002).

One aspect of the invention is thus directed to the treatment of peripheral nervous system (PNS) and/or central nervous system (CNS) disorders or injuries by treating a subject suffering from such a disorder or injury with a composition comprising a therapeutically effective amount of a MASP-2 inhibitory agent in a pharmaceutical carrier. CNS and PNS disorders and injuries that may be treated in accordance with the present invention are believed to include but are not limited to multiple sclerosis (MS), myasthenia gravis (MG), Huntington's disease (HD), amyotrophic lateral sclerosis (ALS), Guillain Barre syndrome, reperfusion following stroke, degenerative discs, cerebral trauma, Parkinson's disease (PD), Alzheimer's disease (AD), Miller-Fisher syndrome, cerebral trauma and/or hemorrhage, demyelination and, possibly, meningitis.

For treatment of CNS conditions and cerebral trauma, the MASP-2 inhibitory agent may be administered to the subject by intrathecal, intracranial, intraventricular, intra-arterial, intravenous, intramuscular, subcutaneous, or other parenteral administration, and potentially orally for non-peptidergic inhibitors. PNS conditions and cerebral trauma may be treated by a systemic route of administration or alternately by local administration to the site of dysfunction or trauma. Administration of the MASP-2 inhibitory compositions of the present invention may be repeated periodically as determined by a physician until effective relief or control of the symptoms is achieved.

Blood Disorders

Sepsis is caused by an overwhelming reaction of the patient to invading microorganisms. A major function of the complement system is to orchestrate the inflammatory response to invading bacteria and other pathogens. Consistent with this physiological role, complement activation has been shown in numerous studies to have a major role in the pathogenesis of sepsis (Bone, R. C., *Annals. Internal. Med.* 115:457-469, 1991). The definition of the clinical manifestations of sepsis is ever evolving. Sepsis is usually defined as the systemic host response to an infection. However, on many occasions, no clinical evidence for infection (e.g., positive bacterial blood cultures) is found in patients with septic symptoms. This discrepancy was first taken into account at a Consensus Conference in 1992 when the term "systemic inflammatory response syndrome" (SIRS) was established, and for which no definable presence of bacterial infection was required (Bone, R. C., et al., *Crit. Care Med.* 20:724-726, 1992). There is now general agreement that sepsis and SIRS are accompanied by the inability to regulate the inflammatory response. For the purposes of this brief review, we will consider the clinical definition of sepsis to also include severe sepsis, septic shock, and SIRS.

The predominant source of infection in septic patients before the late 1980s was Gram-negative bacteria. Lipopolysaccharide (LPS), the main component of the Gram-negative bacterial cell wall, was known to stimulate release of inflammatory mediators from various cell types and induce acute infectious symptoms when injected into animals (Haeney, M. R., et al., *Antimicrobial Chemotherapy* 41(Suppl. A):41-6, 1998). Interestingly, the spectrum of responsible microorganisms appears to have shifted from predominantly Gram-negative bacteria in the late 1970s and 1980s to predominantly Gram-positive bacteria at present, for reasons that are currently unclear (Martin, G. S., et al., *N. Eng. J. Med.* 348:1546-54, 2003).

Many studies have shown the importance of complement activation in mediating inflammation and contributing to the features of shock, particularly septic and hemorrhagic shock. Both Gram-negative and Gram-positive organisms commonly precipitate septic shock. LPS is a potent activator of complement, predominantly via the alternative pathway, although classical pathway activation mediated by antibodies also occurs (Fearon, D. T., et al., *N. Engl. J. Med.* 292:937-400, 1975). The major components of the Gram-positive cell wall are peptidoglycan and lipoteichoic acid, and both components are potent activators of the alternative complement pathway, although in the presence of specific antibodies they can also activate the classical complement pathway (Joiner, K. A., et al., *Ann. Rev. Immunol.* 2:461-2, 1984).

The complement system was initially implicated in the pathogenesis of sepsis when it was noted by researchers that anaphylatoxins C3a and C5a mediate a variety of inflammatory reactions that might also occur during sepsis. These anaphylatoxins evoke vasodilation and an increase in microvascular permeability, events that play a central role in septic shock (Schumacher, W. A., et al., *Agents Actions* 34:345-349, 1991). In addition, the anaphylatoxins induce bronchospasm, histamine release from mast cells, and aggregation of platelets. Moreover, they exert numerous effects on granulocytes, such as chemotaxis, aggregation, adhesion, release of lysosomal enzymes, generation of toxic super oxide anion and formation of leukotrienes (Shin, H. S., et al., *Science* 162:361-363, 1968; Vogt, W., *Complement* 3:177-86, 1986). These biologic effects are thought to play a role in development of complications of sepsis such as shock or acute respiratory distress syndrome (ARDS) (Hammerschmidt, D. E., et al., *Lancet* 1:947-949, 1980; Slotman, G. T., et al., *Surgery* 99:744-50, 1986). Furthermore, elevated levels of the anaphylatoxin C3a is associated with a fatal outcome in sepsis (Hack, C. E., et al., *Am. J. Med.* 86:20-26, 1989). In some animal models of shock, certain complement-deficient strains (e.g., C5-deficient ones) are more resistant to the effects of LPS infusions (Hseuh, W., et al., *Immunol.* 70:309-14, 1990).

Blockade of C5a generation with antibodies during the onset of sepsis in rodents has been shown to greatly improve survival (Czermak, B. J., et al., *Nat. Med.* 5:788-792, 1999). Similar findings were made when the C5a receptor (C5aR) was blocked, either with antibodies or with a small molecular inhibitor (Huber-Lang, M. S., et al., *FASEB J.* 16:1567-74, 2002; Riedemann, N. C., et al., *J. Clin. Invest.* 110:101-8, 2002). Earlier experimental studies in monkeys have suggested that antibody blockade of C5a attenuated *E. coli*-induced septic shock and adult respiratory distress syndrome (Hangen, D. H., et al., *J. Surg. Res.* 46:195-9, 1989; Stevens, J. H., et al., *J. Clin. Invest.* 77:1812-16, 1986). In humans with sepsis, C5a was elevated and associated with significantly reduced survival rates together with multiorgan failure, when compared with that in less severely septic patients and survivors (Nakae, H., et al., *Res. Commun. Chem. Pathol. Pharmacol.* 84:189-95, 1994; Nakae, et al., *Surg. Today* 26:225-29, 1996; Bengtson, A., et al., *Arch. Surg.* 123:645-649, 1988). The mechanisms by which C5a exerts its harmful effects during sepsis are yet to be investigated in greater detail, but recent data suggest the generation of C5a during sepsis significantly compromises innate immune functions of blood neutrophils (Huber-Lang, M. S., et al., *J. Immunol.* 169:3223-31, 2002), their ability to express a respiratory burst, and their ability to generate cytokines (Riedemann, N. C., et al., *Immunity* 19:193-202, 2003). In addition, C5a generation during sepsis appears to have procoagulant effects (Laudes, I. J., et al., *Am. J. Pathol.* 160:1867-75, 2002). The complement-modulating protein CI INH has also shown efficacy in animal models of sepsis and ARDS (Dickneite, G., *Behring Ins. Mitt.* 93:299-305, 1993).

The lectin pathway may also have a role in pathogenesis of sepsis. MBL has been shown to bind to a range of clinically important microorganisms including both Gram-negative and Gram-positive bacteria, and to activate the lectin pathway (Neth, O., et al., *Infect. Immun.* 68:688, 2000). Lipoteichoic acid (LTA) is increasingly regarded as the Gram-positive counterpart of LPS. It is a potent immunostimulant that induces cytokine release from mononuclear phagocytes and whole blood (Morath, S., et al., *J. Exp. Med.* 195:1635, 2002; Morath, S., et al., *Infect. Immun.* 70:938, 2002). Recently it was demonstrated that L-ficolin specifically binds to LTA isolated from numerous Gram-positive bacteria species, including *Staphylococcus aureus*, and activates the lectin pathway (Lynch, N. J., et al., *J. Immunol.* 172:1198-02, 2004). MBL also has been shown to bind to LTA from *Enterococcus* spp in which the polyglycerophosphate chain is substituted with glycosyl groups), but not to LTA from nine other species including *S. aureus* (Polotsky, V. Y., et al., *Infect. Immun.* 64:380, 1996).

An aspect of the invention thus provides a method for treating sepsis or a condition resulting from sepsis, by administering a composition comprising a therapeutically effective amount of a MASP-2 inhibitory agent in a pharmaceutical carrier to a subject suffering from sepsis or a condition resulting from sepsis including without limitation severe sepsis, septic shock, acute respiratory distress syndrome resulting from sepsis, and systemic inflammatory response syndrome. Related methods are provided for the treatment of other blood disorders, including hemorrhagic shock, hemolytic anemia, autoimmune thrombotic thrombocytopenic purpura (TTP), hemolytic uremic syndrome (HUS), atypical hemolytic uremic syndrome (aHUS), or other marrow/blood destructive conditions, by administering a composition comprising a therapeutically effective amount of a MASP-2 inhibitory agent in a pharmaceutical carrier to a subject suffering from such a condition. The MASP-2 inhibitory agent is administered to the subject systemically, such as by intra-arterial, intravenous, intramuscular, inhalational (particularly in the case of ARDS), subcutaneous or other parenteral administration, or potentially by oral administration for non-peptidergic agents. The MASP-2 inhibitory agent composition may be combined with one or more additional therapeutic agents to combat the sequelae of sepsis and/or shock. For advanced sepsis or shock or a distress condition resulting therefrom, the MASP-2 inhibitory composition may suitably be administered in a fast-acting dosage form, such as by intravenous or intra-arterial delivery of a bolus of a solution containing the MASP-2 inhibitory agent composition. Repeated administration may be carried out as determined by a physician until the condition has been resolved.

Another aspect of the invention provides a method for treating Paroxysmal nocturnal hemoglobinuria (PNH) by administering a composition comprising a therapeutically effective amount of a MASP-2 inhibitory agent in a pharmaceutical carrier to a subject suffering from PNH or a condition resulting from PNH. PNH is an acquired, potentially life threatening disease of the blood, characterized by complement-induced intravascular hemolytic anemia that is a consequence of unregulated activation of the alternative pathway of complement. Lindorfer, M. A. et al., Blood 115 (11) (2010). Conditions resulting from PNH include anemia, hemoglobin in the urine and thrombosis. The MASP-2 inhibitory agent is administered systemically to the subject suffering from PNH or a condition resulting from PNH, such as by intra-arterial, intravenous, intramuscular, inhalational, subcutaneous or other parenteral administration, or potentially by oral administration for non-peptidergic agents.

Another aspect of the invention provides methods for treating Cryoglobulinemia by administering a composition comprising a therapeutically effective amount of a MASP-2 inhibitory agent in a pharmaceutical carrier to a subject suffering from Cryoglobulinemia or a condition resulting from Cryoglobulinemia. Cryoglobulinemia is characterized by the presence of cryoglobulins in the serum, which are single or mixed immmunoglobulins (typically IgM antibodies) that undergo reversible aggregation at low temperatures. Conditions resulting from Cryoglobulinemia include vasculitis, glomerulonepthritis, and systemic inflammation. The MASP-2 inhibitory agent is administered systemically to the subject suffering from Cryoglobulinemia or a condition resulting from Cryoglobulinemia, such as by intra-arterial, intravenous, intramuscular, inhalational, subcutaneous or other parenteral administration, or potentially by oral administration for non-peptidergic agents.

In another aspect, the invention provides methods for treating Cold Agglutinin disease (CAD) by administering a composition comprising a therapeutically effective amount of a MASP-2 inhibitory agent in a pharmaceutical carrier to a subject suffering from CAD or a condition resulting from CAD. CAD disease manifests as anemia and can be caused by an underlying disease or disorder, referred to as "Secondary CAD" such as an infectious disease, lymphoproliferative disease or connective tissue disorder. These patients develop IgM antibodies against their red blood cells that trigger an agglutination reaction at low temperatures. The MASP-2 inhibitory agent is administered systemically to the subject suffering from CAD or a condition resulting from CAD, such as by intra-arterial, intravenous, intramuscular, inhalational, subcutaneous or other parenteral administration, or potentially by oral administration for non-peptidergic agents.

Urogenital Conditions

The complement system has been implicated in several distinct urogenital disorders including painful bladder disease, sensory bladder disease, chronic abacterial cystitis and interstitial cystitis (Holm-Bentzen, M., et al., *J. Urol.* 138: 503-507, 1987), infertility (Cruz, et al., *Biol. Reprod.* 54:1217-1228, 1996), pregnancy (Xu, C., et al., *Science* 287:498-507, 2000), fetomaternal tolerance (Xu, C., et al., *Science* 287:498-507, 2000), and pre-eclampsia (Haeger, M., *Int. J. Gynecol. Obstet.* 43:113-127, 1993).

Painful bladder disease, sensory bladder disease, chronic abacterial cystitis and interstitial cystitis are ill-defined conditions of unknown etiology and pathogenesis, and, therefore, they are without any rational therapy. Pathogenetic theories concerning defects in the epithelium and/or mucous surface coating of the bladder, and theories concerning immunological disturbances, predominate (Holm-Bentzen, M., et al., *J. Urol.* 138:503-507, 1987). Patients with interstitial cystitis were reported to have been tested for immunoglobulins (IgA, G, M), complement components (C1q, C3, C4) and for C1-esterase inhibitor. There was a highly significant depletion of the serum levels of complement component C4 (p less than 0.001) and immunoglobulin G was markedly elevated (p less than 0.001). This study suggests classical pathway activation of the complement system, and supports the possibility that a chronic local immunological process is involved in the pathogenesis of the disease (Mattila, J., et al., *Eur. Urol.* 9:350-352, 1983). Moreover, following binding of autoantibodies to antigens in bladder mucosa, activation of complement could be involved in the production of tissue injury and in the chronic self-perpetuating inflammation typical of this disease (Helin, H., et al., *Clin. Immunol. Immunopathol.* 43:88-96, 1987).

In addition to the role of complement in urogenital inflammatory diseases, reproductive functions may be impacted by the local regulation of the complement pathway. Naturally occurring complement inhibitors have evolved to provide host cells with the protection they need to control the body's complement system. Crry, a naturally-occurring rodent complement inhibitor that is structurally similar to the human complement inhibitors, MCP and DAF, has been investigated to delineate the regulatory control of complement in fetal development. Interestingly, attempts to generate Crry−/− mice were unsuccessful. Instead, it was discovered that homozygous Crry−/− mice died in utero. Crry−/− embryos survived until about 10 days post coitus, and survival rapidly declined with death resulting from developmental arrest. There was also a marked invasion of inflammatory cells into the placental tissue of Crry−/− embryos. In contrast, Crry+/+ embryos appeared to have C3 deposited on the placenta. This suggests that complement activation had occurred at the placenta level, and in the absence of complement regulation, the embryos died. Confirming studies investigated the introduction of the Crry mutation onto a C3 deficient background. This rescue strategy was successful. Together, these data illustrate that the fetomaternal complement interface must be regulated. Subtle alterations in complement regulation within the placenta might contribute to placental dysfunction and miscarriage (Xu, C., et al., *Science* 287:498-507, 2000).

Pre-eclampsia is a pregnancy-induced hypertensive disorder in which complement system activation has been implicated but remains controversial (Haeger, M., *Int. J. Gynecol. Obstet.* 43:113-127, 1993). Complement activation in systemic circulation is closely related to established disease in pre-eclampsia, but no elevations were seen prior to the presence of clinical symptoms and, therefore, complement components cannot be used as predictors of pre-eclampsia (Haeger, et al., *Obstet. Gynecol.* 78:46, 1991). However, increased complement activation at the local environment of the placenta bed might overcome local control mechanisms, resulting in raised levels of anaphylatoxins and C5b-9 (Haeger, et al., *Obstet. Gynecol.* 73:551, 1989).

One proposed mechanism of infertility related to anti-sperm antibodies (ASA) is through the role of complement activation in the genital tract. Generation of C3b and iC3b opsonin, which can potentiate the binding of sperm by phagocytic cells via their complement receptors as well as formation of the terminal C5b-9 complex on the sperm surface, thereby reducing sperm motility, are potential causes associated with reduced fertility. Elevated C5b-9 levels have also been demonstrated in ovarian follicular fluid of infertile women (D'Cruz, O. J., et al., *J. Immunol.* 144:3841-3848, 1990). Other studies have shown impairment in sperm migration, and reduced sperm/egg interactions, which may be complement associated (D'Cruz, O. J., et al., *J. Immunol.* 146:611-620, 1991; Alexander, N. J., *Fertil. Steril.* 41:433-439, 1984). Finally, studies with sCR1 demonstrated a protective effect against ASA- and complement mediated injury to human sperm (D'Cruz, O. J., et al., *Biol. Reprod.* 54:1217-1228, 1996). These data provide several lines of evidence for the use of complement inhibitors in the treatment of urogenital disease and disorders.

An aspect of the invention thus provides a method for inhibiting MASP-2-dependent complement activation in a patient suffering from a urogenital disorder, by administering a composition comprising a therapeutically effective amount of a MASP-2 inhibitory agent in a pharmaceutical carrier to a subject suffering from such a disorder. Urogenital disorders believed to be subject to therapeutic treatment with the methods and compositions of the present invention include, by way of nonlimiting example, painful bladder disease, sensory bladder disease, chronic abacterial cystitis and interstitial cystitis, male and female infertility, placental dysfunction and miscarriage and pre-eclampsia. The MASP-2 inhibitory agent may be administered to the subject systemically, such as by intra-arterial, intravenous, intramuscular, inhalational, subcutaneous or other parenteral administration, or potentially by oral administration for non-peptidergic agents. Alternately, the MASP-2 inhibitory composition may be delivered locally to the urogenital tract, such as by intravesical irrigation or instillation with a liquid solution or gel composition. Repeated administration may be carried out as determined by a physician to control or resolve the condition.

Diabetes and Diabetic Conditions

Diabetic retinal microangiopathy is characterized by increased permeability, leukostasis, microthrombosis, and apoptosis of capillary cells, all of which could be caused or promoted by activation of complement. Glomerular structures and endoneurial microvessels of patients with diabetes show signs of complement activation. Decreased availability or effectiveness of complement inhibitors in diabetes has been suggested by the findings that high glucose in vitro selectively decreases on the endothelial cell surface the expression of CD55 and CD59, the two inhibitors that are glycosylphosphatidylinositol (GPI)-anchored membrane proteins, and that CD59 undergoes nonenzymatic glycation that hinders its complement-inhibitory function.

Studies by Zhang et al. (*Diabetes* 51:3499-3504, 2002), investigated complement activation as a feature of human nonproliferative diabetic retinopathy and its association with changes in inhibitory molecules. It was found that deposition of C5b-9, the terminal product of complement activation, occurs in the wall of retinal vessels of human eye donors with type-2 diabetes, but not in the vessels of age-matched nondiabetic donors. C1q and C4, the complement components unique to the classical pathway, were not detected in the diabetic retinas, which indicates that C5b-9 was generated via the alternative pathway. The diabetic donors showed a prominent reduction in the retinal levels of CD55 and CD59, the two complement inhibitors linked to the plasma membrane by GPI anchors. Similar complement activation in retinal vessels and selective reduction in the levels of retinal CD55 and CD59 were observed in rats with a 10 week duration of streptozotocin-induced diabetes. Thus, diabetes appears to cause defective regulation of complement inhibitors and complement activation that precede most other manifestations of diabetic retinal microangiopathy.

Gerl et al. (*Investigative Ophthalmology and Visual Science* 43:1104-08, 2000) determined the presence of activated complement components in eyes affected by diabetic retinopathy. Immunohistochemical studies found extensive deposits of complement C5b-9 complexes that were detected in the choriocapillaris immediately underlying the Bruch membrane and densely surrounding the capillaries in all 50 diabetic retinopathy specimens. Staining for C3d positively correlated with C5b-9 staining, indicative of the fact that complement activation had occurred in situ. Furthermore, positive staining was found for vitronectin, which forms stable complexes with extracellular C5b-9. In contrast, there was no positive staining for C-reactive protein (CRP), mannan-binding lectin (MBL), C1q, or C4, indicating that complement activation did not occur through a C4-dependent pathway. Thus, the presence of C3d, C5b-9, and vitronectin indicates that complement activation occurs to completion, possibly through the alternative pathway in the choriocapillaris in eyes affected by diabetic retinopathy. Complement activation may be a causative factor in the pathologic sequelae that can contribute to ocular tissue disease and visual impairment. Therefore, the use of a complement inhibitor may be an effective therapy to reduce or block damage to microvessels that occurs in diabetes.

Insulin dependent diabetes mellitus (IDDM, also referred to as Type-I diabetes) is an autoimmune disease associated with the presence of different types of autoantibodies (Nicoloff et al., *Clin. Dev. Immunol.* 11:61-66, 2004). The presence of these antibodies and the corresponding antigens in the circulation leads to the formation of circulating immune complexes (CIC), which are known to persist in the blood for long periods of time. Deposition of CIC in the small blood vessels has the potential to lead to microangiopathy with debilitating clinical consequences. A correlation exists between CIC and the development of microvascular complications in diabetic children. These findings suggest that elevated levels of CIC IgG are associated with the development of early diabetic nephropathy and that an inhibitor of the complement pathway may be effective at blocking diabetic nephropathy (Kotnik, et al., *Croat. Med.* 1 44:707-11, 2003). In addition, the formation of downstream complement proteins and the involvement of the alternative pathway is likely to be a contributory factor in overall islet cell function in IDDM, and the use of a complement inhibitor to reduce potential damage or limit cell death is expected (Caraher et al., *J. Endocrinol.* 162:143-53, 1999).

Circulating MBL concentrations are significantly elevated in patients with type 1 diabetes compared to healthy controls, and these MBL concentrations correlate positively with urinary albumin excretion (Hansen et al., *J. Clin. Endocrinol. Metab.* 88:4857-61, 2003). A recent clinical study found that the frequencies of high- and low-expression MBL genotypes were similar between patients with type 1 diabetes and healthy controls (Hansen et al., *Diabetes* 53:1570-76, 2004). However, the risk of having nephropathy among the diabetes patients was significantly increased if they had a high MBL genotype. This indicates that high MBL levels and lectin pathway complement activation may contribute to the development of diabetic nephropathy. This conclusion is supported by a recent prospective study in which the association between MBL levels and the development of albuminuria in a cohort of newly diagnosed type 1 diabetic patients was examined (Hovind et al., *Diabetes* 54:1523-27, 2005). They found that high levels of MBL early in the course of type 1 diabetes were significantly associated with later development of persistent albuminuria. These results suggest that MBL and the lectin pathway may be involved in the specific pathogenesis of diabetic vascular complications more than merely causing an acceleration of existing alterations. In a recent clinical study (Hansen et al., *Arch. Intern. Med.* 166:2007-13, 2006), MBL levels were measured at baseline in a well-characterized cohort of patients with type 2 diabetes who received more than 15 years of follow up. They found that even after adjustment for known confounders, the risk of dying was significantly higher among patients with high MBL plasma levels (>1000 µg/L) than among patients with low MBL levels (<1000 µg/L).

In another aspect of the invention, methods are provided for inhibiting MASP-2-dependent complement activation in a subject suffering from nonobese diabetes (IDDM) or from angiopathy, neuropathy or retinopathy complications of IDDM or adult onset (Type-2) diabetes, by administering a composition comprising a therapeutically effective amount of a MASP-2 inhibitor in a pharmaceutical carrier. The MASP-2 inhibitory agent may be administered to the subject systemically, such as by intra-arterial, intravenous, intramuscular, subcutaneous or other parenteral administration, or potentially by oral administration for non-peptidergic agents. Alternatively, administration may be by local delivery to the site of angiopathic, neuropathic or retinopathic symptoms. The MASP-2 inhibitory agent may be administered periodically over an extended period of time for treatment or control of a chronic condition, or by a single or series of administrations for treatment of an acute condition.

Perichemotherapeutic Administration and Treatment of Malignancies

Activation of the complement system may also be implicated in the pathogenesis of malignancies. Recently, the neoantigens of the C5b-9 complement complex, IgG, C3, C4, S-protein/vitronectin, fibronectin, and macrophages were localized on 17 samples of breast cancer and on 6 samples of benign breast tumors using polyclonal or monoclonal antibodies and the streptavidin-biotin-peroxidase technique. All the tissue samples with carcinoma in each the TNM stages presented C5b-9 deposits on the membranes of tumor cells, thin granules on cell remnants, and diffuse deposits in the necrotic areas (Niculescu, F., et al., *Am. J. Pathol.* 140:1039-1043, 1992).

In addition, complement activation may be a consequence of chemotherapy or radiation therapy and thus inhibition of complement activation would be useful as an adjunct in the treatment of malignancies to reduce iatrogenic inflammation. When chemotherapy and radiation therapy preceded surgery, C5b-9 deposits were more intense and extended. The C5b-9 deposits were absent in all the samples with benign lesions. S-protein/vitronectin was present as fibrillar deposits in the connective tissue matrix and as diffuse deposits around the tumor cells, less intense and extended than fibronectin. IgG, C3, and C4 deposits were present only in carcinoma samples. The presence of C5b-9 deposits is indicative of complement activation and its subsequent pathogenetic effects in breast cancer (Niculescu, F., et al., *Am. J. Pathol.* 140:1039-1043, 1992).

Pulsed tunable dye laser (577 nm) (PTDL) therapy induces hemoglobin coagulation and tissue necrosis, which is mainly limited to blood vessels. In a PTDL-irradiated normal skin study, the main findings were as follows: 1) C3 fragments, C8, C9, and MAC were deposited in vessel walls; 2) these deposits were not due to denaturation of the proteins since they became apparent only 7 min after irradiation, contrary to immediate deposition of transferrin at the sites of erythrocyte coagulates; 3) the C3 deposits were shown to amplify complement activation by the alternative pathway, a reaction which was specific since tissue necrosis itself did not lead to such amplification; and 4) these reactions preceded the local accumulation of polymorphonuclear leucocytes. Tissue necrosis was more pronounced in the hemangiomas. The larger angiomatous vessels in the center of the necrosis did not fix complement significantly. By contrast, complement deposition in the vessels situated at the periphery was similar to that observed in normal skin with one exception: C8, C9, and MAC were detected in some blood vessels immediately after laser treatment, a finding consistent with assembly of the MAC occurring directly without the formation of a C5 convertase. These results indicate that complement is activated in PTDL-induced vascular necrosis, and might be responsible for the ensuing inflammatory response.

Photodynamic therapy (PDT) of tumors elicits a strong host immune response, and one of its manifestations is a pronounced neutrophilia. In addition to complement fragments (direct mediators) released as a consequence of PDT-induced complement activation, there are at least a dozen secondary mediators that all arise as a result of complement activity. The latter include cytokines IL-1beta, TNF-alpha, IL-6, IL-10, G-CSF and KC, thromboxane, prostaglandins, leukotrienes, histamine, and coagulation factors (Cecic, I., et al., *Cancer Lett.* 183:43-51, 2002).

Finally, the use of inhibitors of MASP-2-dependent complement activation may be envisioned in conjunction with the standard therapeutic regimen for the treatment of cancer. For example, treatment with rituximab, a chimeric anti-CD20 monoclonal antibody, can be associated with moderate to severe first-dose side-effects, notably in patients with high numbers of circulating tumor cells. Recent studies during the first infusion of rituximab measured complement activation products (C3b/c and C4b/c) and cytokines (tumour necrosis factor alpha (TNF-alpha), interleukin 6 (IL-6) and IL-8) in five relapsed low-grade non-Hodgkin's lymphoma (NHL) patients. Infusion of rituximab induced rapid complement activation, preceding the release of TNF-alpha, IL-6 and IL-8. Although the study group was small, the level of complement activation appeared to be correlated both with the number of circulating B cells prior to the infusion (r=0.85; P=0.07), and with the severity of the side-effects. The results indicated that complement plays a pivotal role in the pathogenesis of side-effects of rituximab treatment. As complement activation cannot be prevented by corticosteroids, it may be relevant to study the possible role of complement inhibitors during the first administration of rituximab (van der Kolk, L. E., et al., *Br. J. Haematol.* 115:807-811, 2001).

In another aspect of the invention, methods are provided for inhibiting MASP-2-dependent complement activation in a subject being treated with chemotherapeutics and/or radiation therapy, including without limitation for the treatment of cancerous conditions. This method includes administering a composition comprising a therapeutically effective amount of a MASP-2 inhibitor in a pharmaceutical carrier to a patient perichemotherapeutically, i.e., before and/or during and/or after the administration of chemotherapeutic(s) and/or radiation therapy. For example, administration of a MASP-2 inhibitor composition of the present invention may be commenced before or concurrently with the administration of chemo- or radiation therapy, and continued throughout the course of therapy, to reduce the detrimental effects of the chemo- and/or radiation therapy in the non-targeted, healthy tissues. In addition, the MASP-2 inhibitor composition can be administered following chemo- and/or radiation therapy. It is understood that chemo- and radiation therapy regimens often entail repeated treatments and, therefore, it is possible that administration of a MASP-2 inhibitor composition would also be repetitive and relatively coincident with the chemotherapeutic and radiation treatments. It is also believed that MASP-2 inhibitory agents may be used as chemotherapeutic agents, alone or in combination with other chemotherapeutic agents and/or radiation therapy, to treat patients suffering from malignancies. Administration may suitably be via oral (for non-peptidergic), intravenous, intramuscular or other parenteral route.

In another embodiment, MASP-2 inhibitory agents may be used to treat a subject for acute radiation syndrome (also known as radiation sickness or radiation poisoning) to reduce the detrimental effects of exposure to ionizing radiation (accidental or otherwise). Symptoms associated with acute radiation syndrome include nausea, vomiting, diarrhea, skin damage, hair loss, fatigue, fever, seizures and coma. For treatment of acute radiation syndrome, the MASP-2 inhibitory composition may be administered immediately following the radiation exposure or prophylactically prior to, during, immediately following, or within one to seven days or longer, such as within 24 hours to 72 hours, after exposure. In some embodiments, the methods may be used to treat a subject prior to or after exposure to a dosage of ionizing radiation sufficient to cause acute radiation syndrome (i.e. a whole body dosage of ionizing radiation of at least 1 Gy, or at least 2 Gy, or at least 3 Gy, or at least 4 Gy, or at least 5 Gy, or at least 6 Gy, or at least 7 Gy, or higher). In some embodiments, the MASP-2 inhibitory composition may suitably be administered in a fast-acting dosage form, such as by intravenous or intra-arterial delivery of a bolus of a solution containing the MASP-2 inhibitory agent composition.

In accordance with the foregoing, in one aspect of the invention, methods are provided for inhibiting MASP-2 dependent complement activation in a subject at risk for developing or suffering from acute radiation syndrome comprising administering to the subject a composition comprising an amount of a MASP-2 inhibitory agent effective to inhibit MASP-2 dependent complement activation. In some embodiments, the anti-MASP-2 inhibitory agent is an anti-MASP-2 antibody. In some embodiments, the MASP-2 inhibitory agent is administered prophylactically to the subject prior to radiation exposure (such as prior to treatment with radiation, or prior to an expected exposure to radiation). In some embodiments, the MASP-2 inhibitory agent is administered within 24 to 48 hours after exposure to radiation. In some embodiments, the MASP-2 inhibitory agent is administered prior to and/or after exposure to radiation in an amount sufficient to ameliorate one or more symptoms associated with acute radiation syndrome.

Endocrine Disorders

The complement system has also been recently associated with a few endocrine conditions or disorders including Hashimoto's thyroiditis (Blanchin, S., et al., *Exp. Eye Res.* 73(6):887-96, 2001), stress, anxiety and other potential hormonal disorders involving regulated release of prolactin, growth or insulin-like growth factor, and adrenocorticotropin from the pituitary (Francis, K., et al., *FASEB J.* 17:2266-2268, 2003; Hansen, T. K., *Endocrinology* 144(12):5422-9, 2003).

Two-way communication exists between the endocrine and immune systems using molecules such as hormones and cytokines. Recently, a new pathway has been elucidated by which C3a, a complement-derived cytokine, stimulates anterior pituitary hormone release and activates the hypothalamic-pituitary-adrenal axis, a reflex central to the stress response and to the control of inflammation. C3a receptors are expressed in pituitary-hormone-secreting and non-hormone-secreting (folliculostellate) cells. C3a and C3adesArg (a non-inflammatory metabolite) stimulate pituitary cell cultures to release prolactin, growth hormone, and adrenocorticotropin. Serum levels of these hormones, together with adrenal corticosterone, increase dose dependently with recombinant C3a and C3adesArg administration in vivo. The implication is that complement pathway modulates tissue-specific and systemic inflammatory responses through communication with the endocrine pituitary gland (Francis, K., et al., *FASEB J.* 17:2266-2268, 2003).

An increasing number of studies in animals and humans indicate that growth hormone (GH) and insulin-like growth factor-I (IGF-I) modulate immune function. GH therapy increased the mortality in critically ill patients. The excessive mortality was almost entirely due to septic shock or multi-organ failure, which could suggest that a GH-induced modulation of immune and complement function was involved. Mannan-binding lectin (MBL) is a plasma protein that plays an important role in innate immunity through activation of the complement cascade and inflammation following binding to carbohydrate structures. Evidence supports a significant influence from growth hormone on MBL levels and, therefore, potentially on lectin-dependent complement activation (Hansen, T. K., *Endocrinology* 144 (12):5422-9, 2003).

Thyroperoxidase (TPO) is one of the main autoantigens involved in autoimmune thyroid diseases. TPO consists of a large N-terminal myeloperoxidase-like module followed by a complement control protein (CCP)-like module and an epidermal growth factor-like module. The CCP module is a constituent of the molecules involved in the activation of C4 complement component, and studies were conducted to investigate whether C4 may bind to TPO and activate the complement pathway in autoimmune conditions. TPO via its CCP module directly activates complement without any mediation by Ig. Moreover, in patients with Hashimoto's thyroiditis, thyrocytes overexpress C4 and all the downstream components of the complement pathway. These results indicate that TPO, along with other mechanisms related to activation of the complement pathway, may contribute to the massive cell destruction observed in Hashimoto's thyroiditis (Blanchin, S., et al., 2001).

An aspect of the invention thus provides a method for inhibiting MASP-2-dependent complement activation to treat an endocrine disorder, by administering a composition comprising a therapeutically effective amount of a MASP-2 inhibitory agent in a pharmaceutical carrier to a subject suffering from an endocrine disorder. Conditions subject to treatment in accordance with the present invention include, by way of nonlimiting example, Hashimoto's thyroiditis, stress, anxiety and other potential hormonal disorders involving regulated release of prolactin, growth or insulin-like growth factor, and adrenocorticotropin from the pituitary. The MAS-2 inhibitory agent may be administered to the subject systemically, such as by intra-arterial, intravenous, intramuscular, inhalational, nasal, subcutaneous or other parenteral administration, or potentially by oral administration for non-peptidergic agents. The MASP-2 inhibitory agent composition may be combined with one or more additional therapeutic agents. Administration may be repeated as determined by a physician until the condition has been resolved.

Ophthalmologic Conditions

Age-related macular degeneration (AMD) is a blinding disease that afflicts millions of adults, yet the sequelae of biochemical, cellular, and/or molecular events leading to the development of AMD are poorly understood. AMD results in the progressive destruction of the macula which has been correlated with the formation of extracellular deposits called drusen located in and around the macula, behind the retina and between the retina pigment epithelium (RPE) and the choroid. Recent studies have revealed that proteins associated with inflammation and immune-mediated processes are prevalent among drusen-associated constituents. Transcripts that encode a number of these molecules have been detected in retinal, RPE, and choroidal cells. These data also demonstrate that dendritic cells, which are potent antigen-presenting cells, are intimately associated with drusen development, and that complement activation is a key pathway that is active both within drusen and along the RPE-choroid interface (Hageman, G. S., et al., *Prog. Retin. Eye Res.* 20:705-732, 2001).

Several independent studies have shown a strong association between AMD and a genetic polymorphism in the gene for complement factor H (CFH) in which the likelihood of AMD is increased by a factor of 7.4 in individuals homozygous for the risk allele (Klein, R. J. et al., *Science* 308:362-364, 2005; Haines et al., *Science* 308:362-364. 2005; Edwards et al., *Science* 308:263-264, 2005). The CFH gene has been mapped to chromosome 1q31 a region that had been implicated in AMD by six independent linkage scans (see, e.g., Schultz, D. W., et al., *Hum. Mol. Genet.* 12:3315, 2003). CFH is known to be a key regulator of the complement system. It has been shown that CFH on cells and in circulation regulates complement activity by inhibiting the activation of C3 to C3a and C3b, and by inactivating existing C3b. Deposition of C5b-9 has been observed in Brusch's membrane, the intercapillary pillars and within drusen in patients with AMD (Klein et al.). Immunofluorescence experiments suggest that in AMD, the polymorphism of CFH may give rise to complement deposition in chorodial capillaries and chorodial vessels (Klein et al.).

The membrane-associated complement inhibitor, complement receptor 1, is also localized in drusen, but it is not detected in RPE cells immunohistochemically. In contrast, a second membrane-associated complement inhibitor, membrane cofactor protein, is present in drusen-associated RPE cells, as well as in small, spherical substructural elements within drusen. These previously unidentified elements also show strong immunoreactivity for proteolytic fragments of complement component C3 that are characteristically deposited at sites of complement activation. It is proposed that these structures represent residual debris from degenerating RPE cells that are the targets of complement attack (Johnson, L. V., et al., *Exp. Eye Res.* 73:887-896, 2001).

Identification and localization of these multiple complement regulators as well as complement activation products (C3a, C5a, C3b, C5b-9) have led investigators to conclude that chronic complement activation plays an important role in the process of drusen biogenesis and the etiology of AMD (Hageman et al., *Progress Retinal Eye Res.* 20:705-32, 2001). Identification of C3 and C5 activation products in drusen provides no insight into whether complement is activated via the classical pathway, the lectin pathway or the alternative amplification loop, as understood in accordance with the present invention, since both C3 and C5 are common to all three. However, two studies have looked for drusen immuno-labeling using antibodies specific to C1q, the essential recognition component for activation of the classical pathway (Mullins et al., *FASEB J.* 14:835-846, 2000; Johnson et al., *Exp. Eye Res.* 70:441-449, 2000). Both studies concluded that C1q immuno-labelling in drusen was not generally observed. These negative results with C1q suggest that complement activation in drusen does not occur via the classical pathway. In addition, immuno-labeling of drusen for immune-complex constituents (IgG light chains, IgM) is reported in the Mullins et al., 2000 study as being weak to variable, further indicating that the classical pathway plays a minor role in the complement activation that occurs in this disease process.

Two recent published studies have evaluated the role of complement in the development of laser-induced choroidal neovascularization (CNV) in mice, a model of human CNV. Using immunohistological methods, Bora and colleagues (2005) found significant deposition of the complement activation products C3b and C5b-9 (MAC) in the neovascular complex following laser treatment (Bora et al., *J. Immunol.* 174:491-7, 2005). Importantly, CNV did not develop in mice genetically deficient in C3 (C3-/- mice), the essential component required in all complement activation pathways. RNA message levels for VEGF, TGF-$\beta_2$, and $\beta$-FGF, three angiogenic factors implicated in CNV, were elevated in eye tissue from mice after laser-induced CNV. Significantly, complement depletion resulted in a marked reduction in the RNA levels of these angiogenic factors.

Using ELISA methods, Nozaki and colleagues demonstrated that the potent anaphylatoxins C3a and C5a are generated early in the course of laser-induced CNV (Nozaki et al., *Proc. Natl. Acad. Sci. U.S.A.* 103:2328-33, 2006). Furthermore, these two bioactive fragments of C3 and C5 induced VEGF expression following intravitreal injection in wild-type mice. Consistent with these results Nozaki and colleagues also showed that genetic ablation of receptors for C3a and C5a reduces VEGF expression and CNV formation after laser injury, and that antibody-mediated neutralization of C3a or C5a or pharmacologic blockade of their receptors also reduces CNV. Previous studies have established that recruitment of leukocytes, and macrophages in particular, plays a pivotal role in laser-induced CNV (Sakurai et al., *Invest. Opthomol. Vis. Sci.* 44:3578-85, 2003; Espinosa-Heidmann, et al., *Invest. Opthomol. Vis. Sci.* 44:3586-92, 2003). In their 2006 paper, Nozaki and colleagues report that leukocyte recruitment is markedly reduced in C3aR(-/-) and C5aR(-/-) mice after laser injury.

An aspect of the invention thus provides a method for inhibiting MASP-2-dependent complement activation to treat age-related macular degeneration or other complement mediated ophthalmologic condition by administering a composition comprising a therapeutically effective amount of a MASP-2 inhibitory agent in a pharmaceutical carrier to a subject suffering from such a condition or other complement-mediated ophthalmologic condition. The MASP-2 inhibitory composition may be administered locally to the eye, such as by irrigation or application of the composition in the form of a gel, salve or drops. Alternately, the MASP-2 inhibitory agent may be administered to the subject systemically, such as by intra-arterial, intravenous, intramuscular, inhalational, nasal, subcutaneous or other parenteral administration, or potentially by oral administration for non-peptidergic agents. The MASP-2 inhibitory agent composition may be combined with one or more additional therapeutic agents, such as are disclosed in U.S. Patent Application Publication No. 2004-0072809-A1. Administration may be repeated as determined by a physician until the condition has been resolved or is controlled.

In another aspect, the invention provides a method for inhibiting MASP-2-dependent complement activation to treat a subject suffering from or at risk for developing glaucoma. It has been shown that uncontrolled complement activation contributes to the progression of degenerative injury to retinal ganglion cells (RGCs), their synapses and axons in glaucoma. See Tezel G. et al., *Invest Ophthalmol Vis Sci* 51:5071-5082 (2010). For example, histopathologic studies of human tissues and in vivo studies using different animal models have demonstrated that complement components, including C1q and C3, are synthesized and terminal complement complex is formed in the glaucomatous retina (see Stasi K. et al., *Invest Ophthalmol Vis Sci* 47:1024-1029 (2006), Kuehn M. H. et al., *Exp Eye Res* 83:620-628 (2006)). As described in Tezel G. et al., it has been determined that in addition to the classical pathway, the lectin pathway is likely to be involved in complement activation during glaucomatous neurodegeneration, thereby facilitating the progression of neurodegenerative injury by collateral cell lysis, inflammation and autoimmunity. As described in Tezel G. et al., proteomic analysis of human retinal samples obtained from donor eyes with or without glaucoma detected the expression and differential regulation of several complement components. Notably, expression levels of complement components from the lectin pathway were higher, or only detected, in glaucomatous samples than controls, including MASP-1 and MASP-2, and C-type lectin. As further described in Kuehn M. H. et al., *Experimental Eye Research* 87:89-95 (2008), complement synthesis and deposition is induced by retinal I/R and the disruption of the complement cascade delays RGC degeneration. In this study, mice carrying a targeted disruption of the complement component C3 were found to exhibit delayed RGC degeneration after transient retinal I/R when compared to normal animals.

The findings of these studies suggest that alterations in the physiological balance between complement activation and intrinsic regulation under glaucomatous stress consitions may have an important impact on the progression of neurodegenerative injury, indicating that inhibition of complement activation, such as through the administration of anti-MASP-2 antibodies, can be used as a therapeutic for glaucoma patients.

An aspect of the invention thus provides a method for inhibiting MASP-2-dependent complement activation to treat glaucoma by administering a composition comprising a therapeutically effective amount of a MASP-2 inhibitory agent in a pharmaceutical carrier to a subject suffering from glaucoma. The MASP-2 inhibitory composition may be administered locally to the eye, such as by irrigation or application of the composition in the form of a gel, salve or drops. Alternately, the MASP-2 inhibitory agent may be administered to the subject systemically, such as by intra-arterial, intravenous, intramuscular, inhalational, nasal, subcutaneous or other parenteral administration, or potentially by oral administration for non-peptidergic agents. Administration may be repeated as determined by a physician until the condition has been resolved or is controlled.

Coagulopathies

Evidence has been developed for the role of the complement system in disseminated intravascular coagulation ("DIC"), such as DIC secondary to significant bodily trauma.

Figure 30A:
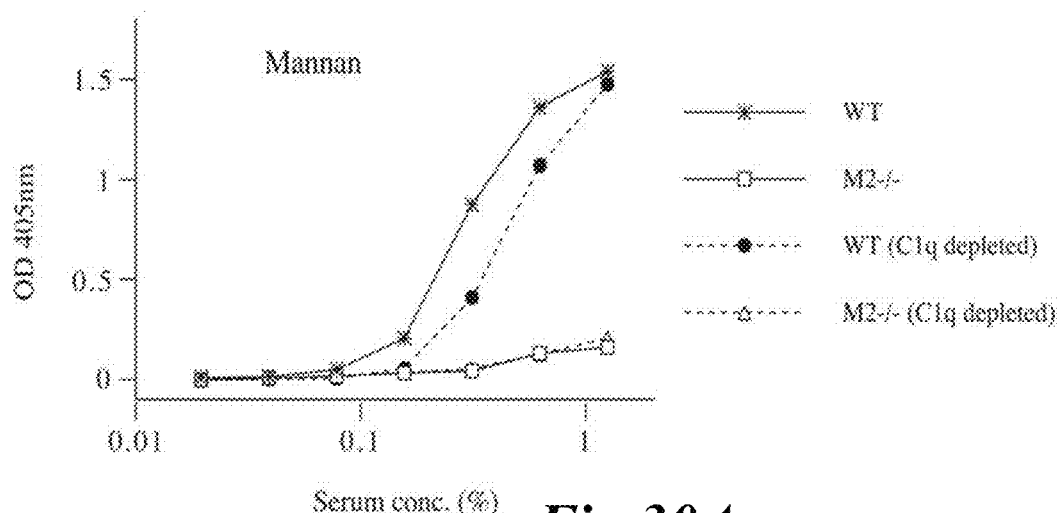
FIGS. 30A-30C illustrate the results of an investigation of C3 turnover in C4−/− plasma in assays specific for either the classical or the lectin pathway activation route.
Figure 30B:
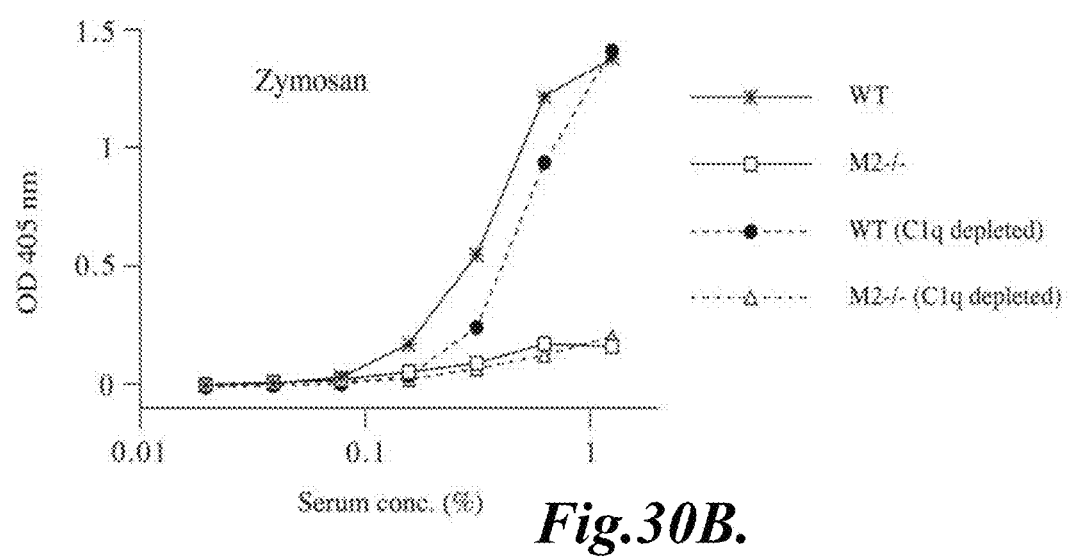
Figure 30C:
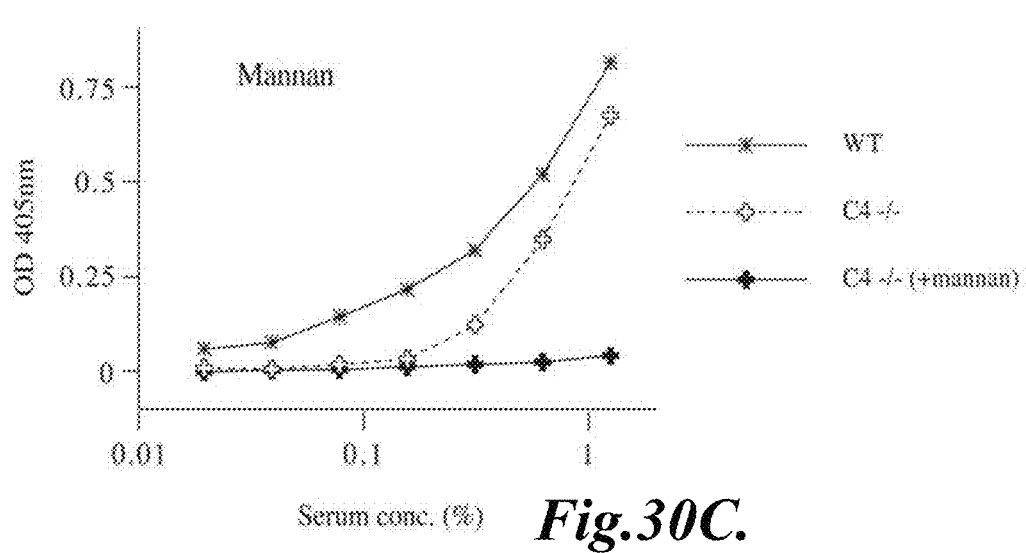

Previous studies have shown that C4-/- mice are not protected from renal reperfusion injury. (Zhou, W., et al, "Predominant role for C5b-9 in renal ischemia/reperfusion injury," *J Clin Invest* 105:1363-1371 (2000)) In order to investigate whether C4-/- mice may still be able to activate complement via either the classical or the lectin pathway, C3 turn-over in C4-/- plasma was measured in assays specific for either the classical, or the lectin pathway activation route. While no C3 cleavage could be observed when triggering activation via the classical, a highly efficient lectin pathway-dependent activation of C3 in C4 deficient serum was observed (FIG. 30). It can be seen that C3b deposition on mannan and zymosan is severely compromised in MASP-2-/- mice, even under experimental conditions, that according to many previously published papers on alternative pathway activation, should be permissive for all three pathways. When using the same sera in wells coated with immunoglobulin complexes instead of mannan or zymosan, C3b deposition and Factor B cleavage are seen in MASP-2+/+ mouse sera and MASP-2-/- sera, but not in C1q depleted sera. This indicates that alternate pathway activation is facilitated in MASP-2-/- sera when the initial C3b is provided via classical activity. FIG. 30C depicts the surprising finding that C3 can efficiently be activated in a lectin pathway-dependent fashion in C4 deficient plasma.

This "C4 bypass" is abolished by the inhibition of lectin pathway-activation through preincubation of plasma with soluble mannan or mannose.

Aberrant, non-immune, activation of the complement system is potentially hazardous to man and may also play an important role in hematological pathway activation, particularly in severe trauma situations wherein both inflammatory and hematological pathways are activated. In normal health, C3 conversion is <5% of the total plasma C3 protein. In rampant infection, including septicaemia and immune complex disease, C3 conversion re-establishes itself at about 30% with complement levels frequently lower than normal, due to increased utilization and changes in pool distribution. Immediate C3 pathway activation of greater than 30% generally produces obvious clinical evidence of vasodilatation and of fluid loss to the tissues. Above 30% C3 conversion, the initiating mechanisms are predominantly non-immune and the resulting clinical manifestations are harmful to the patient. Complement C5 levels in health and in controlled disease appear much more stable than C3. Significant decreases and or conversion of C5 levels are associated with the patient's response to abnormal polytrauma (e.g., road traffic accidents) and the likely development of shock lung syndromes. Thus, any evidence of either complement C3 activation beyond 30% of the vascular pool or of any C5 involvement, or both, may be considered likely to be a harbinger of a harmful pathological change in the patient.

Both C3 and C5 liberate anaphylatoxins (C3a and C5a) that act on mast cells and basophils releasing vasodilatory chemicals. They set up chemotactic gradients to guide polymorphonuclear cells (PMN) to the center of immunological disturbances (a beneficial response), but here they differ because C5a has a specific clumping (aggregating) effect on these phagocytic cells, preventing their random movement away from the reaction site. In normal control of infection, C3 activates C5. However, in polytrauma, C5 appears to be widely activated, generating C5a anaphylatoxins systemically. This uncontrolled activity causes polymorphs to clump within the vascular system, and these clumps are then swept into the capillaries of the lungs, which they occlude and generate local damaging effects as a result of superoxide liberation. While not wishing to be limited by theory, the mechanism is probably important in the pathogenesis of acute respiratory distress syndrome (ARDS), although this view has recently been challenged. The C3a anaphylatoxins in vitro can be shown to be potent platelet aggregators, but their involvement in vivo is less defined and the release of platelet substances and plasmin in wound repair may only secondarily involve complement C3. It is possible that prolonged elevation of C3 activation is necessary to generate DIC.

In addition to cellular and vascular effects of activated complement component outlined above that could explain the link between trauma and DIC, emerging scientific discoveries have identified direct molecular links and functional cross-talk between complement and coagulation systems. Supporting data has been obtained from studies in C3 deficient mice. Because C3 is the shared component for each of the complement pathways, C3 deficient mice are predicted to lack all complement function. Surprisingly, however, C3 deficient mice are perfectly capable of activating terminal complement components. (Huber-Lang, M., et al., "Generation of C5a in the absence of C3: a new complement activation pathway," *Nat. Med* 12:682-687 (2006)) In depth studies revealed that C3-independent activation of terminal complement components is mediated by thrombin, the rate limiting enzyme of the coagulation cascade. (Huber et al., 2006) The molecular components mediating thrombin activation following initial complement activation remained elusive.

The present inventors have elucidated what is believed to be the molecular basis for cross-talk between complement and clotting cascades and identified MASP-2 as a central control point linking the two systems. Biochemical studies into the substrate specificity of MASP-2 have identified prothrombin as a possible substrate, in addition to the well known C2 and C4 complement proteins. MASP-2 specifically cleaves prothrombin at functionally relevant sites, generating thrombin, the rate limiting enzyme of the coagulation cascade. (Krarup, A., et al., "Simultaneous Activation of Complement and Coagulation by MBL-Associated Serine Protease 2," *PLoS. ONE.* 2:e623 (2007)) MASP-2-generated thrombin is capable of promoting fibrin deposition in a defined reconstituted in vitro system, demonstrating the functional relevance of MASP-2 cleavage. (Krarup et al., 2007) As discussed in the examples herein below, the inventors have further corroborated the physiological significance of this discovery by documenting thrombin activation in normal rodent serum following lectin pathway activation, and demonstrated that this process is blocked by neutralizing MASP-2 monoclonal antibodies.

MASP-2 may represent a central branch point in the lectin pathway, capable of promoting activation of both complement and coagulation systems. Because lectin pathway activation is a physiologic response to many types of traumatic injury, the present inventors believe that concurrent systemic inflammation (mediated by complement components) and disseminated coagulation (mediated via the clotting pathway) can be explained by the capacity of MASP-2 to activate both pathways. These findings clearly suggest a role for MASP-2 in DIC generation and therapeutic benefit of MASP-2 inhibition in treating or preventing DIC. MASP-2 may provide the molecular link between complement and coagulation system, and activation of the lectin pathway as it occurs in settings of trauma can directly initiate activation of the clotting system via the MASP-2-thrombin axis, providing a mechanistic link between trauma and DIC. In accordance with an aspect of the present invention, inhibition of MASP-2 would inhibit lectin pathway activation and reduce the generation of both anaphylatoxins C3a and C5a. It is believed that prolonged elevation of C3 activation is necessary to generate DIC.

Therefore, an aspect of the invention thus provides a method for inhibiting MASP-2-dependent complement activation to treat disseminated intravascular coagulation or other complement mediated coagulation disorder by administering a composition comprising a therapeutically effective amount of a MASP-2 inhibitory agent (e.g., anti-MASP-2 antibody or fragment thereof, peptide inhibitors or small molecule inhibitors) in a pharmaceutical carrier to a subject suffering from or at risk for developing such a condition. In some embodiments, the MASP-2 inhibitory agents can block MASP-2 that has already been activated. The MASP-2 inhibitory composition is suitably administered to the subject systemically, such as by intra-arterial, intravenous, intramuscular, inhalational, nasal, subcutaneous or other parenteral administration, or potentially by oral administration for non-peptidergic agents. Administration may be repeated as determined by a physician until the condition has been resolved or is controlled. The methods of this aspect of the present invention may be utilized for treatment of DIC secondary to sepsis, severe trauma, including neurological trauma (e.g., acute head injury, see Kumura, E., et al., *Acta Neurochirurgica* 85:23-28 (1987), infection (bacterial, viral, fungal, parasitic), cancer, obstetrical complications, liver disease, severe toxic reaction (e.g., snake bite, insect bite, transfusion reaction), shock, heat stroke, transplant rejection, vascular aneurysm, hepatic failure, cancer treatment by chemotherapy or radiation therapy, burn, accidental radiation exposure, and other causes. See e.g., Becker J. U. and Wira C. R. "Disseminated Intravascular Coagulation" emedicine.medscape.com/9/10/2009. For DIC secondary to trauma or other acute event, the MASP-2 inhibitory composition may be administered immediately following the traumatic injury or prophylactically prior to, during, immediately following, or within one to seven days or longer, such as within 24 hours to 72 hours, after trauma-inducing injury or situations such as surgery in patients deemed at risk of DIC. In some embodiments, the MASP-2 inhibitory composition may suitably be administered in a fast-acting dosage form, such as by intravenous or intra-arterial delivery of a bolus of a solution containing the MASP-2 inhibitory agent composition.

In another aspect, the present invention provides methods of treating a subject suffering from or at risk for developing thrombosis, microcirculatory coagulation or multi-organ failure subsequent to microcirculatory coagulation. Physiological thrombus (blood clot) forms in response to vascular insult to prevent leakage of blood from a damaged blood vessel.

The lectin pathway may play a role in pathological thrombosis triggered by an underlying vascular inflammation linked to various etiologies. For example, a thrombus can form around atherosclerotic plaques, which is a known initiator of the lectin pathway. Thus, treatment with a MASP-2 inhibitor may be used to block thrombus formation in patients with underlying atheroscelorsis.

Figure 29A:
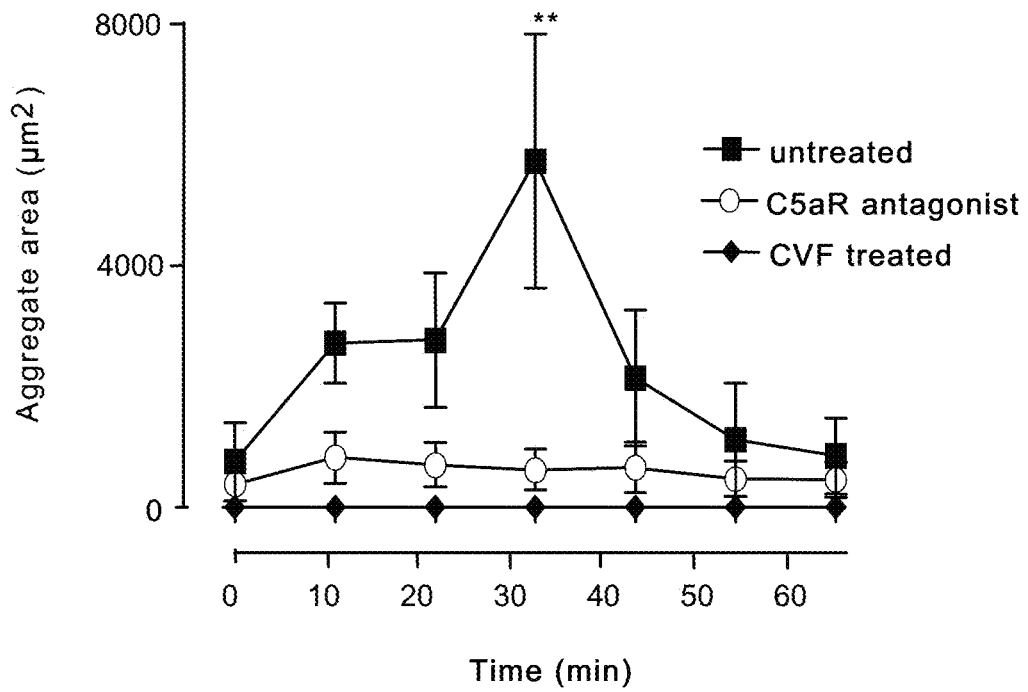
FIGS. 29A and 29B present measured platelet aggregation (expressed as aggregate area) in MASP-2 (−/−) mice (FIG. 29B) as compared to platelet aggregation in untreated wild type mice and wild type mice in which the complement pathway is inhibited by depletory agent cobra venom factor (CVF) and a terminal pathway inhibitor (C5aR antagonist) (FIG. 29A) in a localized Schwartzman reaction model of disseminated intravascular coagulation, as described in Example 33.
Figure 29B:
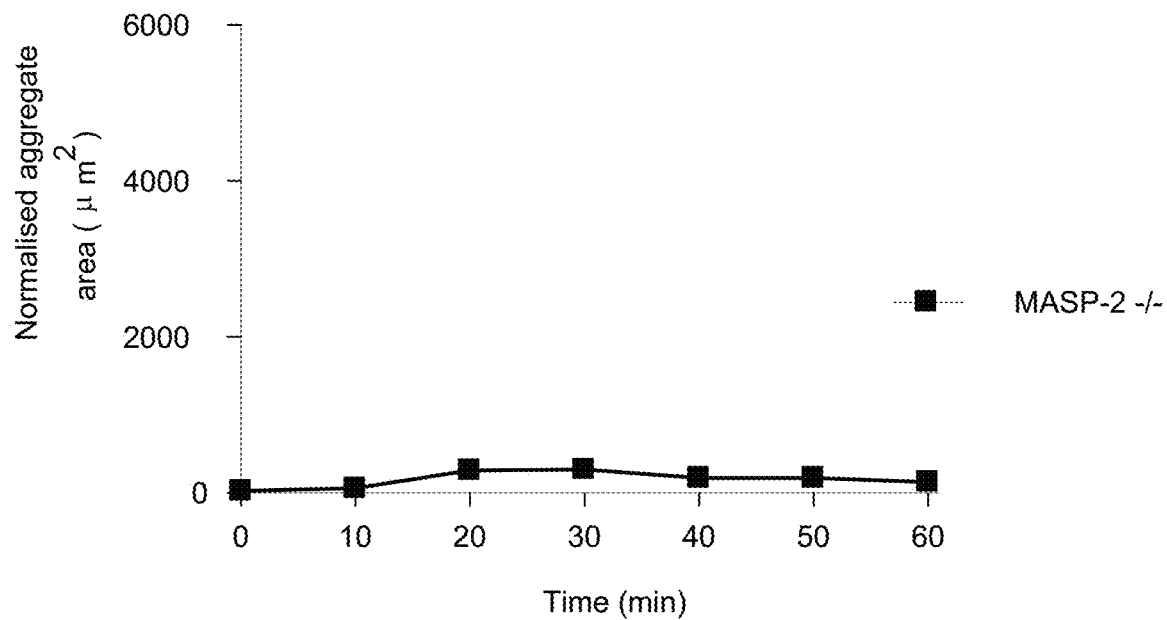

Microcirculatory coagulation (blot clots in capillaries and small blood vessels) occurs in settings such a septic shock. A role of the lectin pathway in septic shock is established, as evidenced by the protected phenotype of MASP-2 (−/−) mouse models of sepsis, described in Example 36 and FIGS. 33 and 34. Furthermore, as demonstrated in Example 33 and FIGS. 29A and 29B, MASP-2 (−/−) mice are protected in the localized Schwartzman reaction model of disseminated intravascular coagulation (DIC), a model of localized coagulation in microvessels.

IV. Masp-2 Inhibitory Agents

In one aspect, the present invention provides methods of inhibiting the adverse effects of MASP-2-dependent complement activation. MASP-2 inhibitory agents are administered in an amount effective to inhibit MASP-2-dependent complement activation in a living subject. In the practice of this aspect of the invention, representative MASP-2 inhibitory agents include: molecules that inhibit the biological activity of MASP-2 (such as small molecule inhibitors, anti-MASP-2 antibodies or blocking peptides which interact with MASP-2 or interfere with a protein-protein interaction), and molecules that decrease the expression of MASP-2 (such as MASP-2 antisense nucleic acid molecules, MASP-2 specific RNAi molecules and MASP-2 ribozymes), thereby preventing MASP-2 from activating the alternative complement pathways. The MASP-2 inhibitory agents can be used alone as a primary therapy or in combination with other therapeutics as an adjuvant therapy to enhance the therapeutic benefits of other medical treatments.

The inhibition of MASP-2-dependent complement activation is characterized by at least one of the following changes in a component of the complement system that occurs as a result of administration of a MASP-2 inhibitory agent in accordance with the methods of the invention: the inhibition of the generation or production of MASP-2-dependent complement activation system products C4b, C3a, C5a and/or C5b-9 (MAC) (measured, for example, as described in Example 2), the reduction of alternative complement activation assessed in a hemolytic assay using unsensitized rabbit or guinea pig red blood cells, the reduction of C4 cleavage and C4b deposition (measured, for example as described in Example 2), or the reduction of C3 cleavage and C3b deposition (measured, for example, as described in Example 2).

According to the present invention, MASP-2 inhibitory agents are utilized that are effective in inhibiting the MASP-2-dependent complement activation system. MASP-2 inhibitory agents useful in the practice of this aspect of the invention include, for example, anti-MASP-2 antibodies and fragments thereof, MASP-2 inhibitory peptides, small molecules, MASP-2 soluble receptors and expression inhibitors. MASP-2 inhibitory agents may inhibit the MASP-2-dependent complement activation system by blocking the biological function of MASP-2. For example, an inhibitory agent may effectively block MASP-2 protein-to-protein interactions, interfere with MASP-2 dimerization or assembly, block $Ca^{2+}$ binding, interfere with the MASP-2 serine protease active site, or may reduce MASP-2 protein expression.

In some embodiments, the MASP-2 inhibitory agents selectively inhibit MASP-2 complement activation, leaving the C1q-dependent complement activation system functionally intact.

In one embodiment, a MASP-2 inhibitory agent useful in the methods of the invention is a specific MASP-2 inhibitory agent that specifically binds to a polypeptide comprising SEQ ID NO:6 with an affinity of at least ten times greater than to other antigens in the complement system. In another embodiment, a MASP-2 inhibitory agent specifically binds to a polypeptide comprising SEQ ID NO:6 with a binding affinity of at least 100 times greater than to other antigens in the complement system. The binding affinity of the MASP-2 inhibitory agent can be determined using a suitable binding assay.

Figure 2:
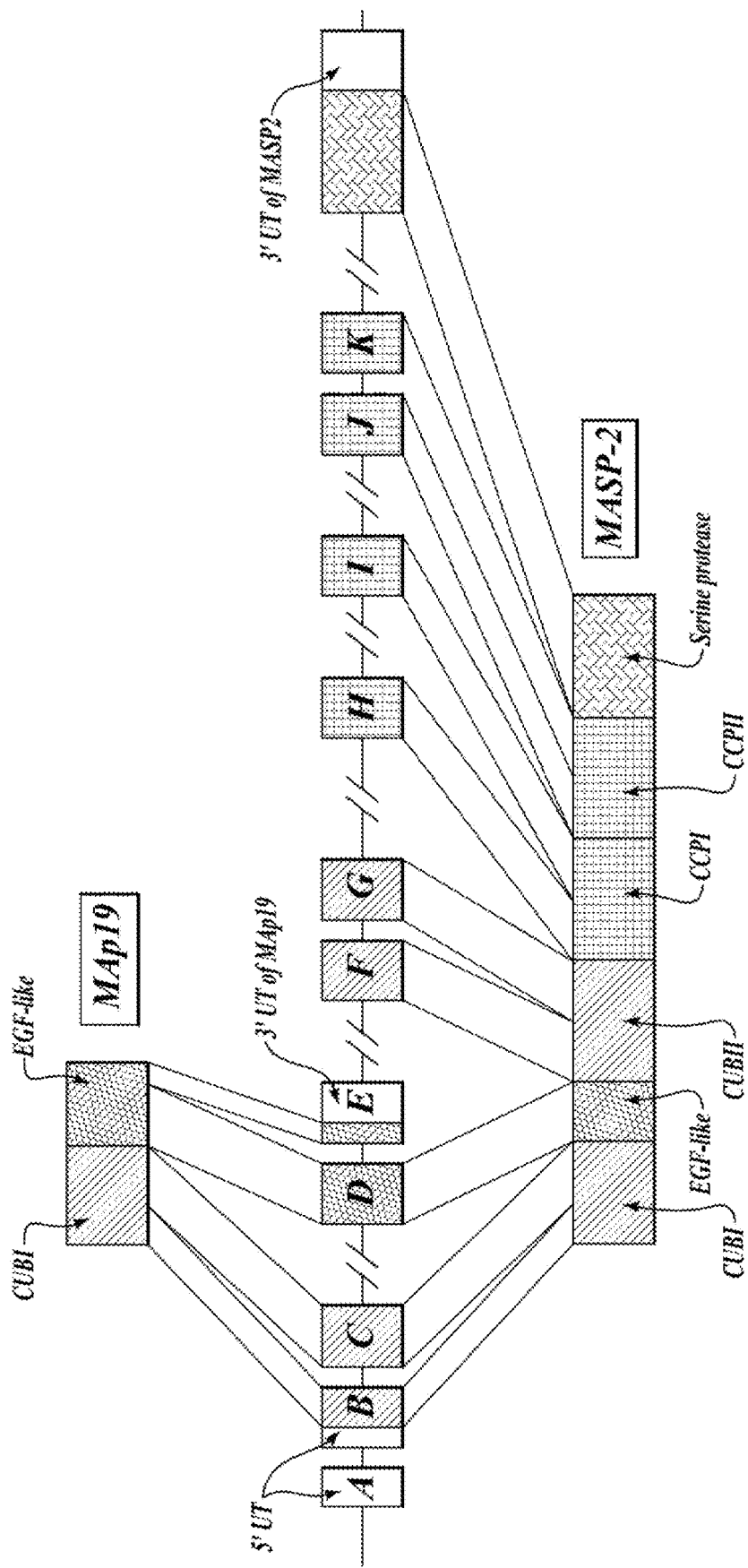
FIG. 2 is a diagram illustrating the genomic structure of human MASP-2.

The MASP-2 polypeptide exhibits a molecular structure similar to MASP-1, MASP-3, and C1r and C1s, the proteases of the C1 complement system. The cDNA molecule set forth in SEQ ID NO:4 encodes a representative example of MASP-2 (consisting of the amino acid sequence set forth in SEQ ID NO:5) and provides the human MASP-2 polypeptide with a leader sequence (aa 1-15) that is cleaved after secretion, resulting in the mature form of human MASP-2 (SEQ ID NO:6). As shown in FIG. 2, the human MASP 2 gene encompasses twelve exons. The human MASP-2 cDNA is encoded by exons B, C, D, F, G, H, I, J, K AND L. An alternative splice results in a 20 kDa protein termed MBL-associated protein 19 ("MAp19", also referred to as "sMAP") (SEQ ID NO:2), encoded by (SEQ ID NO:1) arising from exons B, C, D and E as shown in FIG. 2. The cDNA molecule set forth in SEQ ID NO:50 encodes the murine MASP-2 (consisting of the amino acid sequence set forth in SEQ ID NO:51) and provides the murine MASP-2 polypeptide with a leader sequence that is cleaved after secretion, resulting in the mature form of murine MASP-2 (SEQ ID NO:52). The cDNA molecule set forth in SEQ ID NO:53 encodes the rat MASP-2 (consisting of the amino acid sequence set forth in SEQ ID NO:54) and provides the rat MASP-2 polypeptide with a leader sequence that is cleaved after secretion, resulting in the mature form of rat MASP-2 (SEQ ID NO:55).

Those skilled in the art will recognize that the sequences disclosed in SEQ ID NO:4, SEQ ID NO:50 and SEQ ID NO:53 represent single alleles of human, murine and rat MASP-2 respectively, and that allelic variation and alternative splicing are expected to occur. Allelic variants of the nucleotide sequences shown in SEQ ID NO:4, SEQ ID NO:50 and SEQ ID NO:53, including those containing silent mutations and those in which mutations result in amino acid sequence changes, are within the scope of the present invention. Allelic variants of the MASP-2 sequence can be cloned by probing cDNA or genomic libraries from different individuals according to standard procedures.

Figure 3A:
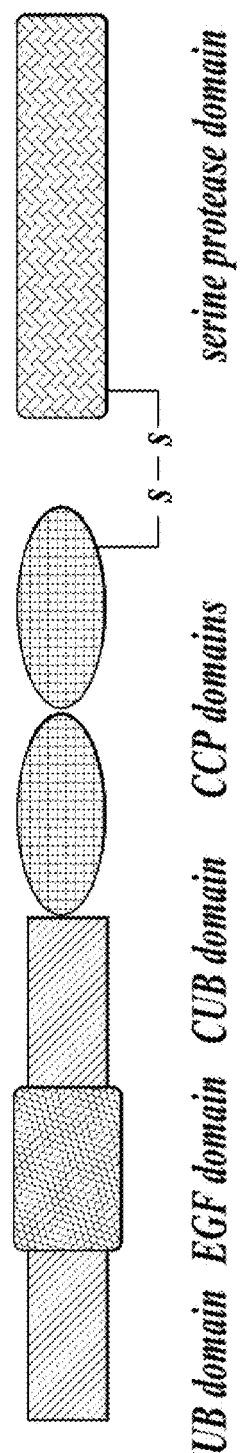
FIG. 3A is a schematic diagram illustrating the domain structure of human MASP-2 protein.
Figure 3B:
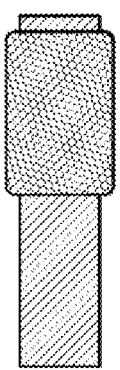
FIG. 3B is a schematic diagram illustrating the domain structure of human MAp19 protein.

The domains of the human MASP-2 protein (SEQ ID NO:6) are shown in FIG. 3A and include an N-terminal C1r/C1s/sea urchin Vegf/bone morphogenic protein (CUBI) domain (aa 1-121 of SEQ ID NO:6), an epidermal growth factor-like domain (aa 122-166), a second CUBI domain (aa 167-293), as well as a tandem of complement control protein domains and a serine protease domain. Alternative splicing of the MASP 2 gene results in MAp19 shown in FIG. 3B. MAp19 is a nonenzymatic protein containing the N-terminal CUB1-EGF region of MASP-2 with four additional residues (EQSL) derived from exon E as shown in FIG. 2.

Several proteins have been shown to bind to, or interact with MASP-2 through protein-to-protein interactions. For example, MASP-2 is known to bind to, and form $Ca^{2+}$ dependent complexes with, the lectin proteins MBL, H-ficolin and L-ficolin. Each MASP-2/lectin complex has been shown to activate complement through the MASP-2-dependent cleavage of proteins C4 and C2 (Ikeda, K., et al., *J. Biol. Chem.* 262:7451-7454, 1987; Matsushita, M., et al., *J. Exp. Med.* 176:1497-2284, 2000; Matsushita, M., et al., *J. Immunol.* 168:3502-3506, 2002). Studies have shown that the CUB1-EGF domains of MASP-2 are essential for the association of MASP-2 with MBL (Thielens, N. M., et al., *J. Immunol.* 166:5068, 2001). It has also been shown that the CUB1EGFCUBII domains mediate dimerization of MASP-2, which is required for formation of an active MBL complex (Wallis, R., et al., *J. Biol. Chem.* 275:30962-30969, 2000). Therefore, MASP-2 inhibitory agents can be identified that bind to or interfere with MASP-2 target regions known to be important for MASP-2-dependent complement activation.

Anti-MASP-2 Antibodies

In some embodiments of this aspect of the invention, the MASP-2 inhibitory agent comprises an anti-MASP-2 antibody that inhibits the MASP-2-dependent complement activation system. The anti-MASP-2 antibodies useful in this aspect of the invention include polyclonal, monoclonal or recombinant antibodies derived from any antibody producing mammal and may be multispecific, chimeric, humanized, anti-idiotype, and antibody fragments. Antibody fragments include Fab, Fab', F(ab)$_2$, F(ab')$_2$, Fv fragments, scFv fragments and single-chain antibodies as further described herein.

Several anti-MASP-2 antibodies have been described in the literature, some of which are listed below in TABLE 1.

These previously described anti-MASP-2 antibodies can be screened for the ability to inhibit the MASP-2-dependent complement activation system using the assays described herein. For example, anti rat MASP-2 Fab2 antibodies have been identified that block MASP-2 dependent complement activation, as described in more detail in Examples 24 and 25 herein. Once an anti-MASP-2 antibody is identified that functions as a MASP-2 inhibitory agent, it can be used to produce anti-idiotype antibodies and used to identify other MASP-2 binding molecules as further described below.

TABLE 1

MASP-2 SPECIFIC ANTIBODIES FROM THE LITERATURE

| ANTIGEN | ANTIBODY TYPE | REFERENCE |
|---|---|---|
| Recombinant MASP-2 | Rat Polyclonal | Peterson, S.V., et al., Mol. Immunol. 37:803-811, 2000 |
| Recombinant human CCP1/2-SP fragment (MoAb 8B5) | Rat MoAb (subclass IgG1) | Moller-Kristensen, M., et al., J. of Immunol. Methods 282:159-167, 2003 |
| Recombinant human MAp19 (MoAb 6G12) (cross reacts with MASP-2) | Rat MoAb (subclass IgG1) | Moller-Kristensen, M., et al., J. of Immunol. Methods 282:159-167, 2003 |
| hMASP-2 | Mouse MoAb (S/P) Mouse MoAb (N-term) | Peterson, S.V., et al., Mol. Immunol. 35:409, April 1998 |
| hMASP-2 (CCP1-CCP2-SP domain | rat MoAb: Nimoab101, produced by hybridoma cell line 03050904 (ECACC) | WO 2004/106384 |
| hMASP-2 (full length-his tagged) | murine MoAbs: NimoAb104, produced by hybridoma cell line M0545YM035 (DSMZ) NimoAb108, produced by hybridoma cell line M0545YM029 (DSMZ) NimoAb109 produced by hybridoma cell line M0545YM046 (DSMZ) NimoAb110 produced by hybridoma cell line M0545YM048 (DSMZ) | WO 2004/106384 |

Anti-MASP-2 Antibodies with Reduced Effector Function

In some embodiments of this aspect of the invention, the anti-MASP-2 antibodies have reduced effector function in order to reduce inflammation that may arise from the activation of the classical complement pathway. The ability of IgG molecules to trigger the classical complement pathway has been shown to reside within the Fc portion of the molecule (Duncan, A. R., et al., Nature 332:738-740 1988). IgG molecules in which the Fc portion of the molecule has been removed by enzymatic cleavage are devoid of this effector function (see Harlow, *Antibodies: A Laboratory Manual*, Cold Spring Harbor Laboratory, New York, 1988). Accordingly, antibodies with reduced effector function can be generated as the result of lacking the Fc portion of the molecule by having a genetically engineered Fc sequence that minimizes effector function, or being of either the human $IgG_2$ or $IgG_4$ isotype.

Antibodies with reduced effector function can be produced by standard molecular biological manipulation of the Fc portion of the IgG heavy chains as described in Example 9 herein and also described in Jolliffe et al., Int'l Rev. Immunol. 10:241-250, 1993, and Rodrigues et al., *J. Immunol.* 151:6954-6961, 1998. Antibodies with reduced effector function also include human IgG2 and IgG4 isotypes that have a reduced ability to activate complement and/or interact with Fc receptors (Ravetch, J. V., et al., *Annu. Rev. Immunol.* 9:457-492, 1991; Isaacs, J. D., et al., *J. Immunol.* 148:3062-3071, 1992; van de Winkel, J. G., et al., *Immunol. Today* 14:215-221, 1993). Humanized or fully human antibodies specific to human MASP-2 comprised of IgG2 or IgG4 isotypes can be produced by one of several methods known to one of ordinary skilled in the art, as described in Vaughan, T. J., et al., *Nature Biotechnical* 16:535-539, 1998.

Production of Anti-MASP-2 Antibodies

Anti-MASP-2 antibodies can be produced using MASP-2 polypeptides (e.g., full length MASP-2) or using antigenic MASP-2 epitope-bearing peptides (e.g., a portion of the MASP-2 polypeptide). Immunogenic peptides may be as small as five amino acid residues. For example, the MASP-2 polypeptide including the entire amino acid sequence of SEQ ID NO:6 may be used to induce anti-MASP-2 antibodies useful in the method of the invention. Particular MASP-2 domains known to be involved in protein-protein interactions, such as the CUBI, and CUBIEGF domains, as well as the region encompassing the serine-protease active site, may be expressed as recombinant polypeptides as described in Example 5 and used as antigens. In addition, peptides comprising a portion of at least 6 amino acids of the MASP-2 polypeptide (SEQ ID NO:6) are also useful to induce MASP-2 antibodies. Additional examples of MASP-2 derived antigens useful to induce MASP-2 antibodies are provided below in TABLE 2. The MASP-2 peptides and polypeptides used to raise antibodies may be isolated as natural polypeptides, or recombinant or synthetic peptides and catalytically inactive recombinant polypeptides, such as MASP-2A, as further described in Examples 5-7. In some embodiments of this aspect of the invention, anti-MASP-2 antibodies are obtained using a transgenic mouse strain as described in Examples 8 and 9 and further described below.

Antigens useful for producing anti-MASP-2 antibodies also include fusion polypeptides, such as fusions of MASP-2 or a portion thereof with an immunoglobulin polypeptide or with maltose-binding protein. The polypeptide immunogen may be a full-length molecule or a portion thereof. If the polypeptide portion is hapten-like, such portion may be advantageously joined or linked to a macromolecular carrier (such as keyhole limpet hemocyanin (KLH), bovine serum albumin (BSA) or tetanus toxoid) for immunization.

TABLE 2

MASP-2 DERIVED ANTIGENS

| SEQ ID NO: | Amino Acid Sequence |
|---|---|
| SEQ ID NO: 6 | Human MASP-2 protein |
| SEQ ID NO: 51 | Murine MASP-2 protein |
| SEQ ID NO: 8 | CUBI domain of human MASP-2 (aa 1-121 of SEQ ID NO: 6) |
| SEQ ID NO: 9 | CUBIEGF domains of human MASP-2 (aa 1-166 of SEQ ID NO: 6) |
| SEQ ID NO: 10 | CUBIEGFCUBII domains of human MASP-2 (aa 1-293 of SEQ ID NO: 6) |
| SEQ ID NO: 11 | EGF domain of human MASP-2 (aa 122-166 of SEQ ID NO: 6) |

TABLE 2-continued

MASP-2 DERIVED ANTIGENS

| SEQ ID NO: | Amino Acid Sequence |
|---|---|
| SEQ ID NO: 12 | Serine-Protease domain of human MASP-2 (aa 429-671 of SEQ ID NO: 6) |
| SEQ ID NO: 13 GKDSCRGDAGGALV FL | Serine-Protease inactivated mutant form (aa 610-625 of SEQ ID NO: 6 with mutated Ser 618) |
| SEQ ID NO: 14 TPLGPKWPEPVFGR L | Human CUBI peptide |
| SEQ ID NO: 15: TAPPGYRLRLYFTH FDLELSHLCEYDFV KLSSGAKVLATLCG Q | Human CUBI peptide |
| SEQ ID NO: 16: TFRSDYSN | MBL binding region in human CUBI domain |
| SEQ ID NO: 17: FYSLGSSLDITFRS DYSNEKPFTGF | MBL binding region in human CUBI domain |
| SEQ ID NO: 18 IDECQVAPG | EGF peptide |
| SEQ ID NO: 19 ANMLCAGLESGGK DSCRGDSGGALV | Peptide from serine-protease active site |

Polyclonal Antibodies

Polyclonal antibodies against MASP-2 can be prepared by immunizing an animal with MASP-2 polypeptide or an immunogenic portion thereof using methods well known to those of ordinary skill in the art. See, for example, Green et al., "Production of Polyclonal Antisera," in *Immunochemical Protocols* (Manson, ed.), page 105, and as further described in Example 6. The immunogenicity of a MASP-2 polypeptide can be increased through the use of an adjuvant, including mineral gels, such as aluminum hydroxide or Freund's adjuvant (complete or incomplete), surface active substances such as lysolecithin, pluronic polyols, polyanions, oil emulsions, keyhole limpet hemocyanin and dinitrophenol. Polyclonal antibodies are typically raised in animals such as horses, cows, dogs, chicken, rats, mice, rabbits, guinea pigs, goats, or sheep. Alternatively, an anti-MASP-2 antibody useful in the present invention may also be derived from a subhuman primate. General techniques for raising diagnostically and therapeutically useful antibodies in baboons may be found, for example, in Goldenberg et al., International Patent Publication No. WO 91/11465, and in Losman, M. J., et al., *Int. J. Cancer* 46:310, 1990. Sera containing immunologically active antibodies are then produced from the blood of such immunized animals using standard procedures well known in the art.

Monoclonal Antibodies

In some embodiments, the MASP-2 inhibitory agent is an anti-MASP-2 monoclonal antibody. Anti-MASP-2 monoclonal antibodies are highly specific, being directed against a single MASP-2 epitope. As used herein, the modifier "monoclonal" indicates the character of the antibody as being obtained from a substantially homogenous population of antibodies, and is not to be construed as requiring production of the antibody by any particular method. Monoclonal antibodies can be obtained using any technique that provides for the production of antibody molecules by continuous cell lines in culture, such as the hybridoma method described by Kohler, G., et al., *Nature* 256:495, 1975, or they may be made by recombinant DNA methods (see, e.g., U.S. Pat. No. 4,816,567 to Cabilly). Monoclonal antibodies may also be isolated from phage antibody libraries using the techniques described in Clackson, T., et al., *Nature* 352:624-628, 1991, and Marks, J. D., et al., *J. Mol. Biol.* 222:581-597, 1991. Such antibodies can be of any immunoglobulin class including IgG, IgM, IgE, IgA, IgD and any subclass thereof.

For example, monoclonal antibodies can be obtained by injecting a suitable mammal (e.g., a BALB/c mouse) with a composition comprising a MASP-2 polypeptide or portion thereof. After a predetermined period of time, splenocytes are removed from the mouse and suspended in a cell culture medium. The splenocytes are then fused with an immortal cell line to form a hybridoma. The formed hybridomas are grown in cell culture and screened for their ability to produce a monoclonal antibody against MASP-2. An example further describing the production of anti-MASP-2 monoclonal antibodies is provided in Example 7. (See also *Current Protocols in Immunology*, Vol. 1., John Wiley & Sons, pages 2.5.1-2.6.7, 1991.)

Human monoclonal antibodies may be obtained through the use of transgenic mice that have been engineered to produce specific human antibodies in response to antigenic challenge. In this technique, elements of the human immunoglobulin heavy and light chain locus are introduced into strains of mice derived from embryonic stem cell lines that contain targeted disruptions of the endogenous immunoglobulin heavy chain and light chain loci. The transgenic mice can synthesize human antibodies specific for human antigens, such as the MASP-2 antigens described herein, and the mice can be used to produce human MASP-2 antibody-secreting hybridomas by fusing B-cells from such animals to suitable myeloma cell lines using conventional Kohler-Milstein technology as further described in Example 7. Transgenic mice with a human immunoglobulin genome are commercially available (e.g., from Abgenix, Inc., Fremont, Calif., and Medarex, Inc., Annandale, N.J.). Methods for obtaining human antibodies from transgenic mice are described, for example, by Green, L. L., et al., *Nature Genet.* 7:13, 1994; Lonberg, N., et al., *Nature* 368:856, 1994; and Taylor, L. D., et al., *Int. Immun.* 6:579, 1994.

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in *Methods in Molecular Biology*, The Humana Press, Inc., Vol. 10, pages 79-104, 1992).

Once produced, polyclonal, monoclonal or phage-derived antibodies are first tested for specific MASP-2 binding. A variety of assays known to those skilled in the art may be utilized to detect antibodies which specifically bind to MASP-2. Exemplary assays include Western blot or immunoprecipitation analysis by standard methods (e.g., as described in Ausubel et al.), immunoelectrophoresis, enzyme-linked immuno-sorbent assays, dot blots, inhibition or competition assays and sandwich assays (as described in Harlow and Land, *Antibodies: A Laboratory Manual*, Cold Spring Harbor Laboratory Press, 1988). Once antibodies are identified that specifically bind to MASP-2, the anti- MASP-2 antibodies are tested for the ability to function as a MASP-2 inhibitory agent in one of several assays such as, for example, a lectin-specific C4 cleavage assay (described in Example 2), a C3b deposition assay (described in Example 2) or a C4b deposition assay (described in Example 2).

The affinity of anti-MASP-2 monoclonal antibodies can be readily determined by one of ordinary skill in the art (see, e.g., Scatchard, A., *NY Acad. Sci.* 51:660-672, 1949). In one embodiment, the anti-MASP-2 monoclonal antibodies useful for the methods of the invention bind to MASP-2 with a binding affinity of <100 nM, preferably <10 nM and most preferably <2 nM.

Chimeric/Humanized Antibodies

Monoclonal antibodies useful in the method of the invention include chimeric antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies (U.S. Pat. No. 4,816,567, to Cabilly; and Morrison, S. L., et al., *Proc. Nat'l Acad. Sci. USA* 81:6851-6855, 1984).

One form of a chimeric antibody useful in the invention is a humanized monoclonal anti-MASP-2 antibody. Humanized forms of non-human (e.g., murine) antibodies are chimeric antibodies, which contain minimal sequence derived from non-human immunoglobulin. Humanized monoclonal antibodies are produced by transferring the non-human (e.g., mouse) complementarity determining regions (CDR), from the heavy and light variable chains of the mouse immunoglobulin into a human variable domain. Typically, residues of human antibodies are then substituted in the framework regions of the non-human counterparts. Furthermore, humanized antibodies may comprise residues that are not found in the recipient antibody or in the donor antibody. These modifications are made to further refine antibody performance. In general, the humanized antibody will comprise substantially all of at least one, and typically two variable domains, in which all or substantially all of the hypervariable loops correspond to those of a non-human immunoglobulin and all or substantially all of the Fv framework regions are those of a human immunoglobulin sequence. The humanized antibody optionally also will comprise at least a portion of an immunoglobulin constant region (Fc), typically that of a human immunoglobulin. For further details, see Jones, P. T., et al., *Nature* 321:522-525, 1986; Reichmann, L., et al., *Nature* 332:323-329, 1988; and Presta, *Curr. Op. Struct. Biol.* 2:593-596, 1992.

The humanized antibodies useful in the invention include human monoclonal antibodies including at least a MASP-2 binding CDR3 region. In addition, the Fc portions may be replaced so as to produce IgA or IgM as well as human IgG antibodies. Such humanized antibodies will have particular clinical utility because they will specifically recognize human MASP-2 but will not evoke an immune response in humans against the antibody itself. Consequently, they are better suited for in vivo administration in humans, especially when repeated or long-term administration is necessary.

An example of the generation of a humanized anti-MASP-2 antibody from a murine anti-MASP-2 monoclonal antibody is provided herein in Example 10. Techniques for producing humanized monoclonal antibodies are also described, for example, by Jones, P. T., et al., *Nature* 321:522, 1986; Carter, P., et al., *Proc. Nat'l. Acad. Sci. USA* 89:4285, 1992; Sandhu, J. S., *Crit. Rev. Biotech.* 12:437, 1992; Singer, et al., *J. Immun.* 150:2844, 1993; Sudhir (ed.), *Antibody Engineering Protocols*, Humana Press, Inc., 1995; Kelley, "Engineering Therapeutic Antibodies," in *Protein Engineering: Principles and Practice*, Cleland et al. (eds.), John Wiley & Sons, Inc., pages 399-434, 1996; and by U.S. Pat. No. 5,693,762, to Queen, 1997. In addition, there are commercial entities that will synthesize humanized antibodies from specific murine antibody regions, such as Protein Design Labs (Mountain View, Calif.).

Recombinant Antibodies

Anti-MASP-2 antibodies can also be made using recombinant methods. For example, human antibodies can be made using human immunoglobulin expression libraries (available for example, from Stratagene, Corp., La Jolla, Calif.) to produce fragments of human antibodies ($V_H$, $V_L$, Fv, Fd, Fab or F(ab')$_2$). These fragments are then used to construct whole human antibodies using techniques similar to those for producing chimeric antibodies.

Anti-Idiotype Antibodies

Once anti-MASP-2 antibodies are identified with the desired inhibitory activity, these antibodies can be used to generate anti-idiotype antibodies that resemble a portion of MASP-2 using techniques that are well known in the art. See, e.g., Greenspan, N. S., et al., *FASEB J.* 7:437, 1993. For example, antibodies that bind to MASP-2 and competitively inhibit a MASP-2 protein interaction required for complement activation can be used to generate anti-idiotypes that resemble the MBL binding site on MASP-2 protein and therefore bind and neutralize a binding ligand of MASP-2 such as, for example, MBL.

Immunoglobulin Fragments

The MASP-2 inhibitory agents useful in the method of the invention encompass not only intact immunoglobulin molecules but also the well known fragments including Fab, Fab', F(ab)$_2$, F(ab')$_2$ and Fv fragments, scFv fragments, diabodies, linear antibodies, single-chain antibody molecules and multispecific antibodies formed from antibody fragments.

It is well known in the art that only a small portion of an antibody molecule, the paratope, is involved in the binding of the antibody to its epitope (see, e.g., Clark, W. R., *The Experimental Foundations of Modern Immunology*, Wiley & Sons, Inc., NY, 1986). The pFc' and Fc regions of the antibody are effectors of the classical complement pathway, but are not involved in antigen binding. An antibody from which the pFc' region has been enzymatically cleaved, or which has been produced without the pFc' region, is designated an F(ab')$_2$ fragment and retains both of the antigen binding sites of an intact antibody. An isolated F(ab')$_2$ fragment is referred to as a bivalent monoclonal fragment because of its two antigen binding sites. Similarly, an antibody from which the Fc region has been enzymatically cleaved, or which has been produced without the Fc region, is designated a Fab fragment, and retains one of the antigen binding sites of an intact antibody molecule.

Antibody fragments can be obtained by proteolytic hydrolysis, such as by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, U.S. Pat. No. 4,331,647 to Goldenberg; Nisonoff, A., et al., *Arch. Biochem. Biophys.* 89:230, 1960; Porter, R. R., *Biochem.* 1 73:119, 1959; Edelman, et al., in *Methods in Enzymology* 1:422, Academic Press, 1967; and by Coligan at pages 2.8.1-2.8.10 and 2.10.-2.10.4.

In some embodiments, the use of antibody fragments lacking the Fc region are preferred to avoid activation of the classical complement pathway which is initiated upon binding Fc to the Fcγ receptor. There are several methods by which one can produce a MoAb that avoids Fcγ receptor interactions. For example, the Fc region of a monoclonal antibody can be removed chemically using partial digestion by proteolytic enzymes (such as ficin digestion), thereby generating, for example, antigen-binding antibody fragments such as Fab or F(ab)$_2$ fragments (Marian, M., et al., *Mol. Immunol.* 28:69-71, 1991). Alternatively, the human γ4 IgG isotype, which does not bind Fcγ receptors, can be used during construction of a humanized antibody as described herein. Antibodies, single chain antibodies and antigen-binding domains that lack the Fc domain can also be engineered using recombinant techniques described herein.

Single-Chain Antibody Fragments

Alternatively, one can create single peptide chain binding molecules specific for MASP-2 in which the heavy and light chain Fv regions are connected. The Fv fragments may be connected by a peptide linker to form a single-chain antigen binding protein (scFv). These single-chain antigen binding proteins are prepared by constructing a structural gene comprising DNA sequences encoding the $V_H$ and $V_L$ domains which are connected by an oligonucleotide. The structural gene is inserted into an expression vector, which is subsequently introduced into a host cell, such as *E. coli*. The recombinant host cells synthesize a single polypeptide chain with a linker peptide bridging the two V domains. Methods for producing scFvs are described for example, by Whitlow, et al., "Methods: A Companion to Methods in Enzymology" 2:97, 1991; Bird, et al., *Science* 242:423, 1988; U.S. Pat. No. 4,946,778, to Ladner; Pack, P., et al., *Bio/Technology* 11:1271, 1993.

As an illustrative example, a MASP-2 specific scFv can be obtained by exposing lymphocytes to MASP-2 polypeptide in vitro and selecting antibody display libraries in phage or similar vectors (for example, through the use of immobilized or labeled MASP-2 protein or peptide). Genes encoding polypeptides having potential MASP-2 polypeptide binding domains can be obtained by screening random peptide libraries displayed on phage or on bacteria such as *E. coli*. These random peptide display libraries can be used to screen for peptides which interact with MASP-2. Techniques for creating and screening such random peptide display libraries are well known in the art (U.S. Pat. No. 5,223,409, to Lardner; U.S. Pat. No. 4,946,778, to Ladner; U.S. Pat. No. 5,403,484, to Lardner; U.S. Pat. No. 5,571, 698, to Lardner; and Kay et al., *Phage Display of Peptides and Proteins* Academic Press, Inc., 1996) and random peptide display libraries and kits for screening such libraries are available commercially, for instance from CLONTECH Laboratories, Inc. (Palo Alto, Calif.), Invitrogen Inc. (San Diego, Calif.), New England Biolabs, Inc. (Beverly, Mass.), and Pharmacia LKB Biotechnology Inc. (Piscataway, N.J.).

Another form of an anti-MASP-2 antibody fragment useful in this aspect of the invention is a peptide coding for a single complementarity-determining region (CDR) that binds to an epitope on a MASP-2 antigen and inhibits MASP-2-dependent complement activation. CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106, 1991; Courtenay-Luck, "Genetic Manipulation of Monoclonal Antibodies," in *Monoclonal Antibodies: Production, Engineering and Clinical Application*, Ritter et al. (eds.), page 166, Cambridge University Press, 1995; and Ward et al., "Genetic Manipulation and Expression of Antibodies," in *Monoclonal Antibodies: Principles and Applications*, Birch et al. (eds.), page 137, Wiley-Liss, Inc., 1995).

The MASP-2 antibodies described herein are administered to a subject in need thereof to inhibit MASP-2-dependent complement activation. In some embodiments, the MASP-2 inhibitory agent is a high-affinity human or humanized monoclonal anti-MASP-2 antibody with reduced effector function.

Peptide Inhibitors

In some embodiments of this aspect of the invention, the MASP-2 inhibitory agent comprises isolated MASP-2 peptide inhibitors, including isolated natural peptide inhibitors and synthetic peptide inhibitors that inhibit the MASP-2-dependent complement activation system. As used herein, the term "isolated MASP-2 peptide inhibitors" refers to peptides that inhibit MASP-2 dependent complement activation by binding to, competing with MASP-2 for binding to another recognition molecule (e.g., MBL, H-ficolin, M-ficolin, or L-ficolin) in the lectin pathway, and/or directly interacting with MASP-2 to inhibit MASP-2-dependent complement activation that are substantially pure and are essentially free of other substances with which they may be found in nature to an extent practical and appropriate for their intended use.

Peptide inhibitors have been used successfully in vivo to interfere with protein-protein interactions and catalytic sites. For example, peptide inhibitors to adhesion molecules structurally related to LFA-1 have recently been approved for clinical use in coagulopathies (Ohman, E. M., et al., *European Heart J.* 16:50-55, 1995). Short linear peptides (<30 amino acids) have been described that prevent or interfere with integrin-dependent adhesion (Murayama, O., et al., *J. Biochem.* 120:445-51, 1996). Longer peptides, ranging in length from 25 to 200 amino acid residues, have also been used successfully to block integrin-dependent adhesion (Zhang, L., et al., *J. Biol. Chem.* 271(47):29953-57, 1996). In general, longer peptide inhibitors have higher affinities and/or slower off-rates than short peptides and may therefore be more potent inhibitors. Cyclic peptide inhibitors have also been shown to be effective inhibitors of integrins in vivo for the treatment of human inflammatory disease (Jackson, D. Y., et al., *J. Med. Chem.* 40:3359-68, 1997). One method of producing cyclic peptides involves the synthesis of peptides in which the terminal amino acids of the peptide are cysteines, thereby allowing the peptide to exist in a cyclic form by disulfide bonding between the terminal amino acids, which has been shown to improve affinity and half-life in vivo for the treatment of hematopoietic neoplasms (e.g., U.S. Pat. No. 6,649,592, to Larson).

Synthetic MASP-2 Peptide Inhibitors

MASP-2 inhibitory peptides useful in the methods of this aspect of the invention are exemplified by amino acid sequences that mimic the target regions important for MASP-2 function. The inhibitory peptides useful in the practice of the methods of the invention range in size from about 5 amino acids to about 300 amino acids. TABLE 3 provides a list of exemplary inhibitory peptides that may be useful in the practice of this aspect of the present invention. A candidate MASP-2 inhibitory peptide may be tested for the ability to function as a MASP-2 inhibitory agent in one of several assays including, for example, a lectin specific C4 cleavage assay (described in Example 2), and a C3b deposition assay (described in Example 2).

In some embodiments, the MASP-2 inhibitory peptides are derived from MASP-2 polypeptides and are selected from the full length mature MASP-2 protein (SEQ ID NO:6), or from a particular domain of the MASP-2 protein such as, for example, the CUBI domain (SEQ ID NO:8), the CUBIEGF domain (SEQ ID NO:9), the EGF domain (SEQ ID NO:11), and the serine protease domain (SEQ ID NO:12). As previously described, the CUBEGFCUBII regions have been shown to be required for dimerization and binding with MBL (Thielens et al., supra). In particular, the peptide sequence TFRSDYN (SEQ ID NO:16) in the CUBI domain of MASP-2 has been shown to be involved in binding to MBL in a study that identified a human carrying a homozygous mutation at Asp105 to Gly105, resulting in the loss of MASP-2 from the MBL complex (Stengaard-Pedersen, K., et al., *New England J. Med.* 349:554-560, 2003).

MASP-2 inhibitory peptides may also be derived from MAp19 (SEQ ID NO:3). As described in Example 30, MAp19 (SEQ ID NO:3) (also referred to as sMAP), has the ability to down-regulate the lectin pathway, which is activated by the MBL complex. Iwaki et al., *J. Immunol.* 177:8626-8632, 2006. While not wishing to be bound by theory, it is likely that sMAP is able to occupy the MASP-2/sMAP binding site in MBL and prevent MASP-2 from binding to MBL. It has also been reported that sMAP competes with MASP-2 in association with ficolin A and inhibits complement activation by the ficolin A/MASP-2 complex. Endo, Y., et al., *Immunogenetics* 57:837-844 (2005).

In some embodiments, MASP-2 inhibitory peptides are derived from the lectin proteins that bind to MASP-2 and are involved in the lectin complement pathway. Several different lectins have been identified that are involved in this pathway, including mannan-binding lectin (MBL), L-ficolin, M-ficolin and H-ficolin. (Ikeda, K., et al., *J. Biol. Chem.* 262:7451-7454, 1987; Matsushita, M., et al., *J. Exp. Med.* 176:1497-2284, 2000; Matsushita, M., et al., *J. Immunol.* 168:3502-3506, 2002). These lectins are present in serum as oligomers of homotrimeric subunits, each having N-terminal collagen-like fibers with carbohydrate recognition domains. These different lectins have been shown to bind to MASP-2, and the lectin/MASP-2 complex activates complement through cleavage of proteins C4 and C2. H-ficolin has an amino-terminal region of 24 amino acids, a collagen-like domain with 11 Gly-Xaa-Yaa repeats, a neck domain of 12 amino acids, and a fibrinogen-like domain of 207 amino acids (Matsushita, M., et al., *J. Immunol.* 168:3502-3506, 2002). H-ficolin binds to GlcNAc and agglutinates human erythrocytes coated with LPS derived from *S. typhimurium*, *S. minnesota* and *E. coli*. H-ficolin has been shown to be associated with MASP-2 and MAp19 and activates the lectin pathway. Id. L-ficolin/P35 also binds to GlcNAc and has been shown to be associated with MASP-2 and MAp19 in human serum and this complex has been shown to activate the lectin pathway (Matsushita, M., et al., *J. Immunol.* 164:2281, 2000). Accordingly, MASP-2 inhibitory peptides useful in the present invention may comprise a region of at least 5 amino acids selected from the MBL protein (SEQ ID NO:21), the H-ficolin protein (Genbank accession number NM_173452), the M-ficolin protein (Genbank accession number O00602) and the L-ficolin protein (Genbank accession number NM_015838).

More specifically, scientists have identified the MASP-2 binding site on MBL to be within the 12 Gly-X-Y triplets "GKD GRD GTK GEK GEP GQG LRG LQG POG KLG POG NOG PSG SOG PKG QKG DOG KS" (SEQ ID NO:26) that lie between the hinge and the neck in the C-terminal portion of the collagen-like domain of MBP (Wallis, R., et al., *J. Biol. Chem.* 279:14065, 2004). This MASP-2 binding site region is also highly conserved in human H-ficolin and human L-ficolin. A consensus binding site has been described that is present in all three lectin proteins comprising the amino acid sequence "OGK-X-GP" (SEQ ID NO:22) where the letter "O" represents hydroxyproline and the letter "X" is a hydrophobic residue (Wallis et al., 2004, supra). Accordingly, in some embodiments, MASP-2 inhibitory peptides useful in this aspect of the invention are at least 6 amino acids in length and comprise SEQ ID NO:22. Peptides derived from MBL that include the amino acid sequence "GLR GLQ GPO GKL GPO G" (SEQ ID NO:24) have been shown to bind MASP-2 in vitro (Wallis, et al., 2004, supra). To enhance binding to MASP-2, peptides can be synthesized that are flanked by two GPO triplets at each end ("GPO GPO GLR GLQ GPO GKL GPO GGP OGP O" SEQ ID NO:25) to enhance the formation of triple helices as found in the native MBL protein (as further described in Wallis, R., et al., *J. Biol. Chem.* 279:14065, 2004).

MASP-2 inhibitory peptides may also be derived from human H-ficolin that include the sequence "GAO GSO GEK GAO GPQ GPO GPO GKM GPK GEO GDO" (SEQ ID NO:27) from the consensus MASP-2 binding region in H-ficolin. Also included are peptides derived from human L-ficolin that include the sequence "GCO GLO GAO GDK GEA GTN GKR GER GPO GPO GKA GPO GPN GAO GEO" (SEQ ID NO:28) from the consensus MASP-2 binding region in L-ficolin.

MASP-2 inhibitory peptides may also be derived from the C4 cleavage site such as "LQRALEILPNRVTIKANRP-FLVFI" (SEQ ID NO:29) which is the C4 cleavage site linked to the C-terminal portion of antithrombin III (Glover, G. I., et al., *Mol. Immunol.* 25:1261 (1988)).

TABLE 3

EXEMPLARY MASP-2 INHIBITORY PEPTIDES

| SEQ ID NO | Source |
|---|---|
| SEQ ID NO: 6 | Human MASP-2 protein |
| SEQ ID NO: 8 | CUBI domain of MASP-2 (aa 1-121 of SEQ ID NO: 6) |
| SEQ ID NO: 9 | CUBIEGF domains of MASP-2 (aa 1-166 of SEQ ID NO: 6) |
| SEQ ID NO: 10 | CUBIEGFCUBII domains of MASP-2 (aa 1-293 of SEQ ID NO: 6) |
| SEQ ID NO: 11 | EGF domain of MASP-2 (aa 122-166) |
| SEQ ID NO: 12 | Serine-protease domain of MASP-2 (aa 429-671) |
| SEQ ID NO: 16 | MBL binding region in MASP-2 |

TABLE 3-continued

EXEMPLARY MASP-2 INHIBITORY PEPTIDES

| SEQ ID NO | Source |
|---|---|
| SEQ ID NO: 3 | Human MAp19 |
| SEQ ID NO: 21 | Human MBL protein |
| SEQ ID NO: 22<br>OGK-X-GP,<br>Where "O" =<br>hydroxyproline<br>and "X" is a<br>hydrophobic amino<br>acid residue | Synthetic peptide<br>Consensus binding site<br>from Human MBL and Human<br>ficolins |
| SEQ ID NO: 23<br>OGKLG | Human MBL core binding<br>site |
| SEQ ID NO: 24<br>GLR GLQ GPO GKL<br>GPO G | Human MBP Triplets 6-10-<br>demonstrated binding to<br>MASP-2 |
| SEQ ID NO: 25<br>GPOGPOGLRGLQGPO<br>GKLGPOGGPOGPO | Human MBP Triplets with<br>GPO added to enhance<br>formation of triple<br>helices |
| SEQ ID NO: 26<br>GKDGRDGTKGEKGEP<br>GQGLRGLQGPOGKLG<br>POGNOGPSGSOGPKG<br>QKGDOGKS | Human MBP Triplets 1-17 |
| SEQ ID NO: 27<br>GAOGSOGEKGAOGPQ<br>GPOGPOGKMGPKGEO<br>GDO | Human H-Ficolin (Hataka) |
| SEQ ID NO: 28<br>GCOGLOGAOGDKGE<br>AGTNGKRGERGPOGP<br>OGKAGPOGPNGAOGE<br>O | Human L-Ficolin P35 |
| SEQ ID NO: 29<br>LQRALEILPNRVTIKA<br>NRPFLVFI | Human C4 cleavage site |

Note:
The letter "O" represents hydroxyproline.
The letter "X" is a hydrophobic residue.

Peptides derived from the C4 cleavage site as well as other peptides that inhibit the MASP-2 serine protease site can be chemically modified so that they are irreversible protease inhibitors. For example, appropriate modifications may include, but are not necessarily limited to, halomethyl ketones (Br, Cl, I, F) at the C-terminus, Asp or Glu, or appended to functional side chains; haloacetyl (or other α-haloacetyl) groups on amino groups or other functional side chains; epoxide or imine-containing groups on the amino or carboxy termini or on functional side chains; or imidate esters on the amino or carboxy termini or on functional side chains. Such modifications would afford the advantage of permanently inhibiting the enzyme by covalent attachment of the peptide. This could result in lower effective doses and/or the need for less frequent administration of the peptide inhibitor.

In addition to the inhibitory peptides described above, MASP-2 inhibitory peptides useful in the method of the invention include peptides containing the MASP-2-binding CDR3 region of anti-MASP-2 MoAb obtained as described herein. The sequence of the CDR regions for use in synthesizing the peptides may be determined by methods known in the art. The heavy chain variable region is a peptide that generally ranges from 100 to 150 amino acids in length. The light chain variable region is a peptide that generally ranges from 80 to 130 amino acids in length. The CDR sequences within the heavy and light chain variable regions include only approximately 3-25 amino acid sequences that may be easily sequenced by one of ordinary skill in the art.

Those skilled in the art will recognize that substantially homologous variations of the MASP-2 inhibitory peptides described above will also exhibit MASP-2 inhibitory activity. Exemplary variations include, but are not necessarily limited to, peptides having insertions, deletions, replacements, and/or additional amino acids on the carboxy-terminus or amino-terminus portions of the subject peptides and mixtures thereof. Accordingly, those homologous peptides having MASP-2 inhibitory activity are considered to be useful in the methods of this invention. The peptides described may also include duplicating motifs and other modifications with conservative substitutions. Conservative variants are described elsewhere herein, and include the exchange of an amino acid for another of like charge, size or hydrophobicity and the like.

MASP-2 inhibitory peptides may be modified to increase solubility and/or to maximize the positive or negative charge in order to more closely resemble the segment in the intact protein. The derivative may or may not have the exact primary amino acid structure of a peptide disclosed herein so long as the derivative functionally retains the desired property of MASP-2 inhibition. The modifications can include amino acid substitution with one of the commonly known twenty amino acids or with another amino acid, with a derivatized or substituted amino acid with ancillary desirable characteristics, such as resistance to enzymatic degradation or with a D-amino acid or substitution with another molecule or compound, such as a carbohydrate, which mimics the natural confirmation and function of the amino acid, amino acids or peptide; amino acid deletion; amino acid insertion with one of the commonly known twenty amino acids or with another amino acid, with a derivatized or substituted amino acid with ancillary desirable characteristics, such as resistance to enzymatic degradation or with a D-amino acid or substitution with another molecule or compound, such as a carbohydrate, which mimics the natural confirmation and function of the amino acid, amino acids or peptide; or substitution with another molecule or compound, such as a carbohydrate or nucleic acid monomer, which mimics the natural conformation, charge distribution and function of the parent peptide. Peptides may also be modified by acetylation or amidation.

The synthesis of derivative inhibitory peptides can rely on known techniques of peptide biosynthesis, carbohydrate biosynthesis and the like. As a starting point, the artisan may rely on a suitable computer program to determine the conformation of a peptide of interest. Once the conformation of peptide disclosed herein is known, then the artisan can determine in a rational design fashion what sort of substitutions can be made at one or more sites to fashion a derivative that retains the basic conformation and charge distribution of the parent peptide but which may possess characteristics which are not present or are enhanced over those found in the parent peptide. Once candidate derivative molecules are identified, the derivatives can be tested to determine if they function as MASP-2 inhibitory agents using the assays described herein.

Screening for MASP-2 Inhibitory Peptides

One may also use molecular modeling and rational molecular design to generate and screen for peptides that mimic the molecular structures of key binding regions of MASP-2 and inhibit the complement activities of MASP-2. The molecular structures used for modeling include the CDR regions of anti-MASP-2 monoclonal antibodies, as well as the target regions known to be important for MASP-2 function including the region required for dimerization, the region involved in binding to MBL, and the serine protease active site as previously described. Methods for identifying peptides that bind to a particular target are well known in the art. For example, molecular imprinting may be used for the de novo construction of macromolecular structures such as peptides that bind to a particular molecule. See, for example, Shea, K. J., "Molecular Imprinting of Synthetic Network Polymers: The De Novo synthesis of Macromolecular Binding and Catalytic Sties," *TRIP* 2(5) 1994.

As an illustrative example, one method of preparing mimics of MASP-2 binding peptides is as follows. Functional monomers of a known MASP-2 binding peptide or the binding region of an anti-MASP-2 antibody that exhibits MASP-2 inhibition (the template) are polymerized. The template is then removed, followed by polymerization of a second class of monomers in the void left by the template, to provide a new molecule that exhibits one or more desired properties that are similar to the template. In addition to preparing peptides in this manner, other MASP-2 binding molecules that are MASP-2 inhibitory agents such as polysaccharides, nucleosides, drugs, nucleoproteins, lipoproteins, carbohydrates, glycoproteins, steroid, lipids and other biologically active materials can also be prepared. This method is useful for designing a wide variety of biological mimics that are more stable than their natural counterparts because they are typically prepared by free radical polymerization of function monomers, resulting in a compound with a nonbiodegradable backbone.

Peptide Synthesis

The MASP-2 inhibitory peptides can be prepared using techniques well known in the art, such as the solid-phase synthetic technique initially described by Merrifield, in *J. Amer. Chem. Soc.* 85:2149-2154, 1963. Automated synthesis may be achieved, for example, using Applied Biosystems 431A Peptide Synthesizer (Foster City, Calif.) in accordance with the instructions provided by the manufacturer. Other techniques may be found, for example, in Bodanszky, M., et al., *Peptide Synthesis*, second edition, John Wiley & Sons, 1976, as well as in other reference works known to those skilled in the art.

The peptides can also be prepared using standard genetic engineering techniques known to those skilled in the art. For example, the peptide can be produced enzymatically by inserting nucleic acid encoding the peptide into an expression vector, expressing the DNA, and translating the DNA into the peptide in the presence of the required amino acids. The peptide is then purified using chromatographic or electrophoretic techniques, or by means of a carrier protein that can be fused to, and subsequently cleaved from, the peptide by inserting into the expression vector in phase with the peptide encoding sequence a nucleic acid sequence encoding the carrier protein. The fusion protein-peptide may be isolated using chromatographic, electrophoretic or immunological techniques (such as binding to a resin via an antibody to the carrier protein). The peptide can be cleaved using chemical methodology or enzymatically, as by, for example, hydrolases.

The MASP-2 inhibitory peptides that are useful in the method of the invention can also be produced in recombinant host cells following conventional techniques. To express a MASP-2 inhibitory peptide encoding sequence, a nucleic acid molecule encoding the peptide must be operably linked to regulatory sequences that control transcriptional expression in an expression vector and then introduced into a host cell. In addition to transcriptional regulatory sequences, such as promoters and enhancers, expression vectors can include translational regulatory sequences and a marker gene, which are suitable for selection of cells that carry the expression vector.

Nucleic acid molecules that encode a MASP-2 inhibitory peptide can be synthesized with "gene machines" using protocols such as the phosphoramidite method. If chemically synthesized double-stranded DNA is required for an application such as the synthesis of a gene or a gene fragment, then each complementary strand is made separately. The production of short genes (60 to 80 base pairs) is technically straightforward and can be accomplished by synthesizing the complementary strands and then annealing them. For the production of longer genes, synthetic genes (double-stranded) are assembled in modular form from single-stranded fragments that are from 20 to 100 nucleotides in length. For reviews on polynucleotide synthesis, see, for example, Glick and Pasternak, "*Molecular Biotechnology, Principles and Applications of Recombinant DNA*", ASM Press, 1994; Itakura, K., et al., *Annu. Rev. Biochem.* 53:323, 1984; and Climie, S., et al., *Proc. Nat'l Acad. Sci. USA* 87:633, 1990.

Small Molecule Inhibitors

In some embodiments, MASP-2 inhibitory agents are small molecule inhibitors including natural and synthetic substances that have a low molecular weight, such as for example, peptides, peptidomimetics and nonpeptide inhibitors (including oligonucleotides and organic compounds). Small molecule inhibitors of MASP-2 can be generated based on the molecular structure of the variable regions of the anti-MASP-2 antibodies.

Small molecule inhibitors may also be designed and generated based on the MASP-2 crystal structure using computational drug design (Kuntz I. D., et al., *Science* 257:1078, 1992). The crystal structure of rat MASP-2 has been described (Feinberg, H., et al., *EMBO J.* 22:2348-2359, 2003). Using the method described by Kuntz et al., the MASP-2 crystal structure coordinates are used as an input for a computer program such as DOCK, which outputs a list of small molecule structures that are expected to bind to MASP-2. Use of such computer programs is well known to one of skill in the art. For example, the crystal structure of the HIV-1 protease inhibitor was used to identify unique nonpeptide ligands that are HIV-1 protease inhibitors by evaluating the fit of compounds found in the Cambridge Crystallographic database to the binding site of the enzyme using the program DOCK (Kuntz, I. D., et al., *J. Mol. Biol.* 161:269-288, 1982; DesJarlais, R. L., et al., *PNAS* 87:6644-6648, 1990).

The list of small molecule structures that are identified by a computational method as potential MASP-2 inhibitors are screened using a MASP-2 binding assay such as described in Example 7. The small molecules that are found to bind to MASP-2 are then assayed in a functional assay such as described in Example 2 to determine if they inhibit MASP-2-dependent complement activation.

MASP-2 Soluble Receptors

Other suitable MASP-2 inhibitory agents are believed to include MASP-2 soluble receptors, which may be produced using techniques known to those of ordinary skill in the art.

Expression Inhibitors of MASP-2

In another embodiment of this aspect of the invention, the MASP-2 inhibitory agent is a MASP-2 expression inhibitor capable of inhibiting MASP-2-dependent complement activation. In the practice of this aspect of the invention, representative MASP-2 expression inhibitors include MASP-2 antisense nucleic acid molecules (such as antisense mRNA, antisense DNA or antisense oligonucleotides), MASP-2 ribozymes and MASP-2 RNAi molecules.

Anti-sense RNA and DNA molecules act to directly block the translation of MASP-2 mRNA by hybridizing to MASP-2 mRNA and preventing translation of MASP-2 protein. An antisense nucleic acid molecule may be constructed in a number of different ways provided that it is capable of interfering with the expression of MASP-2. For example, an antisense nucleic acid molecule can be constructed by inverting the coding region (or a portion thereof) of MASP-2 cDNA (SEQ ID NO:4) relative to its normal orientation for transcription to allow for the transcription of its complement.

The antisense nucleic acid molecule is usually substantially identical to at least a portion of the target gene or genes. The nucleic acid, however, need not be perfectly identical to inhibit expression. Generally, higher homology can be used to compensate for the use of a shorter antisense nucleic acid molecule. The minimal percent identity is typically greater than about 65%, but a higher percent identity may exert a more effective repression of expression of the endogenous sequence. Substantially greater percent identity of more than about 80% typically is preferred, though about 95% to absolute identity is typically most preferred.

The antisense nucleic acid molecule need not have the same intron or exon pattern as the target gene, and non-coding segments of the target gene may be equally effective in achieving antisense suppression of target gene expression as coding segments. A DNA sequence of at least about 8 or so nucleotides may be used as the antisense nucleic acid molecule, although a longer sequence is preferable. In the present invention, a representative example of a useful inhibitory agent of MASP-2 is an antisense MASP-2 nucleic acid molecule which is at least ninety percent identical to the complement of the MASP-2 cDNA consisting of the nucleic acid sequence set forth in SEQ ID NO:4. The nucleic acid sequence set forth in SEQ ID NO:4 encodes the MASP-2 protein consisting of the amino acid sequence set forth in SEQ ID NO:5.

The targeting of antisense oligonucleotides to bind MASP-2 mRNA is another mechanism that may be used to reduce the level of MASP-2 protein synthesis. For example, the synthesis of polygalacturonase and the muscarine type 2 acetylcholine receptor is inhibited by antisense oligonucleotides directed to their respective mRNA sequences (U.S. Pat. No. 5,739,119, to Cheng, and U.S. Pat. No. 5,759,829, to Shewmaker). Furthermore, examples of antisense inhibition have been demonstrated with the nuclear protein cyclin, the multiple drug resistance gene (MDG1), ICAM-1, E-selectin, STK-1, striatal GAB AA receptor and human EGF (see, e.g., U.S. Pat. No. 5,801,154, to Baracchini; U.S. Pat. No. 5,789,573, to Baker; U.S. Pat. No. 5,718,709, to Considine; and U.S. Pat. No. 5,610,288, to Reubenstein).

A system has been described that allows one of ordinary skill to determine which oligonucleotides are useful in the invention, which involves probing for suitable sites in the target mRNA using Rnase H cleavage as an indicator for accessibility of sequences within the transcripts. Scherr, M., et al., *Nucleic Acids Res.* 26:5079-5085, 1998; Lloyd, et al., *Nucleic Acids Res.* 29:3665-3673, 2001. A mixture of antisense oligonucleotides that are complementary to certain regions of the MASP-2 transcript is added to cell extracts expressing MASP-2, such as hepatocytes, and hybridized in order to create an RNAseH vulnerable site. This method can be combined with computer-assisted sequence selection that can predict optimal sequence selection for antisense compositions based upon their relative ability to form dimers, hairpins, or other secondary structures that would reduce or prohibit specific binding to the target mRNA in a host cell. These secondary structure analysis and target site selection considerations may be performed using the OLIGO primer analysis software (Rychlik, I., 1997) and the BLASTN 2.0.5 algorithm software (Altschul, S. F., et al., *Nucl. Acids Res.* 25:3389-3402, 1997). The antisense compounds directed towards the target sequence preferably comprise from about 8 to about 50 nucleotides in length. Antisense oligonucleotides comprising from about 9 to about 35 or so nucleotides are particularly preferred. The inventors contemplate all oligonucleotide compositions in the range of 9 to 35 nucleotides (i.e., those of 9, 10, 11, 12, 13, 14, 15, 16, 17, 18, 19, 20, 21, 22, 23, 24, 25, 26, 27, 28, 29, 30, 31, 32, 33, 34, or 35 or so bases in length) are highly preferred for the practice of antisense oligonucleotide-based methods of the invention. Highly preferred target regions of the MASP-2 mRNA are those that are at or near the AUG translation initiation codon, and those sequences that are substantially complementary to 5' regions of the mRNA, e.g., between the −10 and +10 regions of the MASP-2 gene nucleotide sequence (SEQ ID NO:4). Exemplary MASP-2 expression inhibitors are provided in TABLE 4.

TABLE 4

EXEMPLARY EXPRESSION INHIBITORS OF MASP-2

| | |
|---|---|
| SEQ ID NO: 30 (nucleotides 22-680 of SEQ ID NO: 4) | Nucleic acid sequence of MASP-2 cDNA (SEQ ID NO: 4) encoding CUBIEGF |
| SEQ ID NO: 31 5'CGGGCACACCA TGAGGCTGCTGAC CCTCCTGGGC3' | Nucleotides 12-45 of SEQ ID NO: 4 including the MASP-2 translation start site (sense) |
| SEQ ID NO: 32 5'GACATTACCTT CCGCTCCGACTCC AACGAGAAG3' | Nucleotides 361-396 of SEQ ID NO: 4 encoding a region comprising the MASP-2 MBL binding site (sense) |
| SEQ ID NO: 33 5'AGCAGCCCTGA ATACCCACGGCCG TATCCCAAA3' | Nucleotides 610-642 of SEQ ID NO: 4 encoding a region comprising the CUBII domain |

As noted above, the term "oligonucleotide" as used herein refers to an oligomer or polymer of ribonucleic acid (RNA) or deoxyribonucleic acid (DNA) or mimetics thereof. This term also covers those oligonucleobases composed of naturally occurring nucleotides, sugars and covalent internucleoside (backbone) linkages as well as oligonucleotides having non-naturally occurring modifications. These modifications allow one to introduce certain desirable properties that are not offered through naturally occurring oligonucleotides, such as reduced toxic properties, increased stability against nuclease degradation and enhanced cellular uptake. In illustrative embodiments, the antisense compounds of the invention differ from native DNA by the modification of the phosphodiester backbone to extend the life of the antisense oligonucleotide in which the phosphate substituents are replaced by phosphorothioates. Likewise, one or both ends of the oligonucleotide may be substituted by one or more acridine derivatives that intercalate between adjacent base-pairs within a strand of nucleic acid.

Another alternative to antisense is the use of "RNA interference" (RNAi). Double-stranded RNAs (dsRNAs) can provoke gene silencing in mammals in vivo. The natural function of RNAi and co-suppression appears to be protection of the genome against invasion by mobile genetic elements such as retrotransposons and viruses that produce aberrant RNA or dsRNA in the host cell when they become active (see, e.g., Jensen, J., et al., *Nat. Genet.* 21:209-12, 1999). The double-stranded RNA molecule may be prepared by synthesizing two RNA strands capable of forming a double-stranded RNA molecule, each having a length from about 19 to 25 (e.g., 19-23 nucleotides). For example, a dsRNA molecule useful in the methods of the invention may comprise the RNA corresponding to a sequence and its complement listed in TABLE 4. Preferably, at least one strand of RNA has a 3' overhang from 1-5 nucleotides. The synthesized RNA strands are combined under conditions that form a double-stranded molecule. The RNA sequence may comprise at least an 8 nucleotide portion of SEQ ID NO:4 with a total length of 25 nucleotides or less. The design of siRNA sequences for a given target is within the ordinary skill of one in the art. Commercial services are available that design siRNA sequence and guarantee at least 70% knockdown of expression (Qiagen, Valencia, Calif.).

The dsRNA may be administered as a pharmaceutical composition and carried out by known methods, wherein a nucleic acid is introduced into a desired target cell. Commonly used gene transfer methods include calcium phosphate, DEAE-dextran, electroporation, microinjection and viral methods. Such methods are taught in Ausubel et al., *Current Protocols in Molecular Biology*, John Wiley & Sons, Inc., 1993.

Ribozymes can also be utilized to decrease the amount and/or biological activity of MASP-2, such as ribozymes that target MASP-2 mRNA. Ribozymes are catalytic RNA molecules that can cleave nucleic acid molecules having a sequence that is completely or partially homologous to the sequence of the ribozyme. It is possible to design ribozyme transgenes that encode RNA ribozymes that specifically pair with a target RNA and cleave the phosphodiester backbone at a specific location, thereby functionally inactivating the target RNA. In carrying out this cleavage, the ribozyme is not itself altered, and is thus capable of recycling and cleaving other molecules. The inclusion of ribozyme sequences within antisense RNAs confers RNA-cleaving activity upon them, thereby increasing the activity of the antisense constructs.

Ribozymes useful in the practice of the invention typically comprise a hybridizing region of at least about nine nucleotides, which is complementary in nucleotide sequence to at least part of the target MASP-2 mRNA, and a catalytic region that is adapted to cleave the target MASP-2 mRNA (see generally, EPA No. 0 321 201; WO88/04300; Haseloff, J., et al., *Nature* 334:585-591, 1988; Fedor, M. J., et al., *Proc. Natl. Acad. Sci. USA* 87:1668-1672, 1990; Cech, T. R., et al., *Ann. Rev. Biochem.* 55:599-629, 1986).

Ribozymes can either be targeted directly to cells in the form of RNA oligonucleotides incorporating ribozyme sequences, or introduced into the cell as an expression vector encoding the desired ribozymal RNA. Ribozymes may be used and applied in much the same way as described for antisense polynucleotides.

Anti-sense RNA and DNA, ribozymes and RNAi molecules useful in the methods of the invention may be prepared by any method known in the art for the synthesis of DNA and RNA molecules. These include techniques for chemically synthesizing oligodeoxyribonucleotides and oligoribonucleotides well known in the art, such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well known modifications of the DNA molecules may be introduced as a means of increasing stability and half-life. Useful modifications include, but are not limited to, the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

V. Pharmaceutical Compositions and Delivery Methods Dosing

In another aspect, the invention provides compositions for inhibiting the adverse effects of MASP-2-dependent complement activation comprising a therapeutically effective amount of a MASP-2 inhibitory agent and a pharmaceutically acceptable carrier. The MASP-2 inhibitory agents can be administered to a subject in need thereof, at therapeutically effective doses to treat or ameliorate conditions associated with MASP-2-dependent complement activation. A therapeutically effective dose refers to the amount of the MASP-2 inhibitory agent sufficient to result in amelioration of symptoms of the condition.

Toxicity and therapeutic efficacy of MASP-2 inhibitory agents can be determined by standard pharmaceutical procedures employing experimental animal models, such as the murine MASP-2–/– mouse model expressing the human MASP-2 transgene described in Example 3. Using such animal models, the NOAEL (no observed adverse effect level) and the MED (the minimally effective dose) can be determined using standard methods. The dose ratio between NOAEL and MED effects is the therapeutic ratio, which is expressed as the ratio NOAEL/MED. MASP-2 inhibitory agents that exhibit large therapeutic ratios or indices are most preferred. The data obtained from the cell culture assays and animal studies can be used in formulating a range of dosages for use in humans. The dosage of the MASP-2 inhibitory agent preferably lies within a range of circulating concentrations that include the MED with little or no toxicity. The dosage may vary within this range depending upon the dosage form employed and the route of administration utilized.

For any compound formulation, the therapeutically effective dose can be estimated using animal models. For example, a dose may be formulated in an animal model to achieve a circulating plasma concentration range that includes the MED. Quantitative levels of the MASP-2 inhibitory agent in plasma may also be measured, for example, by high performance liquid chromatography.

In addition to toxicity studies, effective dosage may also be estimated based on the amount of MASP-2 protein present in a living subject and the binding affinity of the MASP-2 inhibitory agent. It has been shown that MASP-2 levels in normal human subjects is present in serum in low levels in the range of 500 ng/ml, and MASP-2 levels in a particular subject can be determined using a quantitative assay for MASP-2 described in Moller-Kristensen M., et al., *J. Immunol. Methods* 282:159-167, 2003.

Generally, the dosage of administered compositions comprising MASP-2 inhibitory agents varies depending on such factors as the subject's age, weight, height, sex, general medical condition, and previous medical history. As an illustration, MASP-2 inhibitory agents, such as anti-MASP-2 antibodies, can be administered in dosage ranges from about 0.010 to 10.0 mg/kg, preferably 0.010 to 1.0 mg/kg, more preferably 0.010 to 0.1 mg/kg of the subject body weight. In some embodiments the composition comprises a combination of anti-MASP-2 antibodies and MASP-2 inhibitory peptides.

Therapeutic efficacy of MASP-2 inhibitory compositions and methods of the present invention in a given subject, and appropriate dosages, can be determined in accordance with complement assays well known to those of skill in the art. Complement generates numerous specific products. During the last decade, sensitive and specific assays have been developed and are available commercially for most of these activation products, including the small activation fragments C3a, C4a, and C5a and the large activation fragments iC3b, C4d, Bb, and sC5b-9. Most of these assays utilize monoclonal antibodies that react with new antigens (neoantigens) exposed on the fragment, but not on the native proteins from which they are formed, making these assays very simple and specific. Most rely on ELISA technology, although radioimmunoassay is still sometimes used for C3a and C5a. These latter assays measure both the unprocessed fragments and their 'desArg' fragments, which are the major forms found in the circulation. Unprocessed fragments and $C5a_{desArg}$ are rapidly cleared by binding to cell surface receptors and are hence present in very low concentrations, whereas $C3a_{desArg}$ does not bind to cells and accumulates in plasma. Measurement of C3a provides a sensitive, pathway-independent indicator of complement activation. Alternative pathway activation can be assessed by measuring the Bb fragment. Detection of the fluid-phase product of membrane attack pathway activation, sC5b-9, provides evidence that complement is being activated to completion. Because both the lectin and classical pathways generate the same activation products, C4a and C4d, measurement of these two fragments does not provide any information about which of these two pathways has generated the activation products.

Additional Agents

The compositions and methods comprising MASP-2 inhibitory agents may optionally comprise one or more additional therapeutic agents, which may augment the activity of the MASP-2 inhibitory agent or that provide related therapeutic functions in an additive or synergistic fashion. For example, one or more MASP-2 inhibitory agents may be administered in combination with one or more anti-inflammatory and/or analgesic agents. The inclusion and selection of additional agent(s) will be determined to achieve a desired therapeutic result. Suitable anti-inflammatory and/or analgesic agents include: serotonin receptor antagonists; serotonin receptor agonists; histamine receptor antagonists; bradykinin receptor antagonists; kallikrein inhibitors; tachykinin receptor antagonists, including neurokinin₁ and neurokinin₂ receptor subtype antagonists; calcitonin gene-related peptide (CGRP) receptor antagonists; interleukin receptor antagonists; inhibitors of enzymes active in the synthetic pathway for arachidonic acid metabolites, including phospholipase inhibitors, including $PLA_2$ isoform inhibitors and $PLC_\gamma$ isoform inhibitors, cyclooxygenase (COX) inhibitors (which may be either COX-1, COX-2, or nonselective COX-1 and -2 inhibitors), lipooxygenase inhibitors; prostanoid receptor antagonists including eicosanoid EP-1 and EP-4 receptor subtype antagonists and thromboxane receptor subtype antagonists; leukotriene receptor antagonists including leukotriene $B_4$ receptor subtype antagonists and leukotriene $D_4$ receptor subtype antagonists; opioid receptor agonists, including μ-opioid, δ-opioid, and κ-opioid receptor subtype agonists; purinoceptor agonists and antagonists including $P_{2X}$ receptor antagonists and $P_{2Y}$ receptor agonists; adenosine triphosphate (ATP)-sensitive potassium channel openers; MAP kinase inhibitors; nicotinic acetylcholine inhibitors; and alpha adrenergic receptor agonists (including alpha-1, alpha-2, and nonselective alpha-1 and 2 agonists).

When used in the prevention or treatment of restenosis, the MASP-2 inhibitory agent of the present invention may be combined with one or more anti-restenosis agents for concomitant administration. Suitable anti-restenosis agents include: antiplatelet agents including: thrombin inhibitors and receptor antagonists, adenosine diphosphate (ADP) receptor antagonists (also known as purinoceptor₁ receptor antagonists), thromboxane inhibitors and receptor antagonists and platelet membrane glycoprotein receptor antagonists; inhibitors of cell adhesion molecules, including selectin inhibitors and integrin inhibitors; anti-chemotactic agents; interleukin receptor antagonists; and intracellular signaling inhibitors including: protein kinase C (PKC) inhibitors and protein tyrosine phosphatases, modulators of intracellular protein tyrosine kinase inhibitors, inhibitors of src homology₂ (SH2) domains, and calcium channel antagonists.

The MASP-2 inhibitory agents of the present invention may also be administered in combination with one or more other complement inhibitors. No complement inhibitors are currently approved for use in humans, however some pharmacological agents have been shown to block complement in vivo. Many of these agents are also toxic or are only partial inhibitors (Asghar, S. S., *Pharmacol. Rev.* 36:223-44, 1984), and use of these has been limited to use as research tools. K76COOH and nafamstat mesilate are two agents that have shown some effectiveness in animal models of transplantation (Miyagawa, S., et al., *Transplant Proc.* 24:483-484, 1992). Low molecular weight heparins have also been shown to be effective in regulating complement activity (Edens, R. E., et al., *Complement Today*, pp. 96-120, Basel: Karger, 1993). It is believed that these small molecule inhibitors may be useful as agents to use in combination with the MASP-2 inhibitory agents of the present invention.

Other naturally occurring complement inhibitors may be useful in combination with the MASP-2 inhibitory agents of the present invention. Biological inhibitors of complement include soluble complement factor 1 (sCR1). This is a naturally-occurring inhibitor that can be found on the outer membrane of human cells. Other membrane inhibitors include DAF, MCP, and CD59. Recombinant forms have been tested for their anti-complement activity in vitro and in vivo. sCR1 has been shown to be effective in xenotransplantation, wherein the complement system (both alternative and classical) provides the trigger for a hyperactive rejection syndrome within minutes of perfusing blood through the newly transplanted organ (Platt, J. L., et al., *Immunol. Today* 11:450-6, 1990; Marino, I. R., et al., *Transplant Proc.* 1071:6, 1990; Johnstone, P. S., et al., *Transplantation* 54:573-6, 1992). The use of sCR1 protects and extends the survival time of the transplanted organ, implicating the complement pathway in the pathogenesis of organ survival (Leventhal, J. R., et al., *Transplantation* 55:857-66, 1993; Pruitt, S. K., et al., *Transplantation* 57:363-70, 1994).

Suitable additional complement inhibitors for use in combination with the compositions of the present invention also include, by way of example, MoAbs such as those being developed by Alexion Pharmaceuticals, Inc., New Haven, Conn., and anti-properdin MoAbs.

When used in the treatment of arthritides (e.g., osteoarthritis and rheumatoid arthritis), the MASP-2 inhibitory agent of the present invention may be combined with one or more chondroprotective agents, which may include one or more promoters of cartilage anabolism and/or one or more inhibitors of cartilage catabolism, and suitably both an anabolic agent and a catabolic inhibitory agent, for concomitant administration. Suitable anabolic promoting chondroprotective agents include interleukin (IL) receptor agonists including IL-4, IL-10, IL-13, rhIL-4, rhIL-10 and rhIL-13, and chimeric IL-4, IL-10, or IL-13; Transforming growth factor-β superfamily agonists, including TGF-β, TGF-β1, TGF-β2, TGF-β3, bone morphogenic proteins including BMP-2, BMP-4, BMP-5, BMP-6, BMP-7 (OP-1), and OP-2/BMP-8, growth-differentiation factors including GDF-5, GDF-6 and GDF-7, recombinant TGF-βs and BMPs, and chimeric TGF-βs and BMPs; insulin-like growth factors including IGF-1; and fibroblast growth factors including bFGF. Suitable catabolic inhibitory chondroprotective agents include Interleukin-1 (IL-1) receptor antagonists (IL-1 ra), including soluble human IL-1 receptors (shuIL-1R), rshuIL-1R, rhIL-1ra, anti-IL1-antibody, AF11567, and AF12198; Tumor Necrosis Factor (TNF) Receptor Antagonists (TNF-α), including soluble receptors including sTNFR1 and sTNFRII, recombinant TNF soluble receptors, and chimeric TNF soluble receptors including chimeric rhTNFR:Fc, Fc fusion soluble receptors and anti-TNF antibodies; cyclooxygenase-2 (COX-2 specific) inhibitors, including DuP 697, SC-58451, celecoxib, rofecoxib, nimesulide, diclofenac, meloxicam, piroxicam, NS-398, RS-57067, SC-57666, SC-58125, flosulide, etodolac, L-745,337 and DFU-T-614; Mitogen-activated protein kinase (MAPK) inhibitors, including inhibitors of ERK1, ERK2, SAPK1, SAPK2a, SAPK2b, SAPK2d, SAPK3, including SB 203580, SB 203580 iodo, SB202190, SB 242235, SB 220025, RWJ 67657, RWJ 68354, FR 133605, L-167307, PD 98059, PD 169316; inhibitors of nuclear factor kappa B (NFκB), including caffeic acid phenylethyl ester (CAPE), DM-CAPE, SN-50 peptide, hymenialdisine and pyrolidone dithiocarbamate; nitric oxide synthase (NOS) inhibitors, including $N^G$-monomethyl-L-arginine, 1400W, diphenyleneiodium, S-methyl isothiourea, S-(aminoethyl) isothiourea, L-$N^6$-(1-iminoethyl)lysine, 1,3-PBITU, 2-ethyl-2-thiopseudourea, aminoguanidine, $N^\omega$-nitro-L-arginine, and $N^\omega$-nitro-L-arginine methyl ester, inhibitors of matrix metalloproteinases (MMPs), including inhibitors of MMP-1, MMP-2, MMP-3, MMP-7, MMP-8, MMP-9, MMP-10, MMP-11, MMP-12, MMP-13, MMP-14 and MMP-15, and including U-24522, minocycline, 4-Abz-Gly-Pro-D-Leu-D-Ala-NHOH, Ac-Arg-Cys-Gly-Val-Pro-Asp-NH2, rhuman TIMP1, rhuman TIMP2, and phosphoramidon; cell adhesion molecules, including integrin agonists and antagonists including αVβ3 MoAb LM 609 and echistatin; anti-chemotactic agents including F-Met-Leu-Phe receptors, IL-8 receptors, MCP-1 receptors and MIP1-I/RANTES receptors; intracellular signaling inhibitors, including (a) protein kinase inhibitors, including both (i) protein kinase C (PKC) inhibitors (isozyme) including calphostin C, G-6203 and GF 109203X, and (ii) protein tyrosine kinase inhibitors; (b) modulators of intracellular protein tyrosine phosphatases (PTPases); and (c) inhibitors of SH2 domains (src Homology2 domains).

For some applications, it may be beneficial to administer the MASP-2 inhibitory agents of the present invention in combination with a spasm inhibitory agent. For example, for urogenital applications, it may be beneficial to include at least one smooth muscle spasm inhibitory agent and/or at least one anti-inflammation agent, and for vascular procedures it may be useful to include at least one vasospasm inhibitor and/or at least one anti-inflammation agent and/or at least one anti-restenosis agent. Suitable examples of spasm inhibitory agents include: serotonin$_2$ receptor subtype antagonists; tachykinin receptor antagonists; nitric oxide donors; ATP-sensitive potassium channel openers; calcium channel antagonists; and endothelin receptor antagonists.

Pharmaceutical Carriers and Delivery Vehicles

In general, the MASP-2 inhibitory agent compositions of the present invention, combined with any other selected therapeutic agents, are suitably contained in a pharmaceutically acceptable carrier. The carrier is non-toxic, biocompatible and is selected so as not to detrimentally affect the biological activity of the MASP-2 inhibitory agent (and any other therapeutic agents combined therewith). Exemplary pharmaceutically acceptable carriers for peptides are described in U.S. Pat. No. 5,211,657 to Yamada. The anti-MASP-2 antibodies and inhibitory peptides useful in the invention may be formulated into preparations in solid, semi-solid, gel, liquid or gaseous forms such as tablets, capsules, powders, granules, ointments, solutions, depositories, inhalants and injections allowing for oral, parenteral or surgical administration. The invention also contemplates local administration of the compositions by coating medical devices and the like.

Suitable carriers for parenteral delivery via injectable, infusion or irrigation and topical delivery include distilled water, physiological phosphate-buffered saline, normal or lactated Ringer's solutions, dextrose solution, Hank's solution, or propanediol. In addition, sterile, fixed oils may be employed as a solvent or suspending medium. For this purpose any biocompatible oil may be employed including synthetic mono- or diglycerides. In addition, fatty acids such as oleic acid find use in the preparation of injectables. The carrier and agent may be compounded as a liquid, suspension, polymerizable or non-polymerizable gel, paste or salve.

The carrier may also comprise a delivery vehicle to sustain (i.e., extend, delay or regulate) the delivery of the agent(s) or to enhance the delivery, uptake, stability or pharmacokinetics of the therapeutic agent(s). Such a delivery vehicle may include, by way of non-limiting example, microparticles, microspheres, nanospheres or nanoparticles composed of proteins, liposomes, carbohydrates, synthetic organic compounds, inorganic compounds, polymeric or copolymeric hydrogels and polymeric micelles. Suitable hydrogel and micelle delivery systems include the PEO:PHB:PEO copolymers and copolymer/cyclodextrin complexes disclosed in WO 2004/009664 A2 and the PEO and PEO/cyclodextrin complexes disclosed in U.S. Patent Application Publication No. 2002/0019369 A1. Such hydrogels may be injected locally at the site of intended action, or subcutaneously or intramuscularly to form a sustained release depot.

For intra-articular delivery, the MASP-2 inhibitory agent may be carried in above-described liquid or gel carriers that are injectable, above-described sustained-release delivery vehicles that are injectable, or a hyaluronic acid or hyaluronic acid derivative.

For oral administration of non-peptidergic agents, the MASP-2 inhibitory agent may be carried in an inert filler or diluent such as sucrose, cornstarch, or cellulose.

For topical administration, the MASP-2 inhibitory agent may be carried in ointment, lotion, cream, gel, drop, suppository, spray, liquid or powder, or in gel or microcapsular delivery systems via a transdermal patch.

Various nasal and pulmonary delivery systems, including aerosols, metered-dose inhalers, dry powder inhalers, and nebulizers, are being developed and may suitably be adapted for delivery of the present invention in an aerosol, inhalant, or nebulized delivery vehicle, respectively.

For intrathecal (IT) or intracerebroventricular (ICV) delivery, appropriately sterile delivery systems (e.g., liquids; gels, suspensions, etc.) can be used to administer the present invention.

The compositions of the present invention may also include biocompatible excipients, such as dispersing or wetting agents, suspending agents, diluents, buffers, penetration enhancers, emulsifiers, binders, thickeners, flavouring agents (for oral administration).

Pharmaceutical Carriers for Antibodies and Peptides

More specifically with respect to anti-MASP-2 antibodies and inhibitory peptides, exemplary formulations can be parenterally administered as injectable dosages of a solution or suspension of the compound in a physiologically acceptable diluent with a pharmaceutical carrier that can be a sterile liquid such as water, oils, saline, glycerol or ethanol. Additionally, auxiliary substances such as wetting or emulsifying agents, surfactants, pH buffering substances and the like can be present in compositions comprising anti-MASP-2 antibodies and inhibitory peptides. Additional components of pharmaceutical compositions include petroleum (such as of animal, vegetable or synthetic origin), for example, soybean oil and mineral oil. In general, glycols such as propylene glycol or polyethylene glycol are preferred liquid carriers for injectable solutions.

The anti-MASP-2 antibodies and inhibitory peptides can also be administered in the form of a depot injection or implant preparation that can be formulated in such a manner as to permit a sustained or pulsatile release of the active agents.

Pharmaceutically Acceptable Carriers for Expression Inhibitors

More specifically with respect to expression inhibitors useful in the methods of the invention, compositions are provided that comprise an expression inhibitor as described above and a pharmaceutically acceptable carrier or diluent. The composition may further comprise a colloidal dispersion system.

Pharmaceutical compositions that include expression inhibitors may include, but are not limited to, solutions, emulsions, and liposome-containing formulations. These compositions may be generated from a variety of components that include, but are not limited to, preformed liquids, self-emulsifying solids and self-emulsifying semisolids. The preparation of such compositions typically involves combining the expression inhibitor with one or more of the following: buffers, antioxidants, low molecular weight polypeptides, proteins, amino acids, carbohydrates including glucose, sucrose or dextrins, chelating agents such as EDTA, glutathione and other stabilizers and excipients. Neutral buffered saline or saline mixed with non-specific serum albumin are examples of suitable diluents.

In some embodiments, the compositions may be prepared and formulated as emulsions which are typically heterogeneous systems of one liquid dispersed in another in the form of droplets (see, Idson, in *Pharmaceutical Dosage Forms*, Vol. 1, Rieger and Banker (eds.), Marcek Dekker, Inc., N.Y., 1988). Examples of naturally occurring emulsifiers used in emulsion formulations include acacia, beeswax, lanolin, lecithin and phosphatides.

In one embodiment, compositions including nucleic acids can be formulated as microemulsions. A microemulsion, as used herein refers to a system of water, oil, and amphiphile, which is a single optically isotropic and thermodynamically stable liquid solution (see Rosoff in Pharmaceutical Dosage Forms, Vol. 1). The method of the invention may also use liposomes for the transfer and delivery of antisense oligonucleotides to the desired site.

Pharmaceutical compositions and formulations of expression inhibitors for topical administration may include transdermal patches, ointments, lotions, creams, gels, drops, suppositories, sprays, liquids and powders. Conventional pharmaceutical carriers, as well as aqueous, powder or oily bases and thickeners and the like may be used.

Modes of Administration

The pharmaceutical compositions comprising MASP-2 inhibitory agents may be administered in a number of ways depending on whether a local or systemic mode of administration is most appropriate for the condition being treated. Additionally, as described herein above with respect to extracorporeal reperfusion procedures, MASP-2 inhibitory agents can be administered via introduction of the compositions of the present invention to recirculating blood or plasma. Further, the compositions of the present invention can be delivered by coating or incorporating the compositions on or into an implantable medical device.

Systemic Delivery

As used herein, the terms "systemic delivery" and "systemic administration" are intended to include but are not limited to oral and parenteral routes including intramuscular (IM), subcutaneous, intravenous (IV), intra-arterial, inhalational, sublingual, buccal, topical, transdermal, nasal, rectal, vaginal and other routes of administration that effectively result in dispersement of the delivered agent to a single or multiple sites of intended therapeutic action. Preferred routes of systemic delivery for the present compositions include intravenous, intramuscular, subcutaneous and inhalational. It will be appreciated that the exact systemic administration route for selected agents utilized in particular compositions of the present invention will be determined in part to account for the agent's susceptibility to metabolic transformation pathways associated with a given route of administration. For example, peptidergic agents may be most suitably administered by routes other than oral.

MASP-2 inhibitory antibodies and polypeptides can be delivered into a subject in need thereof by any suitable means. Methods of delivery of MASP-2 antibodies and polypeptides include administration by oral, pulmonary, parenteral (e.g., intramuscular, intraperitoneal, intravenous (IV) or subcutaneous injection), inhalation (such as via a fine powder formulation), transdermal, nasal, vaginal, rectal, or sublingual routes of administration, and can be formulated in dosage forms appropriate for each route of administration.

By way of representative example, MASP-2 inhibitory antibodies and peptides can be introduced into a living body by application to a bodily membrane capable of absorbing the polypeptides, for example the nasal, gastrointestinal and rectal membranes. The polypeptides are typically applied to the absorptive membrane in conjunction with a permeation enhancer. (See, e.g., Lee, V. H. L., *Crit. Rev. Ther. Drug Carrier Sys.* 5:69, 1988; Lee, V. H. L., *J. Controlled Release* 13:213, 1990; Lee, V. H. L., Ed., *Peptide and Protein Drug Delivery*, Marcel Dekker, New York (1991); DeBoer, A. G., et al., *J. Controlled Release* 13:241, 1990.) For example, STDHF is a synthetic derivative of fusidic acid, a steroidal surfactant that is similar in structure to the bile salts, and has been used as a permeation enhancer for nasal delivery. (Lee, W. A., *Biopharm.* 22, November/December 1990.)

The MASP-2 inhibitory antibodies and polypeptides may be introduced in association with another molecule, such as a lipid, to protect the polypeptides from enzymatic degradation. For example, the covalent attachment of polymers, especially polyethylene glycol (PEG), has been used to protect certain proteins from enzymatic hydrolysis in the body and thus prolong half-life (Fuertges, F., et al., *J. Controlled Release* 11:139, 1990). Many polymer systems have been reported for protein delivery (Bae, Y. H., et al., *J. Controlled Release* 9:271, 1989; Hori, R., et al., *Pharm. Res.* 6:813, 1989; Yamakawa, I., et al., *J. Pharm. Sci.* 79:505, 1990; Yoshihiro, I., et al., *J. Controlled Release* 10:195, 1989; Asano, M., et al., *J. Controlled Release* 9:111, 1989; Rosenblatt, J., et al., *J. Controlled Release* 9:195, 1989; Makino, K., *J. Controlled Release* 12:235, 1990; Takakura, Y., et al., *J. Pharm. Sci.* 78:117, 1989; Takakura, Y., et al., *J. Pharm. Sci.* 78:219, 1989).

Recently, liposomes have been developed with improved serum stability and circulation half-times (see, e.g., U.S. Pat. No. 5,741,516, to Webb). Furthermore, various methods of liposome and liposome-like preparations as potential drug carriers have been reviewed (see, e.g., U.S. Pat. No. 5,567,434, to Szoka; U.S. Pat. No. 5,552,157, to Yagi; U.S. Pat. No. 5,565,213, to Nakamori; U.S. Pat. No. 5,738,868, to Shinkarenko; and U.S. Pat. No. 5,795,587, to Gao).

For transdermal applications, the MASP-2 inhibitory antibodies and polypeptides may be combined with other suitable ingredients, such as carriers and/or adjuvants. There are no limitations on the nature of such other ingredients, except that they must be pharmaceutically acceptable for their intended administration, and cannot degrade the activity of the active ingredients of the composition. Examples of suitable vehicles include ointments, creams, gels, or suspensions, with or without purified collagen. The MASP-2 inhibitory antibodies and polypeptides may also be impregnated into transdermal patches, plasters, and bandages, preferably in liquid or semi-liquid form.

The compositions of the present invention may be systemically administered on a periodic basis at intervals determined to maintain a desired level of therapeutic effect. For example, compositions may be administered, such as by subcutaneous injection, every two to four weeks or at less frequent intervals. The dosage regimen will be determined by the physician considering various factors that may influence the action of the combination of agents. These factors will include the extent of progress of the condition being treated, the patient's age, sex and weight, and other clinical factors. The dosage for each individual agent will vary as a function of the MASP-2 inhibitory agent that is included in the composition, as well as the presence and nature of any drug delivery vehicle (e.g., a sustained release delivery vehicle). In addition, the dosage quantity may be adjusted to account for variation in the frequency of administration and the pharmacokinetic behavior of the delivered agent(s).

Local Delivery

As used herein, the term "local" encompasses application of a drug in or around a site of intended localized action, and may include for example topical delivery to the skin or other affected tissues, ophthalmic delivery, intrathecal (IT), intracerebroventricular (ICV), intra-articular, intracavity, intracranial or intravesicular administration, placement or irrigation. Local administration may be preferred to enable administration of a lower dose, to avoid systemic side effects, and for more accurate control of the timing of delivery and concentration of the active agents at the site of local delivery. Local administration provides a known concentration at the target site, regardless of interpatient variability in metabolism, blood flow, etc. Improved dosage control is also provided by the direct mode of delivery.

Local delivery of a MASP-2 inhibitory agent may be achieved in the context of surgical methods for treating a disease or condition, such as for example during procedures such as arterial bypass surgery, atherectomy, laser procedures, ultrasonic procedures, balloon angioplasty and stent placement. For example, a MASP-2 inhibitor can be administered to a subject in conjunction with a balloon angioplasty procedure. A balloon angioplasty procedure involves inserting a catheter having a deflated balloon into an artery. The deflated balloon is positioned in proximity to the atherosclerotic plaque and is inflated such that the plaque is compressed against the vascular wall. As a result, the balloon surface is in contact with the layer of vascular endothelial cells on the surface of the blood vessel. The MASP-2 inhibitory agent may be attached to the balloon angioplasty catheter in a manner that permits release of the agent at the site of the atherosclerotic plaque. The agent may be attached to the balloon catheter in accordance with standard procedures known in the art. For example, the agent may be stored in a compartment of the balloon catheter until the balloon is inflated, at which point it is released into the local environment. Alternatively, the agent may be impregnated on the balloon surface, such that it contacts the cells of the arterial wall as the balloon is inflated. The agent may also be delivered in a perforated balloon catheter such as those disclosed in Flugelman, M. Y., et al., *Circulation* 85:1110-1117, 1992. See also published PCT Application WO 95/23161 for an exemplary procedure for attaching a therapeutic protein to a balloon angioplasty catheter. Likewise, the MASP-2 inhibitory agent may be included in a gel or polymeric coating applied to a stent, or may be incorporated into the material of the stent, such that the stent elutes the MASP-2 inhibitory agent after vascular placement.

MASP-2 inhibitory compositions used in the treatment of arthritides and other musculoskeletal disorders may be locally delivered by intra-articular injection. Such compositions may suitably include a sustained release delivery vehicle. As a further example of instances in which local delivery may be desired, MASP-2 inhibitory compositions used in the treatment of urogenital conditions may be suitably instilled intravesically or within another urogenital structure.

Coatings on a Medical Device

MASP-2 inhibitory agents such as antibodies and inhibitory peptides may be immobilized onto (or within) a surface of an implantable or attachable medical device. The modified surface will typically be in contact with living tissue after implantation into an animal body. By "implantable or attachable medical device" is intended any device that is implanted into, or attached to, tissue of an animal body, during the normal operation of the device (e.g., stents and implantable drug delivery devices). Such implantable or attachable medical devices can be made from, for example, nitrocellulose, diazocellulose, glass, polystyrene, polyvinylchloride, polypropylene, polyethylene, dextran, Sepharose, agar, starch, nylon, stainless steel, titanium and biodegradable and/or biocompatible polymers.

Linkage of the protein to a device can be accomplished by any technique that does not destroy the biological activity of the linked protein, for example by attaching one or both of the N-C-terminal residues of the protein to the device. Attachment may also be made at one or more internal sites in the protein. Multiple attachments (both internal and at the ends of the protein) may also be used. A surface of an implantable or attachable medical device can be modified to include functional groups (e.g., carboxyl, amide, amino, ether, hydroxyl, cyano, nitrido, sulfanamido, acetylinic, epoxide, silanic, anhydric, succinimic, azido) for protein immobilization thereto. Coupling chemistries include, but are not limited to, the formation of esters, ethers, amides, azido and sulfanamido derivatives, cyanate and other linkages to the functional groups available on MASP-2 antibodies or inhibitory peptides. MASP-2 antibodies or inhibitory fragments can also be attached non-covalently by the addition of an affinity tag sequence to the protein, such as GST (D. B. Smith and K. S. Johnson, *Gene* 67:31, 1988), polyhistidines (E. Hochuli et al., *J. Chromatog.* 411:77, 1987), or biotin. Such affinity tags may be used for the reversible attachment of the protein to a device.

Proteins can also be covalently attached to the surface of a device body, for example, by covalent activation of the surface of the medical device. By way of representative example, matricellular protein(s) can be attached to the device body by any of the following pairs of reactive groups (one member of the pair being present on the surface of the device body, and the other member of the pair being present on the matricellular protein(s)): hydroxyl/carboxylic acid to yield an ester linkage; hydroxyl/anhydride to yield an ester linkage; hydroxyl/isocyanate to yield a urethane linkage. A surface of a device body that does not possess useful reactive groups can be treated with radio-frequency discharge plasma (RFGD) etching to generate reactive groups in order to allow deposition of matricellular protein(s) (e.g., treatment with oxygen plasma to introduce oxygen-containing groups; treatment with propyl amino plasma to introduce amine groups).

MASP-2 inhibitory agents comprising nucleic acid molecules such as antisense, RNAi- or DNA-encoding peptide inhibitors can be embedded in porous matrices attached to a device body. Representative porous matrices useful for making the surface layer are those prepared from tendon or dermal collagen, as may be obtained from a variety of commercial sources (e.g., Sigma and Collagen Corporation), or collagen matrices prepared as described in U.S. Pat. No. 4,394,370, to Jefferies, and U.S. Pat. No. 4,975,527, to Koezuka. One collagenous material is termed UltraFiber™ and is obtainable from Norian Corp. (Mountain View, Calif.).

Certain polymeric matrices may also be employed if desired, and include acrylic ester polymers and lactic acid polymers, as disclosed, for example, in U.S. Pat. Nos. 4,526,909 and 4,563,489, to Urist. Particular examples of useful polymers are those of orthoesters, anhydrides, propylene-cofumarates, or a polymer of one or more α-hydroxy carboxylic acid monomers, (e.g., α-hydroxy acetic acid (glycolic acid) and/or α-hydroxy propionic acid (lactic acid)).

Treatment Regimens

In prophylactic applications, the pharmaceutical compositions are administered to a subject susceptible to, or otherwise at risk of, a condition associated with MASP-2-dependent complement activation in an amount sufficient to eliminate or reduce the risk of developing symptoms of the condition. In therapeutic applications, the pharmaceutical compositions are administered to a subject suspected of, or already suffering from, a condition associated with MASP-2-dependent complement activation in a therapeutically effective amount sufficient to relieve, or at least partially reduce, the symptoms of the condition. In both prophylactic and therapeutic regimens, compositions comprising MASP-2 inhibitory agents may be administered in several dosages until a sufficient therapeutic outcome has been achieved in the subject. Application of the MASP-2 inhibitory compositions of the present invention may be carried out by a single administration of the composition, or a limited sequence of administrations, for treatment of an acute condition, e.g., reperfusion injury or other traumatic injury. Alternatively, the composition may be administered at periodic intervals over an extended period of time for treatment of chronic conditions, e.g., arthritides or psoriasis.

The methods and compositions of the present invention may be used to inhibit inflammation and related processes that typically result from diagnostic and therapeutic medical and surgical procedures. To inhibit such processes, the MASP-2 inhibitory composition of the present invention may be applied periprocedurally. As used herein "periprocedurally" refers to administration of the inhibitory composition preprocedurally and/or intraprocedurally and/or postprocedurally, i.e., before the procedure, before and during the procedure, before and after the procedure, before, during and after the procedure, during the procedure, during and after the procedure, or after the procedure. Periprocedural application may be carried out by local administration of the composition to the surgical or procedural site, such as by injection or continuous or intermittent irrigation of the site or by systemic administration. Suitable methods for local perioperative delivery of MASP-2 inhibitory agent solutions are disclosed in U.S. Pat. No. 6,420,432 to Demopulos and U.S. Pat. No. 6,645,168 to Demopulos. Suitable methods for local delivery of chondroprotective compositions including MASP-2 inhibitory agent(s) are disclosed in International PCT Patent Application WO 01/07067 A2. Suitable methods and compositions for targeted systemic delivery of chondroprotective compositions including MASP-2 inhibitory agent(s) are disclosed in International PCT Patent Application WO 03/063799 A2.

VI. EXAMPLES

The following examples merely illustrate the best mode now contemplated for practicing the invention, but should not be construed to limit the invention. All literature citations herein are expressly incorporated by reference.

Example 1

This example describes the generation of a mouse strain deficient in MASP-2 (MASP-2−/−) but sufficient of MAp19 (MAp19+/+).

Figure 4:
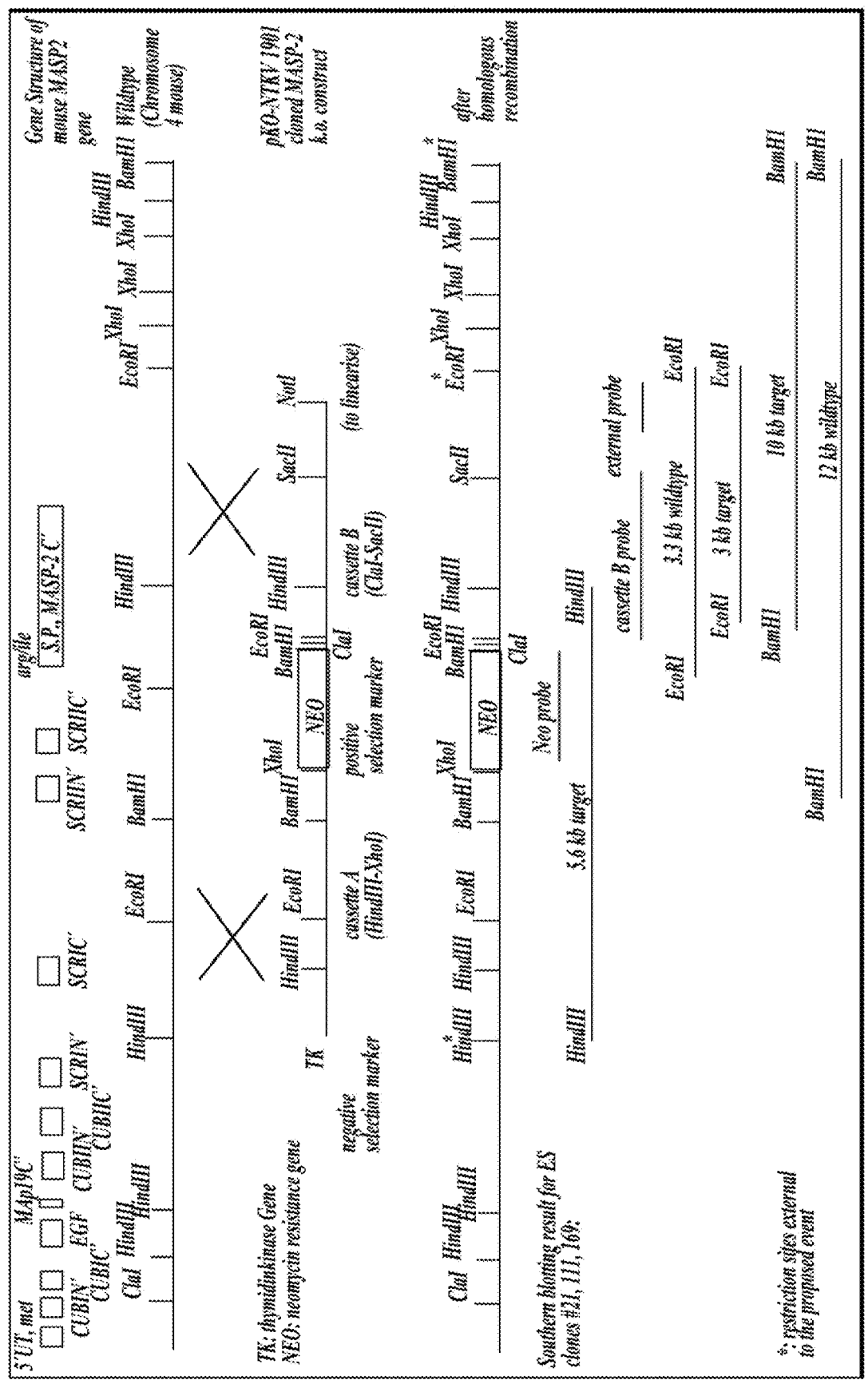
FIG. 4 is a diagram illustrating the murine MASP-2 knockout strategy.

Materials and Methods: The targeting vector pKO-NTKV 1901 was designed to disrupt the three exons coding for the C-terminal end of murine MASP-2, including the exon that encodes the serine protease domain, as shown in FIG. 4. PKO-NTKV 1901 was used to transfect the murine ES cell line E14.1a (SV129 Ola). Neomycin-resistant and Thymidine Kinase-sensitive clones were selected. 600 ES clones were screened and, of these, four different clones were identified and verified by southern blot to contain the expected selective targeting and recombination event as shown in FIG. 4. Chimeras were generated from these four positive clones by embryo transfer. The chimeras were then backcrossed in the genetic background C57/BL6 to create transgenic males. The transgenic males were crossed with females to generate F1s with 50% of the offspring showing heterozygosity for the disrupted MASP-2 gene. The heterozygous mice were intercrossed to generate homozygous MASP-2 deficient offspring, resulting in heterozygous and wild-type mice in the ration of 1:2:1, respectively.

Results and Phenotype: The resulting homozygous MASP-2-/- deficient mice were found to be viable and fertile and were verified to be MASP-2 deficient by southern blot to confirm the correct targeting event, by Northern blot to confirm the absence of MASP-2 mRNA, and by Western blot to confirm the absence of MASP-2 protein (data not shown). The presence of MAp19 mRNA and the absence of MASP-2 mRNA were further confirmed using time-resolved RT-PCR on a LightCycler machine. The MASP-2-/- mice do continue to express MAp19, MASP-1, and MASP-3 mRNA and protein as expected (data not shown). The presence and abundance of mRNA in the MASP-2-/- mice for Properdin, Factor B, Factor D, C4, C2, and C3 was assessed by LightCycler analysis and found to be identical to that of the wild-type littermate controls (data not shown). The plasma from homozygous MASP-2-/- mice is totally deficient of lectin-pathway-mediated complement activation and alternative pathway complement activation as further described in Example 2.

Generation of a MASP-2-/- strain on a pure C57BL6 Background: The MASP-2-/- mice are back-crossed with a pure C57BL6 line for nine generations prior to use of the MASP-2-/- strain as an experimental animal model.

Example 2

This example demonstrates that MASP-2 is required for complement activation via the alternative and the lectin pathway.

Methods and Materials:

Lectin pathway specific C4 Cleavage Assay: A C4 cleavage assay has been described by Petersen, et al., *J. Immunol. Methods* 257:107 (2001) that measures lectin pathway activation resulting from lipoteichoic acid (LTA) from *S. aureus*, which binds L-ficolin. The assay described in Example 11 was adapted to measure lectin pathway activation via MBL by coating the plate with LPS and mannan or zymosan prior to adding serum from MASP-2-/- mice as described below. The assay was also modified to remove the possibility of C4 cleavage due to the classical pathway. This was achieved by using a sample dilution buffer containing 1 M NaCl, which permits high affinity binding of lectin pathway recognition components to their ligands but prevents activation of endogenous C4, thereby excluding the participation of the classical pathway by dissociating the C1 complex. Briefly described, in the modified assay serum samples (diluted in high salt (1 M NaCl) buffer) are added to ligand-coated plates, followed by the addition of a constant amount of purified C4 in a buffer with a physiological concentration of salt. Bound recognition complexes containing MASP-2 cleave the C4, resulting in C4b deposition.

Assay Methods:

1) Nunc Maxisorb microtiter plates (Maxisorb, Nunc, Cat. No. 442404, Fisher Scientific) were coated with 1 µg/ml mannan (M7504 Sigma) or any other ligand (e.g., such as those listed below) diluted in coating buffer (15 mM $Na_2CO_3$, 35 mM $NaHCO_3$, pH 9.6).

The following reagents were used in the assay:
a. mannan (1 µg/well mannan (M7504 Sigma) in 100 µl coating buffer):
b. zymosan (1 µg/well zymosan (Sigma) in 100 µl coating buffer);
c. LTA (1 µg/well in 100 µl coating buffer or 2 µg/well in 20 µl methanol)
d. 1 µg of the H-ficolin specific Mab 4H5 in coating buffer
e. PSA from Aerococcus viridans (2 µg/well in 100 µl coating buffer)
f. 100 µl/well of formalin-fixed *S. aureus* DSM20233 ($OD_{550}$=0.5) in coating buffer.

2) The plates were incubated overnight at 4° C.

3) After overnight incubation, the residual protein binding sites were saturated by incubated the plates with 0.1% HSA-TBS blocking buffer (0.1% (w/v) HSA in 10 mM Tris-CL, 140 mM NaCl, 1.5 mM $NaN_3$, pH 7.4) for 1-3 hours, then washing the plates 3× with TBS/tween/$Ca^{2+}$ (TBS with 0.05% Tween 20 and 5 mM $CaCl_2$, 1 mM $MgCl_2$, pH 7.4).

4) Serum samples to be tested were diluted in MBL-binding buffer (1 M NaCl) and the diluted samples were added to the plates and incubated overnight at 4° C. Wells receiving buffer only were used as negative controls.

5) Following incubation overnight at 4° C., the plates were washed 3× with TBS/tween/Ca2+. Human C4 (100 µl/well of 1 µg/ml diluted in BBS (4 mM barbital, 145 mM NaCl, 2 mM $CaCl_2$, 1 mM $MgCl_2$, pH 7.4)) was then added to the plates and incubated for 90 minutes at 37° C. The plates were washed again 3× with TB Shween/$Ca^{2+}$.

6) C4b deposition was detected with an alkaline phosphatase-conjugated chicken anti-human C4c (diluted 1:1000 in TBS/tween/$Ca^{2+}$), which was added to the plates and incubated for 90 minutes at room temperature. The plates were then washed again 3× with TBS/tween/$Ca^{2+}$.

7) Alkaline phosphatase was detected by adding 100 µl of p-nitrophenyl phosphate substrate solution, incubating at room temperature for 20 minutes, and reading the $OD_{405}$ in a microtiter plate reader.

Results: FIGS. 6A-B show the amount of C4b deposition on mannan (FIG. 6A) and zymosan (FIG. 6B) in serum dilutions from MASP-2+/+ (crosses), MASP-2+/- (closed circles) and MASP-2-/- (closed triangles). FIG. 6C shows the relative C4 convertase activity on plates coated with zymosan (white bars) or mannan (shaded bars) from MASP-2-/+ mice (n=5) and MASP-2-/- mice (n=4) relative to wild-type mice (n=5) based on measuring the amount of C4b deposition normalized to wild-type serum. The error bars represent the standard deviation. As shown in FIGS. 6A-C, plasma from MASP-2-/- mice is totally deficient in lectin-pathway-mediated complement activation on mannan and on zymosan coated plates. These results clearly demonstrate that MASP-2, but not MASP-1 or MASP-3, is the effector component of the lectin pathway.

C3b Deposition Assay:

1) Nunc Maxisorb microtiter plates (Maxisorb, Nunc, cat. No. 442404, Fisher Scientific) are coated with 1 µg/well mannan (M7504 Sigma) or any other ligand diluted in coating buffer (15 mM $Na_2CO_3$, 35 mM $NaHCO_3$, pH 9.6) and incubated overnight at 4° C.

2) Residual protein binding sites are saturated by incubating the plate with 0.1% HSA-TBS blocking buffer (0.1% (w/v) HSA in 10 mM Tris-CL, 140 mM NaCl, 1.5 mM $NaN_3$, pH 7.4) for 1-3 hours.

3) Plates are washed in TBS/tw/$Ca^{++}$ (TBS with 0.05% Tween 20 and 5 mM $CaCl_2$) and diluted BBS is added to serum samples (4 mM barbital, 145 mM NaCl, 2 mM $CaCl_2$, 1 mM $MgCl_2$, pH 7.4). Wells receiving only buffer are used as negative controls. A control set of serum samples obtained from wild-type or MASP-2−/− mice are C1q depleted prior to use in the assay. C1q-depleted mouse serum was prepared using protein-A-coupled Dynabeads (Dynal Biotech, Oslo, Norway) coated with rabbit anti-human C1q IgG (Dako, Glostrup, Denmark), according to the supplier's instructions.

4) Following incubation overnight at 4° C., and another wash with TBS/tw/Ca$^{++}$, converted and bound C3 is detected with a polyclonal anti-human-C3c Antibody (Dako A 062) diluted in TBS/tw/Ca$^{++}$ at 1:1000). The secondary antibody is goat anti-rabbit IgG (whole molecule) conjugated to alkaline-phosphatase (Sigma Immunochemicals A-3812) diluted 1:10,000 in TBS/tw/Ca$^{++}$. The presence of alternative complement pathway (AP) is determined by addition of 100 μl substrate solution (Sigma Fast p-Nitrophenyl Phosphate tablet sets, Sigma) and incubation at room temperature. Hydrolysis is monitored quantitatively by measuring the absorption at 405 nm in a microtiter plate reader. A standard curve is prepared for each analysis using serial dilutions of plasma/serum samples.

Results: The results shown in FIGS. 7A and 7B are from pooled serum from several mice. The crosses represent MASP-2+/+ serum, the filled circles represent C1q depleted MASP-2+/+ serum, the open squares represent MASP-2−/− serum and the open triangles represent C1q depleted MASP-2−/− serum. As shown in FIGS. 7A-B, serum from MASP-2−/− mice tested in a C3b deposition assay results in very low levels of C3 activation on mannan (FIG. 7A) and on zymosan (FIG. 7B) coated plates. This result clearly demonstrates that MASP-2 is required to contribute the initial C3b generation from C3 to initiate the alternative complement pathway. This is a surprising result in view of the widely accepted view that complement factors C3, factor B, factor D and properdin form an independent functional alternative pathway in which C3 can undergo a spontaneous conformational change to a "C3b-like" form which then generates a fluid phase convertase iC3Bb and deposits C3b molecules on activation surfaces such as zymosan.

Recombinant MASP-2 Reconstitutes Lectin Pathway-Dependent C4 Activation in Serum from the MASP-2−/− Mice In order to establish that the absence of MASP-2 was the direct cause of the loss of lectin pathway-dependent C4 activation in the MASP-2−/− mice, the effect of adding recombinant MASP-2 protein to serum samples was examined in the C4 cleavage assay described above. Functionally active murine MASP-2 and catalytically inactive murine MASP-2A (in which the active-site serine residue in the serine protease domain was substituted for the alanine residue) recombinant proteins were produced and purified as described below in Example 5. Pooled serum from 4 MASP-2−/− mice was pre-incubated with increasing protein concentrations of recombinant murine MASP-2 or inactive recombinant murine MASP-2A and C4 convertase activity was assayed as described above.

Figure 8:
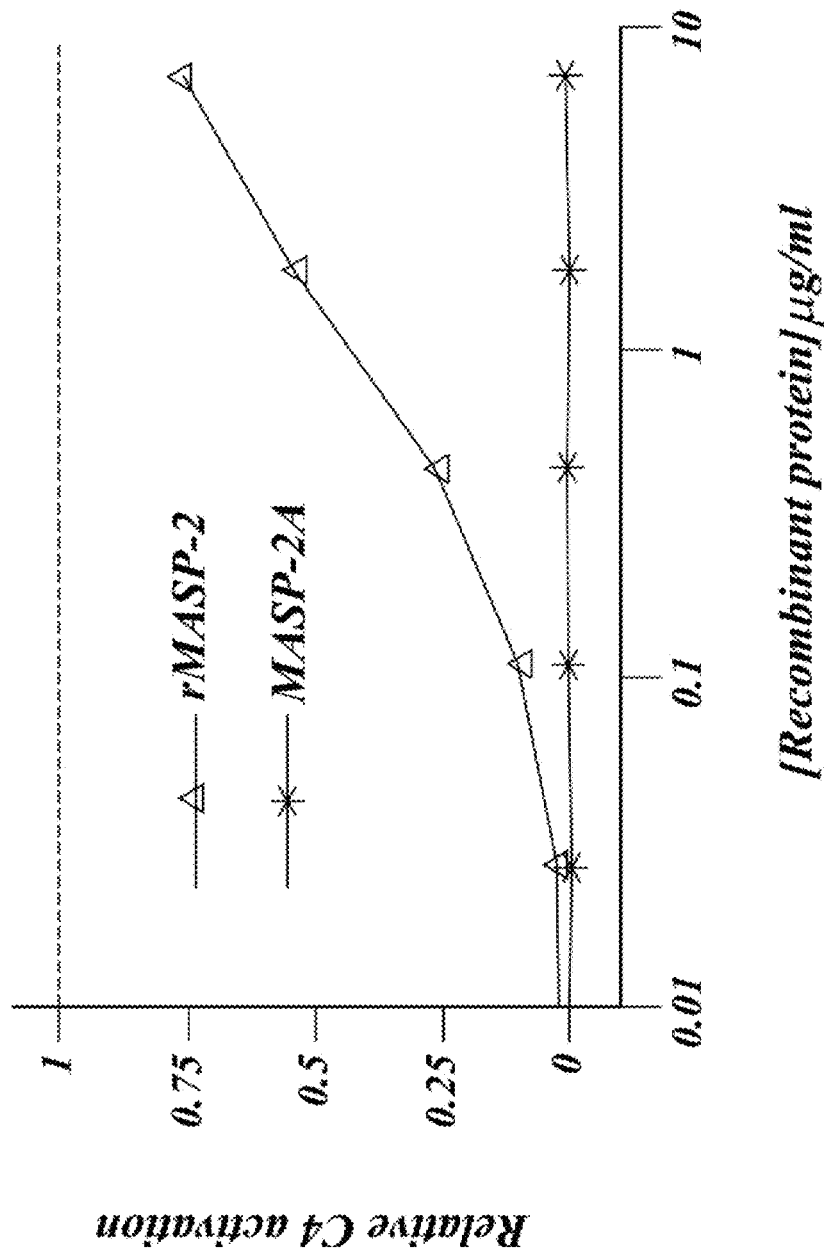
FIG. 8 presents results demonstrating that the addition of murine recombinant MASP-2 to MASP-2−/− serum samples recovers lectin-pathway-mediated C4 activation in a protein concentration dependent manner, as measured by C4b deposition on mannan.

Results: As shown in FIG. 8, the addition of functionally active murine recombinant MASP-2 protein (shown as open triangles) to serum obtained from the MASP-2−/− mice restored lectin pathway-dependent C4 activation in a protein concentration dependent manner, whereas the catalytically inactive murine MASP-2A protein (shown as stars) did not restore C4 activation. The results shown in FIG. 8 are normalized to the C4 activation observed with pooled wild-type mouse serum (shown as a dotted line).

Example 3

This example describes the generation of a transgenic mouse strain that is murine MASP-2−/−, MAp19+/+ and that expresses a human MASP-2 transgene (a murine MASP-2 knock-out and a human MASP-2 knock-in).

Figure 5:
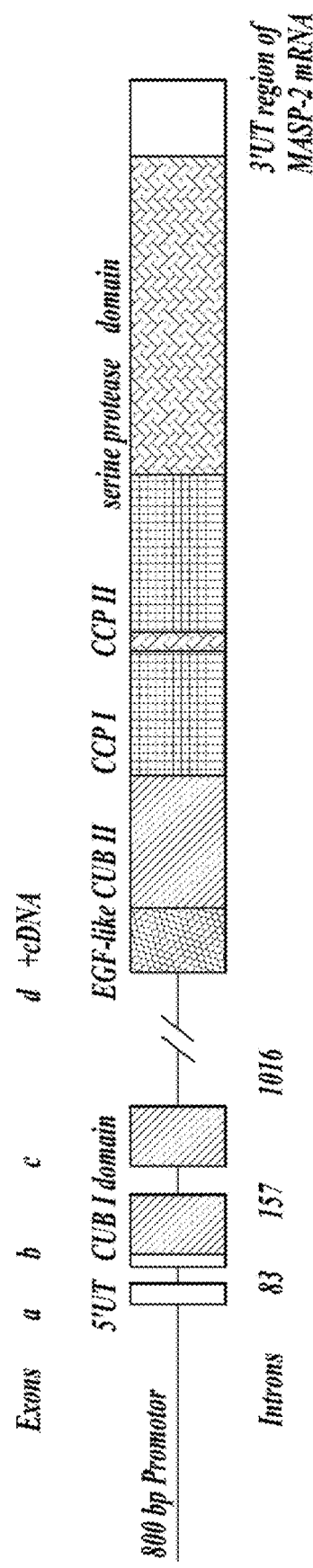
FIG. 5 is a diagram illustrating the human MASP-2 minigene construct.

Materials and Methods: A minigene encoding human MASP-2 called "mini hMASP-2" (SEQ ID NO:49) as shown in FIG. 5 was constructed which includes the promoter region of the human MASP 2 gene, including the first 3 exons (exon 1 to exon 3) followed by the cDNA sequence that represents the coding sequence of the following 8 exons, thereby encoding the full-length MASP-2 protein driven by its endogenous promoter. The mini hMASP-2 construct was injected into fertilized eggs of MASP-2−/− in order to replace the deficient murine MASP 2 gene by transgenically expressed human MASP-2.

Example 4

This example describes the isolation of human MASP-2 protein in proenzyme form from human serum.

Method of human MASP-2 isolation: A method for isolating MASP-2 from human serum has been described in Matsushita et al., *J. Immunol.* 165:2637-2642, 2000. Briefly, human serum is passed through a yeast mannan-Sepharose column using a 10 mM imidazole buffer (pH 6.0) containing 0.2 M NaCl, 20 mM CaCl$_2$, 0.2 mM NPGB, 20 μM p-APMSF, and 2% mannitol. The MASP-1 and MASP-2 proenzymes complex with MBL and elute with the above buffer containing 0.3 M mannose. To separate proenzymes MASP-1 and MASP-2 from MBL, preparations containing the complex are applied to anti-MBL-Sepharose and then MASPs are eluted with imidazole buffer containing 20 mM EDTA and 1 M NaCl. Finally, proenzymes MASP-1 and MASP-2 are separated from each other by passing through anti-MASP-1-Sepharose in the same buffer as used for the anti-MBL-Sepharose. MASP-2 is recovered in the effluents, whereas MASP-1 is eluted with 0.1 M glycine buffer (pH 2.2).

Example 5

This example describes the recombinant expression and protein production of recombinant full-length human, rat and murine MASP-2, MASP-2 derived polypeptides, and catalytically inactivated mutant forms of MASP-2

Expression of Full-Length Human, Murine and Rat MASP-2:

The full length cDNA sequence of human MASP-2 (SEQ ID NO: 4) was also subcloned into the mammalian expression vector pCI-Neo (Promega), which drives eukaryotic expression under the control of the CMV enhancer/promoter region (described in Kaufman R. J. et al., *Nucleic Acids Research* 19:4485-90, 1991; Kaufman, *Methods in Enzymology,* 185:537-66 (1991)). The full length mouse cDNA (SEQ ID NO:50) and rat MASP-2 cDNA (SEQ ID NO:53) were each subcloned into the pED expression vector. The MASP-2 expression vectors were then transfected into the adherent Chinese hamster ovary cell line DXB1 using the standard calcium phosphate transfection procedure described in Maniatis et al., 1989. Cells transfected with these constructs grew very slowly, implying that the encoded protease is cytotoxic.

In another approach, the minigene construct (SEQ ID NO:49) containing the human cDNA of MASP-2 driven by its endogenous promoter is transiently transfected into Chinese hamster ovary cells (CHO). The human MASP-2 protein is secreted into the culture media and isolated as described below.

Expression of Full-Length Catalytically Inactive MASP-2:

Rationale: MASP-2 is activated by autocatalytic cleavage after the recognition subcomponents MBL or ficolins (either L-ficolin, H-ficolin or M-ficolin) bind to their respective carbohydrate pattern. Autocatalytic cleavage resulting in activation of MASP-2 often occurs during the isolation procedure of MASP-2 from serum, or during the purification following recombinant expression. In order to obtain a more stable protein preparation for use as an antigen, a catalytically inactive form of MASP-2, designed as MASP-2A was created by replacing the serine residue that is present in the catalytic triad of the protease domain with an alanine residue in rat (SEQ ID NO:55 Ser617 to Ala617); in mouse (SEQ ID NO:52 Ser617 to Ala617); or in human (SEQ ID NO:3 Ser618 to Ala618).

In order to generate catalytically inactive human and murine MASP-2A proteins, site-directed mutagenesis was carried out using the oligonucleotides shown in TABLE 5. The oligonucleotides in TABLE 5 were designed to anneal to the region of the human and murine cDNA encoding the enzymatically active serine and oligonucleotide contain a mismatch in order to change the serine codon into an alanine codon. For example, PCR oligonucleotides SEQ ID NOS: 56-59 were used in combination with human MASP-2 cDNA (SEQ ID NO:4) to amplify the region from the start codon to the enzymatically active serine and from the serine to the stop codon to generate the complete open reading from of the mutated MASP-2A containing the Ser618 to Ala618 mutation. The PCR products were purified after agarose gel electrophoresis and band preparation and single adenosine overlaps were generated using a standard tailing procedure. The adenosine tailed MASP-2A was then cloned into the pGEM-T easy vector, transformed into *E. coli*.

A catalytically inactive rat MASP-2A protein was generated by kinasing and annealing SEQ ID NO:64 and SEQ ID NO:65 by combining these two oligonucleotides in equal molar amounts, heating at 100° C. for 2 minutes and slowly cooling to room temperature. The resulting annealed fragment has PstI and XbaI compatible ends and was inserted in place of the PstI-XbaI fragment of the wild-type rat MASP-2 cDNA (SEQ ID NO:53) to generate rat MASP-2A.

(SEQ ID NO: 64)
5'GAGGTGACGCAGGAGGGGCATTAGTGTTT 3'

(SEQ ID NO: 65)
5'CTAGAAACACTAATGCCCCTCCTGCGTCACCTCTGCA 3'

The human, murine and rat MASP-2A were each further subcloned into either of the mammalian expression vectors pED or pCI-Neo and transfected into the Chinese Hamster ovary cell line DXB1 as described below.

In another approach, a catalytically inactive form of MASP-2 is constructed using the method described in Chen et al., *J. Biol. Chem.*, 276(28):25894-25902, 2001. Briefly, the plasmid containing the full-length human MASP-2 cDNA (described in Thiel et al., *Nature* 386:506, 1997) is digested with Xho1 and EcoR1 and the MASP-2 cDNA (described herein as SEQ ID NO:4) is cloned into the corresponding restriction sites of the pFastBac1 baculovirus transfer vector (Life Technologies, NY). The MASP-2 serine protease active site at Ser618 is then altered to Ala618 by substituting the double-stranded oligonucleotides encoding the peptide region amino acid 610-625 (SEQ ID NO:13) with the native region amino acids 610 to 625 to create a MASP-2 full length polypeptide with an inactive protease domain. Construction of Expression Plasmids Containing Polypeptide Regions Derived from Human Masp-2.

The following constructs are produced using the MASP-2 signal peptide (residues 1-15 of SEQ ID NO:5) to secrete various domains of MASP-2. A construct expressing the human MASP-2 CUBI domain (SEQ ID NO:8) is made by PCR amplifying the region encoding residues 1-121 of MASP-2 (SEQ ID NO:6) (corresponding to the N-terminal CUB1 domain). A construct expressing the human MASP-2 CUBIEGF domain (SEQ ID NO:9) is made by PCR amplifying the region encoding residues 1-166 of MASP-2 (SEQ ID NO:6) (corresponding to the N-terminal CUB 1EGF domain). A construct expressing the human MASP-2 CUBIEGFCUBII domain (SEQ ID NO:10) is made by PCR amplifying the region encoding residues 1-293 of MASP-2 (SEQ ID NO:6) (corresponding to the N-terminal CUBIEGFCUBII domain). The above mentioned domains are amplified by PCR using VentR polymerase and pBS-MASP-2 as a template, according to established PCR methods. The 5' primer sequence of the sense primer (5'-CGG-GATCCATGAGGCTGCTGACCCTC-3' SEQ ID NO:34) introduces a BamHI restriction site (underlined) at the 5' end of the PCR products. Antisense primers for each of the MASP-2 domains, shown below in TABLE 5, are designed to introduce a stop codon (boldface) followed by an EcoRI site (underlined) at the end of each PCR product. Once amplified, the DNA fragments are digested with BamHI and EcoRI and cloned into the corresponding sites of the pFast-Bac1 vector. The resulting constructs are characterized by restriction mapping and confirmed by dsDNA sequencing.

TABLE 5

MASP-2 PCR PRIMERS

| MASP-2 domain | 5' PCR Primer | 3' PCR Primer |
|---|---|---|
| SEQ ID NO: 8<br>CUBI<br>(aa 1-121 of<br>SEQ ID NO: 6) | 5'CGGGATCCATG<br>AGGCTGCTGACCC<br>TC-3'<br>(SEQ ID NO: 34) | 5'GGAATTCCTAG<br>GCTGCATA<br>(SEQ ID NO: 35) |
| SEQ ID NO: 9<br>CUBIEGF<br>(aa 1-166 of<br>SEQ ID NO: 6) | 5'CGGGATCCATG<br>AGGCTGCTGACCC<br>TC-3'<br>(SEQ ID NO: 34) | 5'GGAATTCCTAC<br>AGGGCGCT-3'<br>(SEQ ID NO: 36) |
| SEQ ID NO: 10<br>CUBIEGFCUBII<br>(aa 1-293 of<br>SEQ ID NO: 6) | 5'CGGGATCCATG<br>AGGCTGCTGACCC<br>TC-3'<br>(SEQ ID NO: 34) | 5'GGAATTCCTAG<br>TAGTGGAT 3'<br>(SEQ ID NO: 37) |
| SEQ ID NO: 4<br>human MASP-2 | 5'ATGAGGCTGCT<br>GACCCTCCTGGGC<br>CTTC 3'<br>(SEQ ID NO: 56)<br>hMASP-2_forward | 5'TTAAAATCACT<br>AATTATGTTCTCG<br>ATC 3'<br>(SEQ ID NO: 59)<br>hMASP-2_reverse |
| SEQ ID NO: 4<br>human MASP-2<br>cDNA | 5'CAGAGGTGACGC<br>AGGAGGGGCAC 3'<br>(SEQ ID NO: 58)<br>hMASP-<br>2_ala_forward | 5'GTGCCCCTCCTG<br>CGTCACCTCTG 3'<br>(SEQ ID NO: 57)<br>hMASP-<br>2_ala_reverse |
| SEQ ID NO: 50<br>Murine MASP-2<br>cDNA | 5'ATGAGGCTACTC<br>ATCTTCCTGG3'<br>(SEQ ID NO: 60)<br>mMASP-2 forward | 5'TTAGAAATTACT<br>TATTATGTTCTCAA<br>TCC3'<br>(SEQ ID NO: 63)<br>mMASP-2_reverse |

TABLE 5-continued

MASP-2 PCR PRIMERS

| MASP-2 domain | 5' PCR Primer | 3' PCR Primer |
|---|---|---|
| SEQ ID NO: 50 Murine MASP-2 cDNA | 5'CCCCCCCTGCGT CACCTCTGCAG3' (SEQ ID NO: 62) mMASP-2_ala_forward | 5'CTGCAGAGGTGA CGCAGGGGGGG 3' (SEQ ID NO: 61) mMASP-2_ala_reverse |

Recombinant Eukaryotic Expression of MASP-2 and Protein Production of Enzymatically Inactive Mouse, Rat, and Human MASP-2A.

The MASP-2 and MASP-2A expression constructs described above were transfected into DXB1 cells using the standard calcium phosphate transfection procedure (Maniatis et al., 1989). MASP-2A was produced in serum-free medium to ensure that preparations were not contaminated with other serum proteins. Media was harvested from confluent cells every second day (four times in total). The level of recombinant MASP-2A averaged approximately 1.5 mg/liter of culture medium for each of the three species.

MASP-2A protein purification: The MASP-2A (Ser-Ala mutant described above) was purified by affinity chromatography on MBP-A-agarose columns. This strategy enabled rapid purification without the use of extraneous tags. MASP-2A (100-200 ml of medium diluted with an equal volume of loading buffer (50 mM Tris-Cl, pH 7.5, containing 150 mM NaCl and 25 mM CaCl$_2$) was loaded onto an MBP-agarose affinity column (4 ml) pre-equilibrated with 10 ml of loading buffer. Following washing with a further 10 ml of loading buffer, protein was eluted in 1 ml fractions with 50 mM Tris-Cl, pH 7.5, containing 1.25 M NaCl and 10 mM EDTA. Fractions containing the MASP-2A were identified by SDS-polyacrylamide gel electrophoresis. Where necessary, MASP-2A was purified further by ion-exchange chromatography on a MonoQ column (HR 5/5). Protein was dialysed with 50 mM Tris-Cl pH 7.5, containing 50 mM NaCl and loaded onto the column equilibrated in the same buffer. Following washing, bound MASP-2A was eluted with a 0.05-1 M NaCl gradient over 10 ml.

Results: Yields of 0.25-0.5 mg of MASP-2A protein were obtained from 200 ml of medium. The molecular mass of 77.5 kDa determined by MALDI-MS is greater than the calculated value of the unmodified polypeptide (73.5 kDa) due to glycosylation. Attachment of glycans at each of the N-glycosylation sites accounts for the observed mass. MASP-2A migrates as a single band on SDS-polyacrylamide gels, demonstrating that it is not proteolytically processed during biosynthesis. The weight-average molecular mass determined by equilibrium ultracentrifugation is in agreement with the calculated value for homodimers of the glycosylated polypeptide.

Production of Recombinant Human MASP-2 Polypeptides

Another method for producing recombinant MASP-2 and MASP2A derived polypeptides is described in Thielens, N. M., et al., *J. Immunol.* 166:5068-5077, 2001. Briefly, the *Spodoptera frugiperda* insect cells (Ready-Plaque Sf9 cells obtained from Novagen, Madison, Wis.) are grown and maintained in SP900II serum-free medium (Life Technologies) supplemented with 50 IU/ml penicillin and 50 mg/ml streptomycin (Life Technologies). The *Trichoplusia ni* (High Five) insect cells (provided by Jadwiga Chroboczek, Institut de Biologie Structurale, Grenoble, France) are maintained in TC100 medium (Life Technologies) containing 10% FCS (Dominique Dutscher, Brumath, France) supplemented with 50 IU/ml penicillin and 50 mg/ml streptomycin. Recombinant baculoviruses are generated using the Bac-to-Bac system (Life Technologies). The bacmid DNA is purified using the Qiagen midiprep purification system (Qiagen) and is used to transfect Sf9 insect cells using cellfectin in Sf900 II SFM medium (Life Technologies) as described in the manufacturer's protocol. Recombinant virus particles are collected 4 days later, titrated by virus plaque assay, and amplified as described by King and Possee, in *The Baculovirus Expression System: A Laboratory Guide*, Chapman and Hall Ltd., London, pp. 111-114, 1992.

High Five cells ($1.75 \times 10^7$ cells/175-cm$^2$ tissue culture flask) are infected with the recombinant viruses containing MASP-2 polypeptides at a multiplicity of infection of 2 in Sf900 II SFM medium at 28° C. for 96 h. The supernatants are collected by centrifugation and diisopropyl phosphorofluoridate is added to a final concentration of 1 mM.

The MASP-2 polypeptides are secreted in the culture medium. The culture supernatants are dialyzed against 50 mM NaCl, 1 mM CaCl$_2$, 50 mM triethanolamine hydrochloride, pH 8.1, and loaded at 1.5 ml/min onto a Q-Sepharose Fast Flow column (Amersham Pharmacia Biotech) (2.8×12 cm) equilibrated in the same buffer. Elution is conducted by applying a1.2 liter linear gradient to 350 mM NaCl in the same buffer. Fractions containing the recombinant MASP-2 polypeptides are identified by Western blot analysis, precipitated by addition of (NH$_4$)$_2$SO$_4$ to 60% (w/v), and left overnight at 4° C. The pellets are resuspended in 145 mM NaCl, 1 mM CaCl2, 50 mM triethanolamine hydrochloride, pH 7.4, and applied onto a TSK G3000 SWG column (7.5×600 mm) (Tosohaas, Montgomeryville, Pa.) equilibrated in the same buffer. The purified polypeptides are then concentrated to 0.3 mg/ml by ultrafiltration on Microsep microconcentrators (m.w. cut-off=10,000) (Filtron, Karl stein, Germany).

Example 6

This example describes a method of producing polyclonal antibodies against MASP-2 polypeptides.

Materials and Methods:

MASP-2 Antigens: Polyclonal anti-human MASP-2 antiserum is produced by immunizing rabbits with the following isolated MASP-2 polypeptides: human MASP-2 (SEQ ID NO:6) isolated from serum as described in Example 4; recombinant human MASP-2 (SEQ ID NO:6), MASP-2A containing the inactive protease domain (SEQ ID NO:13), as described in Examples 4-5; and recombinant CUBI (SEQ ID NO:8), CUBEGFI (SEQ ID NO:9), and CUBEGFCUBII (SEQ ID NO:10) expressed as described above in Example 5.

Polyclonal antibodies: Six-week old Rabbits, primed with BCG (bacillus Calmette-Guerin vaccine) are immunized by injecting 100 µg of MASP-2 polypeptide at 100 µg/ml in sterile saline solution. Injections are done every 4 weeks, with antibody titer monitored by ELISA assay as described in Example 7. Culture supernatants are collected for antibody purification by protein A affinity chromatography.

Example 7

This example describes a method for producing murine monoclonal antibodies against rat or human MASP-2 polypeptides.

Materials and Methods:

Male A1J mice (Harlan, Houston, Tex.), 8-12 weeks old, are injected subcutaneously with 100 μg human or rat rMASP-2 or rMASP-2A polypeptides (made as described in Example 4 or Example 5) in complete Freund's adjuvant (Difco Laboratories, Detroit, Mich.) in 200 μl of phosphate buffered saline (PBS) pH 7.4. At two-week intervals the mice are twice injected subcutaneously with 50 μg of human or rat rMASP-2 or rMASP-2A polypeptide in incomplete Freund's adjuvant. On the fourth week the mice are injected with 50 μg of human or rat rMASP-2 or rMASP-2A polypeptide in PBS and are fused 4 days later.

For each fusion, single cell suspensions are prepared from the spleen of an immunized mouse and used for fusion with Sp2/0 myeloma cells. $5 \times 10^8$ of the Sp2/0 and $5 \times 10^8$ spleen cells are fused in a medium containing 50% polyethylene glycol (M.W. 1450) (Kodak, Rochester, N.Y.) and 5% dimethylsulfoxide (Sigma Chemical Co., St. Louis, Mo.). The cells are then adjusted to a concentration of $1.5 \times 10^5$ spleen cells per 200 μl of the suspension in Iscove medium (Gibco, Grand Island, N.Y.), supplemented with 10% fetal bovine serum, 100 units/ml of penicillin, 100 μg/ml of streptomycin, 0.1 mM hypoxanthine, 0.4 μM aminopterin and 16 μM thymidine. Two hundred microliters of the cell suspension are added to each well of about twenty 96-well microculture plates. After about ten days culture supernatants are withdrawn for screening for reactivity with purified factor MASP-2 in an ELISA assay.

ELISA Assay: Wells of Immulon 2 (Dynatech Laboratories, Chantilly, Va.) microtest plates are coated by adding 50 μl of purified hMASP-2 at 50 ng/ml or rat rMASP-2 (or rMASP-2A) overnight at room temperature. The low concentration of MASP-2 for coating enables the selection of high-affinity antibodies. After the coating solution is removed by flicking the plate, 200 μl of BLOTTO (non-fat dry milk) in PBS is added to each well for one hour to block the non-specific sites. An hour later, the wells are then washed with a buffer PBST (PBS containing 0.05% Tween 20). Fifty microliters of culture supernatants from each fusion well is collected and mixed with 50 μl of BLOTTO and then added to the individual wells of the microtest plates. After one hour of incubation, the wells are washed with PBST. The bound murine antibodies are then detected by reaction with horseradish peroxidase (HRP) conjugated goat anti-mouse IgG (Fc specific) (Jackson ImmunoResearch Laboratories, West Grove, Pa.) and diluted at 1:2,000 in BLOTTO. Peroxidase substrate solution containing 0.1% 3,3,5,5 tetramethyl benzidine (Sigma, St. Louis, Mo.) and 0.0003% hydrogen peroxide (Sigma) is added to the wells for color development for 30 minutes. The reaction is terminated by addition of 50 μl of 2M $H_2SO_4$ per well. The Optical Density at 450 nm of the reaction mixture is read with a BioTek ELISA Reader (BioTek Instruments, Winooski, Vt.).

MASP-2 Binding Assay:

Culture supernatants that test positive in the MASP-2 ELISA assay described above can be tested in a binding assay to determine the binding affinity the MASP-2 inhibitory agents have for MASP-2. A similar assay can also be used to determine if the inhibitory agents bind to other antigens in the complement system.

Polystyrene microtiter plate wells (96-well medium binding plates, Corning Costar, Cambridge, Mass.) are coated with MASP-2 (20 ng/100 μl/well, Advanced Research Technology, San Diego, Calif.) in phosphate-buffered saline (PBS) pH 7.4 overnight at 4° C. After aspirating the MASP-2 solution, wells are blocked with PBS containing 1% bovine serum albumin (BSA; Sigma Chemical) for 2 h at room temperature. Wells without MASP-2 coating serve as the background controls. Aliquots of hybridoma supernatants or purified anti-MASP-2 MoAbs, at varying concentrations in blocking solution, are added to the wells. Following a 2 h incubation at room temperature, the wells are extensively rinsed with PBS. MASP-2-bound anti-MASP-2 MoAb is detected by the addition of peroxidase-conjugated goat anti-mouse IgG (Sigma Chemical) in blocking solution, which is allowed to incubate for 1 h at room temperature. The plate is rinsed again thoroughly with PBS, and 100 μl of 3,3',5,5'-tetramethyl benzidine (TMB) substrate (Kirkegaard and Perry Laboratories, Gaithersburg, Md.) is added. The reaction of TMB is quenched by the addition of 100 μl of 1M phosphoric acid, and the plate is read at 450 nm in a microplate reader (SPECTRA MAX 250, Molecular Devices, Sunnyvale, Calif.).

The culture supernatants from the positive wells are then tested for the ability to inhibit complement activation in a functional assay such as the C4 cleavage assay as described in Example 2. The cells in positive wells are then cloned by limiting dilution. The MoAbs are tested again for reactivity with hMASP-2 in an ELISA assay as described above. The selected hybridomas are grown in spinner flasks and the spent culture supernatant collected for antibody purification by protein A affinity chromatography.

Example 8

This example describes the generation of a MASP-2−/− knockout mouse expressing human MASP-2 for use as a model in which to screen for MASP-2 inhibitory agents.

Materials and Methods: A MASP-2−/− mouse as described in Example 1 and a MASP-2−/− mouse expressing a human MASP-2 transgene construct (human MASP-2 knock-in) as described in Example 3 are crossed, and progeny that are murine MASP-2−/−, murine MAp19+, human MASP-2+ are used to identify human MASP-2 inhibitory agents.

Such animal models can be used as test substrates for the identification and efficacy of MASP-2 inhibitory agents such as human anti-MASP-2 antibodies, MASP-2 inhibitory peptides and nonpeptides, and compositions comprising MASP-2 inhibitory agents. For example, the animal model is exposed to a compound or agent that is known to trigger MASP-2-dependent complement activation, and a MASP-2 inhibitory agent is administered to the animal model at a sufficient time and concentration to elicit a reduction of disease symptoms in the exposed animal.

In addition, the murine MASP-2−/−, MAp19+, human MASP-2+ mice may be used to generate cell lines containing one or more cell types involved in a MASP-2-associated disease which can be used as a cell culture model for that disorder. The generation of continuous cell lines from transgenic animals is well known in the art, for example see Small, J. A., et al., *Mol. Cell Biol.*, 5:642-48, 1985.

Example 9

This example describes a method of producing human antibodies against human MASP-2 in a MASP-2 knockout mouse that expresses human MASP-2 and human immunoglobulins.

Materials and Methods:

A MASP-2−/− mouse was generated as described in Example 1. A mouse was then constructed that expresses human MASP-2 as described in Example 3. A homozygous MASP-2−/− mouse and a MASP-2−/− mouse expressing human MASP-2 are each crossed with a mouse derived from an embryonic stem cell line engineered to contain targeted disruptions of the endogenous immunoglobulin heavy chain and light chain loci and expression of at least a segment of the human immunoglobulin locus. Preferably, the segment of the human immunoglobulin locus includes unrearranged sequences of heavy and light chain components. Both inactivation of endogenous immunoglobulin genes and introduction of exogenous immunoglobulin genes can be achieved by targeted homologous recombination. The transgenic mammals resulting from this process are capable of functionally rearranging the immunoglobulin component sequences and expressing a repertoire of antibodies of various isotypes encoded by human immunoglobulin genes, without expressing endogenous immunoglobulin genes. The production and properties of mammals having these properties is described, for example see Thomson, A. D., *Nature* 148:1547-1553, 1994, and Sloane, B. F., *Nature Biotechnology* 14:826, 1996. Genetically engineered strains of mice in which the mouse antibody genes are inactivated and functionally replaced with human antibody genes is commercially available (e.g., XenoMouse®, available from Abgenix, Fremont Calif.). The resulting offspring mice are capable of producing human MoAb against human MASP-2 that are suitable for use in human therapy.

Example 10

This example describes the generation and production of humanized murine anti-MASP-2 antibodies and antibody fragments.

A murine anti-MASP-2 monoclonal antibody is generated in Male A/J mice as described in Example 7. The murine antibody is then humanized as described below to reduce its immunogenicity by replacing the murine constant regions with their human counterparts to generate a chimeric IgG and Fab fragment of the antibody, which is useful for inhibiting the adverse effects of MASP-2-dependent complement activation in human subjects in accordance with the present invention.

1. Cloning of anti-MASP-2 variable region genes from murine hybridoma cells. Total RNA is isolated from the hybridoma cells secreting anti-MASP-2 MoAb (obtained as described in Example 7) using RNAzol following the manufacturer's protocol (Biotech, Houston, Tex.). First strand cDNA is synthesized from the total RNA using oligo dT as the primer. PCR is performed using the immunoglobulin constant C region-derived 3' primers and degenerate primer sets derived from the leader peptide or the first framework region of murine $V_H$ or $V_K$ genes as the 5' primers. Anchored PCR is carried out as described by Chen and Platsucas (Chen, P. F., *Scand. J. Immunol.* 35:539-549, 1992). For cloning the $V_K$ gene, double-stranded cDNA is prepared using a NotI-MAK1 primer (5'-TGCGGCCGCTGTAGGTGCTGTCTTT-3' SEQ ID NO:38). Annealed adaptors AD1 (5'-GGAATTCACTCGT-TATTCTCGGA-3' SEQ ID NO:39) and AD2 (5'-TCCGAGAATAACGAGTG-3' SEQ ID NO:40) are ligated to both 5' and 3' termini of the double-stranded cDNA. Adaptors at the 3' ends are removed by NotI digestion. The digested product is then used as the template in PCR with the AD1 oligonucleotide as the 5' primer and MAK2 (5'-CAT-TGAAAGCTTTGGGGTAGAAGTTGTTC-3' SEQ ID NO:41) as the 3' primer. DNA fragments of approximately 500 bp are cloned into pUC19. Several clones are selected for sequence analysis to verify that the cloned sequence encompasses the expected murine immunoglobulin constant region. The NotI-MAK1 and MAK2 oligonucleotides are derived from the $V_K$ region and are 182 and 84 bp, respectively, downstream from the first base pair of the C kappa gene. Clones are chosen that include the complete $V_K$ and leader peptide.

For cloning the $V_H$ gene, double-stranded cDNA is prepared using the Not1 MAG1 primer (5'-CGCGGCCGCAGCTGCTCAGAGTGTAGA-3' SEQ ID NO:42). Annealed adaptors AD1 and AD2 are ligated to both 5' and 3' termini of the double-stranded cDNA. Adaptors at the 3' ends are removed by NotI digestion. The digested product are used as the template in PCR with the AD1 oligonucleotide and MAG2 (5'-CGGTAAGCTT-CACTGGCTCAGGGAAATA-3' SEQ ID NO:43) as primers. DNA fragments of 500 to 600 bp in length are cloned into pUC19. The NotI-MAG1 and MAG2 oligonucleotides are derived from the murine Cγ.7.1 region, and are 180 and 93 bp, respectively, downstream from the first bp of the murine Cγ.7.1 gene. Clones are chosen that encompass the complete $V_H$ and leader peptide.

2. Construction of Expression Vectors for Chimeric MASP-2 IgG and Fab. The cloned $V_H$ and $V_K$ genes described above are used as templates in a PCR reaction to add the Kozak consensus sequence to the 5' end and the splice donor to the 3' end of the nucleotide sequence. After the sequences are analyzed to confirm the absence of PCR errors, the $V_H$ and $V_K$ genes are inserted into expression vector cassettes containing human C.γ1 and C. kappa respectively, to give pSV2neoV$_H$-huCγ1 and pSV2neoV-huCγ. CsCl gradient-purified plasmid DNAs of the heavy- and light-chain vectors are used to transfect COS cells by electroporation. After 48 hours, the culture supernatant is tested by ELISA to confirm the presence of approximately 200 ng/ml of chimeric IgG. The cells are harvested and total RNA is prepared. First strand cDNA is synthesized from the total RNA using oligo dT as the primer. This cDNA is used as the template in PCR to generate the Fd and kappa DNA fragments. For the Fd gene, PCR is carried out using 5'-AAGAAGCTTGCCGCCACCATGGATTGGCTGTG-GAACT-3' (SEQ ID NO:44) as the 5' primer and a CH1-derived 3' primer (5'-CGGGATCCTCAAACTTTCTTGTC-CACCTTGG-3' SEQ ID NO:45). The DNA sequence is confirmed to contain the complete $V_H$ and the CH1 domain of human IgG1. After digestion with the proper enzymes, the Fd DNA fragments are inserted at the HindIII and BamHI restriction sites of the expression vector cassette pSV2dhfr-TUS to give pSV2dhfrFd. The pSV2 plasmid is commercially available and consists of DNA segments from various sources: pBR322 DNA (thin line) contains the pBR322 origin of DNA replication (pBR ori) and the lactamase ampicillin resistance gene (Amp); SV40 DNA, represented by wider hatching and marked, contains the SV40 origin of DNA replication (SV40 ori), early promoter (5' to the dhfr and neo genes), and polyadenylation signal (3' to the dhfr and neo genes). The SV40-derived polyadenylation signal (pA) is also placed at the 3' end of the Fd gene.

For the kappa gene, PCR is carried out using 5'-AAGAAAGCTTGCCGCCACCATGTTCT-CACTAGCTCT-3' (SEQ ID NO:46) as the 5' primer and a $C_K$-derived 3' primer (5'-CGG-GATCCTTCTCCCTCTAACACTCT-3' SEQ ID NO:47). DNA sequence is confirmed to contain the complete $V_K$ and human $C_K$ regions. After digestion with proper restriction enzymes, the kappa DNA fragments are inserted at the HindIII and BamHI restriction sites of the expression vector cassette pSV2neo-TUS to give pSV2neoK. The expression of both Fd and .kappa genes are driven by the HCMV-derived enhancer and promoter elements. Since the Fd gene does not include the cysteine amino acid residue involved in the inter-chain disulfide bond, this recombinant chimeric Fab contains non-covalently linked heavy- and light-chains. This chimeric Fab is designated as cFab.

To obtain recombinant Fab with an inter-heavy and light chain disulfide bond, the above Fd gene may be extended to include the coding sequence for additional 9 amino acids (EPKSCDKTH SEQ ID NO:48) from the hinge region of human IgG1. The BstEII-BamHI DNA segment encoding 30 amino acids at the 3' end of the Fd gene may be replaced with DNA segments encoding the extended Fd, resulting in pSV2dhfrFd/9aa.

3. Expression and Purification of Chimeric Anti-MASP-2 IgG

To generate cell lines secreting chimeric anti-MASP-2 IgG, NSO cells are transfected with purified plasmid DNAs of pSV2neoV$_H$-huC.γ1 and pSV2neoV-huC kappa by electroporation. Transfected cells are selected in the presence of 0.7 mg/ml G418. Cells are grown in a 250 ml spinner flask using serum-containing medium.

Culture supernatant of 100 ml spinner culture is loaded on a 10-ml PROSEP-A column (Bioprocessing, Inc., Princeton, N.J.). The column is washed with 10 bed volumes of PBS. The bound antibody is eluted with 50 mM citrate buffer, pH 3.0. Equal volume of 1 M Hepes, pH 8.0 is added to the fraction containing the purified antibody to adjust the pH to 7.0. Residual salts are removed by buffer exchange with PBS by Millipore membrane ultrafiltration (M.W. cut-off: 3,000). The protein concentration of the purified antibody is determined by the BCA method (Pierce).

4. Expression and Purification of Chimeric Anti-MASP-2 Fab

To generate cell lines secreting chimeric anti-MASP-2 Fab, CHO cells are transfected with purified plasmid DNAs of pSV2dhfrFd (or pSV2dhfrFd/9aa) and pSV2neokappa, by electroporation. Transfected cells are selected in the presence of G418 and methotrexate. Selected cell lines are amplified in increasing concentrations of methotrexate. Cells are single-cell subcloned by limiting dilution. High-producing single-cell subcloned cell lines are then grown in 100 ml spinner culture using serum-free medium.

Chimeric anti-MASP-2 Fab is purified by affinity chromatography using a mouse anti-idiotypic MoAb to the MASP-2 MoAb. An anti-idiotypic MASP-2 MoAb can be made by immunizing mice with a murine anti-MASP-2 MoAb conjugated with keyhole limpet hemocyanin (KLH) and screening for specific MoAb binding that can be competed with human MASP-2. For purification, 100 ml of supernatant from spinner cultures of CHO cells producing cFab or cFab/9aa are loaded onto the affinity column coupled with an anti-idiotype MASP-2 MoAb. The column is then washed thoroughly with PBS before the bound Fab is eluted with 50 mM diethylamine, pH 11.5. Residual salts are removed by buffer exchange as described above. The protein concentration of the purified Fab is determined by the BCA method (Pierce).

The ability of the chimeric MASP-2 IgG, cFab, and cFAb/9aa to inhibit MASP-2-dependent complement pathways may be determined by using the inhibitory assays described in Example 2.

Example 11

This example describes an in vitro C4 cleavage assay used as a functional screen to identify MASP-2 inhibitory agents capable of blocking MASP-2-dependent complement activation via L-ficolin/P35, H-ficolin, M-ficolin or mannan.

C4 Cleavage Assay: A C4 cleavage assay has been described by Petersen, S. V., et al., *J. Immunol. Methods* 257:107, 2001, which measures lectin pathway activation resulting from lipoteichoic acid (LTA) from *S. aureus* which binds L-ficolin.

Reagents: Formalin-fixed *S. aureous* (DSM20233) is prepared as follows: bacteria is grown overnight at 37° C. in tryptic soy blood medium, washed three times with PBS, then fixed for 1 h at room temperature in PBS/0.5% formalin, and washed a further three times with PBS, before being resuspended in coating buffer (15 mM $Na_2Co_3$, 35 mM $NaHCO_3$, pH 9.6).

Assay: The wells of a Nunc Maxi Sorb microtiter plate (Nalgene Nunc International, Rochester, N.Y.) are coated with: 100 μl of formalin-fixed *S. aureus* DSM20233 ($OD_{550}$=0.5) in coating buffer with 1 ug of L-ficolin in coating buffer. After overnight incubation, wells are blocked with 0.1% human serum albumin (HSA) in TBS (10 mM Tris-HCl, 140 mM NaCl, pH 7.4), then are washed with TBS containing 0.05% Tween 20 and 5 mM $CaCl_2$ (wash buffer). Human serum samples are diluted in 20 mM Tris-HCl, 1 M NaCl, 10 mM $CaCl_2$, 0.05% Triton X-100, 0.1% HSA, pH 7.4, which prevents activation of endogenous C4 and dissociates the C1 complex (composed of C1q, C1r and C1s). MASP-2 inhibitory agents, including anti-MASP-2 MoAbs and inhibitory peptides are added to the serum samples in varying concentrations. The diluted samples are added to the plate and incubated overnight at 4° C. After 24 hours, the plates are washed thoroughly with wash buffer, then 0.1 μg of purified human C4 (obtained as described in Dodds, A. W., *Methods Enzymol.* 223:46, 1993) in 100 μl of 4 mM barbital, 145 mM NaCl, 2 mM $CaCl_2$, 1 mM $MgCl_2$, pH 7.4 is added to each well. After 1.5 h at 37° C., the plates are washed again and C4b deposition is detected using alkaline phosphatase-conjugated chicken anti-human C4c (obtained from Immunsystem, Uppsala, Sweden) and measured using the colorimetric substrate ρ-nitrophenyl phosphate.

C4 Assay on mannan: The assay described above is adapted to measure lectin pathway activation via MBL by coating the plate with LSP and mannan prior to adding serum mixed with various MASP-2 inhibitory agents.

C4 assay on H-ficolin (Hakata Ag): The assay described above is adapted to measure lectin pathway activation via H-ficolin by coating the plate with LPS and H-ficolin prior to adding serum mixed with various MASP-2 inhibitory agents.

Example 12

The following assay demonstrates the presence of classical pathway activation in wild-type and MASP-2-/- mice.

Methods: Immune complexes were generated in situ by coating microtiter plates (Maxisorb, Nunc, cat. No. 442404, Fisher Scientific) with 0.1% human serum albumin in 10 mM Tris, 140 mM NaCl, pH 7.4 for 1 hours at room temperature followed by overnight incubation at 4° C. with sheep anti whole serum antiserum (Scottish Antibody Production Unit, Carluke, Scotland) diluted 1:1000 in TBS/tween/$Ca^{2+}$. Serum samples were obtained from wild-type and MASP-2-/- mice and added to the coated plates. Control samples were prepared in which C1q was depleted from wild-type and MASP-2-/- serum samples. C1q-depleted mouse serum was prepared using protein-A-coupled Dynabeads (Dynal Biotech, Oslo, Norway) coated with rabbit anti-human C1q IgG (Dako, Glostrup, Denmark), according to the supplier's instructions. The plates were incubated for 90 minutes at 37° C. Bound C3b was detected with a polyclonal anti-human-C3c Antibody (Dako A 062) diluted in TBS/tw/Ca$^{++}$ at 1:1000. The secondary antibody is goat anti-rabbit IgG.

Figure 9:
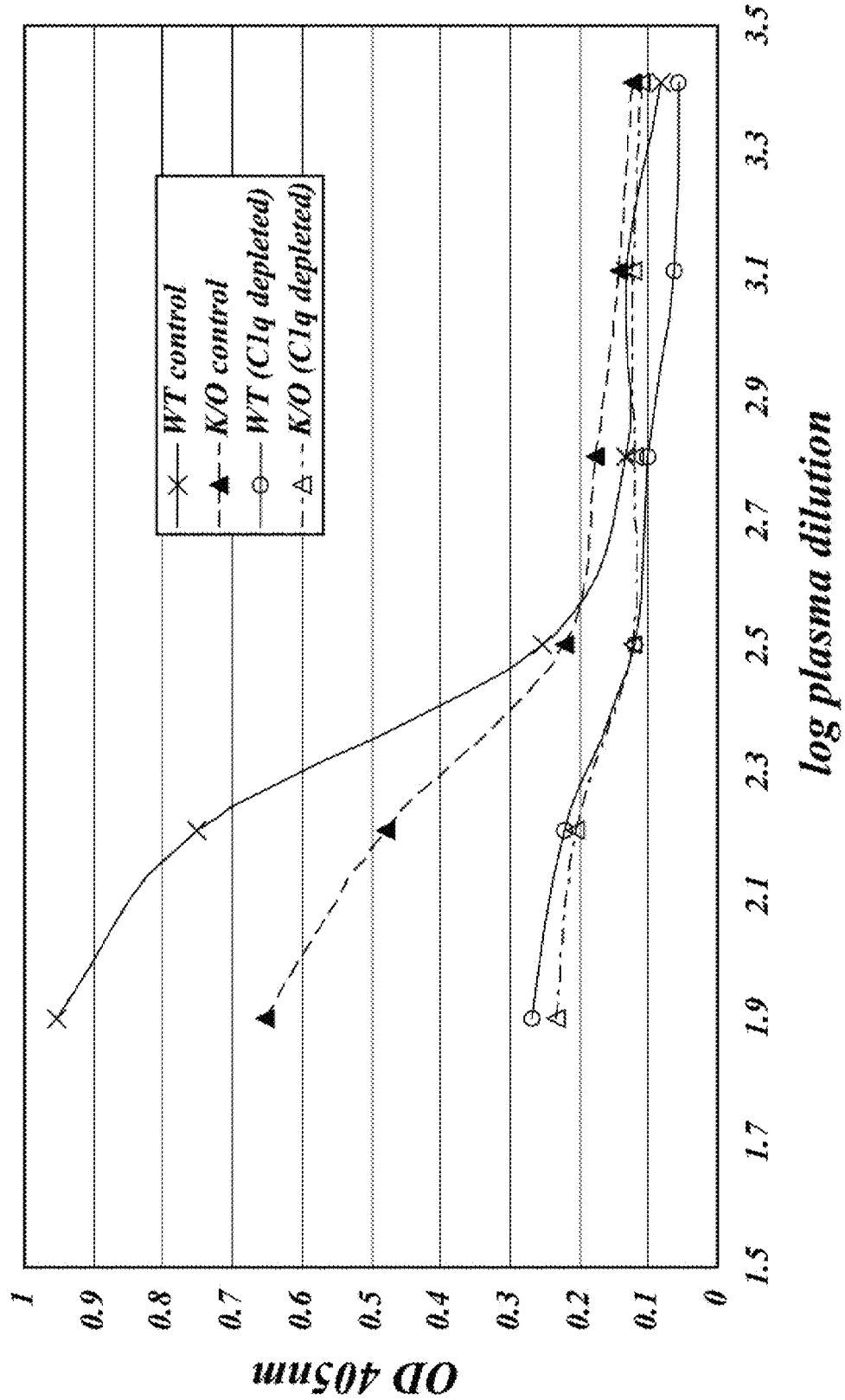
FIG. 9 presents results demonstrating that the classical pathway is functional in the MASP-2−/− strain.

Results: FIG. 9 shows the relative C3b deposition levels on plates coated with IgG in wild-type serum, MASP-2−/− serum, C1q-depleted wild-type and C1q-depleted MASP-2−/− serum. These results demonstrate that the classical pathway is intact in the MASP-2−/− mouse strain.

Example 13

The following assay is used to test whether a MASP-2 inhibitory agent blocks the classical pathway by analyzing the effect of a MASP-2 inhibitory agent under conditions in which the classical pathway is initiated by immune complexes.

Methods: To test the effect of a MASP-2 inhibitory agent on conditions of complement activation where the classical pathway is initiated by immune complexes, triplicate 50 µl samples containing 90% NHS are incubated at 37° C. in the presence of 10 µg/ml immune complex (IC) or PBS, and parallel triplicate samples (+/−IC) are also included which contain 200 nM anti-properdin monoclonal antibody during the 37° C. incubation. After a two hour incubation at 37° C., 13 mM EDTA is added to all samples to stop further complement activation and the samples are immediately cooled to 5° C. The samples are then stored at −70° C. prior to being assayed for complement activation products (C3a and sC5b-9) using ELISA kits (Quidel, Catalog Nos. A015 and A009) following the manufacturer's instructions.

Example 14

This example demonstrates that the lectin-dependent MASP-2 complement activation system is activated in the ischemia/reperfusion phase following abdominal aortic aneurysm repair.

Experimental Rationale and Design: Patients undergoing abdominal aortic aneurysm (AAA) repair are subject to an ischemia-reperfusion injury, which is largely mediated by complement activation. We investigated the role of the MASP-2-dependent lectin pathway of complement activation in ischemia-reperfusion injury in patients undergoing AAA repair. The consumption of mannan-binding lectin (MBL) in serum was used to measure the amount of MASP-2-dependent lectin pathway activation that occurred during reperfusion.

Patient Serum Sample Isolation: A total of 23 patients undergoing elective infrarenal AAA repair and 8 control patients undergoing major abdominal surgery were included in this study.

For the patients under going AAA repair, systemic blood samples were taken from each patient's radial artery (via an arterial line) at four defined time points during the procedure: time point 1: induction of anaesthesia; time point 2: just prior to aortic clamping; time point 3: just prior to aortic clamp removal; and time point 4: during reperfusion.

For the control patients undergoing major abdominal surgery, systemic blood samples were taken at induction of anaesthesia and at two hours after the start of the procedure.

Assay for levels of MBL: Each patient plasma sample was assayed for levels of mannan-binding lectin (MBL) using ELISA techniques.

Figure 10:
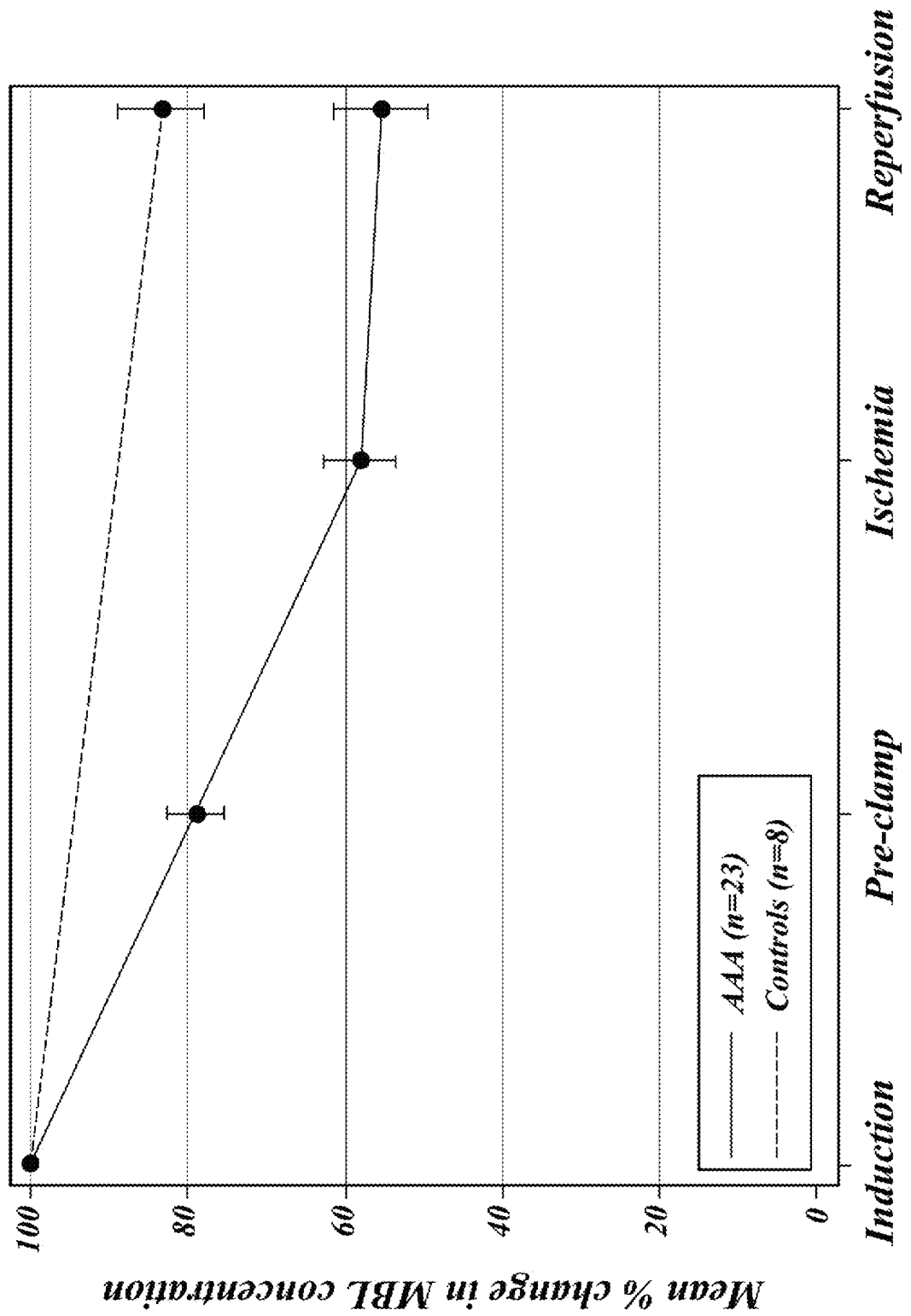
FIG. 10 presents results demonstrating that the MASP-2-dependent complement activation system is activated in the ischemia/reperfusion phase following abdominal aortic aneurysm repair.

Results: The results of this study are shown in FIG. 10, which presents a graph showing the mean percentage change in MBL levels (y axis) at each of the various time points (x axis). Starting values for MBL are 100%, with relative decreases shown thereafter. As shown in FIG. 10, AAA patients (n=23) show a significant decrease in plasma MBL levels, averaging an approximate 41% decrease at time of ischemia/reperfusion following AAA. In contrast, in control patients (n=8) undergoing major abdominal surgery only a minor consumption of MBL was observed in the plasma samples.

The data presented provides a strong indication that the MASP-2-dependent lectin pathway of the complement system is activated in the ischemia/reperfusion phase following AAA repair. The decrease in MBL levels appears to be associated with ischaemia-reperfusion injury because the MBL levels drop significantly and rapidly when the clamped major vessel is reperfused after the end of the operation. In contrast, control sera of patients undergoing major abdominal surgery without a major ischemia-reperfusion insult only show a slight decrease in MBL plasma levels. In view of the well-established contribution of complement activation in reperfusion injury, we conclude that activation of the MASP-2-dependent lectin pathway on ischemic endothelial cells is a major factor in the pathology of ischemia/reperfusion injury. Therefore, a specific transient blockade or reduction in the MASP-2-dependent lectin pathway of complement activation would be expected to have a significant beneficial therapeutic impact to improve the outcome of clinical procedures and diseases that involve a transient ischemic insult, e.g., myocardial infarction, gut infarction, burns, transplantation and stroke.

Example 15

This example describes the use of the MASP-2−/− strain as an animal model for testing MASP-2 inhibitory agents useful to treat Rheumatoid Arthritis.

Background and Rationale: Murine Arthritis Model: K/BxN T cell receptor (TCR) transgenic (tg) mice, is a recently developed model of inflammatory arthritis (Kouskoff, V., et al., *Cell* 87:811-822, 1996; Korganow, A. S., et al., *Immunity* 10:451-461, 1999; Matsumoto, I., et al., *Science* 286:1732-1735, 1999; Maccioni M. et al., *J. Exp. Med.* 195(8):1071-1077, 2002). The K/BxN mice spontaneously develop an autoimmune disease with most of the clinical, histological and immunological features of RA in humans (Ji, H., et al., *Immunity* 16:157-168, 2002). The murine disorder is joint specific, but is initiated then perpetuated by T, then B cell autoreactivity to glucose-6-phosphate isomerase ("GPI"), a ubiquitously expressed antigen. Further, transfer of serum (or purified anti-GPI Igs) from arthritic K/BxN mice into healthy animals provokes arthritis within several days. It has also been shown that polyclonal anti-GPI antibodies or a pool of anti-GPI monoclonal antibodies of the IgG1 isotype induce arthritis when injected into healthy recipients (Maccioni et al., 2002). The murine model is relevant to human RA, because serum from RA patients has also been found to contain anti-GPI antibodies, which is not found in normal individuals. A CS-deficient mouse was tested in this system and found to block the development of arthritis (Ji, H., et al., 2002, supra). There was also strong inhibition of arthritis in C3 null mice, implicating the alternative pathway, however, MBP-A null mice did develop arthritis. In mice however, the presence of MBP-C may compensate for the loss of MBP-A.

Based on the observations described herein that MASP-2 plays an essential role in the initiation of both the lectin and alternative pathways, the K/BxN arthritic model is useful to screen for MASP-2 inhibitory agents that are effective for use as a therapeutic agents to treat RA.

Methods: Serum from arthritic K/BxN mice is obtained at 60 days of age, pooled and injected (150-200 µl i.p.) into MASP-2−/− recipients (obtained as described in Example 1); and control littermates with or without MASP-2 inhibitory agents (MoAb, inhibitory peptides and the like as described herein) at days 0 and 2. A group of normal mice are also pretreated with a MASP-2 inhibitory agent for two days prior to receiving the injection of serum. A further group of mice receive an injection of serum at day 0, followed by a MASP-2 inhibitory agent at day 6. A clinical index is evaluated over time with one point scored for each affected paw, ½ point scored for a paw with only mild swelling. Ankle thickness is also measured by a caliper (thickness is defined as the difference from day 0 measurement).

Example 16

This example describes an assay for inhibition of complement-mediated tissue damage in an ex vivo model of rabbit hearts perfused with human plasma.

Background and Rationale: Activation of the complement system contributes to hyperacute rejection of xenografts. Previous studies have shown that hyperacute rejection can occur in the absence of anti-donor antibodies via activation of the alternative pathway (Johnston, P. S., et al., *Transplant Proc.* 23:877-879, 1991).

Methods: To determine whether isolated anti-MASP-2 inhibitory agents such as anti-MASP-2 antibodies obtained as described in Example 7 are able to inhibit complement pathway in tissue damage, the anti-MASP-2 MoAbs and antibody fragments may be tested using an ex vivo model in which isolated rabbit hearts are perfused with diluted human plasma. This model was previously shown to cause damage to the rabbit myocardium due to the activation of the alternative complement pathway (Gralinski, M. R., et al., *Immunopharmacology* 34:79-88, 1996).

Example 17

This example describes an assay that measures neutrophil activation which is useful as a measure of an effective dose of a MASP-2 inhibitory agent for the treatment of conditions associated with the lectin-dependent pathway in accordance with the methods of the invention.

Methods: A method for measuring neutrophil elastase has been described in Gupta-Bansal, R., et al., *Molecular Immunol.* 37:191-201, 2000. Briefly, the complex of elastase and serum a1-antitrypsin is measured with a two-site sandwich assay that utilizes antibodies against both elastase and $\alpha_1$-antitrypsin. Polystyrene microtiter plates are coated with a 1:500 dilution of anti-human elastase antibody (The Binding Site, Birmingham, UK) in PBS overnight at 4° C. After aspirating the antibody solution, wells are blocked with PBS containing 0.4% HAS for 2 h at room temperature. Aliquots (100 µl) of plasma samples that are treated with or without a MASP-2 inhibitory agent are added to the wells. Following a 2 h incubation at room temperature, the wells are extensively rinsed with PBS. Bound elastase-$\alpha_1$-antitrypsin complex is detected by the addition of a 1:500 dilution of peroxidase conjugated-$\alpha_1$-antitrypsin antibody in blocking solution that is allowed to incubate for 1 h at room temperature. After washing the plate with PBS, 100 µl aliquots of TMB substrate are added. The reaction of TMB is quenched by the addition of 100 µl of phosphoric acid, and the plate is read at 450 nm in a microplate reader.

Example 18

This example describes an animal model for testing MASP-2 inhibitory agents useful to treat myocardial ischemia/reperfusion.

Methods: A myocardial ischemia-reperfusion model has been described by Vakeva et al., *Circulation* 97:2259-2267, 1998, and Jordan et al., *Circulation* 104(12):1413-1418, 2001. The described model may be modified for use in MASP-2−/− and MASP-2+/+ mice as follows. Briefly, adult male mice are anesthetized. Jugular vein and trachea are cannulated and ventilation is maintained with 100% oxygen with a rodent ventilator adjusted to maintain exhaled $CO_2$ between 3.5% and 5%. A left thoracotomy is performed and a suture is placed 3 to 4 mm from the origin of the left coronary artery. Five minutes before ischemia, animals are given a MASP-2 inhibitory agent, such as anti-MASP-2 antibodies (e.g., in a dosage range of between 0.01 to 10 mg/kg). Ischemia is then initiated by tightening the suture around the coronary artery and maintained for 30 minutes, followed by four hours of reperfusion. Sham-operated animals are prepared identically without tightening the suture.

Analysis of Complement C3 Deposition: After reperfusion, samples for immunohistochemistry are obtained from the central region of the left ventricle, fixed and frozen at −80° C. until processed. Tissue sections are incubated with an HRP-conjugated goat anti-rat C3 antibody. Tissue sections are analyzed for the presence of C3 staining in the presence of anti-MASP-2 inhibitory agents as compared with sham-operated control animals and MASP-2−/− animals to identify MASP-2 inhibitory agents that reduce C3 deposition in vivo.

Example 19

This example describes the use of the MASP-2−/− strain as an animal model for testing MASP-2 inhibitory agents for the ability to protect transplanted tissue from ischemia/reperfusion injury.

Background/Rationale: It is known that ischemia/reperfusion injury occurs in a donor organ during transplantation. The extent of tissue damage is related to the length of ischemia and is mediated by complement, as demonstrated in various models of ischemia and through the use of complement inhibiting agents such as soluble receptor type 1 (CR1) (Weisman et al., *Science* 249:146-151, 1990; Mulligan et al., *J. Immunol.* 148:1479-1486, 1992; Pratt et al., *Am. J. Path.* 163(4):1457-1465, 2003). An animal model for transplantation has been described by Pratt et al., *Am. J. Path.* 163(4):1457-1465, which may be modified for use with the MASP-2−/− mouse model and/or for use as a MASP-2+/+ model system in which to screen MASP-2 inhibitory agents for the ability to protect transplanted tissue from ischemia/reperfusion injury. The flushing of the donor kidney with perfusion fluid prior to transplantation provides an opportunity to introduce anti-MASP-2 inhibitory agents into the donor kidney.

Methods: MASP-2−/− and/or MASP-2+/+ mice are anesthetized. The left donor kidney is dissected and the aorta is ligated cephalad and caudad to the renal artery. A portex tube catheter (Portex Ltd, Hythe, UK) is inserted between the ligatures and the kidney is perfused with 5 ml of Soltran Kidney Perfusion Solution (Baxter Health Care, UK) containing MASP-2 inhibitory agents such as anti-MASP-2 monoclonal antibodies (in a dosage range of from 0.01 mg/kg to 10 mg/kg) for a period of at least 5 minutes. Renal transplantation is then performed and the mice are monitored over time.

Analysis of Transplant Recipients: Kidney transplants are harvested at various time intervals and tissue sections are analyzed using anti-C3 to determine the extent of C3 deposition.

Example 20

This example describes the use of a collagen-induced arthritis (CIA) animal model for testing MASP-2 inhibitory agents useful to treat rheumatoid arthritis (RA).

Background and Rationale: Collagen-induced arthritis (CIA) represents an autoimmune polyarthritis inducible in susceptible strains of rodents and primates after immunization with native type II collagen and is recognized as a relevant model for human rheumatoid arthritis (RA) (see Courtney et al., *Nature* 283:666 (1980); Trenthan et al., *J. Exp. Med.* 146:857 (1977)). Both RA and CIA are characterized by joint inflammation, pannus formation and cartilage and bone erosion. The CIA susceptible murine strain DBA/1LacJ is a developed model of CIA in which mice develop clinically severe arthritis after immunization with Bovine type II collagen (Wang et al., *J. Immunol.* 164:4340-4347 (2000). A C5-deficient mouse strain was crossed with DBA/1LacJ and the resulting strain was found to be resistant to the development of CIA arthritis (Wang et al., 2000, supra).

Based on the observations described herein that MASP-2 plays an essential role in the initiation of both the lectin and alternative pathways, the CIA arthritic model is useful to screen for MASP-2 inhibitory agents that are effective for use as therapeutic agents to treat RA.

Methods: A MASP-2-/- mouse is generated as described in Example 1. The MASP-2-/- mouse is then crossed with a mouse derived from the DBA/1LacJ strain (The Jackson Laboratory). F1 and subsequent offspring are intercrossed to produce homozygous MASP-2-/- in the DBA/1LacJ line.

Collagen immunization is carried out as described in Wang et al., 2000, supra. Briefly, wild-type DBA/1LacJ mice and MASP-2-/- DBA/1LacJ mice are immunized with Bovine type II collagen (BCII) or mouse type II collagen (MCII) (obtained from Elastin Products, Owensville, Mo.), dissolved in 0.01 M acetic acid at a concentration of 4 mg/ml. Each mouse is injected intradermally at the base of the tail with 200 ug CII and 100 ug mycobacteria. Mice are re-immunized after 21 days and are examined daily for the appearance of arthritis. An arthritic index is evaluated over time with respect to the severity of arthritis in each affected paw.

MASP-2 inhibitory agents are screened in the wild-type DBA/1LacJ CIA mice by injecting a MASP-2 inhibitory agent such as anti-MASP-2 monoclonal antibodies (in a dosage range of from 0.01 mg/kg to 10 mg/kg) at the time of collagen immunization, either systemically, or locally at one or more joints and an arthritic index is evaluated over time as described above. Anti-hMASP-2 monoclonal antibodies as therapeutic agents can be easily evaluated in a MASP-2-/-, hMASP-+/+ knock-in DBA/1LacJ CIA mouse model.

Example 21

This example describes the use of a (NZB/W) $F_1$ animal model for testing MASP-2 inhibitory agents useful to treat immune-complex mediated glomerulonephritis.

Background and Rationale: New Zealand black×New Zealand white (NZB/W) F1 mice spontaneously develop an autoimmune syndrome with notable similarities to human immune-complex mediated glomerulonephritis. The NZB/W F1 mice invariably succumb to glomerulonephritis by 12 months of age. As discussed above, it has been demonstrated that complement activation plays a significant role in the pathogenesis of immune-complex mediated glomerulonephritis. It has been further shown that the administration of an anti-C5 MoAb in the NZB/W F1 mouse model resulted in significant amelioration of the course of glomerulonepthritis (Wang et al., *Proc. Natl. Acad. Sci.* 93:8563-8568 (1996)). Based on the observations described herein that MASP-2 plays an essential role in the initiation of both the lectin and alternative pathways, the NZB/W $F_1$ animal model is useful to screen for MASP-2 inhibitory agents that are effective for use as therapeutic agents to treat glomerulonephritis.

Methods: A MASP-2-/- mouse is generated as described in Example 1. The MASP-2-/- mouse is then separately crossed with a mouse derived both from the NZB and the NZW strains (The Jackson Laboratory). F1 and subsequent offspring are intercrossed to produce homozygous MASP-2-/- in both the NZB and NZW genetic backgrounds. To determine the role of MASP-2 in the pathogenesis of glomerulonephritis in this model, the development of this disease in F1 individuals resulting from crosses of either wild-type NZB×NZW mice or MASP-2-/-NZB×MASP-2-/-NZW mice are compared. At weekly intervals urine samples will be collected from the MASP-2+/+ and MASP-2-/- F1 mice and urine protein levels monitored for the presence of anti-DNA antibodies (as described in Wang et al., 1996, supra). Histopathological analysis of the kidneys is also carried out to monitor the amount of mesangial matrix deposition and development of glomerulonephritis.

The NZB/W F1 animal model is also useful to screen for MASP-2 inhibitory agents that are effective for use as therapeutic agents to treat glomerulonephritis. At 18 weeks of age, wild-type NZB/W F1 mice are injected intraperitoneally with anti-MASP-2 inhibitory agents, such as anti-MASP-2 monoclonal antibodies (in a dosage range of from 0.01 mg/kg to 10 mg/kg) at a frequency of weekly or biweekly. The above-mentioned histopathological and biochemical markers of glomerulonephritis are used to evaluate disease development in the mice and to identify useful MASP-2 inhibitory agents for the treatment of this disease.

Example 22

This example describes the use of a tubing loop as a model for testing MASP-2 inhibitory agents useful to prevent tissue damage resulting from extracorporeal circulation (ECC) such as a cardiopulmonary bypass (CPB) circuit.

Background and Rationale: As discussed above, patients undergoing ECC during CPB suffer a systemic inflammatory reaction, which is partly caused by exposure of blood to the artificial surfaces of the extracorporeal circuit, but also by surface-independent factors like surgical trauma and ischemia-reperfusion injury (Butler, J., et al., *Ann. Thorac. Surg.* 55:552-9, 1993; Edmunds, L. H., *Ann. Thorac. Surg.* 66(Suppl):S12-6, 1998; Asimakopoulos, G., *Perfusion* 14:269-77, 1999). It has further been shown that the alternative complement pathway plays a predominant role in complement activation in CPB circuits, resulting from the interaction of blood with the artificial surfaces of the CPB circuits (see Kirklin et al., 1983, 1986, discussed supra). Therefore, based on the observations described herein that MASP-2 plays an essential role in the initiation of both the lectin and alternative pathways, the tubing loop model is useful to screen for MASP-2 inhibitory agents that are effective for use as therapeutic agents to prevent or treat an extracorporeal exposure-triggered inflammatory reaction.

Methods: A modification of a previously described tubing loop model for cardiopulmonary bypass circuits is utilized (see Gong et al., *J. Clinical Immunol.* 16(4):222-229 (1996)) as described in Gupta-Bansal et al., *Molecular Immunol.* 37:191-201 (2000). Briefly, blood is freshly collected from a healthy subject in a 7 ml vacutainer tube (containing 7 units of heparin per ml of whole blood). Polyethylene tubing similar to what is used during CPB procedures (e.g., I.D. 2.92 mm; O.D. 3.73 mm, length: 45 cm) is filled with 1 ml of blood and closed into a loop with a short piece of silicone tubing. A control tubing containing heparinized blood with 10 mM EDTA was included in the study as a background control. Sample and control tubings were rotated vertically in a water bath for 1 hour at 37° C. After incubation, the blood samples were transferred into 1.7 ml microfuge tubes containing EDTA, resulting in a final concentration of 20 mM EDTA. The samples were centrifuged and the plasma was collected. MASP-2 inhibitory agents, such as anti-MASP-2 antibodies are added to the heparinized blood immediately before rotation. The plasma samples are then subjected to assays to measure the concentration C3a and soluble C5b-9 as described in Gupta-Bansal et al., 2000, supra.

Example 23

This example describes the use of a rodent caecal ligation and puncture (CLP) model system for testing MASP-2 inhibitory agents useful to treat sepsis or a condition resulting from sepsis, including severe sepsis, septic shock, acute respiratory distress syndrome resulting from sepsis and systemic inflammatory response syndrome.

Background and Rationale: As discussed above, complement activation has been shown in numerous studies to have a major role in the pathogenesis of sepsis (see Bone, R. C., *Annals. Internal. Med.* 115:457-469, 1991). The CLP rodent model is a recognized model that mimics the clinical course of sepsis in humans and is considered to be a reasonable surrogate model for sepsis in humans (see Ward, P., *Nature Review Immunology* 4:133-142 (2004). A recent study has shown that treatment of CLP animals with anti-C5a antibodies resulted in reduced bacteremia and greatly improved survival Huber-Lang et al., *J. of Immunol.* 169:3223-3231 (2002). Therefore, based on the observations described herein that MASP-2 plays an essential role in the initiation of both the lectin and alternative pathways, the CLP rodent model is useful to screen for MASP-2 inhibitory agents that are effective for use as therapeutic agents to prevent or treat sepsis or a condition resulting from sepsis.

Methods: The CLP model is adapted from the model described in Huber-Lang et al., 2004, supra as follows. MASP-2−/− and MASP-2+/+ animals are anesthetized. A 2 cm midline abdominal incision is made and the cecum is tightly ligated below the ileocecal valve, avoiding bowel obstruction. The cecum is then punctured through and through with a 21-gauge needle. The abdominal incision was then closed in layers with silk suture and skin clips (Ethicon, Summerville, N.J.). Immediately after CLP, animals receive an injection of a MASP-2 inhibitory agent such as anti-MASP-2 monoclonal antibodies (in a dosage range of from 0.01 mg/kg to 10 mg/kg). Anti-hMASP-2 monoclonal antibodies as therapeutic agents can be easily evaluated in a MASP-2−/−, hMASP-+/+ knock-in CLP mouse model. The plasma of the mice are then analyzed for levels of complement-derived anaphylatoxins and respiratory burst using the assays described in Huber-Lang et al., 2004, supra.

Example 24

This example describes the identification of high affinity anti-MASP-2 Fab2 antibody fragments that block MASP-2 activity.

Background and rationale: MASP-2 is a complex protein with many separate functional domains, including: binding site(s) for MBL and ficolins, a serine protease catalytic site, a binding site for proteolytic substrate C2, a binding site for proteolytic substrate C4, a MASP-2 cleavage site for auto-activation of MASP-2 zymogen, and two $Ca^{++}$ binding sites. Fab2 antibody fragments were identified that bind with high affinity to MASP-2, and the identified Fab2 fragments were tested in a functional assay to determine if they were able to block MASP-2 functional activity.

To block MASP-2 functional activity, an antibody or Fab2 antibody fragment must bind and interfere with a structural epitope on MASP-2 that is required for MASP-2 functional activity. Therefore, many or all of the high affinity binding anti-MASP-2 Fab2s may not inhibit MASP-2 functional activity unless they bind to structural epitopes on MASP-2 that are directly involved in MASP-2 functional activity.

A functional assay that measures inhibition of lectin pathway C3 convertase formation was used to evaluate the "blocking activity" of anti-MASP-2 Fab2s. It is known that the primary physiological role of MASP-2 in the lectin pathway is to generate the next functional component of the lectin-mediated complement pathway, namely the lectin pathway C3 convertase. The lectin pathway C3 convertase is a critical enzymatic complex (C4bC2a) that proteolytically cleaves C3 into C3a and C3b. MASP-2 is not a structural component of the lectin pathway C3 convertase (C4bC2a); however, MASP-2 functional activity is required in order to generate the two protein components (C4b, C2a) that comprise the lectin pathway C3 convertase. Furthermore, all of the separate functional activities of MASP-2 listed above appear to be required in order for MASP-2 to generate the lectin pathway C3 convertase. For these reasons, a preferred assay to use in evaluating the "blocking activity" of anti-MASP-2 Fab2s is believed to be a functional assay that measures inhibition of lectin pathway C3 convertase formation.

Generation of High Affinity Fab2s: A phage display library of human variable light and heavy chain antibody sequences and automated antibody selection technology for identifying Fab2s that react with selected ligands of interest was used to create high affinity Fab2s to rat MASP-2 protein (SEQ ID NO:55). A known amount of rat MASP-2 (~1 mg, >85% pure) protein was utilized for antibody screening. Three rounds of amplification were utilized for selection of the antibodies with the best affinity. Approximately 250 different hits expressing antibody fragments were picked for ELISA screening. High affinity hits were subsequently sequenced to determine uniqueness of the different antibodies.

Fifty unique anti-MASP-2 antibodies were purified and 250 µg of each purified Fab2 antibody was used for characterization of MASP-2 binding affinity and complement pathway functional testing, as described in more detail below.

Assays used to Evaluate the Inhibitory (Blocking) Activity of Anti-MASP-2 Fab2s

1. Assay to Measure Inhibition of Formation of Lectin Pathway C3 Convertase:

Background: The lectin pathway C3 convertase is the enzymatic complex (C4bC2a) that proteolytically cleaves C3 into the two potent proinflammatory fragments, anaphylatoxin C3a and opsonic C3b. Formation of C3 convertase appears to a key step in the lectin pathway in terms of mediating inflammation. MASP-2 is not a structural component of the lectin pathway C3 convertase (C4bC2a); therefore anti-MASP-2 antibodies (or Fab2) will not directly inhibit activity of preexisting C3 convertase. However, MASP-2 serine protease activity is required in order to generate the two protein components (C4b, C2a) that comprise the lectin pathway C3 convertase. Therefore, anti-MASP-2 Fab2 which inhibit MASP-2 functional activity (i.e., blocking anti-MASP-2 Fab2) will inhibit de novo formation of lectin pathway C3 convertase. C3 contains an unusual and highly reactive thioester group as part of its structure. Upon cleavage of C3 by C3 convertase in this assay, the thioester group on C3b can form a covalent bond with hydroxyl or amino groups on macromolecules immobilized on the bottom of the plastic wells via ester or amide linkages, thus facilitating detection of C3b in the ELISA assay.

Yeast mannan is a known activator of the lectin pathway. In the following method to measure formation of C3 convertase, plastic wells coated with mannan were incubated for 30 min at 37° C. with diluted rat serum to activate the lectin pathway. The wells were then washed and assayed for C3b immobilized onto the wells using standard ELISA methods. The amount of C3b generated in this assay is a direct reflection of the de novo formation of lectin pathway C3 convertase. Anti-MASP-2 Fab2s at selected concentrations were tested in this assay for their ability to inhibit C3 convertase formation and consequent C3b generation.

Methods:

96-well Costar Medium Binding plates were incubated overnight at 5° C. with mannan diluted in 50 mM carbonate buffer, pH 9.5 at 1 ug/50 Tl/well. After overnight incubation, each well was washed three times with 200 Tl PBS. The wells were then blocked with 100 Tl/well of 1% bovine serum albumin in PBS and incubated for one hour at room temperature with gentle mixing. Each well was then washed three times with 200 Tl of PBS. The anti-MASP-2 Fab2 samples were diluted to selected concentrations in $Ca^{++}$ and $Mg^{++}$ containing GVB buffer (4.0 mM barbital, 141 mM NaCl, 1.0 mM $MgCl_2$, 2.0 mM $CaCl_2$, 0.1% gelatin, pH 7.4) at 5 C. A 0.5% rat serum was added to the above samples at 5 C and 100 Tl was transferred to each well. Plates were covered and incubated for 30 minutes in a 37 C waterbath to allow complement activation. The reaction was stopped by transferring the plates from the 37 C waterbath to a container containing an ice-water mix. Each well was washed five times with 200 Tl with PBS-Tween 20 (0.05% Tween 20 in PBS), then washed two times with 200 Tl PBS. A 100 Tl/well of 1:10,000 dilution of the primary antibody (rabbit anti-human C3c, DAKO A0062) was added in PBS containing 2.0 mg/ml bovine serum albumin and incubated 1 hr at room temperature with gentle mixing. Each well was washed 5×200 Tl PBS. 100 Tl/well of 1:10,000 dilution of the secondary antibody (peroxidase-conjugated goat anti-rabbit IgG, American Qualex A102PU) was added in PBS containing 2.0 mg/ml bovine serum albumin and incubated for one hour at room temperature on a shaker with gentle mixing. Each well was washed five times with 200 Tl with PBS. 100 Tl/well of the peroxidase substrate TMB (Kirkegaard & Perry Laboratories) was added and incubated at room temperature for 10 min. The peroxidase reaction was stopped by adding 100 Tl/well of 1.0 M $H_3PO_4$ and the $OD_{450}$ was measured.

2. Assay to Measure Inhibition of MASP-2-Dependent C4 Cleavage

Background: The serine protease activity of MASP-2 is highly specific and only two protein substrates for MASP-2 have been identified; C2 and C4. Cleavage of C4 generates C4a and C4b. Anti-MASP-2 Fab2 may bind to structural epitopes on MASP-2 that are directly involved in C4 cleavage (e.g., MASP-2 binding site for C4; MASP-2 serine protease catalytic site) and thereby inhibit the C4 cleavage functional activity of MASP-2.

Yeast mannan is a known activator of the lectin pathway. In the following method to measure the C4 cleavage activity of MASP-2, plastic wells coated with mannan were incubated for 30 minutes at 37 C with diluted rat serum to activate the lectin pathway. Since the primary antibody used in this ELISA assay only recognizes human C4, the diluted rat serum was also supplemented with human C4 (1.0 Tg/ml). The wells were then washed and assayed for human C4b immobilized onto the wells using standard ELISA methods. The amount of C4b generated in this assay is a measure of MASP-2 dependent C4 cleavage activity. Anti-MASP-2 Fab2 at selected concentrations were tested in this assay for their ability to inhibit C4 cleavage.

Methods: 96-well Costar Medium Binding plates were incubated overnight at 5 C with mannan diluted in 50 mM carbonate buffer, pH 9.5 at 1.0 Tg/50 Tl/well. Each well was washed 3× with 200 Tl PBS. The wells were then blocked with 100 Tl/well of 1% bovine serum albumin in PBS and incubated for one hour at room temperature with gentle mixing. Each well was washed 3× with 200 Tl of PBS. Anti-MASP-2 Fab2 samples were diluted to selected concentrations in $Ca^{++}$ and $Mg^{++}$ containing GVB buffer (4.0 mM barbital, 141 mM NaCl, 1.0 mM $MgCl_2$, 2.0 mM $CaCl_2$, 0.1% gelatin, pH 7.4) at 5 C. 1.0 Tg/ml human C4 (Quidel) was also included in these samples. 0.5% rat serum was added to the above samples at 5 C and 100 Tl was transferred to each well. The plates were covered and incubated for 30 min in a 37 C waterbath to allow complement activation. The reaction was stopped by transferring the plates from the 37 C waterbath to a container containing an ice-water mix. Each well was washed 5×200 Tl with PBS-Tween 20 (0.05% Tween 20 in PBS), then each well was washed with 2× with 200 Tl PBS. 100 Tl/well of 1:700 dilution of biotin-conjugated chicken anti-human C4c (Immunsystem AB, Uppsala, Sweden) was added in PBS containing 2.0 mg/ml bovine serum albumin (BSA) and incubated one hour at room temperature with gentle mixing. Each well was washed 5×200 Tl PBS. 100 Tl/well of 0.1 Tg/ml of peroxidase-conjugated streptavidin (Pierce Chemical #21126) was added in PBS containing 2.0 mg/ml BSA and incubated for one hour at room temperature on a shaker with gentle mixing. Each well was washed 5×200 Tl with PBS. 100 Tl/well of the peroxidase substrate TMB (Kirkegaard & Perry Laboratories) was added and incubated at room temperature for 16 min. The peroxidase reaction was stopped by adding 100 Tl/well of 1.0 M $H_3PO_4$ and the $OD_{450}$ was measured.

3. Binding Assay of Anti-Rat MASP-2 Fab2 to 'Native' Rat MASP-2

Background: MASP-2 is usually present in plasma as a MASP-2 dimer complex that also includes specific lectin molecules (mannose-binding protein (MBL) and ficolins).

Therefore, if one is interested in studying the binding of anti-MASP-2 Fab2 to the physiologically relevant form of MASP-2, it is important to develop a binding assay in which the interaction between the Fab2 and 'native' MASP-2 in plasma is used, rather than purified recombinant MASP-2. In this binding assay the 'native' MASP-2-MBL complex from 10% rat serum was first immobilized onto mannan-coated wells. The binding affinity of various anti-MASP-2 Fab2s to the immobilized 'native' MASP-2 was then studied using a standard ELISA methodology.

Methods: 96-well Costar High Binding plates were incubated overnight at 5° C. with mannan diluted in 50 mM carbonate buffer, pH 9.5 at 1 Tg/50 Tl/well. Each well was washed 3× with 200 Ti PBS. The wells were blocked with 100 Tl/well of 0.5% nonfat dry milk in PBST (PBS with 0.05% Tween 20) and incubated for one hour at room temperature with gentle mixing. Each well was washed 3× with 200 Tl of TB S/Tween/$Ca^{++}$ Wash Buffer (Tris-buffered saline, 0.05% Tween 20, containing 5.0 mM $CaCl_2$, pH 7.4. 10% rat serum in High Salt Binding Buffer (20 mM Tris, 1.0 M NaCl, 10 mM $CaCl_2$, 0.05% Triton-X100, 0.1% (w/v) bovine serum albumin, pH 7.4) was prepared on ice. 100 Tl/well was added and incubated overnight at 5° C. Wells were washed 3× with 200 Tl of TBS/Tween/$Ca^{++}$ Wash Buffer. Wells were then washed 2× with 200 Tl PBS. 100 Tl/well of selected concentration of anti-MASP-2 Fab2 diluted in $Ca^{++}$ and $Mg^{++}$ containing GVB Buffer (4.0 mM barbital, 141 mM NaCl, 1.0 mM $MgCl_2$, 2.0 mM $CaCl_2$, 0.1% gelatin, pH 7.4) was added and incubated for one hour at room temperature with gentle mixing. Each well was washed 5×200 Ti PBS. 100 Tl/well of HRP-conjugated goat anti-Fab2 (Biogenesis Cat No 0500-0099) diluted 1:5000 in 2.0 mg/ml bovine serum albumin in PBS was added and incubated for one hour at room temperature with gentle mixing. Each well was washed 5×200 Tl PBS. 100 Tl/well of the peroxidase substrate TMB (Kirkegaard & Perry Laboratories) was added and incubated at room temperature for 70 min. The peroxidase reaction was stopped by adding 100 Tl/well of 1.0 M $H_3PO_4$ and $OD_{450}$ was measured.

Results:

Approximately 250 different Fab2s that reacted with high affinity to the rat MASP-2 protein were picked for ELISA screening. These high affinity Fab2s were sequenced to determine the uniqueness of the different antibodies, and 50 unique anti-MASP-2 antibodies were purified for further analysis. 250 ug of each purified Fab2 antibody was used for characterization of MASP-2 binding affinity and complement pathway functional testing. The results of this analysis is shown below in TABLE 6.

TABLE 6

ANTI-MASP-2 FAB2 THAT BLOCK LECTIN PATHWAY COMPLEMENT ACTIVATION

| Fab2 antibody # | C3 Convertase ($IC_{50}$ (nM)) | $K_d$ | C4 Cleavage $IC_{50}$ (nM) |
|---|---|---|---|
| 88 | 0.32 | 4.1 | ND |
| 41 | 0.35 | 0.30 | 0.81 |
| 11 | 0.46 | 0.86 | <2 nM |
| 86 | 0.53 | 1.4 | ND |
| 81 | 0.54 | 2.0 | ND |
| 66 | 0.92 | 4.5 | ND |
| 57 | 0.95 | 3.6 | <2 nM |
| 40 | 1.1 | 7.2 | 0.68 |
| 58 | 1.3 | 2.6 | ND |
| 60 | 1.6 | 3.1 | ND |
| 52 | 1.6 | 5.8 | <2 nM |
| 63 | 2.0 | 6.6 | ND |
| 49 | 2.8 | 8.5 | <2 nM |
| 89 | 3.0 | 2.5 | ND |
| 71 | 3.0 | 10.5 | ND |
| 87 | 6.0 | 2.5 | ND |
| 67 | 10.0 | 7.7 | ND |

Figure 11A:
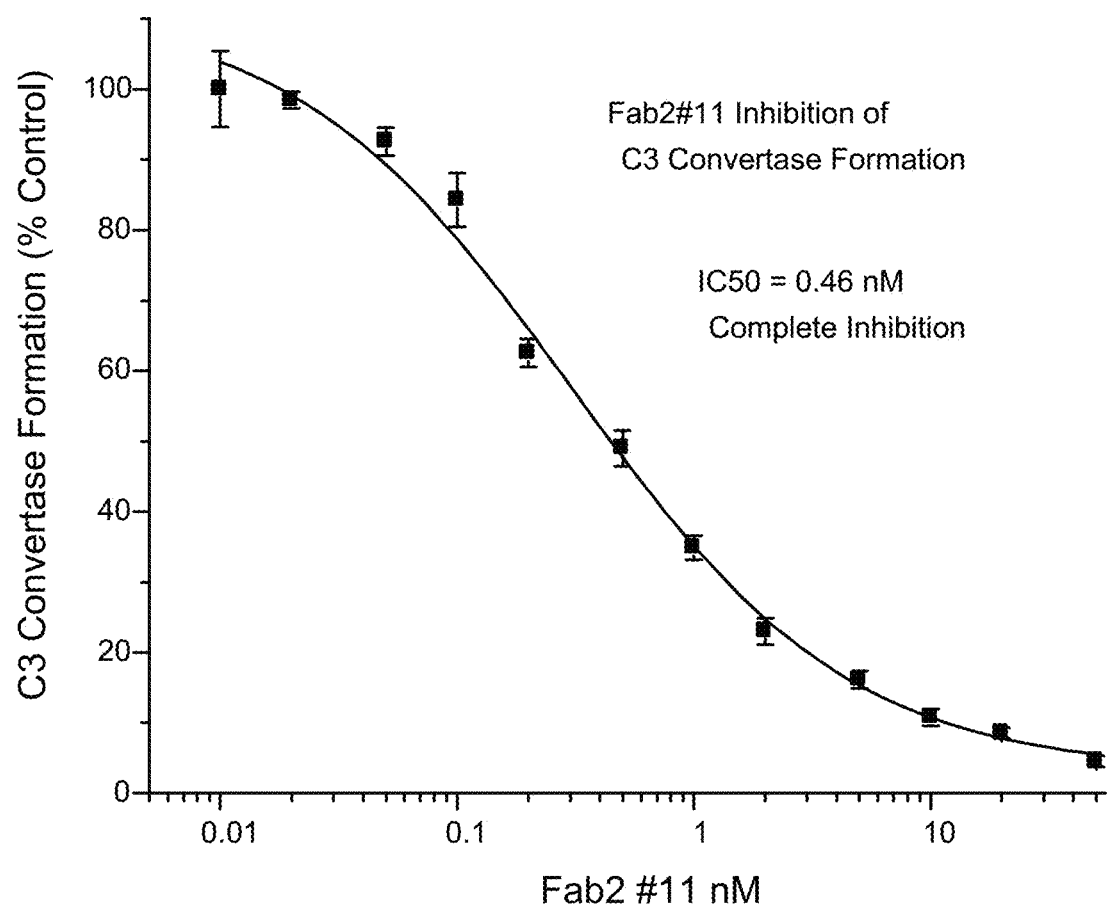
FIG. 11A presents results demonstrating that anti-MASP-2 Fab2 antibody #11 inhibits C3 convertase formation, as described in Example 24.

As shown above in TABLE 6, of the 50 anti-MASP-2 Fab2s tested, seventeen Fab2s were identified as MASP-2 blocking Fab2 that potently inhibit C3 convertase formation with $IC_{50}$ equal to or less than 10 nM Fab2s (a 34% positive hit rate). Eight of the seventeen Fab2s identified have $IC_{50}$s in the subnanomolar range. Furthermore, all seventeen of the MASP-2 blocking Fab2s shown in TABLE 6 gave essentially complete inhibition of C3 convertase formation in the lectin pathway C3 convertase assay. FIG. 11A graphically illustrates the results of the C3 convertase formation assay for Fab2 antibody #11, which is representative of the other Fab2 antibodies tested, the results of which are shown in TABLE 6. This is an important consideration, since it is theoretically possible that a "blocking" Fab2 may only fractionally inhibit MASP-2 function even when each MASP-2 molecule is bound by the Fab2.

Although mannan is a known activator of the lectin pathway, it is theoretically possible that the presence of anti-mannan antibodies in the rat serum might also activate the classical pathway and generate C3b via the classical pathway C3 convertase. However, each of the seventeen blocking anti-MASP-2 Fab2s listed in this example potently inhibits C3b generation (>95%), thus demonstrating the specificity of this assay for lectin pathway C3 convertase.

Figure 11B:
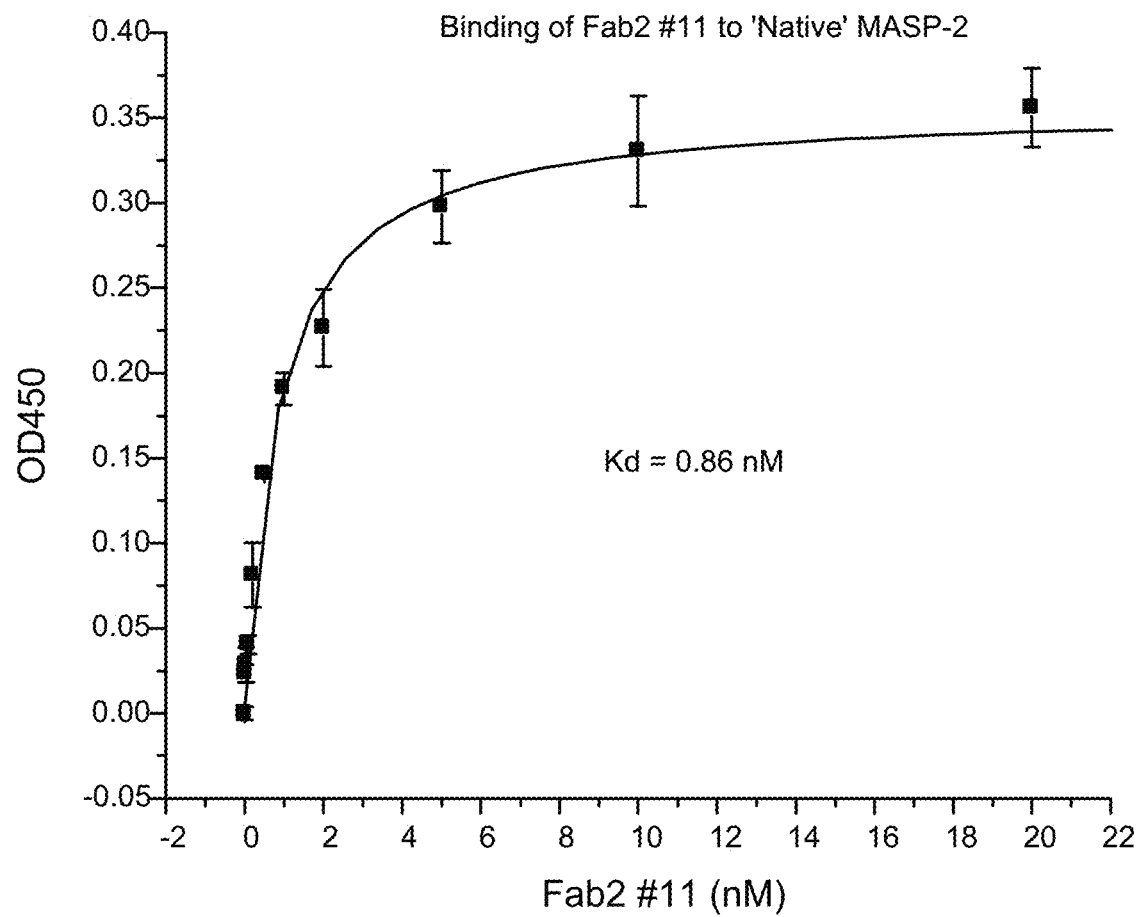
FIG. 11B presents results demonstrating that anti-MASP-2 Fab2 antibody #11 binds to native rat MASP-2, as described in Example 24.

Binding assays were also performed with all seventeen of the blocking Fab2s in order to calculate an apparent $K_d$ for each. The results of the binding assays of anti-rat MASP-2 Fab2s to native rat MASP-2 for six of the blocking Fab2s are also shown in TABLE 6. FIG. 11B graphically illustrates the results of a binding assay with the Fab2 antibody #11. Similar binding assays were also carried out for the other Fab2s, the results of which are shown in TABLE 6. In general, the apparent $K_d$s obtained for binding of each of the six Fab2s to 'native' MASP-2 corresponds reasonably well with the $IC_{50}$ for the Fab2 in the C3 convertase functional assay. There is evidence that MASP-2 undergoes a conformational change from an 'inactive' to an 'active' form upon activation of its protease activity (Feinberg et al., *EMBO J* 22:2348-59 (2003); Gal et al., *J. Biol. Chem.* 280:33435-44 (2005)). In the normal rat plasma used in the C3 convertase formation assay, MASP-2 is present primarily in the 'inactive' zymogen conformation. In contrast, in the binding assay, MASP-2 is present as part of a complex with MBL bound to immobilized mannan; therefore, the MASP-2 would be in the 'active' conformation (Petersen et al., *J. Immunol Methods* 257:107-16, 2001). Consequently, one would not necessarily expect an exact correspondence between the $IC_{50}$ and $K_d$ for each of the seventeen blocking Fab2 tested in these two functional assays since in each assay the Fab2 would be binding a different conformational form of MASP-2. Never-the-less, with the exception of Fab2 #88, there appears to be a reasonably close correspondence between the $IC_{50}$ and apparent Kd for each of the other sixteen Fab2 tested in the two assays (see TABLE 6).

Figure 11C:
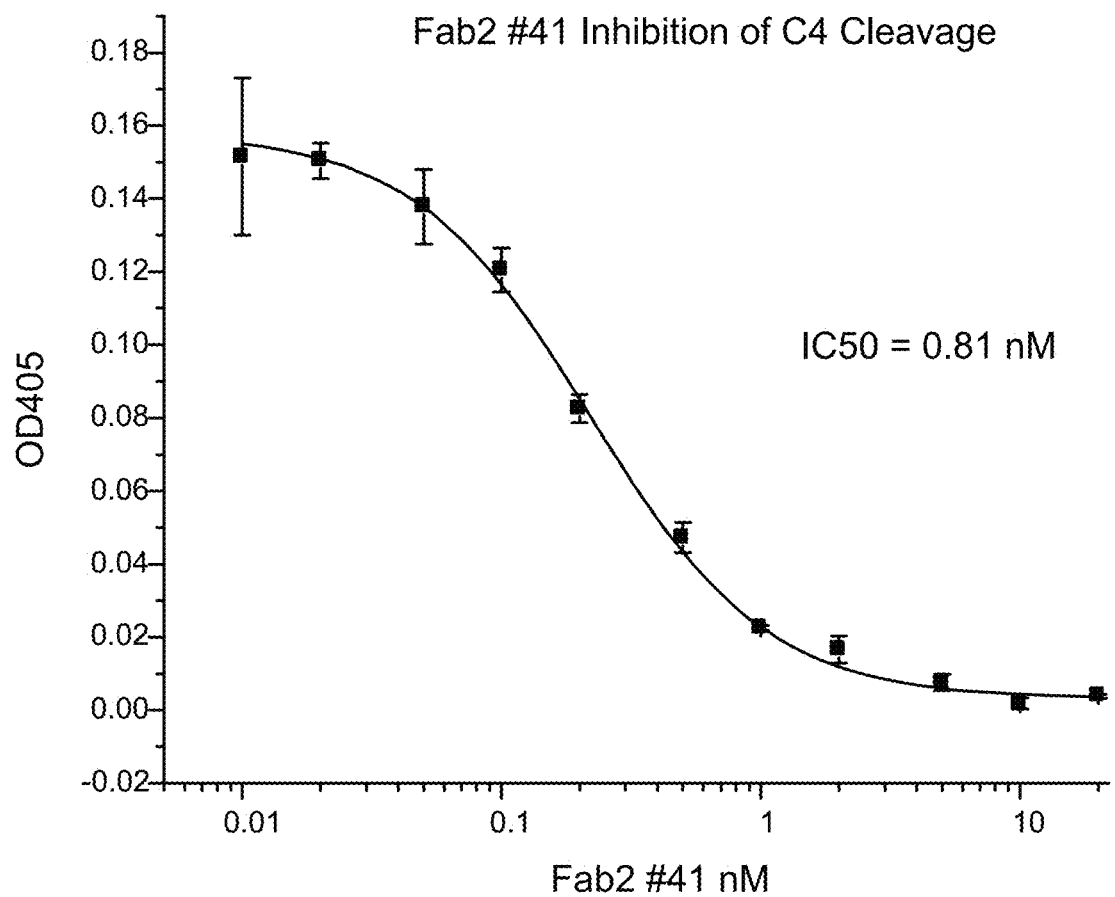
FIG. 11C presents results demonstrating that anti-MASP-2 Fab2 antibody #41 inhibits C4 cleavage, as described in Example 24.
Figure 12:
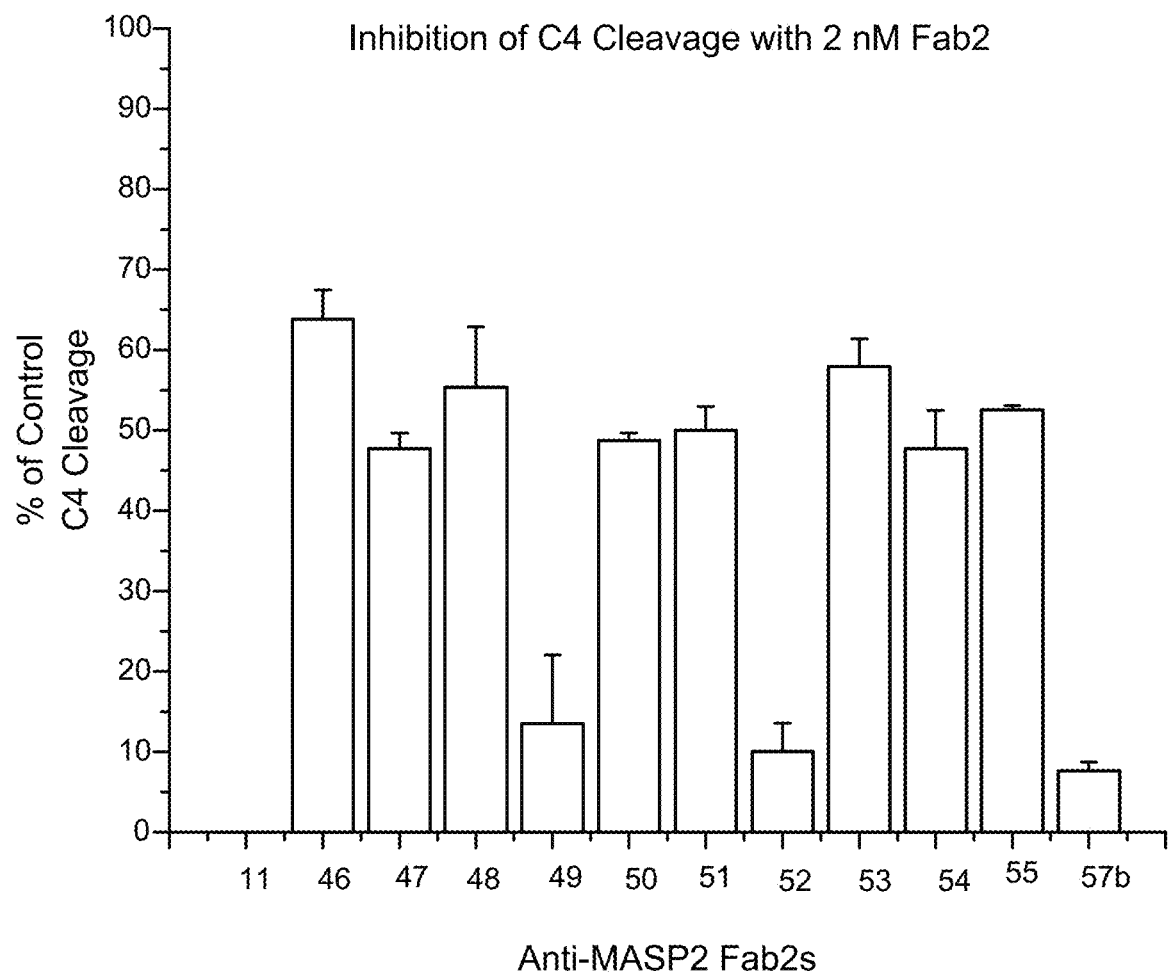
FIG. 12 presents results demonstrating that all of the anti-MASP-2 Fab2 antibodies tested that inhibited C3 convertase formation also were found to inhibit C4 cleavage, as described in Example 24.

Several of the blocking Fab2s were evaluated for inhibition of MASP-2 mediated cleavage of C4. FIG. 11C graphically illustrates the results of a C4 cleavage assay, showing inhibition with Fab2 #41, with an $IC_{50}$=0.81 nM (see TABLE 6). As shown in FIG. 12, all of the Fab2s tested were found to inhibit C4 cleavage with $IC_{50}$s similar to those obtained in the C3 convertase assay (see TABLE 6).

Although mannan is a known activator of the lectin pathway, it is theoretically possible that the presence of anti-mannan antibodies in the rat serum might also activate the classical pathway and thereby generate C4b by C1s-mediated cleavage of C4. However, several anti-MASP-2 Fab2s have been identified which potently inhibit C4b generation (>95%), thus demonstrating the specificity of this assay for MASP-2 mediated C4 cleavage. C4, like C3, contains an unusual and highly reactive thioester group as part of its structure. Upon cleavage of C4 by MASP-2 in this assay, the thioester group on C4b can form a covalent bond with hydroxyl or amino groups on macromolecules immobilized on the bottom of the plastic wells via ester or amide linkages, thus facilitating detection of C4b in the ELISA assay.

These studies clearly demonstrate the creation of high affinity FAB2s to rat MASP-2 protein that functionally block both C4 and C3 convertase activity, thereby preventing lectin pathway activation.

Example 25

This Example describes the epitope mapping for several of the blocking anti-rat MASP-2 Fab2 antibodies that were generated as described in Example 24.

Figure 13:
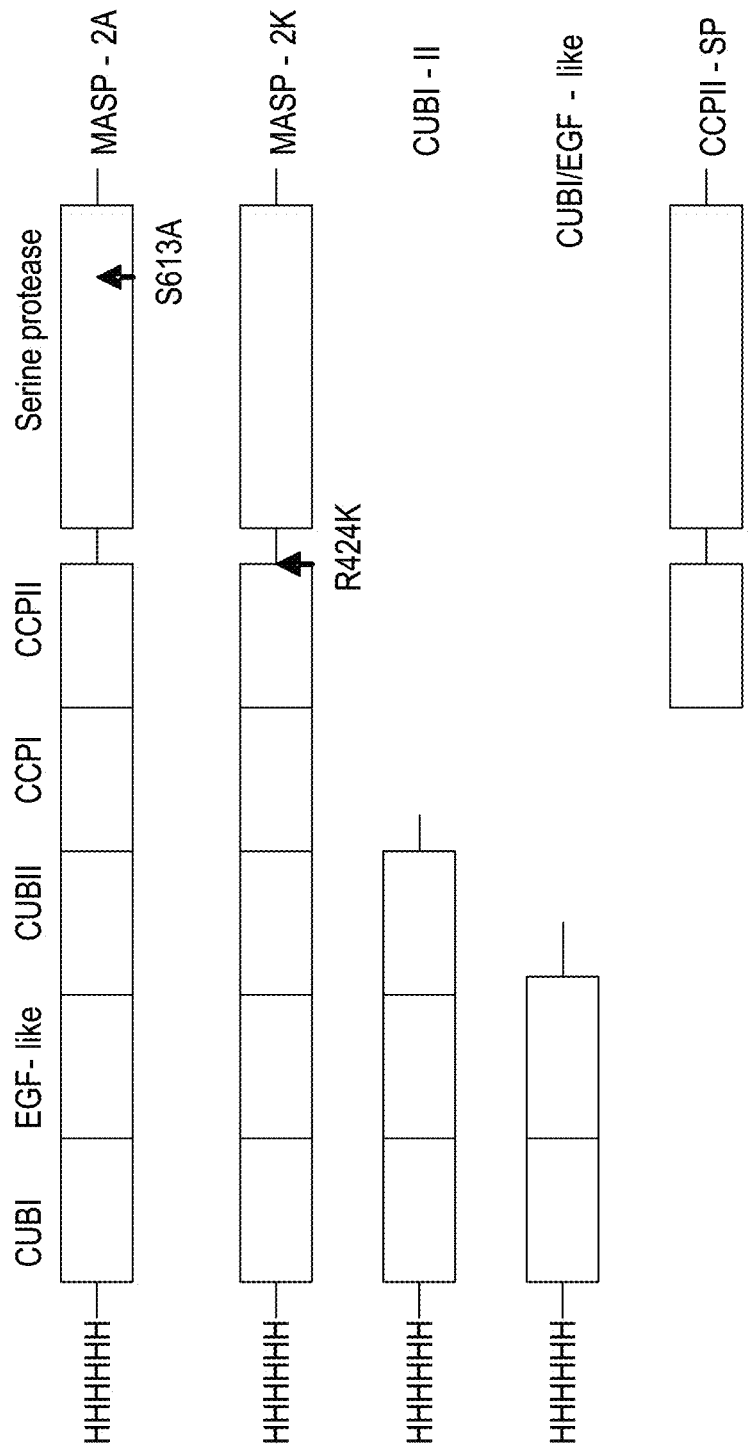
FIG. 13 is a diagram illustrating the recombinant polypeptides derived from rat MASP-2 that were used for epitope mapping of the anti-MASP-2 blocking Fab2 antibodies, as described in Example 25.

Methods:

As shown in FIG. 13, the following proteins, all with N-terminal 6× His tags were expressed in CHO cells using the pED4 vector:

rat MASP-2A, a full length MASP-2 protein, inactivated by altering the serine at the active center to alanine (S613A);

rat MASP-2K, a full-length MASP-2 protein altered to reduce autoactivation (R424K);

CUBI-II, an N-terminal fragment of rat MASP-2 that contains the CUBI, EGF-like and CUBII domains only; and CUBI/EGF-like, an N-terminal fragment of rat MASP-2 that contains the CUBI and EGF-like domains only.

These proteins were purified from culture supernatants by nickel-affinity chromatography, as previously described (Chen et al., *J. Biol. Chem.* 276:25894-02 (2001)).

A C-terminal polypeptide (CCPII-SP), containing CCPII and the serine protease domain of rat MASP-2, was expressed in *E. coli* as a thioredoxin fusion protein using pTrxFus (Invitrogen). Protein was purified from cell lysates using Thiobond affinity resin. The thioredoxin fusion partner was expressed from empty pTrxFus as a negative control.

All recombinant proteins were dialyzed into TBS buffer and their concentrations determined by measuring the OD at 280 nm.

Dot Blot Analysis:

Serial dilutions of the five recombinant MASP-2 polypeptides described above and shown in FIG. 13 (and the thioredoxin polypeptide as a negative control for CCPII-serine protease polypeptide) were spotted onto a nitrocellulose membrane. The amount of protein spotted ranged from 100 ng to 6.4 pg, in five-fold steps. In later experiments, the amount of protein spotted ranged from 50 ng down to 16 pg, again in five-fold steps. Membranes were blocked with 5% skimmed milk powder in TBS (blocking buffer) then incubated with 1.0 μg/ml anti-MASP-2 Fab2s in blocking buffer (containing 5.0 mM $Ca^{2+}$). Bound Fab2s were detected using HRP-conjugated anti-human Fab (AbD/Serotec; diluted 1/10,000) and an ECL detection kit (Amersham). One membrane was incubated with polyclonal rabbit-anti human MASP-2 Ab (described in Stover et al., *J Immunol* 163: 6848-59 (1999)) as a positive control. In this case, bound Ab was detected using HRP-conjugated goat anti-rabbit IgG (Dako; diluted 1/2,000).

MASP-2 Binding Assay

ELISA plates were coated with 1.0 μg/well of recombinant MASP-2A or CUBI-II polypeptide in carbonate buffer (pH 9.0) overnight at 4° C. Wells were blocked with 1% BSA in TBS, then serial dilutions of the anti-MASP-2 Fab2s were added in TBS containing 5.0 mM $Ca^{2+}$. The plates were incubated for one hour at RT. After washing three times with TBS/tween/$Ca^{2+}$, HRP-conjugated anti-human Fab (AbD/Serotec) diluted 1/10,000 in TBS/$Ca^{2+}$ was added and the plates incubated for a further one hour at RT. Bound antibody was detected using a TMB peroxidase substrate kit (Biorad).

Results:

Results of the dot blot analysis demonstrating the reactivity of the Fab2s with various MASP-2 polypeptides are provided below in TABLE 7. The numerical values provided in TABLE 7 indicate the amount of spotted protein required to give approximately half-maximal signal strength. As shown, all of the polypeptides (with the exception of the thioredoxin fusion partner alone) were recognized by the positive control Ab (polyclonal anti-human MASP-2 sera, raised in rabbits).

TABLE 7

REACTIVITY WITH VARIOUS RECOMBINANT RAT MASP-2 POLYPEPTIDES ON DOT BLOTS

| Fab2 Antibody # | MASP-2A | CUBI-II | CUBI/ EGF-like | CCPII-SP | Thioredoxin |
|---|---|---|---|---|---|
| 40 | 0.16 ng | NR | NR | 0.8 ng | NR |
| 41 | 0.16 ng | NR | NR | 0.8 ng | NR |
| 11 | 0.16 ng | NR | NR | 0.8 ng | NR |
| 49 | 0.16 ng | NR | NR | >20 ng | NR |
| 52 | 0.16 ng | NR | NR | 0.8 ng | NR |
| 57 | 0.032 ng | NR | NR | NR | NR |
| 58 | 0.4 ng | NR | NR | 2.0 ng | NR |
| 60 | 0.4 ng | 0.4 ng | NR | NR | NR |
| 63 | 0.4 ng | NR | NR | 2.0 ng | NR |
| 66 | 0.4 ng | NR | NR | 2.0 ng | NR |
| 67 | 0.4 ng | NR | NR | 2.0 ng | NR |
| 71 | 0.4 ng | NR | NR | 2.0 ng | NR |
| 81 | 0.4 ng | NR | NR | 2.0 ng | NR |
| 86 | 0.4 ng | NR | NR | 10 ng | NR |
| 87 | 0.4 ng | NR | NR | 2.0 ng | NR |
| Positive Control | <0.032 ng | 0.16 ng | 0.16 ng | <0.032 ng | NR |

NR = No reaction. The positive control antibody is polyclonal anti-human MASP-2 sera, raised in rabbits.

Figure 14:
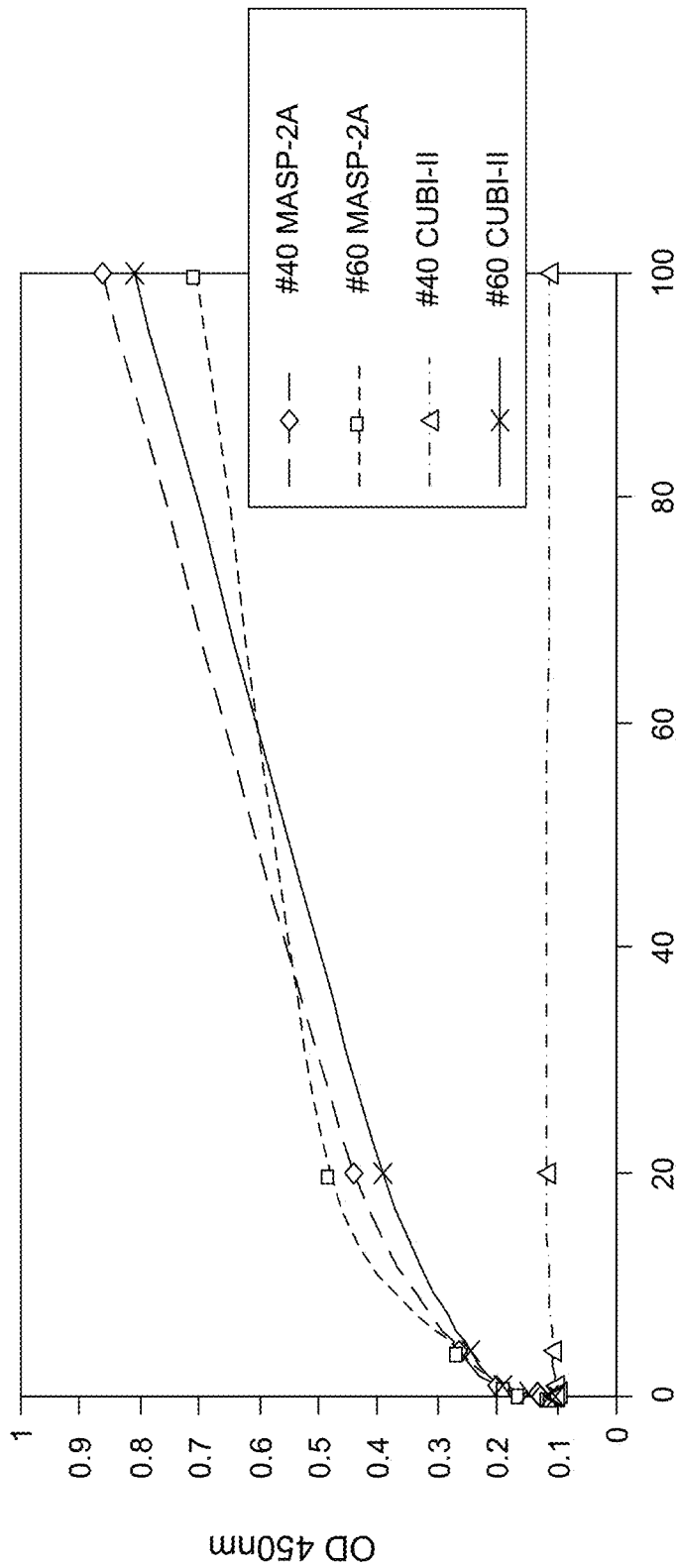
FIG. 14 presents results demonstrating the binding of anti-MASP-2 Fab2 #40 and #60 to rat MASP-2 polypeptides, as described in Example 25.

All of the Fab2s reacted with MASP-2A as well as MASP-2K (data not shown). The majority of the Fab2s recognized the CCPII-SP polypeptide but not the N-terminal fragments. The two exceptions are Fab2 #60 and Fab2 #57. Fab2 #60 recognizes MASP-2A and the CUBI-II fragment, but not the CUBFEGF-like polypeptide or the CCPII-SP polypeptide, suggesting it binds to an epitope in CUBII, or spanning the CUBII and the EGF-like domain. Fab2 #57 recognizes MASP-2A but not any of the MASP-2 fragments tested, perhaps indicating that this Fab2 recognizes an epitope in CCP1. Fab2 #40 and #49 bound only to complete MASP-2A. In the ELISA binding assay shown in FIG. 14, Fab2 #60 also bound to the CUBI-II polypeptide, albeit with a slightly lower apparent affinity.

These finding demonstrate the identification of unique blocking Fab2s to multiple regions of the MASP-2 protein Example 26

This example describes the analysis of MASP-2−/− mice in a Murine Renal Ischemia/Reperfusion Model.

Background/Rationale: Ischemia-Reperfusion (I/R) injury in kidney at body temperature has relevance in a number of clinical conditions, including hypovolaemic shock, renal artery occlusion and cross-clamping procedures.

Kidney ischemia-reperfusion (I/R) is an important cause of acute renal failure, associated with a mortality rate of up to 50% (Levy et al., *JAMA* 275:1489-94, 1996; Thadhani et al., *N. Engl. J Med.* 334:1448-60, 1996). Post-transplant renal failure is a common and threatening complication after renal transplantation (Nicholson et al., *Kidney Int.* 58:2585-91, 2000). Effective treatment for renal I/R injury is currently not available and hemodialysis is the only treatment available. The pathophysiology of renal I/R injury is complicated. Recent studies have shown that the lectin pathway of complement activation may have an important role in the pathogenesis of renal I/R injury (deVries et al., *Am. J. Path.* 165:1677-88, 2004).

Methods:

A MASP-2(−/−) mouse was generated as described in Example 1 and backcrossed for at least 10 generations with C57B1/6. Six male MASP-2(−/−) and six wildtype (+/+) mice weighing between 22-25 g were administered an intraperitoneal injection of Hypnovel (6.64 mg/kg; Roche products Ltd. Welwyn Garden City, UK), and subsequently anaesthetized by inhalation of isoflurane (Abbott Laboratories Ltd., Kent, UK). Isoflurane was chosen because it is a mild inhalation anaesthetic with minimal liver toxicity; the concentrations are produced accurately and the animal recovers rapidly, even after prolonged anaesthesia. Hypnovel was administered because it produces a condition of neuroleptanalgesia in the animal and means that less isoflurane needs to be administered. A warm pad was placed beneath the animal in order to maintain a constant body temperature. Next, a midline abdominal incision was performed and the body cavity held open using a pair of retractors. Connective tissue was cleared above and below the renal vein and artery of both right and left kidneys, and the renal pedicle was clamped via the application of microaneurysm clamps for a period of 55 minutes. This period of ischemia was based initially on a previous study performed in this laboratory (Zhou et al., *J. Clin. Invest.* 105:1363-71 (2000)). In addition, a standard ischemic time of 55 minutes was chosen following ischemic titration and it was found that 55 minutes gave consistent injury that was also reversible, with low mortality, less than 5%. After occlusion, 0.4 ml of warm saline (37° C.) was placed in the abdominal cavity and then the abdomen was closed for the period of ischemia. Following removal of the microaneurysm clamps, the kidneys were observed until color change, an indication of blood re-flow to the kidneys. A further 0.4 ml of warm saline was placed in the abdominal cavity and the opening was sutured, whereupon animals were returned to their cages. Tail blood samples were taken at 24 hours after removing the clamps, and at 48 hours the mice were sacrificed and an additional blood sample was collected.

Figure 15:
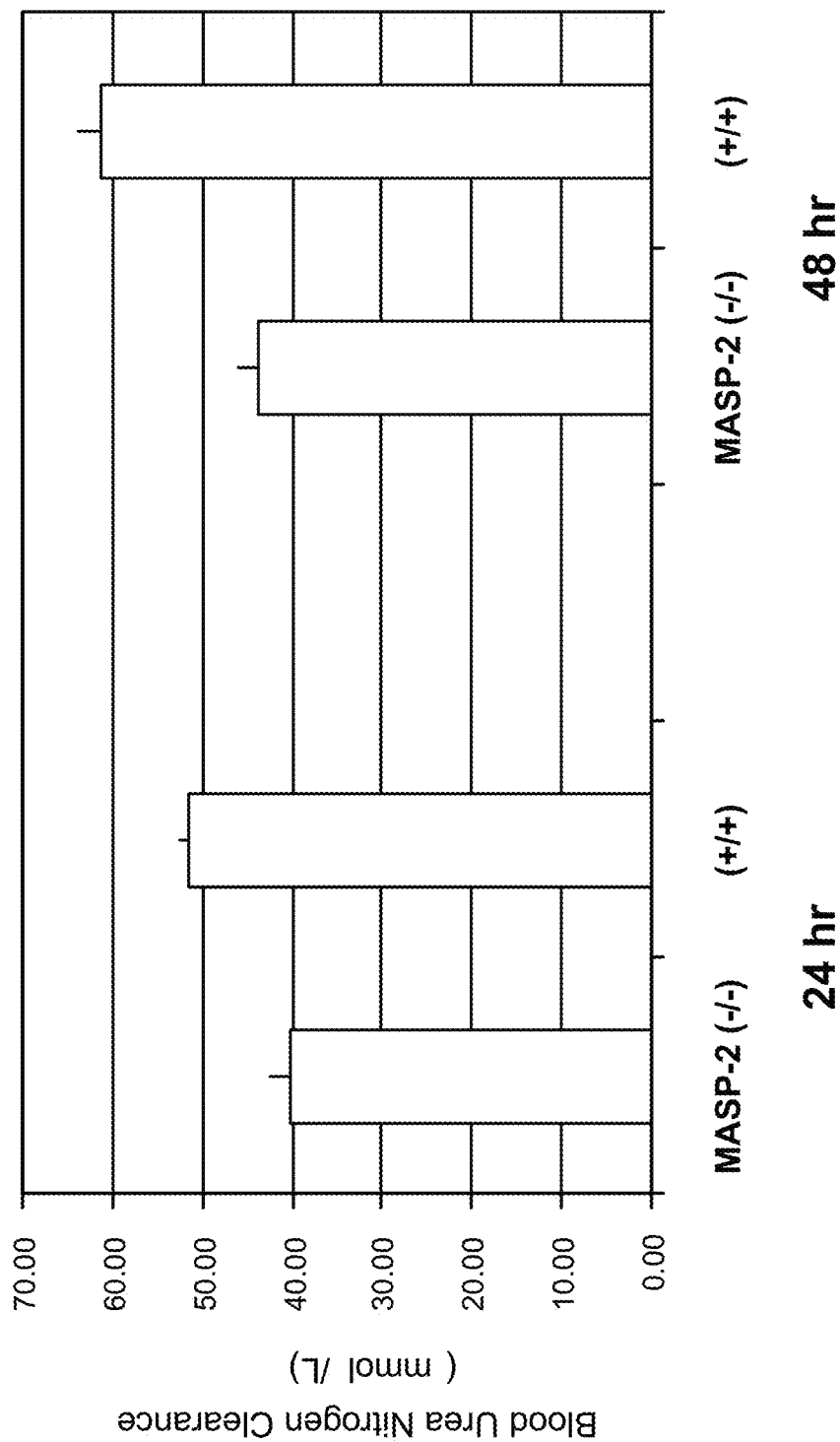
FIG. 15 presents results demonstrating the blood urea nitrogen clearance for wild type (+/+) and MASP-2 (−/−) mice at 24 and 48 hours after reperfusion in a renal ischemia/reperfusion injury model, as described in Example 26.

Assessment of Renal Injury: Renal function was assessed at 24 and 48 hours after reperfusion in six male MASP-2 (−/−) and six WT (+/+) mice. Blood creatinine measurement was determined by mass spectrometry, which provides a reproducible index of renal function (sensitivity<1.0 μmol/L). FIG. 15 graphically illustrates the blood urea nitrogen clearance for wildtype C57B1/6 controls and MASP-2 (−/−) at 24 hours and 48 hours after reperfusion. As shown in FIG. 15, MASP-2(−/−) mice displayed a significant reduction in the amount of blood urea at 24 and 48 hours, in comparison to wildtype control mice, indicating a protective functional effect from renal damage in the ischemia reperfusion injury model.

Overall, increased blood urea was seen in both the WT (+/+) and MASP-2 (−/−) mice at 24 and 48 hours following the surgical procedure and ischemic insult. Levels of blood urea in a non-ischemic WT (+/+) surgery animal was separately determined to be 5.8 mmol/L. In addition to the data presented in FIG. 15, one MASP-2 (−/−) animal showed nearly complete protection from the ischemic insult, with values of 6.8 and 9.6 mmol/L at 24 and 48 hours, respectively. This animal was excluded from the group analysis as a potential outlier, wherein no ischemic injury may have been present. Therefore, the final analysis shown in FIG. 15 included 5 MASP-2(−/−) mice and 6 WT (+/+) mice and a statistically significant reduction in blood urea was seen at 24 and 48 hours in the MASP-2 (−/−) mice (Student t-test $p<0.05$). These findings indicate inhibition of MASP-2 activity would be expected to have a protective or therapeutic effect from renal damage due to ischemic injury.

Example 27

This example describes the analysis of MASP-2(−/−) mice in a Mouse Myocardial Ischemia/Reperfusion Model.

Background/Rationale:

The mannose-binding lectin (MBL) is a circulating molecule that initiates complement activation in an immune complex-independent fashion, in response to a wide range of carbohydrate structures. These structures can be components of infectious agents or altered endogenous carbohydrate moieties particularly within necrotic, oncotic or apoptotic cells. These forms of cell death occur in reperfused myocardium where the activation of complement likely extends injury beyond the boundary that exists at the moment when ischemia is terminated by reperfusion. Although there is compelling evidence that complement activation aggravates myocardial reperfusion, the mechanism of such activation is not well understood and inhibition of all known pathways is likely to have intolerable adverse effects. A recent study suggests that activation may involve the MBL, rather than classical pathway or alternative amplification loop (as defined in the present invention), since infarction was reduced in MBL(A/C)−, but not C1q−, null mice (Walsh M. C. et al., *Jour of Immunol.* 175:541-546 (2005)). However, although encouraging, these mice still harbor circulating components, such as Ficolin A, capable of activating complement through the lectin pathway.

This study investigated MASP-2(−/−) mice versus wild type (+/+) controls to determine if the MASP-2(−/−) would be less sensitive to myocardial ischemia and reperfusion injury. MASP-2(−/−) mice were subjected to regional ischemia and infarct size was compared to their wild type littermates.

Methods: The following protocol was based on a procedure for inducing ischemia/reperfusion injury previously described by Marber et al., *J. Clin Invest.* 95:1446-1456 (1995)).

A MASP-2(-/-) mouse was generated as described in Example 1 and backcrossed for at least 10 generations with C57B1/6. Seven MASP-2 (-/-) mice and seven wildtype (+/+) mice were anesthetized with ketamine/medetomidine (100 mg/kg and 0.2 mg/kg respectively) and placed supine on a thermostatically controlled heating pad to maintain rectal temperature at 37±0.3° C. The mice were intubated under direct vision and ventilated with room air at a respiratory rate of 110/min and a tidal volume of 225 µl/min (Ventilator—Hugo Sachs Elektronic MiniVent Type 845, Germany).

Fur hair was shaved and an anterolateral skin incision made from the left axilla to the processus xiphoideus. The pectoralis major muscle was dissected, cut at its sternal margin and moved into the axillary pit. The pectoralis minor muscle was cut at its cranial margin and moved caudally. The muscle was later used as a muscle flap covering the heart during coronary artery occlusion. Muscles of the 5th intercostal space and the pleura parietalis were penetrated with tweezers at a point slightly medial to the margin of the left lung, thus avoiding damage of the lung or the heart. After penetration of the pleura the tweezers were carefully directed beyond the pleura towards the sternum without touching the heart, and pleura and intercostal muscles were dissected with a battery driven cauterizer (Harvard Apparatus, UK). Special care was exercised in avoiding any bleeding. Using the same technique, the thoracotomy was extended to the mid axillary line. After cutting the 4th rib at its sternal margin the intercostal space was widened until the whole heart exposed from base to apex. With two small artery forceps the pericardium was opened and a pericardial cradle fashioned to move the heart slightly anterior. The left anterior descending coronary artery (LAD) was exposed and a 8-0 monofilament suture with a round needle was then passed under the LAD. The site of ligation of the LAD lies just caudal of the tip of the left atrium, about ¼ along the line running from the atrioventricular crest to the apex of the left ventricle.

All experiments were carried out in a blinded manner, with the investigator being unaware of the genotype of each animal. After completion of instrumentation and surgical procedures, mice were allowed a 15 min equilibration period. Mice then underwent 30 min of coronary artery occlusion with 120 min of reperfusion time.

Coronary Artery Occlusion and Reperfusion Model

Coronary artery occlusion was achieved using the hanging weight system as previously described (Eckle et al., *Am J Physiol Heart Circ Physiol* 291:H2533-H2540, 2006). Both ends of the monofilament ligature were passed through a 2 mm long piece of a polythene PE-10 tube and attached to a length of 5-0 suture using cyanoacrylate glue. The suture was then directed over two horizontally mounted movable metal rods, and masses of 1 g each were attached to both ends of the suture. By elevation of the rods, the masses were suspended and the suture placed under controlled tension to occlude the LAD with a defined and constant pressure. LAD occlusion was verified by paleness of the area at risk, turning color of the LAD perfusion zone from bright red to violet, indicating cessation of blood flow. Reperfusion was achieved by lowering the rods until the masses lay on the operating pad and the tension of the ligature was relieved. Reperfusion was verified by the same three criteria used to verify occlusion. Mice were excluded from further analysis if all three criteria were not met at either start of coronary artery occlusion or within 15 min of reperfusion, respectively. During coronary artery occlusion, temperature and humidity of the heart surface were maintained by covering the heart with the pectoralis minor muscle flap and by sealing the thoracotomy with a 0.9% saline wet gauze.

Measurement of Myocardial Infarct Size:

Infarct size (INF) and area at risk (AAR) were determined by planometry. After i.v. injection of 500 I.U. heparin the LAD was re-occluded and 300 µl 5% (w/vol) Evans Blue (Sigma-Aldrich, Poole, UK) was slowly injected into the jugular vein to delineate the area at risk (AAR). This causes dye to enter the non-ischemic region of the left ventricle and leaves the ischemic AAR unstained. After mice had been euthanized by cervical dislocation, the heart was rapidly removed. The heart was cooled on ice and mounted in a block of 5% agarose and then cut into 8 transverse slices of 800 µm thickness. All slices were incubated at 37° C. for 20 min with 3% 2,3,5-triphenyltetrazolium chloride (Sigma Aldrich, Poole, UK) dissolved in 0.1 M $Na_2HPO_4/NaH_2PO_4$ buffer adjusted to pH 7.4. Slices were fixed overnight in 10% formaldehyde. Slices were placed between two cover slips and sides of each slice were digitally imaged using a high-resolution optical scanner. The digital images were then analyzed using SigmaScan software (SPSS, US). The size of infarcted area (pale), left ventricle (LV) area at risk (red) and normally perfused LV zone (blue) were outlined in each section by identification of their color appearance and color borders. Areas were quantified on both sides of each slice and averaged by an investigator. Infarct size was calculated as a % of risk zone for each animal.

Figure 16A:
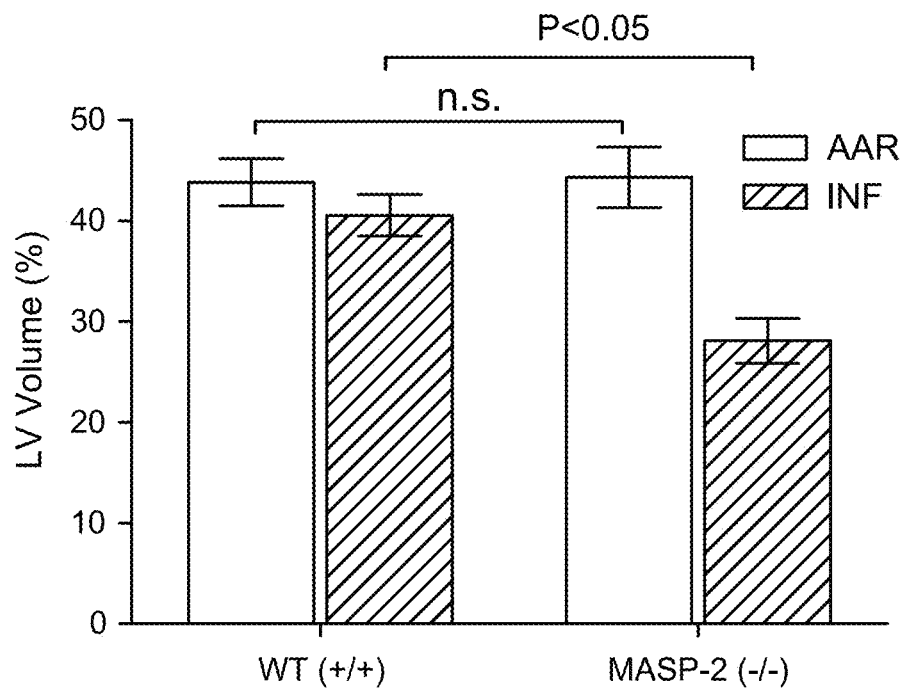
FIG. 16A presents results demonstrating the infarct size for wild type (+/+) and reduced infarct size in MASP-2 (−/−) mice after injury in a coronary artery occlusion and reperfusion model, as described in Example 27.
Figure 16B:
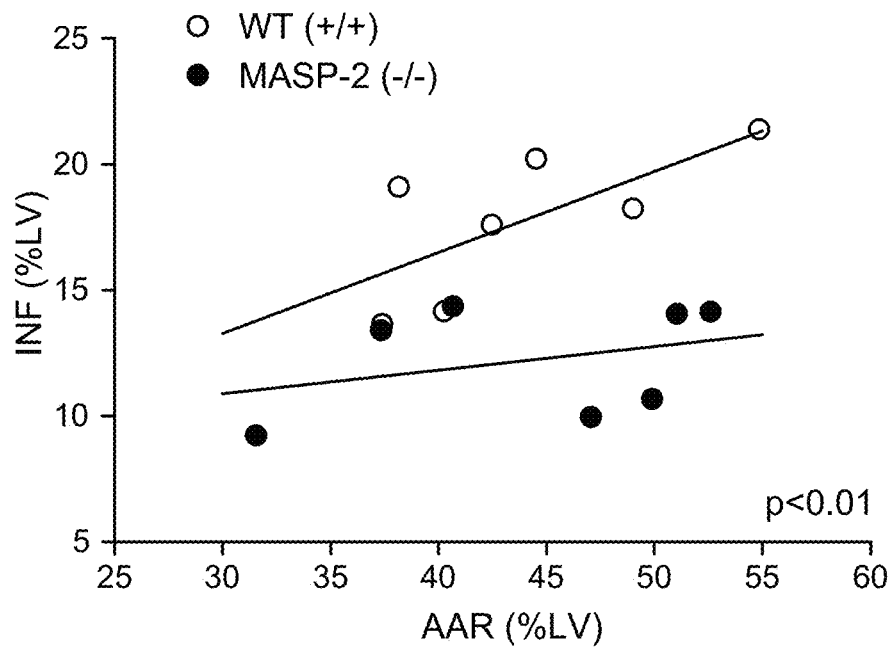
FIG. 16B presents results showing the distribution of the individual animals tested in the coronary artery occlusion and reperfusion model, as described in Example 27.

Results: The size of infarcted area (pale), LV area at risk (red) and normally perfused LV zone (blue) were outlined in each section by identification of their color appearance and color borders. Areas were quantified on both sides of each slice and averaged by an investigator. Infarct size was calculated as a % of risk zone for each animal. FIG. 16A shows the evaluation of seven WT (+/+) mice and seven MASP-2 (-/-) mice for the determination of their infarct size after undergoing the coronary artery occlusion and reperfusion technique described above. As shown in FIG. 16A, MASP-2 (-/-) mice displayed a statistically significant reduction (p<0.05) in the infarct size versus the wildtype (+/+) mice, indicating a protective myocardial effect from damage in the ischemia reperfusion injury model. FIG. 16B shows the distribution of the individual animals tested, indicating a clear protective effect for the MASP-2 (-/-) mice.

Example 28

This example describes the results of MASP-2-/- in a Murine Macular Degeneration Model.

Background/Rationale: Age-related macular degeneration (AMD) is the leading cause of blindness after age 55 in the industrialized world. AMD occurs in two major forms: neovascular (wet) AMD and atrophic (dry) AMD. The neovascular (wet) form accounts for 90% of severe visual loss associated with AMD, even though only ~20% of individuals with AMD develop the wet form. Clinical hallmarks of AMD include multiple drusen, geographic atrophy, and choroidal neovascularization (CNV). In December, 2004, the FDA approved Macugen (pegaptanib), a new class of ophthalmic drugs to specifically target and block the effects of vascular endothelial growth factor (VEGF), for treatment of the wet (neovascular) form of AMD (Ng et al., *Nat Rev. Drug Discov* 5:123-32 (2006)). Although Macugen represents a promising new therapeutic option for a subgroup of AMD patients, there remains a pressing need to develop additional treatments for this complex disease. Multiple, independent lines of investigation implicate a central role for complement activation in the pathogenesis of AMD. The pathogenesis of choroidal neovascularization (CNV), the most serious form of AMD, may involve activation of complement pathways.

Over twenty-five years ago, Ryan described a laser-induced injury model of CNV in animals (Ryan, S. J., *Tr. Am. Opth. Soc.* LXXTII:707-745, 1979). The model was initially developed using rhesus monkeys, however, the same technology has since been used to develop similar models of CNV in a variety of research animals, including the mouse (Tobe et al., *Am. J. Pathol.* 153:1641-46, 1998). In this model, laser photocoagulation is used to break Bruch's membrane, an act which results in the formation of CNV-like membranes. The laser-induced model captures many of the important features of the human condition (for a recent review, see Ambati et al., *Survey Ophthalmology* 48:257-293, 2003). The laser-induced mouse model is now well established, and is used as an experimental basis in a large, and ever increasing, number of research projects. It is generally accepted that the laser-induced model shares enough biological similarity with CNV in humans that preclinical studies of pathogenesis and drug inhibition using this model are relevant to CNV in humans.

Methods:

A MASP-2-/- mouse was generated as described in Example 1 and backcrossed for 10 generations with C57B1/6. The current study compared the results when MASP-2 (-/-) and MASP-2 (+/+) male mice were evaluated in the course of laser-induced CNV, an accelerated model of neovascular AMD focusing on the volume of laser-induced CNV by scanning laser confocal microscopy as a measure of tissue injury and determination of levels of VEGF, a potent angiogenic factor implicated in CNV, in the retinal pigment epithelium (RPE)/choroids by ELISA after laser injury.

Induction of choroidal neovascularization (CNV): Laser photocoagulation (532 nm, 200 mW, 100 ms, 75 μm; Oculight GL, Iridex, Mountain View, Calif.) was performed on both eyes of each animal on day zero by a single individual masked to drug group assignment. Laser spots were applied in a standardized fashion around the optic nerve, using a slit lamp delivery system and a coverslip as a contact lens. The morphologic end point of the laser injury was the appearance of a cavitation bubble, a sign thought to correlate with the disruption of Bruch's membrane. The detailed methods and endpoints that were evaluated are as follows.

Fluorescein Angiography: Fluorescein angiography was performed with a camera and imaging system (TRC 50 1A camera; ImageNet 2.01 system; Topcon, Paramus, N.J.) at 1 week after laser photocoagulation. The photographs were captured with a 20-D lens in contact with the fundus camera lens after intraperitoneal injection of 0.1 ml of 2.5% fluorescein sodium. A retina expert not involved in the laser photocoagulation or angiography evaluated the fluorescein angiograms at a single sitting in masked fashion.

Volume of choroidal neovascularization (CNV): One week after laser injury, eyes were enucleated and fixed with 4% paraformaldehyde for 30 min at 4° C. Eye cups were obtained by removing anterior segments and were washed three times in PBS, followed by dehydration and rehydration through a methanol series. After blocking twice with buffer (PBS containing 1% bovine serumalbumin and 0.5% Triton X-100) for 30 minutes at room temperature, eye cups were incubated overnight at 4° C. with 0.5% FITC-isolectin B4 (Vector laboratories, Burlingame, Calif.), diluted with PBS containing 0.2% BSA and 0.1% Triton X-100, which binds terminal β-D-galactose residues on the surface of endothelial cells and selectively labels the murine vasculature. After two washings with PBS containing 0.1% Triton X-100, the neurosensory retina was gently detached and severed from the optic nerve. Four relaxing radial incisions were made, and the remaining RPE-choroid-sclera complex was flat-mounted in antifade medium (Immu-Mount Vectashield Mounting Medium; Vector Laboratories) and cover-slipped.

Flatmounts were examined with a scanning laser confocal microscope (TCS SP; Leica, Heidelberg, Germany). Vessels were visualized by exciting with blue argon wavelength (488 nm) and capturing emission between 515 and 545 nm. A 40× oil-immersion objective was used for all imaging studies. Horizontal optical sections (1 μm step) were obtained from the surface of the RPE-choroid-sclera complex. The deepest focal plane in which the surrounding choroidal vascular network connecting to the lesion could be identified was judged to be the floor of the lesion. Any vessel in the laser-targeted area and superficial to this reference plane was judged as CNV. Images of each section were digitally stored. The area of CNV-related fluorescence was measured by computerized image analysis with the microscope software (TCS SP; Leica). The summation of whole fluorescent area in each horizontal section was used as an index for the volume of CNV. Imaging was performed by an operator masked to treatment group assignment.

Because the probability of each laser lesion developing CNV is influenced by the group to which it belongs (mouse, eye, and laser spot), the mean lesion volumes were compared using a linear mixed model with a split plot repeated-measures design. The whole plot factor was the genetic group to which the animal belongs, whereas the split plot factor was the eye. Statistical significance was determined at the 0.05 level. Post hoc comparisons of means were constructed with a Bonferroni adjustment for multiple comparisons.

VEGF ELISA. At three days after injury by 12 laser spots, the RPE-choroid complex was sonicated in lysis buffer (20 mM imidazole HCl, 10 mM KCl, 1 mM $MgCL_2$, 10 mM EGTA, 1% Triton X-100, 10 mM NaF, 1 mM Na molybdate, and 1 mM EDTA with protease inhibitor) on ice for 15 min. VEGF protein levels in the supernatant were determined by an ELISA kit (R&D Systems, Minneapolis, Minn.) that recognizes all splice variants, at 450 to 570 nm (Emax; Molecular Devices, Sunnyvale, Calif.), and normalized to total protein. Duplicate measurements were performed in a masked fashion by an operator not involved in photocoagulation, imaging, or angiography. VEGF numbers were represented as the mean+/−SEM of at least three independent experiments and compared using the Mann-Whitney U test. The null hypothesis was rejected at $P<0.05$.

Figure 17A:
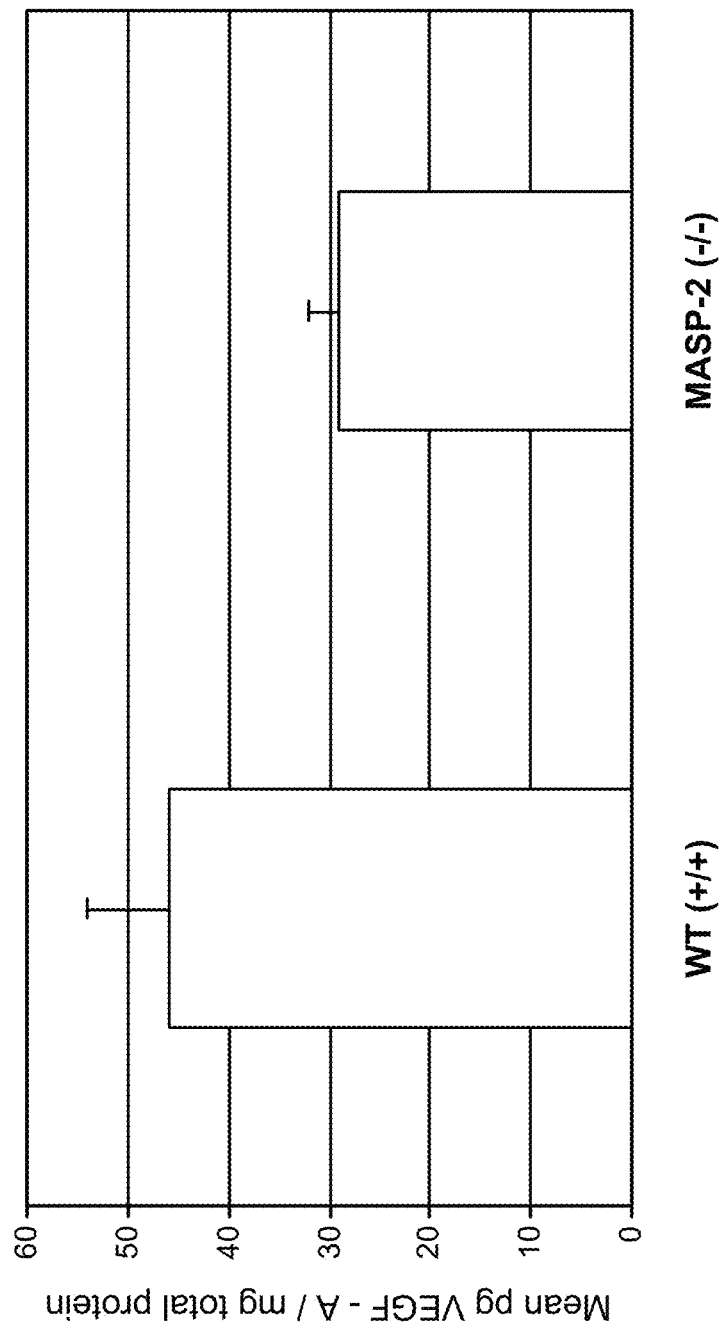
FIG. 17A presents results showing the baseline VEGF protein levels in RPE-choroid complex isolated from wild type (+/+) and MASP-2 (−/−) mice, as described in Example 28.
Figure 17B:
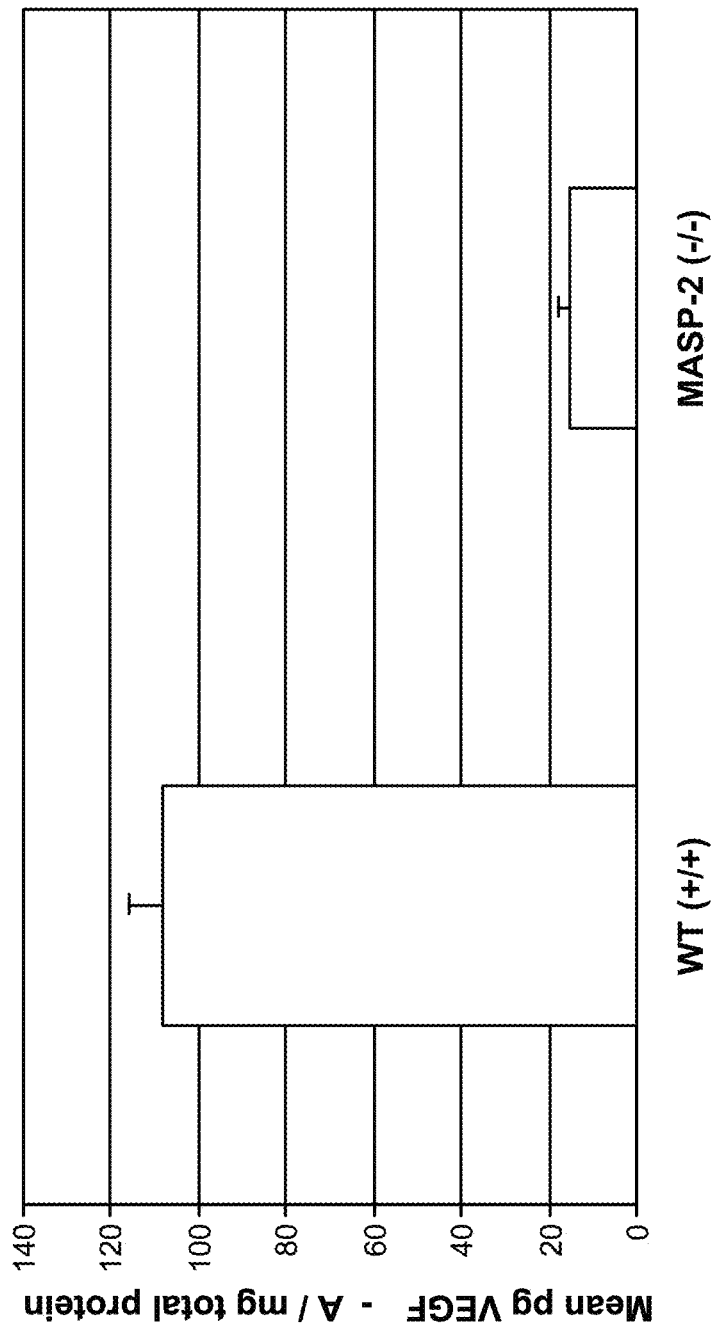
FIG. 17B presents results showing the VEGF protein levels in RPE-choroid complex at day 3 in wild type (+/+) and MASP-2 (−/−) mice following laser induced injury in a macular degeneration model, as described in Example 28.

Results:

Assessment of VEGF Levels:

FIG. 17A graphically illustrates the VEGF protein levels in RPE-choroid complex isolated from C57B16 wildtype and MASP-2(−/−) mice at day zero. As shown in FIG. 17A, the assessment of VEGF levels indicate a decrease in baseline levels for VEGF in the MASP-2 (−/−) mice versus the C57b1 wildtype control mice. FIG. 17B graphically illustrates VEGF protein levels measured at day three following laser induced injury. As shown in FIG. 17B VEGF levels were significantly increased in the wildtype (+/+) mice three days following laser induced injury, consistent with published studies (Nozaki et al., *Proc. Natl. Acad. Sci. USA* 103:2328-33 (2006)). However, surprisingly very low levels of VEGF were seen in the MASP-2 (−/−) mice.

Figure 18:
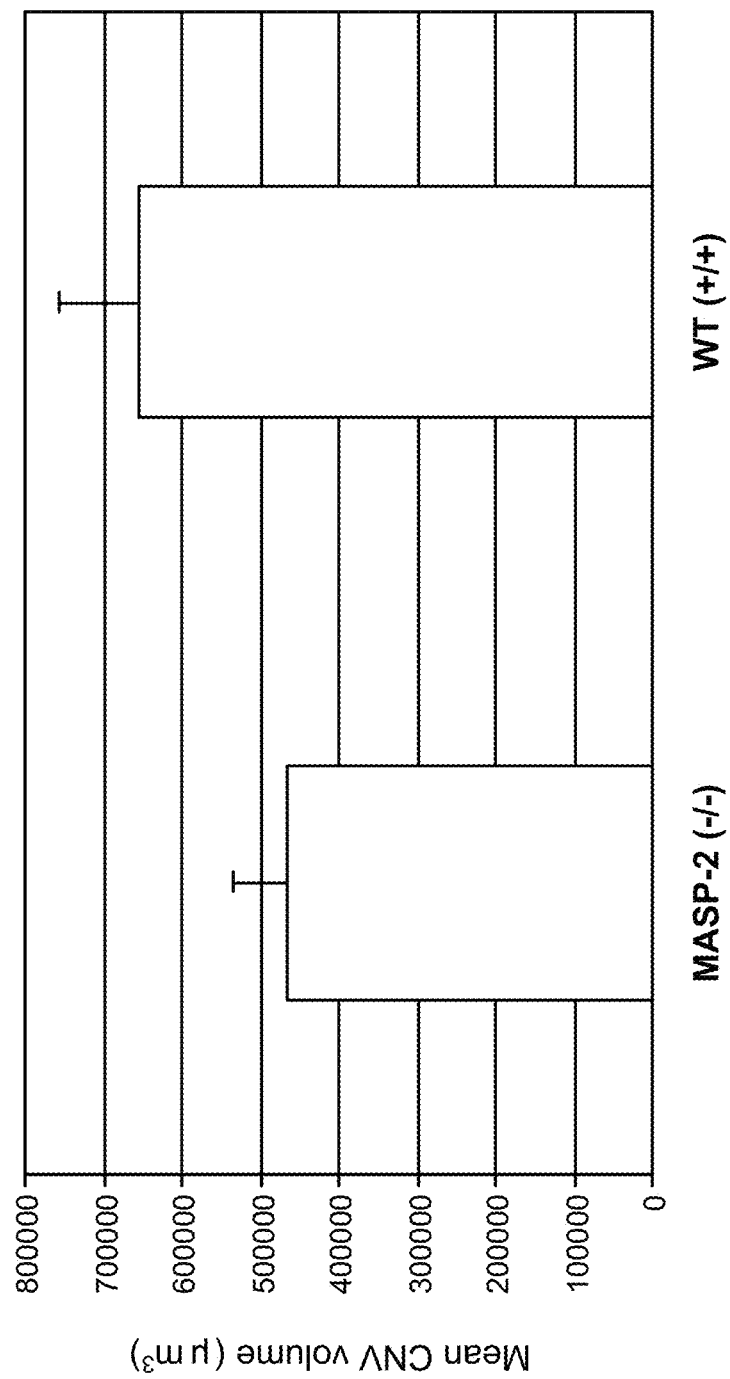
FIG. 18 presents results showing the mean choroidal neovascularization (CNV) volume at day seven following laser induced injury in wild type (+/+) and MASP-2 (−/−) mice, as described in Example 28.

Assessment of Choroidal Neovascularization (CNV):

In addition to the reduction in VEGF levels following laser induced macular degeneration, CNV area was determined before and after laser injury. FIG. 18 graphically illustrates the CNV volume measured in C57bl wildtype mice and MASP-2(−/−) mice at day seven following laser induced injury. As shown in FIG. 18, the MASP-2 (−/−) mice displayed about a 30% reduction in the CNV area following laser induced damage at day seven in comparison to the wildtype control mice.

These findings indicate a reduction in VEGF and CNV as seen in the MASP (−/−) mice versus the wildtype (+/+) control and that blockade of MASP-2 with an inhibitor would have a preventive or therapeutic effect in the treatment of macular degeneration.

Example 29

This example describes the results of MASP-2(−/−) in a Murine Monoclonal Antibody Induced Rheumatoid Arthritis Model Background/Rationale: The most commonly used animal model for rheumatoid arthritis (RA) is the collagen-induced arthritis (CIA) (for recent review, see Linton and Morgan, *Mol. Immunol.* 36:905-14, 1999). Collagen type II (CII) is one of the major constituents of the articular matrix proteins and immunization with native CII in adjuvant induces autoimmune polyarthritis by a cross-reactive autoimmune response to CII in joint cartilage. As in RA, susceptibility to CIA is linked to the expression of certain class II MHC alleles. Some strains of mice, including the C57Bl/6 strain, are resistant to classic CIA because they lack an appropriate MHC haplotype and therefore do not generate high anti-CII antibody titers. However, it has been found that consistent arthritis can be induced in all strains of mice by the i.v. or i.p. administration into mice of a cocktail of four specific monoclonal antibodies against type II collagen. These arthridogenic monoclonal antibodies are commercially available (Chondrex, Inc., Redmond, Wash.). This passive transfer model of CIA has been used successfully in a number of recent published reports using the C57B1/6 mouse strain (Kagari et al., *J. Immunol.* 169:1459-66, 2002; Kato et al., *J. Rheumatol.* 30:247-55, 2003; Banda et al, *J. Immunol.* 177:1904-12, 2006). The following study compared the sensitivity of wild type (+/+) (WT) and MASP-2 (−/−) mice, both sharing the C57B1/6 genetic background, to development of arthritis using the passive transfer model of CIA.

Methods:

Animals: A MASP-2(−/−) mouse was generated as described in Example 1 and backcrossed for 10 generations with C57B1/6. Fourteen male and female C57BL/6 wild type mice that were seven to eight weeks old at the time of antibody injection and ten male and female MASP-2(−/−) and wildtype (+/+) C57B1/6 mice that were seven to eight weeks old at time of antibody injection were used in this study. Twenty mice were injected with a monoclonal antibody cocktail to obtain 20 solid responders (two groups of ten). The animals (ten/group) were housed with five animals/cage, and were acclimated for five to seven days prior to initiating the study.

Mice were injected intravenously with a monoclonal antibody cocktail (Chondrex, Redmond Wash.) (5 mg) on day 0 and day 1. The test agent was a monoclonal antibody+ LPS from Chondrex. On day 2, mice were dosed ip with LPS. Mice were weighed on days 0, 2, 4, 6, 8, 10, 12 and prior to termination on day 14. On day 14 the mice were anesthetized with isoflurane and bled terminally for serum. After blood collection, the mice were euthanized, with removal of both fore and hind limbs with knees, which were placed into formalin for future processing.

Treatment Groups:
Group 1 (control): 4 mice of strain C57/BL/6 WT (+/+);
Group 2 (test): 10 mice of strain C57/BL/6 WT (+/+) (received mAb cocktail plus LPS); and
Group 3 (test): 10 mice of strain C57/BL/MASP-2KO/ 6Ai (−/−) (received mAb cocktail plus LPS)

Clinical arthritic scores were assessed daily using the following scoring system: 0=normal; 1=1 hind or fore paw joint affected; 2=2 hind or fore paw joints affected; 3=3 hind or fore paw joints affected; 4=moderate (erythema and moderate swelling, or 4 digit joints affected); 5=severe (diffuse erythema and severe swelling entire paw, unable to flex digits)

Figure 19:
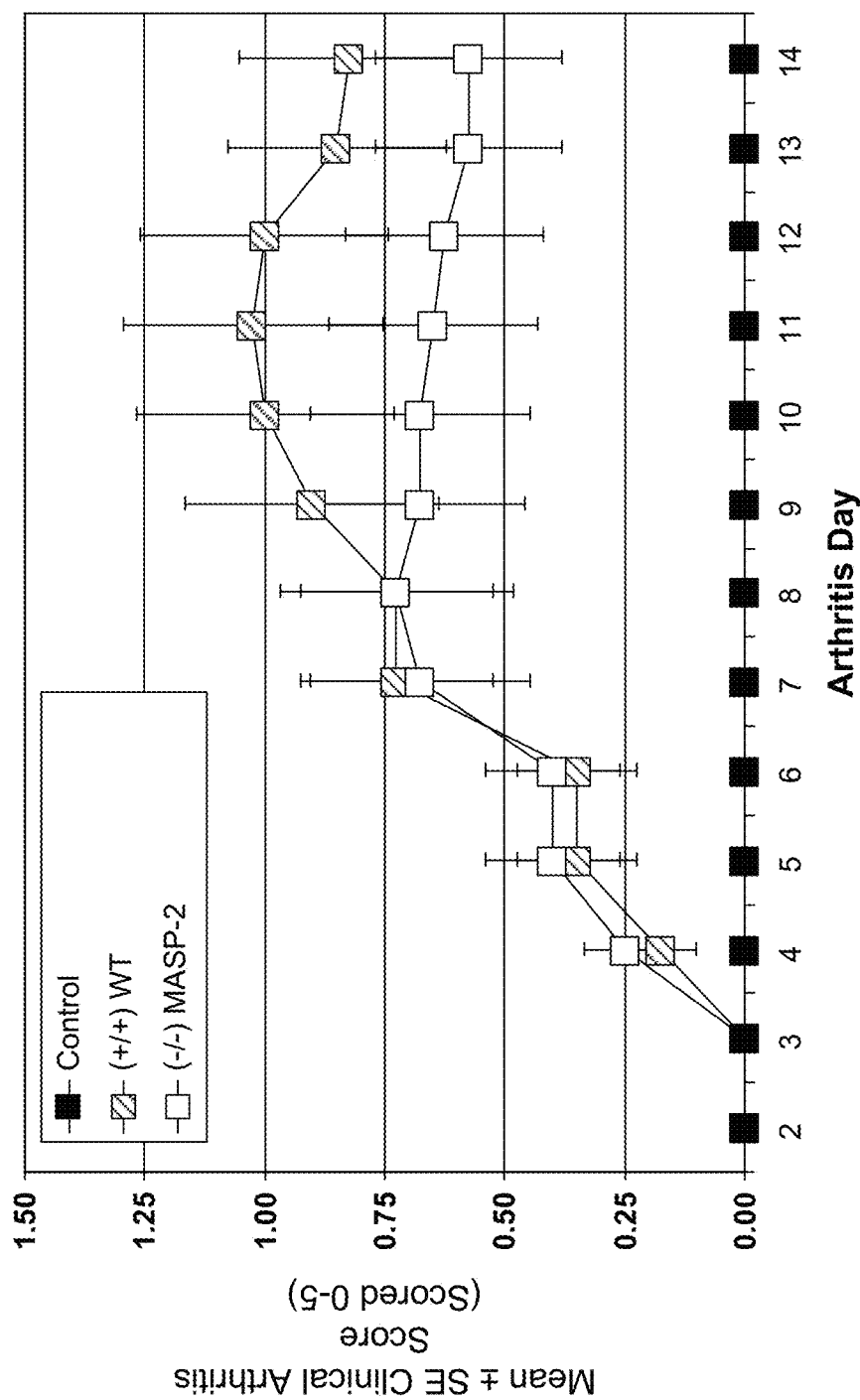
FIG. 19 presents results showing the mean clinical arthritis score of wild type (+/+) and MASP-2 (−/−) mice over time following Col2 mAb-induced rheumatoid arthritis, as described in Example 29.

Results:

FIG. 19 shows the group data plotted for the mean daily clinical arthritis score for up to two weeks. No clinical arthritis score was seen in the control group that did not receive the CoL2 MoAb treatment. The MASP (−/−) mice had a lower clinical arthritis score from day 9 to day 14. The overall clinical arthritis score with area under the curve analysis (AUC) indicated a 21% reduction in the MASP-2 (−/−) group versus the WT (+/+) mice. However, C57B16 mouse background as discussed previously did not provide for a robust overall arthritis clinical score. Due to the small incidence rate and group size, while positively trending, the data provided only trends (p=0.1) and was not statistically significant at the p<0.05 level. Additional animals in the treatment groups would be necessary to show statistical significance. Due to the reduced incidence of arthritis, the affected paw scores were evaluated for severity. No single incidence of a clinical arthritis score of greater than 3 was seen in any of the MASP-2 (−/−) mice, which was seen in 30% of the WT (+/+) mice, further suggesting that (1) the severity of the arthritis may be related to complement pathway activation and (2) that blockade of MASP-2 may have a beneficial effect in arthritis.

Example 30

This Example demonstrates that Small Mannose-Binding Lectin-Associated Protein (Map19 or sMAP) is an inhibitor of MASP-2 dependent complement activation.
Background/Rationale:
Abstract:

Mannose-binding lectin (MBL) and ficolins are pattern recognition proteins acting in innate immunity and trigger the activation of the lectin complement pathway through MBL-associated serine proteases (MASPs). Upon activation of the lectin pathway, MASP-2 cleaves C4 and C2. Small MBL-associated protein (sMAP), a truncated form of MASP-2, is also associated with MBL/ficolin-MASP complexes. To clarify the role of sMAP, we have generated sMAP-deficient (sMAP−/−) mice by targeted disruption of the sMAP-specific exon. Because of the gene disruption, the expression level of MASP-2 was also decreased in sMAP−/− mice. When recombinant sMAP (rsMAP) and recombinant MASP-2 (rMASP-2) reconstituted the MBL-MASP-sMAP complex in deficient serum, the binding of these recombinants to MBL was competitive, and the C4 cleavage activity of the MBL-MASP-sMAP complex was restored by the addition of rMASP-2, whereas the addition of rsMAP attenuated the activity. Therefore, MASP-2 is essential for the activation of C4 and sMAP plays a regulatory role in the activation of the lectin pathway.
Introduction:

The complement system mediates a chain reaction of proteolysis and assembly of protein complexes, playing a major role in biodefense as a part of both the innate and adaptive immune systems. The mammalian complement system consists of three activation pathways, the classical pathway, alternative pathway, and lectin pathway (Fujita, *Nat. Rev. Immunol.* 2: 346-353 (2002); Walport, *N Engl J Med* 344: 1058-1066 (2001)). The lectin pathway provides the primary line of defense against invading pathogens. The pathogen recognition components of this pathway, mannose-binding lectin (MBL) and ficolins, bind to arrays of carbohydrates on the surfaces of bacteria, viruses, and parasites and activate MBL-associated serum proteases (MASPs) to trigger a downstream reaction cascade. The importance of the lectin pathway for innate immune defense is underlined by a number of clinical studies linking a deficiency of MBL with increased susceptibility to a variety of infectious diseases, particularly in early childhood before the adaptive immune system is established (Jack et al., *Immunol Rev* 180:86-99 (2001); Neth et al. *Infect Immun* 68: 688-693 (2000); Summerfield et al., *Lancet* 345:886-889 (1995); Super et al., *Lancet* 2: 1236-1239 (1989)). However, the lectin pathway also contributes to the undesired activation of complement, which is involved in inflammation and tissue damage in a number of pathological conditions, including ischemia/perfusion injury in the heart and kidneys (de Vries et al., *Am J Pathol* 165:1677-1688 (2004); Fiane et al., *Circulation* 108: 849-856 (2003); Jordan et al., *Circulation* 104: 1413-1418 (2001); Walsh et al., *J Immunol* 175:541-546 (2005)).

As mentioned above, the lectin pathway involves carbohydrate recognition by MBL and ficolins (Fujita et al, *Immunol Rev* 198: 185-202 (2004); Holmskov et al, *Annu Rev Immunol* 21: 547-578 (2003); Matsushita and Fujita, *Immunobiology* 205: 490-497 (2002) and these lectins form complexes with MASP-1 (Matsushita and Fujita, *J Exp Med* 176: 1497-1502 (1992); Sato et al, *Int Immunol* 6: 665-669 (1994); Takada et al, *Biochem Biophys Res Commun* 196: 1003-1009 (1993), MASP-2 (Thiel et al, *Nature* 386:506-510 (1997), MASP-3 (Dahl et al, *Immunity* 15: 127-135 (2001), and a truncated protein of MASP-2 (small MBL-associated protein; sMAP or MAp19) (Stover et al, *J Immunol* 162: 3481-3490 (1999); Takahashi et al, *Int Immunol* 11: 8590863 (1999). The MASP family members consist of six domains; two C1r/C1s/Uegf/bone morphogenetic protein (CUB) domains, an epidermal growth factor (EGF)-like domain, two complement control protein (CCP) or short consensus repeats (SCR) domains, and a serine protease domain (Matsushita et al, *Curr Opin Immunol* 10: 29-35 (1998). MASP-2 and sMAP are generated by alternative splicing from a single structural gene, and sMAP consists of the first CUB (CUB1) domain, the EGF-like domain and an extra 4 amino acids at the C-terminal end encoded by a sMAP-specific exon. MASP-1 and MASP-3 are also generated from a single gene by alternative splicing (Schwaeble et al, *Immunobiology* 205: 455-466 (2002). When MBL and ficolins bind to carbohydrates on the surface of microbes, the proenzyme form of MASP is cleaved between the second CCP and the protease domain, resulting in the active form consisting of two polypeptides, called heavy (H)- and light (L)-chains, and thus acquiring proteolytic activities against complement components. Accumulated evidence shows that MASP-2 cleaves C4 and C2 (Matsushita et al, *J Immunol* 165: 2637-2642 (2000) which leads to the formation of the C3 convertase (C4bC2a). We proposed that MASP-1 cleaves C3 directly and subsequently activates the amplification loop (Matsushita and Fujita, *Immunobiology* 194: 443-448 (1995), but this function is controversial (Ambrus et al, *J Immunol* 170: 1374-1382 (2003). Although MASP-3 also contains a serine protease domain in the L-chain and exhibits its proteolytic activity against a synthetic substrate (Zundel et al, *J Immunol* 172: 4342-4350 (2004), its physiological substrates have not been identified. The function of sMAP lacking the serine protease domain remains unknown.

In the present study, to clarify the role of sMAP in activation of the lectin complement pathway, we have disrupted the sMAP-specific exon that encodes 4 amino acid residues (EQSL) at the C-terminal end of sMAP, and generated sMAP−/− mice. We report here for the first time the ability of sMAP to down-regulate activation of the lectin pathway.

Materials and Methods

Mice

Figure 20A:
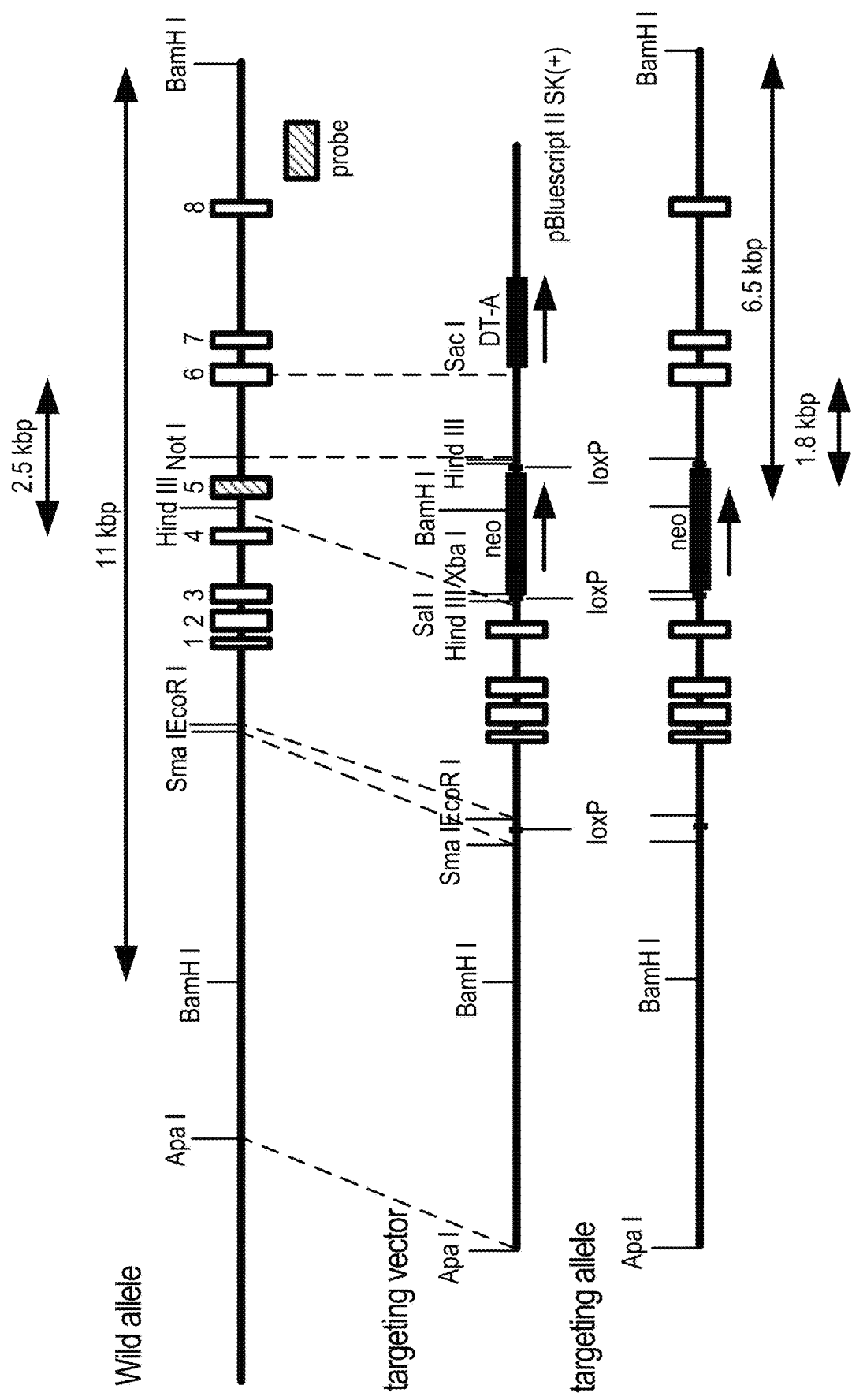
FIG. 20A is a diagram showing the targeted disruption of the sMAP (Map19) gene, as described in Example 30.
Figure 20B:
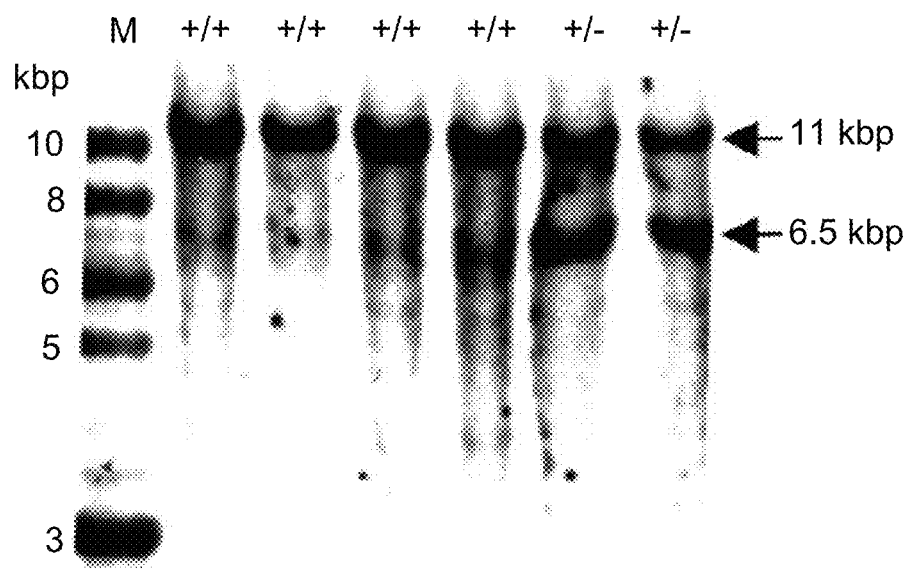
FIG. 20B presents Southern blot analysis of genomic DNA isolated from offspring derived from mating male sMAP (−/−) chimeric mice with female C57BL/6 mice, as described in Example 30.
Figure 20C:
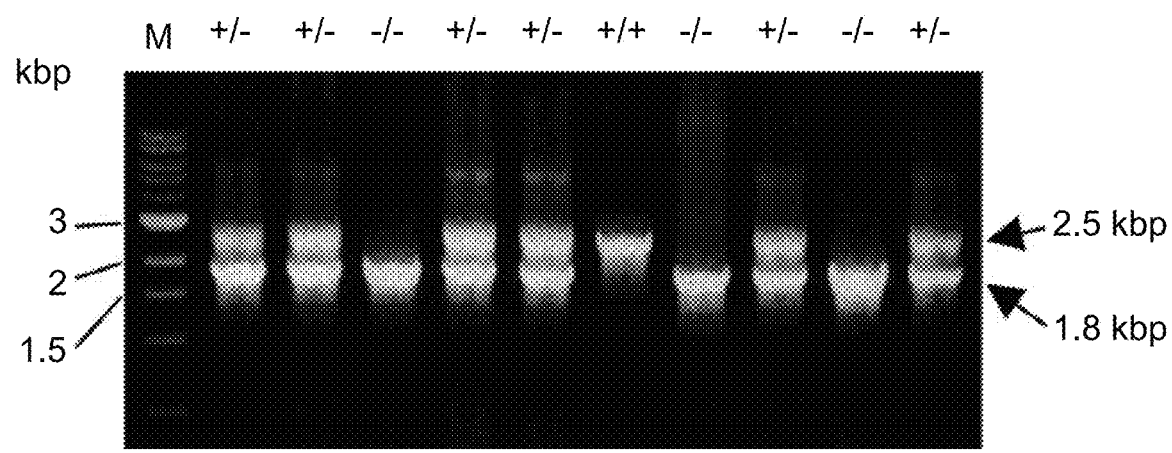
FIG. 20C presents PCR genotyping analysis of wild type (+/+) and sMAP (−/−) mice, as described in Example 30.

A targeting vector was constructed containing exon 1-4 and part of exon 6 of the 129/Sv mouse MASP-2 gene and a neomycin resistance gene cassette instead of exon 5 (FIG. 20A). A DT-A gene was inserted into the 3' end of the vector and three lox p sites were inserted to perform conditional targeting to remove the neomycin cassette and promoter region in the future. The targeting vector was electroporated into 129/Sv ES cells. The targeted ES clones were microinjected into C57BL/6J blastocysts which were implanted into uteri of foster ICR mothers. Male chimeric mice were mated with female C57BL/6J mice to produce heterozygous (+/−) mice. Heterozygous (+/−) mice were screened by Southern blot analysis of tail DNA digested with BamH I using the probe indicated in FIG. 20A. Southern blot analysis showed 6.5-kbp and 11-kbp bands in DNA from heterozygous (+/−) mice (FIG. 20B). Heterozygous (+/−) mice were backcrossed with C57BL/6J mice. To obtain homozygous (−/−) mice, heterozygous (+/−) mice were intercrossed. Homozygous (−/−) mice (C57BL/6J background) were identified by PCR-based genotyping of tail DNA. PCR analysis was performed using a mixture of exon 4-specific and neo gene-specific sense primers and an exon 6-specific antisense primer. DNA from homozygous (−/−) mice yielded a single 1.8-kbp band (FIG. 20C). In all experiments, 8 to 12 week old mice were used according to the guidelines for animal experimentation of Fukushima Medical University.

Northern Blot Analysis

Poly(A)+ RNA (1 μg) from wild-type (+/+) and homozygous (−/−) mouse livers was separated by electrophoresis, transferred to a nylon membrane, and hybridized with a 32P-labeled cDNA probe specific for sMAP, MASP-2 H-chain, MASP-2 L-chain, or the neo gene. The same membrane was stripped and rehybridized with a probe specific for glyceraldehyde-3-phosphate dehydrogenase (GAPDH).

Quantitative RT-PCR

Real-time PCR was performed with the LightCycler System (Roche Diagnostics). cDNAs synthesized from 60 ng of poly(A)+ RNA from wild-type (+/+) and homozygous (−/−) mouse livers were used as templates for real-time PCR and cDNA fragments of MASP-2 H- and L-chains and sMAP were amplified and monitored.

Immunoblotting

The sample was electrophoresed on 10 or 12% SDS-polyacrylamide gels under reducing conditions and proteins were transferred to polyvinylidene difluoride (PVDF) membranes. Proteins on the membranes were detected with anti-MASP-1 antiserum raised against the L-chain of MASP-1 or with anti-MASP-2/sMAP antiserum raised against the peptide from the H-chain of MASP-2.

Detection of MASPs and sMAP in the MBL-MASP-sMAP Complex

Mouse serum (20 μl) was added to 480 μl of TBS-Ca2+ buffer (20 mM Tris-HCl, pH 7.4, 0.15 M NaCl, and 5 mM CaCl2) containing 0.1% (w/v) BSA (TBS-Ca2+/BSA) and incubated with 40 μl of 50% mannan-agarose gel slurry (Sigma-Aldrich, St. Louis, Mo.) in TBS-Ca2+/BSA buffer at 4° C. for 30 min. After incubation each gel was washed with TBS-Ca2+ buffer and the sampling buffer for SDS-PAGE was added to the gel. The gel was boiled and the supernatant was subjected to SDS-PAGE, followed by immunoblotting to detect MASP-1, MASP-2, and sMAP in the MBL complex.

C4 Deposition Assay

Mouse serum was diluted with TBS-Ca2+/BSA buffer up to 100 μl. The diluted sample was added to mannan-coated microtiter wells and incubated at room temperature for 30 min. The wells were washed with the chilled washing buffer (TBS-Ca2+ buffer containing 0.05% (v/v) Tween 20). After the washing, human C4 was added to each well and incubated on ice for 30 min. The wells were washed with the chilled washing buffer and HRP-conjugated anti-human C4 polyclonal antibody (Biogenesis, Poole, England) was added to each well. Following incubation at 37° C. for 30 min, the wells were washed with the washing buffer and 3,3',5,5'-tetramethylbenzidine (TMB) solution was added to each well. After developing, 1 M $H_3PO_4$ was added and the absorbance was measured at 450 nm.

C3 Deposition Assay

Mouse serum was diluted with BBS buffer (4 mM barbital, 145 mM NaCl, 2 mM CaCl2, and 1 mM MgCl2, pH 7.4) containing 0.1% (w/v) HSA up to 100 μl. The diluted sample was added to mannan-coated microtiter wells and incubated at 37° C. for 1 h. The wells were washed with the washing buffer. After the washing, HRP-conjugated anti-human C3c polyclonal antibody (Dako, Glostrup, Denmark) was added to each well. Following incubation at room temperature for 1 h, the wells were washed with the washing buffer and TMB solution was added to each well. The color was measured as described above.

Recombinants

Recombinant mouse sMAP (rsMAP), rMASP-2, and the inactive mouse MASP-2 mutant (MASP-2i) whose active-site serine residue in the serine protease domain was substituted for the alanine residue were prepared as described previously (Iwaki and Fujita, 2005).

Reconstitution of the MBL-MASP-sMAP Complex

Homozygous (−/−) mouse serum (20 μl) and various amounts of MASP-2i and/or rsMAP were incubated in a total volume of 40 μl in TBS-Ca2+ buffer on ice overnight. The mixture was incubated with mannan-agarose gel slurry, and MASP-2i and rsMAP in the MBL-MASP complex bound to the gel were detected as described in "Detection of MASPs and sMAP in the MBL-MASP-sMAP complex".

Reconstitution of the C4 Deposition Activity

Homozygous (−/−) mouse serum (0.5 μl) and various amounts of rMASP-2 and/or rsMAP were incubated in a total volume of 20 μl in TBS-Ca2+ on ice overnight. The mixture was diluted with 80 μl of TBS-Ca2+/BSA buffer and added to mannan-coated wells. All subsequent procedures were performed as described in "C4 deposition assay".

Results

FIG. 20: Targeted disruption of the sMAP gene. (A) Partial restriction maps of the MASP-2/sMAP gene, the targeting vector, and the targeted allele. The sMAP-specific exon (exon 5) was replaced with a neo gene cassette. (B) Southern blot analysis of genomic DNA from offspring derived from mating male chimeric mice with female C57BL/6J mice. Tail DNA was digested with BamH I and hybridized with the probe depicted in (A). A 11-kbp band was derived from the wild-type allele, and a 6.5-kbp band from the targeted allele. (C) PCR genotyping analysis. Tail DNA was analyzed using a mixture of exon 4-specific and neo gene-specific sense primers and an exon 6-specific antisense primer. A 2.5-kbp band was obtained from wild-type allele, a 1.8-kb band from the targeted allele.

FIG. 21: The expression of sMAP and MASP-2 mRNAs in homozygous (−/−) mice. (A) Northern blot analysis. Poly(A)+ RNAs from wild-type (+/+) and homozygous (−/−) mouse livers was electrophoresed, transferred to a nylon membrane, and hybridized with a 32P-labeled probe specific for sMAP, MASP-2 H-chain, MASP-2 L-chain, or the neo gene. A specific band for neo (2.2 kb) was observed in homozygous (−/−) mice. (B) Quantitative RT-PCR. MASP-2 H- and L-chains and sMAP cDNA fragments were amplified by real-time PCR in a LightCycler instrument (Roche Diagnostics). cDNAs synthesized from poly(A)+ RNAs from wild-type (+/+) and homozygous (−/−) mouse livers were used as templates. The data shown are the means of two experiments.

FIG. 22: Deficiency of MASP-2 in homozygous (−/−) mouse serum. (A) Immunoblotting of MASP-2 and sMAP in mouse serum. Wild-type (+/+) or homozygous (−/−) mouse serum (2 μl) was subjected to immunoblotting and detected with anti-MASP-2/sMAP antiserum. (B) Detection of MASPs and sMAP in the MBL-MASP-sMAP complex. Mouse serum was incubated with mannan-agarose gel and sMAP, MASP-1, and MASP-2 in the MBL complex bound to the gel were detected as described in Materials and Methods.

FIG. 23: Decreased cleavage of C4 and C3 in homozygous (−/−) mouse serum. (A) Deposition of C4 on mannan-coated wells. Mouse serum was diluted 2-fold and incubated in mannan-coated wells at room temperature for 30 min. After the washing of the wells, human C4 was added to each well and incubated on ice for 30 min. The amount of human C4 deposited on the wells was measured using HRP-conjugated anti-human C4 polyclonal antibody. (B) Deposition of C3 on mannan-coated wells. Diluted mouse serum was added to mannan-coated wells and incubated at 37° C. for 1 h. The deposition of endogenous C3 on the wells was detected with HRP-conjugated anti-human C3c polyclonal antibody.

FIG. 24: Competitive binding of sMAP and MASP-2 to MBL. (A) Reconstitution of the MBL-MASP-sMAP complex in homozygous (−/−) mouse serum. MASP-2i and/or rsMAP (4 μg) were incubated with homozygous (−/−) mouse serum (20 μl). The mixture was further incubated with mannan-agarose gel, and rsMAP and MASP-2i in the fraction bound to the gel were detected by immunoblotting. (B) Various amounts of MASP-2i (0-5 μg) and a constant amount of rsMAP (5 μg) were incubated with homozygous (−/−) mouse serum (20 μl) and further incubated with mannan-agarose gel. (C) A constant amount of MASP-2i (0.5 μg) and various amounts of rsMAP (0-20 μg) were incubated with homozygous (−/−) mouse serum (20 μl). (D) Various amounts of rsMAP (0-20 μg) was incubated with wild-type (+/+) mouse serum (20 μl).

FIG. 25: Restoration of the C4 deposition activity by addition of rMASP-2. Various amounts of rsMAP (0-5 μg) (A) or rMASP-2 (0-1.5 μg) (B) were incubated with 0.5 μl of homozygous (−/−) mouse serum in a total volume of 20 μl in TBS-Ca2+ buffer on ice overnight. Then the mixture was diluted with 80 μl of TBS-Ca2+/BSA buffer and added to mannan-coated wells and the amount of C4 deposited on the wells was measured.

FIG. 26: Reduction of the C4 deposition activity by addition of sMAP. (A) rMASP-2 (1 μg) and various amounts of rsMAP (0-0.5 μg) were incubated with 0.5 μl of homozygous (−/−) mouse serum. The mixture was added to mannan-coated wells and the amount of C4 deposited on the wells was measured. (B) rsMAP (0-0.7 μg) was incubated with wild-type serum (0.5 μl) and the amount of C4 deposited on mannan-coated wells was measured.

Results:

The Expression of sMAP and MASP-2 in Homozygous (−/−) Mice

To clarify the role of sMAP in vivo, we established a gene targeted mouse which lacks sMAP. A targeting vector was constructed to replace the specific exon for sMAP (exon 5) with a neomycin resistance gene cassette (FIG. 20A). Positive ES clones were injected into C57BL/6 blastocysts, and the founder chimeras bred with C57BL/6J females. Southern blot analysis of tail DNA from agouti-color pups showed a germinal transmission of the targeted allele (FIG. 20B). Heterozygous (+/−) mice were screened by Southern blot analysis of tail DNA digested with BamH I using the probe indicated in FIG. 20A. Southern blot analysis showed 6.5-kbp and 11-kbp bands in DNA from heterozygous (+/−) mice (FIG. 20B). Heterozygous (+/−) mice were back-crossed with C57BL/6J mice. To obtain homozygous (−/−) mice, heterozygous (+/−) mice were intercrossed. Homozygous (−/−) mice (C57BL/6J background) were identified by PCR based genotyping of tail DNA, yielding a single 1.8-kbp band (FIG. 20C).

Figure 21A:
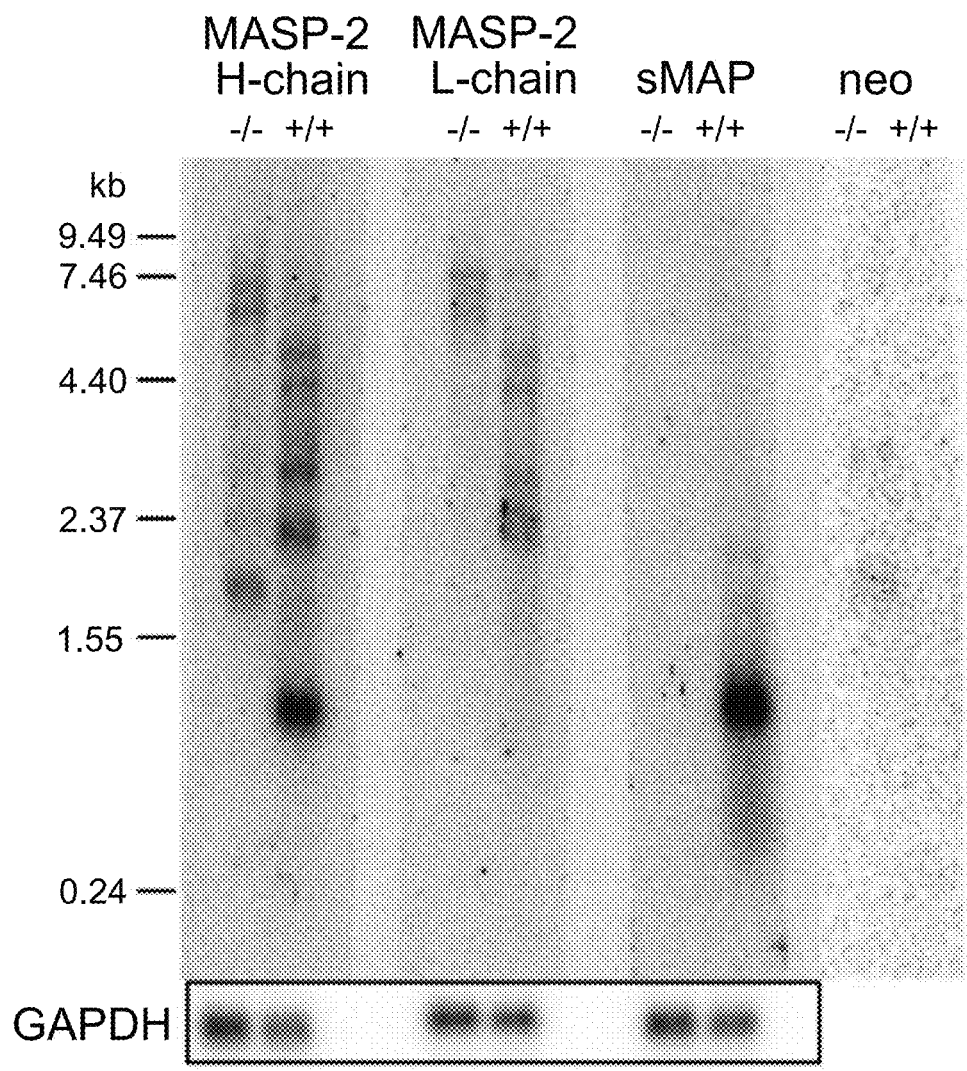
FIG. 21A presents Northern blot analysis of sMAP and MASP-2 mRNA in sMAP (−/−) mice, as described in Example 30.
Figure 21B:
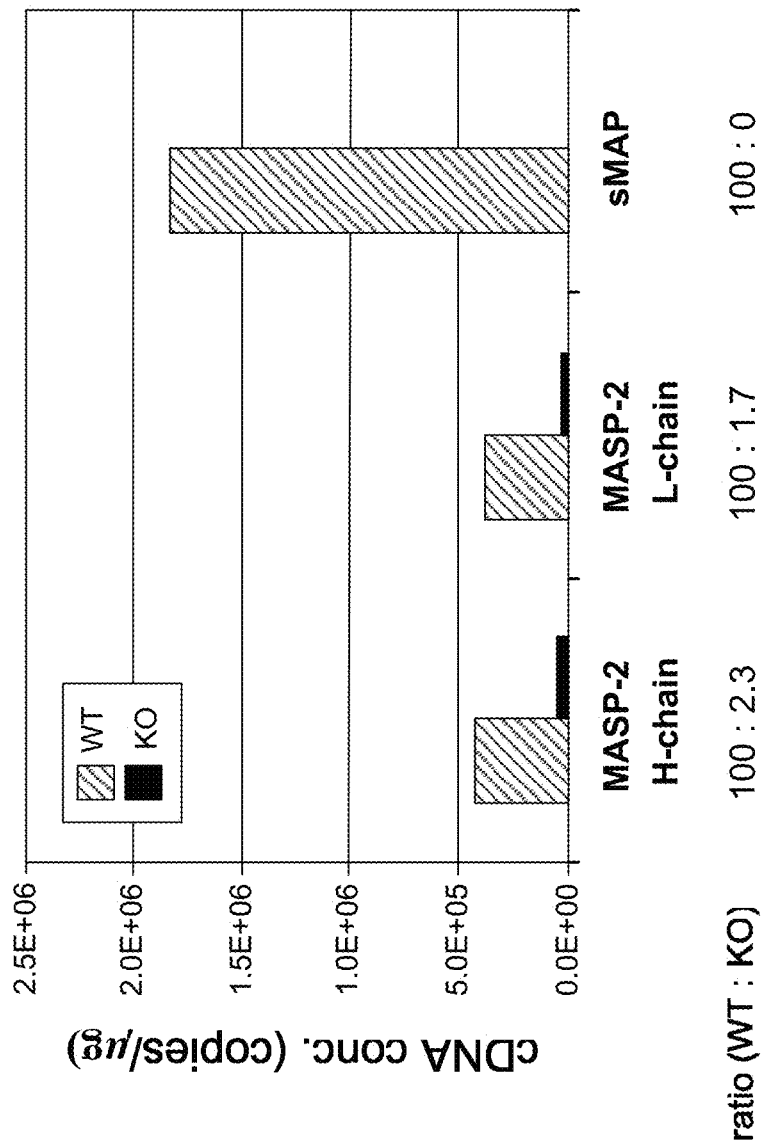
FIG. 21B presents quantitative RT-PCR analysis of cDNA encoding MASP-2 H-chain, MASP-2 L-chain and sMAP, in wild type (+/+) and sMAP (−/−) mice, as described in Example 30.
Figure 22A:
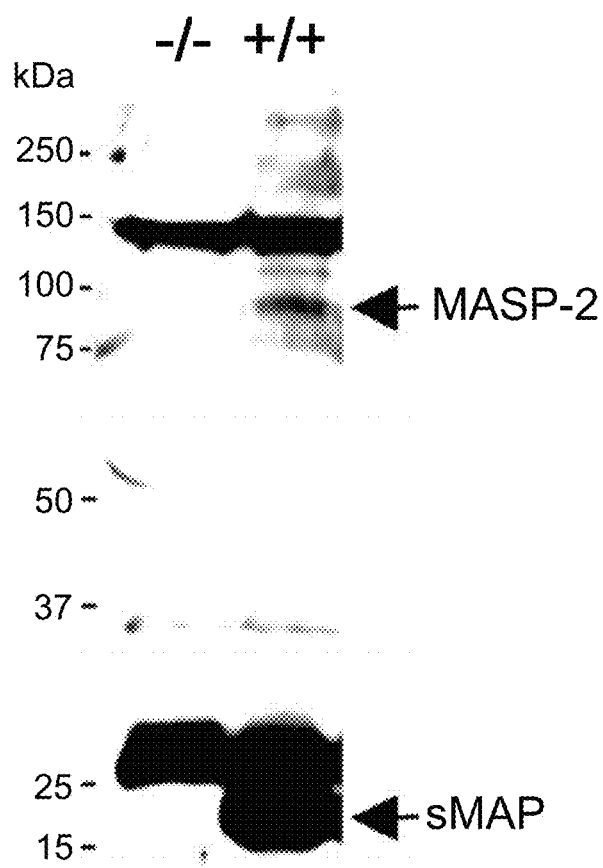
FIG. 22A presents an immunoblot of sMAP (−/−), i.e., MAp19 (−/−), demonstrating deficiency of MASP-2 and sMAP in mouse serum, as described in Example 30.
Figure 22B:
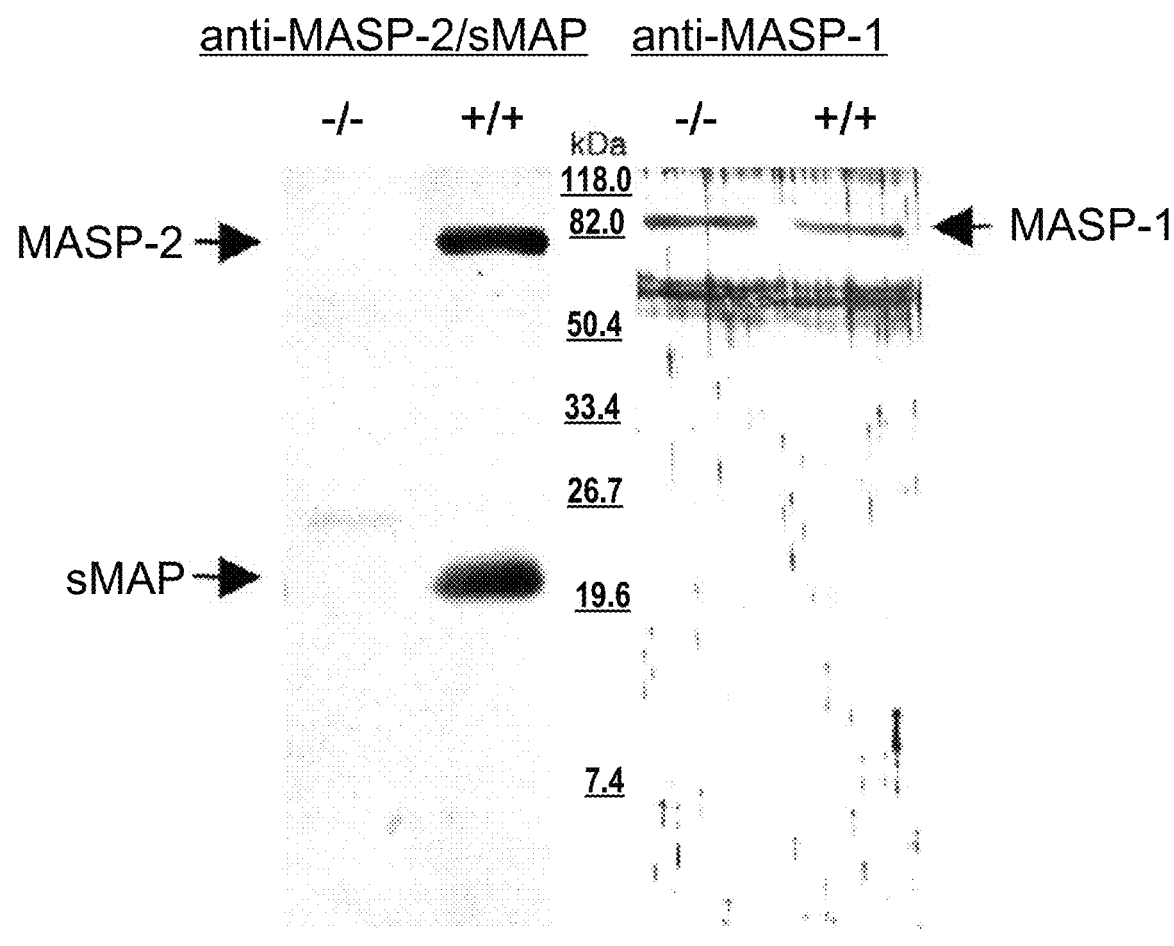
FIG. 22B presents results demonstrating that MASP-2 and sMAP were detected in the MBL-MASP-sMAP complex, as described in Example 30.

Homozygous (−/−) mice developed normally and showed no significant difference in body weight from wild-type (+/+) mice. There were no morphological differences between them either. In a Northern blot analysis, the probe specific for sMAP detected a single 0.9-kb band in wild-type (+/+) mice, whereas no specific bands were detected in homozygous (−/−) mice (FIG. 21A). When the probe specific for MASP-2 H- or L-chain was used, several specific bands were detected in wild-type (+/+) mice as reported previously (Stover et al, 1999) and the H-chain-specific probe also detected the sMAP specific-band. However, in homozygous (−/−) mice the corresponding bands were very weak and several extra bands were detected. We also performed a quantitative RT-PCR analysis to check the expression levels of sMAP and MASP-2 mRNAs. In homozygous (−/−) mice, the expression of sMAP mRNA was completely abolished and that of MASP-2 was also decreased markedly: it was quantitated as about 2% of that of wild-type (+/+) mice in both H- and L-chains by real-time PCR (FIG. 21B). Furthermore, we examined the expression of MASP-2 at the protein level. Both sMAP and MASP-2 were undetectable in homozygous (−/−) mouse serum by immunoblotting (FIG. 22A). After the incubation of homozygous (−/−) mouse serum with mannan-agarose gel, both sMAP and MASP-2 were not detectable in the fraction bound to the gels, although MASP-1 was detected in the complex (FIG. 22B).

Figure 23A:
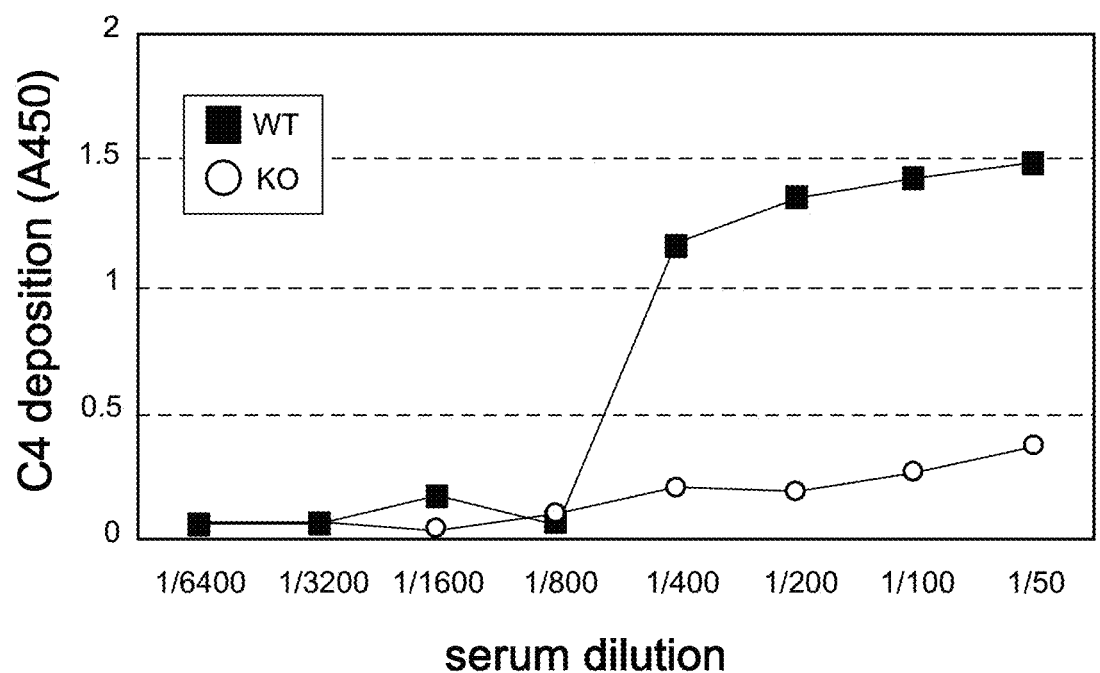
FIG. 23A presents results showing C4 deposition on mannan-coated wells in wild type (+/+) and sMAP (−/−) mouse serum, as described in Example 30.
Figure 23B:
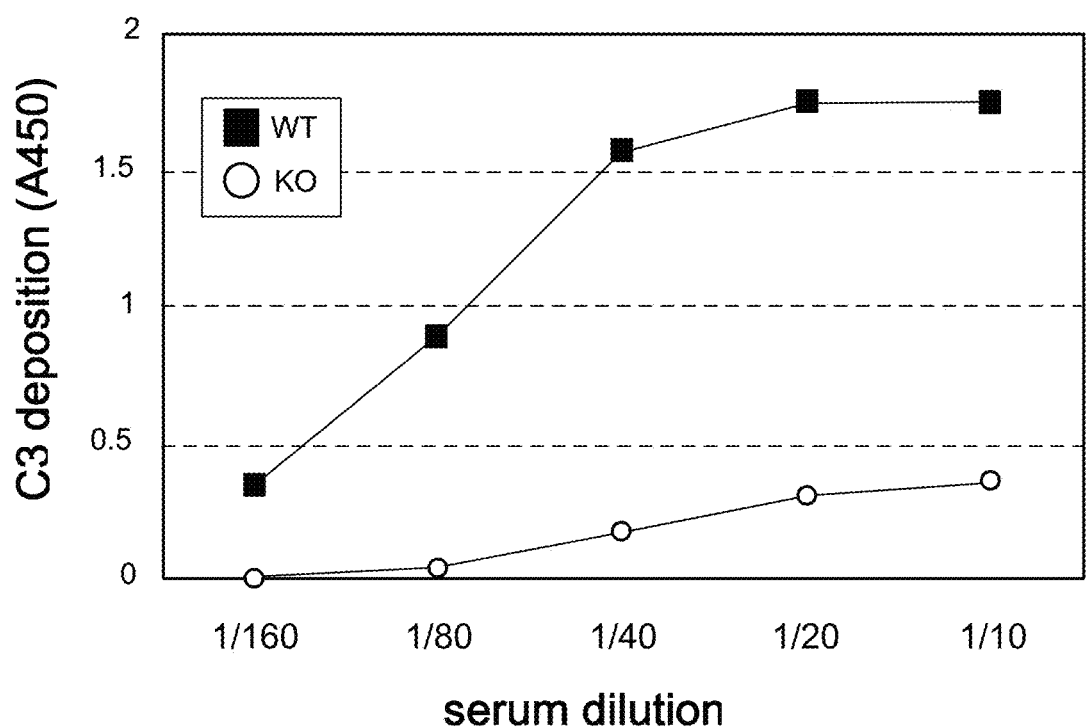
FIG. 23B presents results showing C3 deposition on mannan-coated wells in wild type (+/+) and sMAP (−/−) mouse serum, as described in Example 30.

Cleaving Activities of C4 and C3 through the Lectin Pathway in Homozygous (−/−) Mouse Serum When homozygous (−/−) mouse serum was incubated in mannan-coated wells, the amount of human C4 deposited on the wells was about 20% of that in normal serum at dilutions ranging from 1/400 to 1/50 (FIG. 23A). We also examined the C3 deposition activity of the lectin pathway in homozygous (−/−) mouse serum. The mouse serum was added to mannan-coated wells and the amount of endogenous C3 deposited on the wells was measured. The amount was decreased in the deficient serum and was 21% of that in normal serum at a dilution of 1/10 (FIG. 23B).

Reconstitution of the MBL-MASP-sMAP Complex in Homozygous (−/−) Mouse Serum

Figure 24A:
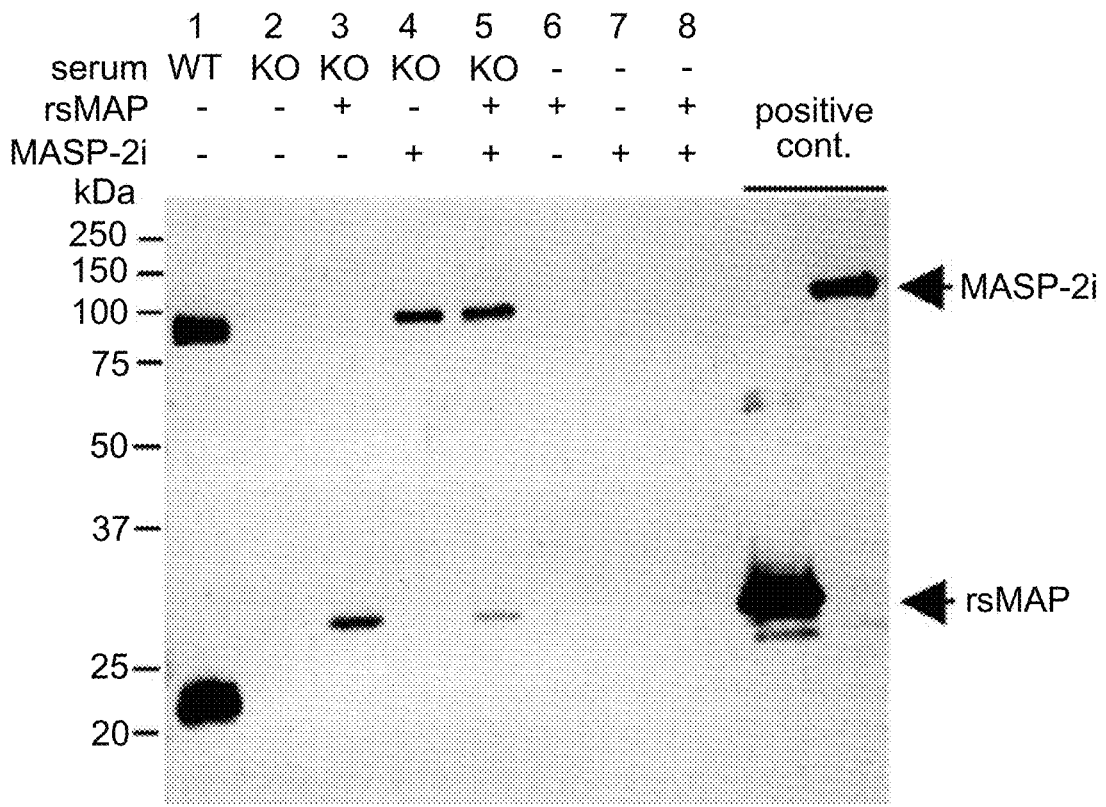
FIG. 24A presents results showing reconstitution of the MBL-MASP-sMAP complex in sMAP (−/−) serum, as described in Example 30.
Figure 24B:
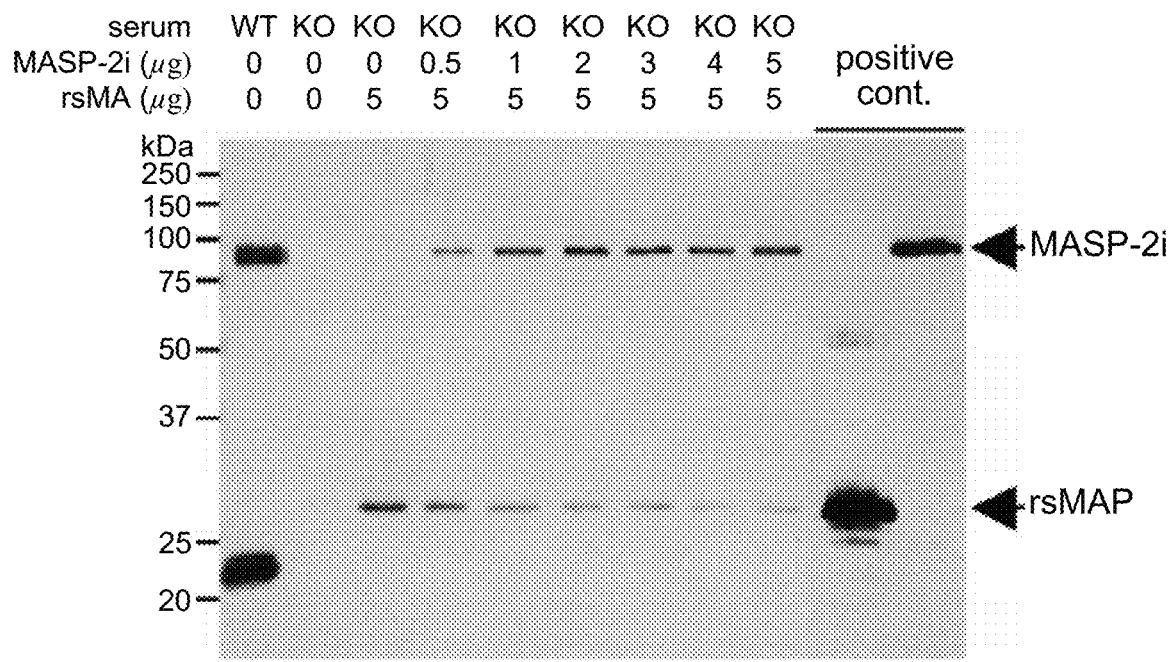
FIGS. 24B-D present results showing competitive binding of rsMAP and MASP-2i to MBL, as described in Example 30.
Figure 24C:
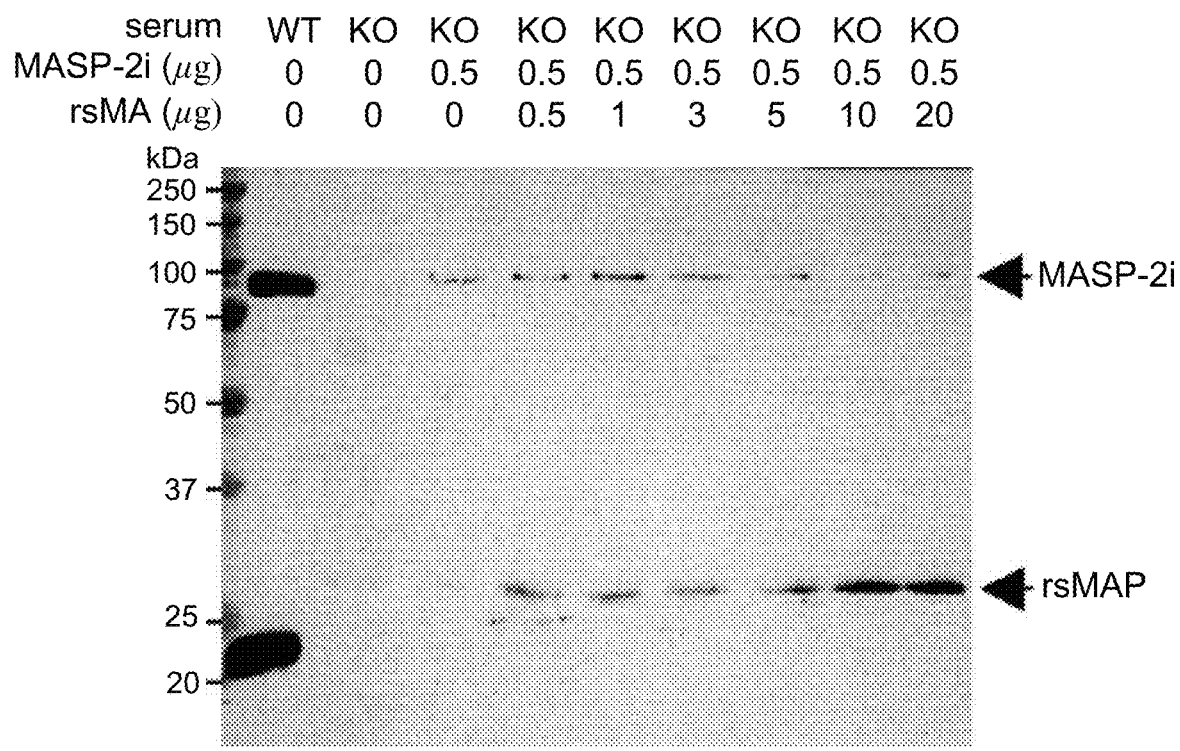
Figure 24D:
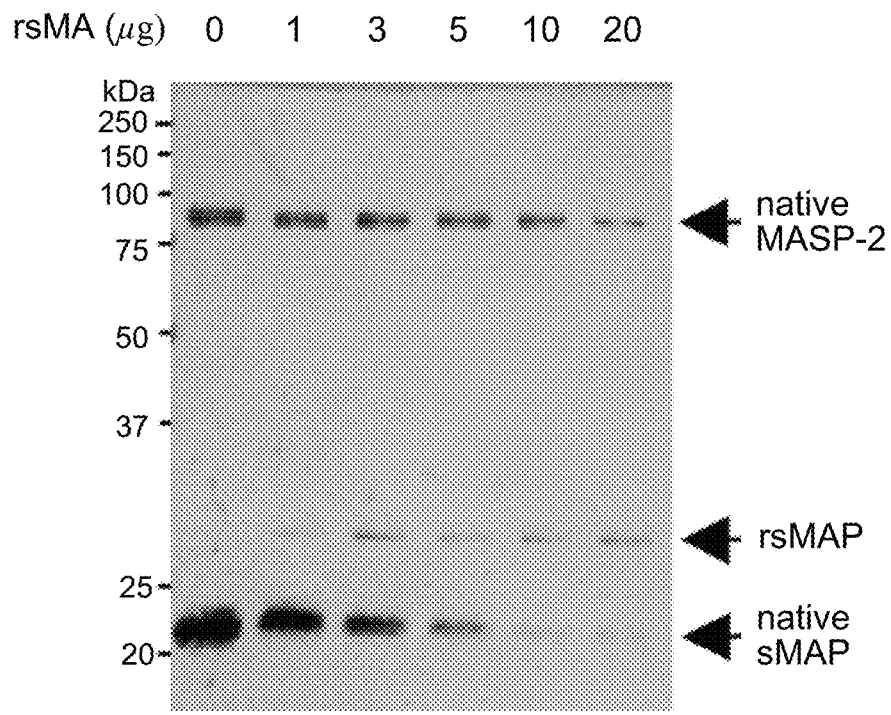

When recombinant mouse sMAP (rsMAP) or the inactive mouse MASP-2 mutant (MASP-2i) was added to homozygous (−/−) mouse serum, both recombinants were able to bind to MBL (FIG. 24A, lanes 3 and 4). When rsMAP and MASP-2i were simultaneously incubated with the serum (FIG. 24A, lane 5), both recombinants were detected in the MBL-MASP-sMAP complex. However the amount of sMAP bound to the complex was less than that when only rsMAP was incubated with the serum. Then we further investigated the competitive binding of sMAP and MASP-2 to MBL. A constant amount of rsMAP and various amounts of MASP-2i were added to the deficient serum. The binding of rsMAP decreased in a dose-dependent manner with increasing amounts of MASP-2i (FIG. 24B). Inversely, the amount of MASP-2i bound to MBL decreased by the addition of rsMAP (FIG. 24C). When rsMAP was added to wild-type serum, the binding both of endogenous sMAP and of MASP-2 to MBL decreased in a dose-dependent manner (FIG. 24D).

Reconstitution of C4 Deposition Activity in Homozygous (−/−) Mouse Serum

Figure 25B:
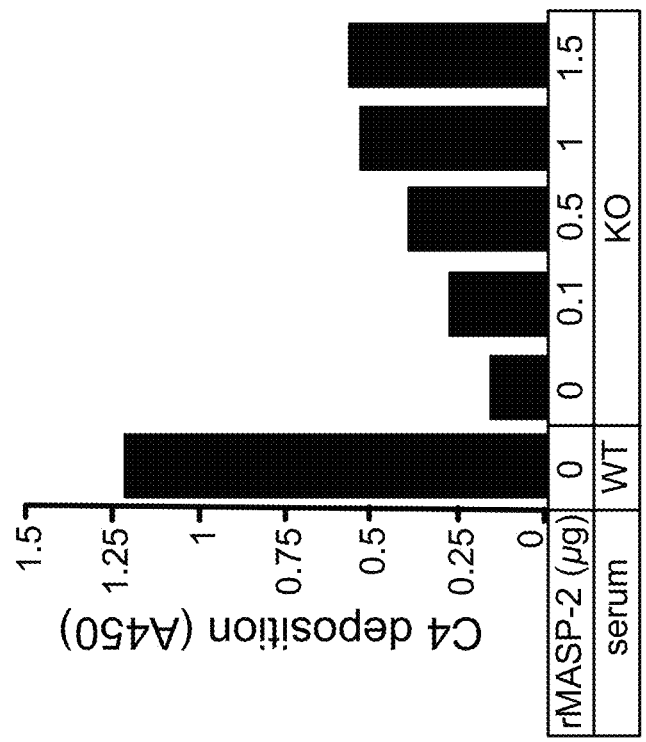
FIGS. 25A-B present results showing restoration of the C4 deposition activity by the addition of rsMAP, as described in Example 30.
Figure 25A:
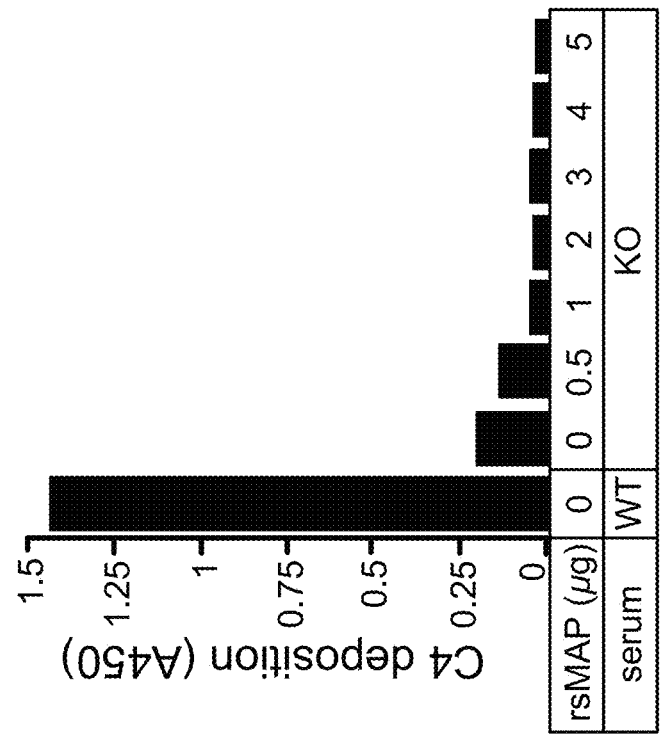

We performed a reconstitution experiment of the deposition of C4 on mannan-coated wells using recombinants. When rsMAP was added to the deficient serum, the amount of C4 deposited actually decreased to basal levels in a dose-dependent manner (FIG. 25A). When rMASP-2 was added to the serum, the amount of C4 was restored by up to 46% of that of wild-type serum in a dose-dependent manner and reached a plateau (FIG. 25B). Next, we investigated the effect of sMAP on the C4 deposition. When a constant amount of rMASP-2 and various amounts of rsMAP were added to the deficient serum, the amount of C4 deposited decreased with the addition of rsMAP in a dose-dependent manner (FIG. 26A) and the addition of rsMAP to wild-type serum also decreased the amount of C4 deposited (FIG. 26B), suggesting that sMAP plays a regulatory role in the activation of the lectin pathway.

Discussion

We have generated sMAP−/− mice through targeted disruption of the sMAP-specific exon. The expression level of MASP-2 was also extremely decreased at both the mRNA and protein levels in these mice (FIGS. 21 and 22). A Northern blot analysis with a MASP-2 probe showed only extra bands in poly(A)+ RNA from sMAP−/− mice, suggesting that the normal splicing of the MASP-2 gene was altered by the targeting of the sMAP gene and therefore, the expression level of MASP-2 was markedly decreased. As a result, the cleavage of C4 by the MBL-MASP complex in the deficient serum was decreased by about 80% compared to that in the normal serum (FIG. 23A). In the reconstitution experiments, the C4 cleavage activity was restored by addition of rMASP-2 but not rsMAP (FIG. 25). The reduction in the deposition of C4 observed in the deficient serum should be caused by the deficiency of MASP-2 in the MBL-MASP complex (FIG. 22B). Therefore, it is clear that MASP-2 is essential for the activation of C4 by the MBL-MASP complex. However, addition of rMASP-2 did not completely restore the cleavage activity and the deposition of C4 reached a plateau. As reported previously (Cseh et al, *J Immunol* 169: 5735-5743 (2002); Iwaki and Fujita, *J Endotoxin Res* 11: 47-50 (2005), most rMASP-2 was converted to the active form by autoactivation during the purification procedures and some lost its protease activity. Since the active or inactive state of MASP-2 has no significant influence on its association with MBL (Zundel et al, *J Immunol* 172: 4342-4350 (2004), it is possible that rMASP-2 which has lost its protease activity binds to MBL and competitively prevents the association of the active form, thereby resulting in an incomplete restoration of C4 deposition. The C3 cleavage activity of the lectin pathway was also attenuated in the deficient serum (FIG. 23B). The decline in the amount of C3 deposited is probably due to the very low level of activity of the C3 convertase, which consists of C4b and C2a fragments generated by MASP-2.

MASP and sMAP each associated as homodimers and formed complexes with MBL or L-ficolin through their N-terminal CUB and EGF-like domains (Chen and Wallis, *J Biol Chem* 276: 25894-25902 (2001); Cseh et al, *J Immunol* 169: 5735-5743 (2002); Thielens et al, *J Immunol* 166: 5068-5077 (2001); Zundel et al, *J Immunol* 172: 4342-4350 (2004)). The crystal structures of sMAP and the CUB1-EGF-CUB2 segment of MASP-2 reveal their homodimeric structure (Feinberg et al, *EMBO J* 22: 2348-2359 (2003); Gregory et al, *J Biol Chem* 278: 32157-32164 (2003)). The collagen-like domain of MBL is involved in associating with MASPs (Wallis and Cheng, *J Immunol* 163: 4953-4959 (1999); Wallis and Drickamer, *J Biol Chem* 279: 14065-14073 (1999) and some mutations introduced into the domain have decreased the binding of MBL to the CUB1-EGF-CUB2 segments of MASP-1 and MASP-2 (Wallis and Dodd, *J Biol Chem* 275: 30962-30969 (2000)). The binding sites for MASP-2 and for MASP-1/3 overlap but are not identical (Wallis et al, *J Biol Chem* 279: 14065-13073 (2004)). Although the sMAP-binding site of MBL has not been identified yet, the binding sites for sMAP and MASP-2 are probably identical, because the CUB1-EGF region is the same in sMAP and MASP-2. Thus, it is reasonable that sMAP and MASP-2 compete with each other to bind MBL in the reconstitution of the MBL-MASP-sMAP complex (FIG. 24). The affinity of sMAP for MBL is lower than that of MASP-2 (Cseh et al, *J Immunol* 169:5735-5743 (2002); Thielens et al, *J Immunol* 166: 5068-5077 (2001)). The concentration of sMAP in mouse serum has not been determined. As shown in FIG. 22A, however, the amount of sMAP in the wild-type serum is much greater than that of MASP-2. Therefore sMAP is able to occupy the MASP-2/sMAP binding site and prevent MASP-2 from binding to MBL and consequently the C4 cleavage activity of the MBL-MASP complex is reduced. The regulatory mechanism of sMAP in the lectin pathway remains to be investigated. It is still unknown whether sMAP plays its regulatory role before or after complement activation. sMAP may prevent inadvertent activation of the MBL-MASP complex before microbial infection or suppress overactivation of the lectin pathway once activated. There is another potential regulator in the lectin pathway. MASP-3 is also a competitor of MASP-2 in binding to MBL and down-regulates the C4 and C2 cleavage activity of MASP-2 (Dahl et al, *Immunity* 15:127-135 (2001)). Although the interaction between sMAP and MASP-3 has not been investigated, it is possible that they are able to down-regulate activation of the lectin pathway cooperatively.

In this report we have demonstrated that sMAP and MASP-2 compete to bind MBL and sMAP has the ability to down-regulate the lectin pathway, which is activated by the MBL-MASP complex. It is reasonable that sMAP also regulates another route of the lectin pathway activated by the ficolin-MASP complex. MASP-2 and sMAP are also compete to bind mouse ficolin A and down-regulate the C4 cleavage activity of the ficolin A-MASP complex (Y Endo et al, in preparation). A study of MBL null mice was recently reported (Shi et al, *J Exp Med* 199: 1379-1390 (2004)). MBL null mice have no C4 cleavage activity in the MBL lectin pathway and are susceptible to *Staphylococcus aureus* infections. In the present study, sMAP-/- mice, which are also deficient in MASP-2, showed reductions in C3 cleavage activity besides C4 cleavage activity in the lectin pathway. Because of their impaired opsonizing activity, the sMAP-deficient mice may be susceptible to bacterial infections. Further investigation of the sMAP-deficient mice will clarify the function of the lectin pathway in protection against infectious diseases.

Figures 26A, 26B:
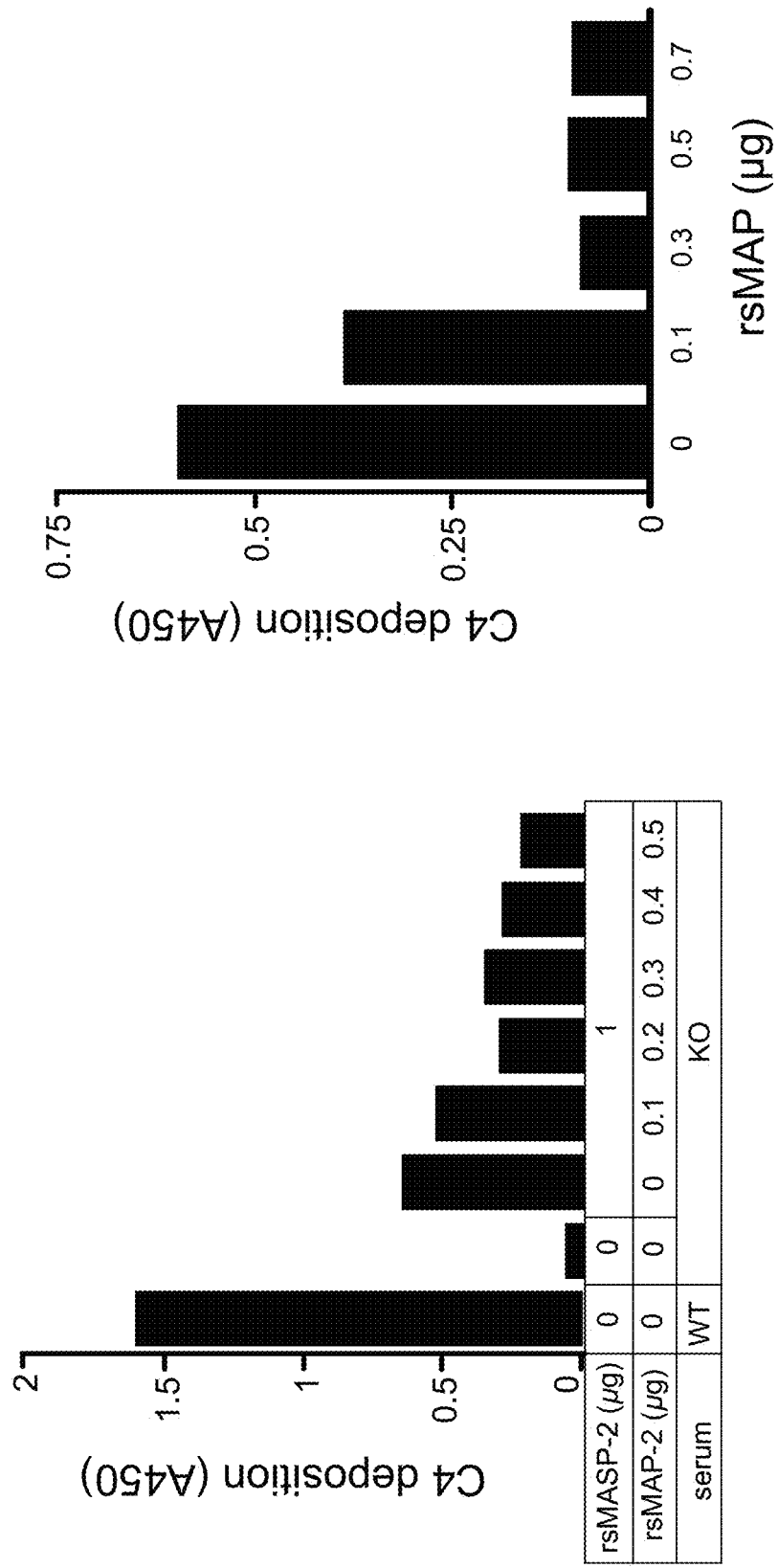
FIGS. 26A-B present results showing reduction of the C4 deposition activity by addition of rsMAP, as described in Example 30.

Another important finding is that the addition of rsMAP to normal serum results in a reduction in the activation of C4 (FIG. 26B). The lectin pathway has been also demonstrated to regulate inflammation and tissue damage in several organs (de Vries et al, *Am J Pathol* 165:1677-1688 (2004); Fiane et al, *Circulation* 108:849-856 (2003); Jordan et al, *Circulation* 104:1413-1418 (2001); Walsh et al, *J Immunol* 175:541-546 (2005)). In MBL-deficient patients undergoing treatment for a thoracic abdominal aortic aneurysm, complement was not activated and levels of proinflammatory markers were reduced following surgery (Fiane et al, *Circulation* 108:849-856 (2003)). Accumulated evidences have demonstrated the potential pathophysiologic role of MBL during conditions of ischemia and reperfusion in a variety of vascular beds. Therefore, the specific blockade of MBL or inhibition of the lectin complement pathway may represent a therapeutically relevant strategy for the prevention of ischemia/perfusion-associated damage. Thus, it is possible that sMAP is one of the candidates for such an inhibitor, since it acts as an attenuator of the lectin pathway's activation.

Example 31

This Example demonstrates that MASP-2 is responsible for the C4 bypass activation of C3.

Background/Rationale: Most recently, it has been shown that inhibiting the alternate pathway protects the kidney from ischemic acute failure (Thurman et al., *J. Immunol* 170:1517-1523 (2003)). The data described herein imply that the lectin pathway instructs alternate pathway-activation, which in turn amplifies complement activation synergistically. We hypothesise that transient inhibition of the lectin pathway may also affect alternate pathway-activation and thus improve the long-term outcome in organ transplantation as limiting complement-mediated graft damage and inflammation, and may moderate the unwanted induction of an adaptive immune response against the graft and reduce the risk of secondary graft rejection through the adaptive immune system. This is supported by recent clinical data showing that a partially impaired lectin pathway, resulting from inherited MBL deficiencies (present in about 30% of the human population), is associated with increased renal allograft survival in humans (Berger, *Am J Transplant* 5:1361-1366 (2005)).

The involvement of complement components C3 and C4 in ischemia-reperfusion (FR) injury was well established in models of transient intestinal and muscular ischemia using gene targeted mouse strains (Weiser et al., *J Exp Med* 183:2342-2348 (1996); Williams et al. *J Appl Physiol* 86:938-42, (1999)). It is well established that C3 has a prominent role in renal FR injury and secondary graft rejection (Zhou et al., *J Clin Invest* 105:1363-1371 (2000); Pratt et al., *Nat Med* 8: 582-587 (2002); Farrar, et al., *Am J.*

*Pathol* 164:133-141 (2004)). It was therefore surprising that a phenotype for C4 deficiency was not observed in the published models of mouse kidney allograft rejection (Lin, 2005 In Press). A subsequent analysis of sera and plasma of these C4 deficient mice, however, indicated that these mice retain a residual functional activity showing LP-dependent cleavage of C3 and further downstream activation of complement (see FIG. 27C).

The existence of a functional C4-bypass (and C2-bypass) is a phenomenon previously described (but not fully characterised) by several investigators (Miller et al., *Proc Natl Acad Sci* 72:418-22 (1975); Knutzen Steuer et al., *J Immunol* 143(7):2256-61 (1989); Wagner et al., *J Immunol* 163: 3549-3558 (1999) and relates to the alternative pathway-independent C3-turnover in C4 (and C2) deficient sera.

Figure 27A:
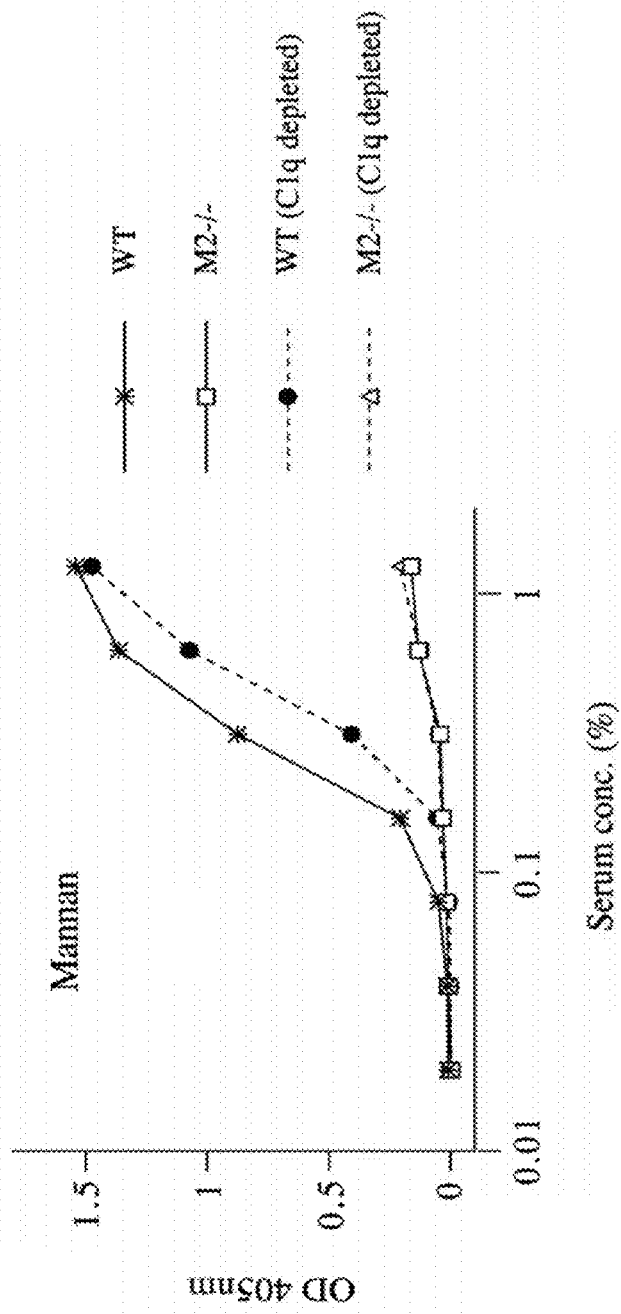
FIGS. 27A-C presents results showing that MASP-2 is responsible for the C4 bypass activation of C3, as described in Example 31.
Figure 27B:
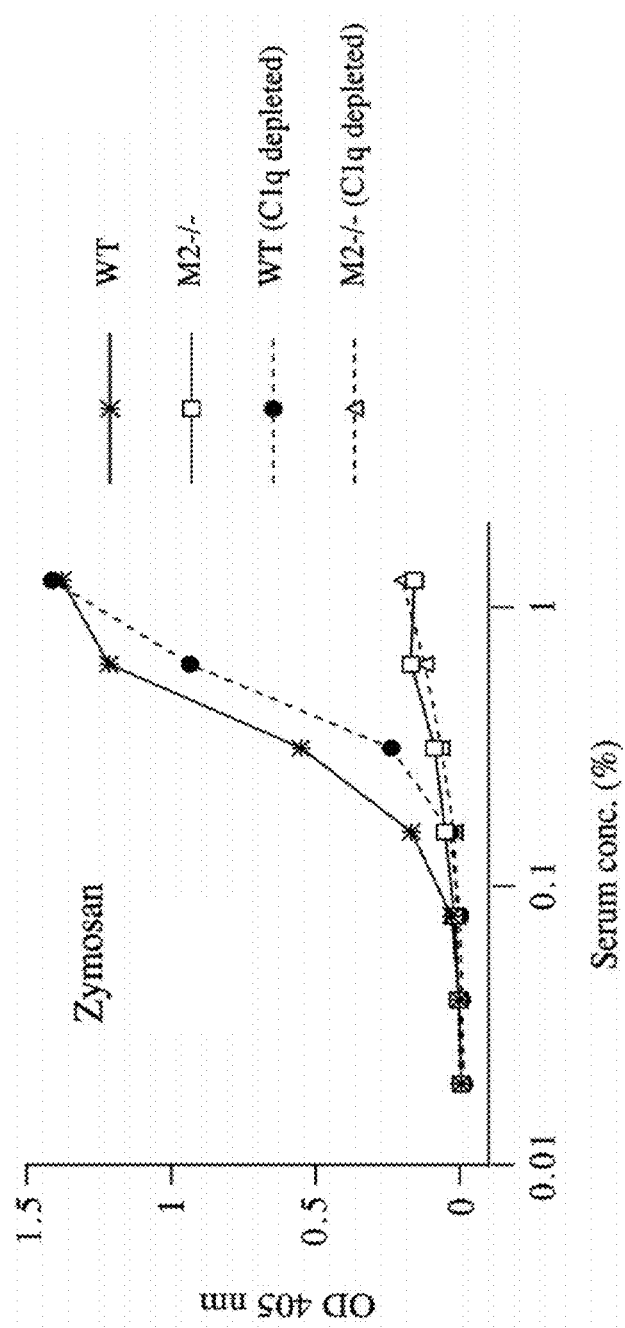
Figure 27C:
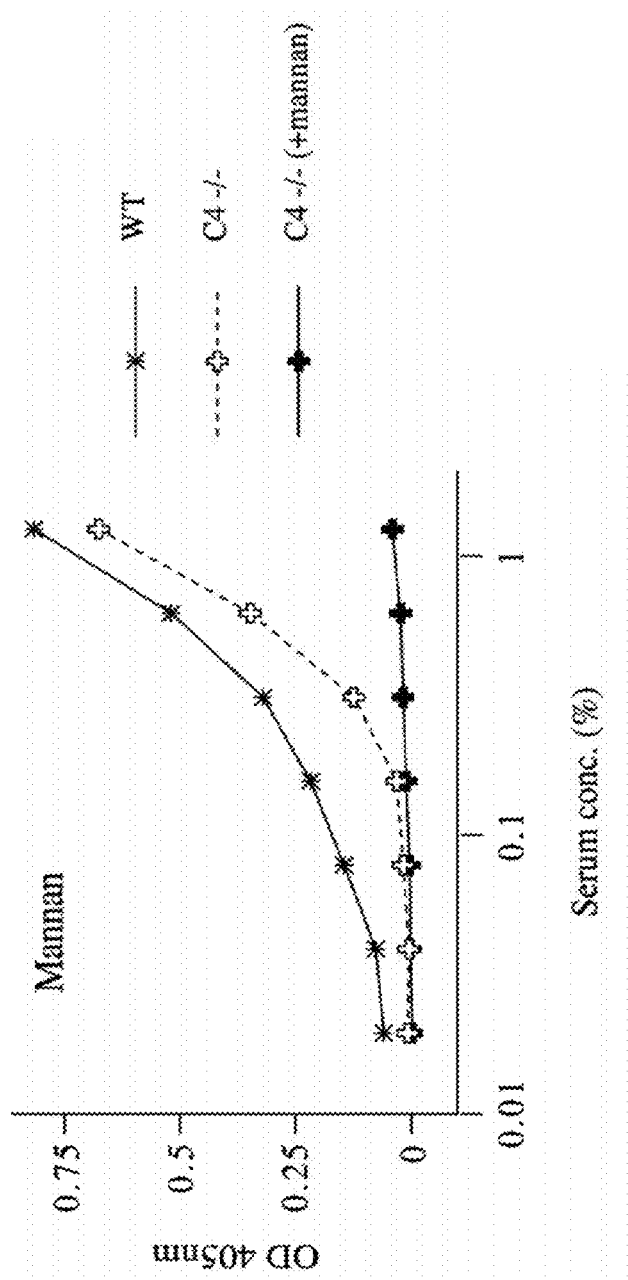

Methods: Effects of the lectin pathway and the classical pathway on C3 deposition. Mouse plasma (with EGTA/$Mg^{2+}$ as anticoagulant) was diluted and re-calcified in 4.0 mM barbital, 145 mM NaCl, 2.0 mM $CaCl_2$, 1.0 mM $MgCl_2$, pH 7.4, then added to microtitre plates coated with mannan (as shown in FIGS. 27A and 27C) or zymosan (as shown in FIG. 27B), and incubated for 90 min at 37° C. The plates were washed 3 times with 10 mM Tris-Cl, 140 mM NaCl, 5.0 mM $CaCl_2$, 0.05% Tween 20, pH 7.4 then C3b deposition was measured using an anti-mouse C3c antibody.

Results: The results shown in FIG. 27A-C are representative of 3 independent experiments. When using the same sera in wells coated with immunoglobulin complexes instead of mannan or zymosan, C3b deposition and Factor B cleavage are seen in WT (+/+) mouse sera and pooled MASP-2(-/-) sera, but not in C1q depleted sera (data not shown). This indicates that alternative pathway activation can be restored in MASP-2-/- sera when the initial C3b is provided via CP activity. FIG. 27C depicts the surprising finding that C3 can efficiently be activated in a lectin pathway-dependant fashion in C4 (-/-) deficient plasma. This "C4 bypass" is abolished by the inhibition of lectin pathway-activation through preincubation of plasma with soluble mannan or mannose.

It can be seen that C3b deposition on mannan and zymosan is severely compromised in MASP-2 (-/-) deficient mice, even under experimental conditions that according to many previously published papers on alterative pathway activation should be permissive for all three pathways. As shown in FIG. 27A-C, MASP-2 (-/-) deficient mouse plasma does not activate C4 via the lectin pathway and does not cleave C3, neither via the lectin pathway nor the alternative pathway. We therefore hypothesise that MASP-2 is required in this C4-bypass. Further progress in the identification of components likely to be involved in the lectin pathway-dependent C4-bypass was most recently reported by Prof. Teizo Fujita. Plasma of C4 deficient mice crossed with Fujita's MASP-1/3 deficient mouse strain loses the residual capacity of C4 deficient plasma to cleave C3 via the lectin pathway. This was restored by adding recombinant MASP-1 to the combined C4 and MASP-1/3 deficient plasma (Takahashi, *Mol Immunol* 43: 153 (2006), suggesting that MASP-1 is involved in the formation of lectin pathway-derived complexes that cleave C3 in absence of C4 (recombinant MASP-1 does not cleave C3, but it cleaves C2; Rossi et al., *J Biol Chem* 276: 40880-7 (2001); Chen et al., *J Biol Chem* 279:26058-65 (2004). We observed that MASP-2 is required for this bypass to be formed.

Although more functional and quantitative parameters and histology are required to consolidate this pilot study, its preliminary results lend strong support to the hypothesis that complement activation via the lectin pathway contributes significantly to the pathophysiology of renal FR injury, as MASP-2-/- mice show a much quicker recovery of renal functions.

Example 32

Figure 28A:
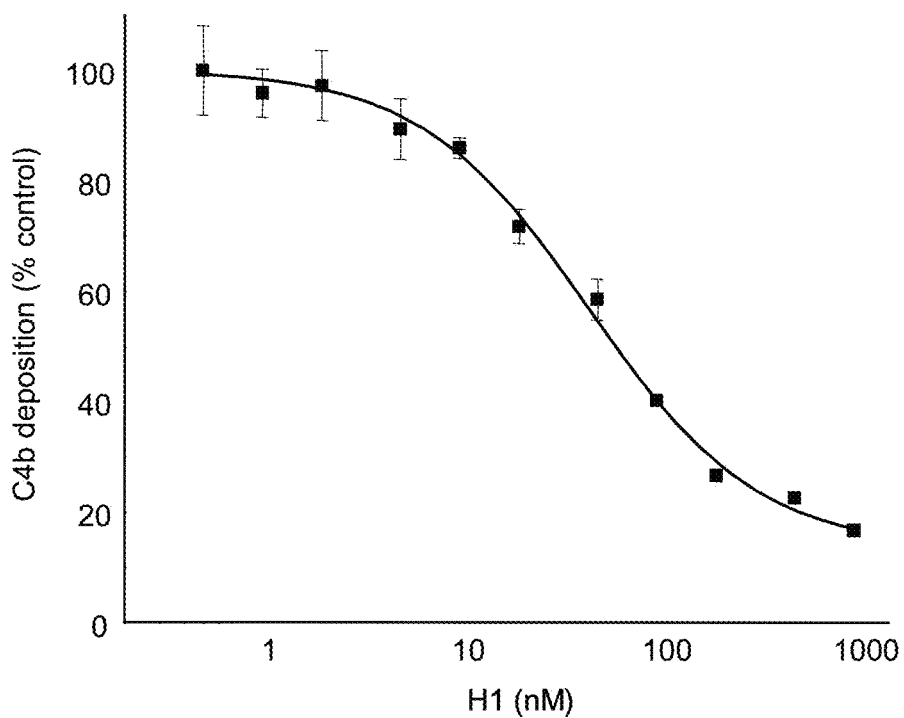
FIGS. 28A and 28B present dose response curves for the inhibition of C4b deposition (FIG. 28A) and the inhibition of thrombin activation following the administration of a MASP-2 Fab2 antibody in normal rat serum, as described in Example 32.
Figure 28B:
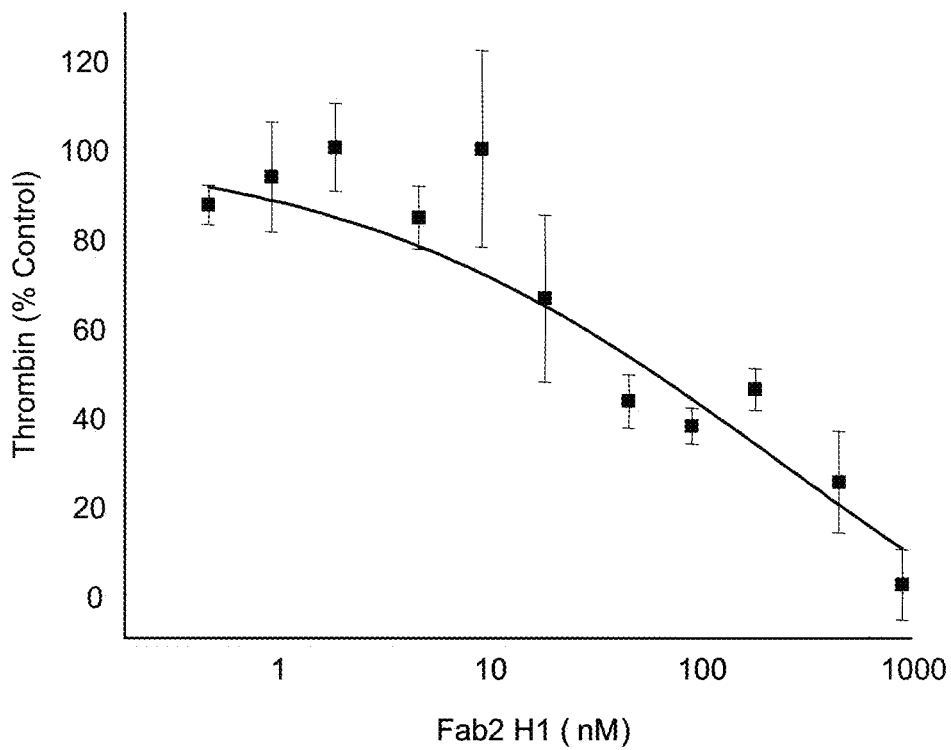

This Example demonstrates that thrombin activation can occur following lectin pathway activation under physiological conditions, and demonstrates the extent of MASP-2 involvement. In normal rat serum, activation of the lectin pathway leads to thrombin activation (assessed as thrombin deposition) concurrent with complement activation (assessed as C4 deposition). As can be seen in FIGS. 28A and 28B, thrombin activation in this system is inhibited by a MASP-2 blocking antibody (Fab2 format), exhibiting an inhibition concentration-response curve (FIG. 28B) that parallels that for complement activation (FIG. 28A). These data suggest that activation of the lectin pathway as it occurs in trauma will lead to activation of both complement and coagulation systems in a process that is entirely dependent on MASP-2. By inference, MASP2 blocking antibodies may prove efficacious in mitigating cases of excessive systemic coagulation, e.g., disseminated intravascular coagulation, which is one of the hallmarks leading to mortality in major trauma cases.

Example 33

This Example provides results generated using a localized Schwartzman reaction model of disseminated intravascular coagulation ("DIC") in MASP-2-/- deficient and MASP-2+/+ sufficient mice to evaluate the role of lectin pathway in DIC.

Background/Rationale:

As described supra, blockade of MASP-2 inhibits lectin pathway activation and reduces the generation of both anaphylatoxins C3a and C5a. C3a anaphylatoxins can be shown to be potent platelet aggregators in vitro, but their involvement in vivo is less well defined and the release of platelet substances and plasmin in wound repair may only secondarily involve complement C3. In this Example, the role of the lectin pathway was analyzed in MASP-2 (-/-) and WT (+/+) mice in order to address whether prolonged elevation of C3 activation is necessary to generate disseminated intravascular coagulation.

Methods:

The MASP-2 (-/-) mice used in this study were generated as described in Example 27. The localized Schwartzman reaction model was used in this experiment. The localized Schwartzman reaction (LSR) is a lipopolysaccharide (LPS)-induced response with well-characterized contributions from cellular and humoral elements of the innate immune system. Dependent of the LSR on complement is well established (Polak, L., et al., *Nature* 223:738-739 (1969); Fong J. S. et al., *J Exp Med* 134:642-655 (1971)). In the LSR model, the mice were primed for 4 hours with TNF alpha (500 ng, intrascrotal), then the mice were anaesthetized and prepared for intravital microscopy of the cremaster muscle. Networks of post-capillary venules (15-60 µm diameter) with good blood flow (1-4 mm/s) were selected for observation. Animals were treated with fluorescent antibodies to selectively label neutrophils, or platelets. The network of vessels was sequentially scanned and images of all vessels were digitally recorded of later analysis. After recording the basal state of the microcirculation, mice received a single intravenous injection of LPS (100 µg), either alone or with the agents listed below. The same network of vessels was then scanned every 10 minutes for 1 hour. Specific accumulation of fluorophores was identified by subtraction of background fluorescence and enhanced by thresholding the image. The magnitude of reactions was measured from recorded images. The primary measure of Schwartzman reactions was aggregate data.

The studies compared the MASP-2+/+ sufficient, or wild type, mice exposed to either a known complement pathway depletory agent, cobra venom factor (CVF), or a terminal pathway inhibitor (C5aR antagonist). The results (FIG. 29A) demonstrate that CVF as well as a C5aR antagonist both prevented the appearance of aggregates in the vasculature. In addition, the MASP-2−/− deficient mice (FIG. 29B) also demonstrated complete inhibition of the localized Schwartzman reaction, supporting lectin pathway involvement. These results clearly demonstrate the role of MASP-2 in DIC generation and support the use of MASP-2 inhibitors for the treatment and prevention of DIC.

Example 34

This Example describes the analysis of MASP-2 (−/−) mice in a Murine Myocardial Ischemia/Reperfusion Model.
Background/Rationale:
To assess the contribution of MASP-2 to inflammatory reperfusion damage following an ischemic insult to the coronary artery, MASP-2 (−/−) and MASP-2 (+/+) mice were compared in the murine ischemia/reperfusion (MIRP) model as described by Marber et al., *J. Clin Invest.* 95:1446-1456 (1995), and in a Langendorff isolated perfused mouse heart model.
Methods:
The MASP-2 (−/−) mice used in this study were generated as described in Example 27. The ischemic insult to the left ventricle was carried out in eight WT (MASP-2 (+/+) and eleven MASP-2 (−/−) mice using the methods described in Example 27. Infarct size (INF) and area at risk (AAR) were determined by planometry as described in Example 27.

Langendorff isolated-perfused mouse heart model: The method of preparing hearts from mice for the Langendorff isolated-perfused mouse heart model was carried out as described in F. J. Sutherland et al., Pharmacol Res 41: 613 (2000). See also, A. M. Kabir et al., Am J Physiol Heart Circ Physiol 291: H1893 (2006); Y. Nishino et al., Circ Res 103:307 (2008) and I. G. Webb et al., Cardiovasc Res (2010)).

Briefly described, six male WT (+/+) and nine male MASP-2 (−/−) mice were anesthetized with pentobarbital (300 mg/kg) and heparin (150 units) intra-peritoneally. Hearts were rapidly isolated and placed in ice cold modified Krebs-Henselit buffer (KH, 118.5 mmol/l NaCl, 25.0 mmol/l $NaHCO_3$, 4.75 mmol KCl, $KH_2PO_4$ 1.18, $MgSO_4$ 1.19, D-glucose 11.0, and $CaCl_2$ 1.41. The excised heart was mounted onto a Langendorff apparatus with a water jacket and retrogradely perfused at a constant pressure of 80 mm Hg with KH buffer equilibrated with 95% $O_2$ and 5% $CO_2$. The temperature of the perfusate was maintained at 37° C. A fluid-filled balloon inserted into the left ventricle monitored contractile function. The balloon was gradually inflated until the end-diastolic pressure was between 1 and 7 mm Hg. Atrial pacing was performed at 580 bpm with a 0.075-mm silver wire (Advent). Coronary flow was measured by timed collection of perfusate.
Infarction Assessment in Vitro
After retrograde perfusion commenced, the hearts were stabilized for 30 min. For inclusion, all hearts had to fulfill the following criteria: coronary flow between 1.5 and 4.5 mL/min, heart rate >300 bpm (unpaced), left ventricular developed pressure >55 mm Hg, time from thoracotomy to aortic cannulation <3 min, and no persistent dysrhythmia during stabilization. Global ischemia and reperfusion was then conducted in the absence of serum. All hearts then underwent 30 mins of global ischemia by clamping the aortic inflow tubing, followed by 2 h of reperfusion.

Electrical pacing was stopped when contraction ceased during ischemia and restarted 30 min into reperfusion. After 2 h of reperfusion. Hearts were perfused for 1 min with 5 ml of 1% triphenyl tetrazolium chloride (TTC) in KH and then placed in an identical solution at 37° C. for 10 min. The atria were then removed, and the hearts were blotted dry, weighed, and stored at −20° C. for up to 1 week.

Hearts were then thawed, placed in 2.5% glutaraldehyde for 1 minute, and set in 5% agarose. The agarose heart blocks were then sectioned from apex to base in 0.7 mm slices using a vibratome (Agar Scientific). After sectioning, slices were placed overnight in 10% formaldehyde at room temperature before transferring into PBS for an additional day at 4° C. Sections were then compressed between Perspex plates (0.57 mm apart) and imaged using a scanner (Epson model G850A). After magnification, planimetry was carried out using image analysis software (SigmaScan Pro 5.0, SPSS) and surface area of the whole, and TTC-negative, left ventricular myocardium was transformed to volume by multiplication with tissue thickness. Within each heart, after summation of individual slices, TTC-negative infarction volume was expressed as a percentage of, or plotted against, left ventricular volume.
Results:
The size of infarcted area (pale), left ventricle (LV) area at risk (red) and normally perfused LV zone (blue) were outlined in each section by identification of their color appearance and color borders. Areas were quantified on both sides of each slice and averaged by an investigator. Infarct volume was calculated as a % of risk zone (% RZ) for each animal.

Figure 31A:
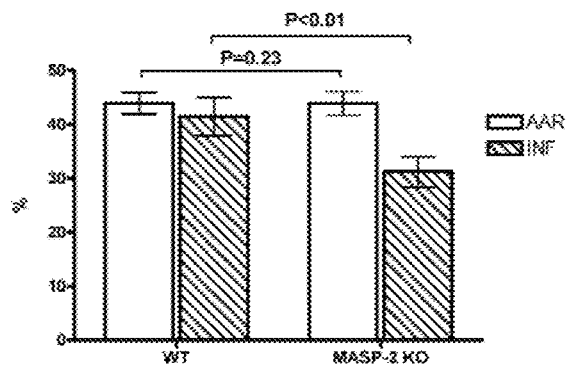
FIG. 31A graphically illustrates the mean area-at-risk (AAR) and infarct volumes (INF) as a percentage of total myocardial volumes in WT (+/+) and MASP-2 (−/−) mice after undergoing left anterior descending coronary artery occlusion and reperfusion, as described in Example 34.

FIG. 31A shows the evaluation of eight WT (+/+) mice and eleven MASP-2 (−/−) mice for the determination of their infarct size after undergoing the coronary artery occlusion and reperfusion technique described above. FIG. 31A graphically illustrates the mean area-at-risk (AAR, a measure of the area affected by ischemia) and infarct volumes (INF, a measure of damage to the myocardium) as a percentage of total myocardial volume. As shown in FIG. 31A), while there is no difference in the AAR between the two groups, the INF volumes are significantly reduced in MASP-2 (−/−) mice as compared with their WT littermates, thus indicating a protective effect from myocardial damage in the absence of MASP-2 in this model of MIRP.

Figure 31B:
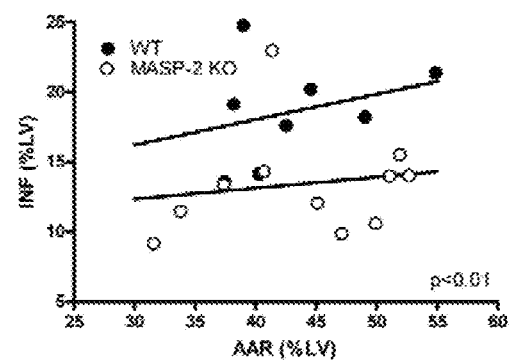
FIG. 31B graphically illustrates the relationship between infarct volume (INF) plotted against the mean area-at-risk (AAR) as a percentage of left ventricle myocardial volume in WT (+/+) and MASP-2 (−/−) mice after undergoing artery occlusion and reperfusion, as described in Example 34.

FIG. 31B graphically illustrates the relationship between INF plotted against the AAR as a % of left ventricle (LV) myocardial volume. As shown in FIG. 31B, for any given AAR, MASP-2 (−/−) animals showed a highly significant reduction in the size of their infarction in comparison with their WT littermates.

Figure 31C:
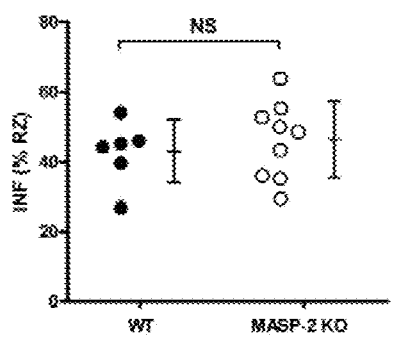
FIG. 31C graphically illustrates the infarct volume (INF) in the buffer-perfused hearts of WT (+/+) and MASP-2 (−/−) mice prepared in accordance with the Langendorff isolated-perfused mouse heart model, in which global ischemia and reperfusion was carried out in the absence of serum, as described in Example 34.
Figure 31D:
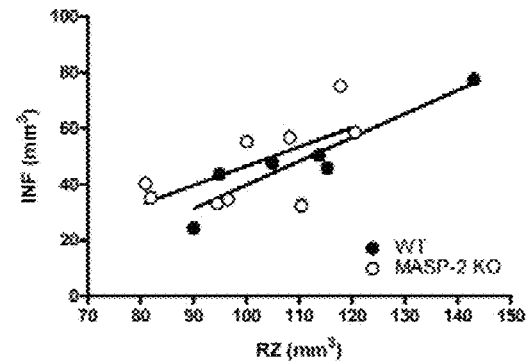
FIG. 31D graphically illustrates the relationship between infarct volume (INF) and risk zone in the buffer-perfused hearts of WT (+/+) and MASP-2 (−/−) mice prepared in accordance with the Langendorff isolated-perfused mouse heart model, as described in Example 34.

FIGS. 31C and 31D show the results of myocardial infarction in the buffer-perfused hearts of WT (+/+) and MASP-2 (−/−) mice prepared in accordance with the Langendorff isolated-perfused mouse heart model, in which global ischemia and reperfusion was carried out in the absence of serum. As shown in FIGS. 31C and 31D, there was no difference observed in the resultant infarct volume (INF) between the hearts of the MASP-2 (−/−) and WT (+/+) mice, suggesting that the difference in infarct sizes shown in FIGS. 31A and 31B are caused by plasma factors, and not by a lower susceptibility of the myocardial tissue of MASP-2 (−/−) mice to ischemic damage.

Taken together, these results demonstrate that MASP-2 deficiency significantly reduces myocardial damage upon reperfusion of an ischemic heart in the Murine Myocardial Ischemia/Reperfusion Model, and support the use of MASP-2 inhibitors to treat and prevent ischemia/reperfusion injury.

Example 35

This Example describes the analysis of MASP-2 (−/−) mice in a Murine Renal Transplantation Model.

Background/Rationale:

The role of MASP-2 in the functional outcome of kidney transplantation was assessed using a mouse model.

Methods:

The functional outcome of kidney transplantation was assessed using a single kidney isograft into uninephrecomized recipient mice, with six WT (+/+) transplant recipients (B6), and six MASP-2 (−/−) transplant recipients. To assess the function of the transplanted kidney, the remaining native kidney was removed from the recipient 5 days after transplantation, and renal function was assessed 24 hours later by measurement of blood urea nitrogen (BUN) levels.

Figure 32:
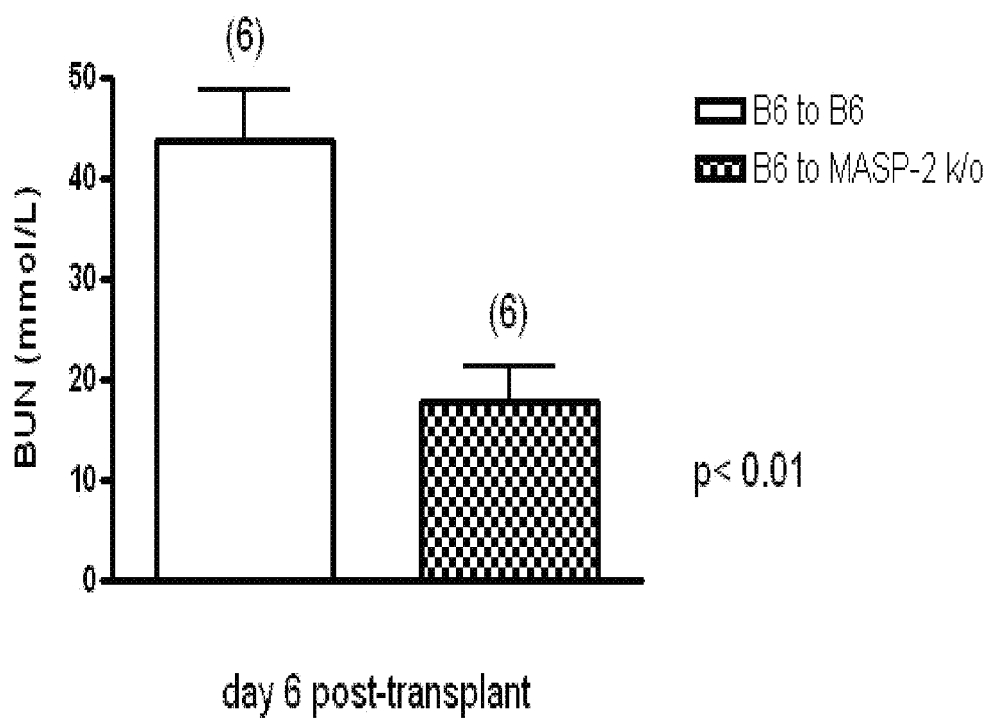
FIG. 32 graphically illustrates the blood urea nitrogen (BUN) levels measured in either WT (+/+) (B6) or MASP-2 (−/−) transplant recipient mice of WT (+/+) donor kidneys, as described in Example 35.

Results:

FIG. 32 graphically illustrates the blood urea nitrogen (BUN) levels of the kidney at 6 days post kidney transplant in the WT (+/+) recipients and the MASP-2 (−/−) recipients. As shown in FIG. 32, strongly elevated BUN levels were observed in the WT (+/+) (B6) transplant recipients (normal BUN levels in mice are <5 mM), indicating renal failure. In contrast, MASP-2 (−/−) isograft recipient mice showed substantially lower BUN levels, suggesting improved renal function. It is noted that these results were obtained using grafts from WT (+/+) kidney donors, suggesting that the absence of a functional lectin pathway in the transplant recipient alone is sufficient to achieve a therapeutic benefit.

Taken together, these results indicate that transient inhibition of the lectin pathway via MASP-2 inhibition provides a method of reducing morbidity and delayed graft function in renal transplantation, and that this approach is likely to be useful in other transplant settings.

Example 36

This Example demonstrates that MASP-2 (−/−) mice are resistant to septic shock in a Murine Polymicrobial Septic Peritonitis Model.

Background/Rationale:

To evaluate the potential effects of MASP-2 (−/−) in infection, the cecal ligation and puncture (CLP) model, a model of polymicrobial septic peritonitis was evaluated. This model is thought to most accurately mimic the course of human septic peritonitis. The cecal ligation and puncture (CLP) model is a model in which the cecum is ligated and punctured by a needle, leading to continuous leakage of the bacteria into the abdominal cavity which reach the blood through the lymph drainage and are then distributed into all the abdominal organs, leading to multi-organ failure and septic shock (Eskandari et al., *J Immunol* 148(9):2724-2730 (1992)). The CLP model mimics the course of sepsis observed in patients and induces an early hyper-inflammatory response followed by a pronounced hypo-inflammatory phase. During this phase, the animals are highly sensitive to bacterial challenges (Wichterman et al., *J. Surg. Res.* 29(2): 189-201 (1980)).

Methods:

The mortality of polymicrobial infection using the cecal ligation and puncture (CLP) model was measured in WT (+/+) (n=18) and MASP-2 (−/−) (n=16) mice as described in Example 23. Briefly described, MASP-2 deficient mice and their wild-type littermates were anaesthetized and the cecum was exteriorized and ligated 30% above the distal end. After that, the cecum was punctured once with a needle of 0.4 mm diameter. The cecum was then replaced into the abdominal cavity and the skin was closed with clamps. The survival of the mice subjected to CLP was monitored over a period of 14 days after CLP. A peritoneal lavage was collected in mice 16 hours post CLP to measure bacterial load. Serial dilutions of the peritoneal lavage were prepared in PBS and inoculated in Mueller Hinton plates with subsequent incubation at 37° C. under anaerobic conditions for 24 hours after which bacterial load was determined.

The TNF-alpha cytokine response to the bacterial infection was also measured in the WT (+/+) and MASP-2 (−/−) mice 16 hours after CLP in lungs and spleens via quantitative real time polymerase chain reaction (qRT-PCR). The serum level of TNF-alpha 16 hours after CLP in the WT (+/+) and MASP-2 (−/−) mice was also quantified by sandwich ELISA.

Figure 33:
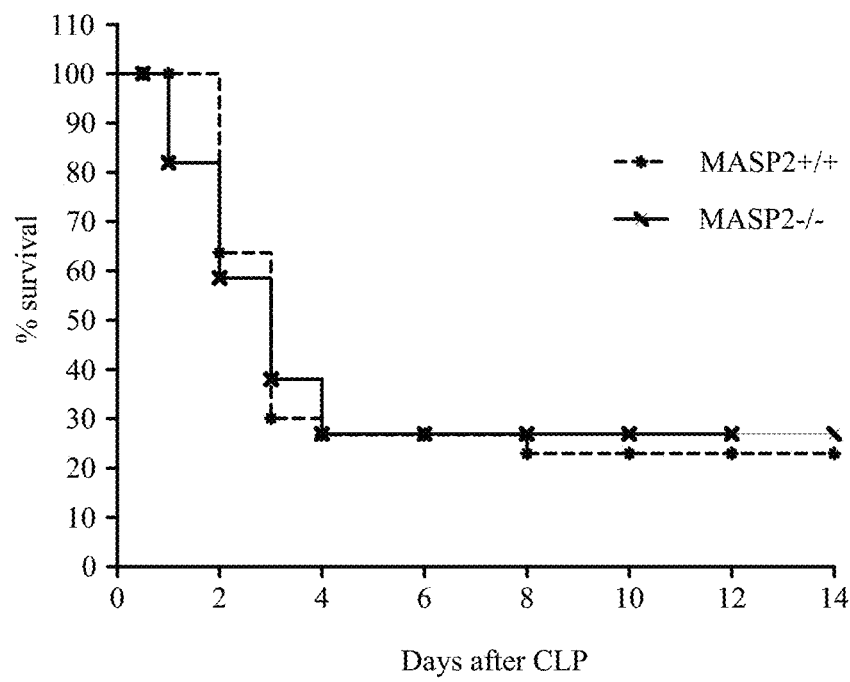
FIG. 33 graphically illustrates the percentage survival of WT (+/+) and MASP-2 (−/−) mice as a function of the number of days after microbial infection in the cecal ligation and puncture (CLP) model, as described in Example 36.
Figure 34:
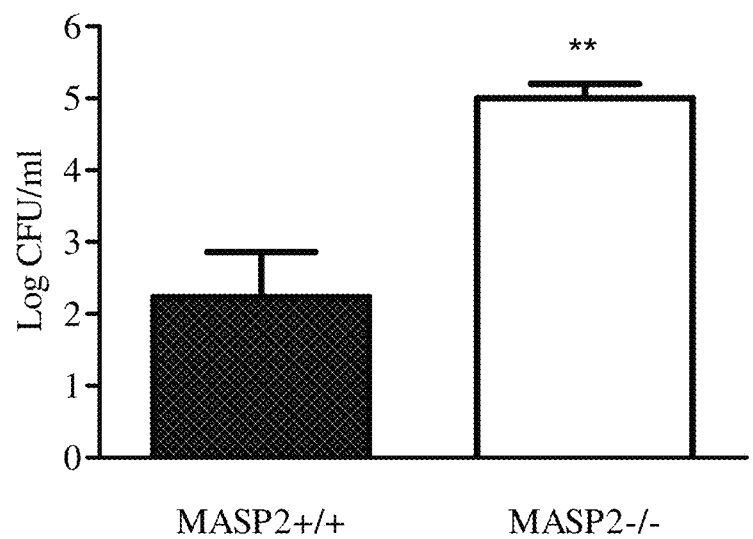
FIG. 34 graphically illustrates the number of bacteria measured in WT (+/+) and MASP-2 (−/−) after microbial infection in the cecal ligation and puncture (CLP) model, as described in Example 36.

Results:

FIG. 33 graphically illustrates the percentage survival of the CLP treated animals as a function of the days after the CLP procedure. As shown in FIG. 33, the lectin pathway deficiency in the MASP-2 (−/−) mice does not increase the mortality of mice after polymicrobial infection using the cecal ligation and puncture model as compared to WT (+/+) mice. However, as shown in FIG. 34, MASP-2 (−/−) mice showed a significantly higher bacterial load (approximately a 1000-fold increase in bacterial numbers) in peritoneal lavage after CLP when compared to their WT (+/+) littermates. These results indicate that MASP-2 (−/−) deficient mice are resistant to septic shock. The reduced bacterial clearance in MASP-2 deficient mice in this model may be due to an impaired C3b mediated phagocytosis, as it was demonstrated that C3 deposition is MASP-2 dependent.

It was determined that the TNF-alpha cytokine response to the bacterial infection was not elevated in the MASP-2 (−/−) mice as compared to the WT (+/+) controls (data not shown). It was also determined that there was a significantly higher serum concentration of TNF-alpha in WT (+/+) mice 16 hours after CLP in contrast to MASP-2 (−/−) mice, where the serum level of TNF-alpha remained nearly unaltered. These results suggest that the intense inflammatory response to the septic condition was tempered in MASP-2 (−/−) mice and allowed the animals to survive in the presence of higher bacterial counts.

Taken together, these results demonstrate the potential deleterious effects of lectin pathway complement activation in the case of septicemia and the increased mortality in patients with overwhelming sepsis. These results further demonstrate that MASP-2 deficiency modulates the inflammatory immune response and reduces the expression levels of inflammatory mediators during sepsis. Therefore, it is believed that inhibition of MASP-2 (−/−) by administration of inhibitory monoclonal antibodies against MASP-2 would be effective to reduce the inflammatory response in a subject suffering from septic shock.

Example 37

This Example describes analysis of MASP-2 (−/−) mice in a Murine Intranasal Infectivity Model.

Background/Rationale:

*Pseudomonas aeruginosa* is a Gram negative opportunistic human bacterial pathogen that causes a wide range of infections, particularly in immune-compromised individuals. It is a major source of acquired nosocomial infections, in particular hospital-acquired pneumonia. It is also responsible for significant morbidity and mortality in cystic fibrosis (CF) patients. *P. aeruginosa* pulmonary infection is characterized by strong neutrophil recruitment and significant lung inflammation resulting in extensive tissue damage (Palanki M. S. et al., *J. Med. Chem* 51:1546-1559 (2008)).

In this Example, a study was undertaken to determine whether the removal of the lectin pathway in MASP-2 (−/−) mice increases the susceptibility of the mice to bacterial infections.

Methods:

Twenty-two WT (+/+) mice, twenty-two MASP-2 (−/−) mice, and eleven C3 (−/−) mice were challenged with intranasal administration of *P. aeruginosa* bacterial strain. The mice were monitored over the six days post-infection and Kaplan-Mayer plots were constructed showing percent survival.

Figure 35:
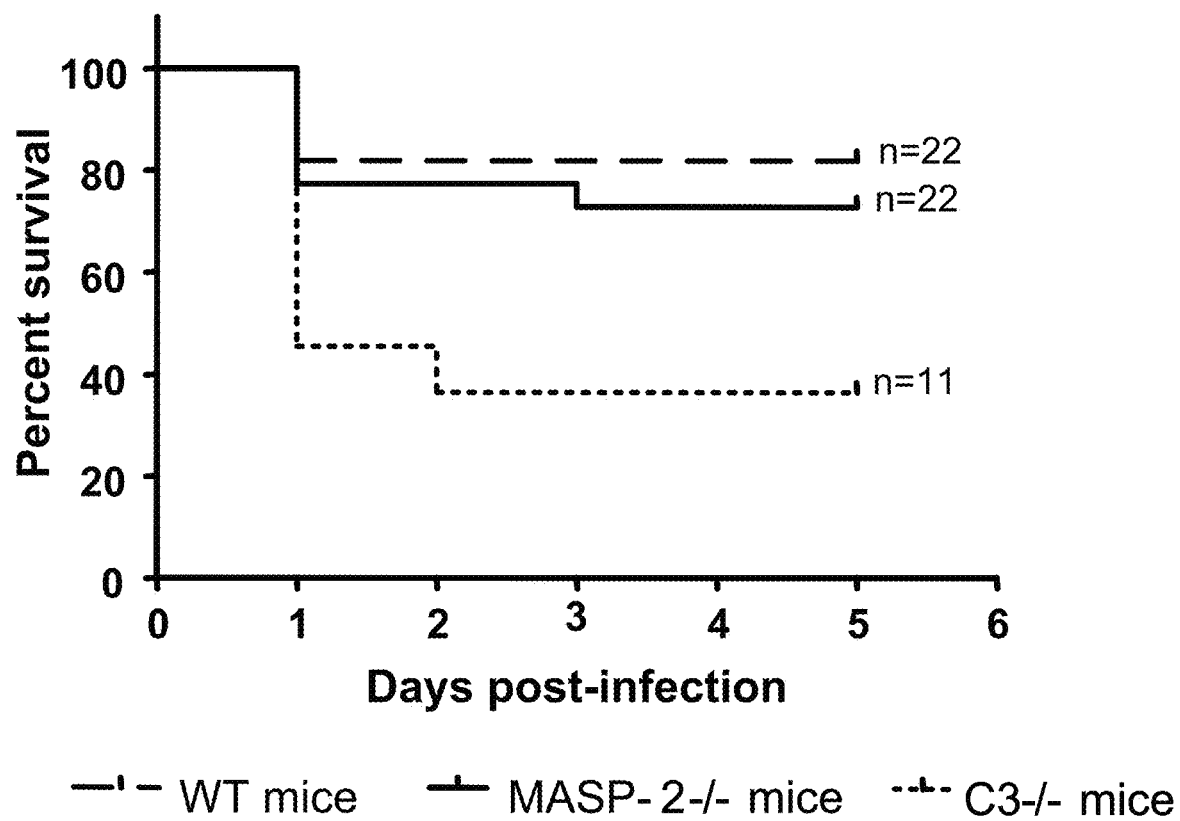
FIG. 35 is a Kaplan-Mayer plot illustrating the percent survival of WT (+/+), MASP-2 (−/−) and C3 (−/−) mice six days after challenge with intranasal administration of Pseudomonas aeruginosa, as described in Example 37.

Results:

FIG. 35 is a Kaplan-Mayer plot of the percent survival of WT (+/+), MASP-2 (−/−) or C3 (−/−) mice six days post-infection. As shown in FIG. 35, no differences were observed in the MASP-2 (−/−) mice versus the WT (+/+) mice. However, removal of the classical (C1q) pathway in the C3 (−/−) mice resulted in a severe susceptibility to bacterial infection. These results demonstrate that MASP-2 inhibition does not increase susceptibility to bacterial infection, indicating that it is possible to reduce undesirable inflammatory complications in trauma patients by inhibiting MASP-2 without compromising the patient's ability to fight infections using the classical complement pathway.

Example 38

This Example describes the pharmacodynamic analysis of representative high affinity anti-MASP-2 Fab2 antibodies that were identified as described in Example 24.

Background/Rationale:

As described in Example 24, in order to identify high-affinity antibodies that block the rat lectin pathway, rat MASP-2 protein was utilized to pan a phage display library. This library was designed to provide for high immunological diversity and was constructed using entirely human immunoglobin gene sequences. As shown in Example 24, approximately 250 individual phage clones were identified that bound with high affinity to the rat MASP-2 protein by ELISA screening. Sequencing of these clones identified 50 unique MASP-2 antibody encoding phage. Fab2 protein was expressed from these clones, purified and analyzed for MASP-2 binding affinity and lectin complement pathway functional inhibition.

As shown in TABLE 6 of Example 24, 17 anti-MASP-2 Fab2s with functional blocking activity were identified as a result of this analysis (a 34% hit rate for blocking antibodies). Functional inhibition of the lectin complement pathway by Fab2s was apparent at the level of C4 deposition, which is a direct measure of C4 cleavage by MASP-2. Importantly, inhibition was equally evident when C3 convertase activity was assessed, demonstrating functional blockade of the lectin complement pathway. The 17 MASP-2 blocking Fab2s identified as described in Example 24 potently inhibit C3 convertase formation with $IC_{50}$ values equal to or less than 10 nM. Eight of the 17 Fab2s identified have $IC_{50}$ values in the sub-nanomolar range. Furthermore, all 17 of the MASP-2 blocking Fab2s gave essentially complete inhibition of the C3 convertase formation in the lectin pathway C3 convertase assay, as shown in FIGS. 11A-C, and summarized in TABLE 6 of Example 24. Moreover, each of the 17 blocking anti-MASP-2 Fab2s shown in TABLE 6 potently inhibit C3b generation (>95%), thus demonstrating the specificity of this assay for lectin pathway C3 convertase.

Rat IgG2c and mouse IgG2a full-length antibody isotype variants were derived from Fab2 #11. This Example describes the in vivo characterization of these isotypes for pharmacodynamic parameters.

Methods:

As described in Example 24, rat MASP-2 protein was utilized to pan a Fab phage display library, from which Fab2 #11 was identified. Rat IgG2c and mouse IgG2a full-length antibody isotype variants were derived from Fab2 #11. Both rat IgG2c and mouse IgG2a full length antibody isotypes were characterized in vivo for pharmacodynamic parameters as follows.

In Vivo Study in Mice:

A pharmacodynamic study was carried out in mice to investigate the effect of anti-MASP-2 antibody dosing on the plasma lectin pathway activity in vivo. In this study, C4 deposition was measured ex vivo in a lectin pathway assay at various time points following subcutaneous (sc) and intraperitoneal (ip) administration of 0.3 mg/kg or 1.0 mg/kg of the mouse anti-MASP-2 MoAb (mouse IgG2a full-length antibody isotype derived from Fab2 #11).

Figure 36:
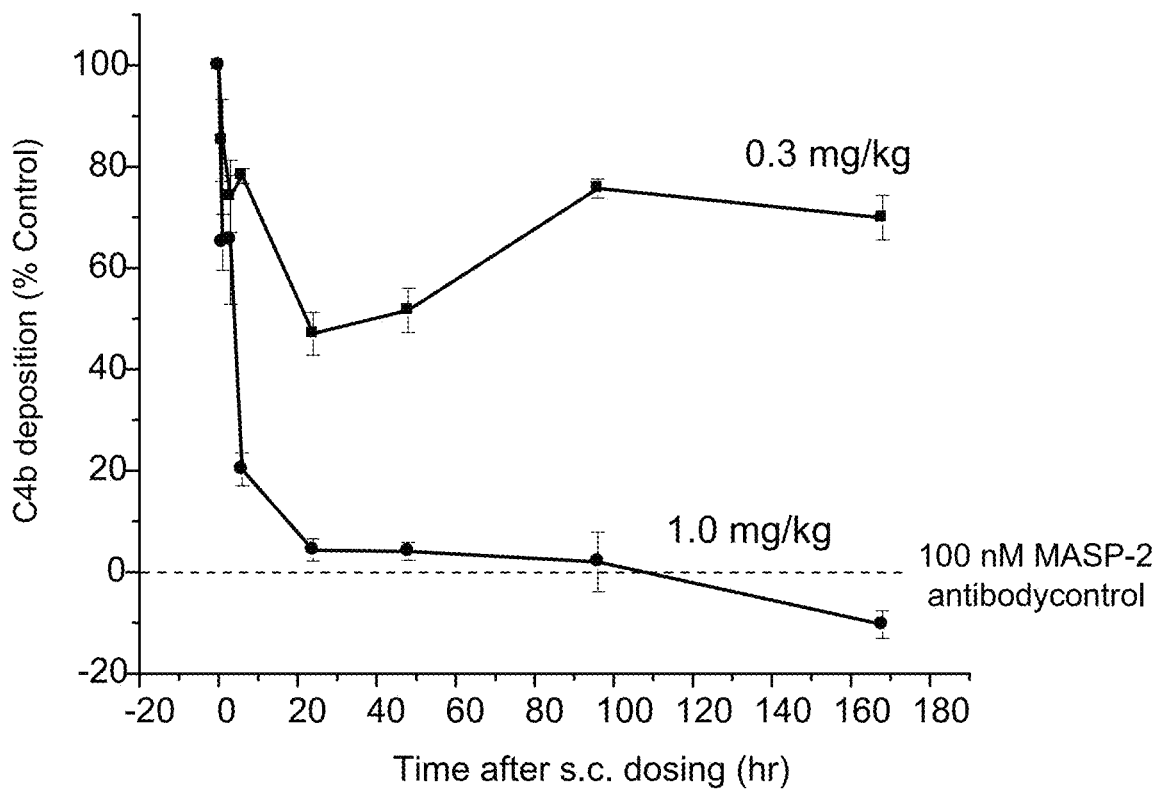
FIG. 36 graphically illustrates the level of C4b deposition, measured as % of control, in samples taken at various time points after subcutaneous dosing of either 0.3 mg/kg or 1.0 mg/kg of mouse anti-MASP-2 monoclonal antibody in WT mice, as described in Example 38.

FIG. 36 graphically illustrates lectin pathway specific C4b deposition, measured ex vivo in undiluted serum samples taken from mice (n=3 mice/group) at various time points after subcutaneous dosing of either 0.3 mg/kg or 1.0 mg/kg of the mouse anti-MASP-2 MoAb. Serum samples from mice collected prior to antibody dosing served as negative controls (100% activity), while serum supplemented in vitro with 100 nM of the same blocking anti-MASP-2 antibody was used as a positive control (0% activity).

The results shown in FIG. 36 demonstrate a rapid and complete inhibition of C4b deposition following subcutaneous administration of 1.0 mg/kg dose of mouse anti-MASP-2 MoAb. A partial inhibition of C4b deposition was seen following subcutaneous administration of 0.3 mg/kg dose of mouse anti-MASP-2 MoAb.

Figure 37:
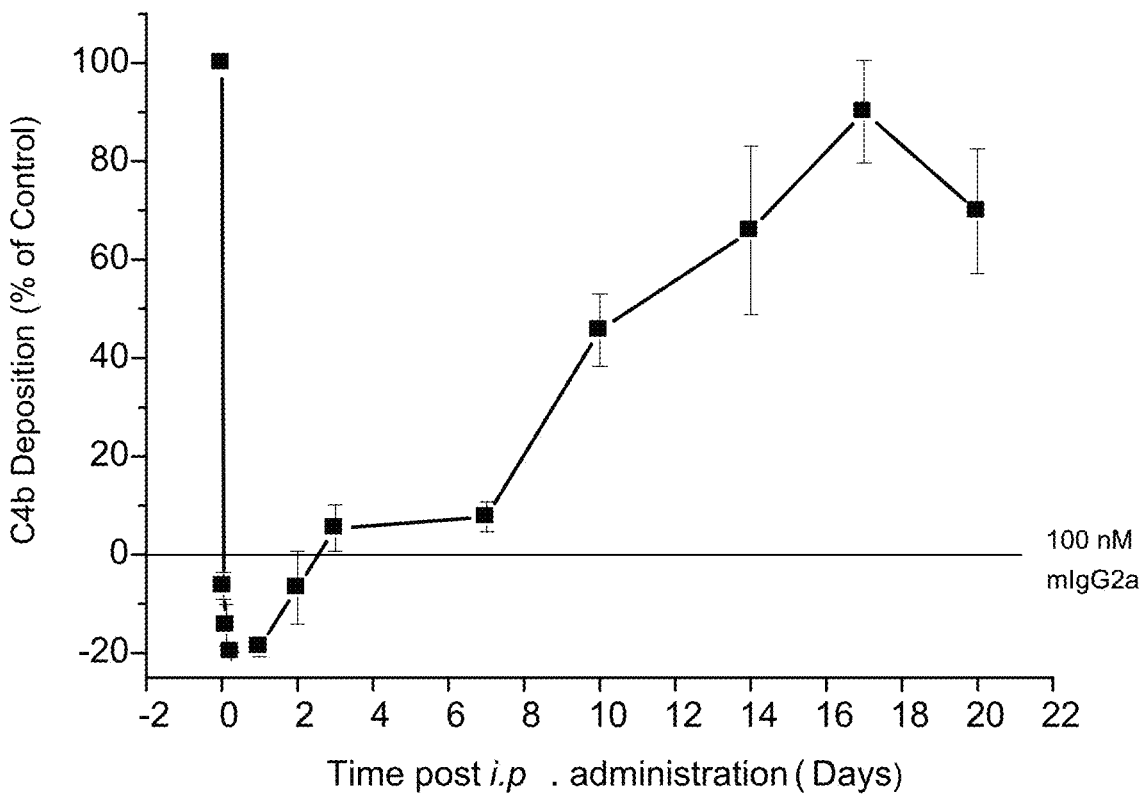
FIG. 37 graphically illustrates the level of C4b deposition, measured as % of control, in samples taken at various time points after ip dosing of 0.6 mg/kg of mouse anti-MASP-2 monoclonal antibody in WT mice, as described in Example 38.

The time course of lectin pathway recovery was followed for three weeks following a single ip administration of mouse anti-MASP-2 MoAb at 0.6 mg/kg in mice. As shown in FIG. 37, a precipitous drop in lectin pathway activity occurred post antibody dosing followed by complete lectin pathway inhibition that lasted for about 7 days after ip administration. Slow restoration of lectin pathway activity was observed over the second and third weeks, with complete lectin pathway restoration in the mice by 17 days post anti-MASP-2 MoAb administration.

These results demonstrate that the mouse anti-MASP-2 Moab derived from Fab2 #11 inhibits the lectin pathway of mice in a dose-responsive manner when delivered systemically.

Example 39

This Example describes analysis of the mouse anti-MASP-2 Moab derived from Fab2 #11 for efficacy in a mouse model for age-related macular degeneration.

Background/Rationale:

As described in Example 24, rat MASP-2 protein was utilized to pan a Fab phage display library, from which Fab2 #11 was identified as a functionally active antibody. Full length antibodies of the rat IgG2c and mouse IgG2a isotypes were generated from Fab2 #11. The full length anti-MASP-2 antibody of the mouse IgG2a isotype was characterized for pharmacodynamic parameters as described in Example 38. In this Example, the mouse anti-MASP-2 full-length antibody derived from Fab2 #11 was analyzed in the mouse model of age-related macular degeneration (AMD), described by Bora P. S. et al, *J Immunol* 174:491-497 (2005).

Methods:

The mouse IgG2a full-length anti-MASP-2 antibody isotype derived from Fab2 #11 as described in Example 38, was tested in the mouse model of age-related macular degeneration (AMD) as described in Example 28 with the following modifications.

Administration of Mouse-Anti-MASP-2 MoAbs

Two different doses (0.3 mg/kg and 1.0 mg/kg) of mouse anti-MASP-2 MoAb along with an isotype control MoAb treatment were injected ip into WT (+/+) mice (n=8 mice per group) 16 hours prior to CNV induction Induction of Choroidal Neovascularization (CNV)

The induction of choroidal neovascularization (CNV) and measurement of the volume of CNV was carried out using laser photocoagulation as described in Example 28.

Figure 38:
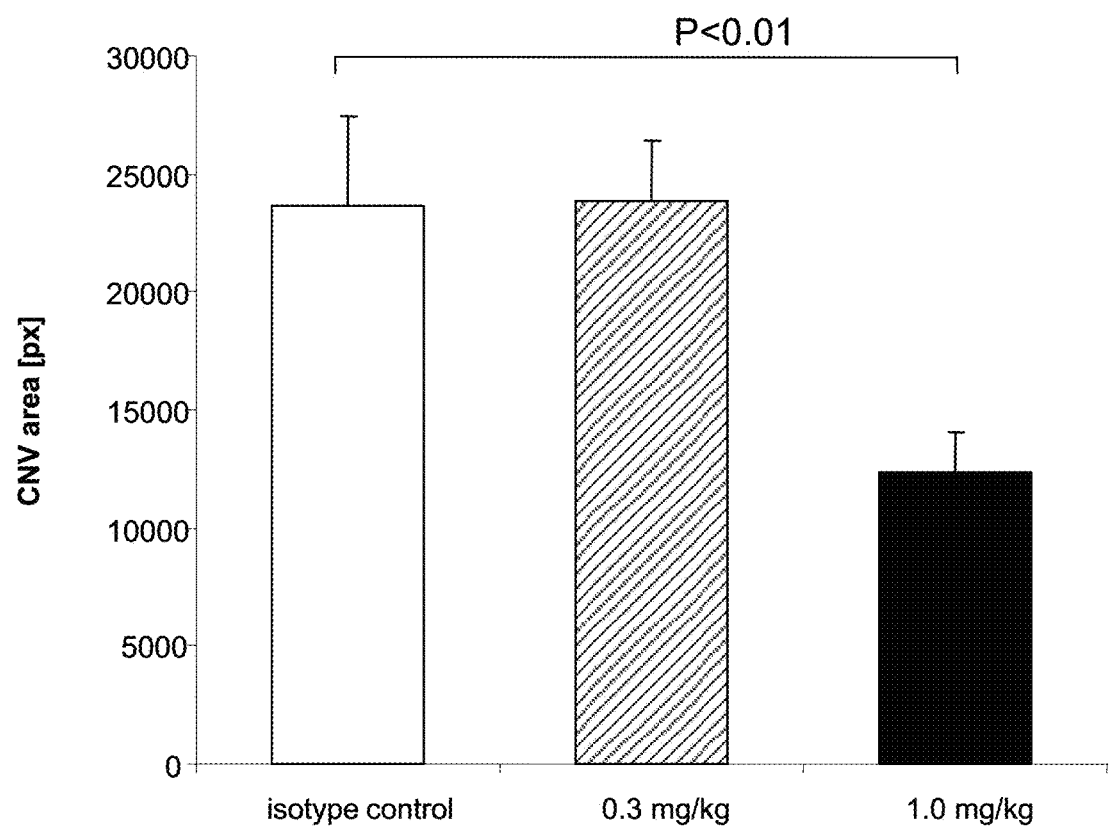
FIG. 38 graphically illustrates the mean choroidal neovascularization (CNV) volume at day seven following laser induced injury in WT (+/+) mice pre-treated with a single ip injection of 0.3 mg/kg or 1.0 mg/kg mouse anti-MASP-2 monoclonal antibody; as described in Example 39.

Results:

FIG. 38 graphically illustrates the CNV area measured at 7 days post laser injury in mice treated with either isotype control MoAb, or mouse anti-MASP-2 MoAb (0.3 mg/kg and 1.0 mg/kg). As shown in FIG. 38, in the mice pre-treated with 1.0 mg/kg anti-MASP-2 MoAb, a statistically significant ($p<0.01$) approximately 50% reduction in CNV was observed seven days post-laser treatment. As further shown in FIG. 38, it was observed that a 0.3 mg/kg dose of anti-MASP-2 MoAb was not efficacious in reducing CNV. It is noted that the 0.3 mg/kg dose of anti-MASP-2 MoAb was shown to have a partial and transient inhibition of C4b deposition following subcutaneous administration, as described in Example 38 and shown in FIG. 36.

The results described in this Example demonstrate that blockade of MASP-2 with an inhibitor, such as anti-MASP-2 MoAb, has a preventative and/or therapeutic effect in the treatment of macular degeneration. It is noted that these results are consistent with the results observed in the study carried out in the MASP-2 (−/−) mice, described in Example 28, in which a 30% reduction in the CNV 7 days post-laser treatment was observed in MASP-2 (−/−) mice in comparison to the wild-type control mice. Moreover, the results in this Example further demonstrate that systemically delivered anti-MASP-2 antibody provides local therapeutic benefit in the eye, thereby highlighting the potential for a systemic route of administration to treat AMD patients. In summary, these results provide evidence supporting the use of MASP-2 MoAb in the treatment of AMD.

Example 40

This Example demonstrates that MASP-2 deficient mice are protected from Neisseria meningitidis induced mortality after infection with *N. meningitidis and have enhanced clearance of bacteraemia as compared to wild type control mice.*

Rationale: Neisseria meningitidis is a heterotrophic gram-negative diplococcal bacterium known for its role in meningitis and other forms of meningococcal disease such as meningococcemia. *N. meningitidis* is a major cause of morbidity and mortality during childhood. Severe complications include septicaemia, Waterhouse-Friderichsen syndrome, adrenal insufficiency and disseminated intravascular coagulation (DIC). See e.g., Rintala E. et al., *Critical Care Medicine* 28(7):2373-2378 (2000). In this Example, the role of the lectin pathway was analyzed in MASP-2 (−/−) and WT (+/+) mice in order to address whether MASP-2 deficient mice would be susceptible to *N. meningitidis* induced mortality.

Methods:

MASP-2 knockout mice were generated as described in Example 27. 10 week old MASP-2 KO mice (n=10) and wild type C57/B6 mice (n=10) were innoculated by intravenous injection with either a dosage of $5\times10^8$ cfu/100 µl, $2\times10^8$ cfu/100 µl or $3\times10^7$ cfu/100 µl of Neisseria meningitidis Serogroup A Z2491 in 400 mg/kg iron dextran. Survival of the mice after infection was monitored over a 72 hour time period. Blood samples were taken from the mice at hourly intervals after infection and analyzed to determine the serum level (log cfu/ml) of *N. meningitidis* in order to verify infection and determine the rate of clearance of the bacteria from the serum.

Figure 39A:
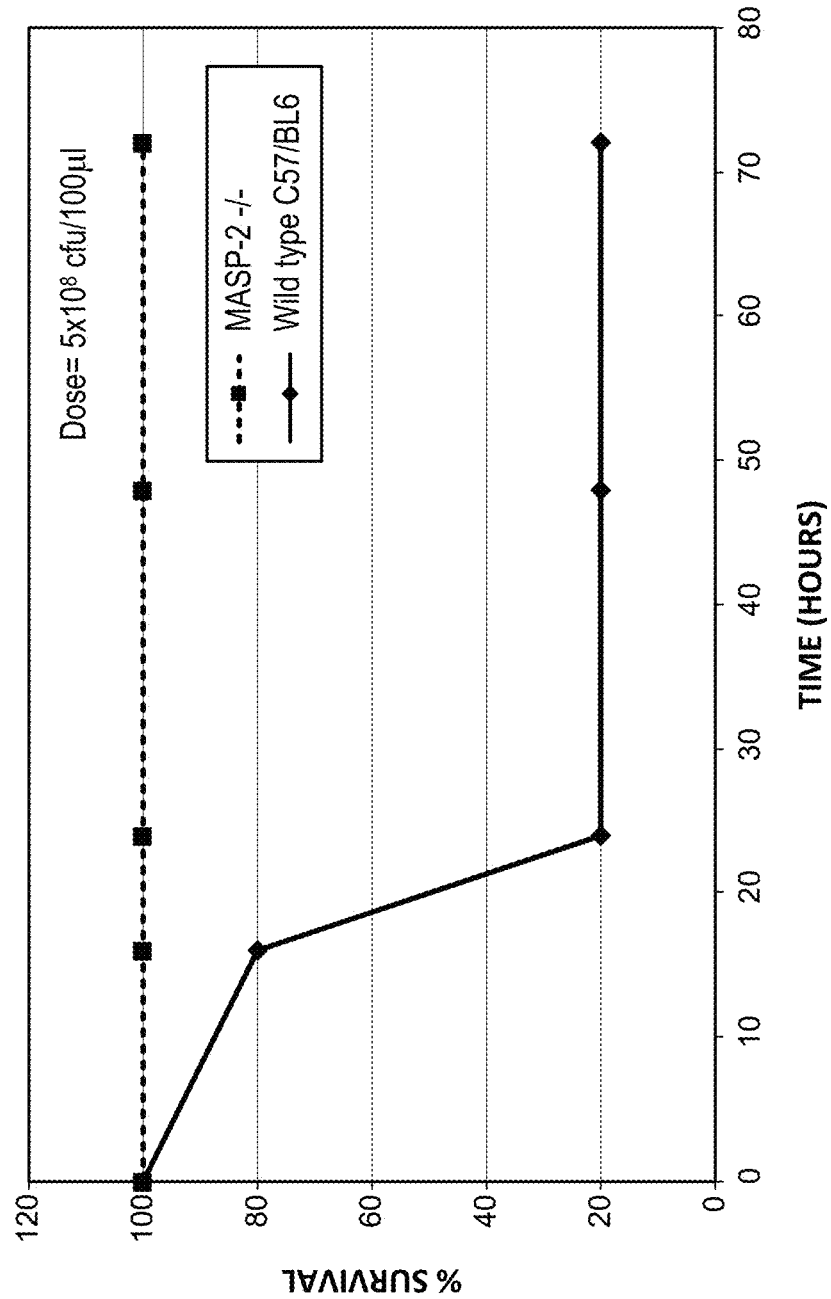
FIG. 39A graphically illustrates the percent survival of MASP-2 (−/−) and WT (+/+) mice after infection with $5\times10^8/100$ μl cfu *N. meningitidis*, as described in Example 40.

Results:

FIG. 39A graphically illustrates the percent survival of MASP-2 KO and WT mice after administration of an infective dose of $5\times10^8/100$ µl cfu *N. meningitidis*. As shown in FIG. 39A, after infection with the highest dose of $5\times10^8/100$ µl cfu *N. meningitidis*, 100% of the MASP-2 KO mice survived throughout the 72 hour period after infection. In contrast, only 20% of the WT mice were still alive 24 hours after infection. These results demonstrate that MASP-2 deficient mice are protected from *N. meningitidis* induced mortality.

Figure 39B:
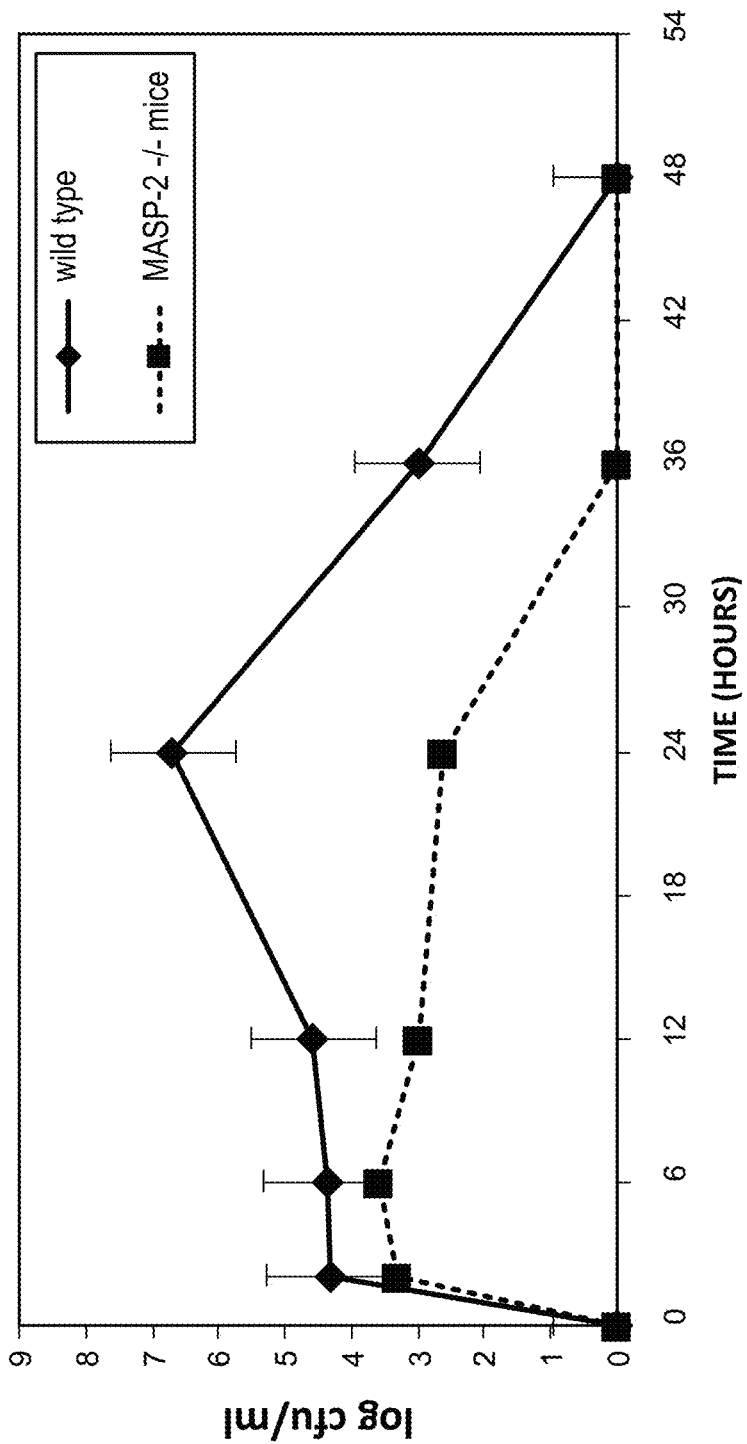
FIG. 39B graphically illustrates the log cfu/ml of *N. meningitidis* recovered at different time points in blood samples taken from the MASP-2 KO (−/−) and WT (+/+) mice infected with $5\times10^8$ cfu/100 μl *N. meningitidis*, as described in Example 40.

FIG. 39B graphically illustrates the log cfu/ml of *N. meningitidis* recovered at different time points in blood samples taken from the MASP-2 KO and WT mice infected with $5\times10^8$ cfu/100 µl *N. meningitidis*. As shown in FIG. 39B, in WT mice the level of *N. meningitidis* in the blood reached a peak of about 6.5 log cfu/ml at 24 hours after infection and dropped to zero by 48 hours after infection. In contrast, in the MASP-2 KO mice, the level of *N. meningitidis* reached a peak of about 3.5 log cfu/ml at 6 hours after infection and dropped to zero by 36 hours after infection.

Figure 40A:
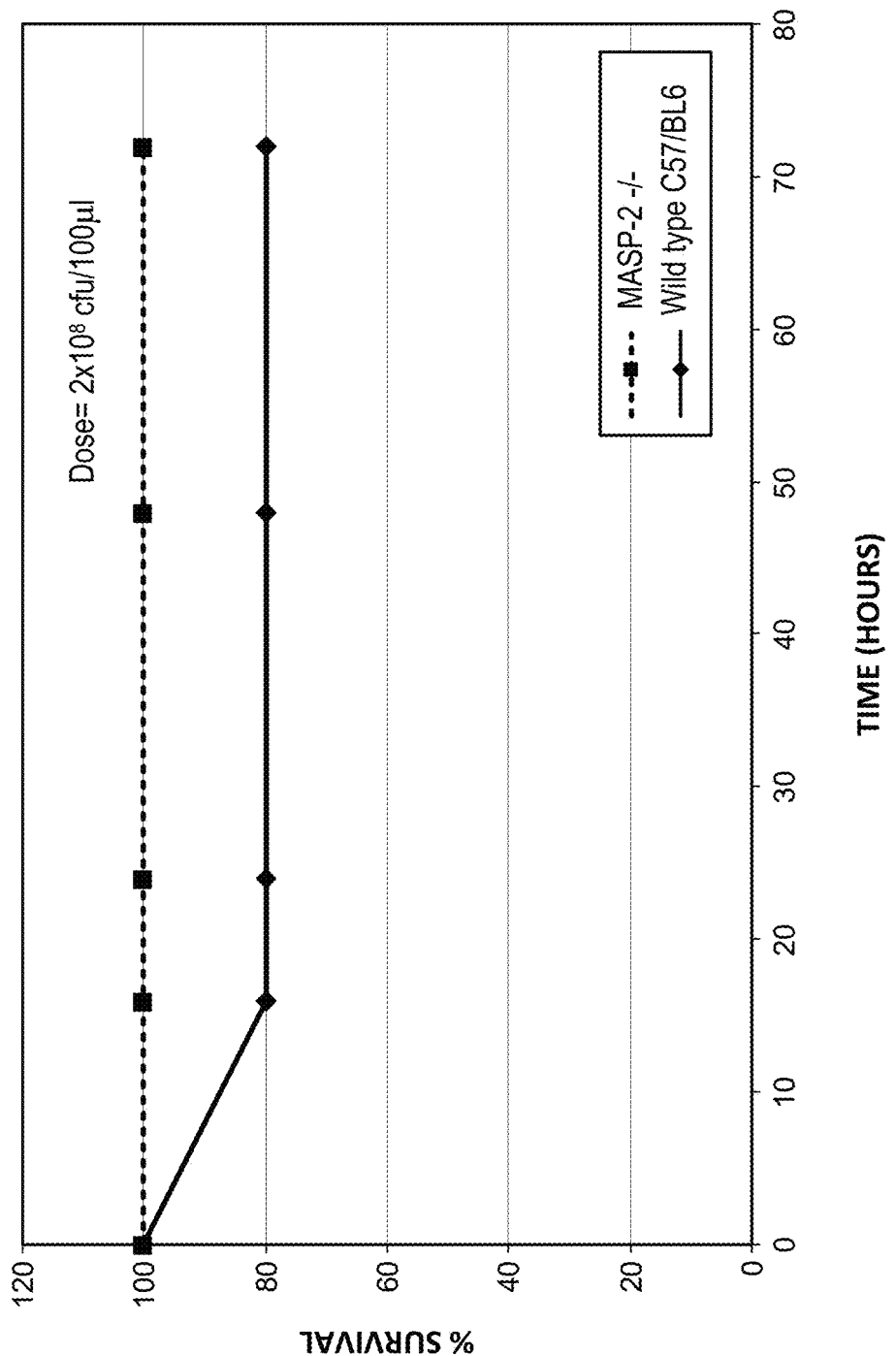
FIG. 40A graphically illustrates the percent survival of MASP-2 KO (−/−) and WT (+/+) mice after infection with $2\times10^8$ cfu/100 μl *N. meningitidis*, as described in Example 40.

FIG. 40A graphically illustrates the percent survival of MASP-2 KO and WT mice after infection with $2\times10^8$ cfu/100 µl *N. meningitidis*. As shown in FIG. 40A, after infection with the dose of $2\times10^8$ cfu/100 µl *N. meningitidis*, 100% of the MASP-2 KO mice survived throughout the 72 hour period after infection. In contrast, only 80% of the WT mice were still alive 24 hours after infection. Consistent with the results shown in FIG. 39A, these results further demonstrate that MASP-2 deficient mice are protected from *N. meningitidis* induced mortality.

Figure 40C:
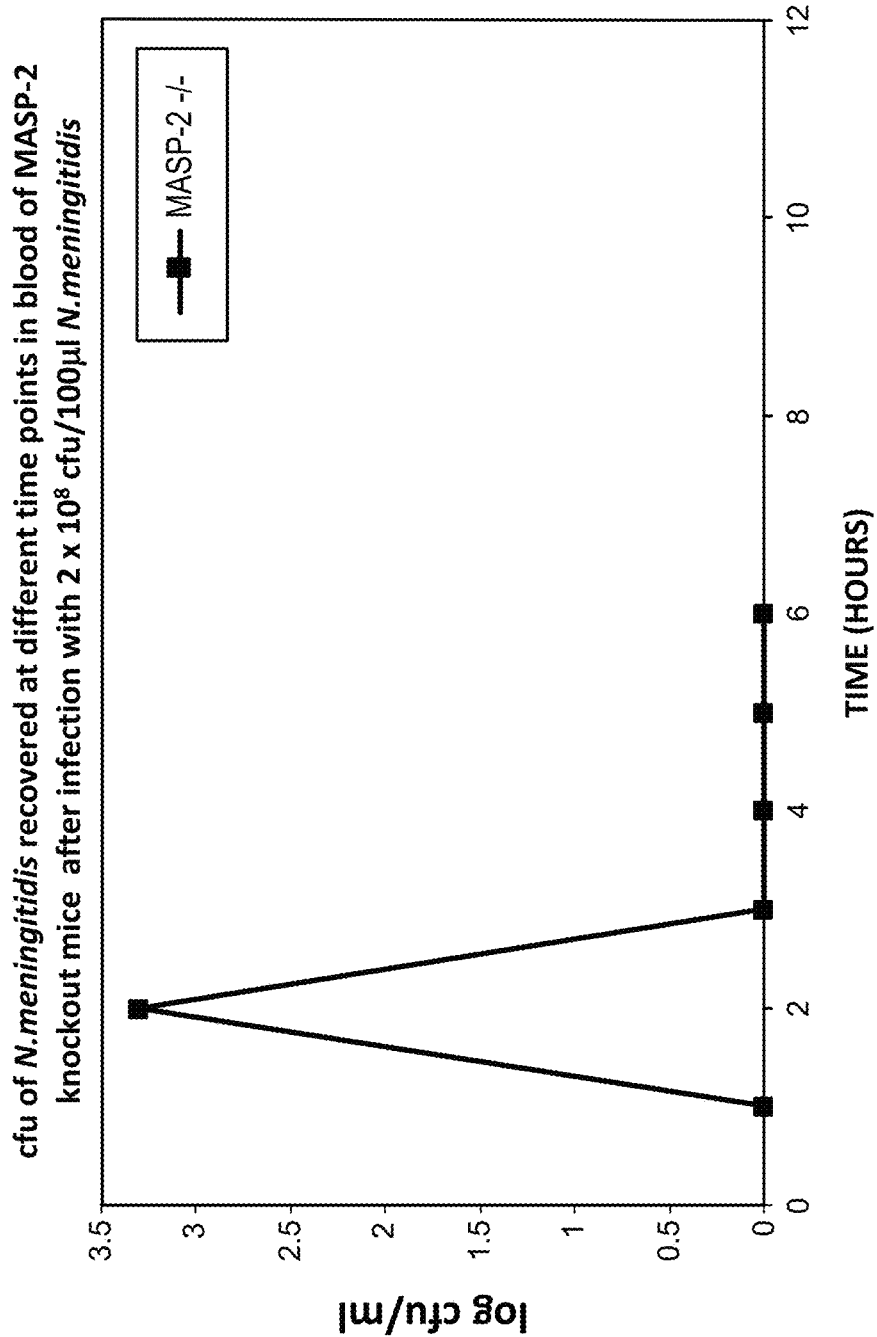
FIG. 40C graphically illustrates the log cfu/ml of *N. meningitidis* recovered at different time points in blood samples taken from the MASP-2 (−/−) mice infected with $2\times10^8$ cfu/100 μl *N. meningitidis*, as described in Example 40.

FIG. 40B graphically illustrates the log cfu/ml of *N. meningitidis* recovered at different time points in blood samples taken from the WT mice infected with $2\times10^8$ cfu/100 µl *N. meningitidis*. As shown in FIG. 40B, the level of *N. meningitidis* in the blood of WT mice infected with $2\times10^8$ cfu reached a peak of about 4 log cfu/ml at 12 hours after infection and dropped to zero by 24 hours after infection. FIG. 40C graphically illustrates the log cfu/ml of *N. meningitidis* recovered at different time points in blood samples taken from the MASP-2 KO mice infected with $2\times10^8$ cfu/100 µl *N. meningitidis*. As shown in FIG. 40C, the level of *N. meningitidis* in the blood of MASP-2 KO mice infected with $2\times10^8$ cfu reached a peak level of about 3.5 log cfu/ml at 2 hours after infection and dropped to zero at 3 hours after infection. Consistent with the results shown in FIG. 39B, these results demonstrate that although the MASP-2 KO mice were infected with the same dose of *N. meningitidis* as the WT mice, the MASP-2 KO mice have enhanced clearance of bacteraemia as compared to WT.

The percent survival of MASP-2 KO and WT mice after infection with the lowest dose of $3 \times 10^7$ cfu/100 µl *N. meningitidis* was 100% at the 72 hour time period (data not shown).

Discussion

These results show that MASP-2 deficient mice are protected from *N. meningitidis* induced mortality and have enhanced clearance of bacteraemia as compared to the WT mice. Therefore, in view of these results, it is expected that therapeutic application of MASP-2 inhibitors, such as MASP-2 MoAb, would be expected to be efficacious to treat, prevent or mitigate the effects of infection with *N. meningitidis* bacteria (i.e., sepsis and DIC). Further, these results indicate that therapeutic application of MASP-2 inhibitors, such as MASP-2 MoAb would not predispose a subject to an increased risk to contract *N. meningitidis* infections.

Example 41

This Example describes the discovery of novel lectin pathway mediated and MASP-2 dependent C4-bypass activation of complement C3.

Rationale:

The principal therapeutic benefit of utilizing inhibitors of complement activation to limit myocardial ischemia/reperfusion injury (MIRI) was convincingly demonstrated in an experimental rat model of myocardial infarction two decades ago: Recombinant sCR1, a soluble truncated derivative of the cell surface complement receptor type-1 (CR1), was given intravenously and its effect assessed in a rat in vivo model of MIRI. Treatment with sCR1 reduced infarct volume by more than 40% (Weisman, H. F., et al., *Science* 249:146-151 (1990)). The therapeutic potential of this recombinant inhibitor was subsequently demonstrated in a clinical trial showing that the administration of sCR1 in patients with MI prevented contractile failure in the post-ischemic heart (Shandelya, S., et al., Circulation 87:536-546 (1993)). The primary mechanism leading to the activation of complement in ischemic tissue, however, has not been ultimately defined, mainly due to the lack of appropriate experimental models, the limited understanding of the molecular processes that lead to complement activation of oxygen-deprived cells, and the cross-talk and synergisms between the different complement activation pathways.

As a fundamental component of the immune response, the complement system provides protection against invading microorganisms through both antibody-dependent and -independent mechanisms. It orchestrates many cellular and humoral interactions within the immune response, including chemotaxis, phagocytosis, cell adhesion, and B-cell differentiation. Three different pathways initiate the complement cascade: the classical pathway, the alternative pathway, and the lectin pathway. The classical pathway recognition subcomponent C1q binds to a variety of targets—most prominently immune complexes—to initiate the step-wise activation of associated serine proteases, C1r and C1s, providing a major mechanism for pathogen and immune complex clearance following engagement by the adaptive immune system. Binding of C1q to immune complexes converts the C1r zymogen dimer into its active form to cleave and thereby activate C1s. C1s translates C1q binding into complement activation in two cleavage steps: It first converts C4 into C4a and C4b and then cleaves C4b-bound C2 to form the C3 convertase C4b2a. This complex converts the abundant plasma component C3 into C3a and C3b. Accumulation of C3b in close proximity of the C4b2a complex shifts the substrate specificity for C3 to C5 to form the C5 convertase $C4b2a(C3b)_n$. The C3 and C5 convertase complexes generated via classical pathway activation are identical to those generated through the lectin pathway activation route. In the alternative pathway, spontaneous low-level hydrolysis of component C3 results in deposition of protein fragments onto cell surfaces, triggering complement activation on foreign cells, while cell-associated regulatory proteins on host tissues avert activation, thus preventing self-damage. Like the alternative pathway, the lectin pathway may be activated in the absence of immune complexes. Activation is initiated by the binding of a multi-molecular lectin pathway activation complex to Pathogen-Associated Molecular Patterns (PAMPs), mainly carbohydrate structures present on bacterial, fungal or viral pathogens or aberrant glycosylation patterns on apoptotic, necrotic, malignant or oxygen-deprived cells (Collard, C. D., et al., *Am. J. Pathol.* 156:1549-1556 (2000); Walport, M. J., *N. Engl. J. Med.* 344:1058-1066 (2001); Schwaeble, W., et al., *Immunobiology* 205:455-466 (2002); and Fujita, T., *Nat. Rev. Immunol.* 2:346-353 (2002)).

Mannan-binding lectin (MBL) was the first carbohydrate recognition subcomponent shown to form complexes with a group of novel serine proteases, named MBL-associated Serine Proteases (MASPs) and numbered according to the sequence of their discovery (i.e., MASP-1, MASP-2 and MASP-3). In man, lectin pathway activation complexes can be formed with four alternative carbohydrate recognition subcomponents with different carbohydrate binding specificities, i.e., MBL 2, and three different members of the ficolin family, namely L-Ficolin, H-ficolin and M-ficolin and MASPs. Two forms of MBL, MBL A and MBL C, and ficolin-A form lectin activation pathway complexes with MASPs in mouse and rat plasma. We have previously cloned and characterised MASP-2 and an additional truncated MASP-2 gene product of 19 kDa, termed MAp19 or sMAP, in human, mouse and rat (Thiel, S., et al., *Nature* 386:506-510 (1997). Stover, C. M., et al., *J. Immunol.* 162:3481-3490 (1999); Takahashi, M., et al., *Int. Immunol.* 11:859-863 (1999); and Stover, C. M., et al., *J. Immunol.* 163:6848-6859 (1999)). MAp19/sMAP is devoid of protease activity, but may regulate lectin pathway activation by competing for the binding of MASPs to carbohydrate recognition complexes (Iwaki, D. et al., *J. Immunol.* 177:8626-8632 (2006)).

There is strong evidence suggesting that of the three MASPs, only MASP-2 is required to translate binding of the lectin pathway recognition complexes into complement activation (Thiel, S., et al. (1997); Vorup-Jensen, T., et al., *J. Immunol.* 165:2093-2100 (2000); Thiel, S., et al., *J. Immunol.* 165:878-887 (2000); Rossi, V., et al., *J. Biol. Chem.* 276:40880-40887 (2001)). This conclusion is underlined by the phenotype of a most recently described mouse strain deficient in MASP-1 and MASP-3. Apart from a delay in the onset of lectin pathway mediated complement activation in vitro –MASP-1/3 deficient mice retain lectin pathway functional activity. Reconstitution of MASP-1 and MASP-3 deficient serum with recombinant MASP-1 overcomes this delay in lectin pathway activation implying that MASP-1 may facilitate MASP-2 activation (Takahashi, M., et al., *J. Immunol.* 180:6132-6138 (2008)). A most recent study has shown that MASP-1 (and probably also MASP-3) are required to convert the alternative pathway activation enzyme Factor D from its zymogen form into its enzymatically active form (Takahashi, M., et al., *J. Exp. Med.* 207:29-37 (2010)). The physiological importance of this process is underlined by the absence of alternative pathway functional activity in plasma of MASP-1/3 deficient mice.

The recently generated mouse strains with combined targeted deficiencies of the lectin pathway carbohydrate recognition subcomponents MBL A and MBL C may still initiate lectin pathway activation via the remaining murine lectin pathway recognition subcomponent ficolin A (Takahashi, K., et al., *Microbes Infect.* 4:773-784 (2002)). The absence of any residual lectin pathway functional activity in MASP-2 deficient mice delivers a conclusive model to study the role of this effector arm of innate humoral immunity in health and disease.

The availability of C4 and MASP-2 deficient mouse strains allowed us to define a novel lectin pathway specific, but MASP-2 dependent, C4-bypass activation route of complement C3. The essential contribution of this novel lectin pathway mediated C4-bypass activation route towards post-ischemic tissue loss is underlined by the prominent protective phenotype of MASP-2 deficiency in MIRI while C4-deficient mice tested in the same model show no protection.

In this Example, we describe a novel lectin pathway mediated and MASP-2 dependent C4-bypass activation of complement C3. The physiological relevance of this new activation route is established by the protective phenotype of MASP-2 deficiency in an experimental model of myocardial ischemia/reperfusion injury (MIRI), where C4 deficient animals were not protected.

Methods:

MASP-2 Deficient Mice Show No Gross Abnormalities.

MASP-2 deficient mice were generated as described in Example 27. Both heterozygous ($+/-$) and homozygous ($-/-$) MASP-2 deficient mice are healthy and fertile, and show no gross abnormalities. Their life expectancy is similar to that of their WT littermates (>18 months). Prior to studying the phenotype of these mice in experimental models of disease, our MASP-2$^{-/-}$ line was backcrossed for eleven generations onto a C57BL/6 background. The total absence of MASP-2 mRNA was confirmed by Northern blotting of poly A+ selected liver RNA preparations, while the 1.2 kb mRNA encoding MAp19 or sMAP (a truncated alternative splicing product of the MASP2 gene) is abundantly expressed.

qRT-PCR analysis using primer pairs specific for either the coding sequence for the serine protease domain of MASP-2 (B chain) or the remainder of the coding sequence for the A-chain showed that no B chain encoding mRNA is detectable in MASP-2$^{-/-}$ mice while the abundance of the disrupted A chain mRNA transcript was significantly increased. Likewise, the abundance of MAp19/sMAP encoding mRNA is increased in MASP-2$^{+/-}$ and MASP-2$^{-/-}$ mice. Plasma MASP-2 levels, determined by ELISA for 5 animals of each genotype, were 300 ng/ml for WT controls (range 260-330 ng/ml), 360 ng/ml for heterozygous mice (range 330-395 ng/ml) and undetectable in MASP-2$^{-/-}$ mice. Using qRT-PCR, mRNA expression profiles were established demonstrating that MASP-2$^{-/-}$ mice express mRNA for MBL A, MBL C, ficolin A, MASP-1, MASP-3, C1q, C1rA, C1sA, Factor B, Factor D, C4, and C3 at an abundance similar to that of their MASP-2 sufficient littermates (data not shown).

Plasma C3 levels of MASP-2$^{-/-}$ (n=8) and MASP-2$^{+/+}$ (n=7) littermates were measured using a commercially available mouse C3 ELISA kit (Kamiya, Biomedical, Seattle, Wash.). C3 levels of MASP-2 deficient mice (average 0.84 mg/ml, +/−0.34) were similar to those of the WT controls (average 0.92, +/−0.37).

Results:

MASP-2 is Essential for Lectin Pathway Functional Activity

As described in Example 2 and shown in FIGS. 6 and 7, the in vitro analyses of MASP-2$^{-/-}$ plasma showed a total absence of lectin pathway functional activity on activating Mannan- and Zymosan-coated surfaces for both the activation of C4 and C3. Likewise, neither lectin pathway-dependent C4 nor C3 cleavage was detectable in MASP-2$^{-/-}$ plasma on surfaces coated with N-acetyl glucosamine, which binds and triggers activation via MBL A, MBL C and ficolin A (data not shown).

The analyses of sera and plasma of MASP-2-/-mice clearly demonstrated that MASP-2 is essentially required to activate complement via the lectin pathway and that neither MASP-1, nor MASP-3 are able to maintain or restore lectin pathway activity in MASP-2 deficiency (data not shown).

Figure 41A:
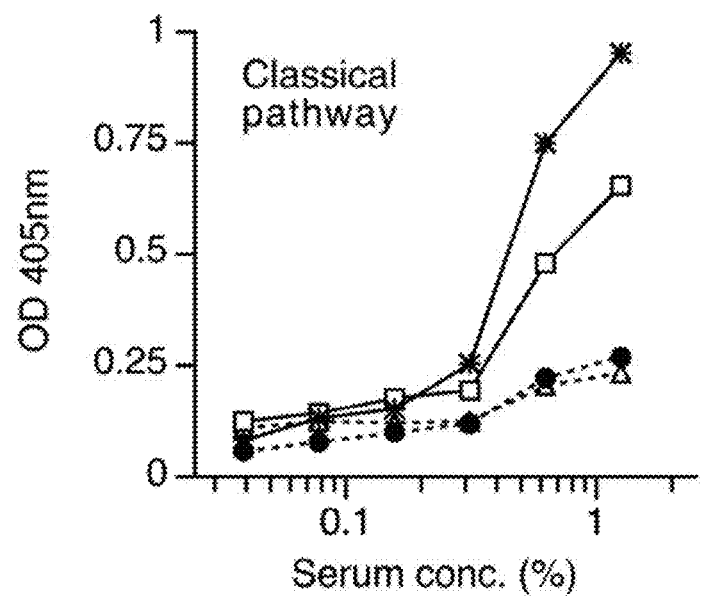
FIG. 41A graphically illustrates the results of a C3b deposition assay demonstrating that MASP-2 (−/−) mice retain a functional classical pathway, as described in Example 41.
Figure 41B:
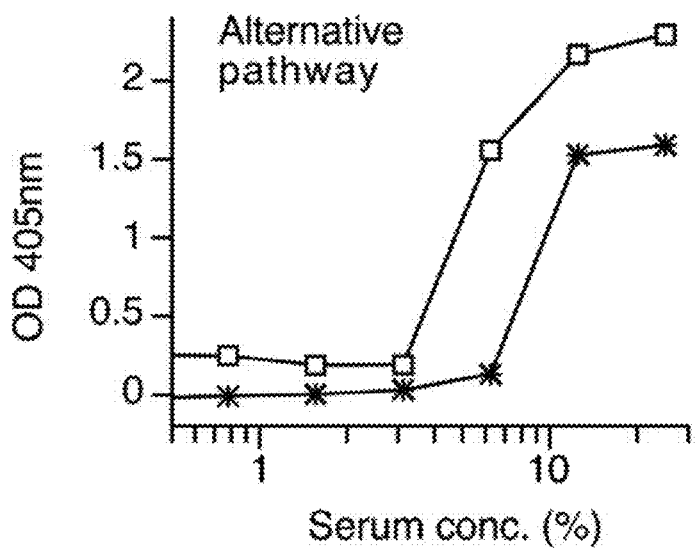
FIG. 41B graphically illustrates the results of a C3b deposition assay on zymosan coated plates, demonstrating that MASP-2 (−/−) mice retain a functional alternative pathway, as described in Example 41.

The total deficiency of lectin pathway functional activity, however, leaves the other complement activation pathways intact: MASP-2-/-plasma can still activate complement via the classical (FIG. 41A) and the alternative pathway (FIG. 41B). In FIGS. 41A and 41B, the symbol "*" indicates serum from WT (MASP-2 (+/+)); the symbol "●" indicates serum from WT (C1q depleted); the symbol "□" indicates serum from MASP-2 (−/−); and the symbol "Δ" indicates serum from MASP-2 (−/−) (C1q depleted).

FIG. 41A graphically illustrates that MASP-2-/- mice retain a functional classical pathway: C3b deposition was assayed on microtiter plates coated with immune complexes (generated in situ by coating with BSA then adding goat anti-BSA IgG). FIG. 41B graphically illustrates MASP-2 deficient mice retain a functional alternative pathway: C3b deposition was assayed on Zymosan coated microtiter plates under conditions that permit only alternative pathway activation (buffer containing Mg$^{2+}$ and EGTA). Results shown in FIG. 41A and FIG. 41B are means of duplicates and are typical of three independent experiments. Same symbols for plasma sources were used throughout. These results show that a functional alternative pathway is present in MASP-2 deficient mice, as evidenced in the results shown in FIG. 41B under experimental conditions designed to directly trigger the alternative pathway, while inactivating both the classical pathway and lectin pathway. However, as demonstrated in FIG. 7A, MASP-2 is required to activate both lectin-pathway mediated C3 activation and subsequent alternative pathway mediated C3 activation. Therefore, although the alternative pathway is functional in MASP-2 deficient mice, it is not activated because the alternative complement pathway requires lectin pathway-dependent MASP-2 activation for complement activation, as illustrated in FIG. 1.

The Lectin Pathway of Complement Activation Critically Contributes to Inflammatory Tissue Loss in Myocardial Ischemia/Reperfusion Injury (MIRI).

As described in Examples 27 and 34, in order to study the contribution of lectin pathway functional activity to MIRI, we compared MASP-2$^{-/-}$ mice and WT littermate controls in a model of MIRI following transient ligation and reperfusion of the left anterior descending branch of the coronary artery (LAD). The results described in Examples 27 and 34 clearly demonstrate that MASP-2 deficient animals show a significant degree of protection with significantly reduced infarct sizes (p<0.01) compared to their lectin pathway sufficient littermates.

Figure 42A:
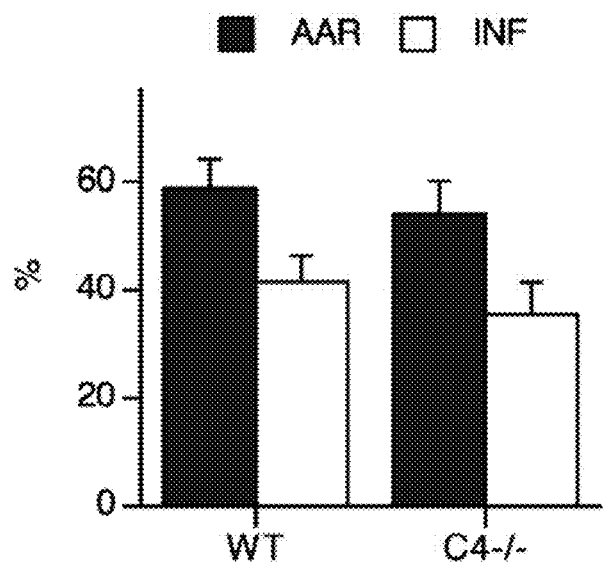
FIG. 42A graphically illustrates myocardial ischemia/reperfusion injury (MIRI)-induced tissue loss following ligation of the left anterior descending branch of the coronary artery (LAD) and reperfusion in C4 (−/−) mice (n=6) and matching WT littermate controls (n=7), showing area at risk (AAR) and infarct size (INF) as described in Example 41.
Figure 42B:
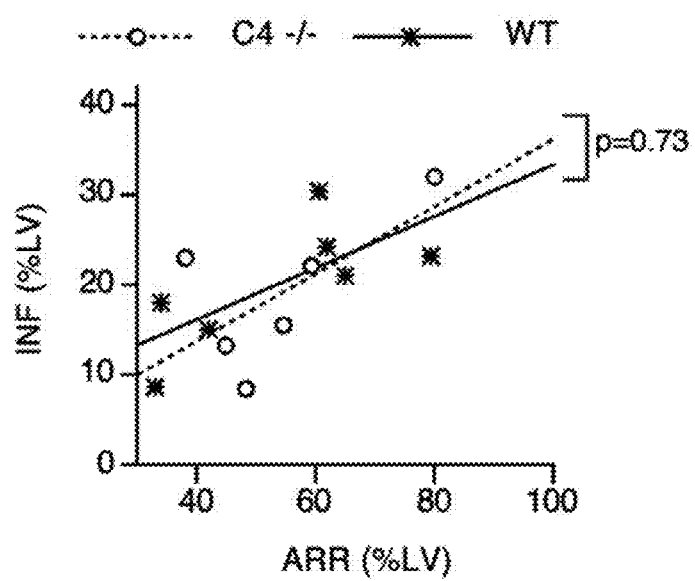
FIG. 42B graphically illustrates infarct size (INF) as a function of area at risk (AAR) in C4 (−/−) and WT mice treated as describe in FIG. 42A, demonstrating that C4 (−/−) mice are as susceptible to MIRI as WT controls (dashed line), as described in Example 41.

The presence or absence of complement C4 has no impact on the degree of ischemic tissue loss in MIRI. Using the same procedure described in Examples 27 and 34, we assessed the impact of C4 deficiency on infarct sizes following experimental MIRI. As shown in FIG. 42A and FIG. 42B, identical infarct sizes were observed in both C4-deficient mice and their WT littermates. FIG. 42A graphically illustrates MIRI-induced tissue loss following LAD ligation and reperfusion in C4−/− mice (n=6) and matching WT littermate controls (n=7). Areas at risk (AAR) and infarct size (INF) were determined as described in FIG. 31. FIG. 42B graphically illustrates INF as a function of AAR, clearly demonstrating that C4−/− mice are as susceptible to MIRI as their WT controls (dashed line).

These results demonstrate that C4 deficient mice are not protected from MIRI. This result was unexpected, as it is in conflict with the widely accepted view that the major C4 activation fragment, C4b, is an essential component of the classical and the lectin pathway C3 convertase C4b2a. We therefore assessed whether a residual lectin pathway specific activation of complement C3 can be detected in C4-deficient mouse and human plasma.

The Lectin Pathway can Activate Complement C3 in Absence of C4 Via a Novel MASP-2 Dependent C4-Bypass Activation Route.

Encouraged by historical reports indicating the existence of a C4-bypass activation route in C4-deficient guinea pig serum (May, J. E., and M. Frank, *J. Immunol.* 111:1671-1677 (1973)), we analyzed whether C4-deficient mice may have residual classical or lectin pathway functional activity and monitored activation of C3 under pathway-specific assay conditions that exclude contributions of the alternative pathway.

Figure 43A:
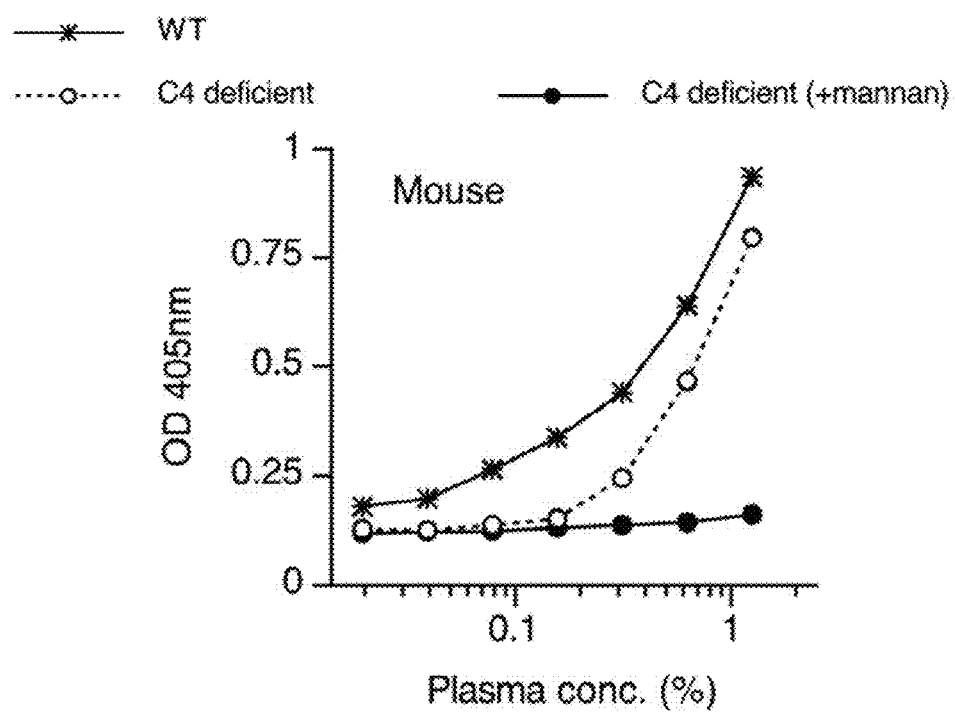
FIG. 43A graphically illustrates the results of a C3b deposition assay using serum from WT mice, C4 (−/−) mice and serum from C4 (−/−) mice pre-incubated with mannan, as described in Example 41.
Figure 43B:
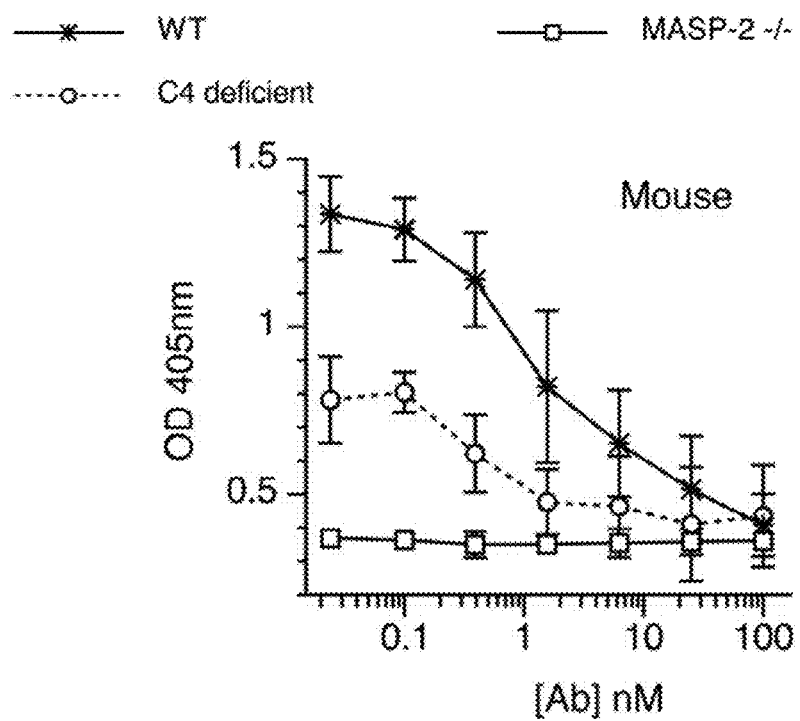
FIG. 43B graphically illustrates the results of a C3b deposition assay on serum from WT, C4 (−/−), and MASP-2 (−/−) mice mixed with various concentrations of an anti-murine MASP-2 mAb (mAbM11), as described in Example 41.

C3b deposition was assayed on Mannan-coated microtiter plates using re-calcified plasma at plasma concentrations prohibitive for alternative pathway activation (1.25% and below). While no cleavage of C3 was detectable in C4-deficient plasma tested for classical pathway activation (data not shown), a strong residual C3 cleavage activity was observed in C4-deficient mouse plasma when initiating complement activation via the lectin pathway. The lectin pathway dependence is demonstrated by competitive inhibition of C3 cleavage following preincubation of C4-deficient plasma dilutions with soluble Mannan (see FIG. 43A). As shown in FIG. 43A-D, MASP-2 dependent activation of C3 was observed in the absence of C4. FIG. 43A graphically illustrates C3b deposition by C4+/+ (crosses) and C4−/− (open circles) mouse plasma. Pre-incubating the C4−/− plasma with excess (1 µg/ml) fluid-phase Mannan prior to the assay completely inhibits C3 deposition (filled circles). Results are typical of 3 independent experiments. FIG. 43B graphically illustrates the results of an experiment in which wild-type, MASP-2 deficient (open squares) and C4−/− mouse plasma (1%) was mixed with various concentrations of anti-rat MASP-2 mAbM11 (abscissa) and C3b deposition assayed on Mannan-coated plates. Results are means (±SD) of 4 assays (duplicates of 2 of each type of plasma).

Figure 43C:
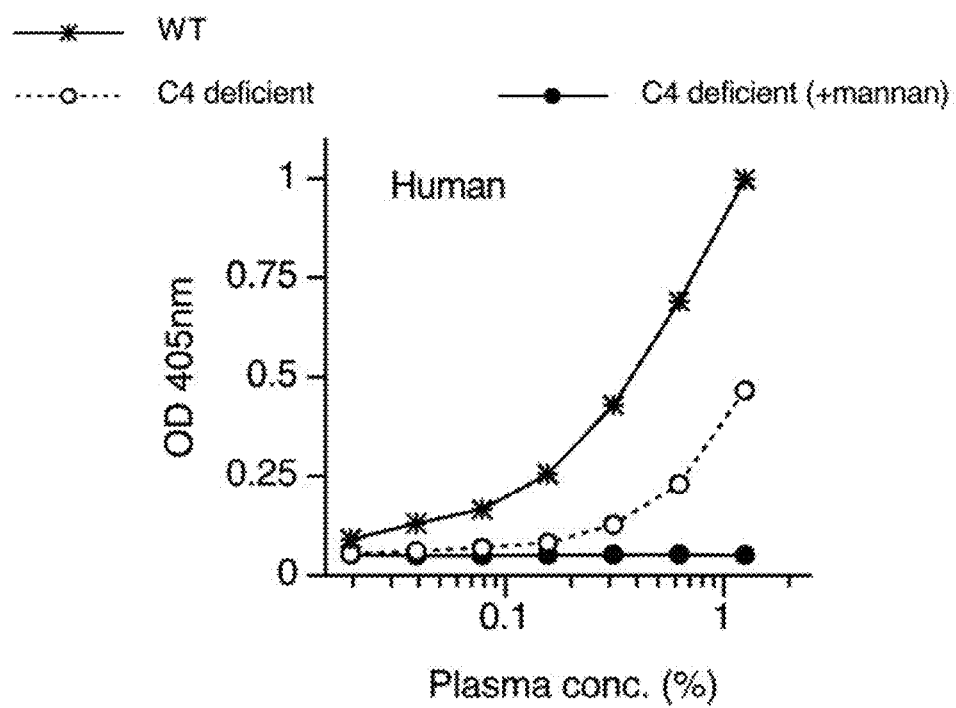
FIG. 43C graphically illustrates the results of a C3b deposition assay on human serum from WT (C4 sufficient) and C4 deficient serum, and serum from C4 deficient subjects pre-incubated with mannan, as described in Example 41.

FIG. 43C graphically illustrates the results of an experiment in which Human plasma: pooled NHS (crosses), C4−/− plasma (open circles) and C4−/− plasma pre-incubated with 1 µg/ml Mannan (filled circles). Results are representative of three independent experiments.

Figure 43D:
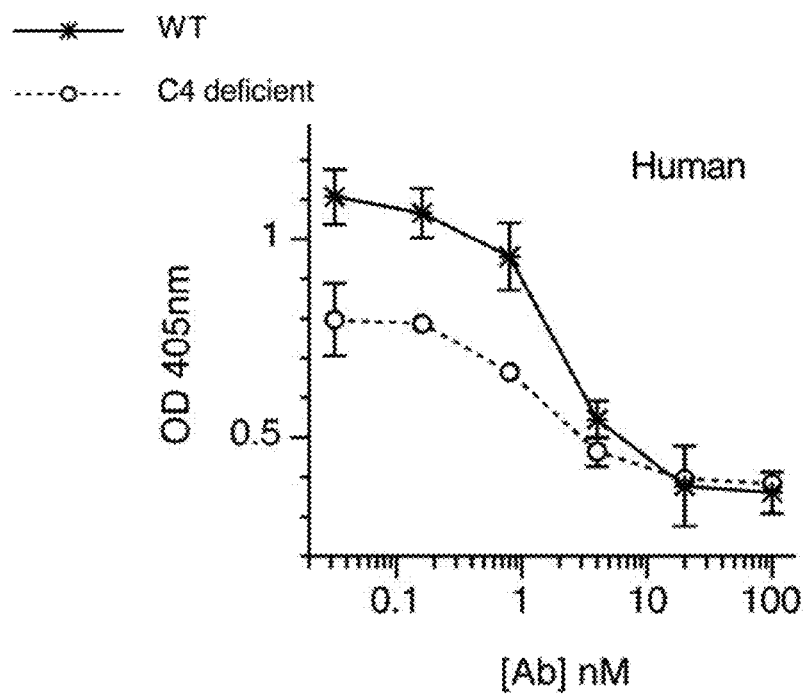
FIG. 43D graphically illustrates the results of a C3b deposition assay on human serum from WT (C4 sufficient) and C4 deficient subjects mixed with anti-human MASP-2 mAb (mAbH3), as described in Example 41.

FIG. 43D graphically illustrates that inhibition of C3b deposition in C4 sufficient and C4 deficient human plasma (1%) by anti-human MASP-2 mAbH3 (Means±SD of triplicates).

As shown in FIG. 43B, no lectin pathway-dependent C3 activation was detected in MASP-2−/−plasma assayed in parallel, implying that this C4-bypass activation route of C3 is MASP-2 dependent.

To further corroborate these findings, we established a series of recombinant inhibitory mAbs isolated from phage display antibody libraries by affinity screening against recombinant human and rat MASP-2A (where the serine residue of the active protease domain was replaced by an alanine residue by site-directed mutagenesis to prevent autolytic degradation of the antigen). Recombinant antibodies against MASP-2 (AbH3 and AbM11) were isolated from Combinatorial Antibody Libraries (Knappik, A., et al., *J. Mol. Biol.* 296:57-86 (2000)), using recombinant human and rat MASP-2A as antigens (Chen, C. B. and Wallis, *J. Biol. Chem.* 276:25894-25902 (2001)). An anti-rat Fab2 fragment that potently inhibited lectin pathway-mediated activation of C4 and C3 in mouse plasma (IC50-1 nM) was converted to a full-length IgG2a antibody. Polyclonal anti-murine MASP-2A antiserum was raised in rats. These tools allowed us to confirm MASP-2 dependency of this novel lectin pathway specific C4-bypass activation route of C3, as further described below.

As shown in FIG. 43B, M211, an inhibitory monoclonal antibody which selectively binds to mouse and rat MASP-2 inhibited the C4-bypass activation of C3 in C4-deficient mouse as well as C3 activation of WT mouse plasma via the lectin pathway in a concentration dependent fashion with similar $IC_{50}$ values. All assays were carried out at high plasma dilutions rendering the alternative pathway activation route dysfunctional (with the highest plasma concentration being 1.25%).

In order to investigate the presence of an analogous lectin pathway specific C4-bypass activation of C3 in humans, we analyzed the plasma of a donor with an inherited deficiency of both human C4 genes (i.e., C4A and C4B), resulting in total absence of C4 (Yang, Y., et al., *J. Immunol.* 173:2803-2814 (2004)). FIG. 43C shows that this patient's plasma efficiently activates C3 in high plasma dilutions (rendering the alternative activation pathway dysfunctional). The lectin pathway specific mode of C3 activation on Mannan-coated plates is demonstrated in murine C4-deficient plasma (FIG. 43A) and human C4 deficient plasma (FIG. 43C) by adding excess concentrations of fluid-phase Mannan. The MASP-2 dependence of this activation mechanism of C3 in human C4-deficient plasma was assessed using AbH3, a monoclonal antibody that specifically binds to human MASP-2 and ablates MASP-2 functional activity. As shown in FIG. 43D, AbH3 inhibited the deposition of C3b (and C3dg) in both C4-sufficient and C4-deficient human plasma with comparable potency.

In order to assess a possible role of other complement components in the C4-bypass activation of C3, we tested plasma of MASP-1/3−/− and Bf/C2−/−mice alongside MASP-2−/−, C4−/− and C1q−/− plasma (as controls) under both lectin pathway specific and classical pathway specific assay conditions. The relative amount of C3 cleavage was plotted against the amount of C3 deposited when using WT plasma.

Figure 44A:
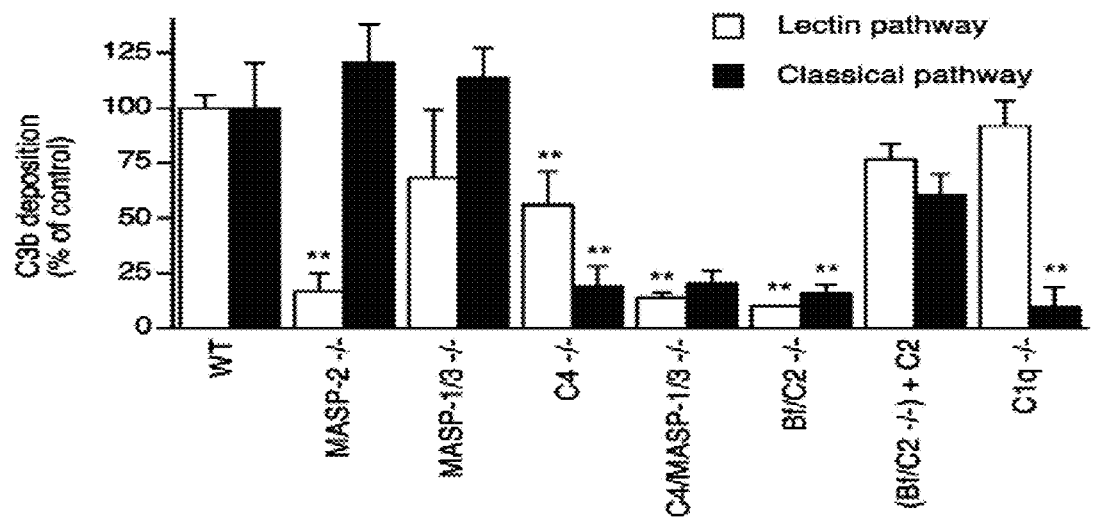
FIG. 44A graphically illustrates a comparative analysis of C3 convertase activity in plasma from various complement deficient mouse strains tested either under lectin activation pathway specific assay conditions, or under classical activation pathway specific assay conditions, as described in Example 41.

FIG. 44A graphically illustrates a comparative analysis of C3 convertase activity in plasma from various complement deficient mouse strains tested either under lectin activation pathway or classical activation pathway specific assay conditions. Diluted plasma samples (1%) of WT mice (n=6), MASP-2−/−mice (n=4), MASP-1/3−/− mice (n=2), C4−/− mice (n=8), C4/MASP-1/3−/− mice (n=8), Bf/C2−/− (n=2) and C1q−/− mice (n=2) were tested in parallel. Reconstitution of Bf/C2−/− plasma with 2.5 µg/ml recombinant rat C2 (Bf/C2−/− +C2) restored C3b deposition. Results are means (±SD). **p<0.01 (compared to WT plasma). As shown in FIG. 44A, substantial C3 deposition is seen in C4−/− plasma tested under lectin pathway specific assay conditions, but not under classical pathway specific conditions. Again, no C3 deposition was seen in MASP-2 deficient plasma via the lectin pathway activation route, while the same plasma deposited C3 via the classical pathway. In MASP-1/3−/− plasma, C3 deposition occurred in both lectin and classical pathway specific assay conditions. No C3 deposition was seen in plasma with a combined deficiency of C4 and MASP-1/3, either using lectin pathway or classical pathway specific conditions. No C3 deposition is detectable in C2/Bf−/− plasma, either via the lectin pathway, or via the classical pathway. Reconstitution of C2/Bf−/− mouse plasma with recombinant C2, however, restored both lectin pathway and classical pathway-mediated C3 cleavage. The assay conditions were validated using C1q−/− plasma.

Figure 44B:
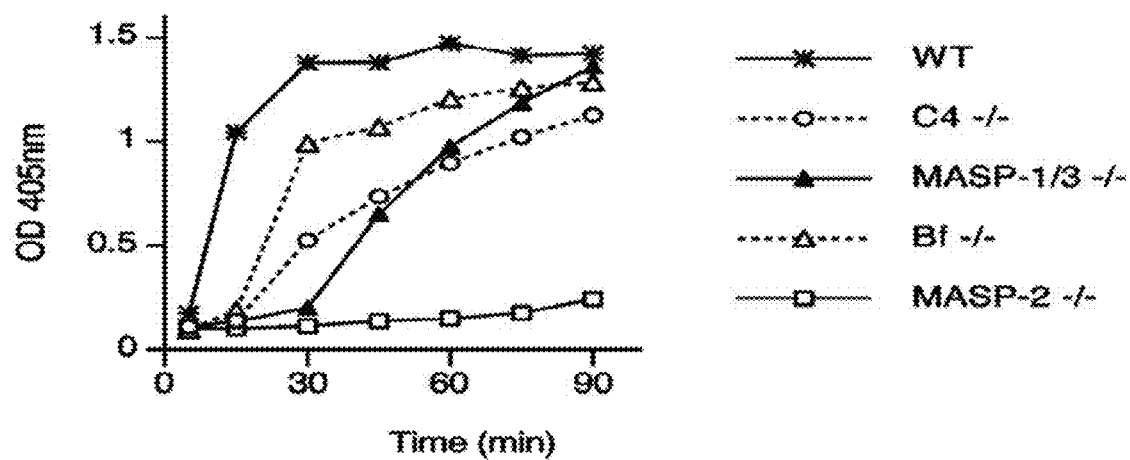
FIG. 44B graphically illustrates the time-resolved kinetics of C3 convertase activity in plasma from various complement deficient mouse strains tested under lectin activation pathway specific conditions, as described in Example 41.

FIG. 44B graphically illustrates time-resolved kinetics of C3 convertase activity in plasma from various complement deficient mouse strains WT, fB−/−, C4−/−, MASP-1/3−/−, and MASP-2−/−plasma, tested under lectin activation pathway specific assay conditions (1% plasma, results are typical of three independent experiments). As shown in FIG. 44B, while no C3 cleavage was seen in MASP-2−/−plasma, fB−/− plasma cleaved C3 with similar kinetics to the WT plasma. A significant delay in the lectin pathway-dependent conversion of C3 to C3b (and C3dg) was seen in C4−/− as well as in MASP-1/3 deficient plasma. This delay of C3 activation in MASP-1/3−/− plasma was recently shown to be MASP-1, rather than MASP-3 dependent (Takahashi, M., et al., *J. Immunol.* 180:6132-6138 (2008)).

Discussion:

The results described in this Example strongly suggest that MASP-2 functional activity is essential for the activation of C3 via the lectin pathway both in presence and absence of C4. Furthermore, C2 and MASP-1 are required for this novel lectin pathway specific C4-bypass activation route of C3 to work. The comparative analysis of lectin pathway functional activity in MASP-2−/− as well as C4−/− plasma revealed the existence of a previously unrecognized C4-independent, but MASP-2-dependent activation route of complement C3 and showed that C3 can be activated in a lectin pathway-dependent mode in total absence of C4. While the detailed molecular composition and the sequence of activation events of this novel MASP-2 dependent C3 convertase remains to be elucidated, our results imply that this C4-bypass activation route additionally requires the presence of complement C2 as well as MASP-1. The loss of lectin pathway-mediated C3 cleavage activity in plasma of mice with combined C4 and MASP-1/3 deficiency may be explained by a most recently described role of MASP-1 to enhance MASP-2 dependent complement activation through direct cleavage and activation of MASP-2 (Takahashi, M., et al., *J. Immunol.* 180:6132-6138 (2008)). Likewise, MASP-1 may aid MASP-2 functional activity through its ability to cleave C2 (Moller-Kristensen, et al., *Int. Immunol.* 19:141-149 (2007)). Both activities may explain the reduced rate by which MASP-1/3 deficient plasma cleaves C3 via the lectin activation pathway and why MASP-1 may be required to sustain C3 conversion via the C4-bypass activation route.

The inability of C2/fB−/− plasma to activate C3 via the lectin pathway was shown to be C2-dependent as the addition of recombinant rat C2 to C2/fB−/− plasma restored the ability of the reconstituted plasma to activate C3 on Mannan-coated plates.

The finding that C4 deficiency specifically disrupts the classical complement activation pathway while the lectin pathway retains a physiologically critical level of C3 convertase activity via a MASP-2 dependent C4-bypass activation route calls for a re-assessment of the role of the lectin pathway in various disease models, including experimental *S. pneumoniae* infection (Brown, J. S., et al., *Proc. Natl. Acad. Sci. U.S.A.* 99:16969-16974 (2002); Experimental Allergic Encephalomyelitis (Boos, L.A., et al., *Glia* 49:158-160 (2005); and models of C3 dependent murine liver regeneration (Clark, A., et al., *Mol. Immunol.* 45:3125-3132 (2008)). The latter group demonstrated that C4-deficient mice can activate C3 in an alternative pathway independent fashion as in vivo inhibition of the alternative pathway by an antibody-mediated depletion of factor B functional activity did not effect C3 cleavage-dependent liver regeneration in C4−/− mice (Clark, A., et al. (2008)). This lectin pathway mediated C4-bypass activation route of C3 may also explain the lack of a protective phenotype of C4 deficiency in our model of MIRI as well as in a previously described model of renal allograft rejection (Lin, T., et al., *Am. J. Pathol.* 168:1241-1248 (2006)). In contrast, our recent results have independently demonstrated a significant protective phenotype of MASP-2−/−mice in models of renal transplantation (Farrar, C. A., et al., *Mol. Immunol.* 46:2832 (2009)).

In summary, the results of this Example support the view that MASP-2 dependent C4-bypass activation of C3 is a physiologically relevant mechanism that may be important under conditions where availability of C4 is limiting C3 activation.

Example 42

This Example demonstrates that the absence of MASP-2 functional activity results in a significant degree of protection from gastrointestinal ischemia/reperfusion injury (GIRI).

Rationale:

We explored the role of MASP-2 in GIRI using an established murine model (Zhang, M. et al. Proc. Natl. Acad. Sci. U.S.A. 101, 3886-3891 (2004); Zhang, M. et al. *J. Exp. Med.* 203, 141-152 (2006).

Methods:

MASP-2 deficient mice were generated as described in Example 27. MASP-2−/− mice and WT littermate controls were subjected to acute intestinal ischemia by surgically clamping of the superior mesenteric artery for 40 minutes followed by reperfusion of three hours. The surgical protocol for GIRI was performed as previously described (Zhang, M., et al., *Proc. Natl. Acad. Sci. U.S.A.* 101:3886-3891 (2004)). Following anesthesia, a laparotomy was performed and a surgical microclip applied to the superior mesenteric artery (SMA). After 40 minutes of ischemia, the microclip was removed and the ischemic tissue allowed to reperfuse for three hours. Sham controls underwent laparotomy without clamping the SMA. Following reperfusion, animals were sacrificed and corresponding segments of the distal jejunum harvested.

Intestinal injury was assessed by semi-quantitative pathology scoring of 200-400 villi in a defined area of jejunum, 4 cm per tissue section. Cryostat sections were stained with Hematoxylin and Eosin, blind-coded, and examined under light microscopy. The pathology score was assessed as described (Zhang, et al., 2004, supra). The first set of experiments assessed GIRL in 8 week old female MASP-2−/− and their MASP-2+/+ littermate controls. In the second set of experiments, six groups of 8 week old female WT C57BL/6 mice were studied: sham operated mice and I/R operated mice pretreated with either saline; orisotype control antibody; or anti-MASP-2 antibody mAbM11. The antibodies (each dosed at 1 mg/kg) or the saline were injected i.p. 18 hours before surgery.

Figure 45A:
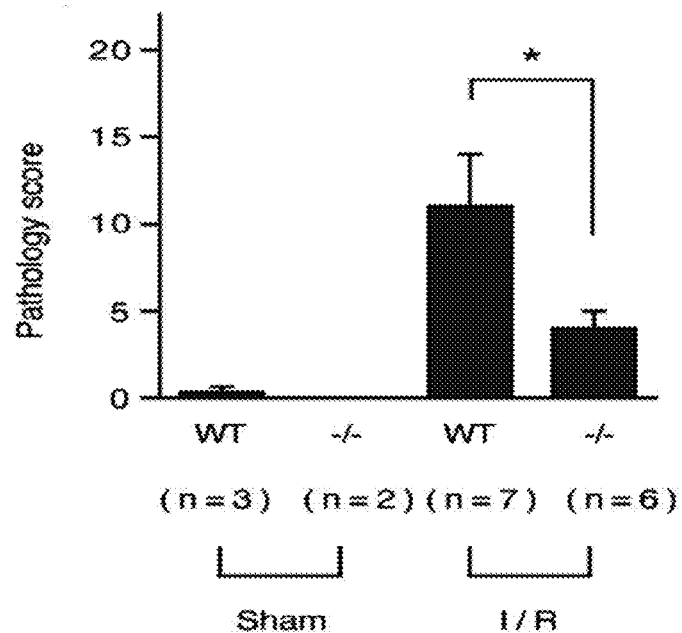
FIG. 45A graphically illustrates the degree of tissue damage in WT and MASP-2 (−/−) mice after induction of transient ischemia/reperfusion injury in the gastrointestinal tract (GIRT), demonstrating that MASP-2 (−/−) mice have a significant degree of protection as compared to WT controls, as described in Example 42.

Results:

FIG. 45A graphically illustrates that MASP-2–/– mice show a significant degree of protection from severe GIRT damage following transient (40 min) occlusion of the mesenteric artery and reperfusion (3 hrs) of ischemic gut tissue. *p<0.05 as determined by Student's test. As shown in FIG. 45A, MASP-2–/– mice had a significant reduction of I/R tissue damage compared with WT littermates (pathology scores of MASP-2–/– I/R group: 4+1, n=6; pathology scores of MASP-2+/+ I/R group: 11+3, n=7; P<0.05).

In order to assess whether a transient inhibition of MASP-2 functional activity can be achieved by applying selective antibody-based MASP-2 inhibitors in vivo, we assessed the degree and duration of lectin pathway inhibitory activity of the murine specific MASP-2 inhibitor mAbM11 following i.p. injection at a dose of 0.6 mg/kg body weight. Following the bolus injection, blood was collected by cardiac puncture at time points 0, 6 hrs, 12 hrs, 24 hrs, 48 hrs, 72 hrs, and 7 days, 10 days, 14 days and 17 days, and plasma assayed for lectin pathway-mediated C4 activation according to the methods described in Petersen, et al., *J. Immunol. Methods* 257:107-116 (2001), incorporated herein by reference.

Figure 45B:
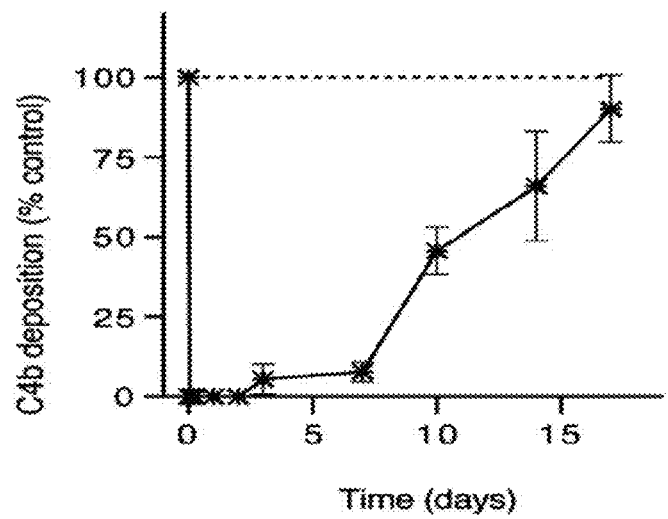
FIG. 45B graphically illustrates the results of a C4b deposition assay carried out on serum obtained from mice (n=3) over time after an intraperitoneal single dose bolus injection of recombinant anti-murine MASP-2 antibody (mAbM11), demonstrating in vivo ablation of lectin pathway functional activity, as described in Example 42.

FIG. 45B illustrates the results obtained over the time course of in vivo ablation of lectin pathway functional activity achieved by an intraperitoneal single dose bolus injection of recombinant anti-murine MASP-2 antibody mAbM11 (0.6 mg/kg body weight). At the indicated time points, groups of mice (n=3) were sacrificed, serum was prepared and assayed for LP-dependent C4 activation. The relative LP functional activity was normalized against to LP activity in pooled sera from naïve mice measured either in the absence (100%) or in the presence of 100 nM blocking antibody(0%). Results are means (±SEM) from plasma samples of 3 different mice for each time point.

The results shown in FIG. 45B depict the relative ablation of lectin pathway dependent C4 activation as a relative percentage of lectin pathway-mediated C4 activation prior to antibody dosing. The results show that the antibody-treatment yields a complete ablation of lectin pathway functional activity within 6 hrs following antibody dosing. Lectin pathway functional activity is completely deficient for up to 48 hrs after dosing and does not recover significantly (less than 10% of the activity levels prior to antibody treatment) for up to seven days.

To test whether a therapeutic depletion of MASP-2 functional activity can protect animals from GIRI, WT mice (male C57BL/6J, 8-10 weeks old) were injected with mAbM11 (i.p., 1 mg/kg body weight), or an identical dose of an irrelevant isotype control antibody (i.p., 1 mg/kg body weight) or saline 18 hrs prior to the intestinal FR or sham surgery.

Figure 45C:
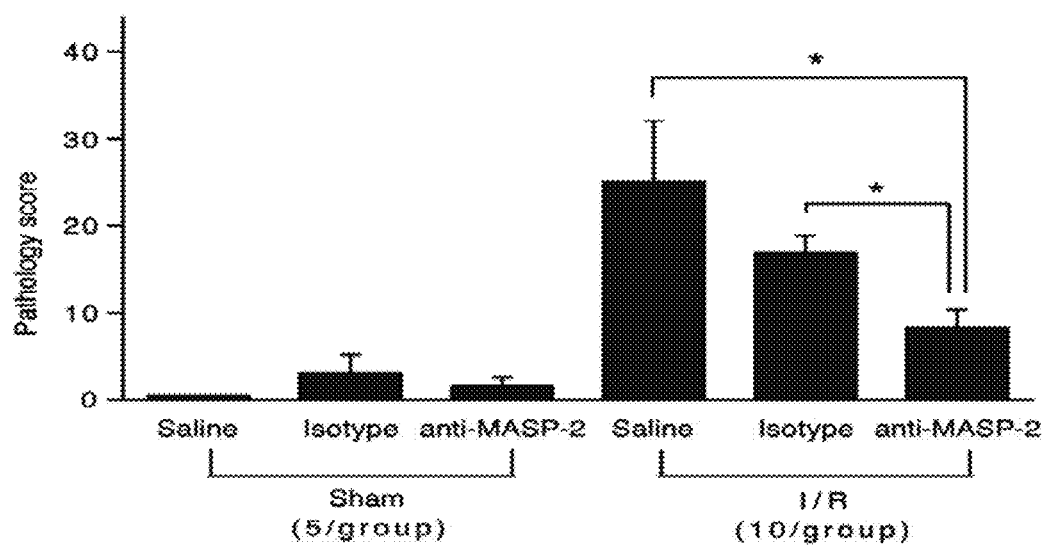
FIG. 45C graphically illustrates the effect of anti-MASP-2 mAb treatment on the severity of GIRL pathology, demonstrating that mice dosed with the anti-murine MASP-2 mAb (mAbM11) 24 hours before being subjected to transient ischemia/reperfusion injury in the gastrointestinal tract (GIRT) had significantly reduced tissue damage as compared to mice dosed with saline, as described in Example 42.

FIG. 45C graphically illustrates the effect of anti-MASP-2 mAb treatment on the severity of GIRT pathology: Mice dosed with 1 mg/kg of mAbM11 (n=10) or a relevant isotype control antibody (n=10) or injected with saline only (n=10) 24 hrs before being subjected to 40 min GI ischemia followed by three hours of reperfusion. (*p<0.05 when comparing animals treated with either the MASP-2 inhibitory antibody mAbM11 or an irrelevant isotype control antibody). Sham animals (n=5 per group) were treated in an identical fashion except that no clamp was applied to the mesenteric artery.

Figure 45D:
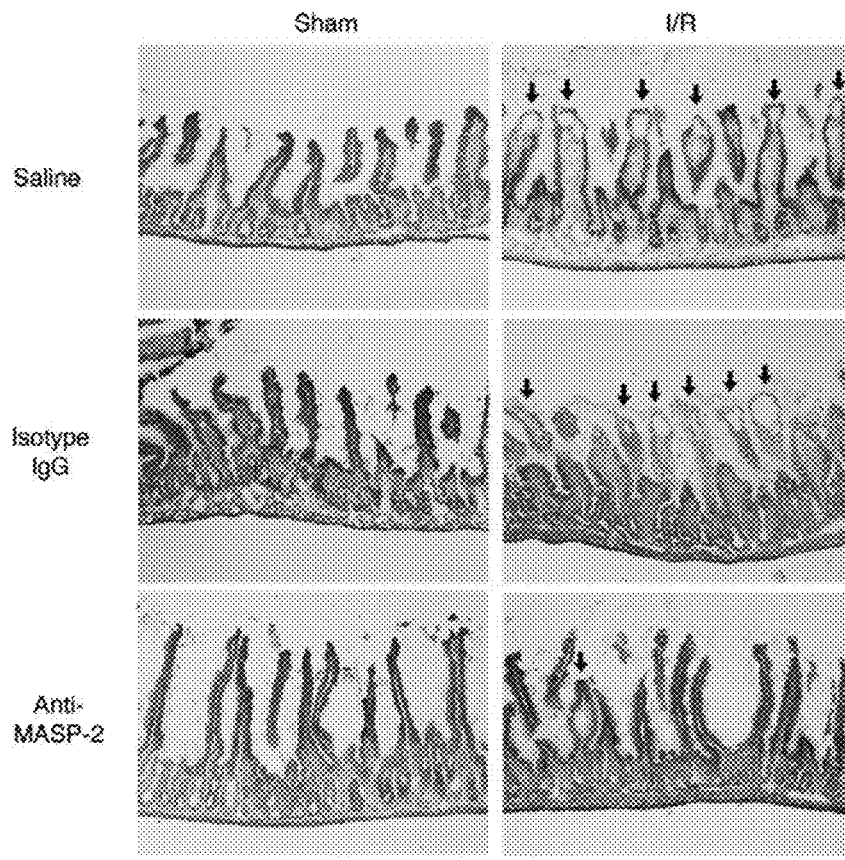
FIG. 45D shows histological presentation of GIRL mediated pathology of the small intestine in mice pre-treated with a single dose intraperitoneal injection of saline, an isotype control antibody, or recombinant anti-murine MASP-2 antibody (mAbM11) 12 hours prior to induction of GIRT, as described in Example 42.

FIG. 45D shows histological presentation of GIRT mediated pathology of the small intestine in WTC57BL/6 mice pre-treated with single dose intraperitoneal injection of either isotonic saline, an isotype control antibody (1 mg/kg body weight), or recombinant anti-murine MASP-2 antibody mAbM11 (1 mg/kg body weight) 12 hours prior to the induction of GIRL and their respective sham controls. The arrowheads indicate subepithelial spaces in the luminal part of the villi (characterized by the lack of cellular content beneath the continuous epithelial layer) as typical features of GIRT pathology. (magnification, X100).

As shown in FIGS. 45C and 45D, when saline-treated mice were subjected to intestinal I/R surgery, they had significant tissue damage compared with sham-operated controls (25±7, n=10; versus 1±0, n=5, P<0.01). Pretreatment with the isotype control antibody gave no protection from I/R injury compared with saline control (17±2 versus 25±7, n=10/per group, P>0.05). In contrast, pretreatment with mAbM11 significantly reduced tissue FR damage by more than 2-fold compared with mice treated with the isotype control antibody (8±2 versus 17±2, n=10/per group, P<0.01). The ischemic intestinal injury in the GIRL group treated with anti-MASP-2 mAb was not reduced down to the baseline levels seen in the sham control group (8±2, n=10, versus 2±1, n=5, p<0.01), but a significant sparing of tissue damage was evident in both MASP-2$^{-/-}$ and anti-MASP-2 mAb treated animals. The anti-Masp-2 mAb results further validate the deleterious role the lectin pathway plays in ischemia reperfusion injury.

Discussion:

Many recent reports aimed to clarify the mechanism(s) and pathway(s) leading to complement activation on oxygen-deprived cells. The involvement of IgM antibodies in complement-dependent GIRT has been well established (Zhang, M., et al., *Proc. Natl. Acad. Sci. U.S.A.* 101I3886-3891 (2004); Zhang, M., et al., *J. Exp. Med.* 203:141-152 (2006)). With IgM being a potent activator of the classical pathway, it was assumed that mice deficient of the classical pathway (such as C1qa–/– mice) would be protected from complement-dependent GIRI and MIRI (described in Example 41). Surprisingly, two recent studies demonstrated that C1qa–/– mice are not protected, either in GIRT, or MIRI, while mice deficient of the lectin pathway recognition molecules MBL A and MBL C showed a significant reduction of both GIRI and MIRI (Hart, M. L., et al., *J. Immunol.* 174:6373-6380 (2005); Walsh, M. C. et al. *J. Immunol.* 175:541-546 (2005)). These findings were confirmed in two subsequent GIRI studies, which identified that the critical pro-inflammatory contributions of IgM-dependent complement activation occurred in absence of classical pathway activity utilizing the lectin activation pathway through direct interactions between autoreactive IgM and MBL (Zhang, M., et al., *J. Immunol.* 177:4727-4734 (2006); McMullen, M. E., et al., *Immunobiology* 211:759-766 (2006)). In contrast, the same MBL null strain (i.e., MBL null mice retain a residual lectin pathway functional activity through ficolin A) was tested in a model of renal IRI, and showed only a moderate degree of protection from tissue injury (Moller-Kristensen, M., et al., *Scand. J. Immunol.* 61:426-434 (2005)).

Taken together, these studies suggest that the degree of protection of MBL null mice may vary between different experimental models of IRI, as the role of the remaining lectin pathway recognition molecule ficolin A in mediating IRI is not yet understood. In humans, we have recently shown that plasma MBL is rapidly consumed in the reperfusion phase following surgically-induced ischemia during abdominal aneurism repair surgery (Norwood, M. G., et al., *Eur. J. Vasc. Endovasc. Surg.* 31:239-243 (2006)). In man, the situation may even be more complex in as—in addition to MBL—three different ficolins may serve as lectin pathway recognition subcomponents.

Utilizing MASP-2-/-mice in a model of MIRI, we have demonstrated that lectin pathway functional activity is an essential component of the inflammatory process leading to major loss of myocardial tissue. MASP-2-/- mice may still activate complement through either the classical or the alternative pathway, but are devoid of any residual lectin pathway functional activity, while having all of the three murine lectin pathway pattern recognition molecules, MBL A, MBL C and ficolin A present in plasma. Moreover, MASP-2 functional activity was also shown to be an essential component in driving post-ischemic inflammatory pathology in a model of GIRI, monitored through scoring GIRI-mediated tissue damage in MASP-2-/- and MASP-2+/+ animals. Our results unequivocally show that neither the classical nor the alternative pathway complement activation route is sufficient to initiate the inflammatory pathology of post-ischemic tissue injury in absence of lectin pathway functional activity. It is, nevertheless, plausible that the alternative pathway may secondarily contribute towards an augmentation of complement activation in other tissues. This would explain why the deficiency of factor B may ameliorate post-ischemic inflammatory tissue loss in a model of ischemic acute renal failure (Thurman, J. M., et al., *J. Immunol.* 170:1517-1523 (2003)).

Finally, with regard to the phenotype of MASP-2 deficiency and the implications for therapeutic intervention, our results demonstrate that a transient and long sustained blockade of MASP-2 and lectin pathway functional activity can be achieved in vivo by systemic application of inhibitory MASP-2 specific monoclonal antibodies. The high efficacy in inhibiting MASP-2 functional activity using relatively low doses of inhibitory antibodies in vivo may be therapeutically viable due to the relatively low abundance of MASP-2 in plasma (ranging between 260 to 330 ng/ml in mouse plasma (see Results) and between 170 to 1196 ng/ml in human plasma (Moller-Kristensen, M., et al., *J. Immunol. Methods* 282:159-167 (2003)), and the strict absence of any extra hepatic MASP-2 biosynthesis (Stover, C. M., et al, *J. Immunol.* 163:6848-6859 (1999)); Endo, Y., et al., *Int. Immunol.* 14:1193-1201 (2002)). Therefore, it is believed that inhibition of MASP-2 (-/-) by administration of inhibitory monoclonal antibodies against MASP-2 would be effective to treat ischemia-induced inflammatory pathologies.

Example 43

This Example describes activation of C3 by thrombin substrates and C3 deposition on mannan in WT (+/+), MASP-2 (-/-), F11 (-/-), F11/C4 (-/-) and C4 (-/-) mice.

Rationale:

As described in Example 32, it was determined that thrombin activation can occur following lectin pathway activation under physiological conditions, and demonstrates the extent of MASP-2 involvement. C3 plays a central role in the activation of complement system. C3 activation is required for both classical and alternative complement activation pathways. An experiment was carried out to determine whether C3 is activated by thrombin substrates.

Methods:

C3 Activation by Thrombin Substrates

Activation of C3 was measured in the presence of the following activated forms of thrombin substrates; human FCXIa, human FVIIa, bovine FXa, human FXa, human activated protein C, and human thrombin. C3 was incubated with the various thrombin substrates, then separated under reducing conditions on 10% SDS-polyacrylamide gels. After electrophoretic transfer using cellulose membrane, the membrane was incubated with monoclonal biotin-coupled rat anti-mouse C3, detected with a streptavidin-HRP kit and developed using ECL reagent.

Figure 46:
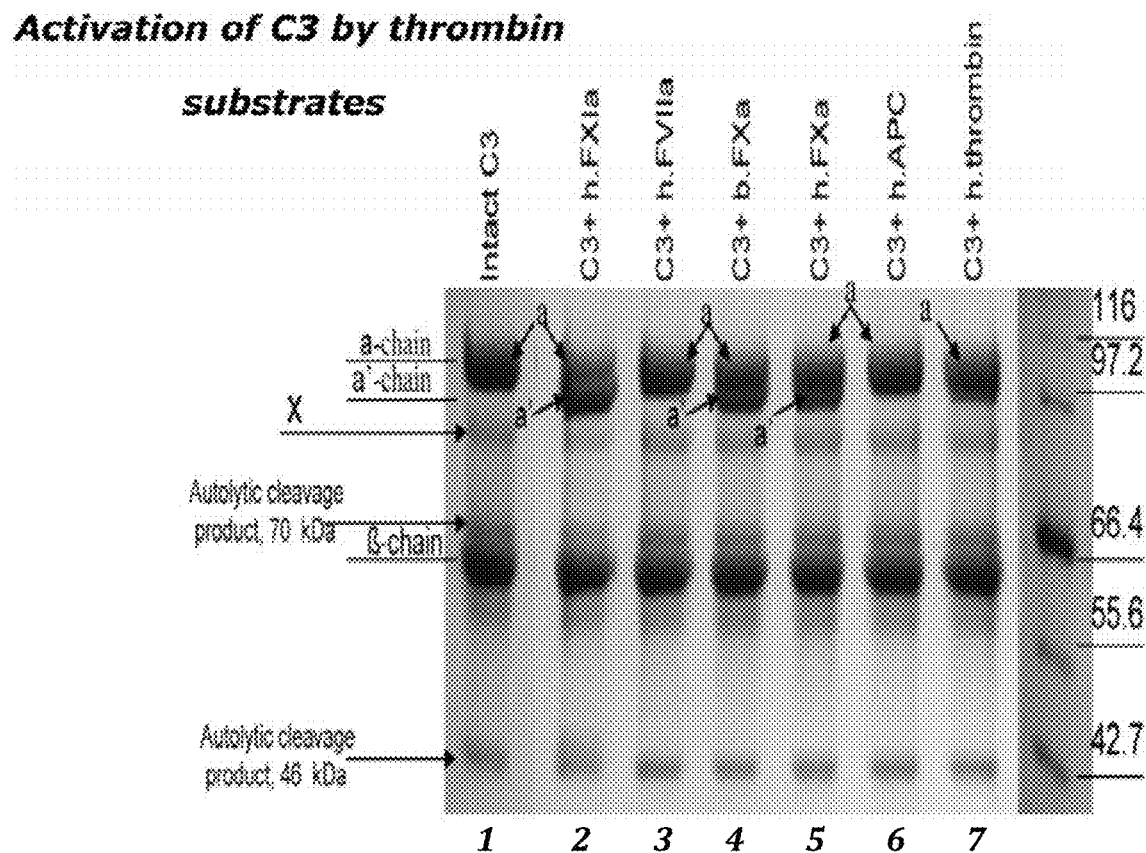
FIG. 46 illustrates the results of a Western blot analysis showing activation of human C3, shown by the presence of the a' chain, by thrombin substrates FXIa and FXa, as described in Example 43.

Results:

Activation of C3 involves cleavage of the intact a-chain into the truncated a' chain and soluble C3a (not shown in FIG. 46). FIG. 46 shows the results of a Western blot analysis on the activation of human C3 by thrombin substrates, wherein the uncleaved C3 alpha chain, and the activation product a' chain are shown by arrows. As shown in FIG. 46, incubation of C3 with the activated forms of human clotting factor XI and factor X, as well as activated bovine clotting factor X, can cleave C3 in vitro in the absence of any complement proteases.

C3 Deposition on Mannan

C3 deposition assays were carried out on serum samples obtained from WT, MASP-2 (-/-), F11(-/-), F11(-/-)/C4 (-/-) and C4(-/-). FII is the gene encoding coagulation factor XI. To measure C3 activation, microtiter plates were coated with mannan (1 µg/well), then adding sheep anti-HSA serum (2 µg/ml) in TBS/tween/Ca$^{2+}$. Plates were blocked with 0.1% HSA in TBS and washed as above. Plasma samples were diluted in 4 mM barbital, 145 mM NaCl, 2 mM CaCl$_2$, 1 mM MgCl$_2$, pH 7.4, added to the plates and incubated for 1.5 h at 37° C. After washing, bound C3b was detected using rabbit anti-human C3c (Dako), followed by alkaline phosphatase-conjugated goat anti-rabbit IgG and pNPP.

Figure 47:
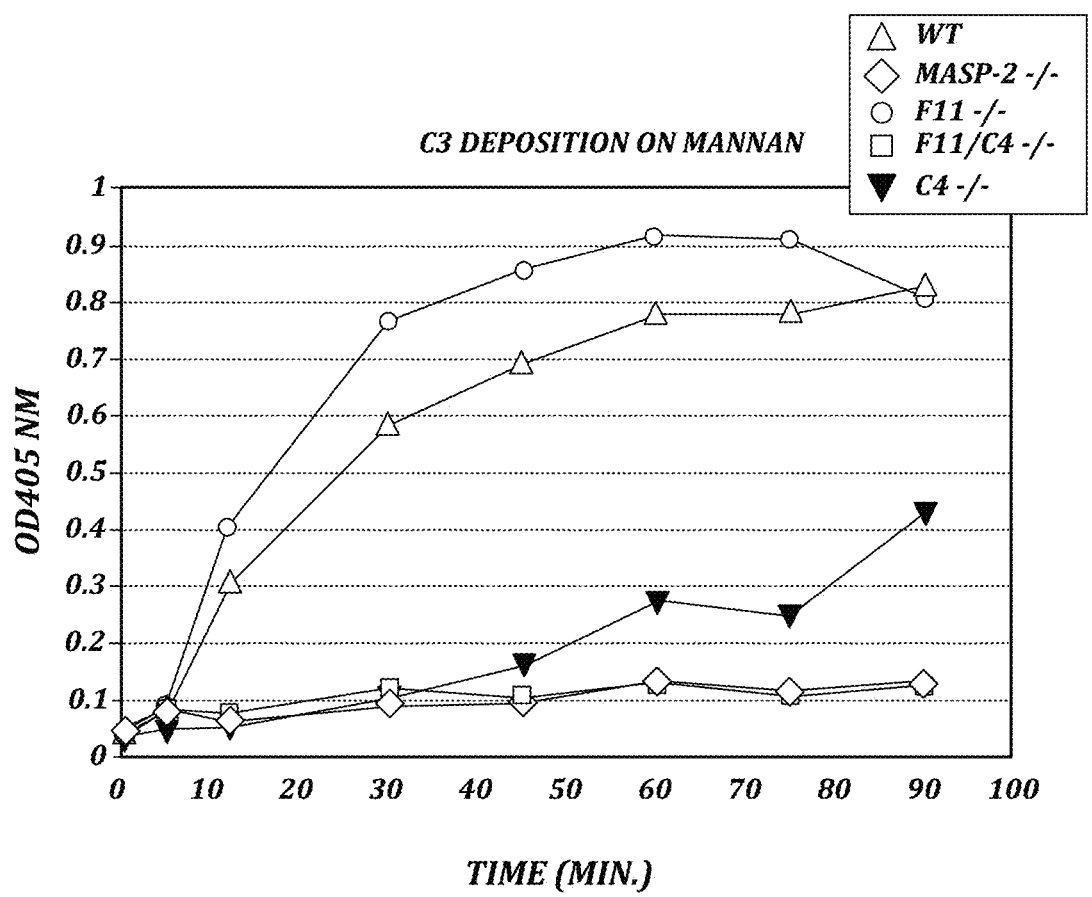
FIG. 47 graphically illustrates the results of a C3b deposition assay on serum samples obtained from WT, MASP-2 (−/−), F11(−/−), F11(−/−)/C4 (−/−) and C4 (−/−) mice, demonstrating that there is a functional lectin pathway even in the complete absence of C4, or F11, while mice with combined F11 (−/−)/C4 (−/−) deficiency lack a functional lectin pathway, as described in Example 43.

Results:

FIG. 47 shows the results of the C3 deposition assay on serum samples obtained from WT, MASP-2 (-/-), F11(-/-), F11(-/-)/C4 (-/-) and C4 (-/-). As shown in FIG. 47, there is a functional lectin pathway even in the complete absence of C4. As further shown in FIG. 47, this novel lectin pathway dependent complement activation requires coagulation factor XI.

Discussion:

Prior to the results obtained in this experiment, it was believed by those in the art that the lectin pathway of complement required C4 for activity. Hence, data from C4 knockout mice (and C4 deficient humans) were interpreted with the assumption that such organisms were lectin pathway deficient (in addition to classical pathway deficiency). The present results demonstrate that this notion is false. Thus, conclusions of past studies suggesting that the lectin pathway was not important in certain disease settings based on the phenotype of C4 deficient animals may be false. As described in Example 41, we have demonstrated this for myocardial infarction models where MASP-2 knockout mice are protected while C4 knockout mice are not.

The data described in this Example also show that in the physiological context of whole serum the lectin pathway can activate components of the coagulation cascade. Thus, it is demonstrated that there is cross-talk between complement and coagulation involving MASP-2.

Example 44

This Example demonstrates the use of pure dust mite allergan as a potent activator of lectin pathway mediated C3 activation as a model of asthma.

Rationale:

A well characterized mouse model of house dust mite (HDM)-induced allergic asthma has been developed. See X. Zhang et al., *J. of Immunol.* 182:5123-5130 (2009), hereby incorporated herein by reference. As described in Zhang et al. (2009), the model involves exposing mice to intratracheal HDM once a week over the course of three weeks. The intratracheal HDM administration significantly increases airway responsiveness, total cell numbers and eosinophil numbers in BAL fluid as well as serum total IgE and allergen-specific IgE levels in WT BALB/c mice. This model can be used to assess the use of anti-MASP-2 mabs as a therapeutic for asthma.

Methods:

C3 deposition assays were carried out on serum samples obtained from WT mice. To measure C3 activation, microtiter plates were coated with mannan (1 μg/well), then adding sheep anti-HSA serum (2 μg/ml) in TBS/tween/$Ca^{2+}$. Plates were blocked with 0.1% HSA in TBS and washed as above. Plasma samples were diluted in 4 mM barbital, 145 mM NaCl, 2 mM $CaCl_2$, 1 mM $MgCl_2$, pH 7.4, added to the plates and incubated for 1.5 h at 37° C. After washing, bound C3b was detected using rabbit anti-human C3c (Dako), followed by alkaline phosphatase-conjugated goat anti-rabbit IgG and pNPP.

Figure 48:
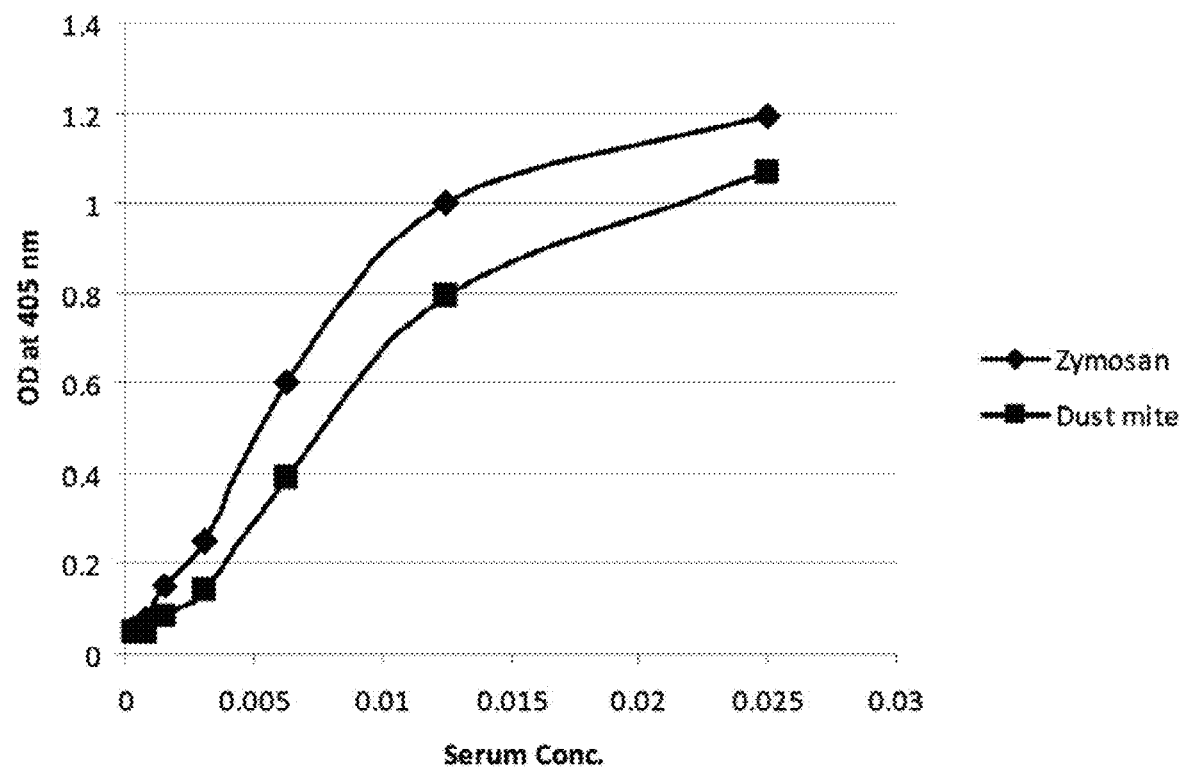
FIG. 48 graphically illustrates the results of the C3 deposition assay on serum samples obtained from WT mice in the presence of house dust mite or zymosan, as described in Example 44.

Results:

FIG. 48 graphically illustrates the results of the C3 deposition assay in serum samples obtained from WT mice in the presence of house dust mite or zymosan. As shown in FIG. 48, dust mite allergen is a potent activator of lectin pathway mediated C3 activation, and activates C3 at nearly the same level as zymosan. These results indicate that dust mite allergen is capable of stimulating the lectin pathway. In view of the fact that anti-MASP-2 antibodies have been shown to block activation of the alternative complement pathway, it is expected that anti-MASP-2 antibodies will be effective as therapeutics in treating asthma that is due to dust mite allergen-sensitized individuals.

Example 45

This Example describes methods to assess the effect of an anti-MASP-2 antibody on lysis of red blood cells from blood samples obtained from Paroxysmal nocturnal hemoglobinuria (PNH) patients.

Background/Rationale:

Paroxysmal nocturnal hemoglobinuria (PNH), also referred to as Marchiafava-Micheli syndrome, is an acquired, potentially life-threatening disease of the blood, characterized by complement-induced intravascular hemolytic anemia. The hallmark of PNH is chronic intravascular hemolysis that is a consequence of unregulated activation of the alternative pathway of complement. Lindorfer, M. A., et al., *Blood* 115(11) (2010). Anemia in PNH is due to destruction of red blood cells in the bloodstream. Symptoms of PNH include red urine, due to appearance of hemoglobin in the urine, and thrombosis. PNH may develop on its own, referred to as "primary PNH" or in the context of other bone marrow disorders such as aplastic anemia, referred to as "secondary PNH". Treatment for PNH includes blood transfusion for anemia, anticoagulation for thrombosis and the use of the monoclonal antibody eculizumab (Soliris), which protects blood cells against immune destruction by inhibiting the complement system (Hillmen P. et al., *N. Engl. J. Med.* 350(6):552-9 (2004)). However, a significant portion of PNH patients treated with eculizumab are left with clinically significant immune-mediated hemolytic anemia because the antibody does not block activation of the alternative pathway of complement.

This Example describes methods to assess the effect of an anti-MASP-2 antibody on lysis of red blood cells from blood samples obtained from PNH patients (not treated with Soliris) that are incubated with ABO-matched acidified normal human serum.

Methods:

Reagents:

Erythrocytes from normal donors and from patients suffering from PNH (not treated with Soliris) are obtained by venipuncture, and prepared as described in Wilcox, L. A., et al., *Blood* 78:820-829 (1991), hereby incorporated herein by reference. Anti-MASP-2 antibodies with functional blocking activity of the lectin pathway may be generated as described in Example 24.

Hemolysis Analysis:

The method for determining the effect of anti-MASP-2 antibodies on the ability to block hemolysis of erythrocytes from PNH patients is carried out using the methods described in Lindorfer, M. A., et al., *Blood* 15(11):2283-91 (2010) and Wilcox, L. A., et al., *Blood* 78:820-829 (1991), both references hereby incorporated herein by reference. As described in Lindorfer et al., erythrocytes from PNH patient samples are centrifuged, the buffy coat is aspirated and the cells are washed in gelatin veronal buffer (GVB) before each experiment. The erythrocytes are tested for susceptibility to APC-mediated lysis as follows. ABO-matched normal human sera are diluted with GVB containing 0.15 mM $CaCl_2$ and 0.5 mM $MgCl_2$ ($GVB^{+2}$) and acidified to pH 6.4 (acidified NHS, aNHS) and used to reconstitute the erythrocytes to a hematocrit of 1.6% in 50% aNHS. The mixtures are then incubated at 37° C., and after 1 hour, the erythrocytes are pelleted by centrifugation. The optical density of an aliquot of the recovered supernate is measured at 405 nM and used to calculate the percent lysis. Samples reconstituted in acidified serum-EDTA are processed similarly and used to define background noncomplement-mediated lysis (typically less than 3%). Complete lysis (100%) is determined after incubating the erythrocytes in distilled water.

In order to determine the effect of anti-MASP-2 antibodies on hemolysis of PNH erythrocytes, erythrocytes from PNH patients are incubated in aNHS in the presence of incremental concentrations of the anti-MASP-2 antibodies, and the presence/amount of hemolysis is subsequently quantified.

In view of the fact that anti-MASP-2 antibodies have been shown to block subsequent activation of the alternative complement pathway, it is expected that anti-MASP-2 antibodies will be effective in blocking alternative pathway-mediated hemolysis of PNH erythrocytes, and will be useful as a therapeutic to treat patients suffering from PNH.

Example 46

This Example describes methods to assess the effect of an anti-MASP-2 blocking antibody on complement activation by cryoglobulins in blood samples obtained from patients suffering from cryoglobulinemia.

Background/Rationale:

Cryoglobulinemia is characterized by the presence of cryoglobulins in the serum. Cryoglobulins are single or mixed immunoglobulins (typically IgM antibodies) that undergo reversible aggregation at low temperatures. Aggregation leads to classical pathway complement activation and inflammation in vascular beds, particularly in the periphery. Clinical presentations of cryoglobulinemia include vasculitis and glomerulonephritis.

Cryoglobulinemia may be classified as follows based on cryoglobulin composition: Type I cryoglobulinemia, or simple cryoglobulinemia, is the result of a monoclonal immunoglobulin, usually immunoglobulin M (IgM); Types II and III cryoglobulinemia (mixed cryoglobulinemia) contain rheumatoid factors (RFs), which are usually IgM in complexes with the Fc portion of polyclonal IgG.

Conditions associated with cryoglobulinemia include hepatitis C infection, lymphoproliferative disorders and other autoimmune diseases. Cryoglobulin-containing immune complexes result in a clinical syndrome of systemic inflammation, possibly due to their ability to activate complement. While IgG immune complexes normally activate the classical pathway of complement, IgM containing complexes can also activate complement via the lectin pathway (Zhang, M., et al., *Mol Immunol* 44(1-3):103-110 (2007) and Zhang. M., et al., *J. Immunol.* 177(7):4727-34 (2006)).

Immunohistochemical studies have further demonstrated the cryoglobulin immune complexes contain components of the lectin pathway, and biopsies from patients with cryoglobulinemic glomerulonephritis showed immunohistochemical evidence of lectin pathway activation in situ (Ohsawa, I., et al., *Clin Immunol* 101(1):59-66 (2001)). These results suggest that the lectin pathway may contribute to inflammation and adverse outcomes in cryoglobulemic diseases.

Methods:

The method for determining the effect of anti-MASP-2 antibodies on the ability to block the adverse effects of Cryoglobulinemia is carried out using the assay for fluid phase C3 conversion as described in Ng Y. C. et al., *Arthritis and Rheumatism* 31(1):99-107 (1988), hereby incorporated herein by reference. As described in Ng et al., in essential mixed cryoglobulinemia (EMC), monoclonal rheumatoid factor (mRF), usually IgM, complexes with polyclonal IgG to form the characteristic cryoprecipitate immune complexes (IC) (type II cryoglobulin). Immunoglobulins and C3 have been demonstrated in vessel walls in affected tissues such as skin, nerve and kidney. As described in Ng et al., $^{125}$I-labeled mRF is added to serum (normal human serum and serum obtained from patients suffering from cryoglobulinemia), incubated at 37° C., and binding to erythrocytes is measured.

Fluid phase C3 conversion is determined in serum (normal human serum and serum obtained from patients suffering from cryoglobulinemia) in the presence or absence of the following IC: BSA-anti BSA, mRF, mRF plus IgG, or cryoglobulins, in the presence or absence of anti-MASP-2 antibodies. The fixation of C3 and C4 to IC is measured using a coprecipitation assay with F(ab')2 anti-C3 and F(ab')2 anti-C4.

In view of the fact that anti-MASP-2 antibodies have been shown to block activation of the lectin pathway and subsequent activation of the alternative complement pathway, it is expected that anti-MASP-2 antibodies will be effective in blocking alternative pathway mediated adverse effects associated with cryoglobulinemia, and will be useful as a therapeutic to treat patients suffering from cryoglobulinemia.

Example 47

This Example describes methods to assess the effect of an anti-MASP-2 antibody on blood samples obtained from patients with Cold Agglutinin Disease, which manifests as anemia.

Background/Rationale:

Cold Agglutinin Disease (CAD), is a type of autoimmune hemolytic anemia. Cold agglutinins antibodies (usually IgM) are activated by cold temperatures and bind to and aggregate red blood cells. The cold agglutinin antibodies combine with complement and attack the antigen on the surface of red blood cells. This leads to opsoniation of red blood cells (hemolysis) which triggers their clearance by the reticuloendothelial system. The temperature at which the agglutination takes place varies from patient to patient.

CAD manifests as anemia. When the rate of destruction of red blood cell destruction exceeds the capacity of the bone marrow to produce an adequate number of oxygen-carrying cells, then anemia occurs. CAD can be caused by an underlying disease or disorder, referred to as "Secondary CAD", such as an infectious disease (mycoplasma pneumonia, mumps, mononucleosis), lymphoproliferative disease (lymphoma, chronic lymphocytic leukemia), or connective tissue disorder. Primary CAD patients are considered to have a low grade lymphoproliferative bone marrow disorder. Both primary and secondary CAD are acquired conditions.

Methods:

Reagents:

Erythrocytes from normal donors and from patients suffering from CAD are obtained by venipuncture. Anti-MASP-2 antibodies with functional blocking activity of the lectin pathway may be generated as described in Example 24.

The effect of anti-MASP-2 antibodies to block cold aggultinin-mediated activation of the lectin pathway may be determined as follows. Erythrocytes from blood group I positive patients are sensitized with cold aggultinins (i.e., IgM antibodies), in the presence or absence of anti-MASP-2 antibodies. The erythrocytes are then tested for the ability to activate the lectin pathway by measuring C3 binding.

In view of the fact that anti-MASP-2 antibodies have been shown to block activation of the lectin pathway and subsequent activation of the alternative pathway, it is expected that anti-MASP-2 antibodies will be effective in blocking cold aggultinin-mediated activation of the lectin pathway.

Example 48

This Example describes methods to assess the effect of an anti-MASP-2 antibody on lysis of red blood cells in blood samples obtained from mice with atypical hemolytic uremic syndrome (aHUS).

Background/Rationale:

Atypical hemolytic uremic syndrome (aHUS) is characterized by hemolytic anemia, thrombocytopenia, and renal failure caused by platelet thrombi in the microcirculation of the kidney and other organs. aHUS is associated with defective complement regulation and can be either sporadic or familial. aHUS is associated with mutations in genes coding for complement activation, including complement factor H, membrane cofactor B and factor I, and well as complement factor H-related 1 (CFHR1) and complement factor H-related 3 (CFHR3). Zipfel, P. F., et al., *PloS Genetics* 3(3):e41 (2007). This Example describes methods to assess the effect of an anti-MASP-2 antibody on lysis of red blood cells from blood samples obtained from aHUS mice.

Methods:

The effect of anti-MASP-2 antibodies to treat aHUS may be determined in a mouse model of this disease in which the endogenouse mouse fH gene has been replaced with a human homologue encoding a mutant form of fH frequently found in aHUS patients. See Pickering M. C. et al., *J. Exp. Med.* 204(6):1249-1256 (2007), hereby incorporated herein by reference. As described in Pickering et al., such mice develop an aHUS like pathology. In order to assess the effect of an anti-MASP-2 antibody for the treatment of aHUS, anti-MASP-2 antibodies are administered to the mutant aHUS mice and lysis of red blood cells obtained from anti-MASP-2 ab treated and untreated controls is compared. In view of the fact that anti-MASP-2 antibodies have been shown to block activation of the lectin pathway which in turn subsequently leads to a significant reduction of complement activation of the alternative pathway (where the availability of C3b is limiting), it is expected that anti-MASP-2 antibodies will be effective in blocking lysis of red blood cells in mammalian subjects suffering from aHUS.

Example 49

This Example describes methods to assess the effect of an anti-MASP-2 antibody for the treatment of glaucoma.

Rationale/Background:

It has been shown that uncontrolled complement activation contributes to the progression of degenerative injury to retinal ganglion cells (RGCs), their synapses and axons in glaucoma. See Tezel G. et al., *Invest Ophthalmol Vis Sci* 51:5071-5082 (2010). For example, histopathologic studies of human tissues and in vivo studies using different animal models have demonstrated that complement components, including C1q and C3, are synthesized and terminal complement complex is formed in the glaucomatous retina (see Stasi K. et al., *Invest Ophthalmol Vis Sci* 47:1024-1029 (2006), Kuehn M. H. et al., *Exp Eye Res* 83:620-628 (2006)). As further described in Kuehn M. H. et al., *Experimental Eye Research* 87:89-95 (2008), complement synthesis and deposition is induced by retinal I/R and the disruption of the complement cascade delays RGC degeneration. In this study, mice carrying a targeted disruption of the complement component C3 were found to exhibit delayed RGC degeneration after transient retinal I/R when compared to normal animals.

Methods:

The method for determining the effect of anti-MASP-2 antibodies on RGC degeneration is carried out in an animal model of retinal I/R as described in Kuehn M. H. et al., *Experimental Eye Research* 87:89-95 (2008), hereby incorporated herein by reference. As described in Kuehn et al., retinal ischemia is induced by anesthetizing the animals, then inserting a 30-gauge needle connected to a reservoir containing phosphate buffered saline through the cornea into the anterior chamber of the eye. The saline reservoir is then elevated to yield an intraocular pressure of 104 mmHg, sufficient to completely prevent circulation through the retinal vasculature. Elevated intraocular ischemia is confirmed by blanching of the iris and retina and ischemia is maintained for 45 minutes in the left eye only; the right eye serves as a control and does not receive cannulation. Mice are then euthanized either 1 or 3 weeks after the ischemic insult. Anti-MASP-2 antibodies are administered to the mice either locally to the eye or systemically to assess the effect of an anti-MASP antibody administered prior to ischemic insult.

Immunohistochemistry of the eyes is carried out using antibodies against C1q and C3 to detect complement deposition. Optic nerve damage can also be assessed using standard electron microscopy methods. Quantitation of surviving retinal RGCs is performed using gamma synuclein labeling.

Results:

As described in Kuehn et al., in normal control mice, transient retinal ischemia results in degenerative changes of the optic nerve and retinal deposits of C1q and C3 detectable by immunohistochemistry. In contrast, C3 deficient mice displayed a marked reduction in axonal degeneration, exhibiting only minor levels of optic nerve damage 1 week after induction. Based on these results, it is expected that similar results would be observed when this assay is carried out in a MASP-2 knockout mouse, and when anti-MASP-2 antibodies are administered to a normal mouse prior to ischemic insult.

Example 50

This Example demonstrates that a MASP-2 inhibitor, such as an anti-MASP-2 antibody, is effective for the treatment of radiation exposure and/or for the treatment, amelioration or prevention of acute radiation syndrome.

Rationale:

Exposure to high doses of ionizing radiation causes mortality by two main mechanisms: toxicity to the bone marrow and gastrointestinal syndrome. Bone marrow toxicity results in a drop in all hematologic cells, predisposing the organism to death by infection and hemorrhage. The gastrointestinal syndrome is more severe and is driven by a loss of intestinal barrier function due to disintegration of the gut epithelial layer and a loss of intestinal endocrine function. This leads to sepsis and associated systemic inflammatory response syndrome which can result in death.

The lectin pathway of complement is an innate immune mechanism that initiates inflammation in response to tissue injury and exposure to foreign surfaces (i.e., bacteria). Blockade of this pathway leads to better outcomes in mouse models of ischemic intestinal tissue injury or septic shock. It is hypothesized that the lectin pathway may trigger excessive and harmful inflammation in response to radiation-induced tissue injury. Blockade of the lectin pathway may thus reduce secondary injury and increase survival following acute radiation exposure.

The objective of the study carried out as described in this Example was to assess the effect of lectin pathway blockade on survival in a mouse model of radiation injury by administering anti-murine MASP-2 antibodies.

Methods and Materials:

Materials. The test articles used in this study were (i) a high affinity anti-murine MASP-2 antibody (mAbM11) and (ii) a high affinity anti-human MASP-2 antibody (mAbH6) that block the MASP-2 protein component of the lectin complement pathway which were produced in transfected mammalian cells. Dosing concentrations were 1 mg/kg of anti-murine MASP-2 antibody (mAbM11), 5 mg/kg of anti-human MASP-2 antibody (mAbH6), or sterile saline. For each dosing session, an adequate volume of fresh dosing solutions were prepared.

Animals. Young adult male Swiss-Webster mice were obtained from Harlan Laboratories (Houston, Tex.). Animals were housed in solid-bottom cages with Alpha-Dri bedding and provided certified PMI 5002 Rodent Diet (Animal Specialties, Inc., Hubbard Oreg.) and water ad libitum. Temperature was monitored and the animal holding room operated with a 12 hour light/12 hour dark light cycle.

Irradiation. After a 2-week acclimation in the facility, mice were irradiated at 6.5 and 7.0 Gy by whole-body exposure in groups of 10 at a dose rate of 0.78 Gy/min using a Therapax X-RAD 320 system equipped with a 320-kV high stability X-ray generator, metal ceramic X-ray tube, variable x-ray beam collimator and filter (Precision X-ray Incorporated, East Haven, Conn.). Dose levels were selected based on prior studies conducted with the same strain of mice indicating the $LD_{50/30}$ was between 6.5 and 7.0 Gy (data not shown).

Drug Formulation and Administration. The appropriate volume of concentrated stock solutions were diluted with ice cold saline to prepare dosing solutions of 0.2 mg/ml anti-murine MASP-2 antibody (mAbM11) or 0.5 mg/ml anti-human MASP-2 antibody (mAbH6) according to protocol. Administration of anti-MASP-2 antibody mAbM11 and mAbH6 was via IP injection using a 25-gauge needle base on animal weight to deliver 1 mg/kg mAbM11, 5 mg/kg mAbH6, or saline vehicle.

Study Design. Mice were randomly assigned to the groups as described in Table 8. Body weight and temperature were measured and recorded daily. Mice in Groups 7, 11 and 13 were sacrificed at post-irradiation day 7 and blood collected by cardiac puncture under deep anesthesia. Surviving animals at post-irradiation day 30 were sacrificed in the same manner and blood collected. Plasma was prepared from collected blood samples according to protocol and returned to Sponsor for analysis.

TABLE 8

STUDY GROUPS

| Group ID | N | Irradiation Level (Gy) | Treatment | Dose Schedule |
|---|---|---|---|---|
| 1 | 20 | 6.5 | Vehicle | 18 hr prior to irradiation, 2 hr post irradiation, weekly booster |
| 2 | 20 | 6.5 | anti-murine MASP-2 ab (mAbM11) | 18 hr prior to irradiation only |
| 3 | 20 | 6.5 | anti-murine MASP-2 ab (mAbM11) | 18 hr prior to irradiation, 2 hr post irradiation, weekly booster |
| 4 | 20 | 6.5 | anti-murine MASP-2 ab (mAbM11) | 2 hr post irradiation, weekly booster |
| 5 | 20 | 6.5 | anti-human MASP-2 ab (mAbH6) | 18 hr prior to irradiation, 2 hr post irradiation, weekly booster |
| 6 | 20 | 7.0 | Vehicle | 18 hr prior to irradiation, 2 hr post irradiation, weekly booster |
| 7 | 5 | 7.0 | Vehicle | 2 hr post irradiation only |
| 8 | 20 | 7.0 | anti-murine MASP-2 ab (mAbM11) | 18 hr prior to irradiation only |
| 9 | 20 | 7.0 | anti-murine MASP-2 ab (mAbM11) | 18 hr prior to irradiation, 2 hr post irradiation, weekly booster |
| 10 | 20 | 7.0 | anti-murine MASP-2 ab (mAbM11) | 2 hr post irradiation, weekly booster |
| 11 | 5 | 7.0 | anti-murine MASP-2 ab (mAbM11) | 2 hr post irradiation only |
| 12 | 20 | 7.0 | anti-human MASP-2 ab (mAbH6) | 18 hr prior to irradiation, 2 hr post irradiation, weekly booster |
| 13 | 5 | None | None | None |

Statistical Analysis. Kaplan-Meier survival curves were generated and used to compare mean survival time between treatment groups using log-Rank and Wilcoxon methods. Averages with standard deviations, or means with standard error of the mean are reported. Statistical comparisons were made using a two-tailed unpaired t-test between controlled irradiated animals and individual treatment groups.

Results

Figure 49A:
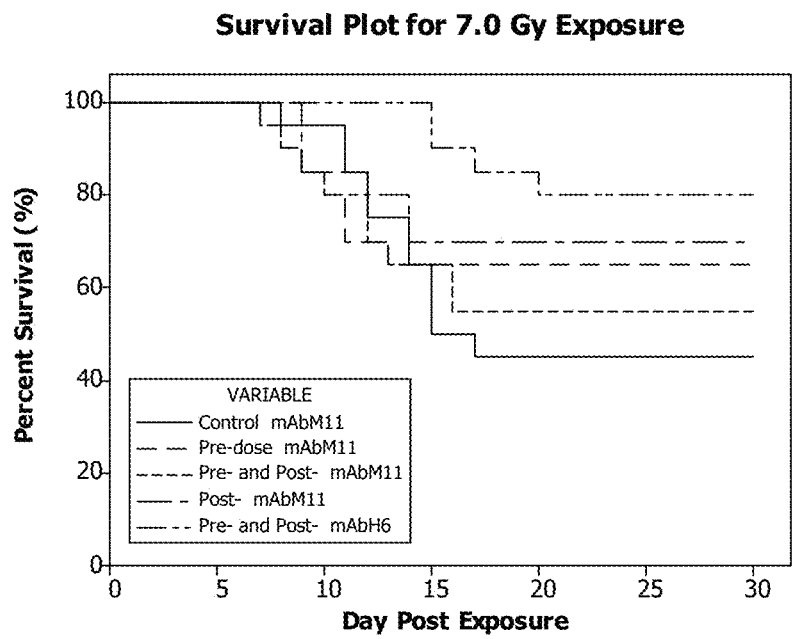
FIG. 49A is a Kaplain-Meier survival plot showing the percent survival over time after exposure to 7.0 Gy radiation in control mice and in mice treated with anti-murine MASP-2 antibody (mAbM11) or anti-human MASP-2 antibody (mAbH6) as described in Example 50.
Figure 49B:
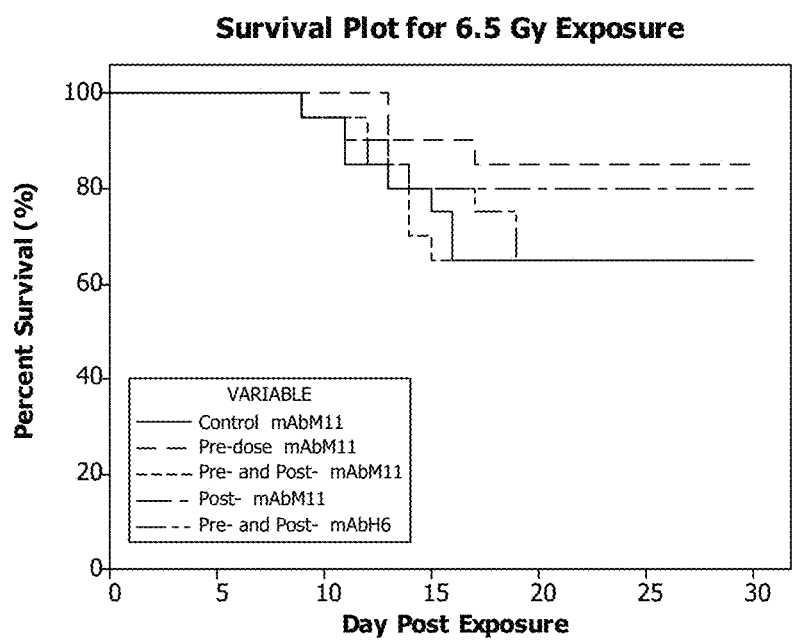
FIG. 49B is a Kaplain-Meier survival plot showing the percent survival over time after exposure to 6.5 Gy radiation in control mice and in mice treated with anti-murine MASP-2 antibody (mAbM11) or anti-human MASP-2 antibody (mAbH6), as described in Example 50.

Kaplan-Meier survival plots for 7.0 and 6.5 Gy exposure groups are provided in FIGS. 49A and 49B, respectively, and summarized below in Table 9. Overall, treatment with anti-murine MASP-2 ab (mAbM11) pre-irradiation increased the survival of irradiated mice compared to vehicle treated irradiated control animals at both 6.5 (20% increase) and 7.0 Gy (30% increase) exposure levels. At the 6.5 Gy exposure level, post-irradiation treatment with anti-murine MASP-2 ab resulted in a modest increase in survival (15%) compared to vehicle control irradiated animals.

In comparison, all treated animals at the 7.0 Gy exposure level showed an increase in survival compared to vehicle treated irradiated control animals. The greatest change in survival occurred in animals receiving mAbH6, with a 45% increase compared to control animals. Further, at the 7.0 Gy exposure level, mortalities in the mAbH6 treated group first occurred at post-irradiation day 15 compared to post-irradiation day 8 for vehicle treated irradiated control animals, an increase of 7 days over control animals. Mean time to mortality for mice receiving mAbH6 (27.3±1.3 days) was significantly increased (p=0.0087) compared to control animals (20.7±2.0 days) at the 7.0 Gy exposure level.

The percent change in body weight compared to pre-irradiation day (day −1) was recorded throughout the study. A transient weight loss occurred in all irradiated animals, with no evidence of differential changes due to mAbM11 or mAbH6 treatment compared to controls (data not shown). At study termination, all surviving animals showed an increase in body weight from starting (day −1) body weight.

TABLE 9

SURVIVAL RATES OF TEST ANIMALS EXPOSED TO RADIATION

| Test Group | Exposure Level | Survival (%) | Time to Death (Mean ± SEM, Day) | First/Last Death (Day) |
|---|---|---|---|---|
| Control Irradiation | 6.5 Gy | 65% | 24.0 ± 2.0 | 9/16 |
| mAbM11 pre-exposure | 6.5 Gy | 85% | 27.7 ± 1.5 | 13/17 |
| mAbM11 pre + post-exposure | 6.5 Gy | 65% | 24.0 ± 2.0 | 9/15 |
| mAbM11 post-exposure | 6.5 Gy | 80% | 26.3 ± 1.9 | 9/13 |
| mAbH6 pre + post-exposure | 6.5 Gy | 65% | 24.6 ± 1.9 | 9/19 |
| Control irraditation | 7.0 Gy | 35% | 20.7 ± 2.0 | 8/17 |
| mAbM11 pre-exposure | 7.0 Gy | 65% | 23.0 ± 2.3 | 7/13 |
| mAbM11 pre + post-exposure | 7.0 Gy | 55% | 21.6 ± 2.2 | 7/16 |
| mAbM11 post-exposure | 7.0 Gy | 70% | 24.3 ± 2.1 | 9/14 |
| mAbH6 pre + post-exposure | 7.0 Gy | 80% | 27.3 ± 1.3* | 15/20 |

*p = 0.0087 by two-tailed unpaired t-test between controlled irradiated animals and treatment group at the same irradiation exposure level.

Discussion

Acute radiation syndrome consists of three defined sub-syndromes: hematopoietic, gastrointestinal, and cerebrovascular. The syndrome observed depends on the radiation dose, with the hematopoietic effects observed in humans with significant partial or whole-body radiation exposures exceeding 1 Gy. The hematopoietic syndrome is characterized by severe depression of bone-marrow function leading to pancytopenia with changes in blood counts, red and white blood cells, and platelets occurring concomitant with damage to the immune system. As nadir occurs, with few neutrophils and platelets present in peripheral blood, neutropenia, fever, complications of sepsis and uncontrollable hemorrhage lead to death.

In the present study, administration of mAbH6 was found to increase survivability of whole-body x-ray irradiation in Swiss-Webster male mice irradiated at 7.0 Gy. Notably, at the 7.0 Gy exposure level, 80% of the animals receiving mAbH6 survived to 30 days compared to 35% of vehicle treated control irradiated animals. Importantly, the first day of death in this treated group did not occur until post-irradiation day 15, a 7-day increase over that observed in vehicle treated control irradiated animals. Curiously, at the lower X-ray exposure (6.5 Gy), administration of mAbH6 did not appear to impact survivability or delay in mortality compared to vehicle treated control irradiated animals. There could be multiple reasons for this difference in response between exposure levels, although verification of any hypothesis may require additional studies, including interim sample collection for microbiological culture and hematological parameters. One explanation may simply be that the number of animals assigned to groups may have precluded seeing any subtle treatment-related differences. For example, with groups sizes of n=20, the difference in survival between 65% (mAbH6 at 6.5 Gy exposure) and 80% (mAbH6 at 7.0 Gy exposure) is 3 animals. On the other hand, the difference between 35% (vehicle control at 7.0 Gy exposure) and 80% (mAbH6 at 7.0 Gy exposure) is 9 animals, and provides sound evidence of a treatment-related difference.

These results demonstrate that anti-MASP-2 antibodies are effective in treating a mammalian subject at risk for, or suffering from the detrimental effects of acute radiation syndrome.

Example 51

This Example demonstrates that a MASP-2 inhibitor, such as an anti-MASP-2 antibody, is effective for the treatment, amelioration or prevention of diabetic neuropathy in a mouse model of type II diabetes.

Rationale:

Obese diabetic db/db mice develop peripheral neuropathy (nerve dysfunction). This study examined if anti-MASP-2 therapy has a beneficial effect on peripheral nerve dysfunction that develops in this mouse model of diabetic nephropathy. Diabetic neuropathy (DN) was assessed using a thermal latency test. The thermal latency test is a test for nociception (perception of pain), which can be defective in diabetic patients and lead to adverse consequences.

Methods:

Animals

Obese diabetic db/db mice on C57BLKS/J background (n=12/group) were treated with anti-murine MASP-2 mAb, isotype matched control mAb, or saline, respectively. Non-obese db/m mice on the same strain background served as non-diabetic controls. Antibody treatment (1 mg/kg ip. once a week) was initiated at 7 weeks of age and continued through 24 weeks of age. Glucose and LP activity levels were measured in blood samples collected every other week from each mouse.

Thermal Latency Test:

Thermal latency tests were conducted at week 17, week 18 and week 20 and were carried out as follows: Mice were placed on a hot plate (Accuscan Instruments) set at a temperature of 55° C. inside a 15 cm×15 cm enclosure. The latency period (ie, number of seconds) for a hind limb response indicative of the perception of pain (shaking or licking) was measured using a stop watch with a maximal cut-off time for 30 seconds.

TABLE 10

STUDY GROUPS

| Group | genotype | number | treatment |
|---|---|---|---|
| A | db/db | n = 12 | untreated diabetic mice |
| B | db/db | n = 12 | anti-murine MASP-2 mAb (IgG2a) |
| C | db/db | n = 12 | isotype control ab (MBT mAb205P) |
| D | db/m | n = 12 | untreated, non-diabetic mice |

Figure 50A:
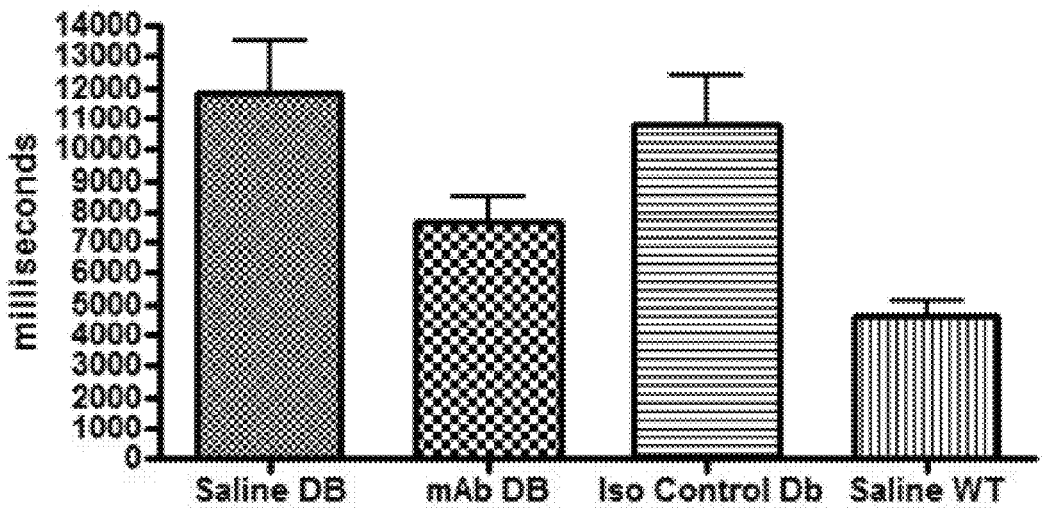
FIG. 50A graphically illustrates the results of thermal plate testing carried out at week 17 in diabetic mice receiving weekly ip administration of anti-murine MASP-2 antibody (mAbM11), as described in Example 51.
Figure 50B:
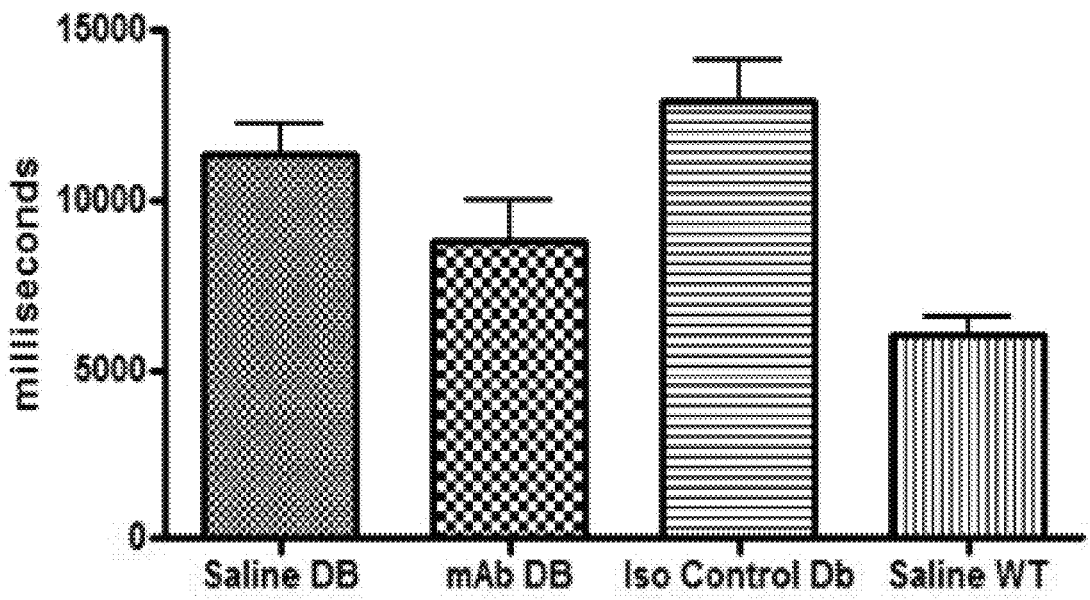
FIG. 50B graphically illustrates the results of thermal plate testing carried out at week 18 in diabetic mice receiving weekly ip administration of anti-murine MASP-2 antibody (mAbM11), as described in Example 51.

Results:

FIG. 50A graphically illustrates the results of the thermal plate testing carried out on week 17. FIG. 50B graphically illustrates the results of thermal plate testing carried out on week 18, and FIG. 50C graphically illustrates the results of thermal plate testing carried out on week 20.

Figure 50C:
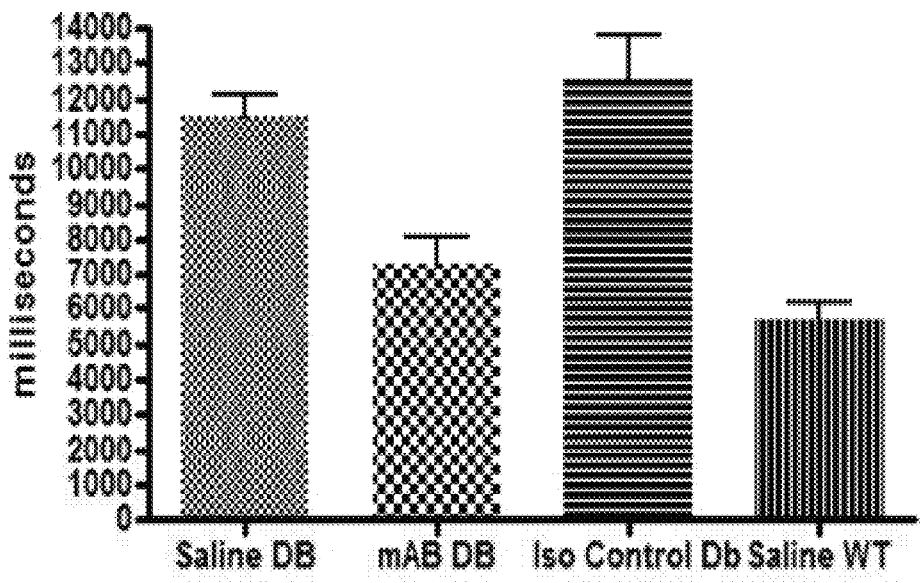
FIG. 50C graphically illustrates the results of thermal plate testing carried out at week 20 in diabetic mice receiving weekly ip administration of anti-murine MASP-2 antibody (mAbM11), as described in Example 51.

As shown in FIGS. 50A-C, the untreated diabetic mice (saline DB) had the longest delay in reacting to the thermal plate. Notably, the reaction time was significantly decreased in the diabetic mice receiving weekly administration of anti-MASP-2 ab (mAb DB). In contrast, the isotype control antibody treated diabetic mice (Iso control db) did not show a decrease in reaction time. The results shown in FIG. 50C (testing at 20 weeks) had the following results of the Ttest: db Iso vs anti-MASP-2 antibody: p<0.003; db Saline vs anti-MASP-2 antibody: p<0.001; and WT vs anti-MASP-2 p=0.01. These results indictate that pre-treatment with anti-MASP-2 antibody is effective to reduce peripheral neuropathy in type II diabetic mice, as measured by increased reaction time in a thermal latency test.

Example 52

This Example demonstrates that the absence of MASP-2 functional activity in a MASP-2 (−/−) mouse model results in a significant degree of protection from cerebral ischaemia/reperfusion injury (stroke).

Methods:

Three vessel occlusion (3VO) Surgery:

Transient ischemia was introduced by the three vessel occlusion (3VO) stroke model as described by Yanamoto et al., *Exp Neurology* 182(2):261-274 (2003). Briefly described, Female C57/B16 mice at the age of 8-18 weeks old were administered with Vetergesic (analgesic) prior to the operation to minimize post-operative pain. The animals were anesthetized with 3% to 4% isofluorane with $O_2/N_2O$ followed by a reduction of isofluorane to 0.5 to 1.5% for maintenance anesthesia. The two common carotid arteries (CCA) were exposed via a ventral midline incision of the neck, followed by clipping the left CCA with an aneurism clip. This reduces bleeding during the procedure to cauterize the ipsilateral middle cerebral artery (MCA). Following the clipping of the left CCA, the left zygomatic arch was removed to enable access to the skull and the middle cerebral artery. A 1 mm thick burr hole was opened to allow access to the MCA followed by its permanent cauterization using a bipolar coagulator (Aura, Kirwan Surgical Products). After the MCA occlusion, ischemia was induced for 30 minutes by the clipping of the right CCA. During the ischemic time the head wound was closed. After the termination of ischemia both clips were removed allowing reperfusion for 24 h and animals were culled afterwards by cervical dislocation.

Infarct Size Determination

Following 24 hours of reperfusion, mice were killed via cervical dislocation and their brains were removed and sliced into 1 mm thick slices using a pre-cooled brain matrix. Infarct volume after ischemia was determined via the reliable method using 2, 3, 5-Triphenyltetrazolium chloride (TTC), which is a metabolic cell indicator of mitochondrial activity, as described in Bederson, J. B. et al., *Stroke* 17:1304-1308 (1986) and Lin T. N. et al, *Stroke* 24:117-121 (1993). In this assay, the red coloring (shown as dark areas in the black and white photographs) in brain sections indicates the normal, non-infracted tissue whereas non-colored, white areas indicate the infracted tissue (Bederson et al., 1986). Upon sectioning of the brain, slices were stained with 2% TTC in saline at room temperature for 30 minutes in the dark. Afterwards the sections were fixed in 10% formalin and stored in the dark in 4° C. Digital images were taken and were analyzed in Scion Image Software to calculate the infarct volume. The infarct volume was calculated as follows to avoid overestimation of the infarct area by edema:

Infarct volume=Infarct area/(ipsilateral area/contralateral area)×1 mm (thickness of the slide)

Figure 51:
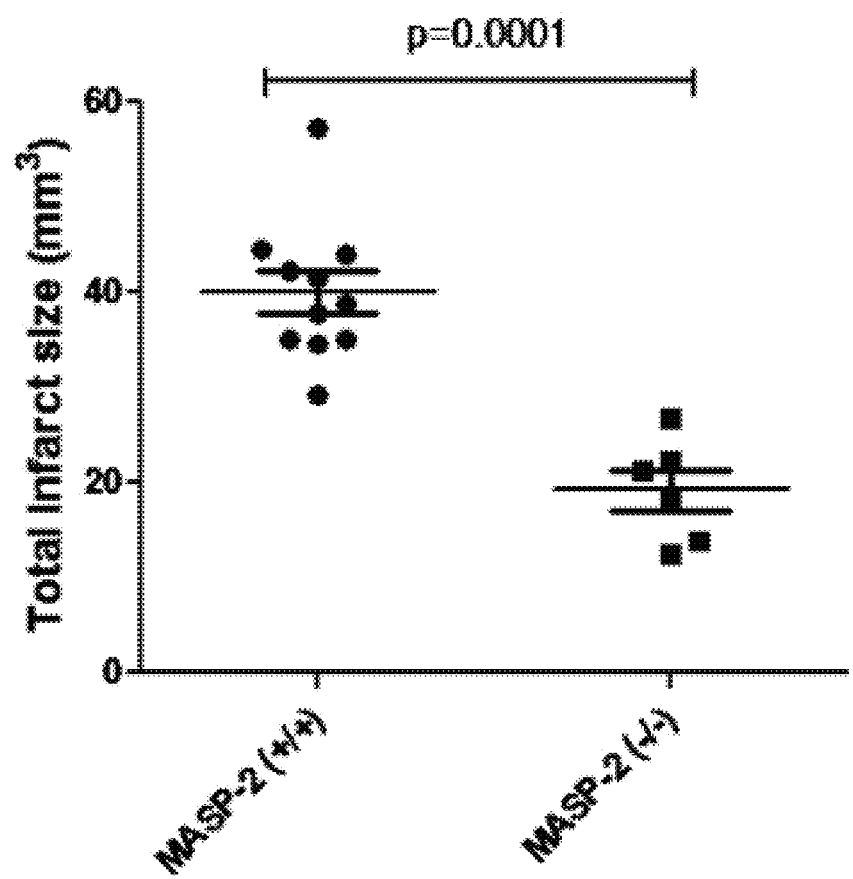
FIG. 51 graphically illustrates the cerebral infarct volume in WT (MASP-2 (+/+)) and MASP-2 (−/−) mice following 30 minutes ischemia and 24 hours reperfusion, as described in Example 52.

Results:

FIG. 51 graphically illustrates the cerebral infarct volume in WT and MASP-2 (−/−) mice following 30 minutes ischemia and 24 hours reperfusion. As shown in FIG. 51, the infarct volume following 3-VO is significantly decreased in MASP-2 (−/−) mice in comparison to WT (MASP-2 (+/+) mice (p=0.0001).

Figure 52A:
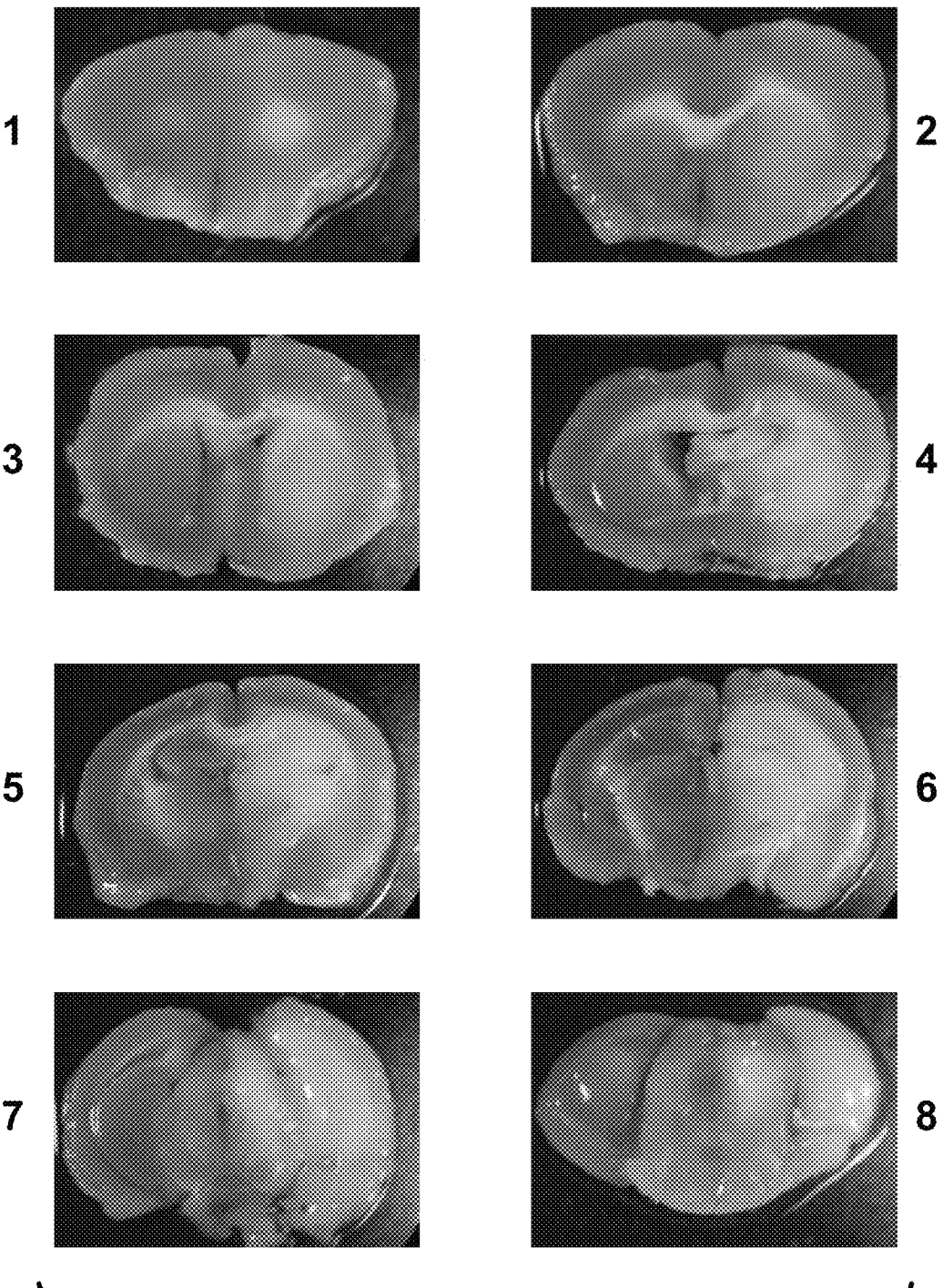
FIG. 52A shows a series of photographs of stained brain sections from a WT (MASP-2+/+) mouse after 30 minutes ischemia and 24 hours reperfusion. Panels 1-8 of FIG. 52A show the different section areas of the brain corresponding to Bregma 1-8, respectively, in relation to the exit of the acoustic nerve (Bregma 0), as described in Example 52.

FIG. 52A shows a series of brain sections of a WT (MASP-2+/+) mouse after 30 minutes ischemia and 24 hours reperfusion. Panels 1-8 of FIG. 52A show the different section areas of the brain corresponding to Bregma 1-8, respectively, in relation to the exit of the acoustic nerve (Bregma 0).

Figure 52B:
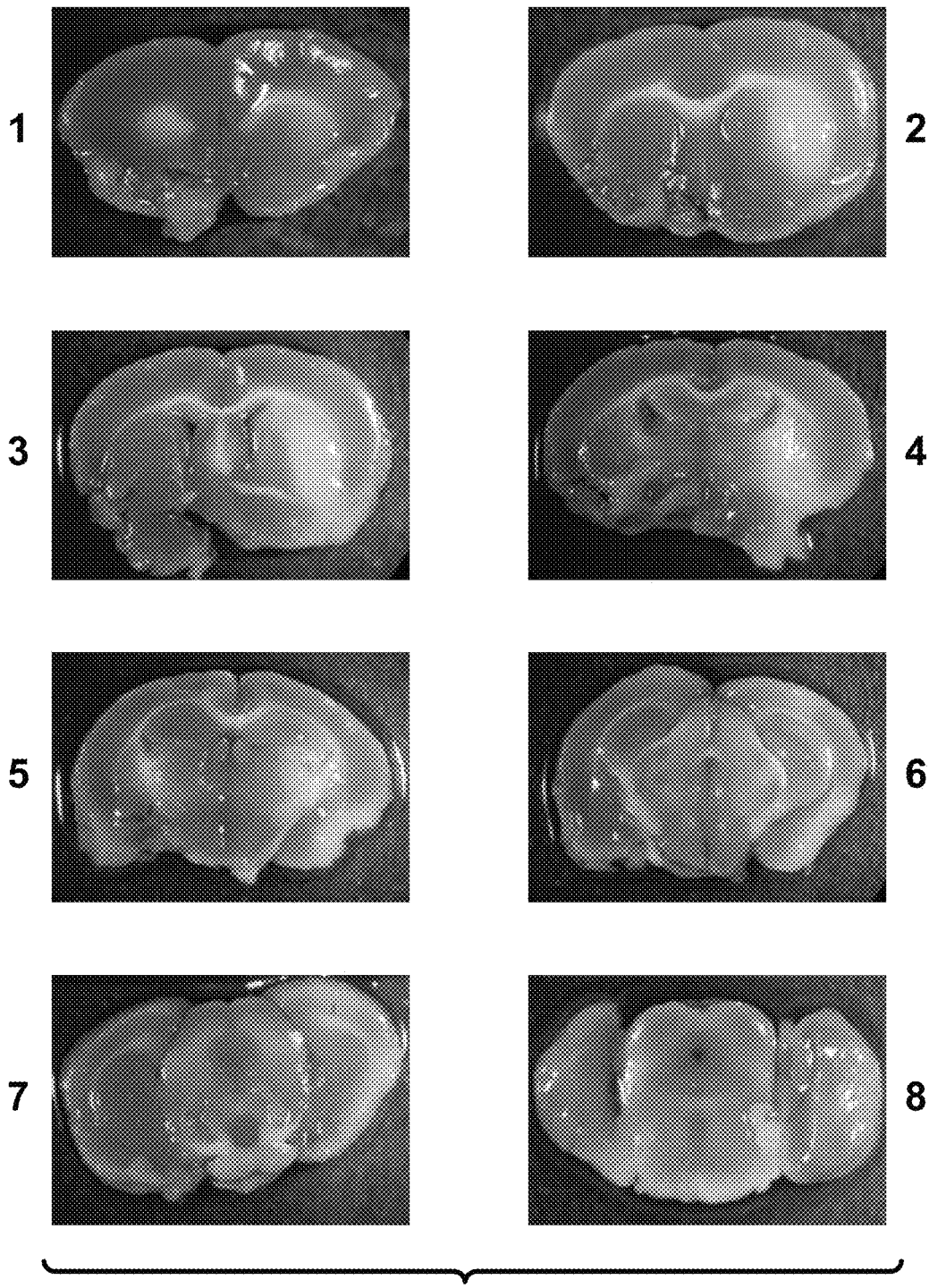
FIG. 52B shows a series of photographs of stained brain sections from a MASP-2 (−/−) mouse after 30 minutes ischemia and 24 hours reperfusion. Panels 1-8 of FIG. 52B show the different sections areas of the brain corresponding to Bregma 1-8, respectively, in relation to the exit of the acoustic nerve (Bregma 0), as described in Example 52.

FIG. 52B shows a series of brain sections of a MASP-2 (−/−) mouse after 30 minutes ischemia and 24 hours reperfusion. Panels 1-8 of FIG. 52B show the different sections areas of the brain corresponding to Bregma 1-8, respectively, in relation to the exit of the acoustic nerve (Bregma 0).

The infarct volumes measured for the brain sections shown in FIGS. 52A and 52B are provided below in TABLE 11.

TABLE 11

INFARCT VOLUME MEASUREMENTS FROM BRAIN SECTIONS OF MICE TREATED WITH MCAO FOR 30 MINUTES FOLLOWED BY 24 HOURS REPERFUSION (SHOWN IN FIGS. 52A AND 52B)

| FIG. (reference panel) | Genotype | BREGMA (in relation to the Exit of the acoustic nerve, Bregma = 0) | Infarct volume |
|---|---|---|---|
| FIG. 52A-1 | WT (MASP2 +/+) | 1 | 1.70 mm |
| FIG. 52A-2 | WT (MASP2 +/+) | 2 | 0.74 mm |
| FIG. 52A-3 | WT (MASP2 +/+) | 3 | −0.10 mm |
| FIG. 52A-4 | WT (MASP2 +/+) | 4 | −0.82 mm |
| FIG. 52A-5 | WT (MASP2 +/+) | 5 | −1.82 mm |
| FIG. 52A-6 | WT (MASP2 +/+) | 6 | −3.08 mm |
| FIG. 52A-7 | WT (MASP2 +/+) | 7 | −4.04 mm |
| FIG. 52A-8 | WT (MASP2 +/+) | 8 | −4.60 mm |
| FIG. 52B-1 | MASP2 (−/−) | 1 | 1.54 mm |
| FIG. 52B-2 | MASP2 (−/−) | 2 | 0.98 mm |
| FIG. 52B-3 | MASP2 (−/−) | 3 | −0.46 mm |
| FIG. 52B-4 | MASP2 (−/−) | 4 | −1.22 mm |
| FIG. 52B-5 | MASP2 (−/−) | 5 | −1.70 mm |
| FIG. 52B-6 | MASP2 (−/−) | 6 | −2.80 mm |
| FIG. 52B-7 | MASP2 (−/−) | 7 | −4.36 mm |
| FIG. 52B-8 | MASP2 (−/−) | 8 | −4.72 mm |

As shown in FIGS. 52A and 52B and TABLE 11, MASP-2 deficiency limits tissue loss following transient cerebral ischemia (MCAO for 30 minutes) followed by 24 hours reperfusion. These results demonstrate that the absence of MASP-2 functional activity in a MASP-2 (−/−) mouse model results in a significant degree of protection from cerebral ischaemia/reperfusion injury (stroke).

While illustrative embodiments have been illustrated and described, it will be appreciated that various changes can be made therein without departing from the spirit and scope of the invention.

The invention claimed is:

1. A method of inhibiting adverse effects of transplantation in a subject that has undergone, is undergoing, or will undergo a liver transplant procedure comprising administering to the subject, or pretreating the liver to be transplanted with, a composition comprising a monoclonal MASP-2 inhibitory antibody, or antigen-binding fragment thereof, that specifically binds to a portion of SEQ ID NO:6 and inhibits MASP 2 dependent complement activation.

2. The method of claim 1, wherein the monoclonal MASP-2 inhibitory antibody, or antigen-binding fragment thereof, specifically binds to a polypeptide comprising SEQ ID NO:6 with an affinity of at least 10 times greater than it binds to a different antigen in the complement system.

3. The method of claim 1, wherein the monoclonal MASP-2 inhibitory antibody, or antigen-binding fragment thereof, selectively inhibits MASP-2 dependent complement activation while leaving C1q-dependent classical complement pathway activation functionally intact.

4. The method of claim 1, wherein the monoclonal MASP-2 inhibitory antibody has reduced effector function.

5. The method of claim 1, wherein the monoclonal MASP-2 inhibitory antibody or antigen-binding fragment thereof is recombinant, chimeric, humanized or human.

6. The method of claim 1, wherein the organ transplant procedure is selected from the group consisting of organ allotransplantation or a tissue graft.

7. The method of claim 1, wherein the subject has undergone, is undergoing, or will undergo a liver transplant.

8. The method of claim 1, wherein the method prevents or reduces an inflammatory reaction resulting from said organ transplantation.

9. The method of claim 1, wherein the composition is administered to the subject by at least one of intra-arterial, intravenous, intramuscular, or subcutaneous administration.

10. The method of claim 1, wherein the method comprises pretreating the organ to be transplanted with the composition comprising the monoclonal MASP-2 inhibitory antibody, or antigen-binding fragment thereof, that specifically binds to a portion of SEQ ID NO:6 and selectively inhibits MASP 2 dependent complement activation without substantially inhibiting C1q-dependent complement activation.

11. The method of claim 1, wherein the method comprises administering the composition to the subject prior to the transplant procedure.

12. The method of claim 1, wherein the method comprises administering the composition to the subject during the transplant procedure.

13. The method of claim 1, wherein the method comprises administering the composition to the subject during the acute period following the transplant procedure.

14. The method of claim 1, wherein the method comprises administering the composition to the subject as a long term post-transplantation therapy.

* * * * *